(12) United States Patent
Chen et al.

(10) Patent No.: US 12,234,479 B2
(45) Date of Patent: *Feb. 25, 2025

(54) BIFUNCTIONAL MOLECULE AND USE THEREOF

(71) Applicant: CYTOCARES (SHANGHAI) INC., Shanghai (CN)

(72) Inventors: Shuai Chen, Shanghai (CN); Huaxing Zhu, Shanghai (CN); Yuanping Liao, Shanghai (CN)

(73) Assignee: CYTOCARES (SHANGHAI) INC., Shanghai (CN)

( * ) Notice: Subject to any disclaimer, the term of this patent is extended or adjusted under 35 U.S.C. 154(b) by 1404 days.

This patent is subject to a terminal disclaimer.

(21) Appl. No.: 16/474,554

(22) PCT Filed: Aug. 9, 2017

(86) PCT No.: PCT/CN2017/096592
§ 371 (c)(1),
(2) Date: Nov. 12, 2019

(87) PCT Pub. No.: WO2018/120842
PCT Pub. Date: Jul. 5, 2018

(65) Prior Publication Data
US 2023/0242876 A1    Aug. 3, 2023

(30) Foreign Application Priority Data

Dec. 30, 2016 (CN) .......................... 201611256643.8
Dec. 30, 2016 (CN) .......................... 201611258667.7
Dec. 30, 2016 (CN) .......................... 201611260781.3
Dec. 30, 2016 (CN) .......................... 201611260818.2

(51) Int. Cl.
*C07K 16/28* (2006.01)
*C12N 5/0783* (2010.01)
*C12N 15/85* (2006.01)

(52) U.S. Cl.
CPC ........ *C12N 5/0636* (2013.01); *C07K 16/2803* (2013.01); *C07K 16/2809* (2013.01); *C07K 16/2818* (2013.01); *C07K 16/2827* (2013.01); *C07K 16/2875* (2013.01); *C07K 16/2878* (2013.01); *C12N 15/85* (2013.01); *C07K 2317/31* (2013.01); *C07K 2317/622* (2013.01); *C07K 2317/74* (2013.01); *C12N 2501/51* (2013.01); *C12N 2501/515* (2013.01); *C12N 2501/599* (2013.01); *C12N 2800/107* (2013.01)

(58) Field of Classification Search
None
See application file for complete search history.

(56) References Cited

U.S. PATENT DOCUMENTS

| | | | |
|---|---|---|---|
| 6,352,694 | B1 | 3/2002 | June et al. |
| 2014/0294833 | A1* | 10/2014 | Desjarlais .......... C07K 16/2809 435/69.6 |

FOREIGN PATENT DOCUMENTS

| | | | |
|---|---|---|---|
| CN | 106132436 A | 11/2016 | |
| CN | 106188305 A | 12/2016 | |
| WO | WO-2004106381 A1 * | 12/2004 | ............. A61P 19/02 |
| WO | WO 2015149077 A1 | 10/2015 | |
| WO | WO 2016061142 A1 | 4/2016 | |
| WO | WO 2016069993 A1 | 5/2016 | |
| WO | WO 2016070061 A1 | 5/2016 | |
| WO | WO 2016138491 A1 | 9/2016 | |
| WO | WO-2016139463 A1 * | 9/2016 | ............. A61K 35/76 |

* cited by examiner

*Primary Examiner* — Michael D Burkhart
(74) *Attorney, Agent, or Firm* — Squire Patton Boggs (US) LLP

(57) ABSTRACT

This disclosure belongs to the field of biomedical technology, and particularly refers to a bifunctional molecule and the application thereof. The structure of the bifunctional molecule includes a first functional domain and a second functional domain. These domains are capable of simultaneously binding to T cells, thereby producing the first and second signals required for T cell activation. The bifunctional molecule is a recombinant protein-peptide, which can be produced by a eukaryotic cell expression system. The product has a single structure, simple purification process, high protein yield, and stable preparation process and product. The bifunctional molecule is superior to the current techniques in expanding T cells in vitro with lower protein dosage and simpler use procedure. It can be directly supplemented as soluble form without optimizing the relative ratio of full-length antibodies.

10 Claims, 30 Drawing Sheets

Specification includes a Sequence Listing.

BIFUNCTIONAL MOLECULE AND USE THEREOF

CROSS REFERENCES TO RELATED APPLICATIONS

This is a Sect. 371 National Stage of PCT International Application No. PCT/CN2017/096592, filed on Aug. 9, 2017, which claims the benefits of priority to Chinese Patent Application No. CN 2016112566438, entitled "A bifunctional molecule combining CD 3 and T cell negative costimulatory molecules, and application thereof", filed with CNIPA on Dec. 30, 2016, claims the benefits of priority to Chinese Patent Application No. 2016112586677, entitled "A bispecific molecule combining CD 3 antibody domain and T cell positive costimulatory molecule ligand, and application thereof", filed with CNIPA on Dec. 30, 2016, claims the benefits of priority to Chinese Patent Application No. 2016112607813, entitled "A bifunctional molecule combining CD 3 and CD28, and application thereof", filed with CNIPA on Dec. 30, 2016, and claims the benefits of priority to Chinese Patent Application No. 2016112608182, entitled "A bifunctional molecule combining CD 3 and T cell positive costimulatory molecule, and application thereof", filed with CNIPA on Dec. 30, 2016, the contents of which are incorporated herein by reference in its entirety.

TECHNICAL FIELD

This disclosure relates to the technical field of biomedicine, and in particular, to a bifunctional molecule and the application thereof.

BACKGROUND

T lymphocyte is derived from Thymus, so it is named as T cell. Mature T cells exist in thymus-dependent peripheral immune organs and play the essential role of adaptive cellular immune response and important assistant role in the thymus-dependent antigen-induced humoral immune response. According to the different functions, T cells can be divided into Cytotoxic T lymphocyte (CTL), helper T cell (Th) and regulatory T cell (Treg). CTLs express CD8, which is the main effect cell in adaptive cellular immune response. The main functions of CTL are specifically recognizing endogenous peptide/MHCI complex on target cells, expressing perforin, granzyme and granulysin to directly kill target cells (tumor cells or parasitic pathogen-infected cells) after self-activation, or inducing target cell apoptosis through Fas/FasL signal pathway. All the Ths express CD4, and regulate the activity of CTL through expression different cytokines or directly interact with other cells to indirectly involve cellular immunity. Additional, Treg negatively regulates cellular immune response through directly inhibiting target cell activation or excrete cytokines like IL-10 and TGFb, which plays important roles in diseases like immune tolerance, autoimmune disease, inflammation and cancer.

The activation and efficient expansion of CD8 positive T cells is the base of effective killing target cells, which depends on a dual signaling pathway. The TCR/CD3 complex on the surface of CD8-positive T cells specifically recognize the endogenous antigen peptide/MHC class I complex on the surface of antigen-presenting cells (APC). This leads to the interaction of CD3 with the cytoplasmic domain of the co-receptor CD8, thus activates the protein tyrosine kinase that links to the tail of the cytoplasmic domain. The activated tyrosine kinase induces tyrosine phosphorylation of immunoreceptor tyrosine-based activation motif (ITAM) of the CD3 cytoplasmic domain. This initiates a signaling cascade that activates transcription factors to initially activate T cells, which is the first signaling of T cell activation. Simultaneously with the costimulatory ligands on the membrane of APC cells (CD80, CD86, 4-1BBL, B7RP-1, OX40L, GITRL, CD40, CD70, PD-L1, PD-L2, and HVEM, etc.) bind to co-stimulatory molecules on the membrane of T cells (such as CD28, 4-1BB, ICOS, OX40, GITR, CD40L, CD27, CTLA-4, PD-1, LAG-3, TIM-3, TIGIT, BTLA, etc.) to produce a second signal which fully activates T cell. Costimulatory molecules can be either positive (co-stimulation) or negative (co-inhibition). Positive co-stimulatory molecules include CD28, 4-1BB, ICOS, OX40, GITR, CD40L and CD27, interacting with the corresponding ligands CD80, CD86, 4-1BBL, B7RP-1, OX40L, GITRL, CD70, etc. The co-stimulatory signal can lead to complete activation of T cells. While CTLA-4, PD-1, LAG-3, TIM-3, TIGIT and BTLA are negative costimulatory (co-inhibition) molecules, and the corresponding ligands such as CD80, CD86, PD-L1, PD-L2, Galectin-9, HVEM, etc. The negative costimulatory signal is primarily the down-regulation and termination of T cell activation.

The studies for the first signaling of T cell activation have been reported by constructing the anti-CD3 monoclonal full-length antibody through gene engineering (Beverley P C et al, Eur J Immunol, 11:329-334, 1981; Lanzavecchia A et al, Eur J Immunol, 17:105-111, 1987; Yannelli J R et al, J Immunol Methods, 130:91-100, 1990). The current experiment data demonstrate these monoclonal antibodies could specifically recognize CD3 molecule on T cell surface and produce first signaling to activate T cells. Studies have shown that the first signaling pathway itself cannot fully activate T cells, which in turn leads to its disability and activation-induced cell death (AICD). To solve this problem, people have designed and constructed monoclonal full-length agonist antibodies against T cell positive costimulatory molecules like anti-CD28, anti-4-1BB and anti-ICOS (US Patent 20100168400A1; US Patent 20100183621A1; US patent 009193789B2) and monoclonal full-length antagonist antibodies against T cell negative co-stimulatory molecules like anti-PD-1, anti-CTLA-4 and LAG-3 (World Patent 2013173223A1; US Patent 007452535B2; US Patent 2015116539A1). These antibodies can be used in combination with full-length anti-CD3 antibody to provide complete dual activation signaling pathways. However, the combination of two full-length antibodies has some inconveniences in practice. It increases the workload and production cost of recombinant antibody expression and purification, and the relative proportion of the two full-length antibodies need to be optimized in activating the expanded T cells. Moreover, in order to promote ligand activation during using of two full-length antibody combination, high density of antibody reagent is needed, or coat plate or microbeads with antibodies to enhance the ligand activation.

SUMMARY

1) The present disclosure is able to fuse a first domain that is capable of binding to and activating a CD3 molecule on a surface of T cell, and a second domain capable of binding to and activating a T cell surface CD28 molecule to the same peptide. The peptide is produced by the eukaryotic cell expression system. The expression product has a single structure. The purification process is simple and the yield of protein yield is high. The preparation process and the product are stable. In contrast, in the using of the anti-CD3/ anti-CD28 monoclonal full-length antibody combination, the two antibodies need to be expressed and purified respectively, and the preparation process is complicated. The workload and production cost are increased. The bifunctional molecule of the disclosure is a single protein, which is better than anti-CD3 and anti-CD28 full-length antibody combination in expanding T cells in vitro, and requires lower protein dosage. The bifunctional molecule is more convenient to use by directly adding protein soluble without optimizing the ratio of the two full-length antibodies. 2) The present disclosure is able to fuse a first domain that is capable of binding to and activating a CD3 molecule on the surface of T cell, and a second domain capable of binding to and activating a T cell surface positive stimulation molecule to the same peptide. The peptide is produced by eukaryotic cell expression system. The expression product has a single structure. The purification process is simple and the yield of protein yield is high. The preparation process and the product are stable. In contrast, in the using of the anti-CD3 and anti-positive costimulatory molecule monoclonal full-length antibody combination, the two antibodies need to be expressed and purified respectively, and the preparation process is complicated. The workload and production cost are increased. The bifunctional molecule of the disclosure is a single protein, which is better than anti-CD3 and anti-positive costimulatory molecule full-length antibody combination in expanding T cells in vitro, and requires lower protein dosage. The bifunctional molecule is more convenient to use by directly adding protein soluble without optimizing the ratio of the two full-length antibodies.

3) The present disclosure is able to fuse a first domain that is capable of binding to and activating a CD3 molecule on the surface of T cell, and a second domain capable of binding to an extracellular domain of T cell positive costimulatory molecule ligand to the same peptide to generate a bifunctional molecule. The peptide is produced by the eukaryotic cell expression system. The expression product has a single structure. The purification process is simple and the yield of protein yield is high. The preparation process and the product are stable. In contrast, in the using of the anti-CD3 and anti-positive costimulatory molecule monoclonal full-length antibody combination, the two antibodies need to be expressed and purified respectively, and the preparation process is complicated. The workload and production cost are increased. The bifunctional molecule of the disclosure is a single protein, which is better than anti-CD3 and anti-positive costimulatory molecule full-length antibody combination in expanding T cells in vitro, and requires lower protein dosage. The bifunctional molecule is more convenient to use by directly adding protein soluble without optimizing the ratio of the two full-length antibodies.

4) The present disclosure is able to fuse a first domain that is capable of binding to and activating a CD3 molecule on the surface of T cell, and a second domain capable of binding to and inhibiting a T cell surface negative stimulation molecule to the same peptide to generate a bifunctional molecule. The peptide is produced by the eukaryotic cell expression system. The expression product has a single structure. The purification process is simple and the yield of protein is high. The preparation process and the product are stable. In contrast, in the using of the anti-CD3 and anti-negative costimulatory molecule monoclonal full-length antibody combination, the two antibodies need to be expressed and purified respectively, and the preparation process is complicated. The increased workload and production cost are increased. The bifunctional molecule of the disclosure is a single protein, which is better than anti-CD3 and anti-negative costimulatory molecule full-length antibody combination in expanding T cells in vitro, and requires lower protein dosage. The bifunctional molecule is more convenient to use by directly adding protein soluble without optimizing the ratio of the two full-length antibodies.

BRIEF DESCRIPTION OF THE DRAWINGS

FIG. 1-2: The SDS-PAGE analysis diagrams of final purified CD3-CD28 BsAb_M and CD3-CD28 BsAb_D.

FIG. 1-3: EILSA results for CD3-CD28 BsAb_M and CD3-CD28 BsAb_D.

FIG. 1-4: The growth curve of CIK cell.

FIG. 1-5: Determination of CD3+CD56+CIK cell percentage by flow cytometry analysis.

FIG. 1-6: Determination of CD4+/CD8+CIK cell percentage by flow cytometry analysis.

FIG. 2-1: The structure diagrams of monomeric anti-CD3/anti-T cell positive costimulatory molecule bifunctional antibody (BsAb_M) and dimeric anti-CD3/anti-T cell positive costimulatory molecule bifunctional antibody (BsAb_D).

FIG. 2-2: The SDS-PAGE analysis diagrams of final purified CD3-4-1BB BsAb_M and CD3-4-1BB BsAb_D.

FIG. 2-3: EILSA results for CD3-4-1BB BsAb_M and CD3-4-1BB BsAb_D.

FIG. 2-4: The growth curve of CIK cell.

FIG. 2-5: Determination of CD4+/CD8+CIK cell percentage by flow cytometry analysis.

FIG. 2-6: The SDS-PAGE analysis diagrams of final purified CD3-ICOS BsAb_M and CD3-ICOS BsAb_D.

FIG. 2-7: EILSA results for CD3-ICOS BsAb_M and CD3-ICOS BsAb_D.

FIG. 2-8: The growth curve of CIK cell.

FIG. 2-9: Determination of CD3+CD56+CIK cell percentage by flow cytometry analysis.

FIG. 2-10: The SDS-PAGE analysis diagrams of final purified CD3-OX40 BsAb_M and CD3-OX40 BsAb_D.

FIG. 2-11: EILSA results for CD3-OX40 BsAb_M and CD3-OX40 BsAb_D.

FIG. 2-12: The growth curve of CIK cells.

FIG. 2-13: Determination cytotoxicity of CIK cell after expansion to kill tumor cells.

FIG. 2-14: The SDS-PAGE analysis diagrams of final purified CD3-GITR BsAb_M and CD3-GITR BsAb_D.

FIG. 2-15: EILSA results for CD3-GITR BsAb_M and CD3-GITR BsAb_D.

FIG. 2-16: The growth curve of CIK cell.

FIG. 2-17: The SDS-PAGE analysis diagrams of final purified CD3-OX40L BsAb_M and CD3-OX40L BsAb_D.

FIG. 2-18: EILSA results for CD3-OX40L BsAb_M and CD3-OX40L BsAb_D.

FIG. 2-19: The growth curve of CIK cell.

FIG. 2-20: The SDS-PAGE analysis diagrams of final purified CD3-CD27 BsAb_M and CD3-CD27 BsAb_D.

FIG. 2-21: EILSA results for CD3-CD27 BsAb_M and CD3-CD27 BsAb_D.

FIG. 2-22: The growth curve of CIK cell.

FIG. 3-1: The structure diagrams of monomeric anti-CD3/anti-T cell positive costimulatory molecule ligand bifunctional molecule (BsM_M) and dimeric anti-CD3/anti-T cell positive costimulatory molecule ligand bifunctional molecule (BsM_D).

FIG. 3-2: The SDS-PAGE analysis diagrams of final purified CD3-4-1BBL BsM_M and CD3-4-1BBL BsM_D.

FIG. 3-3: EILSA results for CD3-4-1BBL BsM_M and CD3-4-1BBL BsM_D.

FIG. 3-4: The growth curve of CIK cell.

FIG. 3-5: The SDS-PAGE analysis diagrams of final purified CD3-B7RP-1 BsM_M and CD3-B7RP-1 BsM_D.

FIG. 3-6: EILSA results for CD3-B7RP-1 BsM_M and CD3-B7RP-1 BsM_D.

FIG. 3-7: The growth curve of CIK cell.

FIG. 3-8: The SDS-PAGE analysis diagrams of final purified CD3-OX40L BsM_M and CD3-OX40L BsM_D.

FIG. 3-9: EILSA results for CD3-OX40L BsM_M and CD3-OX40L BsM_D.

FIG. 3-10: The growth curve of CIK cell.

FIG. 3-11: The SDS-PAGE analysis diagrams of final purified CD3-GITRL BsM_M and CD3-GITRL BsM_D.

FIG. 3-12: EILSA results for CD3-GITRL BsM_M and CD3-GITRL BsM_D.

FIG. 3-13: The growth curve of CIK cell.

FIG. 3-14: The SDS-PAGE analysis diagrams of final purified CD3-CD70 BsM_M and CD3-CD70 BsM_D.

FIG. 3-15: EILSA results for CD3-CD70 BsM_M and CD3-CD27 BsM_D.

FIG. 3-16: The growth curve of CIK cell.

FIG. 4-1: The structure diagrams of monomeric anti-CD3/anti-T cell negative costimulatory molecule bifunctional antibody (BsAb_M) and dimeric anti-CD3/anti-T cell negative costimulatory molecule bifunctional antibody (BsAb_D).

FIG. 4-2: The SDS-PAGE analysis diagrams of final purified CD3-PD-1 BsAb_M and CD3-PD-1 BsAb_D.

FIG. 4-3: EILSA results for CD3-PD-1 BsAb_M and CD3-PD-1 BsAb_D.

FIG. 4-4: The growth curve of CIK cell.

FIG. 4-5: Determination IFN-γ expression of CIK cells mediated by CD3-PD-1 bispecific antibody.

FIG. 4-6: The SDS-PAGE analysis diagram of final purified CD3-CTLA-4 BsAb_M and CD3-CTLA-4 BsAb_D.

FIG. 4-7: EILSA results for CD3-CTLA-4 BsAb_M and CD3-CTLA-4 BsAb_D.

FIG. 4-8: The growth curve of CIK cell.

FIG. 4-9: Determination IFN-γ expression of CIK cells mediated by CD3-CTLA-4 bispecific antibody.

FIG. 4-10: The SDS-PAGE analysis diagram of final purified CD3-LAG-3 BsAb_M and CD3-LAG-3 BsAb_D.

FIG. 4-11: EILSA results for CD3-LAG-3 BsAb_M and CD3-LAG-3 BsAb_D.

FIG. 4-12: The growth curve of CIK cell.

FIG. 4-13: Determination IFN-γ expression of CIK cells mediated by CD3-LAG-3 bispecific antibody.

FIG. 4-14: The SDS-PAGE analysis diagram of final purified CD3-TIM-3 BsAb_M and CD3-TIM-3 BsAb_D.

FIG. 4-15: EILSA results for CD3-TIM-3 BsAb_M and CD3-TIM-3 BsAb_D.

FIG. 4-16: The growth curve of CIK cell.

FIG. 4-17: Determination IFN-γ expression of CIK cells mediated by CD3-TIM-3 bispecific antibody.

FIG. 4-18: The SDS-PAGE analysis diagram of final purified CD3-TIGIT BsAb_M and CD3-TIGIT BsAb_D.

FIG. 4-19: EILSA results for CD3-TIGIT BsAb_M and CD3-TIGIT BsAb_D.

FIG. 4-20: The growth curve of CIK cell.

FIG. 4-21: Determination IFN-γ expression of CIK cells mediated by CD3-TIGIT bispecific antibody.

FIG. 4-22: The SDS-PAGE analysis diagram of final purified CD3-BTLA BsAb_M and CD3-BTLA BsAb_D.

FIG. 4-23: EILSA results for CD3-BTLA BsAb_M and CD3-BTLA BsAb_D.

FIG. 4-24: The growth curve of CIK cell.

FIG. 4-25: Determination IFN-γ expression of CIK cells mediated by CD3-BTLA bispecific antibody.

DETAILED DESCRIPTION OF THE PREFERRED EMBODIMENTS

1, Terms and Abbreviations

Figure 1:
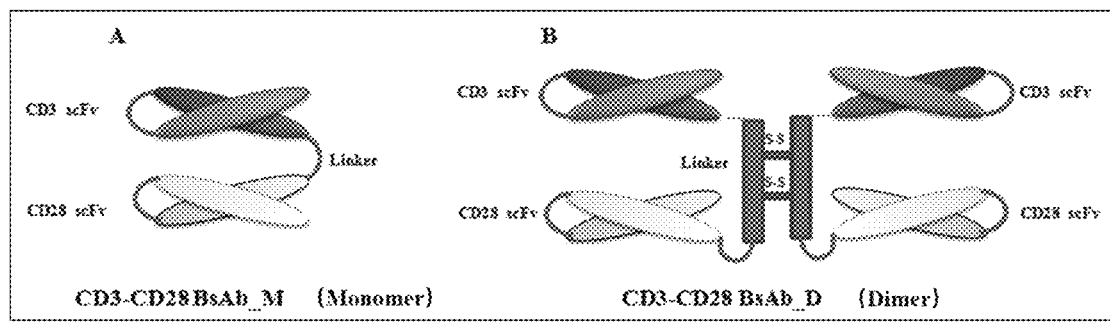
FIG. 1-1: The structure diagrams of CD3-CD28 BsAb_M and CD3-CD28 BsAb_D.

BsAb, Bi-specific Antibody
Fab, Fragment of antigen-binding
Fv, Variable fragment
scFv, Single-chain variable fragment
VH, Heavy chain variable region
VL, Light chain variable region
Linker
Extracellular domain
CD3-CD28 BsAb_M, anti-CD3/anti-CD28 bispecific antibody of monomeric form
CD3-CD28 BsAb_D, anti-CD3/anti-CD28 bispecific antibody of dimeric form
CD3-4-1BB BsAb_M, anti-CD3/anti-4-1BB bispecific antibody of monomeric form
CD3-4-1BB BsAb_D, anti-CD3/anti-4-1BB bispecific antibody of dimeric form
CD3-ICOS BsAb_M, anti-CD3/anti-ICOS bispecific antibody of monomeric form
CD3-ICOS BsAb_D, anti-CD3/anti-ICOS bispecific antibody of dimeric form
CD3-OX40 BsAb_M, anti-CD3/anti-OX40 bispecific antibody of monomeric form
CD3-OX40 BsAb_D, anti-CD3/anti-OX40 bispecific antibody of dimeric form
CD3-GITR BsAb_M, anti-CD3/anti-GITR bispecific antibody of monomeric form
CD3-GITR BsAb_D, anti-CD3/anti-GITR bispecific antibody of dimeric form
CD3-CD40L BsAb_M, anti-CD3/anti-CD40L bispecific antibody of monomeric form
CD3-CD40L BsAb_D, anti-CD3/anti-CD40L bispecific antibody of dimeric form
CD3-CD27 BsAb_M, anti-CD3/anti-CD27 bispecific antibody of monomeric form
CD3-CD27 BsAb_D, anti-CD3/anti-CD27 bispecific antibody of dimeric form
BsM: Bi-specific Molecule
Co-stimulatory molecule
4-1BBL, 4-1BB ligand of T cell positive costimulatory molecule
B7RP-1, ICOS ligand of T cell positive costimulatory molecule
OX4oL, IOX4o ligand of T cell positive costimulatory molecule
GITRL, GITRL ligand of T cell positive costimulatory molecule
CD70, CD27 ligand of T cell positive costimulatory molecule
CD3-4-1BBL BsM_M, anti-CD3/4-BBL bispecific molecules of monomeric form
CD3-4-1BBL BsM_D, anti-CD3/4-1BBL bispecific molecules of dimeric form
CD3-B7RP-1 BsM_M, anti-CD3/B7RP-1 bispecific molecules of monomeric form
CD3-B7RP-1 BsM_D, anti-CD3/B7RP-1 bispecific molecules of dimeric form CD3-OX40L BsM_M, anti-CD3/OX40L bispecific molecules of monomeric form
CD3-OX40L BsM_D, anti-CD3/OX40L bispecific molecules of dimeric form
CD3-GITRL BsM_M, anti-CD3/GITRL bispecific molecules of monomeric form
CD3-GITRL BsM_D: anti-CD3/GITRL bispecific molecules of dimeric form
CD3-CD70 BsM_M, anti-CD3/CD70 bispecific molecules of monomeric form
CD3-CD70 BsM_D, anti-CD3/CD70 bispecific molecules of dimeric form
CD3-PD-1 BsAb_M, anti-CD3/anti-PD-1 bispecific antibody of monomeric form
CD3-PD-1 BsAb_D, anti-CD3/anti-PD-1 bispecific antibody of dimeric form
CD3-CTLA-4 BsAb_M, anti-CD3/anti-CTLA-4 bispecific antibody of monomeric form
CD3-CTLA-4 BsAb_D, anti-CD3/anti-CTLA-4 bispecific antibody of dimeric form
CD3-LAG-3 BsAb_M, anti-CD3/anti-LAG-3 bispecific antibody of monomeric form
CD3-LAG-3 BsAb_D, anti-CD3/anti-LAG-3 bispecific antibody of dimeric form
CD3-TIM-3 BsAb_M, anti-CD3/anti-TIM-3 bispecific antibody of monomeric form
CD3-TIM-3 BsAb_D, anti-CD3/anti-TIM-3 bispecific antibody of dimeric form
CD3-TIGIT BsAb_M, anti-CD3/anti-TIGIT bispecific antibody of monomeric form
CD3-TIGIT BsAb_D, anti-CD3/anti-TIGIT bispecific antibody of dimeric form
CD3-BTLA BsAb_M, anti-CD3/anti-BTLA bispecific antibody of monomeric form
CD3-BTLA BsAb_D, anti-CD3/anti-BTLA bispecific antibody of dimeric form 2. Bifunctional Molecule A bifunctional molecule of the disclosure includes a first domain capable of binding to and activating CD3 molecule on a surface of a T cell, and a second capable of binding to and activating a T cell surface CD28 molecule.

Further, the bifunctional molecule is capable of binding to and activating CD3 molecule on the surface of the T cell and the CD28 molecule, thereby generating a first signal and a second signal required for T cell activation.

The present disclosure has no particular limitation on the first functional domain and the second functional domain, as long as it can bind and activate the CD3 molecule on the surface of T cell and the CD28 molecule, thereby generating the first and second signal for T cell activation. For example, the first functional domain may be an anti-CD3 antibody, and the second functional domain may be an anti-CD28 antibody. The antibody may be in any form. However, regardless of the form of the antibody, the antigen-binding site thereof includes a heavy chain variable region and a light chain variable region. The antibody is preferably a small molecule antibody. The small molecule antibody is a small molecular weight antibody fragment, and the antigen-binding site includes a heavy chain variable region and a light chain variable region. The small molecule antibody has a small molecular weight, but retains the affinity of the parental monoclonal antibody, and has the same specificity as the parental monoclonal antibody. The types of small molecule antibodies include Fab antibodies, Fv antibodies and single-chain antibodies (scFv). The Fab antibody is formed by a disulfide bond between the intact light chain (variable region VL and constant region CL) and the heavy chain Fd segment (variable region VH and first constant region CH1). An Fv antibody is the minimal functional fragment of an antibody molecule that retains the entire antigen-binding site and is joined by a variable region of the light and heavy chains through a non-covalent bond. The scFv is a single-protein peptide chain molecule in which a heavy chain variable region and a light chain variable region are joined by a linker.

The first functional domain and the second functional domain are connected by a linker. The present disclosure has no particular requirements for the order of connection as long as the object of the present disclosure is not limited. For example, the C-terminus of the first functional domain can be linked to the N-terminus of the second functional domain. The number of amino acid of the linker fragment could be more than 1. The linker in the present disclosure is not particularly limited.

Further, the linker is selected from a G4S linker or a hinge domain of immunoglobulin IgD.

The G4S is GGGGS. The G4S linker includes one or more G4S units. For example, one, two, three or more G4S units can be included. In some embodiments of the present disclosure, a bifunctional molecule in a monomeric form is disclosed, the first functional domain and the second functional domain are connected by a G4S linker. The linker contains three G4S units, and the amino acid sequence of the ligated fragment is shown in SEQ ID NO.17.

The hinge domain of the immunoglobulin IgD may be the hinge Ala90-Val170 of IgD. In some embodiments of the disclosure, a bifunctional molecule of a dimeric form is disclosed. The first functional domain and the second functional domain are linked by a hinge domain of immunoglobulin IgD, which is Ala90-Val170. The amino acid sequence of the linker is shown in SEQ ID NO.19. The linker can be linked to each other by a disulfide bond to form a dimer.

In a preferred embodiment of the disclosure, the structure of the bifunctional molecule is shown in FIG. 1-1. The bifunctional molecule may be in a monomeric form or a dimeric form. A structure diagram of the bifunctional molecule in a monomeric form of the present disclosure is shown in FIG. 1-1A. The structure of the bifunctional molecule includes a first functional domain that binds to the CD3 antigen, and a second domain that binds to the CD28 antigen. The first domain is a scFv that binds to the CD3 antigen, and the second domain is a scFv that binds to the CD28 antigen. A structure diagram of the bifunctional molecule in the dimeric form of the present disclosure is shown in FIG. 1-1B. The structure of the bifunctional molecule includes two first domains that bind to the CD3 antigen, and two second domains that bind to the CD28 antigen. The first domain is a scFv that binds to the CD3 antigen, and the second domain is a scFv that binds to the CD28 antigen. The dimeric form of the bifunctional molecule of the disclosure has an antigen-binding affinity that is more than twice of the monomeric form, so the dimer has a better use effect than the monomer in expanding T cells.

Specifically, the first domain is a single-chain antibody against CD3. The anti-CD3 single-chain antibody includes a heavy chain variable region and a light chain variable region. The amino acid sequence of the heavy chain variable region of the anti-CD3 single-chain antibody is shown in SEQ ID NO.6. The amino acid sequence of the light chain variable region of the anti-CD3 single-chain antibody is shown in SEQ ID NO.7. Further, the amino acid sequence of the anti-CD3 single-chain antibody is shown in SEQ ID NO.5. The second domain is a single-chain antibody against CD28. The anti-CD28 single-chain antibody includes a heavy chain variable region and a light chain variable region. The amino acid sequence of the heavy chain variable region of the anti-CD28 single-chain antibody is shown in SEQ ID NO.9. The amino acid sequence of the light chain variable region of the anti-CD28 single-chain antibody is shown in SEQ ID NO.10. The amino acid sequence of the anti-CD28 single-chain antibody is shown in SEQ ID NO.8.

In a preferred embodiment of the present disclosure, the amino acid sequence of the bifunctional molecule in the monomeric form is shown in SEQ ID NO.1. The amino acid sequence of the bifunctional molecule in the dimeric form is shown in SEQ ID NO.3. It is not limited to the specific forms listed in the preferred cases of the present disclosure.

Another bifunctional molecule of the disclosure includes a first domain capable of binding and activating a T cell surface CD3 molecule, and a second functional domain capable of binding to and activating T cell positive costimulatory molecule.

Further, the bifunctional molecule is capable of binding to and activating a CD3 molecule on the surface of T cell and a T cell positive costimulatory molecule, thereby generating a first signal and a second signal required for T cell activation. The T cell positive costimulatory molecules include, but are not limited to, human CD28, 4-1BB, ICOS, OX40, GITR, CD40L or CD27, et al.

The present disclosure has no particular limitation on the first functional domain and the second functional domain. As long as it can bind to and activate CD3 molecules on the surface of T cell and T cell positive costimulatory molecules, thereby producing the first signal and the second signal required for activation of T cells. For example, the first functional domain can be an anti-CD3 antibody, and the second functional domain can be an antibody against a T cell positive costimulatory molecule. The antibody can be in any form. However, regardless of the form of the antibody, the antigen-binding site thereof includes a heavy chain variable region and a light chain variable region. The antibody may preferably be a small molecule antibody. The small molecule antibody is a small molecular weight antibody fragment, and the antigen-binding site includes a heavy chain variable region and a light chain variable region. The small molecule antibody has a small molecular weight, but retains the affinity of the parental monoclonal antibody, and has the same specificity as the parental monoclonal antibody. The types of small molecule antibodies mainly include Fab, Fv and scFv. The Fab antibody is formed by a disulfide bond between the intact light chain (variable region VL and constant region CL) and the heavy chain Fd segment (variable region VH and first constant region CH1). Fv antibodies are joined by non-covalent bonds by the variable regions of the light and heavy chains. They are the minimal functional fragments of the antibody molecule that retain the intact antigen-binding site. A scFv is a single-protein peptide chain molecule in which a heavy chain variable region and a light chain variable region are joined by a linker.

The first functional domain and the second functional domain are connected by a linker. The present disclosure has no particular requirements for the order of connection as long as the object of the present disclosure is not limited. For example, the C-terminus of the first functional domain can be linked to the N-terminus of the second functional domain. The number of amino acid in the linker fragment is preferred to be more than 1. The present disclosure is also not particularly limited to the linker as long as it does not limit the object of the present disclosure.

Further, the linker is selected from a G4S linker and a hinge domain of immunoglobulin IgD.

The G4S is GGGGS. The G4S linker includes one or more G4S units. For example, one, two, three or more G4S units can be included. In some embodiments of the present disclosure, a bifunctional molecule in a monomeric form is disclosed. The first functional domain and the second functional domain are connected by a linker in units of G4S. The linker contains three G4S units, and the amino acid sequence of the ligated fragment is shown in SEQ ID NO.32.

The hinge domain of the immunoglobulin IgD could be the hinge Ala90-Val170 of IgD. In some embodiments of the disclosure, wherein a bifunctional molecule of a dimeric form is disclosed, the first functional domain and the second functional domain are linked by a hinge domain of immunoglobulin IgD, which is Ala90-Val170. The amino acid sequence of the linker is shown in SEQ ID NO.34. The linker can be linked to each other by a disulfide bond to form a dimer.

Figures 1, 2:
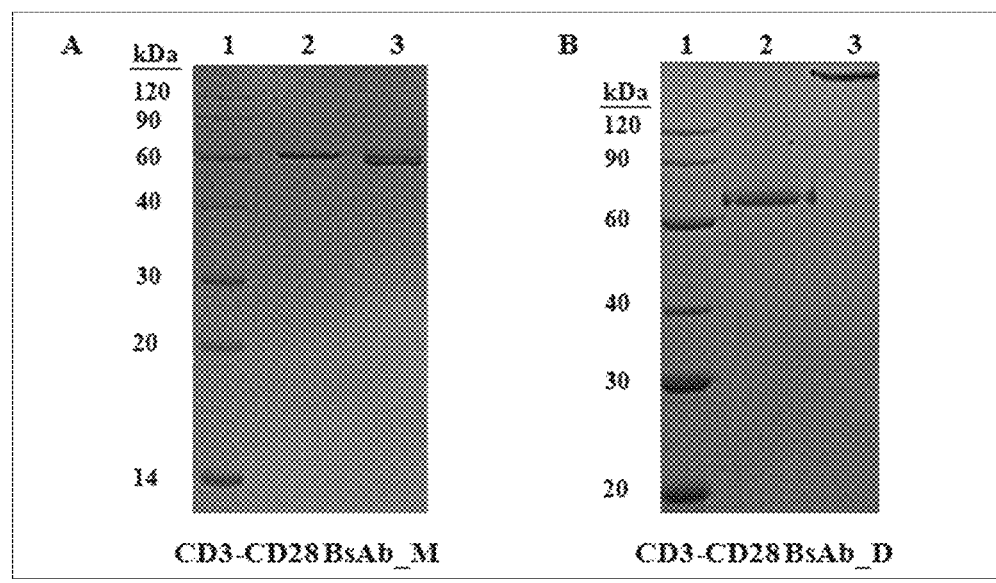

In a preferred embodiment of the disclosure, the schematic structure of the bifunctional molecule is shown in FIG. 2-1. The bifunctional molecule can be in a monomeric form or a dimeric form. A structure diagram of the bifunctional molecule in a monomeric form of the present disclosure is shown in FIG. 2-1A. The bifunctional molecule includes a first functional domain that binds to the CD3 antigen, and a second domain that binds to a T cell positive costimulatory molecule antigen. The first domain is a scFv that binds to the CD3 antigen, and the second domain is a scFv that binds to a T cell positive costimulatory extracellular domain. A structure diagram of the bifunctional molecule in a dimeric form of the present disclosure is shown in FIG. 2-1B. The bifunctional molecule includes two first domains that bind to the CD3 antigen, and two second domains that bind to a T cell positive co-stimulatory molecule antigen. The bifunctional molecule includes two first functional domains that bind to the CD3 antigen, and two second domains that bind to a T cell positive costimulatory molecule antigen. The first domain is a scFv that binds to the CD3 antigen, and the second domain is a scFv that binds to a T cell positive costimulatory molecule extracellular domain. The bifunctional molecule of dimeric form in the disclosure has an antigen-binding affinity that is twice that of the monomeric form, so the dimer has a better use effect than the monomer in expanding T cells in vitro.

The T cell positive costimulatory molecule can be CD28, 4-1BB, ICOS, OX40, GITR, CD40L or CD27, et al.

The amino acid sequence of the human T cell positive costimulatory molecule CD28 extracellular domain is shown in SEQ ID NO. 36 in detail.

The amino acid sequence of the human T cell positive costimulatory molecule 4-1BB extracellular domain is shown in SEQ ID NO. 37 in detail.

The amino acid sequence of the human T cell positive costimulatory molecule ICOS extracellular domain is shown in SEQ ID NO. 38 in detail.

The amino acid sequence of the human T cell positive costimulatory molecule OX40 extracellular domain is shown in SEQ ID NO. 39 in detail.

The amino acid sequence of the human T cell positive costimulatory molecule GITR extracellular domain is shown in SEQ ID NO. 40 in detail.

The amino acid sequence of the human T cell positive costimulatory molecule CD40L extracellular domain is shown in SEQ ID NO. 41 in detail.

The amino acid sequence of the human T cell positive costimulatory molecule CD27 extracellular domain is shown in SEQ ID NO. 42 in detail.

Specifically, the first domain is a single-chain antibody against CD3. The anti-CD3 single-chain antibody includes a heavy chain variable region and a light chain variable region.

The amino acid sequence of the heavy chain variable region of the anti-CD3 single-chain antibody is shown in SEQ ID NO.68. The amino acid sequence of the light chain variable region of the anti-CD3 single-chain antibody is set forth in SEQ ID NO.69. Further, the amino acid sequence of the anti-CD3 single-chain antibody is shown in SEQ ID NO.67.

The second domain is a single-chain antibody against a T cell positive costimulatory molecule. The single-chain antibody of the anti-T cell positive costimulatory molecule includes a heavy chain variable region and a light chain variable region.

The single-chain antibody of the anti-T cell positive costimulatory molecule may be one of any single-chain antibodies against 4-1BB, ICOS, OX40, GITR, CD40L and CD27.

The amino acid sequence of the heavy chain variable region of the anti-4-1BB single-chain antibody is set forth in SEQ ID NO.71. The amino acid sequence of the light chain variable region of the anti-4-1BB single-chain antibody is set forth in SEQ ID NO.72. The amino acid sequence of the anti-4-1BB single-chain antibody is shown in SEQ ID NO.70.

The amino acid sequence of the heavy chain variable region of the anti-ICOS single-chain antibody is set forth in SEQ ID NO.74. The amino acid sequence of the light chain variable region of the anti-ICOS single-chain antibody is set forth in SEQ ID NO.75. The amino acid sequence of the anti-ICOS single-chain antibody is shown in SEQ ID NO.73.

The amino acid sequence of the heavy chain variable region of the anti-OX40 single-chain antibody is set forth in SEQ ID NO.77. The amino acid sequence of the light chain variable region of the anti-OX40 single-chain antibody is set forth in SEQ ID NO.78. The amino acid sequence of the anti-OX40 single-chain antibody is shown in SEQ ID NO.76.

The amino acid sequence of the heavy chain variable region of the anti-GITR single-chain antibody is set forth in SEQ ID NO.80. The amino acid sequence of the light chain variable region of the anti-GITR single-chain antibody is set forth in SEQ ID NO.81. The amino acid sequence of the anti-GITR single-chain antibody is shown in SEQ ID NO.79.

The amino acid sequence of the heavy chain variable region of the anti-CD40L single-chain antibody is set forth in SEQ ID NO.83. The amino acid sequence of the light chain variable region of the anti-CD40L single-chain antibody is set forth in SEQ ID NO.84. The amino acid sequence of the anti-CD40L single-chain antibody is shown in SEQ ID NO.82.

The amino acid sequence of the heavy chain variable region of the anti-CD27 single-chain antibody is set forth in SEQ ID NO.86. The amino acid sequence of the light chain variable region of the anti-CD27 single-chain antibody is set forth in SEQ ID NO.87. The amino acid sequence of the anti-CD27 single-chain antibody is shown in SEQ ID NO.85.

In a preferred embodiment of the disclosure, the amino acid sequence of the bifunctional molecule in monomeric form is shown as any one of SEQ ID NO. 43, SEQ ID NO.47, SEQ ID NO. 51, SEQ ID NO. 55, SEQ ID NO.59 and SEQ ID NO.63. The amino acid sequence of the bifunctional molecule in dimeric form is any one of SEQ ID NO. 45, SEQ ID NO. 49, SEQ ID NO. 53, SEQ ID NO. 57, SEQ ID NO. 61 and SEQ ID NO. 65. However, it is not limited to the specific forms listed in the preferred cases of the present disclosure.

Another bifunctional molecule of the disclosure includes a first domain capable of binding and activating a T cell surface CD3 molecule, and a second functional domain capable of binding to and activating T cell positive costimulatory molecule.

Further, the bifunctional molecule is capable of binding to and activating a CD3 molecule on the surface of T cell and a T cell positive costimulatory molecule, thereby generating a first signal and a second signal required for T cell activation.

The present disclosure has no particular limitation on the first functional domain and the second functional domain. As long as it can bind to and activate CD3 molecule on the surface of T cell and T cell positive costimulatory molecules, thereby producing the first signal and the second signal required for activation of T cells. For example, the first functional domain can be an anti-CD3 antibody, and the second functional domain can be a T cell positive costimulatory molecule ligand extracellular domain. The antibody can be in any form. However, regardless of the form of the antibody, the antigen-binding site thereof includes a heavy chain variable region and a light chain variable region. The antibody may preferably be a small molecule antibody. The small molecule antibody is a small molecular weight antibody fragment, and the antigen-binding site thereof includes a heavy chain variable region and a light chain variable region. The small molecule antibody has a small molecular weight but retains the affinity of the parental monoclonal antibody and has the same specificity as the parental monoclonal antibody. The types of small molecule antibodies mainly include Fab, Fv and scFv. The Fab antibody is formed by a disulfide bond between the intact light chain (variable region VL and constant region CL) and the heavy chain Fd segment (variable region VH and first constant region CH1). Fv antibodies are joined by non-covalent bonds by the variable regions of the light and heavy chains. They are the minimal functional fragments of the antibody molecule that retain the intact antigen-binding site. A scFv is a single-protein peptide chain molecule in which a heavy chain variable region and a light chain variable region are joined by a linker.

The first functional domain and the second functional domain are connected by a linker. The present disclosure has no particular requirements for the order of connection as long as the object of the present disclosure is not limited. For example, the C-terminus of the first functional domain may be linked to the N-terminus of the second functional domain. The number of amino acid in the linker fragment is preferred to be more than 1. The present disclosure is also not particularly limited to the linker as long as it does not limit the object of the present disclosure.

Further, the linker is selected from a G4S linker or a hinge domain of immunoglobulin IgD.

The G4S is GGGGS. The G4S linker includes one or more G4S units. For example, one, two, three or more G4S units can be included. In some embodiments of the present disclosure, a bifunctional molecule in a monomeric form is disclosed. The first functional domain and the second functional domain are connected by a G4S linker. The linker includes three G4S units, and the amino acid sequence of the ligated fragment is set forth in SEQ ID NO.135.

The hinge domain of the immunoglobulin IgD could be the hinge Ala90-Val170 of IgD. In some embodiments of the disclosure, wherein a dimeric form of a bifunctional molecule is exemplified, the first functional domain and the second functional domain are linked by a hinge domain of immunoglobulin IgD, which is Ala90-Val170. The amino acid sequence of the linker is shown in SEQ ID NO.137. The linker may be linked to each other by a disulfide bond to form a dimer.

Figures 1, 2, 3, 3A:
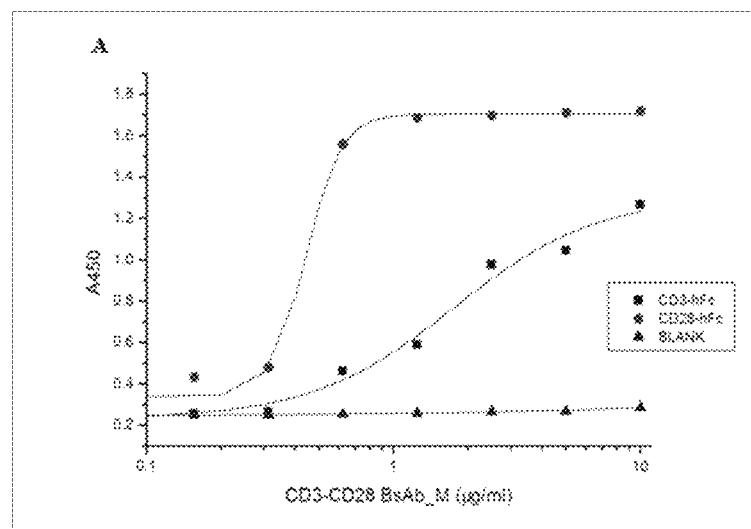

In a preferred embodiment of the disclosure, the schematic structure of the bifunctional molecule is shown in FIG. 3-1. The bifunctional molecule can be in a monomeric form or a dimeric form. A schematic diagram of the structure of the monomeric form of the bifunctional molecule of the present disclosure is shown in FIG. 3-1A. The bifunctional molecule includes a first functional domain that binds to the CD3 antigen, and a T cell costimulatory molecule ligand extracellular domain that binds to a T cell positive costimulatory molecule. A structure schematic diagram of the bifunctional molecule in a dimeric form of the present disclosure is shown in FIG. 3-1B. The structure of the bifunctional molecule includes two first domains that bind to the CD3 antigen, and two T cell costimulatory molecule ligand extracellular domains that bind to T cell positive co-stimulatory molecule. The bifunctional molecule of dimeric form disclosure has an antigen-binding affinity that is twice that of the monomeric form, so the dimer has a better use effect than the monomer to expand T cells in vitro.

Further, the T cell positive costimulatory molecule may be human 4-1BB (UniProt ID: Q07011), the amino acid sequence is shown in SEQ ID No.139. Its ligand is human 4-1BBL (UniProt ID: P41273), the amino acid sequence is shown in SEQ ID No. 140.

The T cell positive costimulatory molecule may be human ICOS (UniProt ID: Q9Y6W8), the amino acid sequence is shown as SEQ ID NO. 141. The ligand is human B7RP-1 (UniProt ID: 075144), and the amino acid sequence is shown in SEQ ID NO.142.

The T cell positive costimulatory molecule may be human OX40 (UniProt ID: P43489), the amino acid sequence is shown as SEQ ID NO. 143. The ligand is human OX40L (UniProt ID: P23510), and the amino acid sequence is shown in SEQ ID NO. 144.

The T cell positive costimulatory molecule may be human GITR (UniProt ID: Q9Y5U5), the amino acid sequence is shown as SEQ ID NO. 145. The ligand is human GITRL (UniProt ID: Q9UNG2), and the amino acid sequence is shown in SEQ ID NO. 146.

The T cell positive costimulatory molecule may be human CD27 (UniProt ID: P26842), the amino acid sequence is shown as SEQ ID NO. 147. The ligand is human CD70 (UniProt ID: P32970), and the amino acid sequence is shown in SEQ ID NO. 148.

Specifically, the first domain is a single-chain antibody against CD3. The anti-CD3 single-chain antibody includes a heavy chain variable region and a light chain variable region. The amino acid sequence of the heavy chain variable region of the anti-CD3 single-chain antibody is set forth in SEQ ID NO.170. The amino acid sequence of the light chain variable region of the anti-CD3 single-chain antibody is set forth in SEQ ID NO.171. Further, the amino acid sequence of the anti-CD3 single-chain antibody is shown in SEQ ID NO.169.

The second domain is the ligand extracellular domain of a T cell positive costimulatory molecule. The ligand extracellular domain of the T cell positive costimulatory molecule may be any one of 4-1BBL extracellular domain, B7RP-1 extracellular domain, OX40L extracellular domain, GITRL extracellular domain or CD70 extracellular domain.

The amino acid sequence of the 4-1BBL extracellular domain is set forth in SEQ ID NO. 172.

The amino acid sequence of the B7RP-1 extracellular domain is set forth in SEQ ID NO.173.

The amino acid sequence of the OX40L extracellular domain is set forth in SEQ ID NO.174.

The amino acid sequence of the GITRL extracellular domain is set forth in SEQ ID NO.175.

The amino acid sequence of the CD70 extracellular domain is set forth in SEQ ID NO.176.

In a preferred embodiment of the present disclosure, the amino acid sequence of the bifunctional molecule in monomeric form is as defined in any one of SEQ ID NO. 149, SEQ ID NO. 153, SEQ ID NO. 157, SEQ ID NO. 161 and SEQ ID NO. 165. The amino acid sequence of the bifunctional molecule in dimeric form is as defined in any one of SEQ ID NO. 151, SEQ ID NO. 155, SEQ ID NO. 159, SEQ ID NO. 163 and SEQ ID NO.167. It is not limited to the specific forms listed in the preferred cases of the present disclosure.

Another bifunctional molecule of the disclosure includes a first domain capable of binding to and activating a T cell surface CD3 molecule, and a second functional domain capable of binding and blocking T cell inhibitory molecule.

Further, the bifunctional molecule is capable of binding to and activating a CD3 molecule on the surface of T cell, binding and blocking a T cell inhibitory molecule, thereby generating a first signal and a second signal required for T cell activation. The T cell inhibitory molecules include, but are not limited to, human PD-1, CTLA-4, LAG-3, TIM-3, TIGIT, and BTLA.

The present disclosure has no particular limitation on the first functional domain and the second functional domain. As long as it can bind to and activate the T cell surface CD3 molecule, bind and block the T cell inhibitory molecule, the first signal and the second signal required for T cell activation can be produced. For example, the first functional domain can be anti-CD3 antibody, and the second functional domain can be an antibody against an anti-T cell inhibitory molecule. The antibody can be in any form. However, regardless of the form of the antibody, the antigen-binding site thereof includes a heavy chain variable region and a light chain variable region. The antibody may preferably be a small molecule antibody. The small molecule antibody is a small molecular weight antibody fragment, and the antigen-binding site thereof includes a heavy chain variable region and a light chain variable region. The small molecule antibody has a small molecular weight but retains the affinity of the parental monoclonal antibody and has the same specificity as the parental monoclonal antibody. The types of small molecule antibodies mainly include Fab, Fv and scFv. The Fab antibody is formed by a disulfide bond between the intact light chain (variable region VL and constant region CL) and the heavy chain Fd segment (variable region VH and first constant region CH1). Fv antibodies are joined by non-covalent bonds by the variable regions of the light and heavy chains. They are the minimal functional fragments of the antibody molecule that retain the intact antigen-binding site. A scFv is a single-protein peptide chain molecule in which a heavy chain variable region and a light chain variable region are joined by a linker.

The first functional domain and the second functional domain are connected by a linker. The present disclosure has no particular requirements for the order of connection as long as the object of the present disclosure is not limited. For example, the C-terminus of the first functional domain may be linked to the N-terminus of the second functional domain. The number of amino acid in the linker fragment is preferred to be more than 1. The present disclosure is also not particularly limited to the linker as long as it does not limit the object of the present disclosure.

Further, the linker is selected from a G4S linker or a hinge domain of immunoglobulin IgD.

The G4S is GGGGS. The G4S linker includes one or more G4S units. For example, one, two, three or more G4S units can be included. In some embodiments of the present disclosure, a bifunctional molecule in a monomeric form is exemplified, wherein the first functional domain and the second functional domain are connected by a linker in units of G4S. The linker contains three G4S units, and the amino acid sequence of the ligated fragment is set forth in SEQ ID NO.208.

The hinge domain of the immunoglobulin IgD could be the hinge Ala90-Val170 of IgD. In some embodiments of the disclosure, wherein a bifunctional molecule in dimeric form is exemplified, the first functional domain and the second functional domain are linked by a hinge domain of immunoglobulin IgD, which is Ala90-Val170. The amino acid sequence of the linker is shown in SEQ ID NO.210. The linker can be linked to each other by a disulfide bond to form a dimer.

Figures 1, 2, 3, 3B:
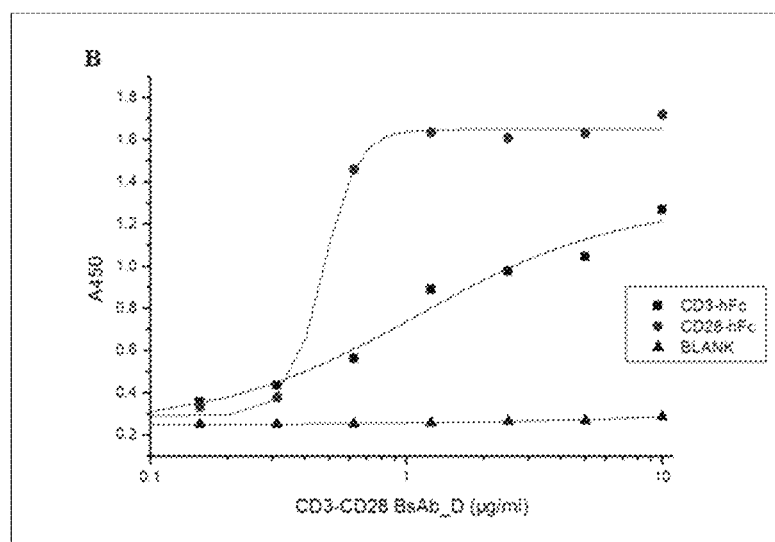
Figures 1, 2, 3, 4:
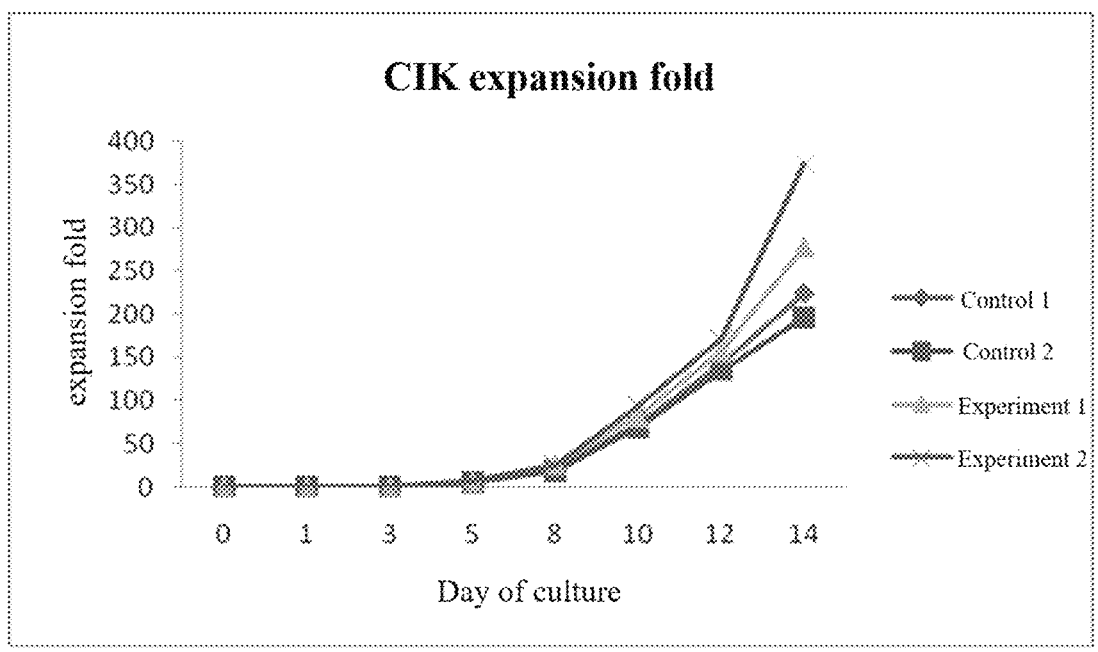

In a preferred embodiment of the disclosure, the schematic structure of the bifunctional molecule is shown in FIG. 4-1. The bifunctional molecule can be in a monomeric form or a dimeric form. A structure diagram of the bifunctional molecule in the monomeric form of the present disclosure is shown in FIG. 4-1A. The bifunctional molecule includes a first functional domain that binds to the CD3 antigen, and a second functional domain that binds to a T cell negative costimulatory molecule. The first domain is a scFv that binds to the CD3 antigen, and the second domain is a scFv that binds to a T cell negative costimulatory molecule extracellular domain. A schematic diagram of the structure of a dimeric form of a bifunctional molecule of the present disclosure is shown in FIG. 4-1B. The structure of the bifunctional molecule contains two first domains that bind to the CD3 antigen, and two second domains that bind to T cell negative co-stimulatory molecule. The first domain is a scFv that binds to the CD3 antigen, and the second domain is a scFv that binds to a T cell negative costimulatory molecule extracellular domain. The dimeric form of the bifunctional molecule of the disclosure has an antigen-binding affinity that is twice that of the monomeric form, so the dimer has a better use effect than the monomer to expand T cells in vitro.

The T cell inhibitory molecules may be PD-1, CTLA-4, LAG-3, TIM-3, TIGIT, BTLA, et al.

The amino acid sequence of the extracellular domain of the human T cell inhibitory molecule PD-1 (Uniprot ID: Q15116) is shown in SEQ ID NO. 212 in detail.

The amino acid sequence of the extracellular domain of the human T cell inhibitory molecule CTLA-4 (Uniprot ID: P16410) is shown in SEQ ID NO. 213.

The amino acid sequence of the extracellular domain of the human T cell inhibitory molecule LAG-3 (Uniprot ID: P18627) is shown in SEQ ID NO. 214.

The amino acid sequence of the extracellular domain of the human T cell inhibitory molecule TIM-3 (Uniprot ID: Q8TDQ0) is shown in SEQ ID NO. 215.

The amino acid sequence of the extracellular domain of the human T cell inhibitory molecule TIGIT (Uniprot ID: Q495A1) is shown in SEQ ID NO. 216.

The amino acid sequence of the extracellular domain of the human T cell inhibitory molecule BTLA (Uniprot ID: Q7Z6A9) is shown in SEQ ID NO. 217.

Specifically, the first domain is a single-chain antibody against CD3. The anti-CD3 single-chain antibody includes a heavy chain variable region and a light chain variable region.

The amino acid sequence of the heavy chain variable region of the anti-CD3 single-chain antibody is set forth in SEQ ID NO.243. The amino acid sequence of the light chain variable region of the anti-CD3 single-chain antibody is set forth in SEQ ID NO.244. Further, the amino acid sequence of the anti-CD3 single-chain antibody is shown in SEQ ID NO.242.

The second domain is a single-chain antibody against an anti-T cell inhibitory molecule. The single-chain antibody of the anti-T cell inhibitive molecule includes a heavy chain variable region and a light chain variable region.

The single-chain antibody against the T cell inhibitory molecule can be a single-chain antibody against PD-1, CTLA-4, LAG-3, TIM-3, TIGIT or BTLA.

The amino acid sequence of the heavy chain variable region of the anti-PD-1 single-chain antibody is set forth in SEQ ID NO.246. The amino acid sequence of the light chain variable region of the anti-PD-1 single-chain antibody is set forth in SEQ ID NO.247. The amino acid sequence of the single-chain antibody against PD-1 is set forth in SEQ ID NO.245.

The amino acid sequence of the heavy chain variable region of the anti-CTLA-4 single-chain antibody is set forth in SEQ ID NO.249. The amino acid sequence of the light chain variable region of the anti-CTLA-4 single-chain antibody is set forth in SEQ ID NO.250. The amino acid sequence of the single-chain antibody against CTLA-4 is set forth in SEQ ID NO.248.

The amino acid sequence of the heavy chain variable region of the anti-LAG-3 single-chain antibody is set forth in SEQ ID NO.252. The amino acid sequence of the light chain variable region of the anti-LAG-3 single-chain antibody is set forth in SEQ ID NO.253. The amino acid sequence of the single-chain antibody against LAG-3 is set forth in SEQ ID NO.251.

The amino acid sequence of the heavy chain variable region of the anti-TIM-3 single-chain antibody is set forth in SEQ ID NO.255. The amino acid sequence of the light chain variable region of the anti-TIM-3 single-chain antibody is set forth in SEQ ID NO.256. The amino acid sequence of the single-chain antibody against TIM-3 is set forth in SEQ ID NO.254.

The amino acid sequence of the heavy chain variable region of the anti-TIGIT single-chain antibody is set forth in SEQ ID NO.258. The amino acid sequence of the light chain variable region of the anti-TIGIT single-chain antibody is set forth in SEQ ID NO.259. The amino acid sequence of the single-chain antibody against TIGIT is set forth in SEQ ID NO.257.

The amino acid sequence of the heavy chain variable region of the anti-BTLA single-chain antibody is set forth in SEQ ID NO.261. The amino acid sequence of the light chain variable region of the anti-BTLA single-chain antibody is set forth in SEQ ID NO.262. The amino acid sequence of the single-chain antibody against BTLA is set forth in SEQ ID NO.260.

In a preferred embodiment of the disclosure, the amino acid sequence of the bifunctional molecule in monomeric form is shown as any of SEQ ID NO. 218, SEQ ID NO. 222, SEQ ID NO. 226, SEQ ID NO. 230, SEQ ID NO. 234, and SEQ ID NO.238. The amino acid sequence of the bifunctional molecule in dimeric form is shown as any one of SEQ ID NO. 220, SEQ ID NO. 224, SEQ ID NO. 228, SEQ ID NO. 232, SEQ ID NO. 236, and SEQ ID NO.240. However, it is not limited to the specific forms listed in the preferred cases of the present disclosure.

3, Polynucleotide Encoding Bifunctional Molecule

The polynucleotide encoding the bifunctional molecule of the present disclosure may be in the form of DNA or RNA. DNA forms include cDNA, genomic DNA or synthetic DNA. DNA can be single-stranded or double-stranded.

The polynucleotide encoding the bifunctional molecule of the disclosure can be prepared by any suitable technique well known to those skilled in the field. Such techniques are described in the general description of the field, such as Molecular Cloning: A Laboratory Manual (J. Sambrook et al., Science Press, 1995). Methods are including, but not limited to, recombinant DNA techniques, chemical synthesis. For example, overlapping extension PCR.

In some preferred embodiments of the disclosure, the nucleotide sequence encoding the heavy chain variable region of the anti-CD3 single-chain antibody is set forth in SEQ ID NO.12.

The nucleotide sequence encoding the light chain variable region of the anti-CD3 single-chain antibody is set forth in SEQ ID NO.13.

The nucleotide sequence encoding the anti-CD3 single-chain antibody is set forth in SEQ ID NO.11.

The nucleotide sequence encoding the heavy chain variable region of the anti-CD28 single-chain antibody is set forth in SEQ ID NO.15.

The nucleotide sequence encoding the light chain variable region of the anti-CD28 single-chain antibody is set forth in SEQ ID NO.16.

The nucleotide sequence encoding the anti-CD28 single-chain antibody is set forth in SEQ ID NO.14.

The nucleotide sequence encoding the amino acid sequence SEQ ID NO.17 of the linker is set forth in SEQ ID NO.18.

The nucleotide sequence encoding the amino acid sequence SEQ ID NO.19 of the linker is set forth in SEQ ID NO.20.

Further, the nucleotide sequence encoding the bifunctional molecule in the monomeric form is set forth in SEQ ID NO.2. The nucleotide sequence encoding the bifunctional molecule in the dimeric form is set forth in SEQ ID NO.4.

In other preferred embodiments of the disclosure, the nucleotide sequence of the heavy chain variable region encoding the anti-CD3 single-chain antibody is set forth in SEQ ID NO.89.

The nucleotide sequence of the light chain variable region encoding the anti-CD3 single-chain antibody is set forth in SEQ ID NO.90. The nucleotide sequence of the single-chain antibody encoding the anti-CD3 is set forth in SEQ ID NO.88.

The nucleotide sequence of the heavy chain variable region encoding the anti-4-1BB single-chain antibody is set forth in SEQ ID NO.92. The nucleotide sequence of the light chain variable region encoding the anti-4-1BB single-chain antibody is set forth in SEQ ID NO.93. The nucleotide sequence of the single-chain antibody encoding the anti-4-1BB is shown in SEQ ID NO.91.

The nucleotide sequence of the heavy chain variable region encoding the anti-ICOS single-chain antibody is set forth in SEQ ID NO.95. The nucleotide sequence of the light chain variable region encoding t the anti-ICOS single-chain antibody is set forth in SEQ ID NO.96.

The nucleotide sequence of the single-chain antibody encoding the anti-ICOS is shown in SEQ ID NO.94.

The nucleotide sequence of the heavy chain variable region encoding the anti-OX40 single-chain antibody is set forth in SEQ ID NO.98. The nucleotide sequence of the light chain variable region encoding the s anti-OX40 single-chain antibody is set forth in SEQ ID NO.99. The nucleotide sequence of the single-chain antibody encoding the anti-OX40 is shown in SEQ ID NO.97.

The nucleotide sequence of the heavy chain variable region encoding the anti-GITR single-chain antibody is set forth in SEQ ID NO.101. The nucleotide sequence of the light chain variable region encoding the s anti-GITR single-chain antibody is set forth in SEQ ID NO.102.

The nucleotide sequence of the single-chain antibody encoding the anti-GITR is shown in SEQ ID NO.100.

The nucleotide sequence of the heavy chain variable region encoding the anti-CD40L single-chain antibody is set forth in SEQ ID NO.104. The nucleotide sequence of the light chain variable region encoding the s anti-CD40L single-chain antibody is set forth in SEQ ID NO.105. The nucleotide sequence of the single-chain antibody encoding the anti-CD40L is shown in SEQ ID NO.103.

The nucleotide sequence of the heavy chain variable region encoding the anti-CD27 single-chain antibody is set forth in SEQ ID NO.107. The nucleotide sequence of the light chain variable region encoding the s anti-CD27 single-chain antibody is set forth in SEQ ID NO.108. The nucleotide sequence of the single-chain antibody encoding the anti-CD27 is shown in SEQ ID NO.106.

The nucleotide sequence encoding the amino acid sequence SEQ ID NO.32 of the linker is set forth in SEQ ID NO.33.

The nucleotide sequence encoding the amino acid sequence SEQ ID NO.34 of the linker is set forth in SEQ ID NO.35.

Further, the nucleotide sequence encoding the bifunctional molecule in monomeric form is set forth in any one of SEQ ID NO.44, SEQ ID NO.48, SEQ ID NO.52, SEQ ID NO.56, SEQ ID NO.60 and SEQ ID NO.64. The nucleotide sequence encoding the bifunctional molecule in the dimeric form is set forth in any one of SEQ ID NO.46, SEQ ID NO.50, SEQ ID NO.54, SEQ ID NO.58, SEQ ID NO.62 and SEQ ID NO.66.

In other preferred embodiments of the disclosure, the nucleotide sequence of the heavy chain variable region encoding the anti-CD3 single-chain antibody is set forth in SEQ ID NO.178. The nucleotide sequence of the light chain variable region encoding the anti-CD3 single-chain antibody is set forth in SEQ ID NO.179. The nucleotide sequence of the anti-CD3 single-chain antibody is shown in SEQ ID NO.177.

The nucleotide sequence encoding the 4-1BBL extracellular domain is set forth in SEQ ID NO.180.

The nucleotide sequence encoding the B7RP-1 extracellular domain is set forth in SEQ ID NO.181.

The nucleotide sequence encoding the OX40L extracellular domain is set forth in SEQ ID NO.182.

The nucleotide sequence encoding the GITRL extracellular domain is set forth in SEQ ID NO.183.

The nucleotide sequence encoding the CD70 extracellular domain is set forth in SEQ ID NO.184.

The nucleotide sequence encoding the amino acid sequence SEQ ID NO.135 of the linker is set forth in SEQ ID NO.136.

The nucleotide sequence encoding the amino acid sequence SEQ ID NO.137 of the linker is set forth in SEQ ID NO.138.

Further, the nucleotide sequence encoding the bifunctional molecule in monomeric form is set forth in any one of SEQ ID NO.150, SEQ ID NO.154, SEQ ID NO.158, SEQ ID NO.162 and SEQ ID NO.166. The nucleotide sequence encoding the bifunctional molecule in the dimeric form is set forth in any one of SEQ ID NO.152, SEQ ID NO.156, SEQ ID NO.160, SEQ ID NO.164 and SEQ ID NO.168.

In other preferred embodiments of the disclosure, the nucleotide sequence encoding the heavy chain variable region of the anti-CD3 single-chain antibody is set forth in SEQ ID NO.264. The nucleotide sequence encoding the light chain variable region of the anti-CD3 single-chain antibody is set forth in SEQ ID NO.265. The nucleotide sequence encoding the anti-CD3 single-chain antibody is shown in SEQ ID NO.263.

The nucleotide sequence encoding the heavy chain variable region of the anti-PD-1 single-chain antibody is set forth in SEQ ID NO.267. The nucleotide sequence encoding the light chain variable region of the anti-PD-1 single-chain antibody is set forth in SEQ ID NO.268. The nucleotide sequence encoding the anti-PD-1 single-chain antibody is shown in SEQ ID NO.266.

The nucleotide sequence encoding the heavy chain variable region of the anti-CTLA-4 single-chain antibody is set forth in SEQ ID NO.270. The nucleotide sequence encoding the light chain variable region of the anti-CTLA-4 single-chain antibody is set forth in SEQ ID NO.271. The nucleotide sequence encoding the anti-CTLA-4 single-chain antibody is shown in SEQ ID NO.269.

The nucleotide sequence encoding the heavy chain variable region of the anti-LAG-3 single-chain antibody is set forth in SEQ ID NO.273. The nucleotide sequence encoding the light chain variable region of the anti-LAG-3 single-chain antibody is set forth in SEQ ID NO.274. The nucleotide sequence encoding the anti-LAG-3 single-chain antibody is shown in SEQ ID NO.272.

The nucleotide sequence encoding the heavy chain variable region of the anti-TIM-3 single-chain antibody is set forth in SEQ ID NO.276. The nucleotide sequence encoding the light chain variable region of the anti-TIM-3 single-chain antibody is set forth in SEQ ID NO.277. The nucleotide sequence encoding the anti-TIM-3 single-chain antibody is shown in SEQ ID NO.275.

The nucleotide sequence encoding the heavy chain variable region of the anti-TIGIT single-chain antibody is set forth in SEQ ID NO.279. The nucleotide sequence encoding the light chain variable region of the anti-TIGIT single-chain antibody is set forth in SEQ ID NO.280.

The nucleotide sequence encoding the anti-TIGIT single-chain antibody is shown in SEQ ID NO.278.

The nucleotide sequence encoding the heavy chain variable region of the anti-BTLA single-chain antibody is set forth in SEQ ID NO.282. The nucleotide sequence encoding the light chain variable region of the anti-BTLA single-chain antibody is set forth in SEQ ID NO.283. The nucleotide sequence encoding the anti-BTLA single-chain antibody is shown in SEQ ID NO.281.

The nucleotide sequence encoding the amino acid sequence SEQ ID NO.1 of the linker is set forth in SEQ ID NO.209.

The nucleotide sequence encoding the amino acid sequence SEQ ID NO.3 of the linker is set forth in SEQ ID NO.211.

Further, the nucleotide sequence encoding the bifunctional molecule in monomeric form is set forth in any one of SEQ ID NO.219, SEQ ID NO.223, SEQ ID NO.227, SEQ ID NO.231, SEQ ID NO.235 and SEQ ID NO.239. The nucleotide sequence encoding the bifunctional molecule in the dimeric form is set forth in any one of SEQ ID NO.221, SEQ ID NO.225, SEQ ID NO.229, SEQ ID NO.233, SEQ ID NO.237 and SEQ ID NO.241.

4, Expression Vector

The expression vector of the present disclosure includes the polynucleotide encoding the bifunctional molecule. Methods well known to those skilled in the field can be used to construct the expression vector. These methods include recombinant DNA techniques, DNA synthesis techniques, et al. The DNA encoding the fusion protein can be cloned to a multiple cloning site in the vector to direct mRNA synthesis to express the protein, or for homologous recombination. In a preferred embodiment of the disclosure, the expression vector is pcDNA3.1. The host cell line is Chinese hamster ovary cell (CHO).

5, Method for Preparing Bifunctional Molecules

The method for preparing the bifunctional molecule of the present disclosure includes: constructing an expression vector containing a DNA sequence of a bifunctional molecule, followed by transforming vector into a host cell to induce expression, and separating bifunctional molecule from the expression product. In a preferred embodiment of the disclosure, the expression vector is pcDNA3.1. The host cell line is Chinese hamster ovary cell (CHO).

6, Use of Bifunctional Molecules

The bifunctional molecule of the present disclosure can be used to expand T cells in vitro.

In some preferred embodiments of the present disclosure, human peripheral blood mononuclear cells (PBMC) are used in the experiment. The bifunctional molecule prepared by the present disclosure includes first domain binding to and activating T cell CD3 and second domain binding to and activating CD28, as well as anti-CD3/anti-CD28 monoclonal full-length antibody combination, works on PBMC from the same donor blood, respectively. Cells were counted after culturing, compared the expansion factor. The results indicated that the bifunctional molecule including first domain binding to and activating T cell CD3 and second domain binding to and activating CD28 can effectively promote Cytokine-induced killer (CIK) cell expansion, and the bifunctional molecule including first domain binding to and activating T cell CD3 and second domain binding to and activating CD28 works better than anti-CD3/anti-CD28 monoclonal full-length antibody combination to promote CIK cell expansion with less protein dosage.

In other preferred embodiments of the present disclosure, it has been found that the bifunctional molecule includes a first functional domain capable of binding to and activating T cell surface CD3 molecules, and a second functional domain capable of binding and activating T cell positive costimulatory molecule. Both bifunctional molecules in both monomeric and dimeric form can bind to CD3 and positive costimulatory molecule recombinant antigens in vitro, and can be used in T cell expansion in vitro, among which, dimer has a better effect than monomer.

In other preferred embodiments of the present disclosure, it has been found that the bifunctional molecule includes a first functional domain capable of binding to and activating T cell surface CD3 molecules, and a second functional domain capable of binding to and activating T cell positive costimulatory molecule. Bifunctional molecules in both monomeric and dimeric form can bind to the CD3 recombinant antigen and positive costimulatory molecule recombinant antigens in vitro, and can be used in T cell expansion in vitro, among which, dimer has better effect than monomer.

In other preferred embodiments of the present disclosure, it has been found that the bifunctional molecule t includes a first functional domain capable of binding to and activating T cell surface CD3 molecules, and a second functional domain capable of binding to and blocking T cell negative costimulatory molecule. Bifunctional molecules in both monomeric and dimeric form can bind to CD3 and negative costimulatory molecule recombinant antigens, and can be used in T cell expansion in vitro, among which, dimer has a better effect than monomer.

7, Method of Expansion T Cell In Vitro

The T cell expansion method in this disclosure includes the aforementioned bifunctional molecule working on T cells. This method can be on nontherapeutic purposes.

In some preferred embodiments of the present disclosure, human peripheral blood mononuclear cells (PBMC) are used as samples. The bifunctional molecule prepared by the present disclosure including a first domain binding to and activating T cell CD3, and a second domain binding to and activating CD28, as well as anti-CD3/anti-CD28 monoclonal full-length antibody combination, works on PBMC from the same donor blood, respectively. Cells were counted after culturing, and compared the expansion factor. The results indicated that the bifunctional molecule including first domain binding to and activating T cell CD3, and second domain binding to and activating CD28 can effectively promote CIK (Cytokine-induced killer) cell expansion, and the bifunctional molecule including first domain binding to and activating T cell CD3 and second domain binding and activating CD28 works better than anti-CD3/anti-CD28 monoclonal full-length antibody combination to promote CIK cell expansion with less protein dosage In order to overcome the disadvantages of anti-CD3 and anti-CD28 monoclonal full-length antibody combination, bifunctional molecule which can activate both CD3 and CD28 was constructed by gene engineering and antibody engineering. This bifunctional molecule not only has the features of anti-CD3 and anti-CD28 monoclonal full-length antibody combination, but also has obvious advantages on preparation process and practical application. When bifunctional molecule is added in soluble form, the effect is even better than that of anti-CD3 and anti-CD28 monoclonal full-length antibody combination or coating plate. It promotes the effect of T cell expansion in vitro and accessibility in application.

In other preferred embodiments of the present disclosure, it has been found that the bifunctional molecules includes a first functional domain capable of binding to and activating T cell surface CD3 molecules, and a second functional domain capable of binding to and activating T cell positive costimulatory molecule. Bifunctional molecules in both monomeric and dimeric form can bind CD3 and positive costimulatory molecule recombinant antigens in vitro, and can be used in T cell expansion in vitro, among which, dimer has a better effect than monomer.

In order to overcome the disadvantages of anti-CD3 and anti-T cell positive stimulatory molecule full-length antibody combination, the bifunctional molecule which can activate both CD3 and any T cell positive costimulatory molecule was constructed by gene engineering and antibody engineering. This bifunctional molecule not only has the features of two antibody combination, but also has obvious advantages on preparation process and practical application. When bifunctional molecule is added in soluble form, the effect is even better than that of anti-CD3 and anti-CD28 single clone full-length antibody combination or coating plate. It promotes the effect of T cell expansion in vitro and accessibility in application.

In other preferred embodiments of the present disclosure, it has been found that the bifunctional molecules includes a first functional domain capable of binding to and activating T cell surface CD3 molecules, and a second functional domain capable of binding to and activating T cell positive costimulatory molecule. Bifunctional molecules n both monomeric and dimeric form can bind CD3 recombinant antigen and positive costimulatory molecule recombinant antigens in vitro, and can be used in T cell expansion in vitro, among which, dimer has a better effect than monomer.

In order to overcome the disadvantages of anti-CD3 and anti-T cell positive stimulatory molecule full-length antibody combination, the bifunctional molecule which can activate both CD3 and any T cell positive costimulatory molecule was constructed by gene engineering and antibody engineering. This bifunctional molecule not only has the features of two antibody combination, but also has obvious advantages on preparation process and practical application. When bifunctional molecule is added in soluble form, the effect is even better effect than that of anti-CD3 and anti-CD28 monoclonal full-length antibody combination or coating plate. It promotes the effect of T cell expansion in vitro and accessibility in application.

In other preferred embodiments of the present disclosure, it has been found that the bifunctional molecules includes a first functional domain capable of binding to and activating T cell surface CD3 molecules, and a second functional domain capable of binding and blocking T cell negative costimulatory molecule. Bifunctional molecules in both monomeric and dimeric form can bind CD3 and negative costimulatory molecule recombinant antigens, and can be used in T cell expansion in vitro, among which, dimer has a better effect than monomer.

In order to overcome the disadvantages of anti-CD3 and anti-T cell positive (negative) stimulatory molecule full-length antibody combination, the bifunctional molecule which can activate both CD3 and any T cell positive costimulatory molecule were constructed by gene engineering and antibody engineering. This bifunctional molecule not only has the features of two antibody combination, but also has obvious advantages on preparation process and practical application. When bifunctional molecule is added in soluble form, the effect is even better effect than that of anti-CD3 and anti-CD28 monoclonal full-length antibody combination or coating plate. It promotes the effect of T cell expansion in vitro and accessibility in application.

Before the present disclosure is further described, it is to be understood that the scope of the present disclosure protection is not limited to the specific embodiments described below. The terms used in the embodiments of the present disclosure are intended to describe specific embodiments, and are not intended to limit the scope of the disclosure protection. The test methods which do not specify the specific conditions in the following examples are usually carried out according to conventional conditions or according to the conditions recommended by each manufacturer.

When the numerical values are given by the embodiments, it is to be understood that two endpoints of each range of values and any value between the two endpoints can be selected. Unless otherwise defined, all technical and scientific terms used in the present disclosure have the same meaning as commonly understood by those skilled in the field. In addition to the specific methods, devices, and materials used in the embodiments, the methods, devices, and materials described in the embodiments of the present disclosure can also be used according to the current technology and the description of the present disclosure by those skilled in the field. Any method, devices, and material of the current technology, similar or equivalent, can be used to practice the disclosure.

Unless otherwise defined, the experimental methods, detection methods, and preparation methods disclosed in the present disclosure employ conventional techniques of molecular biology, biochemistry, chromatin structure and analysis, analytical chemistry, cell culture, recombinant DNA technology, and conventional technology in related fields. These techniques have been well described in the existing literature, according to Sambrook et al. MOLECULAR CLONING: A LABORATORY MANUAL, Second edition, Cold Spring Harbor Laboratory Press, 1989 and Third edition, 2001; Ausubel et al, CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third Edition, Academic Press, San Diego, 1998; METHODS IN ENZYMOLOGY, Vol. 304; Chromatin (P M Wassarman and AP Wolffe, eds.), Academic Press, San Diego, 1999; METHODS IN MOLECULAR BIOLOGY, Vol. 119, Chromatin Protocols (P. B. Becker, ed.) Humana Press, Totowa, 1999, et al.

Embodiment 1-1 Construction of Eukaryotic Expression Vector of CD3-CD28 BsAb_M and CD3-CD28 BsAb_D In this disclosure, the bi-specific antibody targeted CD3 and CD28 on human T cell is named as CD3-CD28 BsAb.
1. Construction of CD3-CD28 BsAb_M and CD3-CD28 BsAb_D Construction of CD3-CD28 BsAb_M Monomer: the sequence of anti-CD3 scFv and anti-CD28 scFv is linked by (GGGGS)3 Linker.

Construction of CD3-CD28 BsAb_D Dimer: the sequence of anti-CD3 scFv and anti-CD28 scFv is linked by IgD hinge region Linker.

In order to express the bi-specific antibody in mammalian cells, codon optimization of the mammalian system was performed for the sequence of anti-CD3 scFv, anti-CD28 scFv and IgD hinge region.

The nucleotide sequence of anti-CD3 scFv heavy chain variable region is shown as SEQ ID NO. 12 in detail.

The nucleotide sequence of anti-CD3 scFv light chain variable region is shown as SEQ ID NO. 13 in detail.

The nucleotide sequence of anti-CD3 scFv is shown as SEQ ID NO. 11 in detail.

The nucleotide sequence of anti-CD28 scFv heavy chain variable region is shown as SEQ ID NO. 15 in detail.

The nucleotide sequence of anti-CD28 scFv light chain variable region is shown as SEQ ID NO. 16 in detail.

The nucleotide sequence of anti-CD28 scFv is shown as SEQ ID NO. 14 in detail.

The nucleotide sequence of the CD3-CD28 BsAb_M monomer linker is shown as SEQ ID NO. 18 in detail.

The nucleotide sequence of CD3-CD28 BsAb_D dimer linker is shown as SEQ ID NO. 20 in detail.

In order to make the bi-specific antibody successfully expressed in CHO-S cells and secreted into medium, signal peptide of antibody secretory expression was selected in this Embodiment.

The amino acid sequence of this secretory signal peptide is shown as SEQ ID NO.21 in detail.

The nucleotide sequence of this secretory signal peptide is shown as SEQ ID NO.22 in detail.

2. Construction of Eukaryotic Expression Vector of CD3-CD28 BsAb_M and CD3-CD28 BsAb_D The construction and expression of bi-specific antibody disclosure selected mammalian cell protein transient expression vector pcDNA3.1 (Purchased from Invitrogen, Shanghai). In order to construct bi-specific antibody of monomer and dimer, primers were designed as in table 1-1. All the primers were synthesized by Genewiz, Suzhou, and DNA template for PCR was synthesized by Synbio Technologies, Suzhou.

The cloning constructs for CD3-CD28 BsAb_M amplified signal peptide by primers pcDNA3.1-Sig-F and Sig-R, and then amplified anti-CD3 scFv, (GGGGS)3 Linker and anti-CD28 scFv sequence by primers Sig-CD3-F&CD3-R, and CD3-(GGGGS)3-CD28-F&pcDNA3.1-CD28-R. The cloning constructs for CD3-CD28 BsAb_D amplified signal peptide first by primers pcDNA3.1-Sig-F and Sig-R, and then amplified anti-CD3 scFv, IgD hinge region Linker, and anti-CD28 scFv sequence by primers Sig-CD3-F&CD3-R, CD3-IgD-F&IgD-R, and IgD-CD28-F&pcDNA3.1-CD28-R. After PCR amplification, the full sequence of bi-specific antibody monomer and dimer were separately ligated and seamlessly cloned into the pcDNA3.1 vector which was linearized by EcoRI and HindIII. The target vector was transformed into E. Coli DH5a, and positive recombinant clones (recombinant plasmid) were selected by PCR with bacteria clones and confirmed by sequencing.

The recombinants (recombinant plasmid) with right sequence were purified by midi-prep, and then transfected into CHO-S cells.

After sequencing, the CD3-CD28 BsAb_M monomer and CD3-CD28 BsAb_D dimer both had the right full-length DNA sequence as expected.

The nucleotide sequence of CD3-CD28 BsAb_M monomer is shown as SEQ ID NO.2.

The nucleotide sequence of CD3-CD28 BsAb_D dimer is shown as SEQ ID NO.4.

TABLE 1-1

| Primers used in bi-specific antibody gene cloning | | |
|---|---|---|
| Primer name | Sequence | No. |
| pcDNA3.1-Sig-F | GTGCTGGATATCTGCAGAATTCGCCGCCACCA TGACCCGGCTGACCGTGCTGGCCCTGC | SEQ ID NO.23 |
| Sig-R | GGCCCTGGAGGAGGCCAGCAGGCCGGCCAGC AGGGCCAGCACGGTCAGC | SEQ ID NO.24 |

TABLE 1-1-continued

Primers used in bi-specific antibody gene cloning

| Primer name | Sequence | No. |
|---|---|---|
| Sig-CD3-F | GCTGGCCTCCTCCAGGGCCGACATCAAGCTG CAGCAGAGCG | SEQ ID NO.25 |
| CD3-R | CTTCAGCTCCAGCTTGGTGC | SEQ ID NO.26 |
| CD3-(GGGGS)₃-CD28-F | GCACCAAGCTGGAGCTGAAGGGCGGCGGCGG CAGCGGCGGCGGCGGCAGCGGCGGCGGCGGC AGCCAGGTGCAGCTGGTGCAGAGC | SEQ ID NO.27 |
| pcDNA3.1-CD28-R | CTGATCAGCGGTTTAAACTTAAGCTTTCAGCG CTTGATCTCCACCTTGGTG | SEQ ID NO.28 |
| CD3-IgD-F | GCACCAAGCTGGAGCTGAAGGCCAGCAAGAG CAAGAAGGAG | SEQ ID NO.29 |
| IgD-R | CACGCCCAGGGGCTGGGTGTG | SEQ ID NO.30 |
| IgD-CD28-F | CACACCCAGCCCCTGGGCGTGCAGGTGCAGC TGGTGCAGAGC | SEQ ID NO.31 |

Embodiment 1-2: The Expression and Purification of CD3-CD28 BsAb_M and CD3-CD28 BsAb_D 1. The expression of CD3-CD28 BsAb_M and CD3-CD28 BsAb_D 1.1 The cell density of CHO-S cells (Purchased from Thermo Fisher Scientific) was 0.5~0.6×106/ml one day before transfection.

1.2 Calculating cell density at the day of transfection, performing plasmid transfection when the density is in the range of 1~1.4×106/ml and the live percentage is >90%.

1.3 Transfecting complex recipes: each project (CD3-CD28 BsAb_M and CD3-CD28 BsAb_D) requires two centrifuge tubes/flasks. Take total 20 ml as an example, the recombinant plasmids from Embodiment 1-1 were taken:

Tube 1: 600 µl PBS, 20 µg recombinant plasmid, mixing well.

Tube 2: 600 µl PBS, 20 µl FreeStyle™ MAX Transfection Reagent (Purchased from Thermo Fisher Scientific), mixing well.

1.4 Adding the diluted transfection reagent into the diluted recombinant plasmid, mixing well, to obtain transfection complex.

1.5 Keeping the transfection complex for 15-20 min, adding it into cell culture dropwise steadily.

1.6 Keeping cell culture at 37° C., CO2 concentration 8%, rotating speed cell shaker of at 130 rpm on. Collecting medium after 5 days for the target protein test.

2. The Purification of CD3-CD28 BsAb_M and CD3-CD28 BsAb_D 2.1 Sample Pretreatment Taking 20 ml cell medium after transfection, adding 20 mM PB, 200 mM NaCl, and adjusting pH to 7.5;

2.2 Purification of Protein L Affinity Chromatography Column

Protein purification chromatography column: Protein L affinity chromatography column
(Purchased from GE Healthcare, column volume: 1.0 ml)
Buffer A: PBS, pH7.4
Buffer B: 0.1M Glycine, pH3.0
Buffer C: 0.1M Glycine, pH2.7
Purification procedure: AKTA explorer 100 protein purification system (Purchased from GE Healthcare) was used for purification. Pretreating Protein L affinity chromatography column with Buffer A, running culture medium sample, and collecting flowthrough sample. After running sample, balancing chromatography column with at least 1.5 ml Buffer A, then washing with Buffer B and Buffer C respectively, collecting flowthrough sample with target protein (the collection tube for flowthrough sample needs to be pretreated with 1% 1M Tris, pH8.0 to neutralize the pH of flowthrough sample, and the final concentration of Tris is about 10 mM), and finally, concentrating and dialysing the flowthrough sample into buffer PBS.

The final purified CD3-CD28 BsAb_M and CD3-CD28 BsAb_D recombinant protein were analyzed by SDS-PAGE, and the protein electrophoresis data under reduced and unreduced conditions were shown as FIG. 1-2. It shows that purity of CD3-CD28 BsAb_M and CD3-CD28 BsAb_D recombinant protein is >95%. The theoretical molecular weight of CD3-CD28 BsAb_M is 54.4 kDa, and protein displayed the same single band under reduced and unreduced conditions. The molecular weight of these bands is consistent with monomer, so this bi-specific antibody is monomer (FIG. 1-2A, Lane 1: protein marker for molecular weight; Lane 2: reduced CD3-CD28 BsAb_M; Lane 3: unreduced CD3-CD28 BsAb_M. B). The theoretical molecular weight for CD3-CD28 BsAb_D is 62.2 kDa, and protein displayed the same molecular weight as monomer under reduced condition, but the molecular weight is consistent with dimer under unreduced condition (FIG. 1-2B, Lane 1: protein marker for molecular weight; Lane 2: reduced CD3-CD28 BsAb_D; Lane 3: unreduced CD3-CD28 BsAb_D), which indicates two proteins link to each other by disulfide bond so that this bi-specific antibody is dimer.

Moreover, the N/C terminal sequence analysis for purified recombinant protein shows the reading frame has no error, and it is consistent with the theoretical N/C terminal amino acid sequence. Mass spectrometry analysis further confirmed that CD3-CD28 BsAb_M is monomer and CD3-CD28 BsAb_D is a dimer.

Therefore, the amino acid sequence of CD3-CD28 BsAb_M monomer is shown as SEQ ID NO.1.

The amino acid sequence of CD3-CD28 BsAb_D dimer is shown as SEQ ID NO.3.

The amino acid sequence of anti-CD3 scFv is shown as SEQ ID NO.5.

The amino acid sequence of anti-CD3 scFv heavy chain variable region is shown as SEQ ID NO.6.

The amino acid sequence of anti-CD3 scFv light chain variable region is shown as SEQ ID NO.7.

The amino acid sequence of anti-CD28 scFv is shown as SEQ ID NO.8.

The amino acid sequence of anti-CD28 scFv heavy chain variable region is shown as SEQ ID NO.9.

The amino acid sequence of anti-CD28 scFv light chain variable region is shown as SEQ ID NO.10.

The amino acid sequence of the CD3-CD28 BsAb_M monomer linker is shown as SEQ ID NO. 17.

The amino acid sequence of the CD3-CD28 BsAb_D dimer linker is shown as SEQ ID NO. 19.

Embodiment 1-3: Antigen-Binding Activity Test of CD3-CD28 BsAb_M and CD3-CD28 BsAb_D by ELISA ELISA Procedure:

1. Recombinant antigen coating: 96-well plates were coated by human CD3-hFc and human CD28-hFc recombinant protein (purchased from Novoprotein, Wujiang) 100 µl per well in concentration 1 µg/ml. The coated plates were kept at 37° C. for 1 hour or at 4° C. overnight. The recipe for the coating buffer is: 3.58 g $Na_2HPO_4$, 0.24 g $NaH_2PO_4$, 0.2 g KCl, 8.2 g NaCl, 950 ml $H_2O$, adjusting pH to 7.4 with 1 mol/L HCl or 1 mol/L NaOH, adding water to 1 L for total volume.

2. Blocking: washing plates with PBS for 4 times, and adding PBSA (PBS+2% BSA (V/W)) 200 µl per well to block at 37° C. for 1 hour.

3. Adding sample: washing plates with PBS for 4 times, add 100 µl per well of bi-specific antibody samples respectively and keeping plates at 37° C. for 1 hour. Sample serial dilution includes: using 10 g/ml of purified CD3-CD28 BsAb_M or CD3-CD28 BsAb_D as starting concentration, diluting it into 6 gradient concentrations, and using 2 duplicate wells for each gradient.

4. Color developing: washing plates with PBST (PBS+ 0.05% Tween-20(V/V)) for 4 times, diluting 1/5000 HRP labeled color-developing antibody (purchased from Abcam) by blocking buffer PBSA, add 100 µl per well and keeping plates at 37° C. for 1 hour. Washing plates with PBS for 4 times, adding 100 µl per well color-developing TMB purchased from KPL), developing in dark for 5-10 min at room temperature.

5. Reaction termination and result test: adding 100 µl per well of stop buffer (1M HCl) to stop the reaction, and reading OD value of 450 nm absorbance on ELISA reader.

The results of ELISA are shown in FIGS. 1-3A and 1-3B. The three lines in the figure represent three test raesults: ■ coated with 1 µg/ml CD3-hFc recombinant antigen; ✤ coated with 1 g/ml CD28-hFc recombinant antigen; ▲ no antigen coated result. FIG. 1-3A indicates that CD3-CD28 BsAb_M has antigen-binding activity with CD3-hFc and CD28-hFc in vitro. CD28 has higher binding activity than CD3. FIG. 1-3B indicates that CD3-CD28 BsAb_D has antigen-binding activity with CD3-hFc and CD28-hFc in vitro as well. CD28 has higher binding activity.

Embodiment 1-4: Cell Proliferation of Cytokine-Induced Killer (CIK) Mediated by CD3-CD28 Bi-Specific Antibody Human PBMC (Peripheral blood mononuclear cell, PBMC) was used as experiment material. CD3-CD28 BsAb_M monomer and CD3-CD28 BsAb_D dimer produced according to this disclosure, as well as full-length antibody anti-CD3/28 combination were added to PBMC from the same donor respectively. Cells are counted after being cultured to compare cell proliferation.

1. Separating PBMC: adding the physiological saline of same volume into the anticoagulant blood, and adding lymphocytes separation solution (purchased from GE Healthcare) of same volume into the mixed-blood slowly along the centrifuge tube wall. Keeping different liquid surface clear, centrifuging at 2000 rpm for 20 min, and extracting the white cell layer in the middle into new centrifuge tube. Adding PBS with volume more than 2 times of the extracted cell layer to wash cells, centrifuging at 1100 rpm for 10 min, washing once more, and adding some pre-cooling X-Vivo 15 serum-free medium (purchased from Lonza) to resuspend cells. Counting cells for use.

2. CIK cell culture and expansion: Resuspending PBMC with CIK basic medium (90% X-vivo15+10% FBS), and adjusting cell density to $1\times10^6$/ml. Experiment groups include: Control 1 (coating plate with anti-CD3 5 g/ml and anti-CD28 5 g/ml, full-length antibodies are all purchased from Novoprotein, Wujiang); Control 2 (add soluble full-length anti-CD3 100 ng/ml and anti-CD28 100 ng/ml in the medium); Experiment 1 (add soluble bi-specific CD3-CD28 BsAb_M 10 ng/ml); Experiment 2 (add soluble bi-specific CD3-CD28 BsAb_D 10 ng/ml). All of the four groups were added with IFN-γ (200 g/ml, purchased from Novoprotein, Wujiang) and IL-10 (2 ng/ml, purchased from Novoprotein, Wujiang), keeping cell culture in incubator with saturated humidity, at 37° C., 5.0% $CO_2$ concentration. After overnight, add 500U/ml of IL-2 (purchased from Novoprotein, Wujiang) into cell medium and keep culture. Every 2-3 days, count cells and passaging cell as $1\times10^6$/ml density in CIK basic medium with 500U/ml of IL-2. Culture cell in this way for 14 days, count cells for expansion factor calculation, and draw the cell growth curve.

The experiment results were shown in Table 1-2 and FIG. 1-4. CD3-CD28 bi-specific antibody monomer and dimer each can induce CIK expansion better than anti-CD3/anti-CD28 monoclonal full-length antibody combination, and the protein dosage is even less (10 ng/ml vs. 100 ng/ml). CD3-CD28 BsAb_D dimer could induce CIK cell expand 373 fold after two weeks, which has the best effect (experiment 2). CD3-CD28 BsAb_M monomer could induce CIK cell expand 278 fold after two weeks, which has the second-best effect (experiment 1).

TABLE 1-2

| | CIK cell expansion fold | | | |
|---|---|---|---|---|
| Experiment group | Control 1 | Control 2 | Experiment 1 | Experiment 2 |
| Expansion fold after 14 days | 224 | 196 | 278 | 373 |

Embodiment 1-5: Characterization of CIK Cells after Expansion Mediated by CD3-CD28 Bi-Specific Antibody 1. Flow Cytometer Analysis for $CD3^+CD56^+$ Double-Positive CIK Cells Four groups of experiment cells in Embodiment 1-4 after 14 days' culture were stained with anti-CD3-FITC and anti-CD56-PE (both purchased from Ebioscience) respectively, and test percentage of CD3+CD56+ double-positive cells by flow cytometer.

Flow Procedure:

1.1 Prepare four cell samples from Control 1, and 1 cell sample each from the other 3 groups (Control 2, Experiment 1, Experiment 2). Each sample has $1 \times 10^6$ cells.

1.2 Centrifugate cells at 1000 rpm for 5 min, discard supernatant, and resuspend cells with 200 µl 2% BSA/PBS. Centrifugate and wash cells twice.

1.3 Four cell samples from Control 1 were added with 5 µl PBS, anti-CD3-FITC, anti-CD56-PE and anti-CD3-FITC&anti-CD56-PE, respectively. Other 3 cell samples were added with anti-CD3-FITC&anti-CD56-PE. Keeping cells at 4° C. for 1 h.

1.4 Wash all cell samples with PBS twice, and resuspend cells with 100 µl PBS. Run cells on the flow cytometer.

The results were shown in FIG. 1-5. After CIK induced expansion by CD3-CD28 BsAb_M for 2 weeks, CD3+CD56+ double-positive percentage is 13.23%. After CIK induced expansion by CD3-CD28 BsAb_D for 2 weeks, CD3+CD56+ double-positive percentage is 13.92%. Both of them have no big difference compared to the effect of anti-CD3/anti-CD28 monoclonal full-length antibody combination (CD3+CD56+ double-positive percentage for antibody coated is 12.90%, and for soluble in medium is 11.40%). This result indicates that CD3-CD28 bispecific antibody of both monomer and dimer can substitute anti-CD3/anti-CD28 full-length antibody recombination.

2. Flow Cytometer Analysis for $CD4^+/CD8^+$ Positive Cells

Four groups of experiment cells in Embodiment 1-4 after 14 days' culture were stained with anti-CD4-FITC and anti-CD8-PE (both purchased from Ebioscience) respectively, and test CD4+ and CD8+ each positive percentage of these cells by flow cytometer.

Flow Procedure:

2.1 Prepare four cell samples from Control 1, and 1 cell sample each from the other 3 groups (Control 2, Experiment 1, Experiment 2). Each sample has $1 \times 10^6$ cells.

2.2 Centrifugate cell down at 1000 rpm for 5 min, discard supernatant, and resuspend cells with 200 µl 2% BSA/PBS. Spin and wash cells twice.

2.3 Four cell samples from Control 1 were added with 5 µl PBS, anti-CD4-FITC, anti-CD8-PE and anti-CD4-FITC&anti-CD8-PE, respectively. Other 3 cell samples were added with anti-CD4-FITC&anti-CD8-PE. Keeping cells at 4° C. for 1 h.

2.4 Wash all cell samples with PBS twice, and resuspend cells with 100 µl PBS. Run cells on the flow cytometer.

Results were shown as FIG. 1-6: After CIK induced expansion by CD3-CD28 BsAb_M for 2 weeks, CD8+ positive percentage is 67.70%. After CIK induced expansion by CD3-CD28 BsAb_D 2 for 2 weeks, CD8+ positive percentage is 78.65%. Both of them have better effect to induce CD8+ positive cells compared to the effect by anti-CD3/anti-CD28 monoclonal full-length antibody combination (CD8+ positive percentage for antibody coated is 48.95%, and for soluble in medium is 48.47%). This result indicates CD3-CD28 bi-specific antibody is better than anti-CD3/anti-CD28 full-length antibody recombination to induce CD8+ cell growth and expansion, and dimer is better than monomer.

Embodiment 2-1 the Eukaryotic Expression Vector Construction of CD3-4-1BB BsAb_M and CD3-4-1BB BsAb_D In this disclosure, the bi-specific antibody targeted CD3 and costimulatory molecule 4-1BB on human T cell is named as CD3-4-1BB BsAb.

1. Construction of CD3-4-1BB BsAb_M and CD3-4-1BB BsAb_D

Construction of CD3-4-1BB BsAb_M Monomer: the sequence of anti-CD3 scFv and anti-4-1BB scFv is linked by (GGGGS) 3 Linker.

Construction of CD3-4-1BB BsAb_D Dimer: the sequence of anti-CD3 scFv and anti-4-1BB scFv is linked by IgD hinge region Linker.

In order to express the bi-specific antibody in mammalian cells, codon optimization of the mammalian system was performed for the sequence of anti-CD3 scFv, anti-4-1BB scFv and linker.

The nucleotide sequence of anti-CD3 scFv heavy chain variable region is shown as SEQ ID NO. 89.

The nucleotide sequence of anti-CD3 scFv light chain variable region is shown as SEQ ID NO. 90.

The nucleotide sequence of anti-CD3 scFv is shown as SEQ ID NO. 88.

The nucleotide sequence of anti-4-1BB scFv heavy chain variable region is shown as SEQ ID NO. 92.

The nucleotide sequence of anti-4-1BB scFv light chain variable region is shown as SEQ ID NO. 93.

The nucleotide sequence of anti-4-1BB scFv is shown as SEQ ID NO. 91.

The nucleotide sequence of the CD3-4-1BB BsAb_M monomer linker is shown as SEQ ID NO. 33.

The nucleotide sequence of CD3-4-1BB BsAb_D dimer linker is shown as SEQ ID NO. 35.

In order to make the bi-specific antibody successfully expressed in CHO-S cells and secreted into medium, signal peptide of antibody secretory expression was selected in this Embodiment.

The amino acid sequence of this secretory signal peptide is shown as SEQ ID NO.109. The nucleotide sequence of this secretory signal peptide is shown as SEQ ID NO.110.

2. Construction of Eukaryotic Expression Vector of CD3-4-1BB BsAb_M and CD3-4-1BB BsAb_D The construction and expression of the bi-specific antibody of the disclosure selected mammalian cell protein transient expression vector pcDNA3.1 (purchased from Invitrogen, Shanghai). In order to construct the bi-specific antibody of monomer and dimer, primers were designed as in table 2-1. All the primers were synthesized by Genewiz, Suzhou, and DNA template for PCR was synthesized by Synbio Technologies, Suzhou.

For the cloning construct of CD3-4-1BB BsAb_M, signal peptide fragments were firstly amplified by primers pcDNA3.1-Sig-F and Sig-R, and then anti-CD3 scFv, (GGGGS) 3 Linker and anti-4-1BB scFv gene sequence were amplified by primers Sig-CD3-F&CD3-R, and CD3-(GGGGS)$_3$-4-1BB-F&pcDNA3.1-4-1BB-R, respectively. For the cloning construct of CD3-4-1BB BsAb_D, similarly, signal peptide fragments were firstly amplified by primers pcDNA3.1-Sig-F and Sig-R, and then anti-CD3 scFv, IgD hinge region Linker, and anti-4-1BB scFv gene sequence were amplified by primers Sig-CD3-F&CD3-R, CD3-IgD-F&IgD-R, and IgD-4-1BB-F&pcDNA3.1-4-1BB-R, respectively. After the PCR amplification, by using NovoRec®PCR one-step cloning kit (purchase from novoprotein, Wujiang), the full-length sequence of bi-specific antibody monomer and dimer were separately spliced and seamlessly cloned into the pcDNA3.1 expression vector which was linearized by EcoRI and HindIII. The target vector was transformed into *E. Coli* DH5a, colony PCR was used for positive cloning identification, and the recombinant (recombinant plasmid) identified as positive was performed sequencing identification. The recombinant (recombinant plasmid) with the right sequence was purified by midi-prep, and then used in the transfection of CHO-S cells.

After sequencing, the CD3-4-1BB BsAb_M monomer and CD3-4-1BB BsAb_D dimer both had the right full DNA sequence as expected.

The nucleotide sequence of CD3-4-1BB BsAb_M monomer is shown as SEQ ID NO.44.

The nucleotide sequence of CD3-4-1BB BsAb_D dimer is shown as SEQ ID NO.46.

TABLE 2-1

Primers used in CD3-4-1BB bi-specific antibody gene cloning

| Primer name | Sequence | No. |
|---|---|---|
| pcDNA3.1-Sig-F | GTGCTGGATATCTGCAGAATTCGCCGCCACCA TGACCCGGCTGACCGTGCTGGCCCTGC | SEQ ID NO.111 |
| Sig-R | GGCCCTGGAGGAGGCCAGCAGGCCGGC CAGCAGGGCCAGCACGGTCAGC | SEQ ID NO.112 |
| Sig-CD3-F | GCTGGCCTCCTCCAGGGCCGACATCAAG CTGCAGCAGAGCG | SEQ ID NO.113 |
| CD3-R | CTTCAGCTCCAGCTTGGTGC | SEQ ID NO.114 |
| CD3-(GGGGS)$_3$-4-1BB-F | GCACCAAGCTGGAGCTGAAGGGCGGCGGCG GCAGCGGCGGCGGCGGCAGCGGCGGCGGCG GCAGCCAGGTGCAGCTGCAGCAGTG | SEQ ID NO.115 |
| pcDNA3.1-4-1BB-R | CTGATCAGCGGTTTAAACTTAAGCTTTCA GCGCTTGATCTCCACCTTGGTG | SEQ ID NO.116 |
| CD3-IgD-F | GCACCAAGCTGGAGCTGAAGGCCAGCAA GAGCAAGAAGGAG | SEQ ID NO.117 |
| IgD-R | CACGCCCAGGGGCTGGGTGTG | SEQ ID NO.118 |
| IgD-4-1BB-F | CACACCCAGCCCCTGGGCGTGCAGGTGC AGCTGCAGCAGTGG | SEQ ID NO.119 |

Embodiment 2-2: The Expression and Purification of CD3-4-1BB BsAb_M and CD3-4-1BB BsAb_D 1. The Expression of CD3-4-1BB BsAb_M and CD3-4-1BB BsAb_D 1.1 The cell density of CHO-S cells (purchased from Thermo Fisher Scientific) was 0.5~0.6×10$^6$/ml one day before transfection.

1.2 Calculating the cell density at the day of transfection, performing plasmid transfection when the density is in the range of 1~1.4×10$^6$/ml and the live percentage is >90%.

1.3 Transfection complex recipes: each project (CD3-4-1BB BsAb_M and CD3-4-1BB BsAb_D) requires two centrifuge tubes/flasks. Take total 20 ml as an example, the centrifuge tubes/flasks were placed, and the recombinant plasmids from Embodiment 2-1 were taken: Tube 1: 600 µl PBS, 20 µg recombinant plasmid, mixing well.

Tube 2: 600 µl PBS, 20 µl FreeStyle™ MAX Transfection Reagent (purchased from Thermo Fisher Scientific), mixing well.

1.4 Adding the diluted transfection reagent into the diluted recombinant plasmid, mixing well to obtain transfection complex.

1.5 After 15~20 min's standing, the transfection complex was added into the cell culture dropwise and at a constant rate.

1.6 Keeping the cell culture at 37° C., with 8% of $CO_2$, and 130 rpm of the shaking speed. Collecting the medium after 5 days for the target protein test.

2. The Purification of CD3-4-1BB BsAb_M and CD3-4-1BB BsAb_D 2.1 Sample Pretreatment Taking 20 ml cell medium after transfection, adding 20 mM PB, 200 mM NaCl, and adjusting pH to 7.5;

2.2 Purification of Protein L Affinity Chromatography Column

Protein purification chromatography column: Protein L affinity chromatography column (purchased from GE Healthcare, column volume: 1.0 ml)

Buffer A: PBS, pH7.4
Buffer B: 0.1M Glycine, pH3.0
Buffer C: 0.1M Glycine, pH2.7

Purification procedure: AKTA explorer 100 protein purification system (purchased from GE Healthcare) was used for purification. Pretreating Protein L affinity chromatography column with Buffer A, running culture medium sample, and collecting the flowthrough sample. After running the sample, balancing the chromatography column with at least 1.5 ml Buffer A, then washing with Buffer B and Buffer C respectively, collecting flowthrough sample with target protein (the collection tube for flowthrough sample needs to be pretreated with 1% 1M Tris, pH8.0 to neutralize the pH of the flowthrough sample, and the final concentration of Tris is about 10 mM), and finally, concentrating and dialyzing the flowthrough sample into buffer PBS.

The final purified CD3-4-1BB BsAb_M and CD3-4-1BB BsAb_D recombinant proteins were analyzed by SDS-PAGE, and the protein electrophoresis data under reduced and unreduced conditions is shown as FIG. 2-2. It shows that both purities of CD3-4-1BB BsAb_M and CD3-4-1BB BsAb_D recombinant protein are >95%. The theoretical molecular weight of CD3-4-1BB BsAb_M is 53.7 kDa, and the protein displayed the same single electrophoretic band under reduced and unreduced conditions. The molecular weight of these bands is consistent with the monomer, so this bi-specific antibody is in monomer form (FIG. 2-2A, Lane 1: protein marker for molecular weight; Lane 2: reduced CD3-4-1BB BsAb_M; Lane 3: unreduced CD3-4-1BB BsAb_M). The theoretical molecular weight of CD3-4-1BB BsAb_D is 61.5 kDa, and the electrophoretic band of the protein displayed the same molecular weight as the monomer under reduced condition, but the molecular weight is consistent with the dimer under unreduced condition (FIG. 2-2B, Lane 1: protein marker for molecular weight; Lane 2: reduced CD3-4-1BB BsAb_D; Lane 3: unreduced CD3-4-1BB BsAb_D), which indicates that two protein could link to each other by disulfide bond, thus this bi-specific antibody is in dimer form.

Moreover, the N/C terminal sequence analysis for purified recombinant protein samples shows that the reading frame has no error, consistent with the theoretical N/C terminal amino acid sequence. Mass spectrometry analysis further confirmed that CD3-4-1BB BsAb_M is monomer and CD3-4-1BB BsAb_D is a dimer.

Therefore, the amino acid sequence of CD3-4-1BB BsAb_M monomer is shown as SEQ ID NO.43.

The amino acid sequence of CD3-4-1BB BsAb_D dimer is shown as SEQ ID NO.45.

The amino acid sequence of anti-CD3 scFv is shown as SEQ ID NO.67.

The amino acid sequence of anti-CD3 scFv heavy chain variable region is shown as SEQ ID NO.68.

The amino acid sequence of anti-CD3 scFv light chain variable region is shown as SEQ ID NO.69.

The amino acid sequence of anti-4-1BB scFv is shown as SEQ ID NO.70.

The amino acid sequence of anti-4-1BB scFv heavy chain variable region is shown as SEQ ID NO.71.

The amino acid sequence of anti-4-1BB scFv light chain variable region is shown as SEQ ID NO.72.

The amino acid sequence of CD3-4-1BB BsAb_D monomer linker is shown as SEQ ID NO.32.

The amino acid sequence of CD3-4-1BB BsAb_D dimer linker is shown as SEQ ID NO.34.

Embodiment 2-3: Antigen-Binding Activity Test of CD3-4-1BB BsAb_M and CD3-4-1BB BsAb_D by ELISA ELISA Procedure:

1. Recombinant antigen coating: 96-well plates were coated by human CD3-hFc and human 4-1BB-hFc recombinant protein (purchased from Novoprotein, Wujiang) 100 μl per well in concentration 1 μg/ml. The coated plates were kept at 37° C. for 1 hour or at 4° C. overnight. The recipe for coating buffer (PBS) is: 3.58 g $Na_2HPO_4$, 0.24 g $NaH_2PO_4$, 0.2 g KCl, 8.2 g NaCl, 950 ml $H_2O$, adjusting pH to 7.4 with 1 mol/L HCl or 1 mol/L NaOH, adding water to 1 L for total volume.

2. Blocking: washing plates with PBS for 4 times, and adding 200 μl per well of PBSA (PBS+2% BSA (V/W)) to block 1 hour at 37° C.

3. Adding sample: washing plates with PBS for 4 times, adding 100 μl per well of bi-specific antibody samples separately and keeping plates at 37° C. for 1 hour. Sample serial dilution includes: using 10 μg/ml of purified CD3-4-1BB BsAb_M or CD3-4-1BB BsAb_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well of the antibody and keeping plates at 37° C. for 1 hour. Washing plates with PBS for 4 times, adding 100 μl per well of color-developing TMB (purchased from KPL), developing in dark for 5~10 min at room temperature.

5. Reaction termination and result test: adding 100 μl per well of stop buffer (1M HCl) to stop the reaction, and reading OD value of 450 nm absorbance on ELISA reader.

The results of ELISA are shown in FIGS. 2-3A and 2-3B. The three curves in the figure represent three test results: ■ coated with 1 μg/ml CD3-hFc recombinant antigen, ● coated with 1 μg/ml 4-1BB-hFc recombinant antigen; ▲ no antigen coated result. FIG. 2-3A displays that CD3-4-1BB BsAb_M has antigen-binding activity with CD3-hFc and 4-1BB-hFc in vitro, among which 4-1BB has higher binding activity than that of CD3. FIG. 2-3B displays that CD3-4-1BB BsAb_D has antigen-binding activity with CD3-hFc and 4-1BB-hFc in vitro as well, and 4-1BB has higher binding activity.

Embodiment 2-4: Cell Proliferation of Cytokine-Induced Killer (CIK) Mediated by CD3-4-1BB Bi-Specific Antibody Human PBMC (Peripheral blood mononuclear cell, PBMC) was used as the experiment material. CD3-4-1BB BsAb_M monomer and CD3-4-1BB BsAb_D dimer produced by this disclosure, as well as full-length antibody anti-CD3/28 combination were added to PBMC from the same donor separately. Cells are counted after being cultured to compare cell proliferation.

1. Separating PBMC: adding the physiological saline of same volume into the anticoagulant blood, and adding ficoll (purchased from GE Healthcare) of same volume into the mixed-blood slowly along the centrifuge tube wall. Keeping the different liquid surface clearly stratified, centrifuging at 2000 rpm for 20 min, and removing the white cell layer in the middle into a new centrifuge tube. Adding PBS with volume more than 2 times of the extracted cell layer to wash the cells, centrifuging 10 min at 1100 rpm, washing once more, and adding some pre-cooling X-Vivo 15 serum-free medium (purchased from Lonza) to the resuspend cells. Counting the cells for use.

2. CIK cell culture and expansion: Resuspending PBMC with CIK basic medium (90% X-vivo15+10% FBS), and adjusting cell density to $1 \times 10^6$/ml. Experiment groups include: Control (coating the plate with 5 μg/ml of anti-CD3 and 5 μg/ml of anti-CD28); Experiment 1 (adding 10 ng/ml of bi-specific CD3-4-1BB BsAb_M in solution); Experiment 2 (adding 10 ng/ml of bi-specific CD3-4-1BB BsAb_D in solution). All of the three groups were added with IFN-γ (200 ng/ml, purchased from Novoprotein, Wujiang) and IL-1β (2 ng/ml, purchased from Novoprotein, Wujiang), the cell culture was kept in an incubator under the condition of saturated humidity, 37° C. and 5.0% $CO_2$. After overnight, 500U/ml of IL-2 (purchased from Novoprotein, Wujiang) was added into the cell medium and keeps culturing. Every 2-3 days, counting the cells and passaging the cells at the density of $1 \times 10^6$ in CIK basic medium with 500U/ml IL-2. Cells were cultured in this way for 14 days, counting the cells to calculate the expansion fold, and drawing the cell growth curve.

The experiment results were shown in FIG. 2-4. Both of CD3-4-1BB bi-specific antibody monomer and dimer better induce CIK expansion than anti-CD3/anti-CD28 monoclonal full-length antibody combination. Anti-CD3/anti-CD28 monoclonal full-length antibody combination induced severe cell death after culturing for 18 days, and cell proliferation rate significantly reduced; meanwhile, neither CD3-4-1BB BsAb_M monomer nor CD3-4-1BB BsAb_D dimer induced cell death, but the cell proliferation rate was relatively slow. Therefore, both monomer and dimer of CD3-4-1BB bi-specific antibody can effectively promote cell expansion and prolong the survival of the CIK cell, among which the dimer has better effect.

Embodiment 2-5: Characterization of CIK Cells after Expansion Mediated by CD3-4-1BB Bi-Specific Antibody: Flow Cytometer Analysis for CD8$^+$CD4$^+$ Positive Cells Three groups of experiment cells in Embodiment 2-4 after 30 days' culturing were stained with anti-CD4-FITC and anti-CD8-PE (both were purchased from Ebioscience) respectively, and the numbers of CD8+ and CD4+ positive cells were detected by flow cytometer to count their proportion, respectively.

Flow Procedure:
1. Preparing four cell samples from Control and 1 cell sample each from the other two groups (Experiment 1, Experiment 2). Each sample has 1×10$^6$ cells.
2. Centrifuging the cell at 1000 rpm for 5 min, discarding the supernatant, and resuspending the cells with 200 µl of 2% BSA/PBS. Centrifuging and washing cells twice.
3. Four cell samples from Control were added with 5 µl of PBS, anti-CD4-FITC, anti-CD8-PE and anti-CD4-FITC&anti-CD8-PE, respectively. Other 2 cell samples were added with anti-CD4-FITC&anti-CD8-PE. The cells were kept at 4° C. for 1 h.
4. Washing all cell samples with PBS twice, and resuspending the cells with 100 µl of PBS. Run cells on the flow cytometer.

Results were shown as FIG. 2-5: After CIK induced expansion by CD3-4-1BB BsAb_D for 30 days, CD8+ positive percentage is 88.17%. After CIK induced expansion by CD3-CD28 BsAb_M for 30 days, CD8+ positive percentage is 78.02%. Both of them have better effect to induce CD8+ positive cells compared to that of anti-CD3/anti-CD28 monoclonal full-length antibody combination (CD8+ positive percentage for antibody coated is 48.47%). This result indicates that CD3-4-1BB bi-specific antibody of both monomer and dimer is better than anti-CD3/anti-CD28 full-length antibody recombination to induce CD8+ cell growth and expansion, and dimer is better than monomer.

Embodiment 2-6 the Eukaryotic Expression Vector Construction of CD3-ICOS BsAb_M and CD3-ICOS BsAb_D In this disclosure, the bi-specific antibody targeted CD3 and ICOS on human T cell is named as CD3-ICOS BsAb.
1. Construction of CD3-ICOS BsAb_M and CD3-ICOS BsAb_D
Construction of CD3-ICOS BsAb_M Monomer: the sequence of anti-CD3 scFv and anti-ICOS scFv is linked by (GGGGS) 3 Linker.
Construction of CD3-ICOS BsAb_D Dimer: the sequence of anti-CD3 scFv and anti-ICOS scFv is linked by IgD hinge region Linker.

In order to express the bi-specific antibody in mammalian cells, codon optimization of the mammalian system was performed for the sequence of anti-CD3 scFv, anti-ICOS scFv and IgD hinge region.

The nucleotide sequence of the anti-CD3 scFv heavy chain variable region is shown as SEQ ID NO. 89 in detail.
The nucleotide sequence of the anti-CD3 scFv light chain variable region is shown as SEQ ID NO. 90 in detail.
The nucleotide sequence of anti-CD3 scFv is shown as SEQ ID NO. 88 in detail.
The nucleotide sequence of anti-ICOS scFv heavy chain variable region is shown as SEQ ID NO. 95.
The nucleotide sequence of anti-ICOS scFv light chain variable region is shown as SEQ ID NO. 96.
The nucleotide sequence of anti-ICOS scFv is shown as SEQ ID NO. 94.
The nucleotide sequence of the CD3-ICOS BsAb_M monomer linker is shown as SEQ ID NO. 33 in detail.
The nucleotide sequence of the CD3-ICOS BsAb_D dimer linker is shown as SEQ ID NO. 35 in detail.
In order to make the bi-specific antibody successfully expressed in CHO-S cells and secreted into the medium, signal peptide of antibody secretory expression was selected in this embodiment.
The amino acid sequence of this secretory signal peptide is shown as SEQ ID NO. 109 in detail.
The nucleotide sequence of this secretory signal peptide is shown as SEQ ID NO.110 in detail.
2. Construction of Eukaryotic Expression Vector of CD3-ICOS BsAb_M and CD3-ICOS BsAb_D The construction and expression of the bi-specific antibody of the disclosure selected mammalian cell protein transient expression vector pcDNA3.1 (purchased from Invitrogen, Shanghai). In order to construct bi-specific antibody of monomer and dimer, primers were designed as in table 2-2. All the primers were synthesized by Genewiz, Suzhou, and DNA template for PCR was synthesized by Synbio Technologies, Suzhou.

For the cloning construct of CD3-ICOS BsAb_M, amplified signal peptide fragment was firstly amplified by primers pcDNA3.1-Sig-F and Sig-R, and then anti-CD3 scFv, (GGGGS) 3 Linker and anti-ICOS scFv sequence were amplified by primers Sig-CD3-F&CD3-R, and CD3-(GGGGS)$_3$-ICOS-F&pcDNA3.1-ICOS-R. For the cloning construct of CD3-ICOS BsAb_D, signal peptide fragment was firstly amplified by primers pcDNA3.1-Sig-F and Sig-R, and then anti-CD3 scFv, IgD hinge region Linker, and anti-ICOS scFv sequence was amplified by primers Sig-CD3-F&CD3-R, CD3-IgD-F&IgD-R, and IgD-ICOS-F&pcDNA3.1-ICOS-R, respectively. After the PCR amplification, by using NovoRec®PCR one-step cloning kit (purchased from novoprotein, Wujiang), the full-length sequence of bi-specific antibody monomer and dimer were separately ligated into the pcDNA3.1 expression vector which was linearized by EcoRI and HindIII. The target vector was transformed into *E. Coli* DH5a, colony PCR was used for positive cloning identification, and the recombinant (recombinant plasmid) identified as positive was performed sequencing identification. The recombinants (recombinant plasmid) with right sequence were purified by midi-prep, and then transfected into CHO-S cells.

After sequencing, the CD3-ICOS BsAb_M monomer and CD3-ICOS BsAb_D dimer both had the right full DNA sequence as expected.
The nucleotide sequence of CD3-ICOS BsAb_M monomer is shown as SEQ ID NO.48.

The nucleotide sequence of CD3-ICOS BsAb_D dimer is shown as SEQ ID NO.50.

TABLE 2-2

Primers used in CD3-ICOS bi-specific antibody gene cloning

| Primer name | Sequence | No. |
| --- | --- | --- |
| CD3-(GGGG S)$_3$-ICOS-F | GCACCAAGCTGGAGCTGAAGGGCGGCGG CGGCAGCGGCGGCGGCGGCAGCGGCGGCGG CGGCAGCCAGGTGCAGCTGGTGCAGAGC | SEQ ID NO.120 |
| pcDNA3.1-I COS-R | CTGATCAGCGGTTTAAACTTAAGCTTTCAC TTGATCTCCACCTTGGTGCC | SEQ ID NO.121 |
| IgD-ICOS-F | CACACCCAGCCCCTGGGCGTGCAGGTGCA GCTGGTGCAGAGC | SEQ ID NO.122 |

Embodiment 2-7: The Expression and Purification of CD3-ICOS BsAb_M and CD3-ICOS BsAb_D 1. The Expression of CD3-ICOS BsAb_M and CD3-ICOS BsAb_D 1.1 The cell density of CHO-S cells (purchased from Thermo Fisher Scientific) was 0.5~0.6×10⁶/ml one day before transfection.

1.2 Calculating the cell density at the day of transfection, performing plasmid transfection when the density is in the range of 1~1.4×10⁶/ml and the live percentage is >90%.

1.3 Transfection complex recipes: each project (CD3-ICOS BsAb_M and CD3-ICOS BsAb_D) requires two centrifuge tubes/flasks. Take total 20 ml as an example, put the recombinant plasmids from Embodiment 2-6 separately:

Tube 1: 600 µl PBS, 20 µg recombinant plasmid, mixing well.
Tube 2: 600 µl PBS, 20 µl FreeStyle™ MAX Transfection Reagent (purchased from Thermo Fisher Scientific), mixing well.

1.4 Adding the diluted transfection reagent into the diluted recombinant plasmid, mixing well to obtain transfection complex.

1.5 After 15~20 min's standing, the transfection complex was added into the cell culture dropwise and at a constant rate.

1.6 Keeping the cell culture at 37° C., with 8% of $CO_2$, and 130 rpm of the shaking speed. Collecting the medium after 5 days for the target protein test.

2. The Purification of CD3-ICOS BsAb_M and CD3-ICOS BsAb_D 2.1 Sample Pretreatment Taking 20 ml cell medium after transfection, adding 20 mM PB, 200 mM NaCl, and adjusting pH to 7.5;

2.2 Purification of Protein L Affinity Chromatography Column

Protein purification chromatography column: Protein L affinity chromatography column (purchased from GE Healthcare, column volume: 1.0 ml)
Buffer A: PBS, pH7.4
Buffer B: 0.1M Glycine, pH3.0
Buffer C: 0.1M Glycine, pH2.7
Purification procedure: AKTA explorer 100 protein purification system (purchased from GE Healthcare) was used for purification. Pretreating Protein L affinity chromatography column with Buffer A, running culture medium sample, and collecting the flowthrough sample. After running the sample, balancing the chromatography column with at least 1.5 ml Buffer A, then washing with Buffer B and Buffer C respectively, and collecting flowthrough sample with target protein (the collection tube for flowthrough sample needs to be pretreated with 1% 1M Tris, pH8.0 to neutralize the pH of the flowthrough sample, and the final concentration of Tris is about 10 mM), and finally, concentrating and dialysing the flowthrough sample into buffer PBS.

The final purified CD3-ICOS BsAb_M and CD3-ICOS BsAb_D recombinant protein were analyzed by SDS-PAGE, and the protein electrophoresis data under reduced and unreduced conditions is shown as FIG. 2-6. It shows that, after the purification of Protein L affinity chromatography column, both purities of CD3-ICOS BsAb_M and CD3-ICOS BsAb_D recombinant protein are >95%. The theoretical molecular weight of CD3-ICOS BsAb_M is 53.8 kDa, and the protein displayed the same single electrophoretic band under reduced and unreduced conditions. The molecular weight of these bands is consistent with monomer, so this bi-specific antibody is monomer (FIG. 2-6A, Lane 1: protein marker for molecular weight; Lane 2: reduced CD3-ICOS BsAb_M; Lane 3: unreduced CD3-ICOS BsAb_M). The theoretical molecular weight of CD3-ICOS BsAb_D is 61.7 kDa, and the electrophoretic band of the protein displayed the same molecular weight as the monomer under reduced condition, but the molecular weight is consistent with dimer under unreduced condition (FIG. 2-6B, Lane 1: protein marker for molecular weight; Lane 2: reduced CD3-ICOS BsAb_D; Lane 3: unreduced CD3-ICOS BsAb_D), which indicates that two protein molecules could link to each other by disulfide bond thus this bi-specific antibody is dimer.

Moreover, the N/C terminal sequence analysis for purified recombinant protein samples shows that the reading frame has no error, consistent with the theoretical N/C terminal amino acid sequence. Mass spectrometry analysis further confirmed that CD3-ICOS BsAb_M is monomer and CD3-ICOS BsAb_D is a dimer.

Therefore, the amino acid sequence of CD3-ICOS BsAb_M monomer is shown as SEQ ID NO.47.

The amino acid sequence of CD3-ICOS BsAb_D dimer is shown as SEQ ID NO.49.

The amino acid sequence of CD3 scFv is shown as SEQ ID NO.67 in detail.

The amino acid sequence of the CD3 scFv heavy chain variable region is shown as SEQ ID NO.68 in detail.

The amino acid sequence of the CD3 scFv light chain variable region is shown as SEQ ID NO.69 in detail.

The amino acid sequence of ICOS scFv is shown as SEQ ID NO.73.

The amino acid sequence of the ICOS scFv heavy chain variable region is shown as SEQ ID NO.74.

The amino acid sequence of the ICOS scFv light chain variable region is shown as SEQ ID NO.75.

The amino acid sequence of the CD3-ICOS_M monomer linker is shown as SEQ ID NO.32 in detail.

The amino acid sequence of the CD3-ICOS BsAb_D dimer linker is shown as SEQ ID NO.34 in detail.

Embodiment 2-8: Antigen-Binding Activity Test of CD3-ICOS BsAb_M and CD3-ICOS BsAb_D by ELISA ELISA Procedure:

1. Recombinant antigen coating: 96-well plates were coated by human CD3-hFc and human ICOS-hFc recombinant protein (purchased from Novoprotein, Wujiang) 100 μl per well in concentration 1 μg/ml. The coated plates were kept at 37° C. for 1 hour or at 4° C. overnight. The recipe for coating buffer (PBS) is: 3.58 g $Na_2HPO_4$, 0.24 g $NaH_2PO_4$, 0.2 g KCl, 8.2 g NaCl, 950 ml $H_2O$, adjusting pH to 7.4 with 1 mol/L HCl or 1 mol/L NaOH, adding water to 1 L for total volume.

2. Blocking: washing plates with PBS for 4 times, and adding 200 μl per well of PBSA (PBS+2% BSA (V/W)) to block 1 hour at 37° C.

3. Adding sample: washing plates with PBS for 4 times, adding 100 μl per well of bi-specific antibody samples respectively and keeping plates at 37° C. for 1 hour. Sample serial dilution includes: using 10 μg/ml of purified CD3-ICOS BsAb_M or CD3-ICOS BsAb_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well of the antibody and keeping plates at 37° C. for 1 hour. Washing plates with PBS for 4 times, adding 100 μl per well of color-developing TMB (purchased from KPL), developing in dark for 5~10 min at room temperature.

5. Reaction termination and result test: add 100 μl per well of stop buffer (1M HCl) to stop the reaction, and reading OD value of 450 nm absorbance on ELISA reader.

The results of ELISA are shown in FIGS. 2-7A and 2-7B. The three lines in the figure represent three test results: ■ coated with 1 μg/ml CD3-hFc recombinant antigen, ✸ coated with 1 μg/ml ICOS-hFc recombinant antigen; ▲ no antigen coated result. FIG. 2-7A displays that CD3-ICOS BsAb_M has antigen-binding activity with CD3-hFc and ICOS-hFc in vitro, among which ICOS has higher binding activity than that of CD3. FIG. 2-7B displays that CD3-ICOS BsAb_D has antigen-binding activity with CD3-hFc and ICOS-hFc in vitro as well, and ICOS has higher binding activity.

Embodiment 2-9: Cell Proliferation of Cytokine-Induced Killer (CIK) Mediated by CD3-ICOS Bi-Specific Antibody Human PBMC (Peripheral blood mononuclear cell, PBMC) was used as experiment material. CD3-ICOS BsAb_M monomer and CD3-ICOS BsAb_D dimer produced by this disclosure, as well as full-length antibody anti-CD3/28 combination were added separately to PBMC from the same donor, respectively. Cells are counted after being cultured to compare cell proliferation.

1. Separating PBMC: adding physiological saline of the same volume into the anticoagulant blood, and adding ficoll (purchased from GE Healthcare) of same volume into the mixed-blood slowly along the centrifuge tube wall. Keeping the different liquid surface clearly stratified, centrifuging at 2000 rpm for 20 min, and removing the white cell layer in the middle into new a centrifuge tube. Adding PBS with volume more than 2 times of the extracted cell layer to wash the cells, centrifuging 10 min at 1100 rpm, washing once more, and adding some pre-cooling X-Vivo 15 serum-free medium (purchased from Lonza) to the resuspend cells. Counting the cells for use.

2. CIK cell culture and expansion: Resuspending PBMC with CIK basic medium (90% X-vivo15+10% FBS), and adjusting cell density to $1\times10^6$/ml. Experiment groups include: Control (coating the plate with 5 μg/ml of anti-CD3 and 5 μg/ml anti-CD28); Experiment 1 (adding 10 ng/ml of bi-specific CD3-ICOS BsAb_M in solution); Experiment 2 (adding 10 ng/ml bi-specific CD3-ICOS BsAb_D in solution). All of the three groups were added with IFN-γ (200 ng/ml, purchased from Novoprotein, Wujiang) and IL-1B (2 ng/ml, purchased from Novoprotein, Wujiang), the cell culture was kept in an incubator under the condition of saturated humidity, 37° C. and 5.0% $CO_2$. After overnight, 500U/ml of IL-2 (purchased from Novoprotein, Wujiang) was added into the cell medium and keeps culturing. Every 2-3 days, counting the cells and passaging the cell at the density of $1\times10^6$/ml in CIK basic medium with 500U/ml of IL-2. Cells were cultured in this way for 14 days, counting the cells to calculate the expansion fold, and drawing the cell growth curve.

The experiment results were shown in FIGS. 2-3 and 2-8. Both of CD3-ICOS bi-specific antibody monomer and dimer each can better induce CIK expansion than anti-CD3/anti-CD28 monoclonal full-length antibody combination, and the protein dosage is even less (10 ng/ml vs. 5 μg/ml). Among them, CD3-ICOS BsAb_D dimer could induce CIK cell to expand 352 fold after two weeks, which has the best effect (experiment 2); CD3-ICOS BsAb_M monomer could induce CIK cell to expand 298 fold after two weeks, which has the second-best effect (experiment 1). CD3/anti-CD28 monoclonal full-length antibody combination could induce CIK cell to expand 224 fold after two weeks with weakest effect (Control).

TABLE 2-3

| CIK cell expansion fold | | | |
|---|---|---|---|
| Experiment group name | Control | Experiment 1 | Experiment 2 |
| Expansion fold after 14 days | 224 | 298 | 352 |

Embodiment 2-10: Characterization of CIK Cells after Expansion Mediated by CD3-ICOS Bi-Specific Antibody: Flow Cytometer Analysis for $CD3^+CD56^+$ Double-Positive CIK Cells Three groups of experiment cells in Embodiment 2-9 after 14 days' culturing were stained with anti-CD3-FITC and anti-CD56-PE (both were purchased from Ebioscience) respectively, and test percentage of CD3+CD56+ double-positive cells by flow cytometer.

Flow Procedure:

1.1 Preparing four cell samples from Control, and 1 cell sample each from the other 2 groups (Experiment 1, Experiment 2). Each sample has $1\times10^6$ cells.

1.2 Centrifugating the cell down, at 1000 rpm for 5 min, discarding the supernatant, and resuspending cells with 200 μl of 2% BSA/PBS. Centrifuging and washing cells twice.

1.3 Four cell samples from Control were added with 5 μl of PBS, anti-CD3-FITC, anti-CD56-PE and anti-CD3-FITC&anti-CD56-PE, respectively. Other 2 cell samples were added with anti-CD3-FITC&anti-CD56-PE. The cells were kept at 4° C. for 1 h.

1.4 Washing all cell samples with PBS twice, and Resuspending cells with 100 μl of PBS. Run cells on the flow cytometer.

Results were shown as FIG. 2-9: After CIK induced by anti-CD3/anti-CD28 monoclonal full-length antibody combination for 2 weeks, CD3+CD56+ double-positive percentage is 12.9% (FIG. 2-9A). After CIK induced expansion by CD3-ICOS BsAb_M for 2 weeks, CD3+CD56+ double-positive percentage is 24.18% (FIG. 2-9B). After CIK induced expansion by CD3-ICOS BsAb_D for 2 weeks, CD3+CD56+ double-positive percentage is 39.71% (FIG. 2-9C). This result indicates that CD3-ICOS bi-specific antibody of both monomer and dimer can substitute anti-CD3/anti-CD28 full-length antibody recombination, and both of them can induce higher CD3+CD56+ double-positive percentage, among which dimer has a better effect than monomer.

Embodiment 2-11 the Eukaryotic Expression Vector Construction of CD3-OX40 BsAb_M and CD3-OX40 Ab D In this disclosure, the bi-specific antibody targeted CD3 and OX40 on human T cell is named as CD3-OX40 BsAb.
1. Construction of CD3-OX40 BsAb_M and CD3-OX40 BsAb_D Construction of CD3-OX40 BsAb_M Monomer: the sequence of anti-CD3 scFv and anti-OX40 scFv is linked by (GGGGS) 3 Linker.

Construction of CD3-OX40 BsAb_D Dimer: the sequence of anti-CD3 scFv and anti-OX40 scFv is linked by IgD hinge region Linker.

In order to express the bi-specific antibody in mammalian cells, codon optimization of the mammalian system was performed for the sequence of anti-CD3 scFv, anti-OX40 scFv and IgD hinge region.

The nucleotide sequence of the anti-CD3 scFv heavy chain variable region is shown as SEQ ID NO. 89 in detail.

The nucleotide sequence of the anti-CD3 scFv light chain variable region is shown as SEQ ID NO. 90 in detail.

The nucleotide sequence of anti-CD3 scFv is shown as SEQ ID NO. 88 in detail.

The nucleotide sequence of anti-OX40 scFv heavy chain variable region is shown as SEQ ID NO. 98.

The nucleotide sequence of anti-OX40 scFv light chain variable region is shown as SEQ ID NO. 99.

The nucleotide sequence of anti-OX40 scFv is shown as SEQ ID NO. 97.

The nucleotide sequence of the CD3-OX40 BsAb_M monomer linker is shown as SEQ ID NO. 33 in detail.

The nucleotide sequence of CD3-OX40 BsAb_D dimer linker is shown as SEQ ID NO. 35 in detail.

In order to make the bi-specific antibody successfully expressed in CHO-S cells and secreted into medium, signal peptide of antibody secretory expression was selected in this Embodiment.

The amino acid sequence of this secretory signal peptide is shown as SEQ ID NO.109 in detail.

The nucleotide sequence of this secretory signal peptide is shown as SEQ ID NO.110 in detail.

2. Construction of Eukaryotic Expression Vector of CD3-OX40 BsAb_M and CD3-OX40 BsAb_D The construction and expression of the bi-specific antibody in this disclosure selected mammalian cell protein transient expression vector pcDNA3.1 (purchased from Invitrogen, Shanghai). In order to construct the bi-specific antibody of monomer and dimer, primers were designed as in table 2-4. All the primers were synthesized by Genewiz, Suzhou, and DNA template for PCR was synthesized by Synbio Technologies, Suzhou.

For the cloning construct of CD3-OX40 BsAb_M, signal peptide fragments were firstly amplified by primers pcDNA3.1-Sig-F and Sig-R, and then anti-CD3 scFv, (GGGGS) 3 Linker and anti-OX40 scFv sequence were amplified by primers Sig-CD3-F&CD3-R, and CD3-(GGGGS)$_3$-OX40-F&pcDNA3.1-OX40-R. For the cloning construct of CD3-OX40 BsAb_D, similarly, signal peptide fragments were firstly amplified by primers pcDNA3.1-Sig-F and Sig-R, and then anti-CD3 scFv, IgD hinge region Linker, and anti-OX40 scFv sequence were amplified by primers Sig-CD3-F&CD3-R, CD3-IgD-F&IgD-R, and IgD-OX40-F&pcDNA3.1-OX40-R. After PCR amplification, by using NovoRec®PCR one-step cloning kit (purchase from novoprotein, Wujiang), the full-length sequence of bi-specific antibody monomer and dimer were separately spliced and seamlessly cloned into the pcDNA3.1 expression vector which was linearized by EcoRI and HindIII. The target vector was transformed into *E. Coli* DH5a, colony PCR was used for positive cloning identification, and the recombinant (recombinant plasmid) identified as positive was performed sequencing identification. The recombinant (recombinant plasmid) with the right sequence was purified by midi-prep, and then used in the transfection of CHO-S cells.

After sequencing, the CD3-OX40 BsAb_M monomer and CD3-OX40 BsAb_D dimer both had the right full DNA sequence as expected.

The nucleotide sequence of CD3-OX40 BsAb_M monomer is shown as SEQ ID NO.52.

The nucleotide sequence of CD3-OX40 BsAb_D dimer is shown as SEQ ID NO.54.

TABLE 2-4

| Primers used in CD3-OX40 bi-specific antibody gene cloning | | |
|---|---|---|
| Primer name | Sequence | No. |
| CD3-(GGGGS)$_3$-OX40-F | GCACCAAGCTGGAGCTGAAGGGCGGCGG CGGCAGCGGCGGCGGCGGCAGCGGCGGCGG CGGCAGCCAGCTGGTGGAGAGCGGCGG | SEQ ID NO.123 |

TABLE 2-4-continued

Primers used in CD3-OX40 bi-specific antibody gene cloning

| Primer name | Sequence | No. |
|---|---|---|
| pcDNA3.1-OX40-R | CTGATCAGCGGTTTAAACTTAAGCTTTCAGCGCTTGATCTCCAGGCGGGTGC | SEQ ID NO.124 |
| IgD-OX40-F | GCCACACCCAGCCCCTGGGCGTGCAGCTGGTGGAGAGCGGCGGCG | SEQ ID NO.125 |

Embodiment 2-12: The Expression and Purification of CD3-OX40 BsAb_M and CD3-OX40 BsAb_D 1. The Expression of CD3-OX40 BsAb_M and CD3-OX40 BsAb_D 1.1 The cell density of CHO-S cells (purchased from Thermo Fisher Scientific) was 0.5~0.6×10⁶/ml one day before transfection.

1.2 Calculating cell density at the day of transfection, performing plasmid transfection when the density is in the range of 1~1.4×10⁶/ml and the live percentage is >90%.

1.3 Transfection complex recipes: each project (CD3-OX40 BsAb_M and CD3-OX40 BsAb_D) requires two centrifuge tubes/flasks. Take total 20 ml as an example, the recombinant plasmids from Embodiment 2-11 were taken:
  Tube 1: 600 μl PBS, 20 μg recombinant plasmid, mixing well.
  Tube 2: 600 μl PBS, 20 μl FreeStyle™ MAX Transfection Reagent (purchased from Thermo Fisher Scientific), mixing well.

1.4 Adding the diluted transfection reagent into the diluted recombinant plasmid, mixing well to obtain transfection complex.

1.5 Keeping the transfection complex for 15~20 min, adding it into cell culture dropwise and at a constant rate.

1.6 Keeping cell culture after transfection at 37° C., CO₂ 8%, CO₂ concentration 8%, rotating speed cell shaker of at 130 rpm. Collecting medium after 5 days for the target protein test.

2. The Purification of CD3-OX40 BsAb_M and CD3-OX40 BsAb_D 2.1 Sample Pretreatment
Taking 20 ml cell medium after transfection, adding 20 mM PB, 200 mM NaCl, and adjusting pH to 7.5;

2.2 Purification of Protein L Affinity Chromatography Column
  Protein purification chromatography column: Protein L affinity chromatography column (purchased from GE Healthcare, column volume: 1.0 ml)
  Buffer A: PBS, pH7.4
  Buffer B: 0.1M Glycine, pH3.0
  Buffer C: 0.1M Glycine, pH2.7
  Purification procedure: AKTA explorer 100 protein purification system (purchased from GE Healthcare) was used for purification. Pretreating Protein L affinity chromatography column with Buffer A, running culture medium sample, and collecting the flowthrough sample. After running sample, balancing the chromatography column with at least 1.5 ml Buffer A, then washing with Buffer B and Buffer C, and collecting flowthrough sample with target protein (the collection tube for flowthrough sample needs to be pretreated with 1% 1M Tris, pH8.0 to neutralize the pH of the flowthrough sample, and the final concentration of Tris is about 10 mM) and finally, concentrating and dialyzing the flowthrough sample into buffer PBS.

The final purified CD3-OX40 BsAb_M and CD3-OX40 BsAb_D recombinant proteins were analyzed by SDS-PAGE, and the protein electrophoresis data under reduced and unreduced conditions is shown as FIG. 2-10. It shows that both purities of CD3-OX40 BsAb_M and CD3-OX40 BsAb_D recombinant protein are >95%. The theoretical molecular weight of CD3-OX40 BsAb_M is 53.2 kDa, and the protein displayed the same single electrophoretic band under reduced and unreduced conditions. The molecular weight of these bands is consistent with the monomer, so this bi-specific antibody is monomer (FIG. 2-10A, Lane 1: protein marker for molecular weight; Lane 2: reduced CD3-OX40 BsAb_M; Lane 3: unreduced CD3-OX40 BsAb_M). The theoretical molecular weight of CD3-OX40 BsAb_D is 61.1 kDa, and the electrophoretic band of the protein displayed the same molecular weight as monomer under reduced condition, but the molecular weight is consistent with dimer under unreduced condition (FIG. 2-10B, Lane 1: protein marker for molecular weight; Lane 2: reduced CD3-OX40 BsAb_D; Lane 3: unreduced CD3-OX40 BsAb_D), which indicates that two protein could link to each other by disulfide bond, thus so that this bi-specific antibody is in dimer form.

Moreover, the N/C terminal sequence analysis for purified recombinant protein shows that the reading frame has no error, consistent with the theoretical N/C terminal amino acid sequence. Mass spectrometry analysis further confirmed that CD3-OX40 BsAb_M is monomer and CD3-OX40 BsAb_D is a dimer.

Therefore, the amino acid sequence of CD3-OX40 BsAb_M monomer is shown as SEQ ID NO.51.

The amino acid sequence of CD3-OX40 BsAb_D dimer is shown as SEQ ID NO.53. The amino acid sequence of CD3 scFv is shown as SEQ ID NO.67 in detail.

The amino acid sequence of the CD3 scFv heavy chain variable region is shown as SEQ ID NO.68 in detail.

The amino acid sequence of the CD3 scFv light chain variable region is shown as SEQ ID NO.69 in detail.

The amino acid sequence of OX40 scFv is shown as SEQ ID NO.76 in detail.

The amino acid sequence of OX40 scFv heavy chain variable region is shown as SEQ ID NO.77 in detail.

The amino acid sequence of OX40 scFv light chain variable region is shown as SEQ ID NO.78 in detail.

The amino acid sequence of the CD3-OX40 BsAb_M monomer linker is shown as SEQ ID NO.32 in detail.

The amino acid sequence of CD3-OX40 BsAb_D dimer linker is shown as SEQ ID NO.34 in detail.

Embodiment 2-13: Antigen-Binding Activity Test of CD3-OX40 BsAb_M and CD3-OX40 BsAb_D by ELISA ELISA Procedure:

1. Recombinant antigen coating: 96-well plates were coated by human CD3-hFc and human OX40-hFc recombinant protein (purchased from Novoprotein, Wujiang) 100 μl per well in concentration 1 μg/ml. The coated plates were kept at 37° C. for 1 hour or at 4° C. overnight. The recipe for coating buffer (PBS) is: 3.58 g $Na_2HPO_4$, 0.24 g $NaH_2PO_4$, 0.2 g KCl, 8.2 g NaCl, 950 ml $H_2O$, adjusting pH to 7.4 with 1 mol/L HCl or 1 mol/L NaOH, adding water to 1 L for total volume.

2. Blocking: washing plates with PBS for 4 times, and adding 200 μl per well of PBSA (PBS+2% BSA (V/W)) to blfock at 37° C. for 1 hour.

3. Adding sample: washing plates with PBS for 4 times, adding 100 μl per well of bi-specific antibody samples respectively and keeping plates at 37° C. for 1 hour. Sample serial dilution includes: using 10 μg/ml of purified CD3-OX40 BsAb_M or CD3-OX40 BsAb_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well color-developing TMB (purchased from KPL), developing in dark for 5~10 min at room temperature.

5. Reaction termination and result test: adding 100 μl per well of stop buffer (1M HCl) to stop the reaction, and reading OD value of 450 nm absorbance on ELISA reader.

The results of ELISA are shown in FIGS. 2-11A and 2-11B. The three curves in the figure represent three test results: ■ coated with 1 μg/ml CD3-hFc recombinant antigen, ◆ coated with 1 μg/ml OX40-hFc recombinant antigen; ▲ no antigen coated result. FIG. 2-11A displays that CD3-OX40 BsAb_M has antigen-binding activity with CD3-hFc and OX40-hFc in vitro, among which OX40 has higher binding activity than that of CD3. FIG. 2-11B displays that CD3-OX40 BsAb_D has antigen-binding activity with CD3-hFc and OX40-hFc in vitro as well, and OX40 has higher binding activity.

Embodiment 2-14: Cell Proliferation of Cytokine-Induced Killer (CIK) Mediated by CD3-OX40 Bi-Specific Antibody Human PBMC (Peripheral blood mononuclear cell, PBMC) was used as experiment material. CD3-OX40 BsAb_M monomer and CD3-OX40 BsAb_D dimer produced by this disclosure, as well as full-length antibody anti-CD3/28 combination were added to PBMC from the same donor, respectively. Cells are counted after being cultured to compare cell proliferation.

1. Separating PBMC: adding the physiological saline of same volume into the anticoagulant blood, and adding Ficoll (purchased from GE Healthcare) of same volume into the mixed-blood slowly along the centrifuge tube wall. Keeping different liquid surface clear, centrifuging at 2000 rpm for 20 min, and removing the white cell in the middle layer into a new centrifuge tube. Adding PBS with volume more than 2 times of the extracted cell layer to wash cells, centrifuging for 10 min at 1000 rpm, repeat washing once more, and adding some pre-cooling X-Vivo 15 serum-free medium (purchased from Lonza) to resuspend cells. Counting the cells for use.

2. CIK cell culture and expansion: Resuspending PBMC with CIK basic medium (90% X-vivo15+10% FBS), and adjusting cell density to 1×106/ml. Setup three experiment groups: Control (coating plate with 5 μg/ml of anti-CD3 and 5 μg/ml of anti-CD28, full-length antibodies are all purchased from Novoprotein, Wujiang); Experiment 1 (adding 10 ng/ml of soluble bi-specific CD3-OX40 BsAb_M); Experiment 2 (adding 10 ng/ml of soluble bi-specific CD3-OX40 BsAb_D). All of the three groups were added with IFN-γ (200 ng/ml, purchased from Novoprotein, Wujiang) and IL-1 (2 ng/ml, purchased from Novoprotein, Wujiang), the cell culture was kept in incubator under the condition of saturated humidity, 37° C. and 5.0% CO2. After overnight, adding 500U/ml of IL-2 (purchased from Novoprotein, Wujiang) into cell medium and keeping culture. Every 2-3 days, counting the cells and passaging cell at the density of 1×106/ml in CIK basic medium with 500U/ml IL-2. Keeping cell culture in this way for 30 days, counting the cells for expansion fold calculation, and make the cell growth curve.

The experiment results were shown in FIG. 2-12. CD3-OX40 bi-specific antibody monomer and dimer can better induce CIK expansion than anti-CD3/anti-CD28 monoclonal full-length antibody combination. Anti-CD3/anti-CD28 monoclonal full-length antibody combination induced severe cell death after culturing for 18 days, and cell proliferation rate significantly reduced; meanwhile, neither CD3-OX40 BsAb_M monomer nor CD3-OX40 BsAb_D dimer induced cell death, but the cell proliferation rate was relatively slow. Therefore, both monomer and dimer of CD3-OX40 bi-specific antibody can effectively promote cell expansion and prolong the survival of CIK cell survival, among which dimer has better effect.

Embodiment 2-15: Cytotoxicity Test of CIK Cells Killing Tumor Cells Mediated by CD3-OX40 Bi-Specific Antibody Three groups of experiment cells in Embodiment 2-14 after 14- or 30-days' culture were used as cytotoxic effector cells, and CCL-86 Raji lymphoma cells (purchased from ATCC) were used as target cells. Two cells were mixed together to test the cytotoxicity of CIK cells killing Raji cells.

Cytotoxicity test of CIK cells killing Raji cells procedure:

Six groups of cells were set up in 96-well plate with 100 μl reaction volume per well: Group 1 (CIK cells after 14-days' culture with 5 μg/ml of Anti-CD3/Anti-CD28 combination), Group 2 (CIK cells after 14-days' culture with 10 ng/ml of CD3-OX40 BsAb_M), Group 3 (CIK cells after 14-days' culture with 10 ng/ml of CD3-OX40 BsAb_D), Group 4 (CIK cells after 30-days' culture with 5 μg/ml of Anti-CD3/Anti-CD28 combination), Group 5 (CIK cells after 30-days' culture with 10 ng/ml of CD3-OX40 BsAb_M), and Group 6 (CIK cells after 30-days' culture with 10 ng/ml of CD3-OX40 BsAb_D). Mixing 1×10⁵ CIK cells from each group with 1×10⁵ Raji cells (CIK target cells: E:T=1:1), after culturing together at 37° C. for 3 h, adding 10 μl CCK8 per well, and keeping reaction 2-3 h at 37° C. Then using OD reader to test OD450, calculate cytotoxicity efficacy by the following formula and repeat 3 times; meanwhile, using the cytotoxicity of CIK cultured without any antibody killing Raji cells as blank control.

The results were shown in FIG. 2-13. CIK cells after culture for 14 days with CD3-OX40 bi-specific antibodies have better killing efficacy than CIK cells cultured with anti-CD3/anti-CD28 antibody recombination: the cytotoxicity efficacy of CIK with CD3-OX40 BsAb_D is 32%, showing the best effect (Group 3); the cytotoxicity efficacy of CIK with CD3-OX40 BsAb_M is 25%, showing the second-best effect (Group 2); the cytotoxicity efficacy of CIK with anti-CD3/anti-CD28 antibody recombination is 22%, showing the weakest effect (Group 1). The killing efficacy of CIK cells with CD3-OX40 bi-specific antibodies is enhanced after culturing for 30 days: the cytotoxicity efficacy of CIK with CD3-OX40 BsAb_D is 40%; the cytotoxicity efficacy of CIK with CD3-OX40 BsAb_M is 35%; the cytotoxicity efficacy of CIK with anti-CD3/anti-CD28 antibody recombination is significantly reduced, only 10% (Group 4).

The Formula of cytotoxicity efficacy:

$$\text{Cytotoxicity efficacy (\%)} = \frac{(OD \text{ value of } Raji \text{ cells } + OD \text{ value of } CIK \text{ cells}) - OD \text{ value of experimental group}}{OD \text{ value of } Raji \text{ cells}}$$

Embodiment 2-16 the Eukaryotic Expression Vector Construction of CD3-GITR BsAb_M and CD3-GITR BsAb_D In this disclosure, the bi-specific antibody targeted CD3 and co-stimulatory molecule GITR on human T cell is named as CD3-GITR BsAb.
1. CD3-GITR BsAb_M and CD3-GITR BsAb_D Construction Design Construction of CD3-GITR BsAb_M Monomer: the sequence of anti-CD3 scFv and anti-GITR scFv is linked by (GGGGS) 3 Linker.

Construction of CD3-GITR BsAb_D Dimer: the sequence of anti-CD3 scFv and anti-GITR scFv is linked by IgD hinge region Linker.

In order to express the bi-specific antibody in mammalian cells, codon optimization of the mammalian system was performed for the sequence of anti-CD3 scFv, anti-GITR scFv and IgD hinge region.

The nucleotide sequence of the anti-CD3 scFv heavy chain variable region is shown as SEQ ID NO. 89 in detail.

The nucleotide sequence of the anti-CD3 scFv light chain variable region is shown as SEQ ID NO. 90 in detail.

The nucleotide sequence of anti-CD3 scFv is shown as SEQ ID NO. 88 in detail.

The nucleotide sequence of anti-GITR scFv heavy chain variable region is shown as SEQ ID NO. 101 in detail.

The nucleotide sequence of anti-GITR scFv light chain variable region is shown as SEQ ID NO. 102 in detail.

The nucleotide sequence of anti-GITR scFv is shown as SEQ ID NO. 100 in detail.

The nucleotide sequence of the CD3-GITR BsAb_M monomer linker is shown as SEQ ID NO. 33 in detail.

The nucleotide sequence of the CD3-GITR BsAb_D dimer linker is shown as SEQ ID NO. 35 in detail.

In order to make the bi-specific antibody successfully expressed in CHO-S cells and secreted into medium, signal peptide of antibody secretory expression was selected in this Embodiment.

The amino acid sequence of this secretory signal peptide is shown as SEQ ID NO.78 in detail.

The nucleotide sequence of this secretory signal peptide is shown as SEQ ID NO.79 in detail.

2. Construction of Eukaryotic Expression Vector of CD3-GITR BsAb_M and CD3-GITR BsAb_D The construction and expression of this bi-specific antibody disclosure chose mammalian cell protein transient expression vector pcDNA3.1 (purchased from Invitrogen, Shanghai). In order to construct the monomer and dimer of bi-specific antibody, primers were designed as in table 2-5. All the primers were synthesized by Genewiz, Suzhou, and DNA template for PCR was synthesized by Synbio Technologies, Suzhou.

The cloning constructs for CD3-GITR BsAb_M amplified signal peptide by primers pcDNA3.1-Sig-F and Sig-R, and then amplified anti-CD3 scFv, (GGGGS); Linker and anti-GITR scFv sequence by primers Sig-CD3-F&CD3-R, and CD3-(GGGGS)$_3$-GITR-F&pcDNA3.1-GITR-R. The cloning constructs for CD3-GITR BsAb_D amplified signal peptide by primers pcDNA3.1-Sig-F and Sig-R, and then amplified anti-CD3 scFv, IgD hinge region Linker, and anti-GITR scFv sequence by primers Sig-CD3-F&CD3-R, CD3-IgD-F&IgD-R, and IgD-GITR-F&pcDNA3.1-GITR-R. After PCR amplification, by using NovoRec®PCR one-step cloning kit (purchase from novoprotein, Wujiang), the full-length sequence of bi-specific antibody monomer and dimer were separately ligated and seamlessly cloned into the pcDNA3.1 vector which was linearized by EcoRI and HindIII. The target vector was transformed into E. Coli DH5a, colony PCR was used for positive cloning identification, and the recombinant (recombinant plasmid) identified as positive was performed sequencing identification. The recombinants (recombinant plasmid) with right sequence were purified by midi-prep, and then transfected into CHO-S cells.

After sequencing, the CD3-GITR BsAb_M monomer and CD3-GITR BsAb_D dimer both had the right full DNA sequence as expected.

The nucleotide sequence of CD3-GITR BsAb_M monomer is shown as SEQ ID NO.56 in detail.

The nucleotide sequence of CD3-GITR BsAb_D dimer is shown as SEQ ID NO.58 in detail.

TABLE 2-5

Primers used in CD3-GITR bi-specific antibody gene cloning

| Primer name | Sequence | No. |
| --- | --- | --- |
| CD3-(GGGGS)$_3$-GITR-F | GCACCAAGCTGGAGCTGAAGGGCGGCGGCG GCAGCGGCGGCGGCGGCAGCGGCGGCGGCG GCAGCCAGGTGACCCTGAAGGAGAG | SEQ ID NO.126 |
| pcDNA3.1-GITR-R | CTGATCAGCGGTTTAAACTTAAGCTTTCAC TTGATCTCCAGCTTGGTGCCGG | SEQ ID NO.127 |

TABLE 2-5-continued

Primers used in CD3-GITR bi-specific antibody gene cloning

| Primer name | Sequence | No. |
|---|---|---|
| IgD-GITR-F | GCCACACCCAGCCCCTGGGCGTGCAGGTG ACCCTGAAGGAGAG | SEQ ID NO.128 |

Embodiment 2-17: The Expression and Purification of CD3-GITR BsAb_M and CD3-GITR BsAb_D 1. The Expression of CD3-GITR BsAb_M and CD3-GITR BsAb_D 1.1 The cell density of CHO-S cells (purchased from Thermo Fisher Scientific) was 0.5~0.6×10⁶/ml one day before transfection.

1.2 Calculating cell density at the day of transfection, performing plasmid transfection when the density is in the range of 1~1.4×10⁶/ml and the live percentage is >90%.

1.3 Transfection complex recipes: each project (CD3-GITR BsAb_M and CD3-GITR BsAb_D) needs two centrifuge tubes/flasks. Take total 20 ml as an example, put the recombinant plasmids from Embodiment 2-16 separately:
Tube 1: 600 µl PBS, 20 µg recombinant plasmid, mixing well.
Tube 2: 600 µl PBS, 20 µl FreeStyle™ MAX Transfection Reagent (purchased from Thermo Fisher Scientific), mixing well.

1.4 Mixing the diluted transfection reagent into the diluted recombinant plasmid, mixing well, which is transfection complex.

1.5 Keeping the transfection complex for 15~20 min, adding it into cell culture by drops steadily.

1.6 Keeping cell culture after transfection at 37° C., $CO_2$ 8%, 130 rpm on cell shaker. Collect medium after 5 days for the target protein test.

2. The Purification of CD3-GITR BsAb_M and CD3-GITR BsAb_D 2.1 Sample pretreatment
Get 20 ml cell medium after transfection, adding 20 mM PB, 200 mM NaCl, and adjusting pH to 7.5;

2.2 Purification of Protein L Affinity Chromatography Column
Protein purification chromatography column: Protein L affinity chromatography column (purchased from GE Healthcare, column volume: 1.0 ml)
Buffer A: PBS, pH7.4
Buffer B: 0.1M Glycine, pH3.0
Buffer C: 0.1M Glycine, pH2.7
Purification procedure: AKTA explorer 100 protein purification system (purchased from GE Healthcare) was used for purification. Pretreat Protein L affinity chromatography column with Buffer A, running culture medium sample, and collecting flowthrough sample. After running sample, balance chromatography column with at least 1.5 ml Buffer A, washing with Buffer B and Buffer C respectively after balance, and collecting flowthrough sample with target protein (the collection tube for flowthrough sample needs to be pretreated with 1% 1M Tris, pH8.0 to neutralize the pH of flowthrough sample, and the final concentration of Tris is about 10 mM). Finally, concentrate and dialyze into buffer PBS.

The final purified CD3-GITR BsAb_M and CD3-GITR BsAb_D recombinant protein were analyzed by SDS-PAGE, and the protein electrophoresis data under reduced and unreduced conditions were shown as FIG. 2-14. It shows that both purity of CD3-GITR BsAb_M and CD3-GITR BsAb_D recombinant protein is >95%. The theoretical molecular weight for CD3-GITR BsAb_M is 53.2 kDa, and protein displayed the same single band under reduced and unreduced conditions. The molecular weight of these bands is consistent with monomer, so this bi-specific antibody is monomer (FIG. 2-14A, Lane 1: protein marker for molecular weight; Lane 2: reduced CD3-GITR BsAb_M; Lane 3: unreduced CD3-GITR BsAb_M). The theoretical molecular weight for CD3-GITR BsAb_D is 61.1 kDa, and protein displayed the same molecular weight as monomer under reduced condition, but the molecular weight is consistent with dimer under unreduced condition (FIG. 2-14B, Lane 1: protein marker for molecular weight; Lane 2: reduced CD3-GITR BsAb_D; Lane 3: unreduced CD3-GITR BsAb_D), which indicate two protein link to each other by disulfide bond so that this bi-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD3-GITR BsAb_M is monomer and CD3-GITR BsAb_D is a dimer.

Therefore, the amino acid sequence of CD3-GITR BsAb_M monomer is shown as SEQ ID NO.55 in detail.

The amino acid sequence of CD3-GITR BsAb_D dimer is shown as SEQ ID NO.57 in detail.

The amino acid sequence of CD3 scFv is shown as SEQ ID NO.67 in detail.

The amino acid sequence of the CD3 scFv heavy chain variable region is shown as SEQ ID NO.68 in detail.

The amino acid sequence of the CD3 scFv light chain variable region is shown as SEQ ID NO.69 in detail.

The amino acid sequence of GITR scFv is shown as SEQ ID NO.79 in detail.

The amino acid sequence of GITR scFv heavy chain variable region is shown as SEQ ID NO.80 in detail.

The amino acid sequence of GITR scFv light chain variable region is shown as SEQ ID NO.81 in detail.

The amino acid sequence of the CD3-GITR BsAb_M monomer linker is shown as SEQ ID NO.32 in detail.

The amino acid sequence of the CD3-GITR BsAb_D dimer linker is shown as SEQ ID NO.34 in detail.

Embodiment 2-18: Antigen-Binding Activity Test of CD3-GITR BsAb_M and CD3-GITR BsAb_D by ELISA ELISA Procedure:
1. Recombinant antigen coating: 96-well plates were coated by human CD3-hFc and human GITR-hFc recombinant protein (purchased from Novoprotein, Wujiang) 100 µl per well in concentration 1 µg/ml. The coated plates were kept at 37° C. for 1 hour or at 4° C. overnight. The recipe for the coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding PBSA (PBS+2% BSA (V/W)) 200 µl per well to block 1 hour at 37° C.

3. Adding sample: washing plates with PBS for 4 times, adding 100 µl per well of bi-specific antibody samples respectively and keeping plates at 37° C. for 1 hour. Sample serial dilution includes: using 10 µg/ml of purified CD3-GITR BsAb_M or CD3-GITR BsAb_D as starting concentration, diluting it into 6 gradient concentrations, and using 2 duplicate wells for each gradient.

4. Color developing: washing plates with PBST (PBS+ 0.05% Tween-20 (V/V)) for 4 times, diluting 1/5000 HRP labeled color-developing antibody (purchased from Abcam) by blocking buffer PBSA, adding 100 µl per well and keeping plates at 37° C. for 1 hour. Washing plates with PBS for 4 times, adding 100 µl per well of color-developing TMB (purchased from KPL), developing in dark for 5~10 min at room temperature.

5. Reaction termination and result test: adding 100 µl per well of stop buffer (1M HCl) to stop the reaction, and reading OD value of 450 nm absorbance on ELISA reader.

The results of ELISA are shown in FIGS. 2-15A and 2-15B. The three curves in the figure represent three test results: ■ coated with 1 µg/ml CD3-hFc recombinant antigen, ✱ coated with 1 µg/ml GITR-hFc recombinant antigen; ▲ no antigen coated result. FIG. 2-15A displays that CD3-GITR BsAb_M has antigen-binding activity with CD3-hFc and GITR-hFc in vitro, among which GITR has higher binding activity than that of CD3. FIG. 2-15B displays that CD3-GITR BsAb_D has antigen-binding activity with CD3-hFc and GITR-hFc in vitro as well, and GITR has higher binding activity.

Embodiment 2-19: Cell Proliferation of Cytokine-Induced Killer (CIK) Mediated by CD3-GITR Bi-Specific Antibody Human PBMC (Peripheral blood mononuclear cell, PBMC) was used as experiment material. CD3-GITR BsAb_M monomer and CD3-GITR BsAb_D dimer produced by this disclosure, as well as full-length antibody anti-CD3/28 combination were added to PBMC from the same donor, respectively. Cells are counted after being cultured to compare cell proliferation.

1. Separating PBMC: adding the physiological saline of same volume into the anticoagulant blood, and adding Ficoll (purchased from GE Healthcare) of same volume into the mixed-blood slowly along the centrifuge tube wall. Keeping different liquid surface clear, centrifuging at 2000 rpm for 20 min, and removing the white cell layer in the middle into a new centrifuge tube. Adding PBS with volume more than 2 times of the extracted cell layer to wash cells, centrifuging for 10 min at 1000 rpm, repeat washing once more, and adding some pre-cooling X-Vivo 15 serum-free medium (purchased from Lonza) to resuspend cells. Counting the cells and ready for use.

2. CIK cell culture and expansion: Resuspending PBMC with CIK basic medium (90% X-vivo15+10% FBS), and adjusting cell density to 1×10⁶/ml. Setup three experiment groups: Control (coating plate with 5 µg/ml of anti-CD3 and 5 µg/ml of anti-CD28, full-length antibodies are all purchased from Novoprotein, Wujiang); Experiment 1 (adding 10 ng/ml of soluble bi-specific CD3-GITR BsAb_M); Experiment 2 (adding 10 ng/ml of soluble bi-specific CD3-GITR BsAb_D). All of the three groups were added with IFN-γ (200 ng/ml, purchased from Novoprotein, Wujiang) and IL-1β (2 ng/ml, purchased from Novoprotein, Wujiang), the cell culture was kept in incubator under the condition of saturated humidity, 37° C. and 5.0% $CO_2$. After overnight, adding 500U/ml of IL-2 (purchased from Novoprotein, Wujiang) into cell medium and keeping culture. Every 2-3 days, counting the cells and passaging cell at the density of 1×10⁶/ml in CIK basic medium with 500U/ml of IL-2. Keeping cell culture in this way for 14 days, counting the cells for expansion fold calculation, and make the cell growth curve.

The experiment results were shown in Table 2-6 and FIG. 2-16. CD3-GITR bi-specific antibody monomer and dimer can induce better CIK expansion than anti-CD3/anti-CD28 monoclonal full-length antibody combination, and the protein dosage is even less (10 ng/ml vs. 5 µg/ml). Among them, CD3-GITR BsAb_D dimer could induce CIK cell expand 287 fold after two weeks, which has the best effect (experiment 2); CD3-GITR BsAb_M monomer could induce CIK cell expand 248 fold after two weeks, which has the second-best effect (experiment 1). Anti-CD3/anti-CD28 monoclonal full-length antibody combination could induce CIK cell expand 224 fold after two weeks, which has the weakest effect (control).

TABLE 2-6

| Experiment group | CIK cell expansion fold | | |
|---|---|---|---|
| | Control | Experiment 1 | Experiment 2 |
| Expansion fold after 14 days | 224 | 248 | 287 |

Embodiment 2-20 the Eukaryotic Expression Vector Construction of CD3-CD40L BsAb_M and CD3-CD4L BsAb_D In this disclosure, the bi-specific antibody targeted CD3 and co-stimulatory molecule CD40L on human T cell is named as CD3-CD40L BsAb.

1. CD3-CD40L BsAb_M and CD3-CD40L BsAb_D construction design CD3-CD40L BsAb_M Monomer construction design: the sequence of anti-CD3 scFv and anti-CD40L scFv is linked by (GGGGS) 3 Linker.

CD3-CD40L BsAb_D Dimer construction design: the sequence of anti-CD3 scFv and anti-CD40L scFv is linked by the IgD hinge region Linker.

In order to express the bi-specific antibody in mammalian cells, codon optimization of the mammalian system was performed for the sequence of anti-CD3 scFv, anti-CD40L scFv and IgD hinge region.

The nucleotide sequence of the anti-CD3 scFv heavy chain variable region is shown as SEQ ID NO. 89 in detail.

The nucleotide sequence of the anti-CD3 scFv light chain variable region is shown as SEQ ID NO. 90 in detail.

The nucleotide sequence of anti-CD3 scFv is shown as SEQ ID NO. 88 in detail.

The nucleotide sequence of anti-CD40L scFv heavy chain variable region is shown as SEQ ID NO. 104 in detail.

The nucleotide sequence of anti-CD40L scFv light chain variable region is shown as SEQ ID NO. 105 in detail.

The nucleotide sequence of anti-CD40L scFv is shown as SEQ ID NO. 103 in detail.

The nucleotide sequence of the CD3-CD40L BsAb_M monomer linker is shown as SEQ ID NO. 33 in detail.

The nucleotide sequence of CD3-CD40L BsAb_D dimer linker is shown as SEQ ID NO. 35 in detail.

In order to make the bi-specific antibody successfully expressed in CHO-S cells and secreted into medium, signal peptide of antibody secretory expression was selected in this Embodiment.

The amino acid sequence of this secretory signal peptide is shown as SEQ ID NO.78 in detail.

The nucleotide sequence of this secretory signal peptide is shown as SEQ ID NO. 79 in detail.

2. Construction of Eukaryotic Expression Vector of CD3-CD40L BsAb_M and CD3-CD40L BsAb_D The construction and expression of this bi-specific antibody disclosure chose mammalian cell protein transient expression vector pcDNA3.1 (purchased from Invitrogen, Shanghai). In order to construct the monomer and dimer of bi-specific antibody, primers were designed as in table 2-7. All the primers were synthesized by Genewiz, Suzhou, and DNA template for PCR was synthesized by Synbio Technologies, Suzhou.

The cloning constructs for CD3-CD40L BsAb_M amplified signal peptide by primers pcDNA3.1-Sig-F and Sig-R, and then amplified anti-CD3 scFv, (GGGGS) 3 Linker and anti-CD40L scFv sequence by primers Sig-CD3-F&CD3-R, and CD3-(GGGGS)$_3$-CD40L-F&pcDNA3.1-CD40L-R. The cloning constructs for CD3-CD40L BsAb_D amplified signal peptide by primers pcDNA3.1-Sig-F and Sig-R, and then amplified anti-CD3 scFv, IgD hinge region Linker, and anti-CD40L scFv sequence by primers Sig-CD3-F&CD3-R, CD3-IgD-F&IgD-R, and IgD-CD40L-F&pcDNA3.1-CD40L-R. After PCR amplification, by using NovoRec®PCR one-step cloning kit (purchased from novoprotein, Wujiang), the full sequence of bi-specific antibody monomer and dimer were separately ligated and seamlessly cloned into the pcDNA3.1 vector which was linearized by EcoRI and HindIII. The target vector was transformed into *E. Coli* DH5a, colony PCR was used for positive cloning identification, and the recombinant (recombinant plasmid) identified as positive was performed sequencing identification. The recombinants (recombinant plasmid) with right sequence were purified by midi-prep, and then transfected into CHO-S cells.

After sequencing, the CD3-CD40L BsAb_M monomer and CD3-CD40L BsAb_D dimer both had the right full DNA sequence as expected.

The nucleotide sequence of CD3-CD40L BsAb_M monomer is shown as SEQ ID NO.60 in detail.

The nucleotide sequence of CD3-CD40L BsAb_D dimer is shown as SEQ ID NO.62 in detail.

Embodiment 2-21: The Expression and Purification of CD3-CD40L BsAb_M and CD3-CD40L BsAb_D 1. The Expression of CD3-CD40L BsAb_M and CD3-CD40L BsAb_D 1.1 The cell density of CHO-S cells (purchased from Thermo Fisher Scientific) was 0.5~0.6×10$^6$/ml one day before transfection.

1.2 Calculating cell density at the day of transfection, performing plasmid transfection when the density is in the range of 1~1.4×10$^6$/ml and the live percentage is >90%.

1.3 Transfection complex recipes: each project (CD3-CD40L BsAb_M and CD3-CD40L BsAb_D) needs two centrifuge tubes/flasks. Take total 20 ml as an example, put the recombinant plasmids from Embodiment 2-20 separately:

Tube 1: 600 μl PBS, 20 μg recombinant plasmid, mixing well.

Tube 2: 600 μl PBS, 20 μl FreeStyle™ MAX Transfection Reagent (purchased from Thermo Fisher Scientific), mixing well.

1.4 Mixing the diluted transfection reagent into the diluted recombinant plasmid, mixing well, which is transfection complex.

1.5 Keeping the transfection complex for 15~20 min, adding it into cell culture by drops steadily.

1.6 Keeping cell culture after transfection at 37° C., CO$_2$ 8%, 130 rpm on cell shaker. Collecting medium after 5 days for the target protein test.

2. The Purification of CD3-CD40L BsAb_M and CD3-CD40L BsAb_D 2.1 Sample Pretreatment Get 20 ml cell medium after transfection, adding 20 mM PB, 200 mM NaCl, and adjusting pH to 7.5;

2.2 Purification of Protein L Affinity Chromatography Column

Protein purification chromatography column: Protein L affinity chromatography column (purchased from GE Healthcare, column volume: 1.0 ml)

Buffer A: PBS, pH7.4

Buffer B: 0.1M Glycine, pH3.0

Buffer C: 0.1M Glycine, pH2.7

Purification procedure: AKTA explorer 100 protein purification system (purchased from GE Healthcare) was used for purification. Pretreat Protein L affinity chromatography column with Buffer A, running culture medium sample, and collecting flowthrough sample. After running sample, balance chromatography column with at least 1.5 ml Buffer A, washing with Buffer B and Buffer C respectively after balance, and collecting flowthrough sample with target

TABLE 2-7

Primers used in CD3-CD40L bi-specific antibody gene cloning

| Primer name | Sequence | No. |
| --- | --- | --- |
| CD3-(GGGG S)$_3$-CD40L-F | GGCACCAAGCTGGAGCTGAAGGGCGGCG GCGGCAGCGGCGGCGGCGGCAGCGGCGGCG GCGGCAGCGAGGTGCAGCTGCTGGAGAGC | SEQ ID NO.129 |
| pcDNA3.1-C D40L-R | CTGATCAGCGGTTTAAACTTAAGCTTTCA GCGCTTGATCTCCACCTTGGTG | SEQ ID NO.130 |
| IgD-CD40L-F | GCCACACCCAGCCCCTGGGCGTGGAGGT GCAGCTGCTGGAGAG | SEQ ID NO.131 | protein (the collection tube for flowthrough sample needs to be pretreated with 1% 1M Tris, pH8.0 to neutralize the pH of flowthrough sample, and the final concentration of Tris is about 10 mM). Finally, concentrate and dialyze into buffer PBS.

The final purified CD3-CD40L BsAb_M and CD3-CD40L BsAb_D recombinant protein were analyzed by SDS-PAGE, and the protein electrophoresis data under reduced and unreduced conditions were shown as FIG. 2-17. It shows that both purity of CD3-CD40L BsAb_M and CD3-CD40L BsAb_D recombinant protein is >95%. The theoretical molecular weight for CD3-CD40L BsAb_M is 53.2 kDa, and protein displayed the same single band under reduced and unreduced conditions. The molecular weight of these bands is consistent with monomer, so this bi-specific antibody is monomer (FIG. 2-17A, Lane 1: protein marker for molecular weight; Lane 2: reduced CD3-OX40L BsAb_M; Lane 3: unreduced CD3-OX40L BsAb_M). The theoretical molecular weight for CD3-CD40L BsAb_D is 61.2 kDa, and protein displayed the same molecular weight as monomer under reduced condition, but the molecular weight is consistent with dimer under unreduced condition (FIG. 2-17B, Lane 1: protein marker for molecular weight; Lane 2: reduced CD3-OX40L BsAb_D; Lane 3: unreduced CD3-OX40L BsAb_D), which indicate two protein link to each other by disulfide bond so that this bi-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD3-CD40L BsAb_M is monomer and CD3-CD40L BsAb_D is a dimer.

Therefore, the amino acid sequence of CD3-CD40L BsAb_M monomer is shown as SEQ ID NO.59 in detail.

The amino acid sequence of CD3-CD40L BsAb_D dimer is shown as SEQ ID NO.61 in detail.

The amino acid sequence of CD3 scFv is shown as SEQ ID NO.67 in detail.

The amino acid sequence of the CD3 scFv heavy chain variable region is shown as SEQ ID NO.68 in detail.

The amino acid sequence of the CD3 scFv light chain variable region is shown as SEQ ID NO.69 in detail.

The amino acid sequence of CD40L scFv is shown as SEQ ID NO.82 in detail.

The amino acid sequence of CD40L scFv heavy chain variable region is shown as SEQ ID NO.83 in detail.

The amino acid sequence of CD40L scFv light chain variable region is shown as SEQ ID NO.84 in detail.

The amino acid sequence of the CD3-CD40L BsAb_M monomer linker is shown as SEQ ID NO.32 in detail.

The amino acid sequence of CD3-CD40L BsAb_D dimer linker is shown as SEQ ID NO.34 in detail.

Embodiment 2-22: Antigen-Binding Activity Test of CD3-CD40L BsAb_M and CD3-CD40L BsAb_D by ELISA ELISA Procedure:
1. Recombinant antigen coating: 96-well plates were coated by human CD3-hFc and human CD40L-hFc recombinant protein (purchased from Novoprotein, Wujiang) 100 μl per well in concentration 1 μg/ml. The coated plates were kept at 37° C. for 1 hour or at 4° C. overnight. The recipe for the coating buffer is: 3.58 g Na$_2$HPO$_4$, 0.24 g NaH$_2$PO$_4$, 0.2 g KCl, 8.2 g NaCl, 950 ml H2O, adjusting pH to 7.4 by 1 mol/L HCl or 1 mol/L NaOH, adding water to 1 L for total volume.

2. Blocking: washing plates with PBS for 4 times, and adding PBSA (PBS+2% BSA (V/W)) 200 μl per well to block 1 hour at 37° C.

3. Adding sample: washing plates with PBS for 4 times, adding 100 μl per well of bi-specific antibody samples respectively and keeping plates at 37° C. for 1 hour. Sample serial dilution includes: using 10 μg/ml of purified CD3-CD40L BsAb_M or CD3-CD40L BsAb_D as starting concentration, diluting it into 6 gradient concentrations, and using 2 duplicate wells for each gradient.

4. Color developing: washing plates with PBST (PBS+0.05% Tween-20 (V/V)) 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well color-developing TMB (purchased from KPL), developing in dark for 5~10 min at room temperature.

5. Reaction termination and result test: adding 100 μl per well of stop buffer (1M HCl) to stop the reaction, and reading OD value of 450 nm absorbance on ELISA reader.

The results of ELISA are shown in FIGS. 2-18A and 2-18B. The three lines in the figure represent three test results: ■ coated with 1 μg/ml CD3-hFc recombinant antigen; ✦ coated with 1 μg/ml OX40L-hFc recombinant antigen; ▲ no antigen coated result. FIG. 2-18A displays that CD3-CD40L BsAb_M has antigen-binding activity with CD3-hFc and CD40L-hFc in vitro, among which CD40L has higher binding activity than that of CD3. FIG. 2-18B displays that CD3-CD40L BsAb_D has antigen-binding activity with CD3-hFc and CD40L-hFc in vitro as well, and CD40L has higher binding activity.

Embodiment 2-23: Cell Proliferation of Cytokine-Induced Killer (CIK) Mediated by CD3-CD40L Bi-Specific Antibody Human PBMC (Peripheral blood mononuclear cell, PBMC) was used as experiment material. CD3-CD40L BsAb_M monomer and CD3-CD40L BsAb_D dimer produced by this disclosure, as well as full-length antibody anti-CD3/28 combination were added to PBMC from the same donor, respectively. Cells are counted after being cultured to compare cell proliferation.

1. Separating PBMC: adding the physiological saline of same volume into the anticoagulant blood, and adding Ficoll (purchased from GE Healthcare) of same volume into the mixed-blood slowly along the centrifuge tube wall. Keep different liquid surface clear, centrifuging at 2000 rpm for 20 min, and removing the white cell layer in the middle into a new centrifuge tube. Adding PBS with volume more than 2 times of the extracted cell layer to wash cells, centrifuging for 10 min at 1000 rpm, repeat washing once more, and adding some pre-cooling X-Vivo 15 serum-free medium (purchased from Lonza) to resuspend cells. Counting the cells for use.

2. CIK cell culture and expansion: Resuspending PBMC with CIK basic medium (90% X-vivo15+10% FBS), and adjusting cell density to 1×10$^6$/ml. Setup three experiment groups: Control (coating plate with 5 μg/ml of anti-CD3 and 5 μg/ml of anti-CD28, full-length antibodies are all purchased from Novoprotein, Wujiang); Experiment 1 (adding 10 ng/ml of soluble bi-specific CD3-CD40L BsAb_M); Experiment 2 (adding 10 ng/ml of soluble bi-specific CD3-

CD40L BsAb_D). All of the three groups were added with IFN-γ (200 ng/ml, purchased from Novoprotein, Wujiang) and IL-1β (2 ng/ml, purchased from Novoprotein, Wujiang), the cell culture was kept in incubator under the condition of saturated humidity, 37° C. and 5.0% $CO_2$. After overnight, adding 500U/ml of IL-2 (purchased from Novoprotein, Wujiang) into cell medium and keeping culture. Every 2-3 days, counting the cells and passaging cell at the density of $1\times10^6$/ml in CIK basic medium with 500U/ml of IL-2. Keeping cell culture in this way for 14 days, counting the cells for expansion fold calculation, and make the cell growth curve.

The experiment results were shown in Table 2-8 and FIG. 2-19. CD3-CD40L bi-specific antibody monomer and dimer can better induce CIK expansion than anti-CD3/anti-CD28 monoclonal full-length antibody combination, and the protein dosage is even less (10 ng/ml Vs. 5 µg/ml). Among them, CD3-CD40L BsAb_D dimer could induce CIK cell expand 367 fold after two weeks, which has the best effect (experiment 2); CD3-CD40L BsAb_M monomer could induce CIK cell expand 301 fold after two weeks, which has the second best effect (experiment 1). Anti-CD3/anti-CD28 monoclonal full-length antibody combination could induce CIK cell expand 224 fold after two weeks, which has the weakest effect (control).

TABLE 2-8

| | CIK cell expansion fold | | |
|---|---|---|---|
| Experiment group | Control | Experiment 1 | Experiment 2 |
| Expansion fold after 14 days | 224 | 301 | 367 |

Embodiment 2-24 the Eukaryotic Expression Vector Construction of CD3-CD27 BsAb_M and CD3-CD27 BsAb_D In this disclosure, the bi-specific antibody targeted CD3 and co-stimulatory molecule CD27 on human T cell is named as CD3-CD27 BsAb.

1. CD3-CD27 BsAb_M and CD3-CD27 BsAb_D Construction Design

CD3-CD27 BsAb_M Monomer construction design: the sequence of anti-CD3 scFv and anti-CD27 scFv is linked by (GGGGS); Linker.

CD3-CD27 BsAb_D Dimer construction design: the sequence of anti-CD3 scFv and anti-CD27 scFv is linked by IgD hinge region Linker.

In order to express the bi-specific antibody in mammalian cells, codon optimization of the mammalian system was performed for the sequence of anti-CD3 scFv, anti-CD27 scFv and IgD hinge region.

The nucleotide sequence of the anti-CD3 scFv heavy chain variable region is shown as SEQ ID NO. 89 in detail.

The nucleotide sequence of anti-CD3 scFv light chain variable region is shown as SEQ ID NO. 90 in detail.

The nucleotide sequence of anti-CD3 scFv is shown as SEQ ID NO. 88 in detail.

The nucleotide sequence of anti-CD27 scFv heavy chain variable region is shown as SEQ ID NO. 107 in detail.

The nucleotide sequence of anti-CD27 scFv light chain variable region is shown as SEQ ID NO. 108 in detail.

The nucleotide sequence of anti-CD27 scFv is shown as SEQ ID NO. 106 in detail.

The nucleotide sequence of the CD3-CD27 BsAb_M monomer linker is shown as SEQ ID NO. 33 in detail.

The nucleotide sequence of the CD3-CD27 BsAb_D dimer linker is shown as SEQ ID NO. 35 in detail.

In order to make the bi-specific antibody successfully expressed in CHO-S cells and secreted into medium, signal peptide of antibody secretory expression was selected in this Embodiment.

The amino acid sequence of this secretory signal peptide is shown as SEQ ID NO.109 in detail.

The nucleotide sequence of this secretory signal peptide is shown as SEQ ID NO. 110 in detail.

2. Construction of Eukaryotic Expression Vector of CD3-CD27 BsAb_M and CD3-CD27 BsAb_D The construction and expression of this bi-specific antibody disclosure chose mammalian cell protein transient expression vector pcDNA3.1 (purchased from Invitrogen, Shanghai). In order to construct the monomer and dimer of bi-specific antibody, primers were designed as in table 2-9. All the primers were synthesized by Genewiz, Suzhou, and DNA template for PCR was synthesized by Synbio Technologies, Suzhou.

The cloning constructs for CD3-CD27 BsAb_M amplified signal peptide by primers pcDNA3.1-Sig-F and Sig-R, and then amplified anti-CD3 scFv, (GGGGS) 3 Linker and anti-CD27 scFv sequence by primers Sig-CD3-F&CD3-R, and CD3-(GGGGS)$_3$-CD27-F&pcDNA3.1-CD27-R. The cloning constructs for CD3-CD27 BsAb_D amplified signal peptide by primers pcDNA3.1-Sig-F and Sig-R, and then amplified anti-CD3 scFv, IgD hinge region Linker, and anti-CD27 scFv sequence by primers Sig-CD3-F&CD3-R, CD3-IgD-F&IgD-R, and IgD-CD27-F&pcDNA3.1-CD27-R. After PCR amplification, by using NovoRec®PCR one-step cloning kit (purchased from novoprotein, Wujiang), the full sequence of bi-specific antibody monomer and dimer were separately ligated and seamlessly cloned into the pcDNA3.1 vector which was linearized by EcoRI and HindIII. The target vector was transformed into E. Coli DH5a, colony PCR was used for positive cloning identification, and the recombinant (recombinant plasmid) identified as positive was performed sequencing identification. The recombinants (recombinant plasmid) with right sequence were purified by midi-prep, and then transfected into CHO-S cells.

After sequencing, the CD3-CD27 BsAb_M monomer and CD3-CD27 BsAb_D dimer both had the right full DNA sequence as expected.

The nucleotide sequence of CD3-CD27 BsAb_M monomer is shown as SEQ ID NO.64 in detail.

The nucleotide sequence of CD3-CD27 BsAb_D dimer is shown as SEQ ID NO.66 in detail.

TABLE 2-9

Primers used in CD3-CD27 bi-specific antibody gene cloning

| Primer name | Sequence | No. |
|---|---|---|
| CD3-(GGG GS)₃-CD27-F | GCACCAAGCTGGAGCTGAAGGGCGGCGG CGGCAGCGGCGGCGGCGGCAGCGGCGGCGG CGGCAGCCAGGTGCAGCTGGTGGAGAGC | SEQ ID NO.132 |
| pcDNA3.1-CD27-R | CTGATCAGCGGTTTAAACTTAAGCTTTCAC TTGATCTCCACCTTGGTGCCC | SEQ ID NO.133 |
| IgD-CD27-F | GCCACACCCAGCCCCTGGGCGTGCAGGT GCAGCTGGTGGAGAG | SEQ ID NO.134 |

Embodiment 2-25: The Expression and Purification of CD3-CD27 BsAb_M and CD3-CD27 BsAb_D 1. The Expression of CD3-CD27 BsAb_M and CD3-CD27 BsAb_D 1.1 The cell density of CHO-S cells (purchased from Thermo Fisher Scientific) was 0.5~0.6×10⁶/ml one day before transfection.

1.2 Calculating cell density at the day of transfection, performing plasmid transfection when the density is in the range of 1~1.4×10⁶/ml and the live percentage is >90%.

1.3 Transfection complex recipes: each project (CD3-CD27 BsAb_M and CD3-CD27 BsAb_D) needs two centrifuge tubes/flasks. Take total 20 ml as an example, put the recombinant plasmids from Embodiment 2-24 separately:

Tube 1: 600 μl PBS, 20 μg recombinant plasmid, mixing well.

Tube 2: 600 μl PBS, 20 μl FreeStyle™ MAX Transfection Reagent (purchased from Thermo Fisher Scientific), mixing well.

1.4 Mixing the diluted transfection reagent into the diluted recombinant plasmid, mixing well, which is transfection complex.

1.5 Keeping the transfection complex for 15~20 min, adding it into cell culture by drops steadily.

1.6 Keeping cell culture after transfection at 37° C., $CO_2$ 8%, 130 rpm on cell shaker. Collecting medium after 5 days for the target protein test.

2. The Purification of CD3-CD27 BsAb_M and CD3-CD27 BsAb_D 2.1 Sample Pretreatment Get 20 ml cell medium after transfection, adding 20 mM PB, 200 mM NaCl, and adjusting pH to 7.5;

2.2 Purification of Protein L Affinity Chromatography Column

Protein purification chromatography column: Protein L affinity chromatography column (purchased from GE Healthcare, column volume: 1.0 ml)

Buffer A: PBS, pH7.4

Buffer B: 0.1M Glycine, pH3.0

Buffer C: 0.1M Glycine, pH2.7

Purification procedure: AKTA explorer 100 protein purification system (purchased from GE Healthcare) was used for purification. Pretreat Protein L affinity chromatography column with Buffer A, running culture medium sample, and collecting flowthrough sample. After running sample, balance chromatography column with at least 1.5 ml Buffer A, washing with Buffer B and Buffer C respectively after balance, and collecting flowthrough sample with target protein (the collection tube for flowthrough sample needs to be pretreated with 1% 1M Tris, pH8.0 to neutralize the pH of flowthrough sample, and the final concentration of Tris is about 10 mM). Finally, concentrate and dialyze into buffer PBS.

The final purified CD3-CD27 BsAb_M and CD3-CD27 BsAb_D recombinant protein were analyzed by SDS-PAGE, and the protein electrophoresis data under reduced and unreduced conditions were shown as FIG. 2-20. It shows that both purity of CD3-CD27 BsAb_M and CD3-CD27 BsAb_D recombinant protein is >95%. The theoretical molecular weight for CD3-CD27 BsAb_M is 53.2 kDa, and protein displayed the same single band under reduced and unreduced conditions. The molecular weight of these bands is consistent with monomer, so this bi-specific antibody is monomer (FIG. 2-20A, Lane 1: protein marker for molecular weight; Lane 2: reduced CD3-CD27 BsAb_M; Lane 3: unreduced CD3-CD27 BsAb_M). The theoretical molecular weight for CD3-CD27 BsAb_D is 61.1 kDa, and protein displayed the same molecular weight as monomer under reduced condition, but the molecular weight is consistent with dimer under unreduced condition (FIG. 2-20B, Lane 1: protein marker for molecular weight; Lane 2: reduced CD3-CD27 BsAb_D; Lane 3: unreduced CD3-CD27 BsAb_D), which indicate two protein link to each other by disulfide bond so that this bi-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD3-CD27 BsAb_M is monomer and CD3-CD27 BsAb_D is dimer.

Therefore, the amino acid sequence of CD3-CD27 BsAb_M monomer is shown as SEQ ID NO.63 in detail.

The amino acid sequence of CD3-CD27 BsAb_D dimer is shown as SEQ ID NO.65 in detail.

The amino acid sequence of CD3 scFv is shown as SEQ ID NO.67 in detail.

The amino acid sequence of CD3 scFv heavy chain variable region is shown as SEQ ID NO.68 in detail.

The amino acid sequence of CD3 scFv light chain variable region is shown as SEQ ID NO.69 in detail.

The amino acid sequence of CD27 scFv is shown as SEQ ID NO.85 in detail.

The amino acid sequence of CD27 scFv heavy chain variable region is shown as SEQ ID NO.86 in detail.

The amino acid sequence of CD27 scFv light chain variable region is shown as SEQ ID NO.87 in detail.

The amino acid sequence of CD3-CD27 BsAb_M monomer linker is shown as SEQ ID NO.32 in detail.

The amino acid sequence of CD3-CD27 BsAb_D dimer linker is shown as SEQ ID NO.34 in detail.

Embodiment 2-26: Antigen-Binding Activity Test of CD3-CD27 BsAb_M and CD3-CD27 BsAb_D by ELISA ELISA Procedure:

1. Recombinant antigen coating: 96-well plates were coated by human CD3-hFc and human CD27-hFc recombinant protein (purchased from Novoprotein, Wujiang) 100 μl per well in concentration 1 μg/ml. The coated plates were kept at 37° C. 1 hour or 4° C. overnight. The recipe for coating buffer is: 3.58 g $Na_2HPO_4$, 0.24 g $NaH_2PO_4$. 0.2 g KCl. 8.2 g NaCl. 950 ml $H_2O$. Adjusting pH to 7.4 by 1 mol/L HCl or 1 mol/L NaOH, adding water to 1 L for total volume.

2. Blocking: washing plates with PBS for 4 times, and adding PBSA (PBS+2% BSA (V/W)) 200 μl per well to block 1 hour at 37° C.

3. Adding sample: washing plates with PBS for 4 times, adding 100 μl per well of bi-specific antibody samples respectively and keeping plates at 37° C. for 1 hour. Sample serial dilution includes: using 10 μg/ml of purified CD3-CD27 BsAb_M or CD3-CD27 BsAb_D as starting concentration, diluting it into 6 gradient concentrations, and using 2 duplicate wells for each gradient.

4. Color developing: washing plates with PBST (PBS+ 0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well color-developing TMB (purchased from KPL), developing in dark for 5~10 min at room temperature.

5. Reaction termination and result test: adding 100 μl per well of stop buffer (1M HCl) to stop the reaction, and reading OD value of 450 nm absorbance on ELISA reader.

The results of ELISA are shown in FIGS. 2-21A and 2-21B. The three lines in the figure represent three test results: ■ coated with 1 μg/ml CD3-hFc recombinant antigen, ✻ coated with 1 μg/ml CD27-hFc recombinant antigen; ▲ no antigen coated result. FIG. 2-21A displays that CD3-CD27 BsAb_M has antigen-binding activity with CD3-hFc and CD27-hFc in vitro, among which CD27 has higher binding activity than that of CD3. FIG. 2-21B displays that CD3-CD27 BsAb_D has antigen-binding activity with CD3-hFc and CD27-hFc in vitro as well, and CD27 has higher binding activity.

Embodiment 2-27: Cell Proliferation of Cytokine Induced Killer (CIK) Mediated by CD3-CD27 Bi-Specific Antibody Human PBMC (Peripheral blood mononuclear cell, PBMC) was used as experiment material. CD3-CD27 BsAb_M monomer and CD3-CD27 BsAb_D dimer produced by this disclosure, as well as full-length antibody anti-CD3/28 combination were added to PBMC from the same donor, respectively. Cells are counted after being cultured to compare cell proliferation.

1. Separating PBMC: adding the physiological saline of same volume into the anticoagulant blood, and adding Ficoll (purchased from GE Healthcare) of same volume into the mixed-blood slowly along the centrifuge tube wall. Keeping different liquid surface clear, centrifuging at 2000 rpm for 20 min, and removing the white cell layer in the middle into a new centrifuge tube. Adding PBS with volume more than 2 times of the extracted cell layer to wash cells, centrifuging for 10 min at 1000 rpm, repeat washing once more, and adding some pre-cooling X-vivo 15 serum-free medium (purchased from Lonza) to resuspend cells. Counting the cells for use.

2. CIK cell culture and expansion: Resuspending PBMC with CIK basic medium (90% X-vivo15+10% FBS), and adjusting cell density to $1\times10^6$/ml. Setup three experiment groups: Control (coating plate with 5 μg/ml of anti-CD3 and 5 μg/ml of anti-CD28, full-length antibodies are all purchased from Novoprotein, Wujiang); Experiment 1 (adding 10 ng/ml of soluble bi-specific CD3-CD27 BsAb_M); Experiment 2 (adding 10 ng/ml of soluble bi-specific CD3-CD27 BsAb_D). All of the three groups were added with IFN-γ (200 ng/ml, purchased from Novoprotein, Wujiang) and IL-1β (2 ng/ml, purchased from Novoprotein, Wujiang), the cell culture was kept in incubator under the condition of saturated humidity, 37° C. and 5.0% $CO_2$. After overnight, adding 500U/ml of IL-2 (purchased from Novoprotein, Wujiang) into cell medium and keeping culture. Every 2-3 days, counting the cells and passaging cell at the density of $1\times10^6$/ml in CIK basic medium with 500U/ml of IL-2. Keeping cell culture in this way for 30 days, counting the cells for expansion fold calculation, and make the cell growth curve.

The experiment results were shown as FIG. 2-22. CD3-CD27 bi-specific antibody monomer and dimer can better induce CIK expansion than anti-CD3/anti-CD28 monoclonal full-length antibody combination. Anti-CD3/anti-CD28 monoclonal full-length antibody combination induced severe cell death after culturing for 18 days, and cell proliferation rate significantly reduced; meanwhile, neither CD3-CD27 BsAb_M monomer nor CD3-CD27 BsAb_D dimer induced cell death, but the cell proliferation rate was relatively slow. Therefore, both monomer and dimer of CD3-CD27 bi-specific antibody can effectively promote cell expansion and prolong the survival of CIK cell, among which dimer has better effect.

Embodiment 3-1 the Eukaryotic Expression Vector Construction of CD3-4-1BBL BsM_M and CD3-4-1BBL BsM_D In this disclosure, the bi-specific molecule targeted CD3 and co-stimulatory molecule ligand 4-1BBL extracellular domain on human T cell is named as CD3-4-1BBL BsM.

1. CD3-4-1BBL BsM_M and CD3-4-1BBL BsM_D Construction Design

CD3-4-1BBL BsM_M Monomer construction design: the sequence of anti-CD3 scFv and 4-1BBL extracellular domain sequence is linked by (GGGGS) 3 Linker.

CD3-4-1BBL BsM_D Dimer construction design: the sequence of anti-CD3 scFv and 4-1BBL extracellular domain sequence is linked by IgD hinge region Linker.

In order to express the bi-specific antibody in mammalian cells, codon optimization of mammalian system was performed for the sequence of anti-CD3 scFv, 4-1BBL extracellular domain and Linker.

The nucleotide sequence of anti-CD3 scFv heavy chain variable region is shown as SEQ ID NO. 178 in detail.

The nucleotide sequence of anti-CD3 scFv light chain variable region is shown as SEQ ID NO. 179 in detail.

The nucleotide sequence of anti-CD3 scFv is shown as SEQ ID NO. 177 in detail.

The nucleotide sequence of 4-1BBL extracellular region is shown as SEQ ID NO. 180 in detail.

The nucleotide sequence of CD3-4-1BBL BsM_M monomer linker is shown as SEQ ID NO. 136 in detail.

The nucleotide sequence of CD3-4-1BBL BsM_D dimer linker is shown as SEQ ID NO. 138 in detail.

In order to make bi-specific molecule successfully expressed in CHO-S cells and secreted into medium, signal peptide of antibody secretory expression was selected in this Embodiment.

The amino acid sequence of this secretory signal peptide is shown as SEQ ID NO.185 in detail.

The nucleotide sequence of this secretory signal peptide is shown as SEQ ID NO. 186 in detail.

was performed sequencing identification. The recombinants (recombinant plasmid) with right sequence were purified by midi-prep, and then transfected into CHO-S cells.

After sequencing, the CD3-4-1BBL BsM_M monomer and CD3-4-1BBL BsM_D dimer both had the right full DNA sequence as expected.

The nucleotide sequence of CD3-4-1BBL BsM_M monomer is shown as SEQ ID NO.150 in detail.

The nucleotide sequence of CD3-4-1BBL BsM_D dimer is shown as SEQ ID NO.152 in detail.

TABLE 3-1

Primers used in CD3-4-1BBL bi-specific molecule gene cloning

| Primer name | Sequence | No. |
|---|---|---|
| pcDNA3.1-Sig-F | GTGCTGGATATCTGCAGAATTCGCCGCCACC ATGACCCGGCTGACCGTGCTGGCCCTGC | SEQ ID NO.187 |
| Sig-R | GGCCCTGGAGGAGGCCAGCAGGCCGGCCAG CAGGGCCAGCACGGTCAGC | SEQ ID NO.188 |
| Sig-CD3-F | GCTGGCCTCCTCCAGGGCCGACATCAAGCTG CAGCAGAGCG | SEQ ID NO.189 |
| CD3-R | CTTCAGCTCCAGCTTGGTGC | SEQ ID NO.190 |
| CD3-(GGGGS)₃-4-1BBL-F | GCACCAAGCTGGAGCTGAAGGGCGGCGGCG GCAGCGGCGGCGGCGGCAGCGGCGGCGGCG GCAGCGCCTGCCCCTGGGCCGTGAGC | SEQ ID NO.191 |
| pcDNA3.1-4-1BBL-R | CTGATCAGCGGTTTAAACTTAAGCTTTCACT CGCTGCGGGGCTGGGCAGGC | SEQ ID NO.192 |
| CD3-IgD-F | GCACCAAGCTGGAGCTGAAGGCCAGCAAGA GCAAGAAGGAG | SEQ ID NO.193 |
| IgD-R | CACGCCCAGGGGCTGGGTGTG | SEQ ID NO.194 |
| IgD-4-1BBL-F | GCCACACCCAGCCCCTGGGCGTGGCCTGCCC CTGGGCCGTGAGC | SEQ ID NO.195 |

2. Construction of Eukaryotic Expression Vector of CD3-4-1BBL BsM_M and CD3-4-1BBL BsM_D The construction and expression of this bi-specific molecule disclosure chose mammalian cell protein transient expression vector pcDNA3.1 (purchased from Invitrogen, Shanghai). In order to construct the monomer and dimer of bi-specific molecules, primers were designed as in table 3-1. All the primers were synthesized by Genewiz, Suzhou, and DNA template for PCR was synthesized by Synbio Technologies, Suzhou.

The cloning construct for CD3-4-1BBL BsM_M amplified signal peptide by primers pcDNA3.1-Sig-F and Sig-R, and then amplified anti-CD3 scFv, (GGGGS) 3 Linker and 4-1BBL extracellular domain sequence by primers Sig-CD3-F&CD3-R, and CD3-(GGGGS)₃-4-1BBL-F&pcDNA3.1-4-1BBL-R. The cloning construct for CD3-4-1BBL BsM_D amplified signal peptide by primers pcDNA3.1-Sig-F and Sig-R, and then amplified anti-CD3 scFv, IgD hinge region Linker, and 4-1BBL extracellular domain sequence by primers Sig-CD3-F&CD3-R, CD3-IgD-F&IgD-R, and IgD-4-1BBL-F&pcDNA3.1-4-1BBL-R. After PCR amplification, by using NovoRec®PCR one-step cloning kit (purchased from novoprotein, Wujiang), the full sequence of bi-specific molecule monomer and dimer were seperately ligated and seamlessly cloned into the pcDNA3.1 vector which was linearized by EcoRI and HindIII. The target vector was transformed into *E. Coli* DH5α, colony PCR was used for positive cloning identification, and the recombinant (recombinant plasmid) identified as positive Embodiment 3-2: The Expression and Purification of CD3-4-1BBL BsM_M and CD3-4-1BBL BsM_D 1. The Expression of CD3-4-1BBL BsM_M and CD3-4-1BBL BsM_D 1.1 The cell density of CHO-S cells (purchased from Thermo Fisher Scientific) was 0.5~0.6×10⁶/ml one day before transfection.

1.2 Calculating cell density at the day of transfection, performing plasmid transfection when the density is in the range of 1~1.4×10⁶/ml and live percentage is >90%.

1.3 Transfection complex recipes: each project (CD3-4-1BBL BsM_M and CD3-4-1BBL BsM_D) needs two centrifuge tubes/flasks. Take total 20 ml as an example, put the recombinant plasmids from Embodiment 3-1 separately:

Tube 1: 600 μl PBS, 20 μg recombinant plasmid, mixing well.

Tube 2: 600 μl PBS, 20 μl FreeStyle™ MAX Transfection Reagent (purchased from Thermo Fisher Scientific), mixing well.

1.4 Mixing the diluted transfection reagent into the diluted recombinant plasmid, mixing well, which is transfection complex.

1.5 Keeping transfection complex for 15~20 min, adding it into cell culture by drops steadily.

1.6 Keeping cell culture after transfection at 37° C., CO₂ 8%, 130 rpm on cell shaker. Collecting medium after 5 days for the target protein test.

2. The Purification of CD3-4-1BBL BsM_M and CD3-4-1BBL BsM_D 2.1 Sample Pretreatment Get 20 ml cell medium after transfection, adding 20 mM PB, 200 mM NaCl, and adjusting pH to 7.5;

2.2 Purification of Protein L Affinity Chromatography Column

Protein purification chromatography column: Protein L affinity chromatography column (purchased from GE Healthcare, column volume: 1.0 ml)

Buffer A: PBS, pH7.4

Buffer B: 0.1M Glycine, pH3.0

Buffer C: 0.1M Glycine, pH2.7

Purification procedure: AKTA explorer 100 protein purification system (purchased from GE Healthcare) was used for purification. Pretreat Protein L affinity chromatography column with Buffer A, running culture medium sample, and collecting flowthrough sample. After running sample, balance chromatography column with at least 1.5 ml Buffer A, washing with Buffer B and Buffer C respectively after balance, and collecting flowthrough sample with target protein (the collection tube for flowthrough sample needs pretreated with 1% 1M Tris, pH8.0 to neutralize the pH of flowthrough sample, and the final concentration of Tris is about 10 mM). Finally, concentrate and dialyse into buffer PBS.

The final purified CD3-4-1BBL BsM_M and CD3-4-1BBL BsM_D recombinant protein was analyzed by SDS-PAGE, and the protein electrophoresis data under reduced and unreduced conditions were shown as FIG. 3-2. It shows that both purity of CD3-4-1BBL BsM_M and CD3-4-1BBL BsM_D recombinant protein are >95%. The theoretical molecular weight for CD3-4-1BBL BsM_M is 48.8 kDa, and protein displayed the same single band under reduced and unreduced conditions. The molecular weight of these bands is consistent with monomer, so this bi-specific antibody is monomer (FIG. 3-2A, Lane 1: protein marker for molecular weight; Lane 2: reduced CD3-4-1BBL BsM_M; Lane 3: unreduced CD3-4-1BBL BsM_M). The theoretical molecular weight for CD3-4-1BBL BsM_D is 56.6 kDa, and protein displayed the same molecular weight as monomer under reduced condition, but the molecular weight is consistent with dimer under unreduced condition (FIG. 3-2B, Lane 1: protein marker for molecular weight; Lane 2: reduced CD3-4-1BBL BsM_D; Lane 3: unreduced CD3-4-1BBL BsM_D), which indicate two protein link to each other by disulfide bond so that this bi-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD3-4-1BBL BsM_M is monomer and CD3-4-1BBL BsM_D is dimer.

Therefore, the amino acid sequence of CD3-4-1BBL BsM_M monomer is shown as SEQ ID NO.149 in detail.

The amino acid sequence of CD3-4-1BBL BsM_D dimer is shown as SEQ ID NO.151 in detail.

The amino acid sequence of anti-CD3 scFv is shown as SEQ ID NO.169 in detail.

The amino acid sequence of anti-CD3 scFv heavy chain variable region is shown as SEQ ID NO.170 in detail.

The amino acid sequence of anti-CD3 scFv light chain variable region is shown as SEQ ID NO.171 in detail.

The amino acid sequence of 4-1BBL extracellular domain is shown as SEQ ID NO.172 in detail.

The amino acid sequence of CD3-4-1BBL BsM_M monomer linker is shown as SEQ ID NO.135 in detail.

The amino acid sequence of CD3-4-1BBL BsM_D dimer linker is shown as SEQ ID NO.137 in detail.

Embodiment 3-3: CD3 Antigen-Binding and Co-Stimulatory Molecule 4-1BB Binding Activity Test of CD3-4-1BBL BsM_M and CD3-4-1BBL BsM_D by ELISA ELISA Procedure:

1. Recombinant antigen coating: 96-well plates were coated by human CD3-hFc and human 4-1BB-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding PBSA (PBS+2% BSA (V/W)) 200 μl per well to block 1 hour at 37° C.

3. Adding sample: washing plates with PBS for 4 times, adding 100 μl per well of bi-specific antibody samples respectively and keeping plates at 37° C. for 1 hour. Sample serial dilution includes: using 10 μg/ml of purified CD3-4-1BBL BsM_M or CD3-4-1BBL BsM_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well color-developing TMB (purchased from KPL), developing in dark for 5~10 min at room temperature.

5. Reaction termination and result test: adding 100 μl per well of stop buffer (1M HCl) to stop the reaction, and reading OD value of 450 nm absorbance on ELISA reader.

The results of ELISA are shown in FIGS. 3-3A and 3-3B. The three lines in the figure represent three test results: ■ coated with 1 μg/ml CD3-hFc recombinant antigen, ● coated with 1 μg/ml 4-1BB-hFc recombinant antigen; ▲ no antigen coated result. FIG. 3-3A displays that CD3-4-1BBL BsM_M has antigen-binding activity with CD3-hFc and 4-1BB-hFc in vitro, among which 4-1BB has higher binding activity than that of CD3. FIG. 3-3B displays that CD3-4-1BBL BsM_D has antigen-binding activity with CD3-hFc and 4-1BB-hFc in vitro as well, and 4-1BB has higher binding activity.

Embodiment 3-4: Cell Proliferation of Cytokine Induced Killer (CIK) Mediated by CD3-4-1BBL Bi-Specific Molecule Human PBMC (Peripheral blood mononuclear cell, PBMC) was used as experiment material. CD3-4-1BBL BsM_M monomer and CD3-4-1BBL BsM_D dimer produced by this disclosure, as well as full-length antibody anti-CD3/28 combination were added to PBMC from the same donor, respectively. Cells are counted after being cultured to compare cell proliferation.

1. Separating PBMC: adding the physiological saline of same volume into the anticoagulant blood, and adding Ficoll (purchased from GE Healthcare) of same volume into the mixed-blood slowly along the centrifuge tube wall. Keeping different liquid surface clear, centrifuging at 2000 rpm for 20 min, and removing the white cell layer in the middle into a new centrifuge tube. Adding PBS with volume more than 2 times of the extracted cell layer to wash cells, centrifuging for 10 min at 1000 rpm, repeat washing once more, and adding some pre-cooling X-vivo 15 serum-free medium (purchased from Lonza) to resuspend cells. Counting the cells for use.

2. CIK cell culture and expansion: Resuspending PBMC with CIK basic medium (90% X-vivo15+10% FBS), and adjusting cell density to $1\times10^6$/ml. Setup three experiment groups: Control (coating plate with 5 μg/ml of anti-CD3 and 5 μg/ml of anti-CD28, full-length antibodies are all purchased from Novoprotein, Wujiang); Experiment 1 (adding 10 ng/ml of soluble bi-specific CD3-4-1BBL BsM_M); Experiment 2 (adding 10 ng/ml of soluble bi-specific CD3-4-1BBL BsM_D). All of the three groups were added with IFN-γ (200 ng/ml, purchased from Novoprotein, Wujiang) and IL-1B (2 ng/ml, purchased from Novoprotein, Wujiang), the cell culture was kept in incubator under the condition of saturated humidity, 37° C. and 5.0% $CO_2$. After overnight, adding 500U/ml of IL-2 (purchased from Novoprotein, Wujiang) into cell medium and keeping culture. Every 2-3 days, counting the cells and passaging cell at the density of $1\times10^6$/ml in CIK basic medium with 500U/ml of IL-2. Keeping cell culture in this way for 30 days, counting the cells for expansion fold calculation, and drawing the cell growth curve.

The experiment results were shown as FIG. 3-4. CD3-4-1BBL bi-specific molecule monomer and dimer can better induce CIK expansion than anti-CD3/anti-CD28 monoclonal full-length antibody combination. Anti-CD3/anti-CD28 monoclonal full-length antibody combination induced severe cell death after culturing 18 days, and cell proliferation rate significantly reduced; meanwhile, neither CD3-4-1BBL BsM_M monomer nor CD3-4-1BBL BsM_D dimer induced cell death, but the cell proliferation rate was relatively slow. Therefore, both monomer and dimer of CD3-4-1BBL bi-specific molecules can effectively promote cell expansion and prolong the survival of CIK cell, among which dimer has better effect.

Embodiment 3-5 the Eukaryotic Expression Vector Construction of CD3-B7RP-1 BsM_M and CD3-B7RP-1 BsM_D In this disclosure, the bi-specific molecule targeted CD3 and co-stimulatory molecule ligand B7RP-1 extracellular domain on human T cell is named as CD3-B7RP-1 BsM.

1. CD3-B7RP-1 BsM_M and CD3-B7RP-1 BsM_D Construction Design

CD3-B7RP-1 BsM_M Monomer construction design: the sequence of anti-CD3 scFv and B7RP-1 extracellular domain sequence is linked by (GGGGS) 3 Linker.

CD3-B7RP-1 BsM_D Dimer construction design: the sequence of anti-CD3 scFv and B7RP-1 extracellular domain sequence is linked by IgD hinge region Linker.

In order to express the bi-specific antibody in mammalian cells, codon optimization of mammalian system was performed for the sequence of anti-CD3 scFv, B7RP-1 extracellular domain and Linker.

The nucleotide sequence of anti-CD3 scFv heavy chain variable region is shown as SEQ ID NO. 178 in detail.

The nucleotide sequence of anti-CD3 scFv light chain variable region is shown as SEQ ID NO. 179 in detail.

The nucleotide sequence of anti-CD3 scFv is shown as SEQ ID NO. 177 in detail.

The nucleotide sequence of B7RP-1 extracellular domain sequence is shown as SEQ ID NO. 181 in detail.

The nucleotide sequence of CD3-B7RP-1 BsM_M monomer linker is shown as SEQ ID NO. 136 in detail.

The nucleotide sequence of CD3-B7RP-1 BsM_D dimer linker is shown as SEQ ID NO. 138 in detail.

In order to make bi-specific molecule successfully expressed in CHO-S cells and secreted into medium, signal peptide of antibody secretory expression was selected in this Embodiment.

The amino acid sequence of this secretory signal peptide is shown as SEQ ID NO.185 in detail.

The nucleotide sequence of this secretory signal peptide is shown as SEQ ID NO. 186 in detail.

2. Construction of Eukaryotic Expression Vector of CD3-B7RP-1 BsM_M and CD3-B7RP-1 BsM_D The construction and expression of this bi-specific molecule disclosure chose mammalian cell protein transient expression vector pcDNA3.1 (purchased from Invitrogen, Shanghai). In order to construct the monomer and dimer of bi-specific molecules, primers were designed as in table 3-2. All the primers were synthesized by Genewiz, Suzhou, and DNA template for PCR was synthesized by Synbio Technologies, Suzhou.

The cloning construct for CD3-B7RP-1 BsM_M amplified signal peptide first by primers pcDNA3.1-Sig-F and Sig-R, and then amplified anti-CD3 scFv, (GGGGS) 3 Linker and B7RP-1 extracellular domain sequence by primers Sig-CD3-F&CD3-R, and CD3-(GGGGS)$_3$-B7RP-1-F&pcDNA3.1-B7RP-1-R. The cloning construct for CD3-B7RP-1BsM_D amplified signal peptide first by primers pcDNA3.1-Sig-F and Sig-R, and then amplified anti-CD3 scFv, IgD hinge region Linker, and B7RP-1 extracellular domain sequence by primers Sig-CD3-F&CD3-R, CD3-IgD-F&IgD-R, and IgD-B7RP-1-F&pcDNA3.1-B7RP-1-R. After PCR amplification, by using NovoRec®PCR one-step cloning kit (purchased from novoprotein, Wujiang), the full sequence of bi-specific molecule monomer and dimer were seperately ligated and seamlessly cloned into the pcDNA3.1 vector which was linearized by EcoRI and HindIII. The target vector was transformed into *E. Coli* DH5a, colony PCR was used for positive cloning identification, and the recombinant (recombinant plasmid) identified as positive was performed sequencing identification. The recombinants (recombinant plasmid) with right sequence were purified by midi-prep, and then transfected into CHO-S cells.

After sequencing, the CD3-B7RP-1 BsM_M monomer and CD3-B7RP-1 BsM_D dimer both had the right full DNA sequence as expected.

The nucleotide sequence of CD3-B7RP-1 BsM_M monomer is shown as SEQ ID NO.154 in detail.

The nucleotide sequence of CD3-B7RP-1 BsM_D dimer is shown as SEQ ID NO.156 in detail.

TABLE 3-2

Primer used in CD3-B7RP-1 bi-specific molecule gene cloning

| Primer name | Sequence | No. |
|---|---|---|
| CD3-(GGGGS)$_3$-B7RP-1-F | CGGCACCAAGCTGGAGCTGAAGGGCGGC GGCGGCAGCGGCGGCGGCGGCAGCGGCG GCGGCGGCAGCGACACCCAGGAGAAGGA GGTGC | SEQ ID NO.196 |
| pcDNA3.1-B7RP-1-R | CTGATCAGCGGTTTAAACTTAAGCTTTCAG GTGGCGGCGTTCTTCTCGCC | SEQ ID NO.197 |
| IgD-B7RP-1-F | GCCACACCCAGCCCCTGGGCGTGGACACC CAGGAGAAGGAGGTGC | SEQ ID NO.198 |

Embodiment 3-6: The Expression and Purification of CD3-B7RP-1 BsM_M and CD3-B7RP-1 BsM_D 1. The Expression of CD3-B7RP-1 BsM_M and CD3-B7RP-1 BsM_D 1.1 The cell density of CHO-S cells (purchased from Thermo Fisher Scientific) was 0.5~0.6×10⁶/ml one day before transfection.

1.2 Calculating cell density at the day of transfection, performing plasmid transfection when the density is in the range of 1~1.4×10⁶/ml and live percentage is >90%.

1.3 Transfection complex recipes: each project (CD3-B7RP-1 BsM_M and CD3-B7RP-1 BsM_D) needs two centrifuge tubes/flasks. Take total 20 ml as an example, put the recombinant plasmids from Embodiment 3-5 separately:
   Tube 1: 600 μl PBS, 20 μg recombinant plasmid, mixing well.
   Tube 2: 600 μl PBS, 20 μl FreeStyle™ MAX Transfection Reagent (purchased from Thermo Fisher Scientific), mixing well.

1.4 Mixing the diluted transfection reagent into the diluted recombinant plasmid, mixing well, which is transfection complex.

1.5 Keeping transfection complex for 15~20 min, adding it into cell culture by drops steadily.

1.6 Keeping cell culture after transfection at 37° C., CO$_2$ 8%, 130 rpm on cell shaker. Collecting medium after 5 days for the target protein test.

2. The Purification of CD3-B7RP-1 BsM_M and CD3-B7RP-1 BsM_D 2.1 Sample Pretreatment Get 20 ml cell medium after transfection, adding 20 mM PB, 200 mM NaCl, and adjusting pH to 7.5;

2.2 Purification of Protein L Affinity Chromatography Column

Protein purification chromatography column: Protein L affinity chromatography column (purchased from GE Healthcare, column volume: 1.0 ml)
Buffer A: PBS, pH7.4
Buffer B: 0.1M Glycine, pH3.0
Buffer C: 0.1M Glycine, pH2.7

Purification procedure: AKTA explorer 100 protein purification system (purchased from GE Healthcare) was used for purification. Pretreat Protein L affinity chromatography column with Buffer A, running culture medium sample, and collecting flowthrough sample. After running sample, balance chromatography column with at least 1.5 ml Buffer A, washing with Buffer B and Buffer C respectively after balance, and collecting flowthrough sample with target protein (the collection tube for flowthrough sample needs pretreated with 1% 1M Tris, pH8.0 to neutralize the pH of flowthrough sample, and the final concentration of Tris is about 10 mM). Finally, concentrate and dialyse into buffer PBS.

Figures 1, 2, 3, 4, 5:
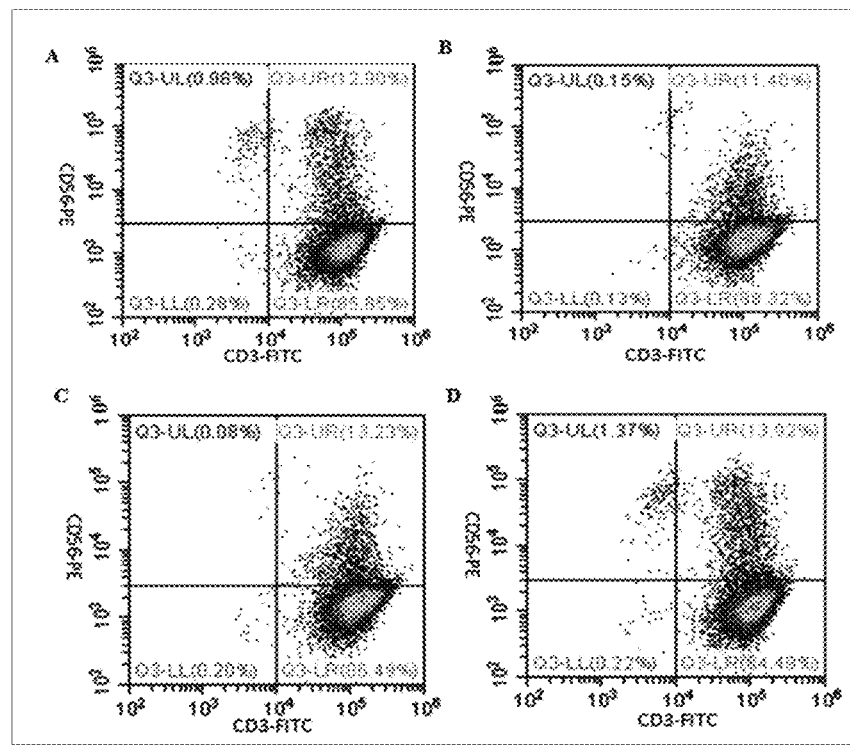

The final purified CD3-B7RP-1 BsM_M and CD3-B7RP-1 BsM_D recombinant protein was analyzed by SDS-PAGE, and the protein electrophoresis data under reduced and unreduced conditions were shown as FIG. 3-5. It shows that both purity of CD3-B7RP-1 BsM_M and CD3-B7RP-1 BsM_D recombinant protein are >95%. The theoretical molecular weight for CD3-B7RP-1 BsM_M is 53.7 kDa, and protein displayed single band under reduced and unreduced conditions. Because of the N-glycosylation modification on B7RP-1 extracellular domain, the real molecular weight of the band is bigger than theoretical value, so this bi-specific molecule is glycosylated monomer (FIG. 3-5A, Lane 1: protein marker for molecular weight; Lane 2: reduced CD3-B7RP-1 BsM_M; Lane 3: unreduced CD3-B7RP-1 BsM_M). The theoretical molecular weight for CD3-B7RP-1 BsM_D is 61.6 kDa, and protein displayed the same molecular weight as glycosylated monomer under reduced condition, but the molecular weight is consistent with glycosylated dimer under unreduced condition (FIG. 3-5B, Lane 1: protein marker for molecular weight; Lane 2: reduced CD3-B7RP-1 BsM_D; Lane 3: unreduced CD3-B7RP-1 BsM_D), which indicate two protein link to each other by disulfide bond so that this bi-specific molecule is dimer.

Moreover, the N/C terminal sequence analysis for purified recombinant protein shows the reading frame has no error, consistent with the theoretical N/C terminal amino acid sequence. Mass spectrometry analysis further confirmed that CD3-B7RP-1 BsM_M is monomer and CD3-B7RP-1 BsM_D is dimer.

Therefore, the amino acid sequence of CD3-B7RP-1 BsM_M monomer is shown as SEQ ID NO.153 in detail.

The amino acid sequence of CD3-B7RP-1 BsM_D dimer is shown as SEQ ID NO.155 in detail.

The amino acid sequence of anti-CD3 scFv is shown as SEQ ID NO.169 in detail.

The amino acid sequence of anti-CD3 scFv heavy chain variable region is shown as SEQ ID NO.170 in detail.

The amino acid sequence of anti-CD3 scFv light chain variable region is shown as SEQ ID NO.171 in detail.

The amino acid sequence of B7RP-1 extracellular domain is shown as SEQ ID NO.173 in detail.

The amino acid sequence of CD3-B7RP-1 BsM_M monomer linker is shown as SEQ ID NO.135 in detail.

The amino acid sequence of CD3-B7RP-1 BsM_D dimer linker is shown as SEQ ID NO.137 in detail.

Embodiment 3-7: CD3 Antigen-Binding and Co-Stimulatory Molecule ICOS Binding Activity Test of CD3-B7RP-1 BsM_M and CD3-B7RP-1 BsM_D by ELISA ELISA Procedure:
1. Recombinant antigen coating: 96-well plates were coated by human CD3-hFc and human ICOS-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.
2. Blocking: washing plates with PBS for 4 times, and adding PBSA (PBS+2% BSA (V/W)) 200 μl per well to block 1 hour at 37° C.
3. Adding sample: washing plates with PBS for 4 times, adding 100 μl per well of bi-specific antibody samples respectively and keeping plates at 37° C. for 1 hour. Sample serial dilution includes: using 10 μg/ml of purified CD3-B7RP-1 BsM_M or CD3-B7RP-1 BsM_D as starting concentration, diluting it into 6 gradient concentrations, and using 2 duplicate wells for each gradient.
4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well color-developing TMB (purchased from KPL), developing in dark for 5~10 min at room temperature.
5. Reaction termination and result test: adding 100 μl per well of stop buffer (1M HCl) to stop the reaction, and reading OD value of 450 nm absorbance on ELISA reader.

The results of ELISA are shown in FIGS. 3-6A and 3-6B. The three lines in the figure represent three test results: ■ coated with 1 μg/ml CD3-hFc recombinant antigen, ♦ coated with 1 μg/ml ICOS-hFc recombinant antigen; ▲ no antigen coated result. FIG. 3-6A displays that CD3-B7RP-1 BsM_M has antigen-binding activity with CD3-hFc and T cell co-stimulatory molecule ICOS-hFc in vitro, among which CD3 has higher binding activity than that of ICOS. FIG. 3-6B displays that CD3-B7RP-1 BsM_D has antigen-binding activity with CD3-hFc and ICOS-hFc in vitro as well, and CD3 has higher binding activity.

Embodiment 3-8: Cell Proliferation of Cytokine Induced Killer (CIK) Mediated by CD3-B7RP-1 Bi-Specific Molecule Human PBMC (Peripheral blood mononuclear cell, PBMC) was used as experiment material. CD3-B7RP-1 BsM_M monomer and CD3-B7RP-1 BsM_D dimer produced by this disclosure, as well as full-length antibody anti-CD3/28 combination were added to PBMC from the same donor, respectively. Cells are counted after being cultured to compare cell proliferation.

1. Separating PBMC: adding the physiological saline of same volume into the anticoagulant blood, and adding Ficoll (purchased from GE Healthcare) of same volume into the mixed-blood slowly along the centrifuge tube wall. Keep different liquid surface clear, centrifuging at 2000 rpm for 20 min, and removing the white cell layer in the middle into new a centrifuge tube. Adding PBS with volume more than 2 times of the extracted cell layer to wash cells, centrifuging for 10 min at 1000 rpm, repeat washing once more, and adding some pre-cooling X-vivo 15 serum-free medium (purchased from Lonza) to resuspend cells. Counting the cells for use.
2. CIK cell culture and expansion: Resuspending PBMC with CIK basic medium (90% X-vivo15+10% FBS), and adjusting cell density to $1 \times 10^6$/ml. Setup three experiment groups: Control (coating plate with 5 μg/ml of anti-CD3 and 5 μg/ml of anti-CD28, full-length antibodies are all purchased from Novoprotein, Wujiang); Experiment 1 (adding 10 ng/ml of soluble bi-specific CD3-B7RP-1 BsM_M); Experiment 2 (adding 10 ng/ml of soluble bi-specific CD3-B7RP-1 BsM_D). All of the three groups were added with IFN-γ (200 ng/ml, purchased from Novoprotein, Wujiang) and IL-1β (2 ng/ml, purchased from Novoprotein, Wujiang), the cell culture was kept in incubator under the condition of saturated humidity, 37° C. and 5.0% $CO_2$. After overnight, adding 500U/ml of IL-2 (purchased from Novoprotein, Wujiang) into cell medium and keeping culture. Every 2-3 days, counting the cells and passaging cell at the density of $1 \times 10^6$/ml in CIK basic medium with 500U/ml of IL-2. Keeping cell culture in this way for 30 days, counting the cells for expansion fold calculation, and drawing the cell growth curve.

The experiment results were shown as FIG. 3-7. CD3-B7RP-1 bi-specific molecule monomer and dimer can better induce CIK expansion than anti-CD3/anti-CD28 monoclonal full-length antibody combination. Anti-CD3/anti-CD28 monoclonal full-length antibody combination induced severe cell death after culturing 18 days, and cell proliferation rate significantly reduced; meanwhile, neither CD3-B7RP-1 BsM_M monomer nor CD3-B7RP-1 BsM_D dimer induced cell death, but the cell proliferation rate was relatively slow. Therefore, both monomer and dimer of CD3-B7RP-1 bi-specific molecules can effectively promote cell expansion and prolong the survival of CIK cell, among which dimer has better effect.

Embodiment 3-9 the Eukaryotic Expression Vector Construction of CD3-OX40L BsM_M and CD3-OX40L BsM_D In this disclosure, the bi-specific molecule targeted CD3 and co-stimulatory molecule ligand OX40L extracellular domain on human T cell is named as CD3-OX40L BsM.

1. CD3-OX40L BsM_M and CD3-OX40L BsM_D Construction Design

CD3-OX40L BsM_M Monomer construction design: the sequence of anti-CD3 scFv and OX40L extracellular domain sequence is linked by (GGGGS) 3 Linker.

CD3-OX40L BsM_D Dimer construction design: the sequence of anti-CD3 scFv and OX40L extracellular domain sequence is linked by IgD hinge region Linker.

In order to express the bi-specific antibody in mammalian cells, codon optimization of mammalian system was performed for the sequence of anti-CD3 scFv, OX40L extracellular domain and Linker.

The nucleotide sequence of anti-CD3 scFv heavy chain variable region is shown as SEQ ID NO. 178 in detail.

The nucleotide sequence of anti-CD3 scFv light chain variable region is shown as SEQ ID NO. 179 in detail.

The nucleotide sequence of anti-CD3 scFv is shown as SEQ ID NO. 177 in detail.

The nucleotide sequence of OX40L extracellular region is shown as SEQ ID NO. 182 in detail.

The nucleotide sequence of CD3-OX40L BsM_M monomer linker is shown as SEQ ID NO. 136 in detail.

The nucleotide sequence of CD3-OX40L BsM_D dimer linker is shown as SEQ ID NO. 138 in detail.

In order to make bi-specific molecule successfully expressed in CHO-S cells and secreted into medium, signal peptide of antibody secretory expression was selected in this Embodiment.

The amino acid sequence of this secretory signal peptide is shown as SEQ ID NO.185 in detail.

The nucleotide sequence of this secretory signal peptide is shown as SEQ ID NO. 186 in detail.

2. Construction of Eukaryotic Expression Vector of CD3-OX40L BsM_M and CD3-OX40L BsM_D The construction and expression of this bi-specific molecule disclosure chose mammalian cell protein transient expression vector pcDNA3.1 (purchased from Invitrogen, Shanghai). In order to construct the monomer and dimer of bi-specific molecules, primers were designed as in table 3-3. All the primers were synthesized by Genewiz, Suzhou, and DNA template for PCR was synthesized by Synbio Technologies, Suzhou.

The cloning construct for CD3-OX40L BsM_M amplified signal peptide first by primers pcDNA3.1-Sig-F and Sig-R, and then amplified anti-CD3 scFv, (GGGGS) 3 Linker and OX40L extracellular domain sequence by primers Sig-CD3-F&CD3-R, and CD3-(GGGGS)$_3$-OX40L-F&pcDNA3.1-OX40L. The cloning construct for CD3-OX40L BsM_D amplified signal peptide first by primers pcDNA3.1-Sig-F and Sig-R, and then amplified anti-CD3 scFv, IgD hinge region Linker, and OX40L extracellular domain sequence by primers Sig-CD3-F&CD3-R, CD3-IgD-F&IgD-R, and IgD-OX40L-F&pcDNA3.1-OX40L-R. After PCR amplification, by using NovoRec®PCR one-step cloning kit (purchased from novoprotein, Wujiang), the full sequence of bi-specific molecule monomer and dimer were seperately ligated and seamlessly cloned into the pcDNA3.1 vector which was linearized by EcoRI and HindIII. The target vector was transformed into *E. Coli* DH5a, colony PCR was used for positive cloning identification, and the recombinant (recombinant plasmid) identified as positive was performed sequencing identification. The recombinants (recombinant plasmid) with right sequence were purified by midi-prep, and then transfected into CHO-S cells.

After sequencing, the CD3-OX40L BsM_M monomer and CD3-OX40L BsM_D dimer both had the right full DNA sequence as expected.

The nucleotide sequence of CD3-OX40L BsM_M monomer is shown as SEQ ID NO.158 in detail.

The nucleotide sequence of CD3-OX40L BsM_D dimer is shown as SEQ ID NO.160 in detail.

Embodiment 3-10: The Expression and Purification of CD3-OX40L BsM_M and CD3-OX40L BsM_D 1. The Expression of CD3-OX40L BsM_M and CD3-OX40L BsM_D 1.1 The cell density of CHO-S cells (purchased from Thermo Fisher Scientific) was 0.5~0.6×10$^6$/ml one day before transfection.

1.2 Calculating cell density at the day of transfection, performing plasmid transfection when the density is in th range of 1~1.4×10$^6$/ml and live percentageis >90%.

1.3 Transfection complex recipes: each project (CD3-OX40L BsM_M and CD3-OX40L BsM_D) needs two centrifuge tubes/flasks. Take total 20 ml as an example, put the recombinant plasmids from Embodiment 3-9 separately:

Tube 1: 600 μl PBS, 20 μg recombinant plasmid, mixing well.

Tube 2: 600 μl PBS, 20 μl FreeStyle™ MAX Transfection Reagent (purchased from Thermo Fisher Scientific), mixing well.

1.4 Mixing the diluted transfection reagent into the diluted recombinant plasmid, mixing well, which is transfection complex.

1.5 Keeping transfection complex for 15~20 min, adding it into cell culture by drops steadily.

1.6 Keeping cell culture after transfection at 37° C., $CO_2$ 8%, 130 rpm on cell shaker. Collecting medium after 5 days for the target protein test.

2. The Purification of CD3-OX40L BsM_M and CD3-OX40L BsM_D 2.1 Sample Pretreatment Get 20 ml cell medium after transfection, adding 20 mM PB, 200 mM NaCl, and adjusting pH to 7.5;

2.2 Purification of Protein L Affinity Chromatography Column

Protein purification chromatography column: Protein L affinity chromatography column (purchased from GE Healthcare, column volume: 1.0 ml)

Buffer A: PBS, pH7.4

Buffer B: 0.1M Glycine, pH3.0

Buffer C: 0.1M Glycine, pH2.7

Purification procedure: AKTA explorer 100 protein purification system (purchased from GE Healthcare) was used for purification. Pretreat Protein L affinity chromatography column with Buffer A, running culture medium sample, and collecting flowthrough sample. After running sample, balance chromatography column with at least 1.5 ml Buffer A, washing with Buffer B and Buffer C respectively after balance, and collecting flowthrough sample with target protein (the collection tube for flowthrough sample needs

TABLE 3-3

Primers used in CD3-OX40L bi-specific molecule gene cloning

| Primer name | Sequence | No. |
| --- | --- | --- |
| CD3-(GGGGS)$_3$-OX40L-F | CGGCACCAAGCTGGAGCTGAAGGGC GGCGGCGGCAGCGGCGGCGGCGGCA GCGGCGGCGGCGGCAGCCAGGTGAG CCACCGCTACCCCCG | SEQ ID NO.199 |
| pcDNA3.1-OX40 L-R | CTGATCAGCGGTTTAAACTTAAGCTT TCACAGCACGCAGAACTCGCCG | SEQ ID NO.200 |
| IgD-OX40L-F | CACACCCAGCCCCTGGGCGTGCAGG TGAGCCACCGCTACCCCCG | SEQ ID NO.201 | pretreated with 1% 1M Tris, pH8.0 to neutralize the pH of flowthrough sample, and the final concentration of Tris is about 10 mM). Finally, concentrate and dialyse into buffer PBS.

The final purified CD3-OX40L BsM_M and CD3-OX40L BsM_D recombinant protein was analyzed by SDS-PAGE, and the protein electrophoresis data under reduced and unreduced conditions were shown as FIG. 3-8. It shows that both purity of CD3-OX40L BsM_M and CD3-OX40L BsM_D recombinant protein are >95%. The theoretical molecular weight for CD3-OX40L BsM_M is 42.7 kDa, and protein displayed single band under reduced and unreduced conditions. Because of the N-glycosylation modification on OX40L extracellular domain, the real molecular weight of the band is bigger than theoretical value, so this bi-specific molecule is glycosylated monomer (FIG. 3-8A, Lane 1: protein marker for molecular weight; Lane 2: reduced CD3-OX40L BsM_M; Lane 3: unreduced CD3-OX40L BsM_M). The theoretical molecular weight for CD3-OX40L BsM_D is 50.6 kDa, and protein displayed the same molecular weight as glycosylated monomer under reduced condition, but the molecular weight is consistent with glycosylated dimer under unreduced condition (FIG. 3-8B, Lane 1: protein marker for molecular weight; Lane 2: reduced CD3-OX40L BsM_D; Lane 3: unreduced CD3-OX40L BsM_D), which indicate two protein link to each other by disulfide bond so that this bi-specific molecule is dimer.

Moreover, the N/C terminal sequence analysis for purified recombinant protein shows the reading frame has no error, consistent with the theoretical N/C terminal amino acid sequence. Mass spectrometry analysis further confirmed that CD3-OX40L BsM_M is monomer and CD3-OX40L BsM_D is dimer.

Therefore, the amino acid sequence of CD3-OX40L BsM_M monomer is shown as SEQ ID NO.157 in detail.

The amino acid sequence of CD3-OX40L BsM_D dimer is shown as SEQ ID NO.159 in detail.

The amino acid sequence of anti-CD3 scFv is shown as SEQ ID NO.169 in detail.

The amino acid sequence of anti-CD3 scFv heavy chain variable region is shown as SEQ ID NO.170 in detail.

The amino acid sequence of anti-CD3 scFv light chain variable region is shown as SEQ ID NO.171 in detail.

The amino acid sequence of OX40L extracellular domain is shown as SEQ ID NO.174 in detail.

The amino acid sequence of CD3-OX40L BsM_M monomer linker is shown as SEQ ID NO.135 in detail.

The amino acid sequence of CD3-OX40L BsM_D dimer linker is shown as SEQ ID NO.137 in detail.

Embodiment 3-11: CD3 Antigen-Binding and Co-Stimulatory Molecule OX40 Binding Activity Test of CD3-OX40L BsM_M and CD3-OX40L BsM_D by ELISA ELISA Procedure:
1. Recombinant antigen coating: 96-well plates were coated by human CD3-hFc and humanOX40-hFc recombinant protein (purchased from Novoprotein, Wujiang) 100 µl per well in concentration 1 µg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding PBSA (PBS+2% BSA (V/W)) 200 µl per well to block 1 hour at 37° C.

3. Adding sample: washing plates with PBS for 4 times, adding 100 µl per well of bi-specific antibody samples respectively and keeping plates at 37° C. for 1 hour. Sample serial dilution includes: using 10 µg/ml of purified CD3-OX40L BsM_M or CD3-OX40L BsM_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 µl per well and keeping plates at 37° C. for 1 hour. Washing plates with PBS for 4 times, adding 100 µl per well color-developing TMB (purchased from KPL), developing in dark for 5~10 min at room temperature.

5. Reaction termination and result test: adding 100 µl per well of stop buffer (1M HCl) to stop the reaction, and reading OD value of 450 nm absorbance on ELISA reader.

The results of ELISA are shown in FIGS. 3-9A and 3-9B. The three lines in the figure represent three test results: ■ coated with 1 µg/ml CD3-hFc recombinant antigen, ● coated with 1 µg/ml OX40-hFc recombinant antigen; ▲ no antigen coated result. FIG. 3-9A displays that CD3-OX40L BsM_M has antigen-binding activity with CD3-hFc and T cell co-stimulatory molecule OX40-hFc in vitro, among which OX40 has higher binding activity than that of CD3. FIG. 3-9B displays that CD3-OX40L BsM_D has antigen-binding activity with CD3-hFc and OX40-hFc in vitro as well, and OX40 has higher binding activity.

Embodiment 3-12: Cell Proliferation of Cytokine Induced Killer (CIK) Mediated by CD3-OX40L Bi-Specific Molecule Human PBMC (Peripheral blood mononuclear cell, PBMC) was used as experiment material. CD3-OX40L BsM_M monomer and CD3-OX40L BsM_D dimer produced by this disclosure, as well as full-length antibody anti-CD3/28 combination were added to PBMC from the same donor, respectively. Cells are counted after being cultured to compare cell proliferation.

1. Separating PBMC: adding the physiological saline of same volume into the anticoagulant blood, and adding Ficoll (purchased from GE Healthcare) of same volume into the mixed-blood slowly along the centrifuge tube wall. Keep different liquid surface clear, centrifuging at 2000 rpm for 20 min, and removing the white cell layer in the middle into a new centrifuge tube. Adding PBS with volume more than 2 times of the extracted cell layer to wash cells, centrifuging for 10 min at 1000 rpm, repeat washing once more, and adding some pre-cooling X-vivo 15 serum-free medium (purchased from Lonza) to resuspend cells. Counting the cells for use.

2. CIK cell culture and expansion: Resuspending PBMC with CIK basic medium (90% X-vivo15+10% FBS), and adjusting cell density to $1\times10^6$/ml. Setup three experiment groups: Control (coating plate with 5 µg/ml of anti-CD3 and 5 µg/ml of anti-CD28, full-length antibodies are all purchased from Novoprotein, Wujiang); Experiment 1 (adding 10 ng/ml of soluble bi-specific CD3-OX40L BsM_M); Experiment 2 (adding 10 ng/ml of soluble bi-specific CD3-OX40L BsM_D). All of the three groups were added with IFN-γ (200 ng/ml, purchased from Novoprotein, Wujiang) and IL-1B (2 ng/ml, purchased from Novoprotein, Wujiang), the cell culture was kept in incubator under the condition of saturated humidity, 37° C. and 5.0% $CO_2$. After overnight, adding 500U/ml of IL-2 (purchased from Novoprotein, Wujiang) into cell medium and keeping culture. Every 2-3 days, counting the cells and passaging cell at the density of $1×10^6$/ml in CIK basic medium with 500U/ml of IL-2. Keeping cell culture in this way for 30 days, counting the cells for expansion fold calculation, and drawing the cell growth curve.

The experiment results were shown as FIG. 3-10. CD3-OX40L bi-specific molecule monomer and dimer can better induce CIK expansion than anti-CD3/anti-CD28 monoclonal full-length antibody combination. Anti-CD3/anti-CD28 monoclonal full-length antibody combination induced severe cell death after culturing 18 days, and cell proliferation rate significantly reduced; meanwhile, neither CD3-OX40L BsM_M monomer nor CD3-OX40L BsM_D dimer induced cell death, but the cell proliferation rate was relatively slow. Therefore, both monomer and dimer of CD3-OX40L bi-specific molecules can effectively promote cell expansion and prolong the survival of CIK cell, among which dimer has better effect.

Embodiment 3-13 the Eukaryotic Expression Vector Construction of CD3-GITRL BsM_M and CD3-GITRL BsM_D In this disclosure, the bi-specific molecule targeted CD3 and co-stimulatory molecule ligand GITRL extracellular domain on human T cell is named as CD3-GITRL BsM.

1. CD3-GITRL BsM_M and CD3-GITRL M_D Construction Design

CD3-GITRL BsM_M Monomer construction design: the sequence of anti-CD3 scFv and GITRL extracellular domain sequence is linked by (GGGGS) 3 Linker.

CD3-GITRL BsM_D Dimer construction design: the sequence of anti-CD3 scFv and GITRL extracellular domain sequence is linked by IgD hinge region Linker.

In order to express the bi-specific antibody in mammalian cells, codon optimization of mammalian system was performed for the sequence of anti-CD3 scFv, GITRL extracellular domain and Linker.

The nucleotide sequence of anti-CD3 scFv heavy chain variable region is shown as SEQ ID NO. 178 in detail.

The nucleotide sequence of anti-CD3 scFv light chain variable region is shown as SEQ ID NO. 179 in detail.

The nucleotide sequence of anti-CD3 scFv is shown as SEQ ID NO. 177 in detail.

The nucleotide sequence of GITRL extracellular region is shown as SEQ ID NO. 183 in detail.

The nucleotide sequence of CD3-GITRL BsM_M monomer linker is shown as SEQ ID NO. 136 in detail.

The nucleotide sequence of CD3-GITRL BsM_D dimer linker is shown as SEQ ID NO. 138 in detail.

In order to make bi-specific molecule successfully expressed in CHO-S cells and secreted into medium, signal peptide of antibody secretory expression was selected in this Embodiment.

The amino acid sequence of this secretory signal peptide is shown as SEQ ID NO.185 in detail.

The nucleotide sequence of this secretory signal peptide is shown as SEQ ID NO. 186 in detail.

2. Construction of Eukaryotic Expression Vector of CD3-GITRL BsM_M and CD3-GITRL BsM_D The construction and expression of this bi-specific molecule disclosure chose mammalian cell protein transient expression vector pcDNA3.1 (purchased from Invitrogen, Shanghai). In order to construct the monomer and dimer of bi-specific molecules, primers were designed as in table 3-4. All the primers were synthesized by Genewiz, Suzhou, and DNA template for PCR was synthesized by Synbio Technologies, Suzhou.

The cloning construct for CD3-GITRL BsM_M amplified signal peptide first by primers pcDNA3.1-Sig-F and Sig-R, and then amplified anti-CD3 scFv, (GGGGS); Linker and GITRL extracellular domain sequence by primers Sig-CD3-F&CD3-R, and CD3-(GGGGS)₃-GITRL-F&pcDNA3.1-GITRL. The cloning construct for CD3-GITRL BsM_D amplified signal peptide first by primers pcDNA3.1-Sig-F and Sig-R, and then amplified anti-CD3 scFv, IgD hinge region Linker, and GITRL extracellular domain sequence by primers Sig-CD3-F&CD3-R, CD3-IgD-F&IgD-R, and IgD-GITRL-F&pcDNA3.1-GITRL-R. After PCR amplification, by using NovoRec®PCR one-step cloning kit (purchased from novoprotein, Wujiang), the full sequence of bi-specific molecule monomer and dimer were seperately ligated and seamlessly cloned into the pcDNA3.1 vector which was linearized by EcoRI and HindIII. The target vector was transformed into E. Coli DH5a, colony PCR was used for positive cloning identification, and the recombinant (recombinant plasmid) identified as positive was performed sequencing identification. The recombinants (recombinant plasmid) with right sequence were purified by midi-prep, and then transfected into CHO-S cells.

After sequencing, the CD3-GITRL BsM_M monomer and CD3-GITRL BsM_D dimer both had the right full DNA sequence as expected.

The nucleotide sequence of CD3-GITRL BsM_M monomer is shown as SEQ ID NO.162 in detail.

The nucleotide sequence of CD3-GITRL BsM_D dimer is shown as SEQ ID NO. 164 in detail.

TABLE 3-4

Primers used in CD3-GITRL bi-specific molecule gene cloning

| Primer name | Sequence | No. |
|---|---|---|
| CD3-(GGGGS)₃-GITRL-F | GGCACCAAGCTGGAGCTGAAGGGCGGCGGC GGCAGCGGCGGCGGCGGCAGCGGCGGCGGC GGCAGCCAGCTGGAGACCGCCAAGGAGC | SEQ ID NO.202 |
| pcDNA3.1-GITRL-R | CTGATCAGCGGTTTAAACTTAAGCTTTCAGC TGATGAACTGGGGGTTGGC | SEQ ID NO.203 |
| IgD-GITRL-F | CACACCCAGCCCCTGGGCGTGCAGCTGGAG ACCGCCAAGGAGC | SEQ ID NO.204 |

Embodiment 3-14: The Expression and Purification of CD3-GITRL BsM_M and CD3-GITRL BsM_D 1. The Expression of CD3-GITRL BsM_M and CD3-GITRL BsM_D 1.1 The cell density of CHO-S cells (purchased from Thermo Fisher Scientific) was 0.5~0.6×10⁶/ml one day before transfection.

1.2 Calculating cell density at the day of transfection, performing plasmid transfection when the density is in the range of 1~1.4×10⁶/ml and live percentage is >90%.

1.3 Transfection complex recipes: each project (CD3-GITRL BsM_M and CD3-GITRL BsM_D) needs two centrifuge tubes/flasks. Take total 20 ml as an example, put the recombinant plasmids from Embodiment 3-13 separately:

Tube 1: 600 µl PBS, 20 µg recombinant plasmid, mixing well.

Tube 2: 600 µl PBS, 20 µl FreeStyle™ MAX Transfection Reagent (purchased from Thermo Fisher Scientific), mixing well.

1.4 Mixing the diluted transfection reagent into the diluted recombinant plasmid, mixing well, which is transfection complex.

1.5 Keeping transfection complex for 15~20 min, adding it into cell culture by drops steadily.

1.6 Keeping cell culture after transfection at 37° C., $CO_2$ 8%, 130 rpm on cell shaker. Collecting medium after 5 days for the target protein test.

2. The Purification of CD3-GITRL BsM_M and CD3-GITRL BsM_D 2.1 Sample Pretreatment Get 20 ml cell medium after transfection, adding 20 mM PB, 200 mM NaCl, and adjusting pH to 7.5;

2.2 Purification of Protein L Affinity Chromatography Column

Protein purification chromatography column: Protein L affinity chromatography column (purchased from GE Healthcare, column volume: 1.0 ml)

Buffer A: PBS, pH7.4

Buffer B: 0.1M Glycine, pH3.0

Buffer C: 0.1M Glycine, pH2.7

Purification procedure: AKTA explorer 100 protein purification system (purchased from GE Healthcare) was used for purification. Pretreat Protein L affinity chromatography column with Buffer A, running culture medium sample, and collecting flowthrough sample. After running sample, balance chromatography column with at least 1.5 ml Buffer A, washing with Buffer B and Buffer C respectively after balance, and collecting flowthrough sample with target protein (the collection tube for flowthrough sample needs pretreated with 1% 1M Tris, pH8.0 to neutralize the pH of flowthrough sample, and the final concentration of Tris is about 10 mM). Finally, concentrate and dialyse into buffer PBS.

The final purified CD3-GITRL BsM_M and CD3-GITRL BsM_D recombinant protein was analyzed by SDS-PAGE, and the protein electrophoresis data under reduced and unreduced conditions were shown as FIG. 3-11. It shows that both purity of CD3-GITRL BsM_M and CD3-GITRL BsM_D recombinant protein are >95%. The theoretical molecular weight for CD3-GITRL BsM_M is 41.8 kDa, and protein displayed single band under reduced and unreduced conditions. Because of the N-glycosylation modification on OX40L extracellular domain, the real molecular weight of the band is bigger than theoretical value, so this bi-specific molecule is glycosylated monomer (FIG. 3-11A, Lane 1: protein marker for molecular weight; Lane 2: reduced CD3-GITRL BsM_M; Lane 3: unreduced CD3-GITRL BsM_M). The theoretical molecular weight for CD3-GITRL BsM_D is 49.7 kDa, and protein displayed the same molecular weight as glycosylated monomer under reduced condition, but the molecular weight is consistent with glycosylated dimer under unreduced condition (FIG. 3-11B, Lane 1: protein marker for molecular weight; Lane 2: reduced CD3-GITRL BsM_D; Lane 3: unreduced CD3-GITRL BsM_D), which indicate two protein link to each other by disulfide bond so that this bi-specific molecule is dimer.

Moreover, the N/C terminal sequence analysis for purified recombinant protein shows the reading frame has no error, consistent with the theoretical N/C terminal amino acid sequence. Mass spectrometry analysis further confirmed that CD3-GITRL BsM_M is monomer and CD3-GITRL BsM_D is dimer.

Therefore, the amino acid sequence of CD3-GITRL BsM_M monomer is shown as SEQ ID NO.161 in detail.

The amino acid sequence of CD3-GITRL BsM_D dimer is shown as SEQ ID NO.163 in detail.

The amino acid sequence of anti-CD3 scFv is shown as SEQ ID NO.169 in detail.

The amino acid sequence of anti-CD3 scFv heavy chain variable region is shown as SEQ ID NO.170 in detail.

The amino acid sequence of anti-CD3 scFv light chain variable region is shown as SEQ ID NO.171 in detail.

The amino acid sequence of GITRL extracellular domain is shown as SEQ ID NO.175 in detail.

The amino acid sequence of CD3-GITRL BsM_M monomer linker is shown as SEQ ID NO.135 in detail.

The amino acid sequence of CD3-GITRL BsM_D dimer linker is shown as SEQ ID NO.137 in detail.

Embodiment 3-15: CD3 Antigen-Binding and Co-Stimulatory Molecule GITR Binding Activity Test of CD3-GITRL BsM_M and CD3-GITRL BsM_D by ELISA ELISA Procedure:

1. Recombinant antigen coating: 96-well plates were coated by human CD3-hFc and human GITR-hFc recombinant protein (purchased from Novoprotein, Wujiang) 100 µl per well in concentration 1 µg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding PBSA (PBS+2% BSA (V/W)) 200 µl per well to block 1 hour at 37° C.

3. Adding sample: washing plates with PBS for 4 times, adding 100 µl per well bi-specific molecule samples respectively and keeping plates at 37° C. for 1 hour. Sample serial dilution includes: using 10 µg/ml of purified CD3GITRL BsM_M or CD3-GITRL BsM_D as starting concentration, diluting it into 6 gradient concentrations, and using 2 duplicate wells for each gradient.

4. Color developing: washing plates with PBST (PBS+ 0.05% Tween-20 (V/V)) for 4 times, diluting 1/5000 HRP labeled color-developing antibody (purchased from Abcam) by blocking buffer PBSA, adding 100 µl per well and keeping plates at 37° C. for 1 hour. Washing plates with PBS for 4 times, adding 100 µl per well color-developing TMB (purchased from KPL), developing in dark for 5~10 min at room temperature.

5. Reaction termination and result test: adding 100 µl per well of stop buffer (1M HCl) to stop the reaction, and reading OD value of 450 nm absorbance on ELISA reader.

The results of ELISA are shown in FIGS. 3-12A and 3-12B. The three lines in the figure represent three test results: ■ coated with 1 µg/ml CD3-hFc recombinant antigen, ✽ coated with 1 µg/ml GITR-hFc recombinant antigen; ▲ no antigen coated result. FIG. 3-12A displays that CD3-GITRL BsM_M has antigen-binding activity with CD3-hFc and T cell co-stimulatory molecule GITR-hFc in vitro, among which GITR has higher binding activity than that of CD3. FIG. 3-12B displays that CD3-GITRL BsM_D has antigen-binding activity with CD3-hFc and GITR-hFc in vitro as well, and GITR has higher binding activity.

Embodiment 3-16: Cell Proliferation of Cytokine Induced Killer (CIK) Mediated by CD3-GITRL Bi-Specific Molecule Human PBMC (Peripheral blood mononuclear cell, PBMC) was used as experiment material. CD3-GITRL BsM_M monomer and CD3-GITRL BsM_D dimer produced by this disclosure, as well as full-length antibody anti-CD3/28 combination were added to PBMC from the same donor, respectively. Cells are counted after being cultured to compare cell proliferation.

1. Separating PBMC: adding the physiological saline of same volume into the anticoagulant blood, and adding Ficoll (purchased from GE Healthcare) of same volume into the mixed-blood slowly along the centrifuge tube wall. Keep different liquid surface clear, centrifuging at 2000 rpm for 20 min, and removing the white cell layer in the middle into a new centrifuge tube. Adding PBS with volume more than 2 times of the extracted cell layer to wash cells, centrifuging for 10 min at 1000 rpm, repeat washing once more, and adding some pre-cooling X-vivo 15 serum-free medium (purchased from Lonza) to resuspend cells. Counting the cells for use.

2. CIK cell culture and expansion: Resuspending PBMC with CIK basic medium (90% X-vivo15+10% FBS), and adjusting cell density to $1\times10^6$/ml. Setup three experiment groups: Control (coating plate with 5 µg/ml of anti-CD3 and 5 µg/ml of anti-CD28, full-length antibodies are all purchased from Novoprotein, Wujiang); Experiment 1 (adding 10 ng/ml of soluble bi-specific CD3-GITRL BsM_M); Experiment 2 (adding 10 ng/ml of soluble bi-specific CD3-GITRL BsM_D). All of the three groups were added with IFN-γ (200 ng/ml, purchased from Novoprotein, Wujiang) and IL-1B (2 ng/ml, purchased from Novoprotein, Wujiang), the cell culture was kept in incubator under the condition of saturated humidity, 37° C. and 5.0% $CO_2$. After overnight, adding 500U/ml of IL-2 (purchased from Novoprotein, Wujiang) into cell medium and keeping culture. Every 2-3 days, counting the cells and passaging cell at the density of $1\times10^6$/ml in CIK basic medium with 500U/ml of IL-2. Keeping cell culture in this way for 30 days, counting the cells for expansion fold calculation, and drawing the cell growth curve.

The experiment results were shown as FIG. 3-13. CD3-GITRL bi-specific molecule monomer and dimer can better induce CIK expansion than anti-CD3/anti-CD28 monoclonal full-length antibody combination. Anti-CD3/anti-CD28 monoclonal full-length antibody combination induced severe cell death after culturing 18 days, and cell proliferation rate significantly reduced; meanwhile, neither CD3-GITRL BsM_M monomer nor CD3-GITRL BsM_D dimer induced cell death, but the cell proliferation rate was relatively slow. Therefore, both monomer and dimer of CD3-GITRL bi-specific molecules can effectively promote cell expansion and prolong the survival of CIK cell, among which dimer has better effect.

Embodiment 3-17 the Eukaryotic Expression Vector Construction of CD3-CD70 BsM_M and CD3-CD70 BsM_D In this disclosure, the bi-specific molecule targeted CD3 and co-stimulatory molecule ligand CD70 extracellular domain on human T cell is named as CD3-CD70 BsM.

1. CD3-CD70 BsM_M and CD3-CD70 M_D Construction Design

CD3-CD70 BsM_M Monomer construction design: the sequence of anti-CD3 scFv and CD70 extracellular domain sequence is linked by (GGGGS)₃ Linker.

CD3-CD70 BsM_D Dimer construction design: the sequence of anti-CD3 scFv and CD70 extracellular domain sequence is linked by IgD hinge region Linker.

In order to express the bi-specific antibody in mammalian cells, codon optimization of mammalian system was performed for the sequence of anti-CD3 scFv, CD70 extracellular domain and Linker.

The nucleotide sequence of anti-CD3 scFv heavy chain variable region is shown as SEQ ID NO. 178 in detail.

The nucleotide sequence of anti-CD3 scFv light chain variable region is shown as SEQ ID NO. 179 in detail.

The nucleotide sequence of anti-CD3 scFv is shown as SEQ ID NO. 177 in detail.

The nucleotide sequence of CD70 extracellular region is shown as SEQ ID NO. 184 in detail.

The nucleotide sequence of CD3-CD70 BsM_M monomer linker is shown as SEQ ID NO. 136 in detail.

The nucleotide sequence of CD3-CD70 BsM_D dimer linker is shown as SEQ ID NO. 138 in detail.

In order to make bi-specific molecule successfully expressed in CHO-S cells and secreted into medium, signal peptide of antibody secretory expression was selected in this Embodiment.

The amino acid sequence of this secretory signal peptide is shown as SEQ ID NO.185 in detail.

The nucleotide sequence of this secretory signal peptide is shown as SEQ ID NO. 186 in detail.

2. Construction of Eukaryotic Expression Vector of CD3-CD70 BsM_M and CD3-CD70 BsM_D The construction and expression of this bi-specific molecule disclosure chose mammalian cell protein transient expression vector pcDNA3.1 (purchased from Invitrogen, Shanghai). In order to construct the monomer and dimer of bi-specific molecules, primers were designed as in table 3-5. All the primers were synthesized by Genewiz, Suzhou, and DNA template for PCR was synthesized by Synbio Technologies, Suzhou.

The cloning construct for CD3-CD70 BsM_M amplified signal peptide first by primers pcDNA3.1-Sig-F and Sig-R, and then amplified anti-CD3 scFv, (GGGGS) 3 Linker and CD70 extracellular domain sequence by primers Sig-CD3-F&CD3-R, and CD3-(GGGGS)₃-CD70-F&pcDNA3.1-CD70-R. The cloning construct for CD3-CD70 BsM_D amplified signal peptide first by primers pcDNA3.1-Sig-F and Sig-R, and then amplified anti-CD3 scFv, IgD hinge region Linker, and CD70 extracellular domain sequence by primers Sig-CD3-F&CD3-R, CD3-IgD-F&IgD-R, and IgD-CD70-F&pcDNA3.1-CD70-R. After PCR amplification, by using NovoRec®PCR one-step cloning kit (purchased from novoprotein, Wujiang), the full sequence of bi-specific molecule monomer and dimer were seperately ligated and seamlessly cloned into the pcDNA3.1 vector which was linearized by EcoRI and HindIII. The target vector was transformed into *E. Coli* DH5a, colony PCR was used for positive cloning identification, and the recombinant (recombinant plasmid) identified as positive was performed sequencing identification. The recombinants (recombinant plasmid) with right sequence were purified by midi-prep, and then transfected into CHO-S cells.

After sequencing, the CD3-CD70 BsM_M monomer and CD3-CD70 BsM_D dimer both had the right full DNA sequence as expected.

The nucleotide sequence of CD3-CD70 BsM_M monomer is shown as SEQ ID NO.166 in detail.

The nucleotide sequence of CD3-CD70 BsM_D dimer is shown as SEQ ID NO.168 in detail.

TABLE 3-5

Primers used in CD3-CD70 bi-specific molecule gene cloning

| Primer name | Sequence | No. |
| --- | --- | --- |
| CD3-(GGGG S)₃-CD70-F | GGCACCAAGCTGGAGCTGAAGGGCGGCGGCGG CAGCGGCGGCGGCGGCAGCGGCGGCGGCGGCA GCCAGCGCTTCGCCCAGGCCCAGC | SEQ ID NO.205 |
| pcDNA3.1-C D70-R | CTGATCAGCGGTTTAAACTTAAGCTTTCAGGGG CGCACCCACTGCACGC | SEQ ID NO.206 |
| IgD-CD70-F | CACACCCAGCCCCTGGGCGTGCAGCGCTTCGCC CAGGCCCAGC | SEQ ID NO.207 |

Embodiment 3-18: The Expression and Purification of CD3-CD70 BsM_M and CD3-CD70 BsM_D 1. The Expression of CD3-CD70 BsM_M and CD3-CD70 BsM_D 1.1 The cell density of CHO-S cells (purchased from Thermo Fisher Scientific) was 0.5~0.6×10⁶/ml one day before transfection.

1.2 Calculating cell density at the day of transfection, performing plasmid transfection when the density is in the range of 1~1.4×10⁶/ml and live percentage is >90%.

1.3 Transfection complex recipes: each project (CD3-CD70 BsM_M and CD3-CD70 BsM_D) needs two centrifuge tubes/flasks. Take total 20 ml as an example, put the recombinant plasmids from Embodiment 3-17 separately:

Tube 1: 600 μl PBS, 20 μg recombinant plasmid, mixing well.

Tube 2: 600 μl PBS, 20 μl FreeStyle™ MAX Transfection Reagent (purchased from Thermo Fisher Scientific), mixing well.

1.4 Mixing the diluted transfection reagent into the diluted recombinant plasmid, mixing well, which is transfection complex.

1.5 Keeping transfection complex for 15~20 min, adding it into cell culture by drops steadily.

1.6 Keeping cell culture after transfection at 37° C., $CO_2$ 8%, 130 rpm on cell shaker. Collecting medium after 5 days for the target protein test.

2. The Purification of CD3-CD70 BsM_M and CD3-CD70 BsM_D 2.1 Sample Pretreatment Get 20 ml cell medium after transfection, adding 20 mM PB, 200 mM NaCl, and adjusting pH to 7.5;

2.2 Purification of Protein L Affinity Chromatography Column

Protein purification chromatography column: Protein L affinity chromatography column (purchased from GE Healthcare, column volume: 1.0 ml)

Buffer A: PBS, pH7.4
Buffer B: 0.1M Glycine, pH3.0
Buffer C: 0.1M Glycine, pH2.7

Purification procedure: AKTA explorer 100 protein purification system (purchased from GE Healthcare) was used for purification. Pretreat Protein L affinity chromatography column with Buffer A, running culture medium sample, and collecting flowthrough sample. After running sample, balance chromatography column with at least 1.5 ml Buffer A, washing with Buffer B and Buffer C respectively after balance, and collecting flowthrough sample with target protein (the collection tube for flowthrough sample needs pretreated with 1% 1M Tris, pH8.0 to neutralize the pH of flowthrough sample, and the final concentration of Tris is about 10 mM). Finally, concentrate and dialyse into buffer PBS.

The final purified CD3-CD70 BsM_M and CD3-CD70 BsM_D recombinant protein was analyzed by SDS-PAGE, and the protein electrophoresis data under reduced and unreduced conditions were shown as FIG. 3-14. It shows that both purity of CD3-CD70 BsM_M and CD3-CD70 BsM_D recombinant protein are >95%. The theoretical molecular weight for CD3-CD70 BsM_M is 44.4 kDa, and protein displayed single band under reduced and unreduced conditions. Because of the N-glycosylation modification on CD70 extracellular domain, the real molecular weight of the band is bigger than theoretical value, so this bi-specific molecule is glycosylated monomer (FIG. 3-14A, Lane 1: protein marker for molecular weight; Lane 2: reduced CD3-CD70 BsM_M; Lane 3: unreduced CD3-CD70 BsM_M). The theoretical molecular weight for CD3-CD70 BsM_D is 52.3 kDa, and protein displayed the same molecular weight as glycosylated monomer under reduced condition, but the molecular weight is consistent with glycosylated dimer under unreduced condition (FIG. 3-14B, Lane 1: protein marker for molecular weight; Lane 2: reduced CD3-CD70 BsM_D; Lane 3: unreduced CD3-CD70 BsM_D), which indicate two protein link to each other by disulfide bond so that this bi-specific molecule is dimer.

Moreover, the N/C terminal sequence analysis for purified recombinant protein shows the reading frame has no error, consistent with the theoretical N/C terminal amino acid sequence. Mass spectrometry analysis further confirmed that CD3-CD70 BsM_M is monomer and CD3-CD70 BsM_D is dimer.

Therefore, the amino acid sequence of CD3-CD70 BsM_M monomer is shown as SEQ ID NO.165 in detail.

The amino acid sequence of CD3-CD70 BsM_D dimer is shown as SEQ ID NO.167 in detail.

The amino acid sequence of anti-CD3 scFv is shown as SEQ ID NO.169 in detail.

The amino acid sequence of anti-CD3 scFv heavy chain variable region is shown as SEQ ID NO.170 in detail.

The amino acid sequence of anti-CD3 scFv light chain variable region is shown as SEQ ID NO.171 in detail.

The amino acid sequence of CD70 extracellular domain is shown as SEQ ID NO.176 in detail.

The amino acid sequence of CD3-CD70 BsM_M monomer linker is shown as SEQ ID NO.135 in detail.

The amino acid sequence of CD3-CD70 BsM_D dimer linker is shown as SEQ ID NO.137 in detail.

Embodiment 3-19: CD3 Antigen-Binding and Co-Stimulatory Molecule CD27 Binding Activity Test of CD3-CD70 BsM_M and CD3-CD70 BsM_D by ELISA ELISA Procedure:

1. Recombinant antigen coating: 96-well plates were coated by human CD3-hFc and human CD27-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding PBSA (PBS+2% BSA (V/W)) 200 μl per well to block 1 hour at 37° C.

3. Adding sample: washing plates with PBS for 4 times, adding 100 μl per well bi-specific molecule samples respectively and keeping plates at 37° C. for 1 hour. Sample serial dilution includes: using 10 μg/ml of purified CD3-CD70 BsM_M or CD3-CD70 BsM_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well color-developing TMB (purchased from KPL), develop in dark for 5~10 min at room temperature.

5. Reaction termination and result test: adding 100 μl per well of stop buffer (1M HCl) to stop the reaction, and reading OD value of 450 nm absorbance on ELISA reader.

The results of ELISA are shown in FIGS. 3-15A and 3-12B. The three lines in the figure represent three test results: ■ coated with 1 μg/ml CD3-hFc recombinant antigen, ✱ coated with 1 μg/ml CD27-hFc recombinant antigen; ▲ no antigen coated result. FIG. 3-15A displays that CD3-CD70 BsM_M has antigen-binding activity with CD3-hFc and T cell co-stimulatory molecule CD27-hFc in vitro, among which CD27 has higher binding activity than that of CD3. FIG. 3-15B displays that CD3-CD70 BsM_D has antigen-binding activity with CD3-hFc and CD27-hFc in vitro as well, and CD27 has higher binding activity.

Embodiment 3-20: Cell Proliferation of Cytokine Induced Killer (CIK) Mediated by CD3-CD70 Bi-Specific Molecule Human PBMC (Peripheral blood mononuclear cell, PBMC) was used as experiment material. CD3-CD70 BsM_M monomer and CD3-CD70 BsM_D dimer produced by this disclosure, as well as full-length antibody anti-CD3/28 combination were added to PBMC from the same donor, respectively. Cells are counted after being cultured to compare cell proliferation.

1. Separating PBMC: adding the physiological saline of same volume into the anticoagulant blood, and adding Ficoll (purchased from GE Healthcare) of same volume into the mixed-blood slowly along the centrifuge tube wall. Keep different liquid surface clear, centrifuging at 2000 rpm for 20 min, and removing the white cell layer in the middle into a new centrifuge tube. Adding PBS with volume more than 2 times of the extracted cell layer to wash cells, centrifuging for 10 min at 1000 rpm, repeat washing once more, and adding some pre-cooling X-vivo 15 serum-free medium (purchased from Lonza) to resuspend cells. Counting the cells for use.

2. CIK cell culture and expansion: Resuspending PBMC with CIK basic medium (90% X-vivo15+10% FBS), and adjusting cell density to $1 \times 10^6$/ml. Setup three experiment groups: Control (coating plate with 5 μg/ml of anti-CD3 and 5 μg/ml of anti-CD28, full-length antibodies are all purchased from Novoprotein, Wujiang); Experiment 1 (adding 10 ng/ml of soluble bi-specific CD3-CD70 BsM_M); Experiment 2 (adding 10 ng/ml of soluble bi-specific CD3-CD70 BsM_D). All of the three groups were added with IFN-γ (200 ng/ml, purchased from Novoprotein, Wujiang) and IL-1B (2 ng/ml, purchased from Novoprotein, Wujiang), the cell culture was kept in incubator under the condition of saturated humidity, 37° C. and 5.0% $CO_2$. After overnight, adding 500U/ml of IL-2 (purchased from Novoprotein, Wujiang) into cell medium and keeping culture. Every 2-3 days, counting the cells and passaging cell at the density of $1 \times 10^6$/ml in CIK basic medium with 500U/ml of IL-2. Keeping cell culture in this way for 30 days, counting the cells for expansion fold calculation, and drawing the cell growth curve.

The experiment results were shown as FIG. 3-16. CD3-CD70 bi-specific molecule monomer and dimer can better induce CIK expansion than anti-CD3/anti-CD28 monoclonal full-length antibody combination. Anti-CD3/anti-CD28 monoclonal full-length antibody combination induced severe cell death after culturing 18 days, and cell proliferation rate significantly reduced; Meanwhile, neither CD3-CD70 BsM_M monomer nor CD3-CD70 BsM_D dimer induced cell death, but the cell proliferation rate was relatively slow. Therefore, both monomer and dimer of CD3-CD70 bi-specific molecules can effectively promote cell expansion and prolong the survival of CIK cell, among which dimer has better effect.

Embodiment 4-1 the Eukaryotic Expression Vector Construction of CD3-PD-1 BsAb_M and CD3-PD-1 BsAb_D In this disclosure, the bi-specific antibody targeted CD3 and inhibitory molecule PD-1 on human T cell is named as CD3-PD-1 BsAb.

1. CD3-PD-1 BsAb_M and CD3-PD-1 BsAb_D Construction Design

CD3-PD-1 BsAb_M Monomer construction design: the sequence of anti-CD3 scFv and PD-1 scFv is linked by (GGGGS) 3 Linker.

CD3-PD-1 BsAb_D Dimer construction design: the sequence of anti-CD3 scFv and PD-1 scFv is linked by IgD hinge region Linker.

In order to express the bi-specific antibody in mammalian cells, codon optimization of mammalian system was performed for the sequence of anti-CD3 scFv, PD-1 scFv and Linker.

The nucleotide sequence of anti-CD3 scFv heavy chain variable region is shown as SEQ ID NO. 264 in detail.

The nucleotide sequence of anti-CD3 scFv light chain variable region is shown as SEQ ID NO. 265 in detail.

The nucleotide sequence of anti-CD3 scFv is shown as SEQ ID NO. 263 in detail.

The nucleotide sequence of PD-1 scFv heavy chain variable region is shown as SEQ ID NO. 267 in detail.

The nucleotide sequence of PD-1 scFv light chain variable region is shown as SEQ ID NO. 268 in detail.

The nucleotide sequence of PD-1 scFv is shown as SEQ ID NO. 266 in detail.

The nucleotide sequence of CD3-PD-1 BsAb_M monomer linker is shown as SEQ ID NO. 209 in detail.

The nucleotide sequence of CD3-PD-1 BsAb_D dimer linker is shown as SEQ ID NO. 211 in detail.

In order to make bi-specific antibody successfully expressed in CHO-S cells and secreted into medium, signal peptide of antibody secretory expression was selected in this Embodiment.

The amino acid sequence of this secretory signal peptide is shown as SEQ ID NO.284 in detail.

The nucleotide sequence of this secretory signal peptide is shown as SEQ ID NO. 285 in detail.

The cloning construct for CD3-PD-1 BsAb_M amplified signal peptide first by primers pcDNA3.1-Sig-F and Sig-R, and then amplified anti-CD3 scFv, (GGGGS) 3 Linker and PD-1 scFv by primers Sig-CD3-F&CD3-R, and CD3-(GGGGS)$_3$-PD-1-F&pcDNA3.1-PD-1-R. The cloning construct for CD3-PD-1 BsAb_D amplified signal peptide first by primers pcDNA3.1-Sig-F and Sig-R, and then amplified anti-CD3 scFv, IgD hinge region Linker, and PD-1 scFv by primers Sig-CD3-F&CD3-R, CD3-IgD-F&IgD-R, and IgD-PD-1-F&pcDNA3.1-PD-1-R. After PCR amplification, by using NovoRec®PCR one-step cloning kit (purchased from novoprotein, Wujiang), the full sequence of bi-specific antibody monomer and dimer were seperately ligated and seamlessly cloned into the pcDNA3.1 vector which was linearized by EcoRI and HindIII. The target vector was transformed into E. Coli DH5a, colony PCR was used for positive cloning identification, and the recombinant (recombinant plasmid) identified as positive was performed sequencing identification. The recombinants (recombinant plasmid) with right sequence were purified by midi-prep, and then transfected into CHO-S cells.

After sequencing, the CD3-PD-1 BsAb_M monomer and CD3-PD-1 BsAb_D dimer both had the right full DNA sequence as expected.

The nucleotide sequence of CD3-PD-1 BsAb_M monomer is shown as SEQ ID NO.219 in detail.

The nucleotide sequence of CD3-PD-1 BsAb_D dimer is shown as SEQ ID NO.221 in detail.

TABLE 4-1

Primers used in CD3-PD-1 bi-specific antibody gene cloning

| Primer name | Sequence | No. |
| --- | --- | --- |
| pcDNA3.1-Sig-F | GTGCTGGATATCTGCAGAATTCGCCGCCACCATG ACCCGGCTGACCGTGCTGGCCCTGC | SEQ ID NO.286 |
| Sig-R | GGCCCTGGAGGAGGCCAGCAGGCCGGCCAGCAG GGCCAGCACGGTCAGC | SEQ ID NO.287 |
| Sig-CD3-F | GCTGGCCTCCTCCAGGGCCGACATCAAGCTGCAG CAGAGCG | SEQ ID NO.288 |
| CD3-R | CTTCAGCTCCAGCTTGGTGC | SEQ ID NO.289 |
| CD3-(GGGGS)$_3$-PD-1-F | GGCACCAAGCTGGAGCTGAAGGGCGGCGGCGGC AGCGGCGGCGGCGGCAGCGGCGGCGGCGGCAGC CAGGTGCAGCTGGTGGAGAGCGGCG | SEQ ID NO.290 |
| pcDNA3.1-PD-1-R | CTGATCAGCGGTTTAAACTTAAGCTTTCAGCGCT TGATCTCCACCTTGG | SEQ ID NO.291 |
| CD3-IgD-F | GCACCAAGCTGGAGCTGAAGGCCAGCAAGAGCA AGAAGGAG | SEQ ID NO.292 |
| IgD-R | CACGCCCAGGGGCTGGGTGTG | SEQ ID NO.293 |
| IgD-PD-1-F | CACACCCAGCCCCTGGGCGTGCAGGTGCAGCTG GTGGAGAGCG | SEQ ID NO.294 |

2. Construction of Eukaryotic Expression Vector of CD3-PD-1 BsAb_M and CD3-PD-1 BsAb_D The construction and expression of this bi-specific antibody disclosure chose mammalian cell protein transient expression vector pcDNA3.1 (purchased from Invitrogen, Shanghai). In order to construct the monomer and dimer of bi-specific antibodys, primers were designed as in table 4-1. All the primers were synthesized by Genewiz, Suzhou, and DNA template for PCR was synthesized by Synbio Technologies, Suzhou.

Embodiment 4-2: The Expression and Purification of CD3-PD-1 BsAb_M and CD3-PD-1 BsAb_D 1. The Expression of CD3-PD-1 BsAb_M and CD3-PD-1 BsAb_D 1.1 The cell density of CHO-S cells (purchased from Thermo Fisher Scientific) was $0.5 \sim 0.6 \times 10^6$/ml one day before transfection.

1.2 Calculating cell density at the day of transfection, performing plasmid transfection when the density is in the range of $1 \sim 1.4 \times 10^6$/ml and live percentage>90%.

1.3 Transfection complex recipes: each project (CD3-PD-1 BsAb_M and CD3-PD-1 BsAb_D) needs two centrifuge tubes/flasks. Take total 20 ml as an example, put the recombinant plasmids from Embodiment 4-1 separately:

Tube 1: 600 μl PBS, 20 μg recombinant plasmid, mixing well.

Tube 2: 600 μl PBS, 20 μl FreeStyle™ MAX Transfection Reagent (purchased from Thermo Fisher Scientific), mixing well.

1.4 Mixing the diluted transfection reagent into the diluted recombinant plasmid, mixing well, which is transfection complex.

1.5 Keeping transfection complex for 15~20 min, adding it into cell culture by drops steadily.

1.6 Keeping cell culture after transfection at 37° C., $CO_2$ 8%, 130 rpm on cell shaker. Collecting medium after 5 days for the target protein test.

2. The Purification of CD3-PD-1 BsAb_M and CD3-PD-1 BsAb_D 2.1 Sample Pretreatment Taking 20 ml cell medium after transfection, adding 20 mM PB, 200 mM NaCl, and adjusting pH to 7.5;

2.2 Purification of Protein L Affinity Chromatography Column

Protein purification chromatography column: Protein L affinity chromatography column (purchased from GE Healthcare, column volume: 1.0 ml)

Buffer A: PBS, pH7.4
Buffer B: 0.1M Glycine, pH3.0
Buffer C: 0.1M Glycine, pH2.7

Purification procedure: AKTA explorer 100 protein purification system (purchased from GE Healthcare) was used for purification. Pretreat Protein L affinity chromatography column with Buffer A, running culture medium sample, and collecting flowthrough sample. After running sample, balance chromatography column with at least 1.5 ml Buffer A, washing with Buffer B and Buffer C respectively after balance, and collecting flowthrough sample with target protein (the collection tube for flowthrough sample needs pretreated with 1% 1M Tris, pH8.0 to neutralize the pH of flowthrough sample, and the final concentration of Tris is about 10 mM). Finally, concentrate and dialyse into buffer PBS.

The final purified CD3-PD-1 BsAb_M and CD3-PD-1 BsAb_D recombinant protein was analyzed by SDS-PAGE, and the protein electrophoresis data under reduced and unreduced conditions were shown as FIG. 4-2. It shows that both purity of CD3-PD-1 BsAb_M and CD3-PD-1 BsAb_D recombinant protein are >95%. The theoretical molecular weight for CD3-PD-1 BsAb_M is 52.5 kDa, and protein displayed the same single band under reduced and unreduced conditions. The molecular weight of these bands is consistent with monomer, so this bi-specific antibody is monomer (FIG. 4-2A, Lane 1: protein marker for molecular weight; Lane 2: reduced CD3-PD-1 BsAb_M; Lane 3: unreduced CD3-PD-1 BsAb_M). The theoretical molecular weight for CD3-PD-1 BsAb_D is 60.4 kDa, and protein displayed the same molecular weight as monomer under reduced condition, but the molecular weight is consistent with dimer under unreduced condition (FIG. 4-2B, Lane 1: protein marker for molecular weight; Lane 2: reduced CD3-PD-1 BsAb_D; Lane 3: unreduced CD3-PD-1 BsAb_D), which indicate two protein link to each other by disulfide bond so that this bi-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD3-PD-1 BsAb_M is monomer and CD3-PD-1 BsAb_D is dimer.

Therefore, the amino acid sequence of CD3-PD-1 BsAb_M monomer is shown as SEQ ID NO.218 in detail.

The amino acid sequence of CD3-PD-1 BsAb_D dimer is shown as SEQ ID NO.220 in detail.

The amino acid sequence of anti-CD3 scFv is shown as SEQ ID NO.242 in detail.

The amino acid sequence of anti-CD3 scFv heavy chain variable region is shown as SEQ ID NO.243 in detail.

The amino acid sequence of anti-CD3 scFv light chain variable region is shown as SEQ ID NO.244 in detail.

The amino acid sequence of anti-PD-1 scFv is shown as SEQ ID NO.245 in detail.

The amino acid sequence of anti-PD-1 scFv heavy chain variable region is shown as SEQ ID NO.246 in detail.

The amino acid sequence of anti-PD-1 scFv light chain variable region is shown as SEQ ID NO.247 in detail.

The amino acid sequence of CD3-PD-1 BsAb_M monomer linker is shown as SEQ ID NO.208 in detail: GGGGSGGGGSGGGGS.

The amino acid sequence of CD3-PD-1 BsAb_D dimer linker is shown as SEQ ID NO.210 in detail.

Embodiment 4-3: Antigen-Binding Activity Test of CD3-PD-1 BsAb_M and CD3-PD-1 BsAb_D by ELISA ELISA Procedure:

1. Recombinant antigen coating: 96-well plates were coated by human CD3-hFc and human PD-1-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding PBSA (PBS+2% BSA (V/W)) 200 μl per well to block 1 hour at 37° C.

3. Adding sample: washing plates with PBS for 4 times, adding 100 μl per well of bi-specific antibody samples respectively and keeping plates at 37° C. for 1 hour. Sample serial dilution includes: using 10 μg/ml of purified CD3-PD-1 BsAb_M or CD3-PD-1 BsAb_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well color-developing TMB (purchased from KPL), develop in dark for 5~10 min at room temperature.

5. Reaction termination and result test: adding 100 μl per well of stop buffer (1M HCl) to stop the reaction, and reading OD value of 450 nm absorbance on ELISA reader.

The results of ELISA are shown in FIGS. 4-3A and 4-3B. The three lines in the figure represent three test results: ■ coated with 1 μg/ml CD3-hFc recombinant antigen, ✱ coated with 1 μg/ml PD-1-hFc recombinant antigen; ▲ no antigen coated result. FIG. 4-3A displays that CD3-PD-1 BsAb_M has antigen-binding activity with CD3-hFc and PD-1-hFc in vitro, among which PD-1 has higher binding activity than that of CD3. FIG. 4-3B displays that CD3-PD-1 BsAb_D has antigen-binding activity with CD3-hFc and PD-1-hFc in vitro as well, and PD-1 has higher binding activity.

Embodiment 4-4: Cell Proliferation of Cytokine Induced Killer (CIK) Mediated by CD3-PD-1 Bi-Specific Antibody Human PBMC (Peripheral blood mononuclear cell, PBMC) was used as experiment material. CD3-PD-1 BsAb_M monomer and CD3-PD-1 BsAb_D dimer produced by this disclosure, as well as full-length antibody anti-CD3/28 combination were added to PBMC from the same donor, respectively. Cells are counted after being cultured to compare cell proliferation.

1. Separating PBMC: adding the physiological saline of same volume into the anticoagulant blood, and adding Ficoll (purchased from GE Healthcare) of same volume into the mixed-blood slowly along the centrifuge tube wall. Keeping different liquid surface clear, centrifuging at 2000 rpm for 20 min, and removing the white cell layer in the middle into a new centrifuge tube. Adding PBS with volume more than 2 times of the extracted cell layer to wash cells, centrifuging for 10 min at 1000 rpm, repeat washing once more, and adding some pre-cooling X-vivo 15 serum-free medium (purchased from Lonza) to resuspend cells. Counting the cells for use.

2. CIK cell culture and expansion: Resuspending PBMC with CIK basic medium (90% X-vivo15+10% FBS), and adjusting cell density to $1\times10^6$/ml. Setup three experiment groups: Control (coating plate with 5 µg/ml of anti-CD3 and 5 µg/ml of anti-CD28, full-length antibodies are all purchased from Novoprotein, Wujiang); Experiment 1 (adding 10 ng/ml of soluble bi-specific CD3-PD-1 BsAb_M); Experiment 2 (adding 10 ng/ml of soluble bi-specific CD3-PD-1 BsAb_D). All of the three groups were added with IFN-γ (200 ng/ml, purchased from Novoprotein, Wujiang) and IL-1B (2 ng/ml, purchased from Novoprotein, Wujiang), the cell culture was kept in incubator under the condition of saturated humidity, 37° C. and 5.0% $CO_2$. After overnight, adding 500U/ml of IL-2 (purchased from Novoprotein, Wujiang) into cell medium and keeping culture. Every 2-3 days, counting the cells and passaging cell at the density of $1\times10^6$/ml in CIK basic medium with 500U/ml of IL-2. Keeping cell culture in this way for 30 days, counting the cells for expansion fold calculation, and drawing the cell growth curve.

The experiment results were shown as FIG. 4-4. CD3-PD-1 bi-specific antibody monomer and dimer can better induce CIK expansion than anti-CD3/anti-CD28 monoclonal full-length antibody combination. Anti-CD3/anti-CD28 monoclonal full-length antibody combination induced severe cell death after culturing 18 days, and cell proliferation rate significantly reduced; meanwhile, neither CD3-PD-1 BsAb_M monomer nor CD3-PD-1 BsAb_D dimer induced cell death, but the cell proliferation rate was relatively slow. Therefore, both monomer and dimer of CD3-PD-1 bi-specific antibodies can effectively promote cell expansion and prolong the survival of CIK cell, among which dimer has better effect.

Embodiment 4-5: IFN-γ of CIK Induced by CD3-PD-1 Bi-Specific Antibody

Procedure:

1. Collecting 100 µl CIK cell culture supernatant after 25 days from Embodiment 4-4 (adjusting to the same cell density, cell number is $2\times10^5$), incubate for 45 min at 37° C., and test by Human IFN-γ ELISA kit (purchased from Boster Biological Technology). Triplet for three group samples.

2. Washing with PBS for three times, adding HRP labeled IFN-γ antibody, and incubate for 45 min at 37° C.

3. Washing with PBS for three times, and then adding TIMB 100 µl to develop color. Developing at room temperature for 5-10 min.

4. Stop reaction with stop buffer HCl (1M), and then read OD value of 450 nm wavelength.

The experiment results were shown as FIG. 4-5. The amount of IFN-γ secreted by CIK cultured with anti-CD3/anti-CD28 monoclonal full-length antibody combination was defined as 1, so the relative amount of IFN-γ secreted by CIK cultured with soluble CD3-PD-1 BsAb_M monomer is 2.45 and the relative amount of IFN-γ secreted by CIK cultured with soluble CD3-PD-1 BsAb_D dimer is 4.12. Therefore, both monomer and dimer of CD3-PD-1 bi-specific antibody can effectively activate CIK cells and induce IFN-γ secretion, among which dimer has better effect.

Embodiment 4-6 the Eukaryotic Expression Vector Construction of CD3-CTLA-4 BsAb_M and CD3-CTLA-4 BsAb_D In this disclosure, the bi-specific antibody targeted CD3 and inhibitory molecule CTLA-4 on human T cell is named as CD3-CTLA-4 BsAb.

1. CD3-CTLA-4 BsAb_M and CD3-CTLA-4 BsAb_D Construction Design

CD3-CTLA-4 BsAb_M Monomer construction design: the sequence of anti-CD3 scFv and CTLA-4 scFv is linked by (GGGGS) 3 Linker.

CD3-CTLA-4 BsAb_D Dimer construction design: the sequence of anti-CD3 scFv and CTLA-4 scFv is linked by IgD hinge region Linker.

In order to express the bi-specific antibody in mammalian cells, codon optimization of mammalian system was performed for the sequence of anti-CD3 scFv, CTLA-4 scFv and Linker.

The nucleotide sequence of anti-CD3 scFv heavy chain variable region is shown as SEQ ID NO. 264 in detail.

The nucleotide sequence of anti-CD3 scFv light chain variable region is shown as SEQ ID NO. 265 in detail.

The nucleotide sequence of anti-CD3 scFv is shown as SEQ ID NO. 263 in detail.

The nucleotide sequence of CTLA-4 scFv heavy chain variable region is shown as SEQ ID NO. 270 in detail.

The nucleotide sequence of CTLA-4 scFv light chain variable region is shown as SEQ ID NO. 271 in detail.

The nucleotide sequence of CTLA-4 scFv is shown as SEQ ID NO. 269 in detail.

The nucleotide sequence of CD3-CTLA-4 BsAb_M monomer linker is shown as SEQ ID NO. 209 in detail.

The nucleotide sequence of CD3-CTLA-4 BsAb_D dimer linker is shown as SEQ ID NO. 211 in detail.

In order to make bi-specific antibody successfully expressed in CHO-S cells and secreted into medium, signal peptide of antibody secretory expression was selected in this Embodiment.

The amino acid sequence of this secretory signal peptide is shown as SEQ ID NO.284 in detail.

The nucleotide sequence of this secretory signal peptide is shown as SEQ ID NO. 285 in detail.

2. Construction of Eukaryotic Expression Vector of CD3-CTLA-4 BsAb_M and CD3-CTLA-4 BsAb_D The construction and expression of this bi-specific antibody disclosure chose mammalian cell protein transient expression vector pcDNA3.1 (purchased from Invitrogen, Shanghai). In order to construct the monomer and dimer of bi-specific antibodys, primers were designed as in table 4-2. All the primers were synthesized by Genewiz, Suzhou, and DNA template for PCR was synthesized by Synbio Technologies, Suzhou.

The cloning construct for CD3-CTLA-4 BsAb_M amplified signal peptide first by primers pcDNA3.1-Sig-F and Sig-R, and then amplified anti-CD3 scFv, (GGGGS)$_3$ Linker and CTLA-4 scFv by primers Sig-CD3-F&CD3-R, and CD3-(GGGGS)$_3$-CTLA-4-F&pcDNA3.1-CTLA-4-R. The cloning construct for CD3-CTLA-4 BsAb_D amplified signal peptide first by primers pcDNA3.1-Sig-F and Sig-R, and then amplified anti-CD3 scFv, IgD hinge region Linker, and CTLA-4 scFv by primers Sig-CD3-F&CD3-R, CD3-IgD-F&IgD-R, and IgD-CTLA-4-F&pcDNA3.1-CTLA-4-R. After PCR amplification, by using NovoRec®PCR one-step cloning kit (purchased from novoprotein, Wujiang), the full sequence of bi-specific antibody monomer and dimer were seperately ligated and seamlessly cloned into the pcDNA3.1 vector which was linearized by EcoRI and HindIII. The target vector was transformed into *E. Coli* DH5α, colony PCR was used for positive cloning identification, and the recombinant (recombinant plasmid) identified as positive was performed sequencing identification. The recombinants (recombinant plasmid) with right sequence were purified by midi-prep, and then transfected into CHO-S cells.

After sequencing, the CD3-CTLA-4 BsAb_M monomer and CD3-CTLA-4 BsAb_D dimer both had the right full DNA sequence as expected.

The nucleotide sequence of CD3-CTLA-4 BsAb_M monomer is shown as SEQ ID NO.223 in detail.

The nucleotide sequence of CD3-CTLA-4 BsAb_D dimer is shown as SEQ ID NO.225 in detail.

centrifuge tubes/flasks. Take total 20 ml as an example, put the recombinant plasmids from Embodiment 4-6 separately:

Tube 1: 600 μl PBS, 20 μg recombinant plasmid, mixing well.

Tube 2: 600 μl PBS, 20 μl FreeStyle™ MAX Transfection Reagent (purchased from Thermo Fisher Scientific), mixing well.

1.4 Mixing the diluted transfection reagent into the diluted recombinant plasmid, mixing well, which is transfection complex.

1.5 Keeping transfection complex for 15~20 min, adding it into cell culture by drops steadily.

1.6 Keeping cell culture after transfection at 37° C., $CO_2$ 8%, 130 rpm on cell shaker. Collecting medium after 5 days for the target protein test.

2. The Purification of CD3-CTLA-4 BsAb_M and CD3-CTLA-4 BsAb_D 2.1 Sample Pretreatment Get 20 ml cell medium after transfection, adding 20 mM PB, 200 mM NaCl, and adjusting pH to 7.5;

2.2 Purification of Protein L Affinity Chromatography Column

Protein purification chromatography column: Protein L affinity chromatography column (purchased from GE Healthcare, column volume: 1.0 ml)

Buffer A: PBS, pH7.4

Buffer B: 0.1M Glycine, pH3.0

Buffer C: 0.1M Glycine, pH2.7

Purification procedure: AKTA explorer 100 protein purification system (purchased from GE Healthcare) was used for purification. Pretreat Protein L affinity chromatography column with Buffer A, running culture medium sample, and collecting flowthrough sample. After running sample, balance chromatography column with at least 1.5 ml Buffer A, washing with Buffer B and Buffer C respectively after balance, and collecting flowthrough sample with target protein (the collection tube for flowthrough sample needs pretreated with 1% 1M Tris, pH8.0 to neutralize the pH of

TABLE 4-2

Primers used in CD3-CTLA-4 bi-specific antibody gene cloning

| Primer name | Sequence | No. |
|---|---|---|
| CD3-(GGGG S)$_3$-CTLA-4-F | GGCACCAAGCTGGAGCTGAAGGGCGGCGGCGG CAGCGGCGGCGGCGGCAGCGGCGGCGGCGGCA GCCAGGTGCAGCTGGTGGAGAGC | SEQ ID NO.295 |
| pcDNA3.1-C TLA-4-R | CTGATCAGCGGTTTAAACTTAAGCTTTCAGCGCT TGATCTCCACCTTGG | SEQ ID NO.296 |
| IgD-CTLA-4-F | ACACCCAGCCCCTGGGCGTGCCAAGGTGGAGAT CAAGCGC | SEQ ID NO.297 |

Embodiment 4-7: The Expression and Purification of CD3-CTLA-4 BsAb_M and CD3-CTLA-4 BsAb_D 1. The Expression of CD3-CTLA-4 BsAb_M and CD3-CTLA-4 BsAb_D 1.1 The cell density of CHO-S cells (purchased from Thermo Fisher Scientific) was 0.5~0.6×10$^6$/ml one day before transfection.

1.2 Calculating cell density at the day of transfection, performing plasmid transfection when the density is in the range of 1~1.4×10$^6$/ml and live percentage>90%.

1.3 Transfection complex recipes: each project (CD3-CTLA-4 BsAb_M and CD3-CTLA-4 BsAb_D) needs two flowthrough sample, and the final concentration of Tris is about 10 mM). Finally, concentrate and dialyse into buffer PBS.

Figures 1, 2, 3, 4, 5, 6:
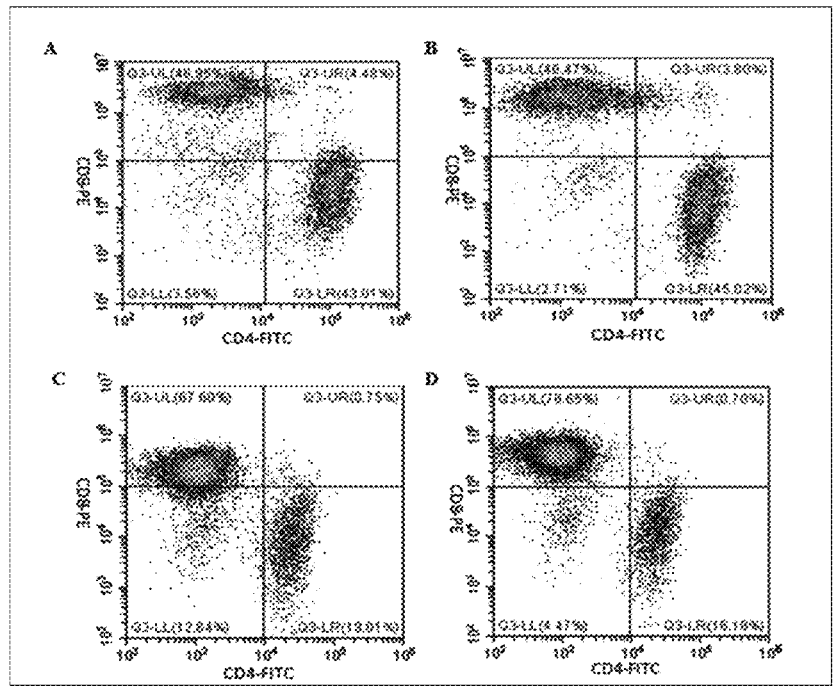
Figures 1, 2:
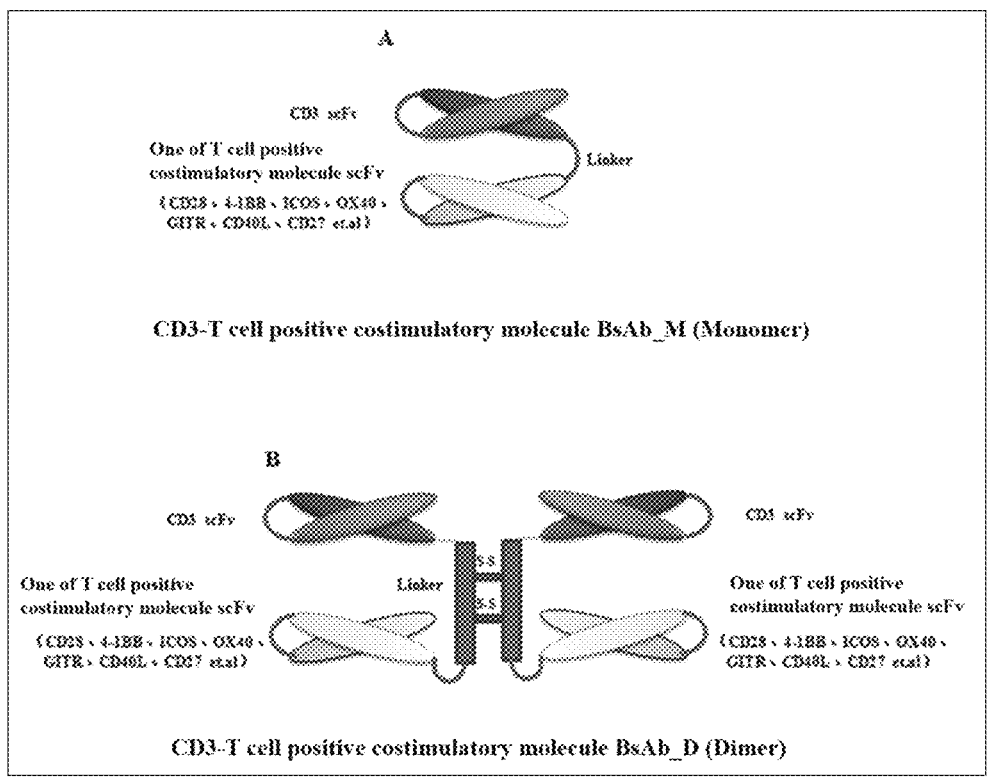
Figure 2:
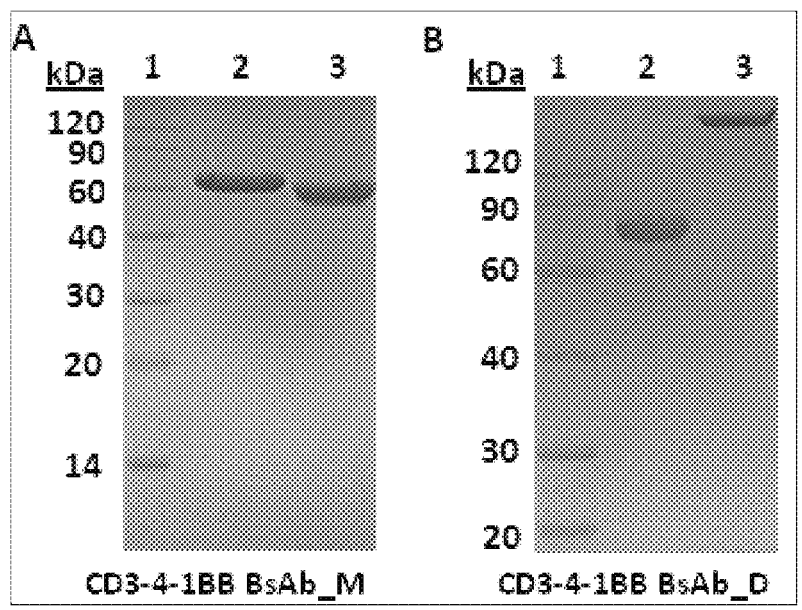
Figures 2, 3, 3A:
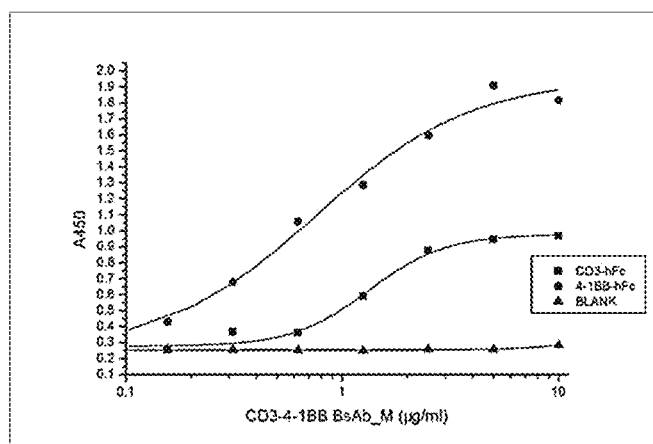
Figures 2, 3, 3B:
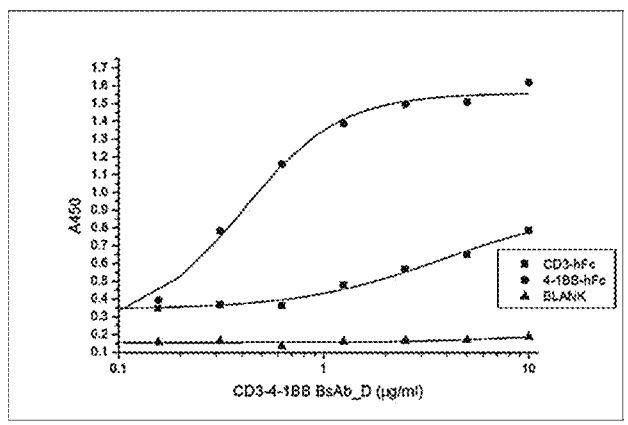
Figures 2, 3, 4:
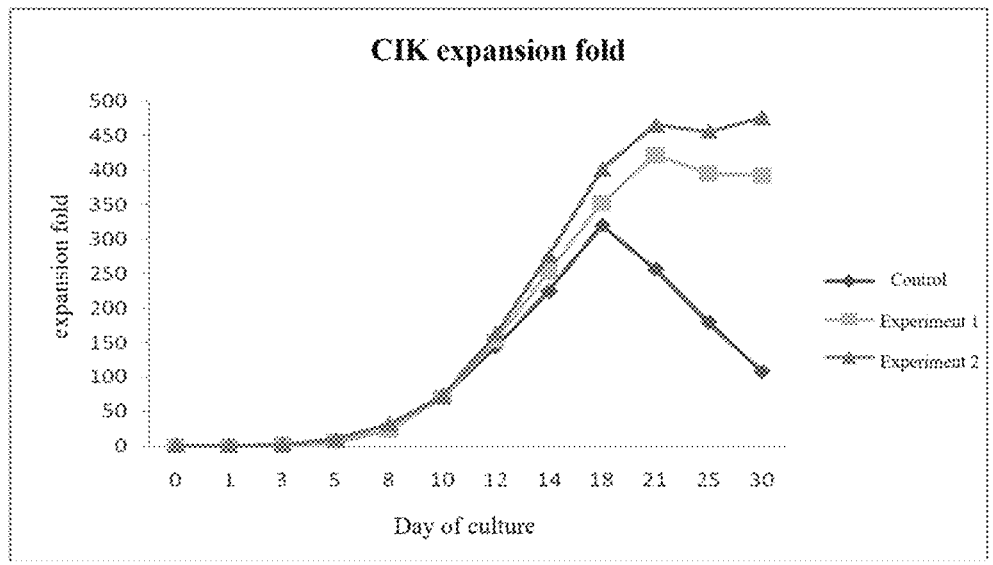
Figures 2, 3, 4, 5:
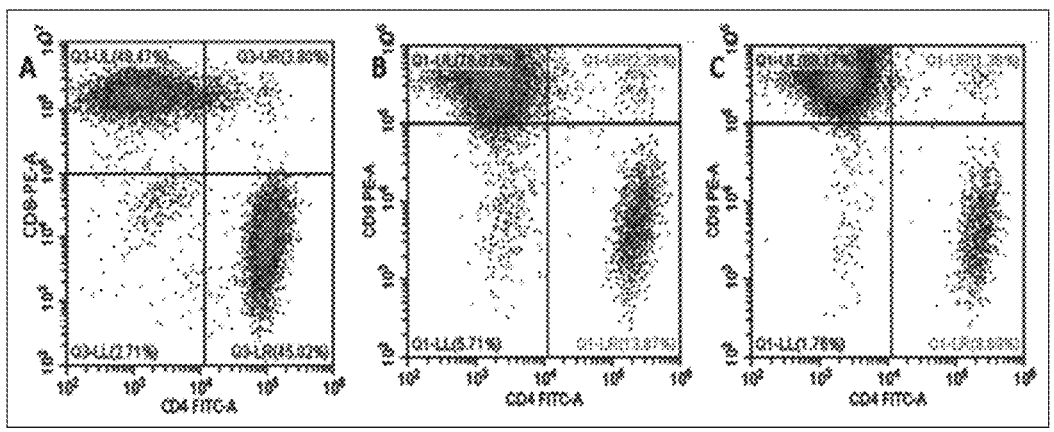
Figures 2, 3, 4, 5, 6:
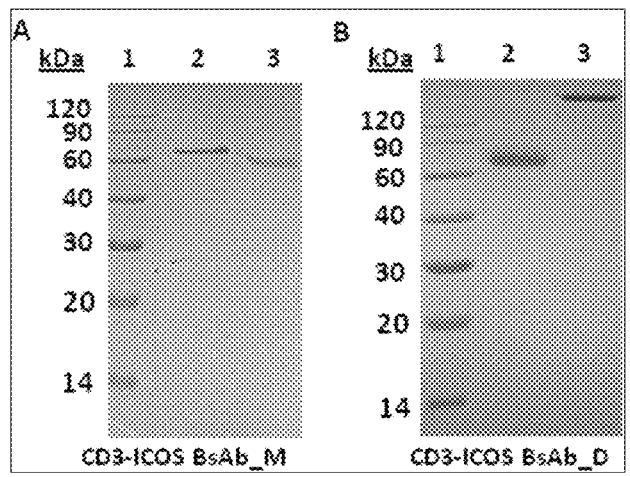
Figures 2, 3, 4, 5, 6, 7, 7A:
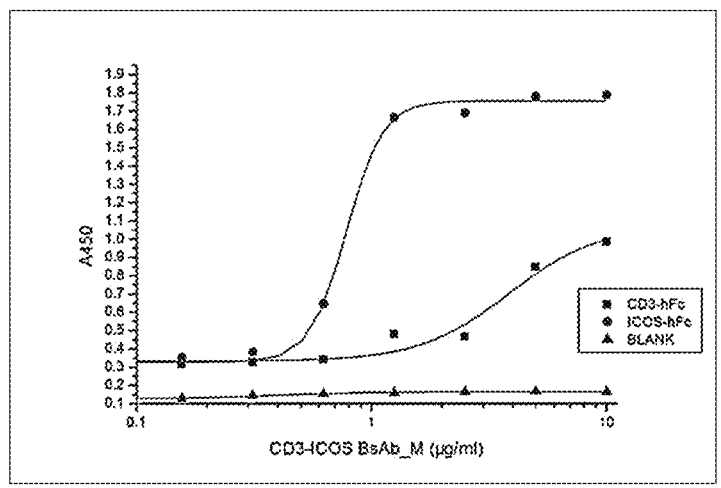
Figures 2, 3, 4, 5, 6, 7, 7B:
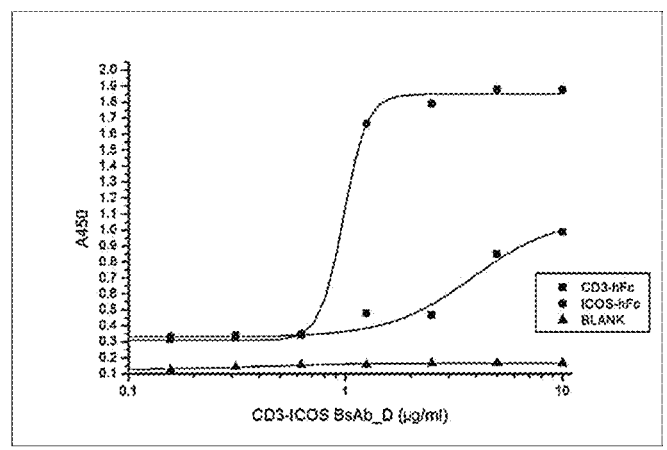
Figures 2, 3, 4, 5, 6, 7, 8:
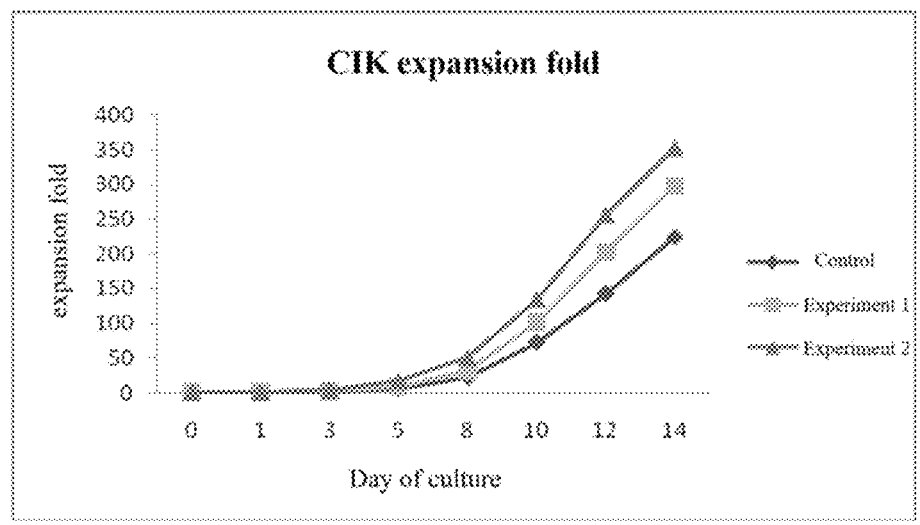
Figures 2, 3, 4, 5, 6, 7, 8, 9:
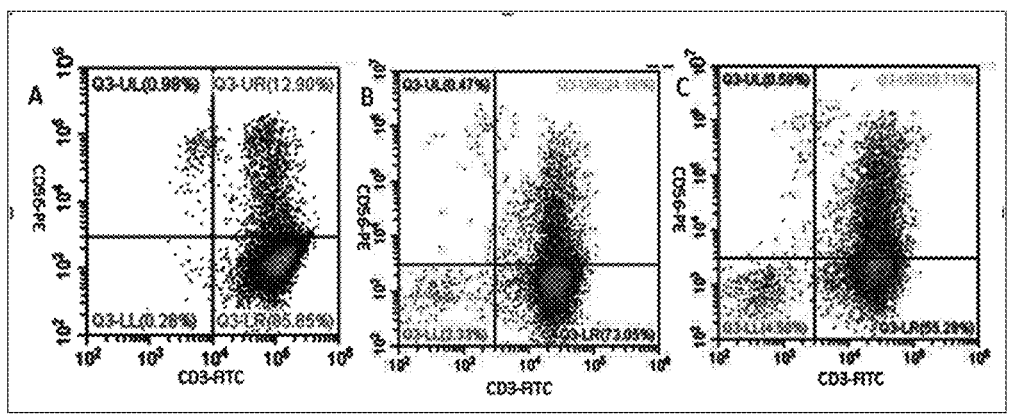
Figures 2, 3, 4, 5, 6, 7, 8, 9, 10:
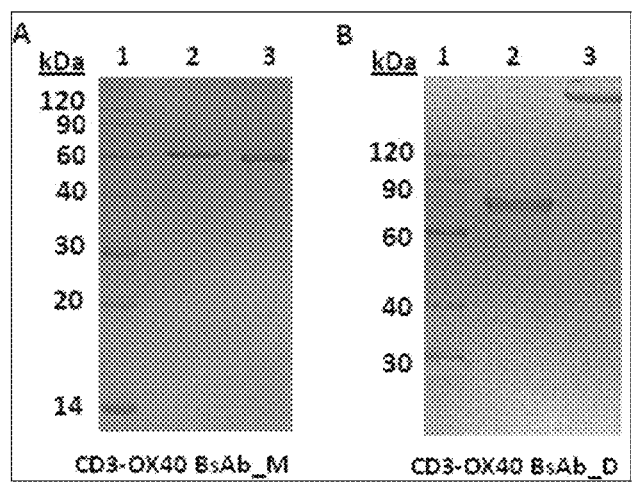
Figures 2, 3, 4, 5, 6, 7, 8, 9, 10, 11, 11A:
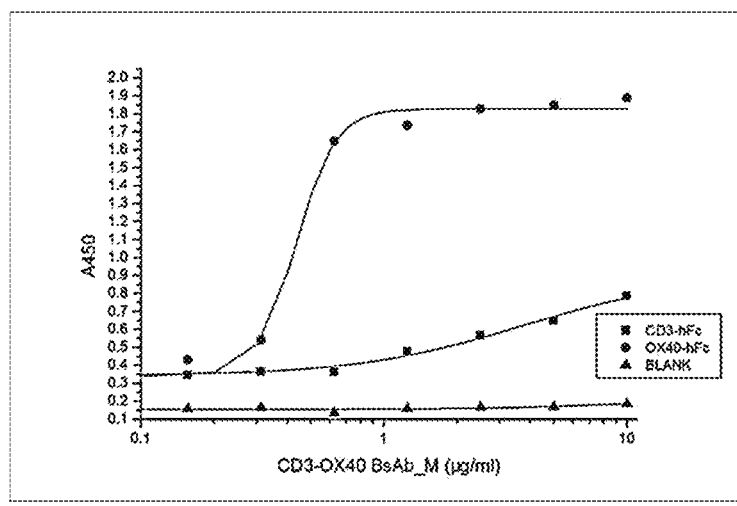
Figures 2, 3, 4, 5, 6, 7, 8, 9, 10, 11, 11B:
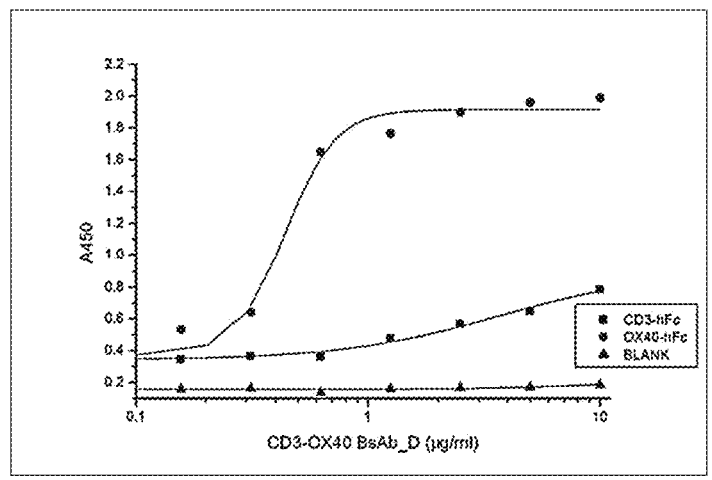
Figures 2, 3, 4, 5, 6, 7, 8, 9, 10, 11, 12:
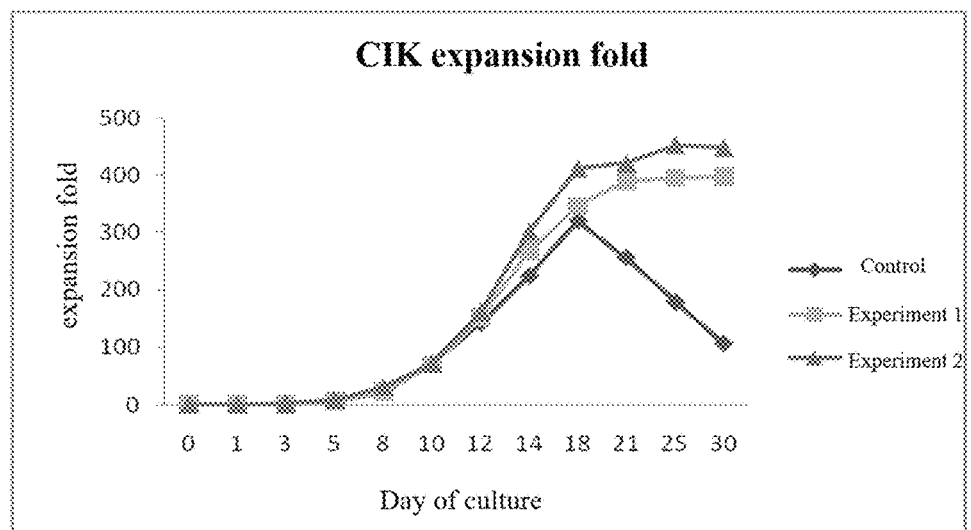
Figures 2, 3, 4, 5, 6, 7, 8, 9, 10, 11, 12, 13:
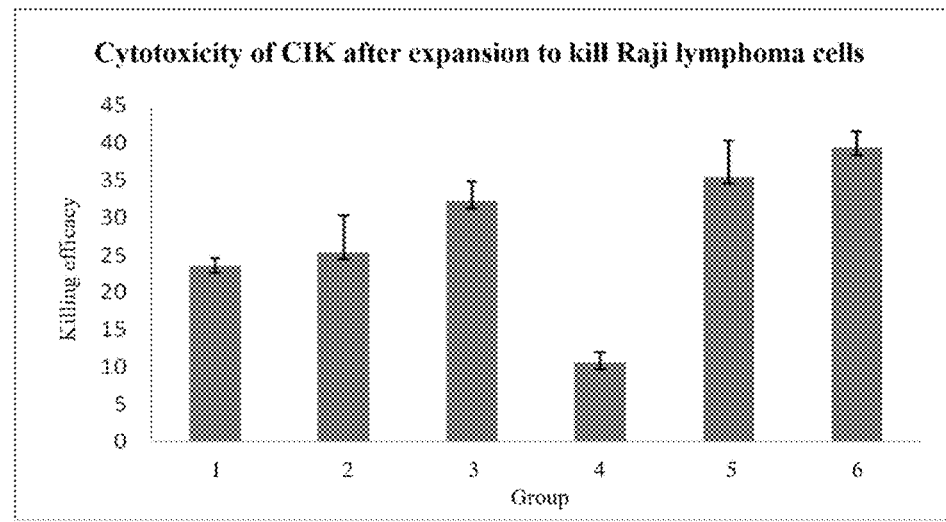
Figures 2, 3, 4, 5, 6, 7, 8, 9, 10, 11, 12, 13, 14:
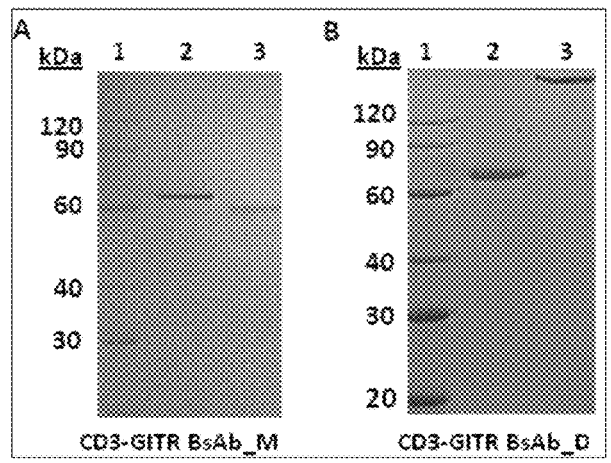
Figures 2, 3, 4, 5, 6, 7, 8, 9, 10, 11, 12, 13, 14, 15, 15A:
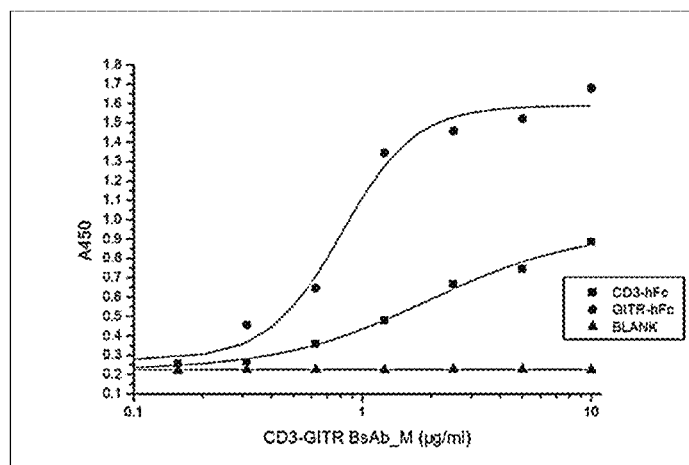
Figures 2, 3, 4, 5, 6, 7, 8, 9, 10, 11, 12, 13, 14, 15, 15B:
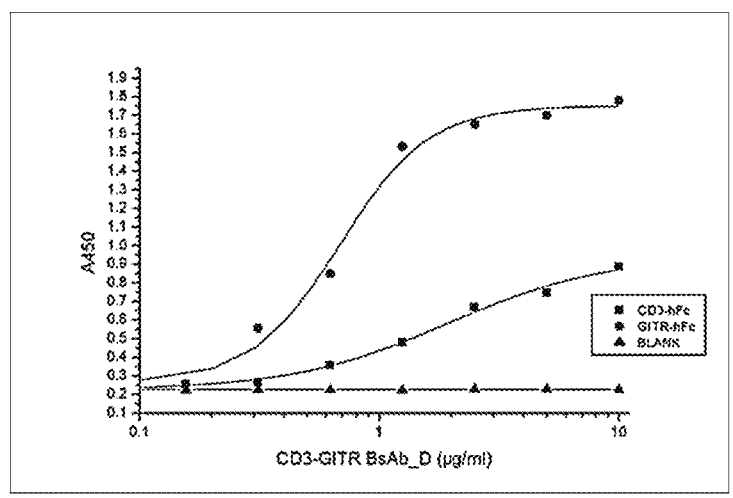
Figures 2, 3, 4, 5, 6, 7, 8, 9, 10, 11, 12, 13, 14, 15, 16:
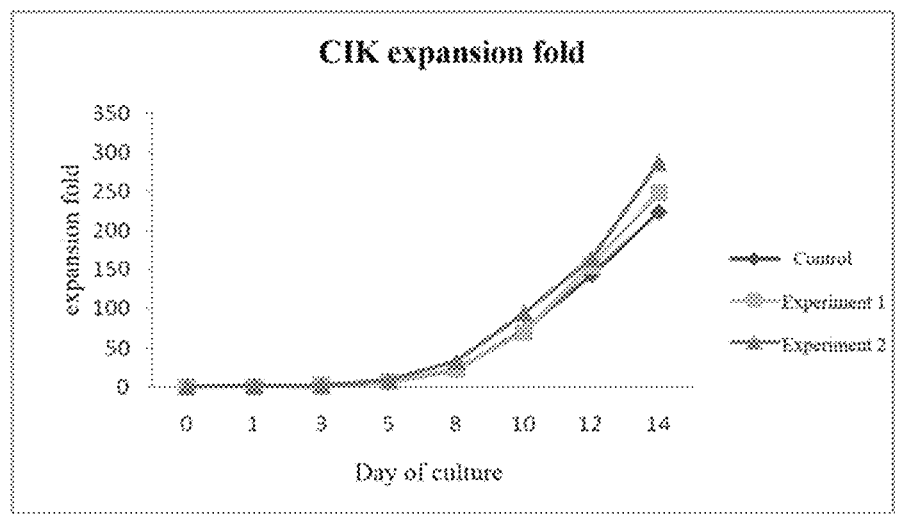
Figures 2, 3, 4, 5, 6, 7, 8, 9, 10, 11, 12, 13, 14, 15, 16, 17:
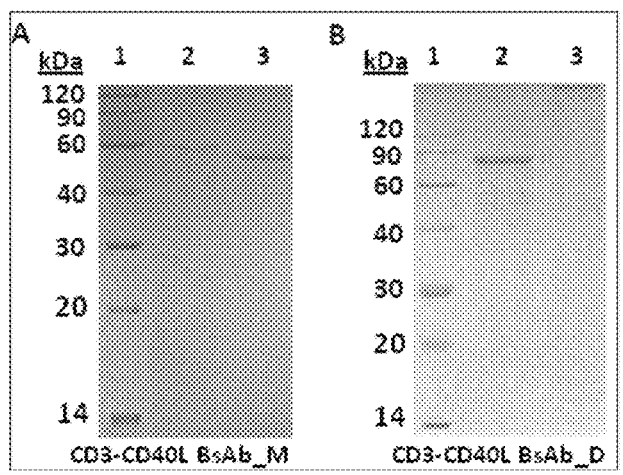
Figures 2, 3, 4, 5, 6, 7, 8, 9, 10, 11, 12, 13, 14, 15, 16, 17, 18, 18A:
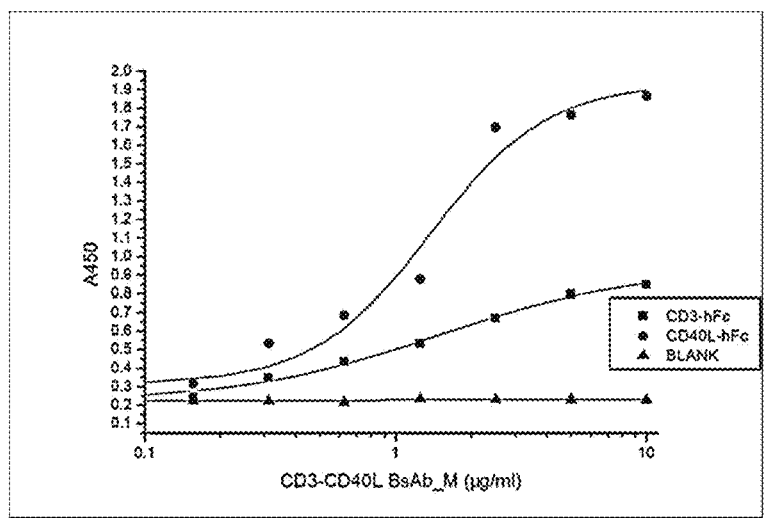
Figures 2, 3, 4, 5, 6, 7, 8, 9, 10, 11, 12, 13, 14, 15, 16, 17, 18, 18B:
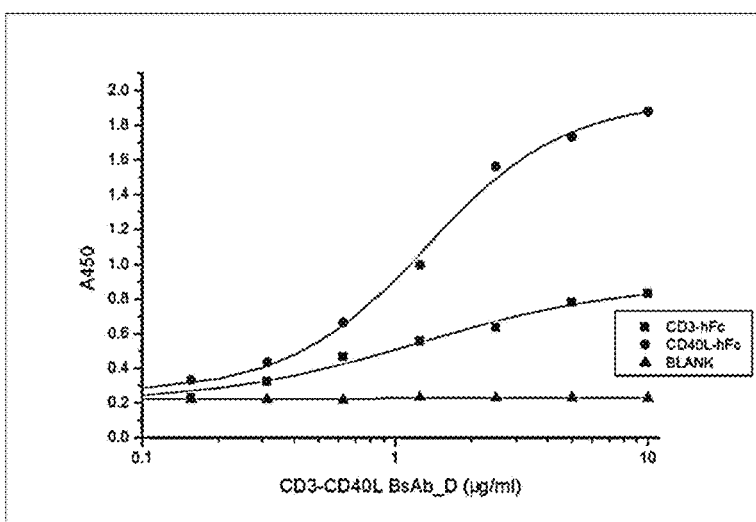
Figures 2, 3, 4, 5, 6, 7, 8, 9, 10, 11, 12, 13, 14, 15, 16, 17, 18, 19:
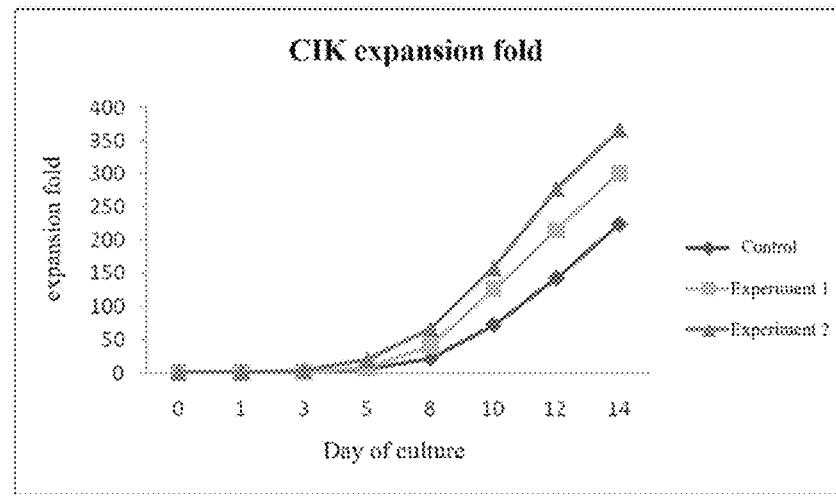
Figures 2, 3, 4, 5, 6, 7, 8, 9, 10, 11, 12, 13, 14, 15, 16, 17, 18, 19, 20:
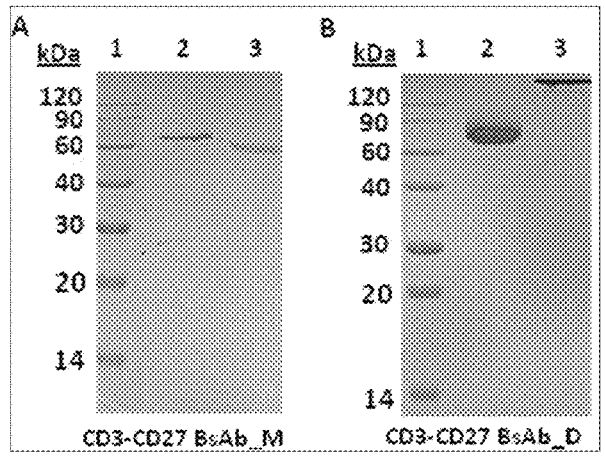
Figures 2, 3, 4, 5, 6, 7, 8, 9, 10, 11, 12, 13, 14, 15, 16, 17, 18, 19, 20, 21, 21A:
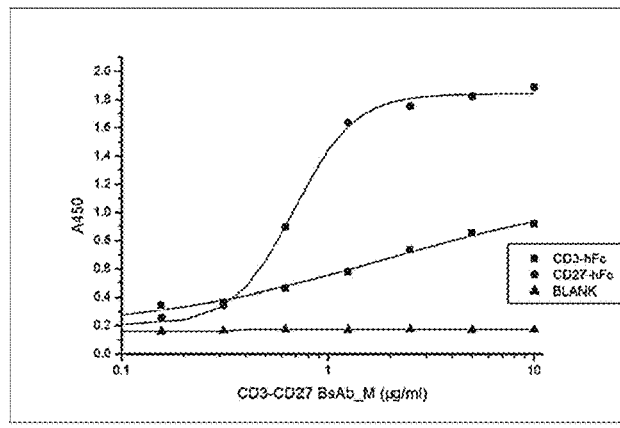
Figures 2, 3, 4, 5, 6, 7, 8, 9, 10, 11, 12, 13, 14, 15, 16, 17, 18, 19, 20, 21, 21B:
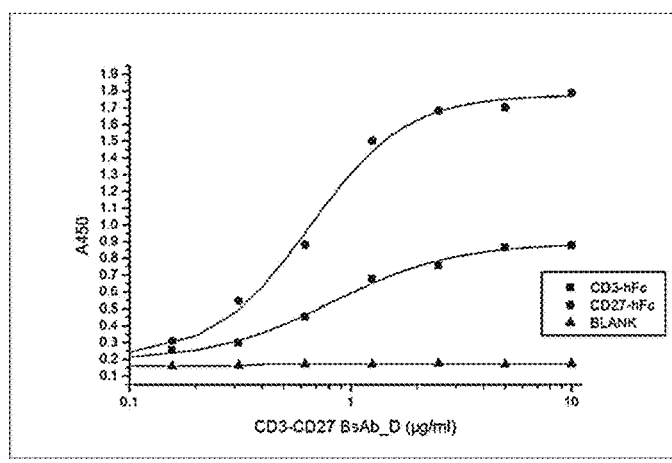
Figures 2, 3, 4, 5, 6, 7, 8, 9, 10, 11, 12, 13, 14, 15, 16, 17, 18, 19, 20, 21, 22:
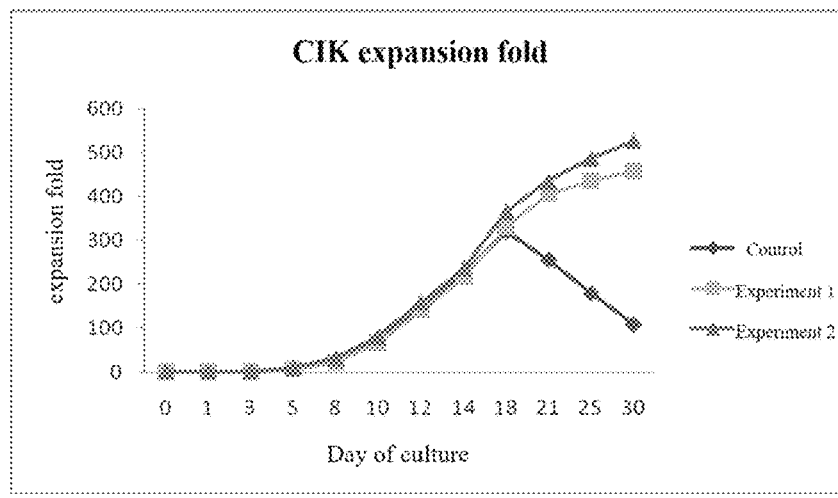
Figures 1, 3:
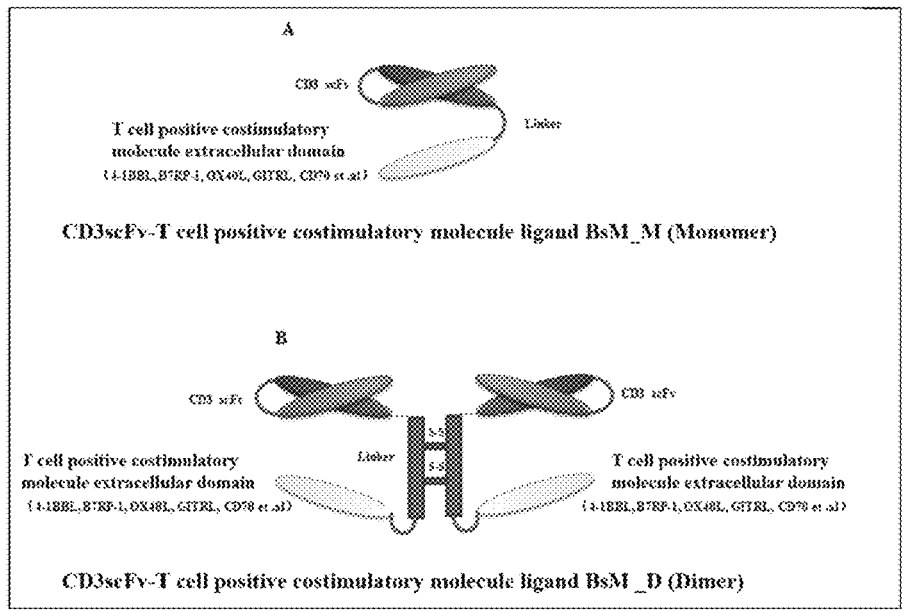
Figures 2, 3:
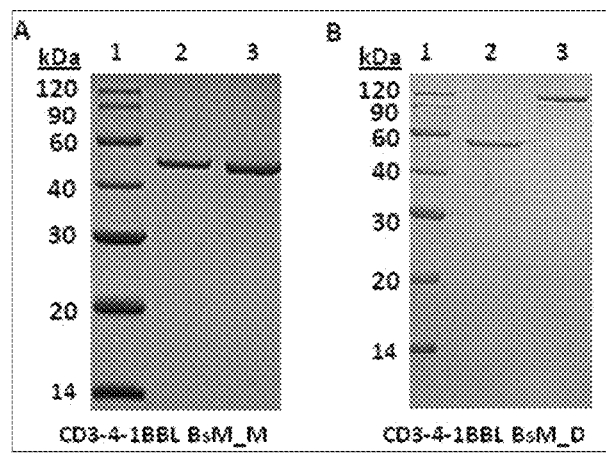
Figures 3, 3A:
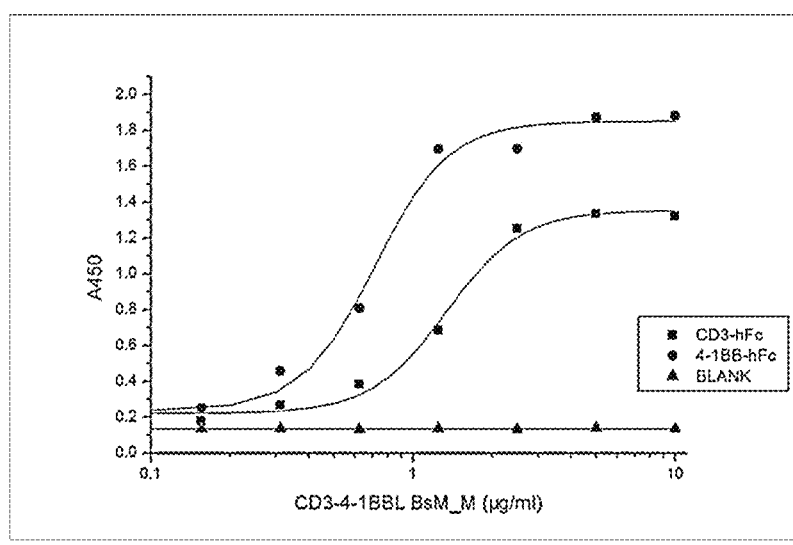
Figures 3, 3B:
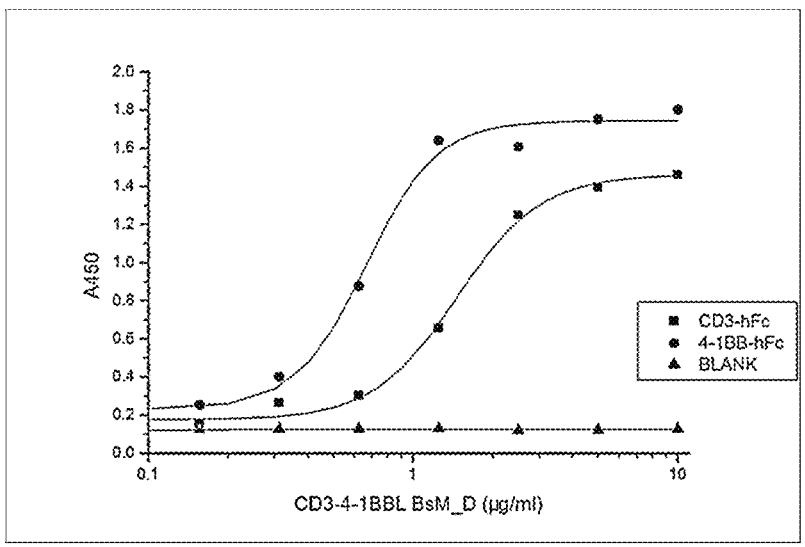
Figures 3, 4:
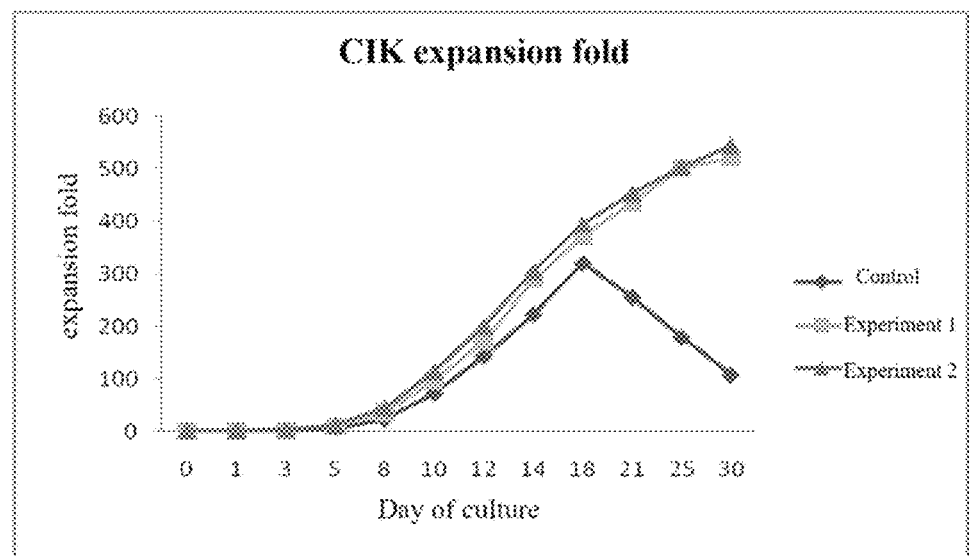
Figures 3, 4, 5:
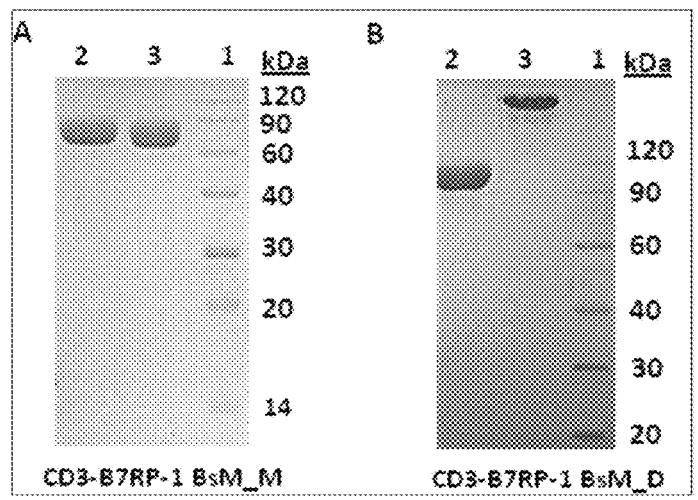
Figures 3, 4, 5, 6, 6A:
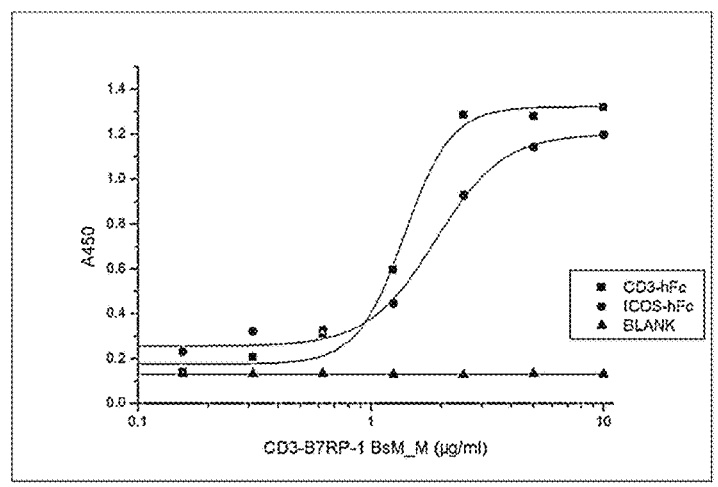
Figures 3, 4, 5, 6, 6B:
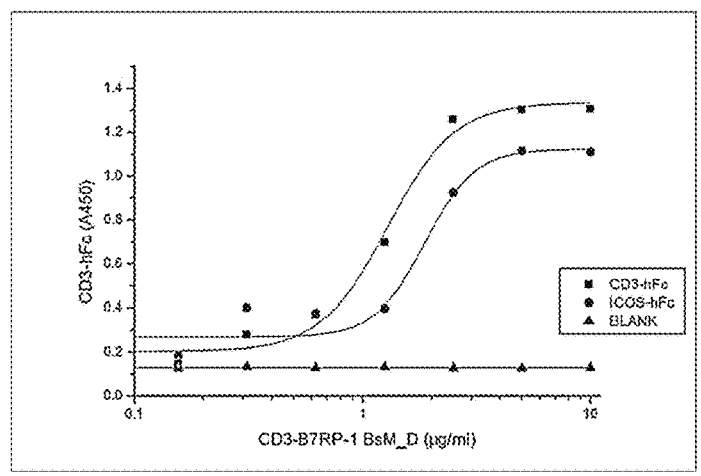
Figures 3, 4, 5, 6, 7:
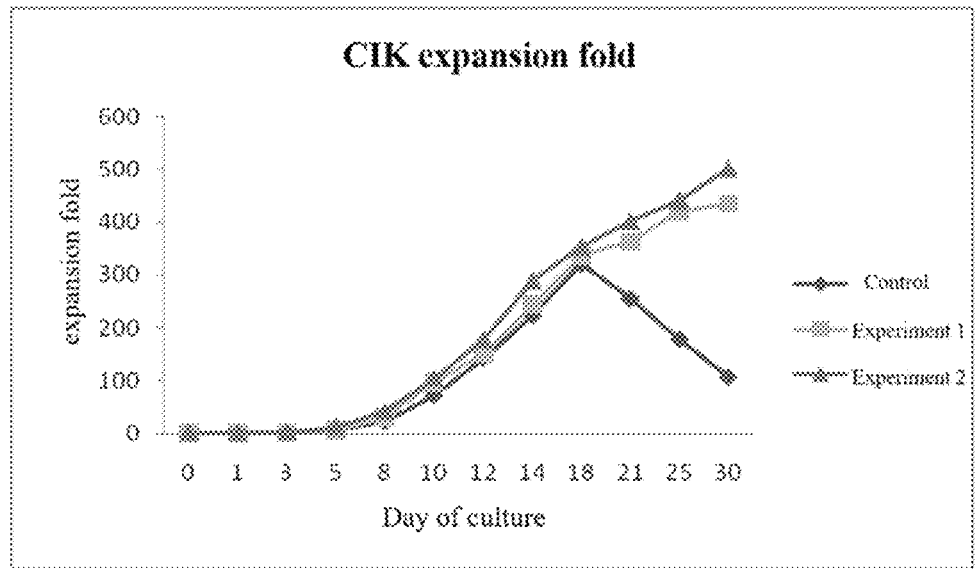
Figures 3, 4, 5, 6, 7, 8:
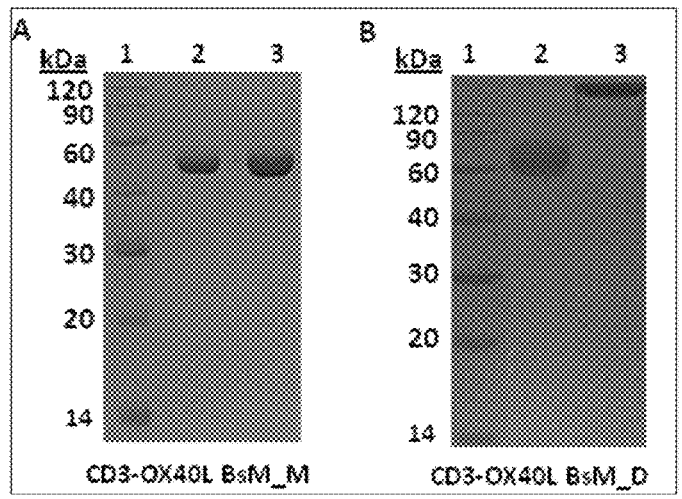
Figures 3, 4, 5, 6, 7, 8, 9, 9A:
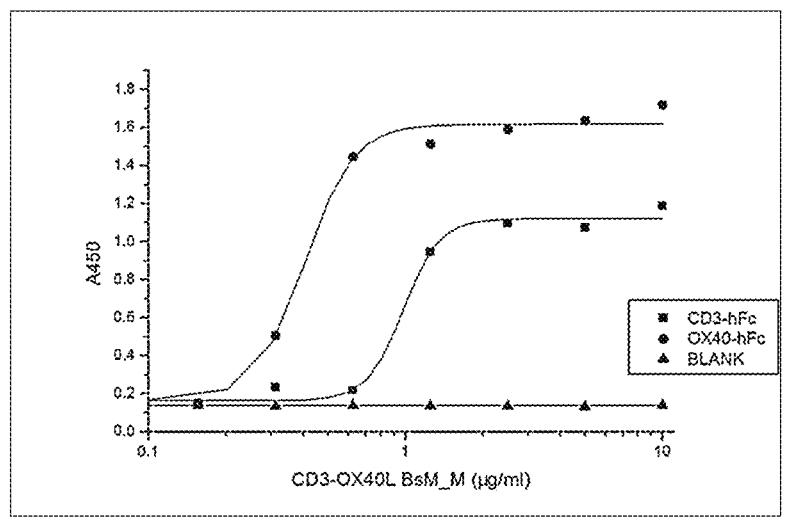
Figures 3, 4, 5, 6, 7, 8, 9, 9B:
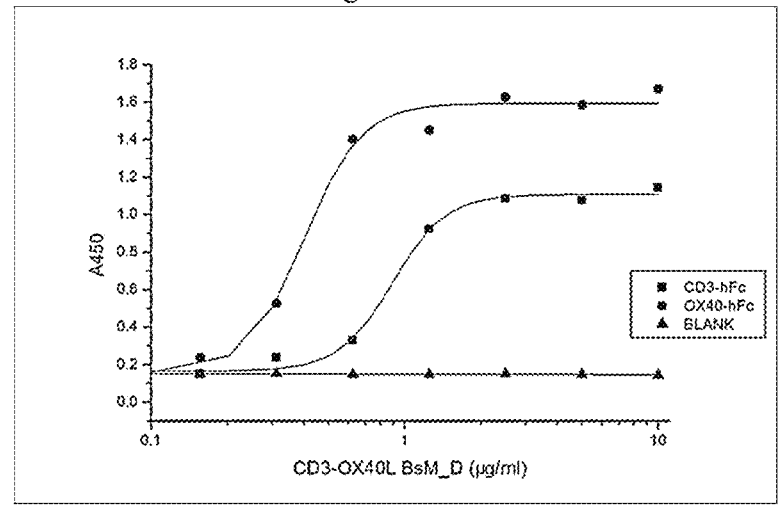
Figures 3, 4, 5, 6, 7, 8, 9, 10:
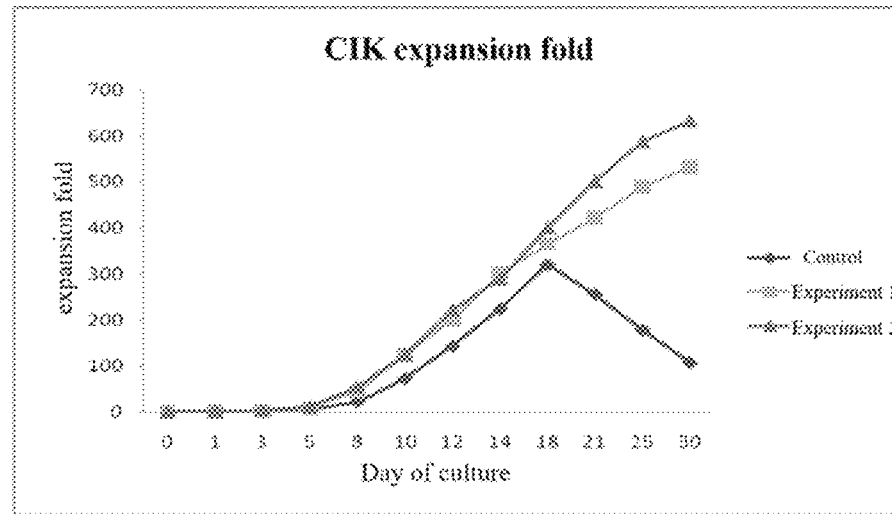
Figures 3, 4, 5, 6, 7, 8, 9, 10, 11:
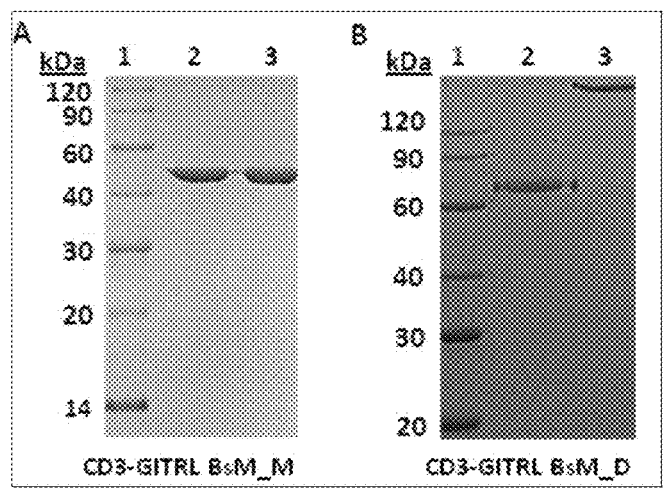
Figures 3, 4, 5, 6, 7, 8, 9, 10, 11, 12, 12A:
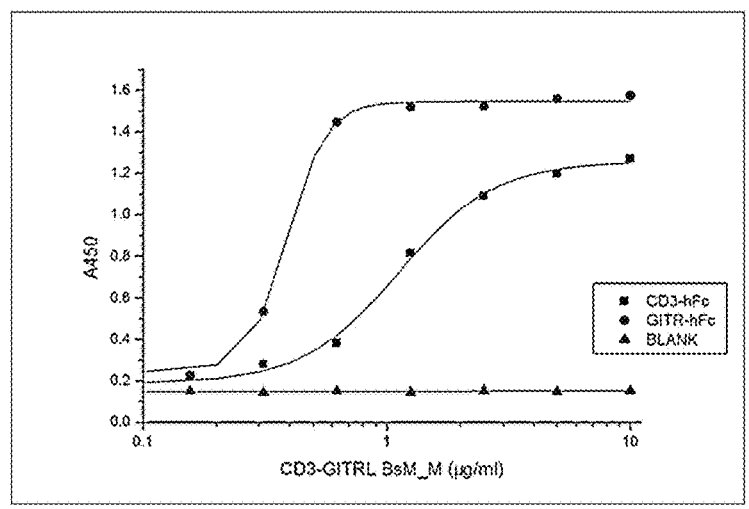
Figures 3, 4, 5, 6, 7, 8, 9, 10, 11, 12, 12B:
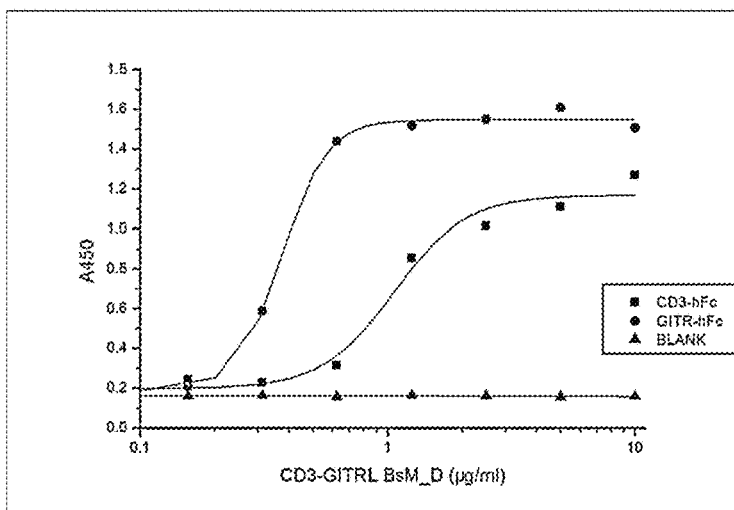
Figures 3, 4, 5, 6, 7, 8, 9, 10, 11, 12, 13:
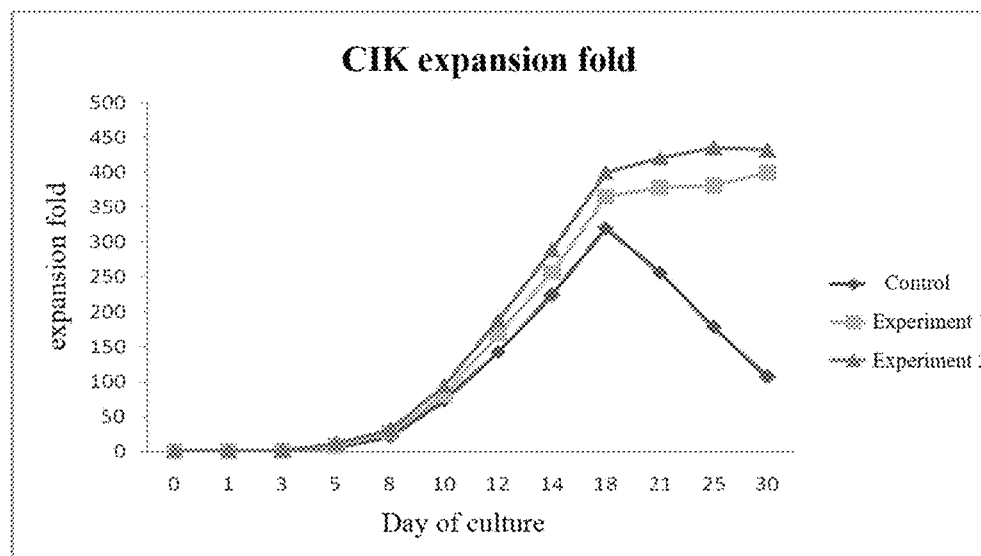
Figures 3, 4, 5, 6, 7, 8, 9, 10, 11, 12, 13, 14:
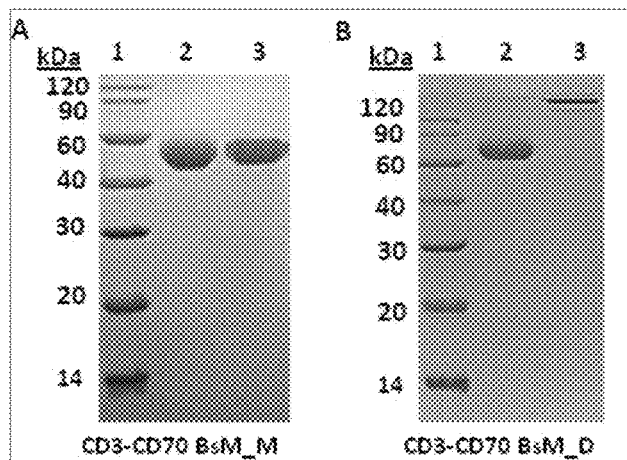
Figures 3, 4, 5, 6, 7, 8, 9, 10, 11, 12, 13, 14, 15, 15A:
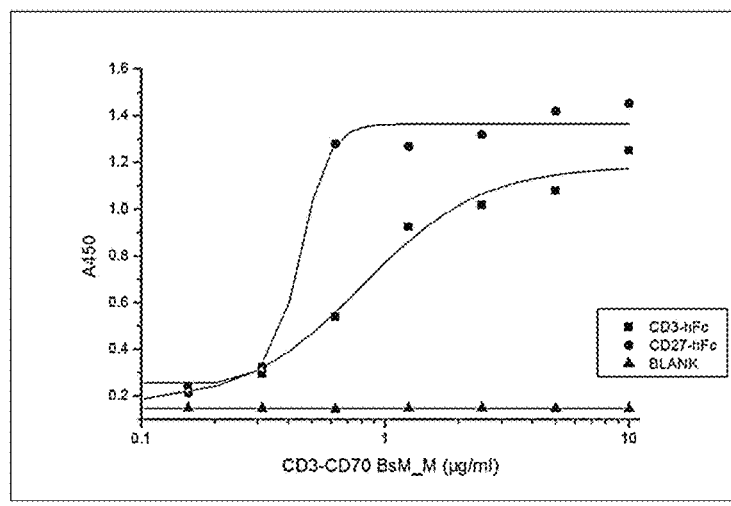
Figures 3, 4, 5, 6, 7, 8, 9, 10, 11, 12, 13, 14, 15, 15B:
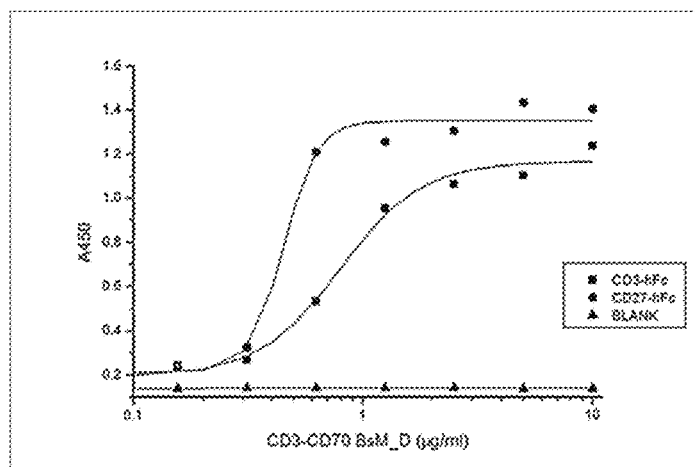
Figures 3, 4, 5, 6, 7, 8, 9, 10, 11, 12, 13, 14, 15, 16:
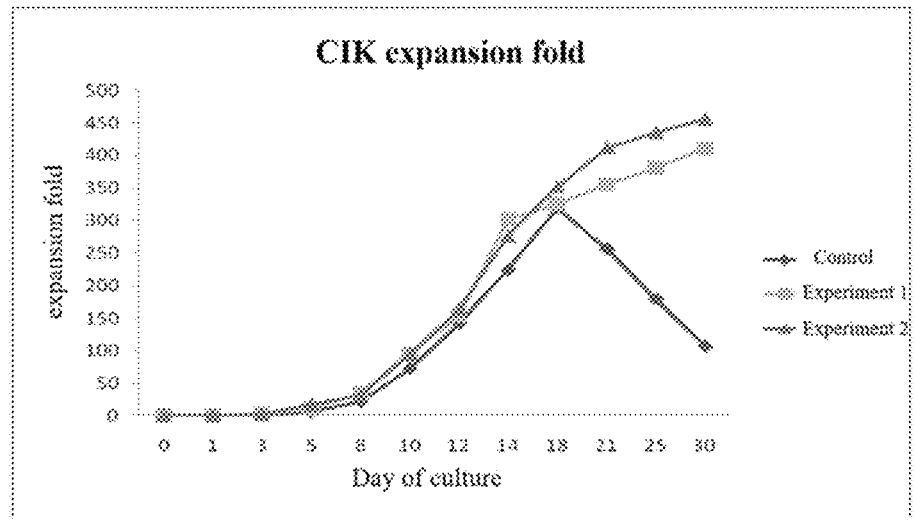
Figures 1, 4:
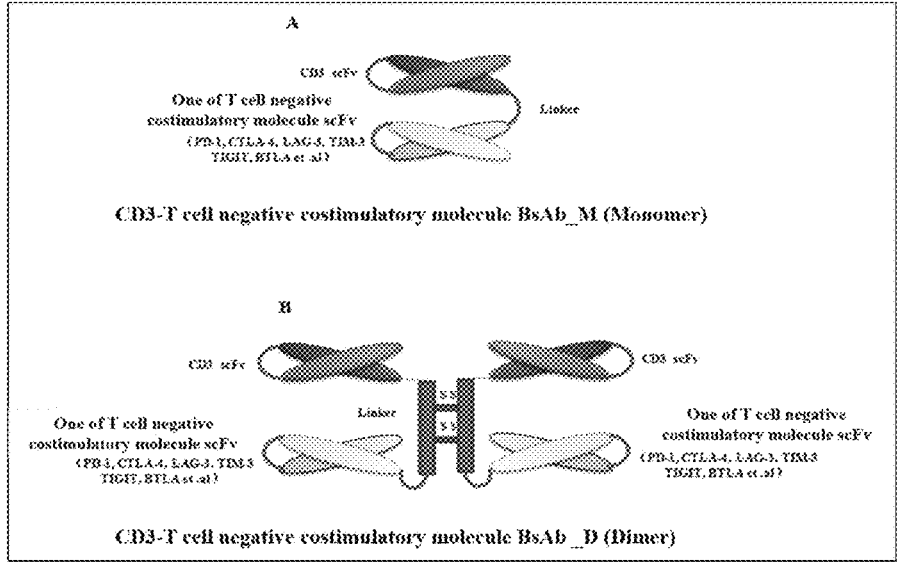
Figures 2, 4:
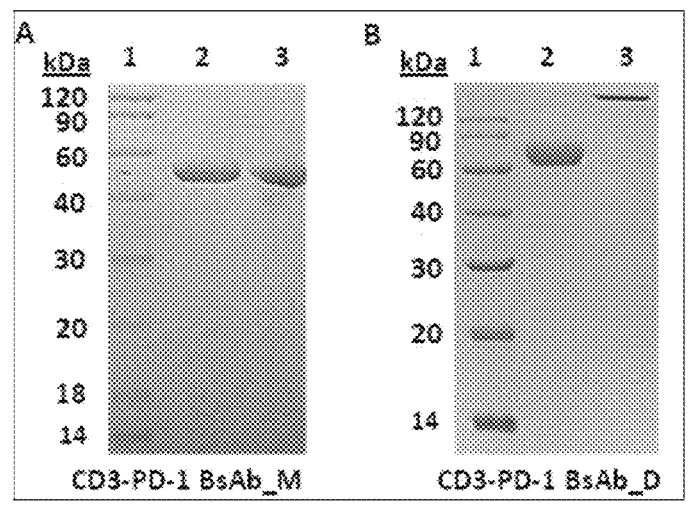
Figures 3A, 4:
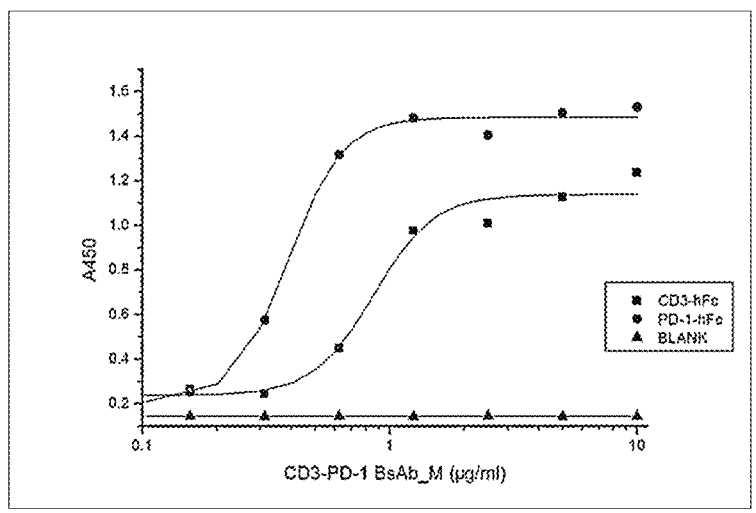
Figures 3B, 4:
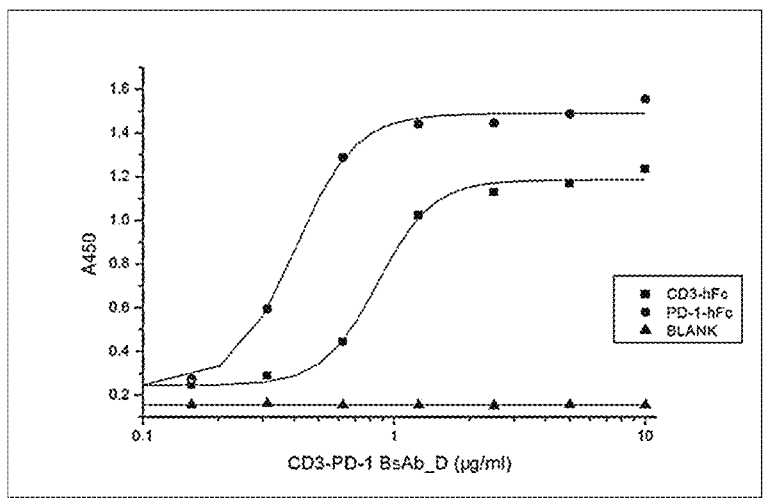
Figure 4:
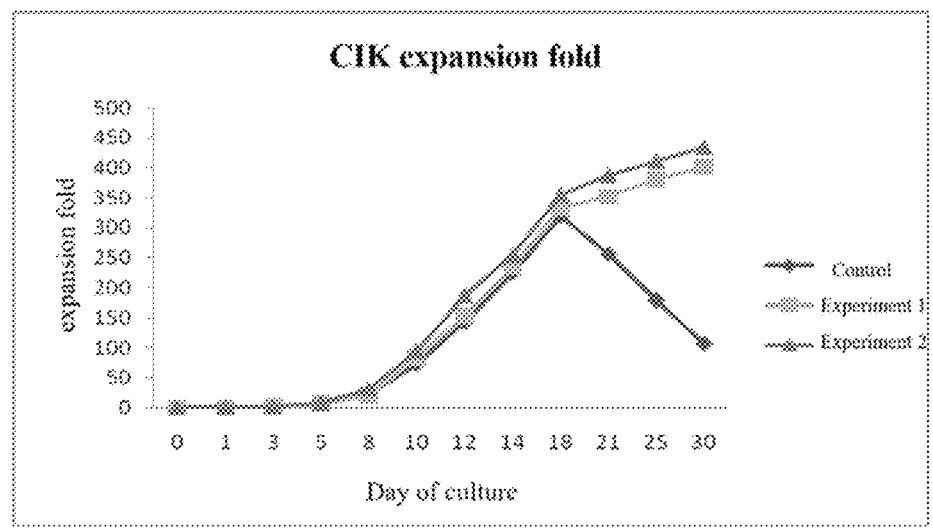
Figures 4, 5:
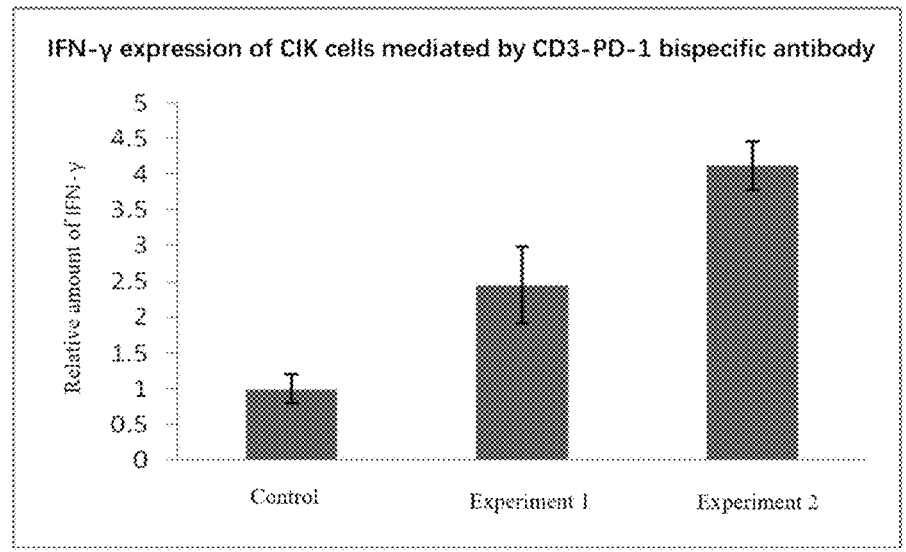
Figures 4, 5, 6:
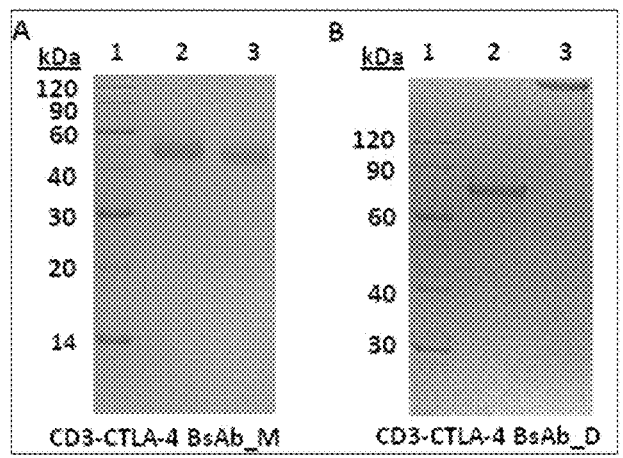
Figures 4, 5, 6, 7, 7A:
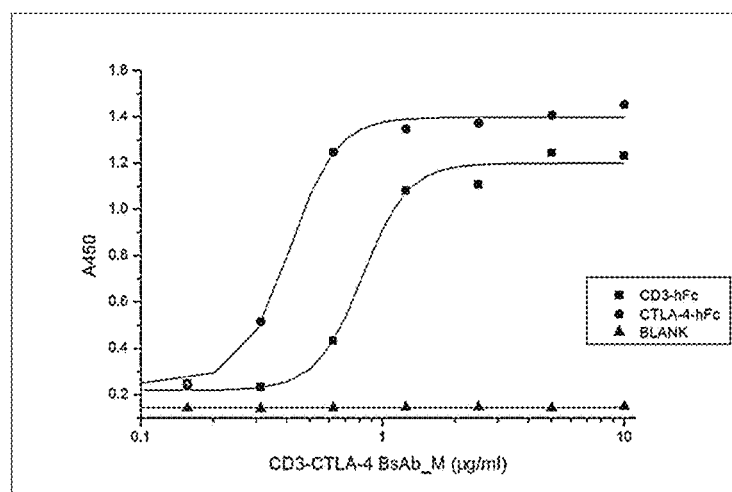
Figures 4, 5, 6, 7, 7B:
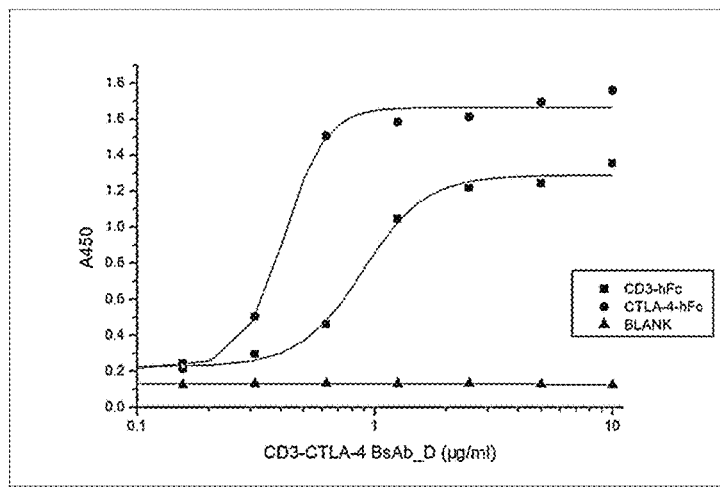
Figures 4, 5, 6, 7, 8:
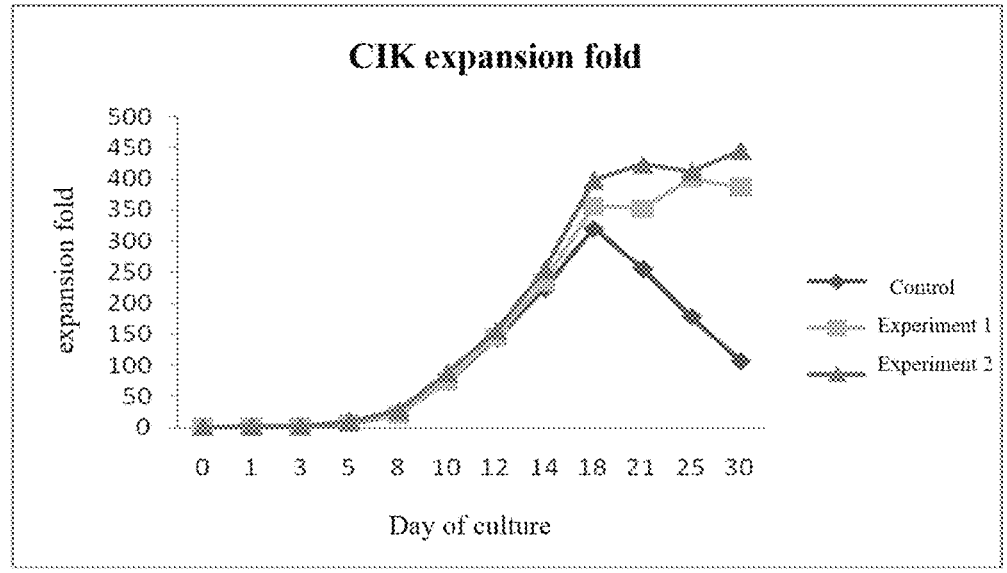
Figures 4, 5, 6, 7, 8, 9:
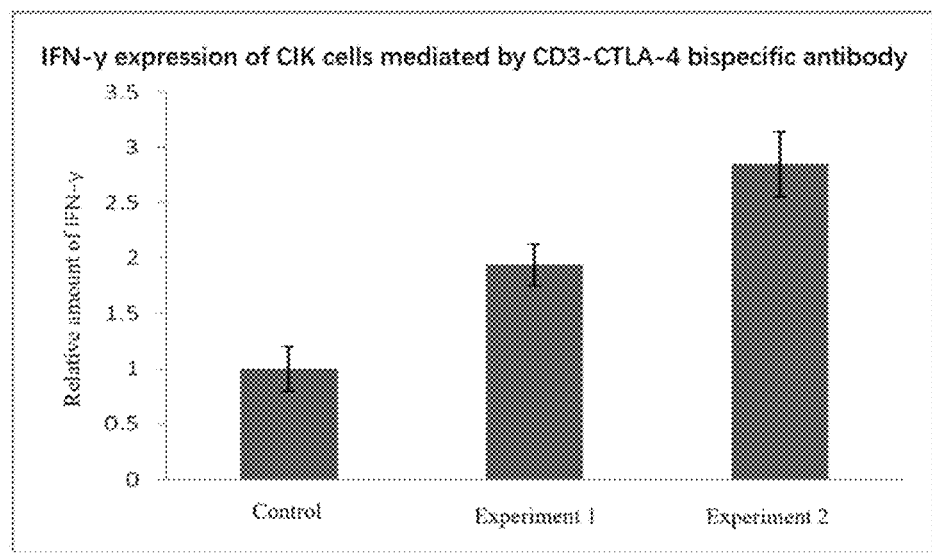
Figures 4, 5, 6, 7, 8, 9, 10:
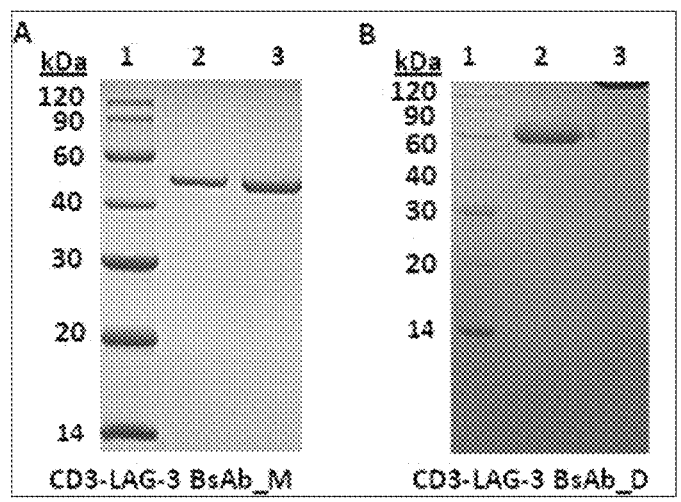
Figures 4, 5, 6, 7, 8, 9, 10, 11, 11A:
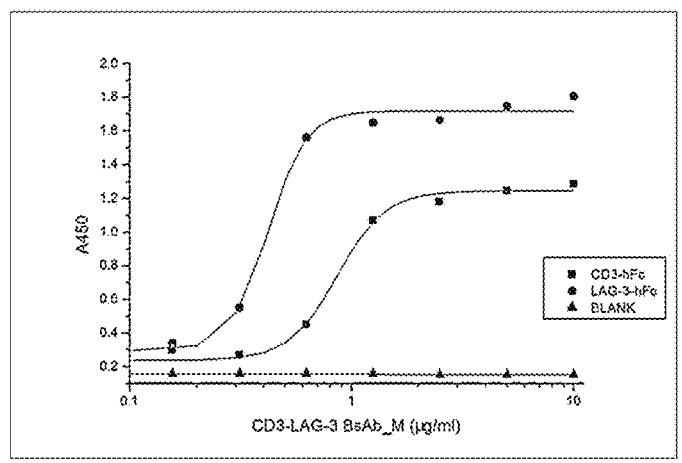
Figures 4, 5, 6, 7, 8, 9, 10, 11, 11B:
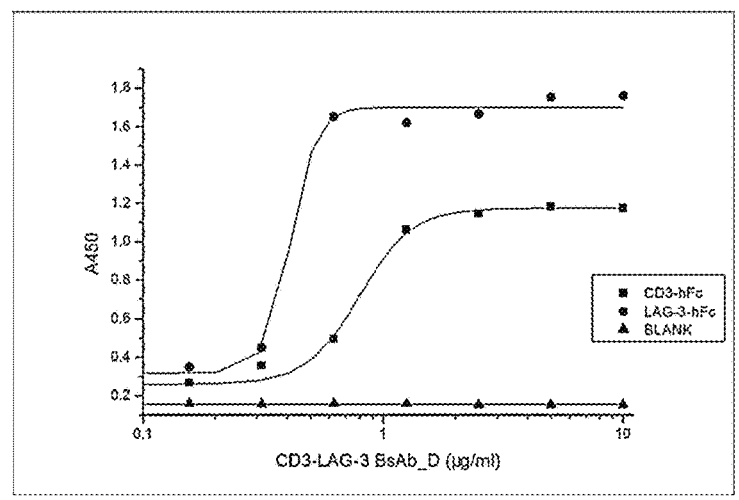
Figures 4, 5, 6, 7, 8, 9, 10, 11, 12:
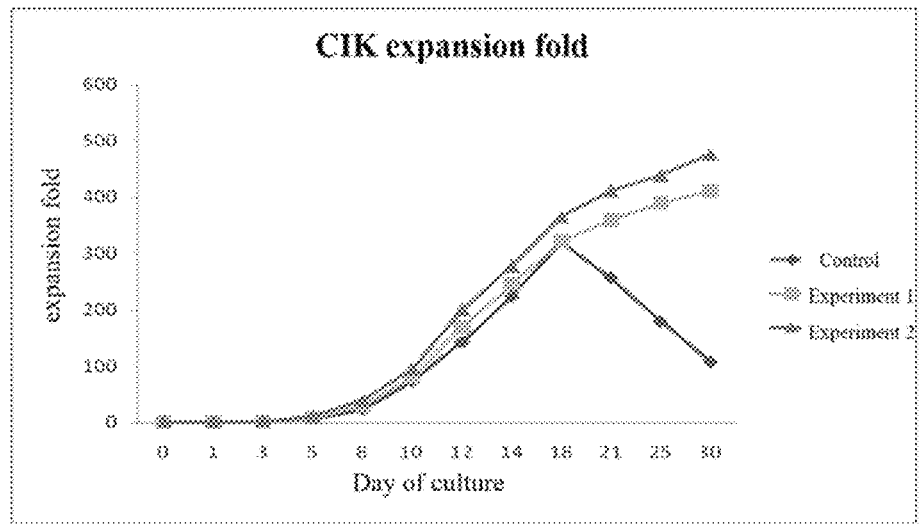
Figures 4, 5, 6, 7, 8, 9, 10, 11, 12, 13:
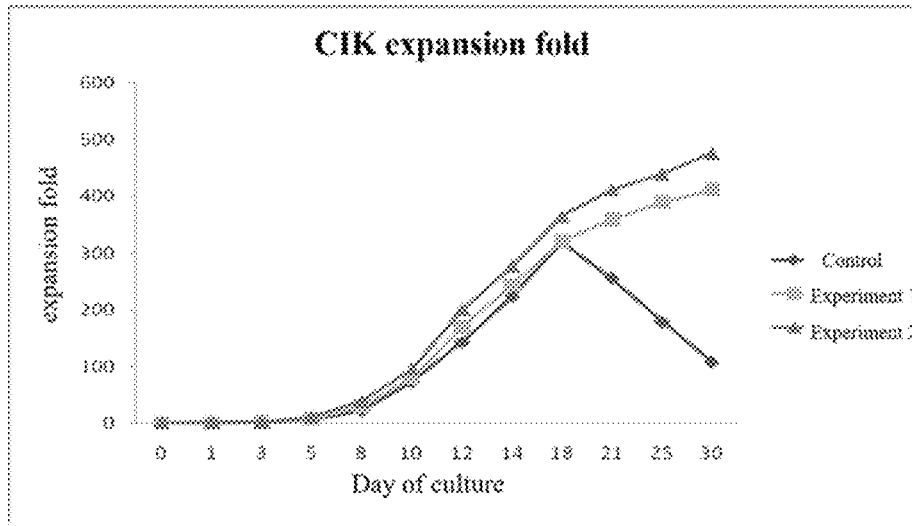
Figures 4, 5, 6, 7, 8, 9, 10, 11, 12, 13, 14:
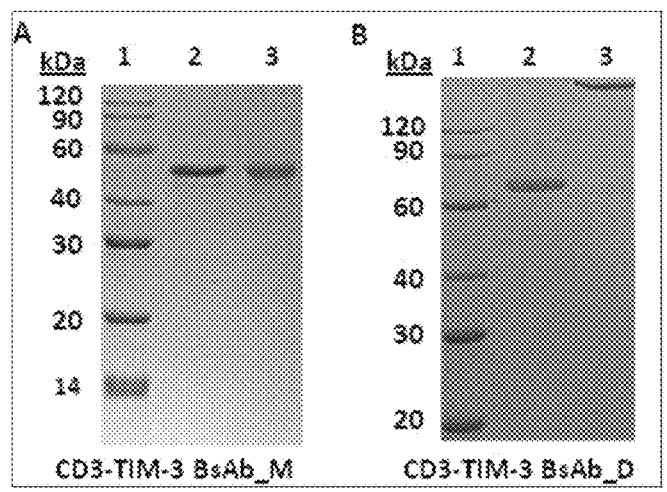
Figures 4, 5, 6, 7, 8, 9, 10, 11, 12, 13, 14, 15, 15A:
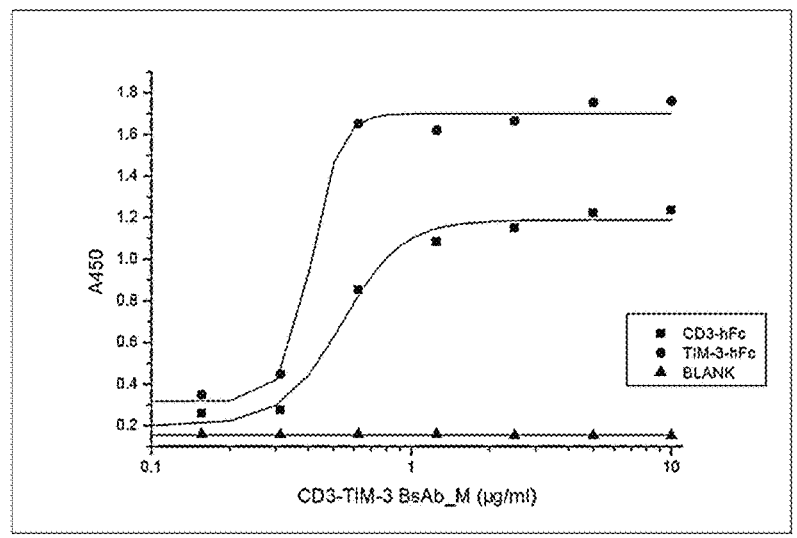
Figures 4, 5, 6, 7, 8, 9, 10, 11, 12, 13, 14, 15, 15B:
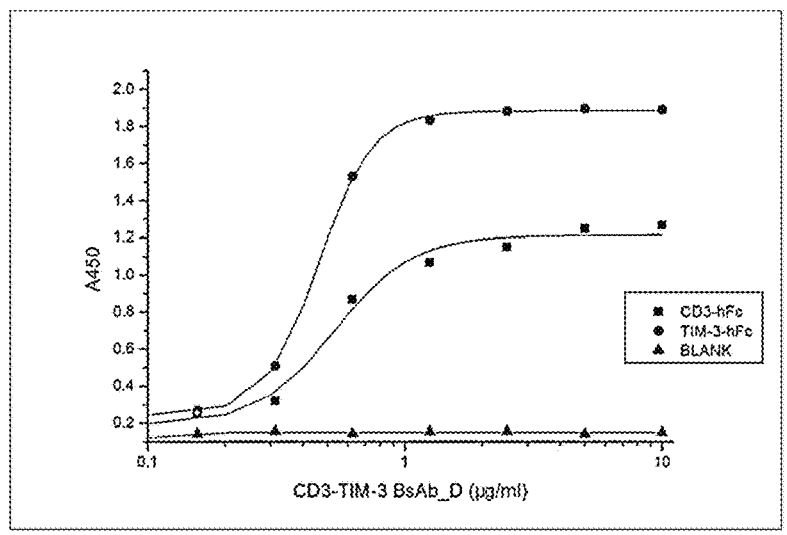
Figures 4, 5, 6, 7, 8, 9, 10, 11, 12, 13, 14, 15, 16:
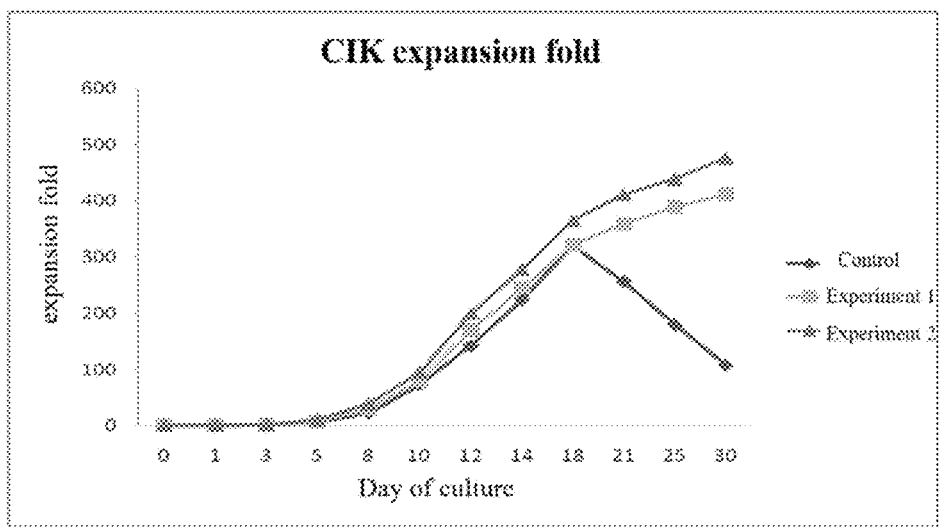
Figures 4, 5, 6, 7, 8, 9, 10, 11, 12, 13, 14, 15, 16, 17:
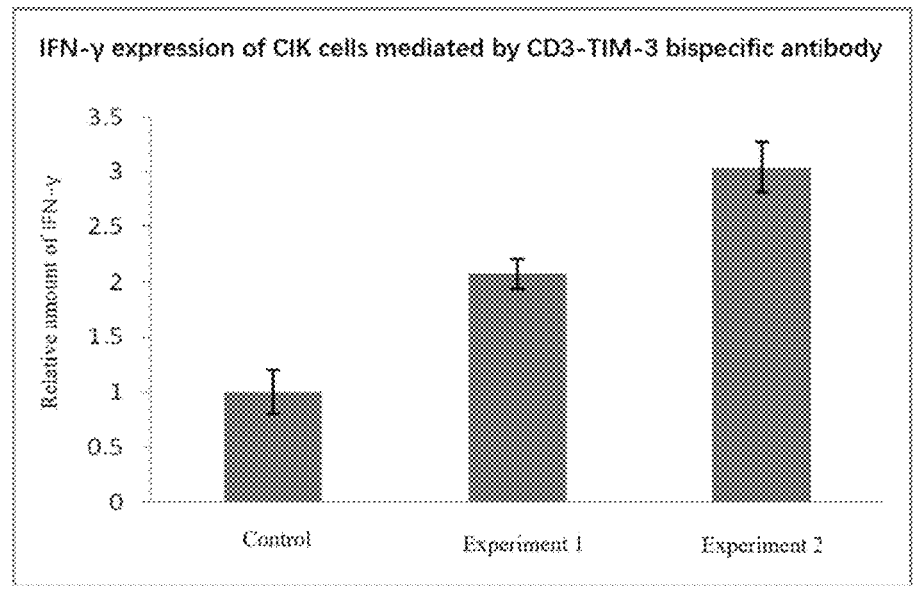
Figures 4, 5, 6, 7, 8, 9, 10, 11, 12, 13, 14, 15, 16, 17, 18:
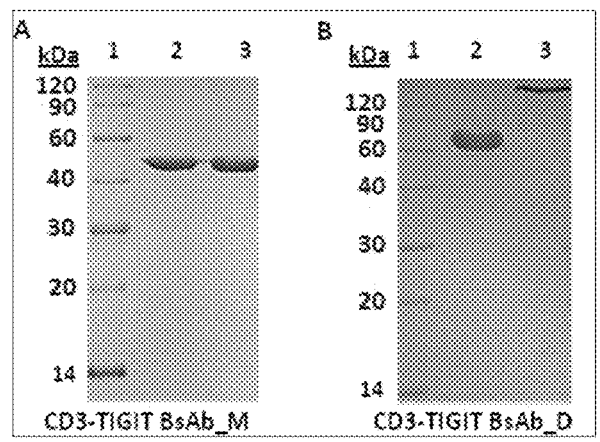
Figures 4, 5, 6, 7, 8, 9, 10, 11, 12, 13, 14, 15, 16, 17, 18, 19, 19A:
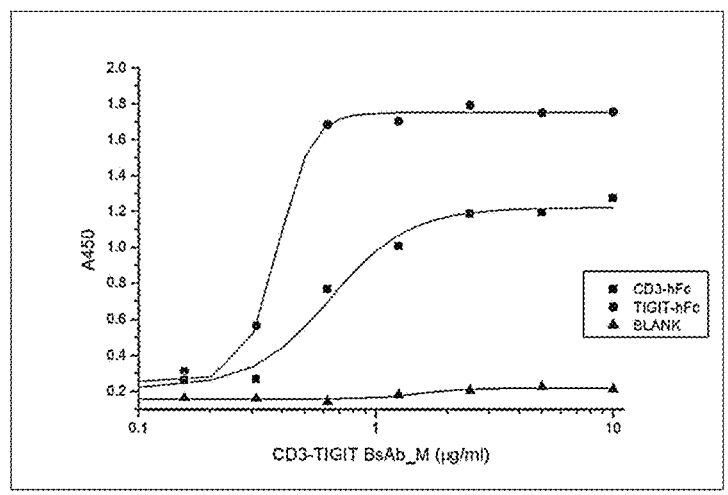
Figures 4, 5, 6, 7, 8, 9, 10, 11, 12, 13, 14, 15, 16, 17, 18, 19, 19B:
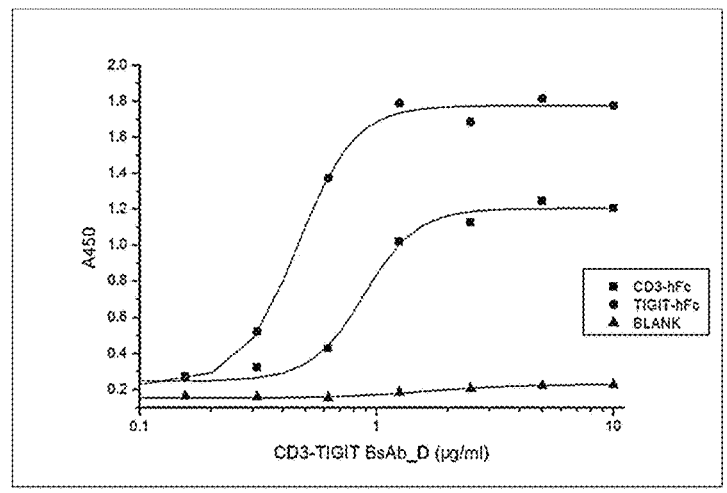
Figures 4, 5, 6, 7, 8, 9, 10, 11, 12, 13, 14, 15, 16, 17, 18, 19, 20:
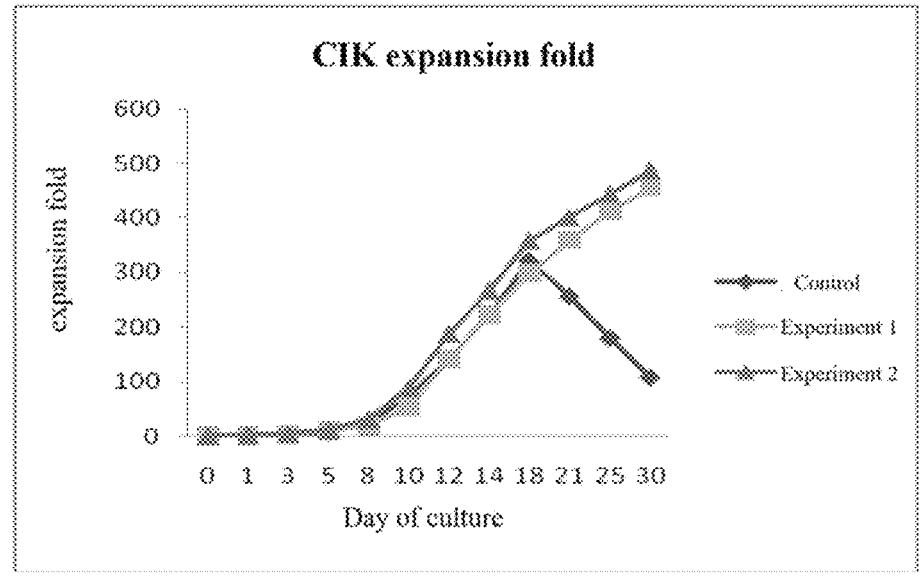
Figures 4, 5, 6, 7, 8, 9, 10, 11, 12, 13, 14, 15, 16, 17, 18, 19, 20, 21:
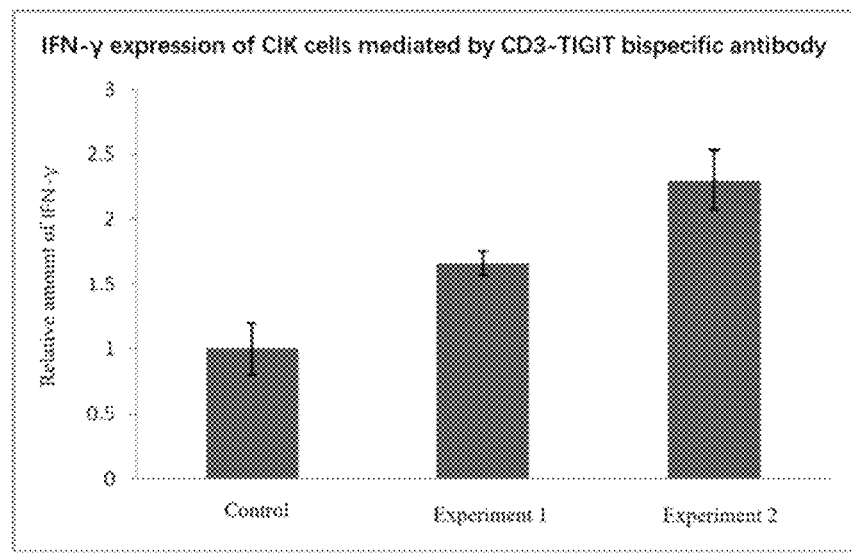
Figures 4, 5, 6, 7, 8, 9, 10, 11, 12, 13, 14, 15, 16, 17, 18, 19, 20, 21, 22:
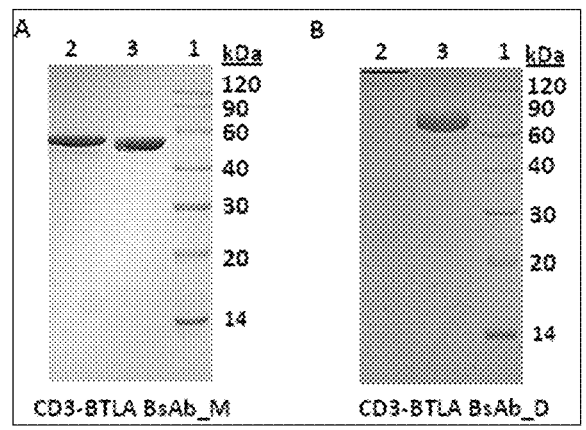
Figures 4, 5, 6, 7, 8, 9, 10, 11, 12, 13, 14, 15, 16, 17, 18, 19, 20, 21, 22, 23, 23A:
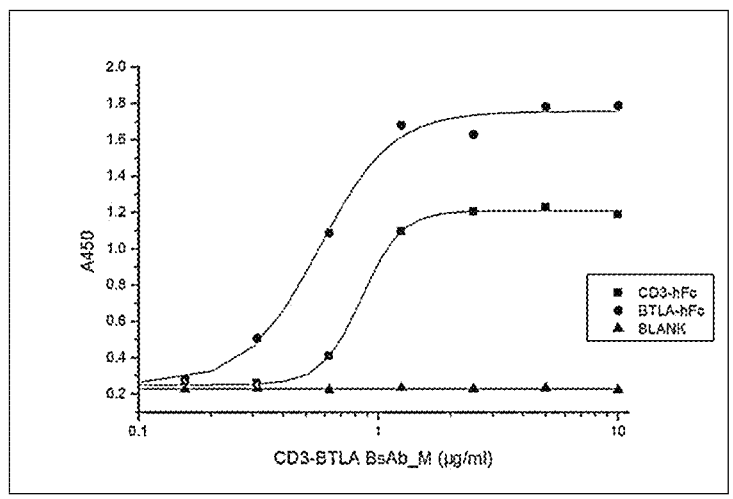
Figures 4, 5, 6, 7, 8, 9, 10, 11, 12, 13, 14, 15, 16, 17, 18, 19, 20, 21, 22, 23, 23B:
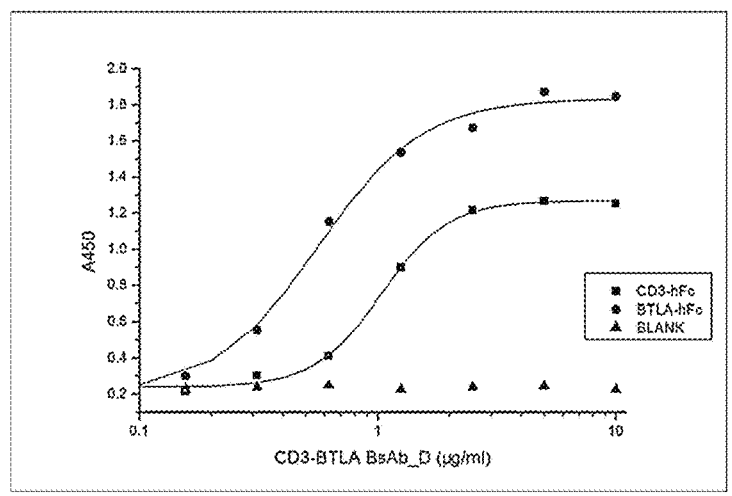
Figures 4, 5, 6, 7, 8, 9, 10, 11, 12, 13, 14, 15, 16, 17, 18, 19, 20, 21, 22, 23, 24:
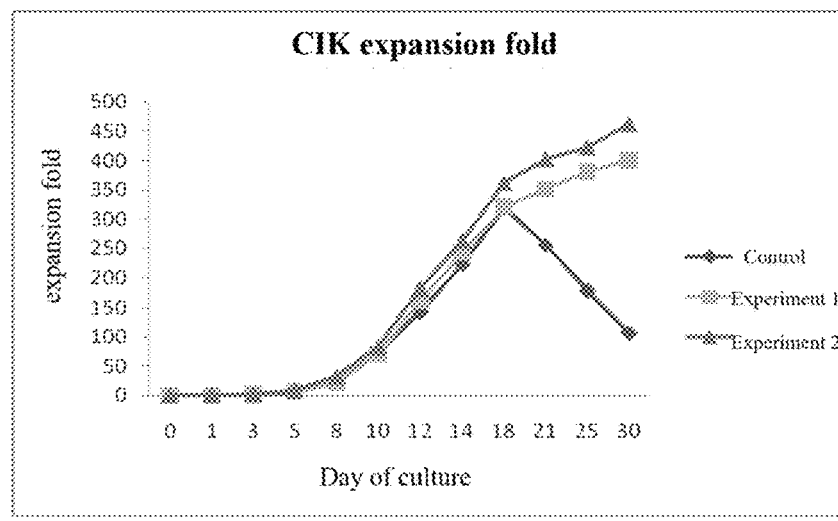
Figures 4, 5, 6, 7, 8, 9, 10, 11, 12, 13, 14, 15, 16, 17, 18, 19, 20, 21, 22, 23, 24, 25:
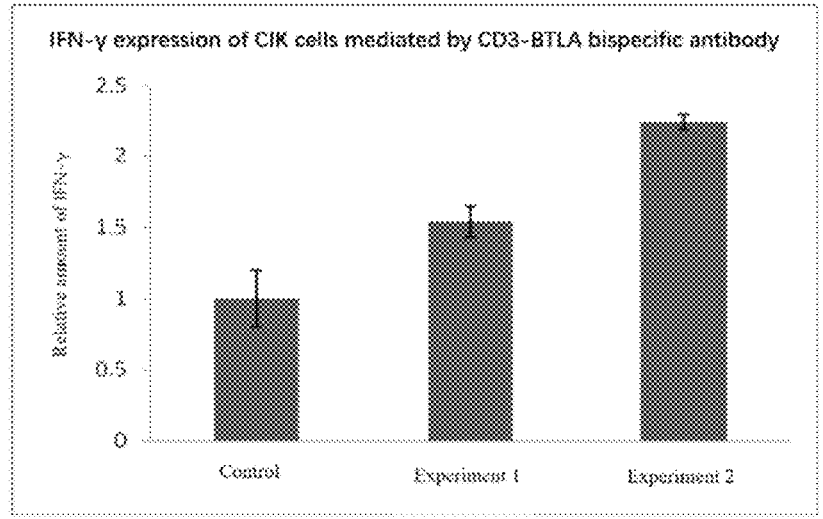

The final purified CD3-CTLA-4 BsAb_M and CD3-CTLA-4 BsAb_D recombinant protein was analyzed by SDS-PAGE, and the protein electrophoresis data under reduced and unreduced conditions were shown as FIG. 4-6. It shows that both purity of CD3-CTLA-4 BsAb_M and CD3-CTLA-4 BsAb_D recombinant protein are >95%. The theoretical molecular weight for CD3-CTLA-4 BsAb_M is 53.2 kDa, and protein displayed the same single band under reduced and unreduced conditions. The molecular weight of these bands is consistent with monomer, so this bi-specific antibody is monomer (FIG. 4-6A, Lane 1: protein marker for molecular weight; Lane 2: reduced CD3-CTLA-4 BsAb_M; Lane 3: unreduced CD3-CTLA-4 BsAb_M). The theoretical molecular weight for CD3-CTLA-4 BsAb_D is 61.2 kDa, and protein displayed the same molecular weight as monomer under reduced condition, but the molecular weight is consistent with dimer under unreduced condition (FIG. 4-6B, Lane 1: protein marker for molecular weight; Lane 2: reduced CD3-CTLA-4 BsAb_D; Lane 3: unreduced CD3-CTLA-4 BsAb_D), which indicate two protein link to each other by disulfide bond so that this bi-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD3-CTLA-4 BsAb_M is monomer and CD3-CTLA-4 BsAb_D is dimer.

Therefore, the amino acid sequence of CD3-CTLA-4 BsAb_M monomer is shown as SEQ ID NO.222 in detail.

The amino acid sequence of CD3-CTLA-4 BsAb_D dimer is shown as SEQ ID NO.224 in detail.

The amino acid sequence of anti-CD3 scFv is shown as SEQ ID NO.242 in detail.

The amino acid sequence of anti-CD3 scFv heavy chain variable region is shown as SEQ ID NO.243 in detail.

The amino acid sequence of anti-CD3 scFv light chain variable region is shown as SEQ ID NO.244 in detail.

The amino acid sequence of anti-CTLA-4 scFv is shown as SEQ ID NO.248 in detail.

The amino acid sequence of anti-CTLA-4 scFv heavy chain variable region is shown as SEQ ID NO.249 in detail.

The amino acid sequence of anti-CTLA-4 scFv light chain variable region is shown as SEQ ID NO.250 in detail.

The amino acid sequence of CD3-CTLA-4 BsAb_M monomer linker is shown as SEQ ID NO.208 in detail.

The amino acid sequence of CD3-CTLA-4 BsAb_D dimer linker is shown as SEQ ID NO.210 in detail.

Embodiment 4-8: Antigen-Binding Activity Test of CD3-CTLA-4 BsAb_M and CD3-CTLA-4 BsAb_D by ELISA ELISA Procedure:
1. Recombinant antigen coating: 96-well plates were coated by human CD3-hFc and human CTLA-4-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding PBSA (PBS+2% BSA (V/W)) 200 μl per well to block 1 hour at 37° C.

3. Adding sample: washing plates with PBS for 4 times, adding 100 μl per well of bi-specific antibody samples respectively and keeping plates at 37° C. for 1 hour. Sample serial dilution includes: using 10 μg/ml of purified CD3-CTLA-4 BsAb_M or CD3-CTLA-4 BsAb_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well color-developing TMB (purchased from KPL), develop in dark for 5~10 min at room temperature.

5. Reaction termination and result test: adding 100 μl per well of stop buffer (1M HCl) to stop the reaction, and reading OD value of 450 nm absorbance on ELISA reader.

The results of ELISA are shown in FIGS. 4-7A and 4-7B. The three lines in the figure represent three test results: ■ coated with 1 μg/ml CD3-hFc recombinant antigen, ● coated with 1 μg/ml CTLA-4-hFc recombinant antigen; ▲ no antigen coated result. FIG. 4-7A displays that CD3-CTLA-4 BsAb_M has antigen-binding activity with CD3-hFc and CTLA-4-hFc in vitro, among which CTLA-4 has higher binding activity than that of CD3. FIG. 4-7B displays that CD3-CTLA-4 BsAb_D has antigen-binding activity with CD3-hFc and CTLA-4-hFc in vitro as well, and CTLA-4 has higher binding activity.

Embodiment 4-9: Cell Proliferation of Cytokine Induced Killer (CIK) Mediated by CD3-CTLA-4 Bi-Specific Antibody Human PBMC (Peripheral blood mononuclear cell, PBMC) was used as experiment material. CD3-CTLA-4 BsAb_M monomer and CD3-CTLA-4 BsAb_D dimer produced by this disclosure, as well as full-length antibody anti-CD3/28 combination were added to PBMC from the same donor, respectively. Cells are counted after being cultured to compare cell proliferation.

1. Separating PBMC: adding the physiological saline of same volume into the anticoagulant blood, and adding Ficoll (purchased from GE Healthcare) of same volume into the mixed-blood slowly along the centrifuge tube wall. Keeping different liquid surface clear, centrifuging at 2000 rpm for 20 min, and removing the white cell layer in the middle into a new centrifuge tube. Adding PBS with volume more than 2 times of the extracted cell layer to washing cells, centrifuging for 10 min at 1000 rpm, repeat washing once more, and adding some pre-cooling X-vivo 15 serum-free medium (purchased from Lonza) to resuspend cells. Counting the cells for use.

2. CIK cell culture and expansion: Resuspending PBMC with CIK basic medium (90% X-vivo15+10% FBS), and adjusting cell density to 1×106/ml. Setup three experiment groups: Control (coating plate with 5 μg/ml of anti-CD3 and 5 μg/ml of anti-CD28, full-length antibodies are all purchased from Novoprotein, Wujiang); Experiment 1 (adding 10 ng/ml of soluble bi-specific CD3-CTLA-4 BsAb_M); Experiment 2 (adding 10 ng/ml of soluble bi-specific CD3-CTLA-4 BsAb_D). All of the three groups were added with IFN-γ (200 ng/ml, purchased from Novoprotein, Wujiang) and IL-1B (2 ng/ml, purchased from Novoprotein, Wujiang), the cell culture was kept in incubator under the condition of saturated humidity, 37° C. and 5.0% CO2. After overnight, adding 500U/ml of IL-2 (purchased from Novoprotein, Wujiang) into cell medium and keeping culture. Every 2-3 days, counting the cells and passaging cell at the density of 1×106/ml in CIK basic medium with 500U/ml of IL-2. Keeping cell culture in this way for 30 days, counting the cells for expansion fold calculation, and drawing the cell growth curve.

The experiment results were shown as FIG. 4-8. CD3-CTLA-4 bi-specific antibody monomer and dimer can better induce CIK expansion than anti-CD3/anti-CD28 monoclonal full-length antibody combination. Anti-CD3/anti-CD28 monoclonal full-length antibody combination induced severe cell death after culturing 18 days, and cell proliferation rate significantly reduced; meanwhile, neither CD3-CTLA-4 BsAb_M monomer nor CD3-CTLA-4 BsAb_D dimer induced cell death, but the cell proliferation rate was relatively slow. Therefore, both monomer and dimer of CD3-CTLA-4 bi-specific antibodies can effectively promote cell expansion and prolong the survival of CIK cell, among which dimer has better effect.

Embodiment 4-10: IFN-γ of CIK Induced by CD3-CTLA-4 Bi-Specific Antibody

Procedure:
1. Collecting 100 μl CIK cell culture supernatant after 25 days from Embodiment 4-9 (adjusting to the same cell density, cell number is 2×10$^5$), incubate for 45 min at 37° C., and test by Human IFN-γ ELISA kit (purchased from Boster Biological Technology). Triplet for three group samples.
2. Washing with PBS for three times, adding HRP labeled IFN-γ antibody, and incubate for 45 min at 37° C.
3. Washing with PBS for three times, and then adding TIMB 100 μl to develop color. Developing at room temperature for 5-10 min.
4. Stop reaction with stop buffer HCL (1M), and then read OD value of 450 nm wavelength.

The experiment results were shown as FIG. 4-9. The amount of IFN-γ secreted by CIK cultured with anti-CD3/anti-CD28 monoclonal full-length antibody combination was defined as 1, so the relative amount of IFN-γ secreted by CIK cultured with soluble CD3-CTLA-4 BsAb_M monomer is 1.94 and the relative amount of IFN-γ secreted by CIK cultured with soluble CD3-CTLA-4 BsAb_D dimer is 2.85. Therefore, both monomer and dimer of CD3-CTLA-4 bi-specific antibody can effectively activate CIK cells and induce IFN-γ secretion, among which dimer has better effect.

Embodiment 4-11 the Eukaryotic Expression Vector Construction of CD3-LAG-3 BsAb_M and CD3-LAG-3 BsAb_D In this disclosure, the bi-specific antibody targeted CD3 and inhibitory molecule LAG-3 on human T cell is named as CD3-LAG-3 BsAb.
1. CD3-LAG-3 BsAb_M and CD3-LAG-3 BsAb_D Construction Design CD3-LAG-3 BsAb_M Monomer construction design: the sequence of anti-CD3 scFv and LAG-3 scFv is linked by (GGGGS) 3 Linker.

CD3-LAG-3 BsAb_D Dimer construction design: the sequence of anti-CD3 scFv and LAG-3 scFv is linked by IgD hinge region Linker.

In order to express the bi-specific antibody in mammalian cells, codon optimization of mammalian system was performed for the sequence of anti-CD3 scFv, LAG-3 scFv and Linker.

The nucleotide sequence of anti-CD3 scFv heavy chain variable region is shown as SEQ ID NO. 264 in detail.

The nucleotide sequence of anti-CD3 scFv light chain variable region is shown as SEQ ID NO. 265 in detail.

The nucleotide sequence of anti-CD3 scFv is shown as SEQ ID NO. 263 in detail.

The nucleotide sequence of LAG-3 scFv heavy chain variable region is shown as SEQ ID NO. 273 in detail.

The nucleotide sequence of LAG-3 scFv light chain variable region is shown as SEQ ID NO. 274 in detail.

The nucleotide sequence of LAG-3 scFv is shown as SEQ ID NO. 272 in detail.

The nucleotide sequence of CD3-LAG-3 BsAb_M monomer linker is shown as SEQ ID NO. 209 in detail.

The nucleotide sequence of CD3-LAG-3 BsAb_D dimer linker is shown as SEQ ID NO. 211 in detail.

In order to make bi-specific antibody successfully expressed in CHO-S cells and secreted into medium, signal peptide of antibody secretory expression was selected in this Embodiment.

The amino acid sequence of this secretory signal peptide is shown as SEQ ID NO.284 in detail.

The nucleotide sequence of this secretory signal peptide is shown as SEQ ID NO. 285 in detail.

2. Construction of Eukaryotic Expression Vector of CD3-LAG-3 BsAb_M and CD3-LAG-3 BsAb_D The construction and expression of this bi-specific antibody disclosure chose mammalian cell protein transient expression vector pcDNA3.1 (purchased from Invitrogen, Shanghai). In order to construct the monomer and dimer of bi-specific antibodys, primers were designed as in table 4-3. All the primers were synthesized by Genewiz, Suzhou, and DNA template for PCR was synthesized by Synbio Technologies, Suzhou.

The cloning construct for CD3-LAG-3 BsAb_M amplified signal peptide first by primers pcDNA3.1-Sig-F and Sig-R, and then amplified anti-CD3 scFv, (GGGGS) 3 Linker and LAG-3 scFv by primers Sig-CD3-F&CD3-R, and CD3-(GGGGS)$_3$-LAG-3-F&pcDNA3.1-LAG-3-R. The cloning construct for CD3-LAG-3 BsAb_D amplified signal peptide first by primers pcDNA3.1-Sig-F and Sig-R, and then amplified anti-CD3 scFv, IgD hinge region Linker, and LAG-3 scFv by primers Sig-CD3-F&CD3-R, CD3-IgD-F&IgD-R, and IgD-LAG-3-F&pcDNA3.1-LAG-3-R. After PCR amplification, by using NovoRec®PCR one-step cloning kit (purchased from novoprotein, Wujiang), the full sequence of bi-specific antibody monomer and dimer were seperately ligated and seamlessly cloned into the pcDNA3.1 vector which was linearized by EcoRI and HindIII. The target vector was transformed into *E. Coli* DH5a, colony PCR was used for positive cloning identification, and the recombinant (recombinant plasmid) identified as positive was performed sequencing identification. The recombinants (recombinant plasmid) with right sequence were purified by midi-prep, and then transfected into CHO-S cells.

After sequencing, the CD3-LAG-3 BsAb_M monomer and CD3-LAG-3 BsAb_D dimer both had the right full DNA sequence as expected.

The nucleotide sequence of CD3-LAG-3 BsAb_M monomer is shown as SEQ ID NO.227 in detail.

The nucleotide sequence of CD3-LAG-3 BsAb_D dimer is shown as SEQ ID NO.229 in detail.

TABLE 4-3

Primers used in CD3-LAG-3 bi-specific antibody gene cloning

| Primer name | Sequence | No. |
|---|---|---|
| CD3-(GGGG S)$_3$-LAG-3-F | GGCACCAAGCTGGAGCTGAAGGGCGGCGGC GGCAGCGGCGGCGGCGGCAGCGGCGGCGGC GGCAGCCAGGTGCAGCTGCAGCAGTGG | SEQ ID NO.298 |

TABLE 4-3-continued

Primers used in CD3-LAG-3 bi-specific antibody gene cloning

| Primer name | Sequence | No. |
|---|---|---|
| pcDNA3.1-LAG-3-R | CTGATCAGCGGTTTAAACTTAAGCTTTCAGCGCTTGATCTCCAGGTTGG | SEQ ID NO.299 |
| IgD-LAG-3-F | ACACCCAGCCCCTGGGCGTGCCAACCTGGAGATCAAGCGC | SEQ ID NO.300 |

Embodiment 4-12: The Expression and Purification of CD3-LAG-3 BsAb_M and CD3-LAG-3 BsAb_D 1. The Expression of CD3-LAG-3 BsAb_M and CD3-LAG-3 BsAb_D 1.1 The cell density of CHO-S cells (purchased from Thermo Fisher Scientific) was 0.5~0.6×10$^6$/ml one day before transfection.

1.2 Calculating cell density at the day of transfection, performing plasmid transfection when the density is in the range of 1~1.4×106/ml and live percentage>90%.

1.3 Transfection complex recipes: each project (CD3-LAG-3 BsAb_M and CD3-LAG-3 BsAb_D) needs two centrifuge tubes/flasks. Take total 20 ml as an example, put the recombinant plasmids from Embodiment 4-11 separately:

Tube 1: 600 μl PBS, 20 μg recombinant plasmid, mixing well.

Tube 2: 600 μl PBS, 20 μl FreeStyle™ MAX Transfection Reagent (purchased from Thermo Fisher Scientific), mixing well.

1.4 Mixing the diluted transfection reagent into the diluted recombinant plasmid, mixing well, which is transfection complex.

1.5 Keeping transfection complex for 15~20 min, adding it into cell culture by drops steadily.

1.6 Keeping cell culture after transfection at 37° C., $CO_2$ 8%, 130 rpm on cell shaker. Collecting medium after 5 days for the target protein test.

2. The Purification of CD3-LAG-3 BsAb_M and CD3-LAG-3 BsAb_D 2.1 Sample Pretreatment Get 20 ml cell medium after transfection, adding 20 mM PB, 200 mM NaCl, and adjusting pH to 7.5;

2.2 Purification of Protein L Affinity Chromatography Column

Protein purification chromatography column: Protein L affinity chromatography column (purchased from GE Healthcare, column volume: 1.0 ml)

Buffer A: PBS, pH7.4

Buffer B: 0.1M Glycine, pH3.0

Buffer C: 0.1M Glycine, pH2.7

Purification procedure: AKTA explorer 100 protein purification system (purchased from GE Healthcare) was used for purification. Pretreat Protein L affinity chromatography column with Buffer A, running culture medium sample, and collecting flowthrough sample. After running sample, balance chromatography column with at least 1.5 ml Buffer A, washing with Buffer B and Buffer C respectively after balance, and collecting flowthrough sample with target protein (the collection tube for flowthrough sample needs pretreated with 1% 1M Tris, pH8.0 to neutralize the pH of flowthrough sample, and the final concentration of Tris is about 10 mM). Finally, concentrate and dialyse into buffer PBS.

The final purified CD3-LAG-3 BsAb_M and CD3-LAG-3 BsAb_D recombinant protein was analyzed by SDS-PAGE, and the protein electrophoresis data under reduced and unreduced conditions were shown as FIG. 4-10. It shows that both purity of CD3-LAG-3 BsAb_M and CD3-LAG-3 BsAb_D recombinant protein are >95%. The theoretical molecular weight for CD3-LAG-3 BsAb_M is 53.5 kDa, and protein displayed the same single band under reduced and unreduced conditions. The molecular weight of these bands is consistent with monomer, so this bi-specific antibody is monomer (FIG. 4-10A, Lane 1: protein marker for molecular weight; Lane 2: reduced CD3-LAG-3 BsAb_M; Lane 3: unreduced CD3-LAG-3 BsAb_M). The theoretical molecular weight for CD3-LAG-3 BsAb_D is 61.4 kDa, and protein displayed the same molecular weight as monomer under reduced condition, but the molecular weight is consistent with dimer under unreduced condition (FIG. 4-10B, Lane 1: protein marker for molecular weight; Lane 2: reduced CD3-LAG-3 BsAb_D; Lane 3: unreduced CD3-LAG-3 BsAb_D), which indicate two protein link to each other by disulfide bond so that this bi-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD3-LAG-3 BsAb_M is monomer and CD3-LAG-3 BsAb_D is dimer.

Therefore, the amino acid sequence of CD3-LAG-3 BsAb_M monomer is shown as SEQ ID NO.226 in detail.

The amino acid sequence of CD3-LAG-3 BsAb_D dimer is shown as SEQ ID NO.228 in detail.

The amino acid sequence of anti-CD3 scFv is shown as SEQ ID NO.242 in detail.

The amino acid sequence of anti-CD3 scFv heavy chain variable region is shown as SEQ ID NO.243 in detail.

The amino acid sequence of anti-CD3 scFv light chain variable region is shown as SEQ ID NO.244 in detail.

The amino acid sequence of anti-LAG-3 scFv is shown as SEQ ID NO.251 in detail.

The amino acid sequence of anti-LAG-3 scFv heavy chain variable region is shown as SEQ ID NO.252 in detail.

The amino acid sequence of anti-LAG-3 scFv light chain variable region is shown as SEQ ID NO.253 in detail.

The amino acid sequence of CD3-LAG-3 BsAb_M monomer linker is shown as SEQ ID NO.208 in detail.

The amino acid sequence of CD3-LAG-3 BsAb_D dimer linker is shown as SEQ ID NO.210 in detail.

Embodiment 4-13: Antigen-Binding Activity Test of CD3-LAG-3 BsAb_M and CD3-LAG-3 BsAb_D by ELISA ELISA Procedure:

1. Recombinant antigen coating: 96-well plates were coated by human CD3-hFc and human LAG-3-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g Na$_2$HPO$_4$, 0.24 g NaH$_2$PO$_4$, 0.2 g KCl, 8.2 g NaCl, 950 ml H$_2$O, adjusting pH to 7.4 by 1 mol/L HCl or 1 mol/L NaOH, adding water to 1 L for total volume.

2. Blocking: washing plates with PBS for 4 times, and adding PBSA (PBS+2% BSA (V/W)) 200 μl per well to block 1 hour at 37° C.

3. Adding sample: washing plates with PBS for 4 times, adding 100 μl per well of bi-specific antibody samples respectively and keeping plates at 37° C. for 1 hour. Sample serial dilution includes: using 10 μg/ml of purified CD3-LAG-3 BsAb_M or CD3-LAG-3 BsAb Das starting concentration, diluting it into 6 gradient concentrations, and using 2 duplicate wells for each gradient.

4. Color developing: washing plates with PBST (PBS+ 0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well color-developing TMB (purchased from KPL), developing in dark for 5~10 min at room temperature.

5. Reaction termination and result test: adding 100 μl per well of stop buffer (1M HCl) to stop the reaction, and reading OD value of 450 nm absorbance on ELISA reader.

The results of ELISA are shown in FIGS. 4-11A and 4-11B. The three lines in the figure represent three test results: ■ coated with 1 μg/ml CD3-hFc recombinant antigen, ◆ coated with 1 μg/ml LAG-3-hFc recombinant antigen; ▲ no antigen coated result. FIG. 4-11A displays that CD3-LAG-3 BsAb_M has antigen-binding activity with CD3-hFc and LAG-3-hFc in vitro, among which LAG-3 has higher binding activity than that of CD3. FIG. 4-11B displays that CD3-LAG-3 BsAb_D has antigen-binding activity with CD3-hFc and LAG-3-hFc in vitro as well, and LAG-3 has higher binding activity.

Embodiment 4-14: Cell Proliferation of Cytokine Induced Killer (CIK) Mediated by CD3-LAG-3 Bi-Specific Antibody Human PBMC (Peripheral blood mononuclear cell, PBMC) was used as experiment material. CD3-LAG-3 BsAb_M monomer and CD3-LAG-3 BsAb_D dimer produced by this disclosure, as well as full-length antibody anti-CD3/28 combination were added to PBMC from the same donor, respectively. Cells are counted after being cultured to compare cell proliferation.

1. Separating PBMC: adding the physiological saline of same volume into the anticoagulant blood, and adding Ficoll (purchased from GE Healthcare) of same volume into the mixed-blood slowly along the centrifuge tube wall. Keeping different liquid surface clear, centrifuging at 2000 rpm for 20 min, and removing the white cell layer in the middle into a new centrifuge tube. Adding PBS with volume more than 2 times of the extracted cell layer to wash cells, centrifuging for 10 min at 1000 rpm, repeat washing once more, and adding some pre-cooling X-vivo 15 serum-free medium (purchased from Lonza) to resuspend cells. Counting the cells for use.

2. CIK cell culture and expansion: Resuspending PBMC with CIK basic medium (90% X-vivo15+10% FBS), and adjusting cell density to 1×106/ml. Setup three experiment groups: Control (coating plate with 5 μg/ml of anti-CD3 and 5 μg/ml of anti-CD28, full-length antibodies are all purchased from Novoprotein, Wujiang); Experiment 1 (adding 10 ng/ml of soluble bi-specific CD3-LAG-3 BsAb_M); Experiment 2 (adding 10 ng/ml of soluble bi-specific CD3-LAG-3 BsAb_D). All of the three groups were added with IFN-γ (200 ng/ml, purchased from Novoprotein, Wujiang) and IL-1B (2 ng/ml, purchased from Novoprotein, Wujiang), the cell culture was kept in incubator under the condition of saturated humidity, 37° C. and 5.0% CO2. After overnight, adding 500U/ml of IL-2 (purchased from Novoprotein, Wujiang) into cell medium and keeping culture. Every 2-3 days, counting the cells and passaging cell at the density of 1×106/ml in CIK basic medium with 500U/ml of IL-2. Keeping cell culture in this way for 30 days, counting the cells for expansion fold calculation, and drawing the cell growth curve.

The experiment results were shown as FIG. 4-12. CD3-LAG-3 bi-specific antibody monomer and dimer can better induce CIK expansion than anti-CD3/anti-CD28 monoclonal full-length antibody combination. Anti-CD3/anti-CD28 monoclonal full-length antibody combination induced severe cell death after culturing 18 days, and cell proliferation rate significantly reduced; Meanwhile, neither CD3-LAG-3 BsAb_M monomer nor CD3-LAG-3 BsAb_D dimer induced cell death, but the cell proliferation rate was relatively slow. Therefore, both monomer and dimer of CD3-LAG-3 bi-specific antibodies can effectively promote cell expansion and prolong the survival of CIK cell, among which dimer has better effect.

Embodiment 4-15: IFN-γ of CIK Induced by CD3-LAG-3 Bi-Specific Antibody

Procedure:

1. Collecting 100 μl CIK cell culture supernatant after 25 days from Embodiment 4-14 (adjusting to the same cell density, cell number is 2×10$^5$), incubate for 45 min at 37° C., and test by Human IFN-γ ELISA kit (purchased from Boster Biological Technology). Triplet for three group samples.

2. Washing with PBS for three times, adding HRP labeled IFN-γ antibody, and incubate for 45 min at 37° C.

3. Washing with PBS for three times, and then adding TIMB 100 μl to develop color. Developing at room temperature for 5-10 min.

4. Stop reaction with stop buffer HCL (1M), and then reading OD value of 450 nm wavelength.

The experiment results were shown as FIG. 4-13. The amount of IFN-γ secreted by CIK cultured with anti-CD3/ anti-CD28 monoclonal full-length antibody combination was defined as 1, so the relative amount of IFN-γ secreted by CIK cultured with soluble CD3-LAG-3 BsAb_M monomer is 2.25 and the relative amount of IFN-γ secreted by CIK cultured with soluble CD3-LAG-3 BsAb_D dimer is 3.37. Therefore, both monomer and dimer of CD3-LAG-3 bi-specific antibody can effectively activate CIK cells and induce IFN-γ secretion, among which dimer has better effect.

Embodiment 4-16 the Eukaryotic Expression Vector Construction of CD3-TIM-3 BsAb_M and CD3-TIM-3 BsAb_D In this disclosure, the bi-specific antibody targeted CD3 and inhibitory molecule TIM-3 on human T cell is named as CD3-TIM-3 BsAb.

1. CD3-TIM-3 BsAb_M and CD3-TIM-3 BsAb_D Construction Design

CD3-TIM-3 BsAb_M Monomer construction design: the sequence of anti-CD3 scFv and TIM-3 scFv is linked by (GGGGS) 3 Linker.

CD3-TIM-3 BsAb_D Dimer construction design: the sequence of anti-CD3 scFv and TIM-3 scFv is linked by IgD hinge region Linker.

In order to express the bi-specific antibody in mammalian cells, codon optimization of mammalian system was performed for the sequence of anti-CD3 scFv, TIM-3 scFv and Linker.

The nucleotide sequence of anti-CD3 scFv heavy chain variable region is shown as SEQ ID NO. 264 in detail.

The nucleotide sequence of anti-CD3 scFv light chain variable region is shown as SEQ ID NO. 265 in detail.

The nucleotide sequence of anti-CD3 scFv is shown as SEQ ID NO. 263 in detail.

The nucleotide sequence of TIM-3 scFv heavy chain variable region is shown as SEQ ID NO. 276 in detail.

The nucleotide sequence of TIM-3 scFv light chain variable region is shown as SEQ ID NO. 277 in detail.

The nucleotide sequence of TIM-3 scFv is shown as SEQ ID NO. 275 in detail.

The nucleotide sequence of CD3-TIM-3 BsAb_M monomer linker is shown as SEQ ID NO. 209 in detail.

The nucleotide sequence of CD3-TIM-3 BsAb_D dimer linker is shown as SEQ ID NO. 211 in detail.

In order to make bi-specific antibody successfully expressed in CHO-S cells and secreted into medium, signal peptide of antibody secretory expression was selected in this Embodiment.

The amino acid sequence of this secretory signal peptide is shown as SEQ ID NO.284 in detail.

The nucleotide sequence of this secretory signal peptide is shown as SEQ ID NO. 285 in detail.

2. Construction of Eukaryotic Expression Vector of CD3-TIM-3 BsAb_M and CD3-TIM-3 BsAb_D The construction and expression of this bi-specific antibody disclosure chose mammalian cell protein transient expression vector pcDNA3.1 (purchased from Invitrogen, Shanghai). In order to construct the monomer and dimer of bi-specific antibodys, primers were designed as in table 4-4. All the primers were synthesized by Genewiz, Suzhou, and DNA template for PCR was synthesized by Synbio Technologies, Suzhou.

The cloning construct for CD3-TIM-3 BsAb_M amplified signal peptide first by primers pcDNA3.1-Sig-F and Sig-R, and then amplified anti-CD3 scFv, (GGGGS) 3 Linker and TIM-3 scFv by primers Sig-CD3-F&CD3-R, and CD3-(GGGGS)₃-TIM-3-F&pcDNA3.1-TIM-3-R. The cloning construct for CD3-TIM-3 BsAb_D amplified signal peptide first by primers pcDNA3.1-Sig-F and Sig-R, and then amplified anti-CD3 scFv, IgD hinge region Linker, and TIM-3 scFv by primers Sig-CD3-F&CD3-R, CD3-IgD-F&IgD-R, and IgD-TIM-3-F&pcDNA3.1-TIM-3-R. After PCR amplification, by using NovoRec®PCR one-step cloning kit (purchased from novoprotein, Wujiang), the full sequence of bi-specific antibody monomer and dimer were seperately ligated and seamlessly cloned into the pcDNA3.1 vector which was linearized by EcoRI and HindIII. The target vector was transformed into E. Coli DH5a, colony PCR was used for positive cloning identification, and the recombinant (recombinant plasmid) identified as positive was performed sequencing identification. The recombinants (recombinant plasmid) with right sequence were purified by midi-prep, and then transfected into CHO-S cells.

After sequencing, the CD3-TIM-3 BsAb_M monomer and CD3-TIM-3 BsAb_D dimer both had the right full DNA sequence as expected.

The nucleotide sequence of CD3-TIM-3 BsAb_M monomer is shown as SEQ ID NO.231 in detail.

The nucleotide sequence of CD3-TIM-3 BsAb_D dimer is shown as SEQ ID NO.233 in detail.

TABLE 4-4

Primers used in CD3-TIM-3 bi-specific antibody gene cloning

| Primer name | Sequence | No. |
|---|---|---|
| CD3-(GGGG S)₃-TIM-3-F | GGCACCAAGCTGGAGCTGAAGGGCGGCGGCGG CAGCGGCGGCGGCGGCAGCGGCGGCGGCGGCA GCCAGGTGCAGCTGGTGCAGAGC | SEQ ID NO.301 |
| pcDNA3.1-TIM-3-R | CTGATCAGCCGGTTTAAACTTAAGCTTTCAGCGCT TGATCTCCACCTTGGT | SEQ ID NO.302 |
| IgD-TIM-3-F | ACACCCAGCCCCTGGGCGTGCCAAGGTGGAGAT CAAGCGC | SEQ ID NO.303 |

Embodiment 4-17: The Expression and Purification of CD3-TIM-3 BsAb_M and CD3-TIM-3 BsAb_D 1. The Expression of CD3-TIM-3 BsAb_M and CD3-TIM-3 BsAb_D 1.1 The cell density of CHO-S cells (purchased from Thermo Fisher Scientific) was $0.5$~$0.6 \times 10^6$/ml one day before transfection.

1.2 Calculating cell density at the day of transfection, performing plasmid transfection when the density is in the range of $1$~$1.4 \times 10^6$/ml and live percentage is >90%.

1.3 Transfection complex recipes: each project (CD3-TIM-3 BsAb_M and CD3-TIM-3 BsAb_D) needs two centrifuge tubes/flasks. Take total 20 ml as an example, put the recombinant plasmids from Embodiment 4-16 separately:

Tube 1: 600 µl PBS, 20 µg recombinant plasmid, mixing well.

Tube 2: 600 µl PBS, 20 µl FreeStyle™ MAX Transfection Reagent (purchased from Thermo Fisher Scientific), mixing well.

1.4 Mixing the diluted transfection reagent into the diluted recombinant plasmid, mixing well, which is transfection complex.

1.5 Keeping transfection complex for 15~20 min, adding it into cell culture by drops steadily.

1.6 Keeping cell culture after transfection at 37° C., $CO_2$ 8%, 130 rpm on cell shaker. Collecting medium after 5 days for the target protein test.

2. The Purification of CD3-TIM-3 BsAb_M and CD3-TIM-3 BsAb_D 2.1 Sample Pretreatment Get 20 ml cell medium after transfection, adding 20 mM PB, 200 mM NaCl, and adjusting pH to 7.5;

2.2 Purification of Protein L Affinity Chromatography Column

Protein purification chromatography column: Protein L affinity chromatography column (purchased from GE Healthcare, column volume: 1.0 ml)

Buffer A: PBS, pH7.4

Buffer B: 0.1M Glycine, pH3.0

Buffer C: 0.1M Glycine, pH2.7

Purification procedure: AKTA explorer 100 protein purification system (purchased from GE Healthcare) was used for purification. Pretreat Protein L affinity chromatography column with Buffer A, running culture medium sample, and collecting flowthrough sample. After running sample, balance chromatography column with at least 1.5 ml Buffer A, washing with Buffer B and Buffer C respectively after balance, and collecting flowthrough sample with target protein (the collection tube for flowthrough sample needs pretreated with 1% 1M Tris, pH8.0 to neutralize the pH of flowthrough sample, and the final concentration of Tris is about 10 mM). Finally, concentrate and dialyse into buffer PBS.

The final purified CD3-TIM-3 BsAb_M and CD3-TIM-3 BsAb_D recombinant protein was analyzed by SDS-PAGE, and the protein electrophoresis data under reduced and unreduced conditions were shown as FIG. 4-14. It shows that both purity of CD3-TIM-3 BsAb_M and CD3-TIM-3 BsAb_D recombinant protein are >95%. The theoretical molecular weight for CD3-TIM-3 BsAb_M is 53.2 kDa, and protein displayed the same single band under reduced and unreduced conditions. The molecular weight of these bands is consistent with monomer, so this bi-specific antibody is monomer (FIG. 4-14A, Lane 1: protein marker for molecular weight; Lane 2: reduced CD3-TIM-3 BsAb_M; Lane 3: unreduced CD3-TIM-3 BsAb_M). The theoretical molecular weight for CD3-TIM-3 BsAb_D is 61.1 kDa, and protein displayed the same molecular weight as monomer under reduced condition, but the molecular weight is consistent with dimer under unreduced condition (FIG. 4-14B, Lane 1: protein marker for molecular weight; Lane 2: reduced CD3-TIM-3 BsAb_D; Lane 3: unreduced CD3-TIM-3 BsAb_D), which indicate two protein link to each other by disulfide bond so that this bi-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD3-TIM-3 BsAb_M is monomer and CD3-TIM-3 BsAb_D is dimer.

Therefore, the amino acid sequence of CD3-TIM-3 BsAb_M monomer is shown as SEQ ID NO.230 in detail.

The amino acid sequence of CD3-TIM-3 BsAb_D dimer is shown as SEQ ID NO.232 in detail.

The amino acid sequence of anti-CD3 scFv is shown as SEQ ID NO.242 in detail.

The amino acid sequence of anti-CD3 scFv heavy chain variable region is shown as SEQ ID NO.243 in detail.

The amino acid sequence of anti-CD3 scFv light chain variable region is shown as SEQ ID NO.244 in detail.

The amino acid sequence of anti-TIM-3 scFv is shown as SEQ ID NO.254 in detail.

The amino acid sequence of anti-TIM-3 scFv heavy chain variable region is shown as SEQ ID NO.255 in detail.

The amino acid sequence of anti-TIM-3 scFv light chain variable region is shown as SEQ ID NO.256 in detail.

The amino acid sequence of CD3-TIM-3 BsAb_M monomer linker is shown as SEQ ID NO.208 in detail.

The amino acid sequence of CD3-TIM-3 BsAb_D dimer linker is shown as SEQ ID NO.210 in detail.

Embodiment 4-18: Antigen-Binding Activity Test of CD3-TIM-3 BsAb_M and CD3-TIM-3 BsAb_D by ELISA ELISA procedure:

1. Recombinant antigen coating: 96-well plates were coated by human CD3-hFc and human TIM-3-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding PBSA (PBS+2% BSA (V/W)) 200 μl per well to block 1 hour at 37° C.

3. Adding sample: washing plates with PBS for 4 times, adding 100 μl per well of bi-specific antibody samples respectively and keeping plates at 37° C. for 1 hour. Sample serial dilution includes: using 10 μg/ml of purified CD3-TIM-3 BsAb_M or CD3-TIM-3 BsAb_D as starting concentration, diluting it into 6 gradient concentrations, and using 2 duplicate wells for each gradient.

4. Color developing: washing plates with PBST (PBS+0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well color-developing TMB (purchased from KPL), developing in dark for 5~10 min at room temperature.

5. Reaction termination and result test: adding 100 μl per well of stop buffer (1M HCl) to stop the reaction, and reading OD value of 450 nm absorbance on ELISA reader.

The results of ELISA are shown in FIGS. 4-15A and 4-15B. The three lines in the figure represent three test results: ■ coated with 1 μg/ml CD3-hFc recombinant antigen, ✤ coated with 1 μg/ml TIM-3-hFc recombinant antigen; ▲ no antigen coated result. FIG. 4-15A displays that CD3-TIM-3 BsAb_M has antigen-binding activity with CD3-hFc and TIM-3-hFc in vitro, among which TIM-3 has higher binding activity than that of CD3. FIG. 4-15B displays that CD3-TIM-3 BsAb_D has antigen-binding activity with CD3-hFc and TIM-3-hFc in vitro as well, and TIM-3 has higher binding activity.

Embodiment 4-19: Cell Proliferation of Cytokine Induced Killer (CIK) Mediated by CD3-TIM-3 Bi-Specific Antibody Human PBMC (Peripheral blood mononuclear cell, PBMC) was used as experiment material. CD3-TIM-3 BsAb_M monomer and CD3-TIM-3 BsAb_D dimer produced by this disclosure, as well as full-length antibody anti-CD3/28 combination were added to PBMC from the same donor, respectively. Cells are counted after being cultured to compare cell proliferation.

1. Separating PBMC: adding the physiological saline of same volume into the anticoagulant blood, and adding Ficoll (purchased from GE Healthcare) of same volume into the mixed-blood slowly along the centrifuge tube wall. Keeping different liquid surface clear, centrifuging at 2000 rpm for 20 min, and removing the white cell layer in the middle into a new centrifuge tube. Adding PBS with volume more than 2 times of the extracted cell layer to wash cells, centrifuging for 10 min at 1000 rpm, repeat washing once more, and adding some pre-cooling X-vivo 15 serum-free medium (purchased from Lonza) to resuspend cells. Counting the cells for use.

2. CIK cell culture and expansion: Resuspending PBMC with CIK basic medium (90% X-vivo15+10% FBS), and adjusting cell density to 1×106/ml. Setup three experiment groups: Control (coating plate with 5 μg/ml of anti-CD3 and 5 μg/ml of anti-CD28, full-length antibodies are all purchased from Novoprotein, Wujiang); Experiment 1 (adding 10 ng/ml of soluble bi-specific CD3-TIM-3 BsAb_M); Experiment 2 (adding 10 ng/ml of soluble bi-specific CD3-TIM-3 BsAb_D). All of the three groups were added with IFN-γ (200 ng/ml, purchased from Novoprotein, Wujiang) and IL-1B (2 ng/ml, purchased from Novoprotein, Wujiang), the cell culture was kept in incubator under the condition of saturated humidity, 37° C. and 5.0% CO2. After overnight, adding 500U/ml of IL-2 (purchased from Novoprotein, Wujiang) into cell medium and keeping culture. Every 2-3 days, counting the cells and passaging cell at the density of 1×106/ml in CIK basic medium with 500U/ml of IL-2. Keeping cell culture in this way for 30 days, counting the cells for expansion fold calculation, and drawing the cell growth curve.

The experiment results were shown as FIG. 4-16. CD3-TIM-3 bi-specific antibody monomer and dimer can better induce CIK expansion than anti-CD3/anti-CD28 monoclonal full-length antibody combination. Anti-CD3/anti-CD28 monoclonal full-length antibody combination induced severe cell death after culturing for 18 days, and cell proliferation rate significantly reduced; meanwhile, neither CD3-TIM-3 BsAb_M monomer nor CD3-TIM-3 BsAb_D dimer induced cell death, but the cell proliferation rate was relatively slow. Therefore, both monomer and dimer of CD3-TIM-3 bi-specific antibodies can effectively promote cell expansion and prolong the survival of CIK cell, among which dimer has better effect.

Embodiment 4-20: IFN-γ of CIK Induced by CD3-TIM-3 Bi-Specific Antibody

Procedure:

1. Collecting 100 μl CIK cell culture supernatant after 25 days from Embodiment 4-19 (adjusting to the same cell density, cell number is 2×10$^5$), incubate for 45 min at 37° C., and test by Human IFN-γ ELISA kit (purchased from Boster Biological Technology). Triplet for three group samples.

2. Washing with PBS for three times, adding HRP labeled IFN-γ antibody, and incubate for 45 min at 37° C.

3. Washing with PBS for three times, and then adding TIMB 100 μl to develop color. Developing at room temperature for 5-10 min.

4. Stop reaction with stop buffer HCL (1M), and then reading OD value of 450 nm wavelength.

The experiment results were shown as FIG. 4-17. The amount of IFN-γ secreted by CIK cultured with anti-CD3/anti-CD28 monoclonal full-length antibody combination was defined as 1, so the relative amount of IFN-γ secreted by CIK cultured with soluble CD3-TIM-3 BsAb_M monomer is 2.07 and the relative amount of IFN-γ secreted by CIK cultured with soluble CD3-TIM-3 BsAb_D dimer is 3.04. Therefore, both monomer and dimer of CD3-TIM-3 bi-specific antibody can effectively activate CIK cells and induce IFN-γ secretion, among which dimer has better effect.

Embodiment 4-21 the Eukaryotic Expression Vector Construction of CD3-TIGIT BsAb_M and CD3-TIGIT BsAb_D In this disclosure, the bi-specific antibody targeted CD3 and inhibitory molecule TIGIT on human T cell is named as CD3-TIGIT BsAb.

1. CD3-TIGIT BsAb_M and CD3-TIGIT BsAb_D Construction Design

CD3-TIGIT BsAb_M Monomer construction design: the sequence of anti-CD3 scFv and TIGIT scFv is linked by (GGGGS) 3 Linker.

CD3-TIGIT BsAb_D Dimer construction design: the sequence of anti-CD3 scFv and TIGIT scFv is linked by IgD hinge region Linker.

In order to express the bi-specific antibody in mammalian cells, codon optimization of mammalian system was performed for the sequence of anti-CD3 scFv, TIGIT scFv and Linker.

The nucleotide sequence of anti-CD3 scFv heavy chain variable region is shown as SEQ ID NO. 264 in detail.

The nucleotide sequence of anti-CD3 scFv light chain variable region is shown as SEQ ID NO. 265 in detail.

The nucleotide sequence of anti-CD3 scFv is shown as SEQ ID NO. 263 in detail.

The nucleotide sequence of TIGIT scFv heavy chain variable region is shown as SEQ ID NO. 279 in detail.

The nucleotide sequence of TIGIT scFv light chain variable region is shown as SEQ ID NO. 280 in detail.

The nucleotide sequence of TIGIT scFv is shown as SEQ ID NO. 278 in detail.

The nucleotide sequence of CD3-TIGIT BsAb_M monomer linker is shown as SEQ ID NO. 209 in detail.

The nucleotide sequence of CD3-TIGIT BsAb_D dimer linker is shown as SEQ ID NO. 211 in detail.

In order to make bi-specific antibody successfully expressed in CHO-S cells and secreted into medium, signal peptide of antibody secretory expression was selected in this Embodiment.

The amino acid sequence of this secretory signal peptide is shown as SEQ ID NO.284 in detail.

The nucleotide sequence of this secretory signal peptide is shown as SEQ ID NO. 285 in detail.

2. Construction of Eukaryotic Expression Vector of CD3-TIGIT BsAb_M and CD3-TIGIT BsAb_D The construction and expression of this bi-specific antibody disclosure chose mammalian cell protein transient expression vector pcDNA3.1 (purchased from Invitrogen, Shanghai). In order to construct the monomer and dimer of bi-specific antibodys, primers were designed as in table 4-5. All the primers were synthesized by Genewiz, Suzhou, and DNA template for PCR was synthesized by Synbio Technologies, Suzhou.

The cloning construct for CD3-TIGIT BsAb_M amplified signal peptide first by primers pcDNA3.1-Sig-F and Sig-R, and then amplified anti-CD3 scFv, (GGGGS) 3 Linker and TIGIT scFv by primers Sig-CD3-F&CD3-R, and CD3-(GGGGS)$_3$-TIGIT-F&pcDNA3.1-TIGIT-R. The cloning construct for CD3-TIGIT BsAb_D amplified signal peptide first by primers pcDNA3.1-Sig-F and Sig-R, and then amplified anti-CD3 scFv, IgD hinge region Linker, and TIGIT scFv by primers Sig-CD3-F&CD3-R, CD3-IgD-F&IgD-R, and IgD-TIGIT-F&pcDNA3.1-TIGIT-R. After PCR amplification, by using NovoRec®PCR one-step cloning kit (purchased from novoprotein, Wujiang), the full sequence of bi-specific antibody monomer and dimer were seperately ligated and seamlessly cloned into the pcDNA3.1 vector which was linearized by EcoRI and HindIII. The target vector was transformed into E. Coli DH5a, colony PCR was used for positive cloning identification, and the recombinant (recombinant plasmid) identified as positive was performed sequencing identification. The recombinants (recombinant plasmid) with right sequence were purified by midi-prep, and then transfected into CHO-S cells.

After sequencing, the CD3-TIGIT BsAb_M monomer and CD3-TIGIT BsAb_D dimer both had the right full DNA sequence as expected.

The nucleotide sequence of CD3-TIGIT BsAb_M monomer is shown as SEQ ID NO.235 in detail.

The nucleotide sequence of CD3-TIGIT BsAb_D dimer is shown as SEQ ID NO.237 in detail.

TABLE 4-5

Primers used in CD3-TIGIT bi-specific antibody gene cloning

| Primer name | Sequence | No. |
|---|---|---|
| CD3-(GGGG S)₃-TIGIT-F | GGCACCAAGCTGGAGCTGAAGGGCGGCGGCGG CAGCGGCGGCGGCGGCAGCGGCGGCGGCGGCA GCGAGGTGCAGCTGCAGGAGAGC | SEQ ID NO.304 |
| pcDNA3.1-TI GIT-R | CTGATCAGCGGTTTAAACTTAAGCTTTCAGCGCT TCAGCTCCACCTTGG | SEQ ID NO.305 |
| IgD-TIGIT-F | ACACCCAGCCCCTGGGCGTGCCAAGGTGGAGCT GAAGCGC | SEQ ID NO.306 |

Embodiment 4-22: The Expression and Purification of CD3-TIGIT BsAb_M and CD3-TIGIT BsAb_D 1. The Expression of CD3-TIGIT BsAb_M and CD3-TIGIT BsAb_D 1.1 The cell density of CHO-S cells (purchased from Thermo Fisher Scientific) was 0.5~0.6×106/ml one day before transfection.

1.2 Calculating cell density at the day of transfection, performing plasmid transfectionwhen the density is in the range of 1~1.4×106/ml and live percentage>90%.

1.3 Transfection complex recipes: each project (CD3-TIGIT BsAb_M and CD3-TIGIT BsAb_D) needs two centrifuge tubes/flasks. Take total 20 ml as an example, put the recombinant plasmids from Embodiment 4-21 separately:

Tube 1: 600 μl PBS, 20 μg recombinant plasmid, mixing well.

Tube 2: 600 μl PBS, 20 μl FreeStyle™ MAX Transfection Reagent (purchased from Thermo Fisher Scientific), mixing well.

1.4 Mixing the diluted transfection reagent into the diluted recombinant plasmid, mixing well, which is transfection complex.

1.5 Keeping transfection complex for 15~20 min, adding it into cell culture by drops steadily.

1.6 Keeping cell culture after transfection at 37° C., $CO_2$ 8%, 130 rpm on cell shaker. Collecting medium after 5 days for the target protein test.

2. The Purification of CD3-TIGIT BsAb_M and CD3-TIGIT BsAb_D 2.1 Sample Pretreatment Get 20 ml cell medium after transfection, adding 20 mM PB, 200 mM NaCl, and adjusting pH to 7.5;

2.2 Purification of Protein L Affinity Chromatography Column

Protein purification chromatography column: Protein L affinity chromatography column (purchased from GE Healthcare, column volume: 1.0 ml)

Buffer A: PBS, pH7.4

Buffer B: 0.1M Glycine, pH3.0

Buffer C: 0.1M Glycine, pH2.7

Purification procedure: AKTA explorer 100 protein purification system (purchased from GE Healthcare) was used for purification. Pretreat Protein L affinity chromatography column with Buffer A, running culture medium sample, and collecting flowthrough sample. After running sample, balance chromatography column with at least 1.5 ml Buffer A, washing with Buffer B and Buffer C respectively after balance, and collecting flowthrough sample with target protein (the collection tube for flowthrough sample needs pretreated with 1% 1M Tris, pH8.0 to neutralize the pH of flowthrough sample, and the final concentration of Tris is about 10 mM). Finally, concentrate and dialyse into buffer PBS.

The final purified CD3-TIGIT BsAb_M and CD3-TIGIT BsAb_D recombinant protein was analyzed by SDS-PAGE, and the protein electrophoresis data under reduced and unreduced conditions were shown as FIG. 4-18. It shows that both purity of CD3-TIGIT BsAb_M and CD3-TIGIT BsAb_D recombinant protein are >95%. The theoretical molecular weight for CD3-TIGIT BsAb_M is 54.0 kDa, and protein displayed the same single band under reduced and unreduced conditions. The molecular weight of these bands is consistent with monomer, so this bi-specific antibody is monomer (FIG. 4-18A, Lane 1: protein marker for molecular weight; Lane 2: reduced CD3-TIGIT BsAb_M; Lane 3: unreduced CD3-TIGIT BsAb_M). The theoretical molecular weight for CD3-TIGIT BsAb_D is 61.9 kDa, and protein displayed the same molecular weight as monomer under reduced condition, but the molecular weight is consistent with dimer under unreduced condition (FIG. 4-18B, Lane 1: protein marker for molecular weight; Lane 2: reduced CD3-TIGIT BsAb_D; Lane 3: unreduced CD3-TIGIT BsAb_D), which indicate two protein link to each other by disulfide bond so that this bi-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD3-TIGIT BsAb_M is monomer and CD3-TIGIT BsAb_D is dimer.

Therefore, the amino acid sequence of CD3-TIGIT BsAb_M monomer is shown as SEQ ID NO.234 in detail.

The amino acid sequence of CD3-TIGIT BsAb_D dimer is shown as SEQ ID NO.236 in detail.

The amino acid sequence of anti-CD3 scFv is shown as SEQ ID NO.242 in detail.
The amino acid sequence of anti-CD3 scFv heavy chain variable region is shown as SEQ ID NO.243 in detail.
The amino acid sequence of anti-CD3 scFv light chain variable region is shown as SEQ ID NO.244 in detail.
The amino acid sequence of anti-TIGIT scFv is shown as SEQ ID NO.257 in detail.
The amino acid sequence of anti-TIGIT scFv heavy chain variable region is shown as SEQ ID NO.258 in detail.
The amino acid sequence of anti-TIGIT scFv light chain variable region is shown as SEQ ID NO.259 in detail.
The amino acid sequence of CD3-TIGIT BsAb_M monomer linker is shown as SEQ ID NO.208 in detail.
The amino acid sequence of CD3-TIGIT BsAb_D dimer linker is shown as SEQ ID NO.210 in detail.

Embodiment 4-23: Antigen-Binding Activity Test of CD3-TIGIT BsAb_M and CD3-TIGIT BsAb_D by ELISA ELISA Procedure:
1. Recombinant antigen coating: 96-well plates were coated by human CD3-hFc and human TIGIT-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.
2. Blocking: washing plates with PBS for 4 times, and adding PBSA (PBS+2% BSA (V/W)) 200 μl per well to block 1 hour at 37° C.
3. Adding sample: washing plates with PBS for 4 times, adding 100 μl per well of bi-specific antibody samples respectively and keeping plates at 37° C. for 1 hour. Sample serial dilution includes: using 10 μg/ml of purified CD3-TIGIT BsAb_M or CD3-TIGIT BsAb_D as starting concentration, diluting it into 6 gradient concentrations, and using 2 duplicate wells for each gradient.
4. Color developing: washing plates with PBST (PBS+ 0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well color-developing TMB (purchased from KPL), developing in dark for 5~10 min at room temperature.
5. Reaction termination and result test: adding 100 μl per well of stop buffer (1M HCl) to stop the reaction, and reading OD value of 450 nm absorbance on ELISA reader.

The results of ELISA are shown in FIGS. 4-19A and 4-19B. The three lines in the figure represent three test results: ■ coated with 1 μg/ml CD3-hFc recombinant antigen, ✱ coated with 1 μg/ml TIGIT-hFc recombinant antigen; ▲ no antigen coated result. FIG. 4-19A displays that CD3-TIGIT BsAb_M has antigen-binding activity with CD3-hFc and TIGIT-hFc in vitro, among which TIGIT has higher binding activity than that of CD3. FIG. 4-19B displays that CD3-TIGIT BsAb_D has antigen-binding activity with CD3-hFc and TIGIT-hFc in vitro as well, and TIGIT has higher binding activity.

Embodiment 4-24: Cell Proliferation of Cytokine Induced Killer (CIK) Mediated by CD3-TIGIT Bi-Specific Antibody Human PBMC (Peripheral blood mononuclear cell, PBMC) was used as experiment material. CD3-TIGIT BsAb_M monomer and CD3-TIGIT BsAb_D dimer produced by this disclosure, as well as full-length antibody anti-CD3/28 combination were added to PBMC from the same donor, respectively. Cells are counted after being cultured to compare cell proliferation.

1. Separating PBMC: adding the physiological saline of same volume into the anticoagulant blood, and adding Ficoll (purchased from GE Healthcare) of same volume into the mixed-blood slowly along the centrifuge tube wall. Keeping different liquid surface clear, centrifuging at 2000 rpm for 20 min, and removing the white cell layer in the middle into a new centrifuge tube. Adding PBS with volume more than 2 times of the extracted cell layer to wash cells, centrifuging for 10 min at 1000 rpm, repeat washing once more, and adding some pre-cooling X-vivo 15 serum-free medium (purchased from Lonza) to resuspend cells. Counting the cells for use.
2. CIK cell culture and expansion: Resuspending PBMC with CIK basic medium (90% X-vivo15+10% FBS), and adjusting cell density to 1×106/ml. Setup three experiment groups: Control (coating plate with 5 μg/ml of anti-CD3 and 5 μg/ml of anti-CD28, full-length antibodies are all purchased from Novoprotein, Wujiang); Experiment 1 (adding 10 ng/ml of soluble bi-specific CD3-TIGIT BsAb_M); Experiment 2 (adding 10 ng/ml of soluble bi-specific CD3-TIGIT BsAb_D). All of the three groups were added with IFN-γ (200 ng/ml, purchased from Novoprotein, Wujiang) and IL-1B (2 ng/ml, purchased from Novoprotein, Wujiang), the cell culture was kept in incubator under the condition of saturated humidity, 37° C. and 5.0% CO2. After overnight, adding 500U/ml of IL-2 (purchased from Novoprotein, Wujiang) into cell medium and keeping culture. Every 2-3 days, counting the cells and passaging cell at the density of 1×106/ml in CIK basic medium with 500U/ml of IL-2. Keeping cell culture in this way for 30 days, counting the cells for expansion fold calculation, and drawing the cell growth curve.

The experiment results were shown as FIG. 4-20. CD3-TIGIT bi-specific antibody monomer and dimer can better induce CIK expansion than anti-CD3/anti-CD28 monoclonal full-length antibody combination. Anti-CD3/anti-CD28 monoclonal full-length antibody combination induced severe cell death after culturing 18 days, and cell proliferation rate significantly reduced; meanwhile, neither CD3-TIGIT BsAb_M monomer nor CD3-TIGIT BsAb_D dimer induced cell death, but the cell proliferation rate was relatively slow. Therefore, both monomer and dimer of CD3-TIGIT bi-specific antibodies can effectively promote cell expansion and prolong the survival of CIK cell, among which dimer has better effect.

Embodiment 4-25: IFN-γ of CIK Induced by CD3-TIGIT Bi-Specific Antibody

Procedure:
1. Collecting 100 μl CIK cell culture supernatant after 25 days from Embodiment 4-24 (adjusting to the same cell density, cell number is 2×10$^5$), incubate for 45 min at 37° C., and test by Human IFN-γ ELISA kit (purchased from Boster Biological Technology). Triplet for three group samples.
2. Washing with PBS for three times, adding HRP labeled IFN-γ antibody, and incubate for 45 min at 37° C.
3. Washing with PBS for three times, and then adding TIMB 100 μl to develop color. Developing at room temperature for 5-10 min.

4. Stop reaction with stop buffer HCL (1M), and then reading OD value of 450 nm wavelength.

The experiment results were shown as FIG. 4-21. The amount of IFN-γ secreted by CIK cultured with anti-CD3/anti-CD28 monoclonal full-length antibody combination was defined as 1, so the relative amount of IFN-γ secreted by CIK cultured with soluble CD3-TIGIT BsAb_M monomer is 1.66 and the relative amount of IFN-γ secreted by CIK cultured with soluble CD3-TIGIT BsAb_D dimer is 2.30. Therefore, both monomer and dimer of CD3-TIGIT bi-specific antibody can effectively activate CIK cells and induce IFN-γ secretion, among which dimer has better effect.

Embodiment 4-26 the Eukaryotic Expression Vector Construction of CD3-BTLA BsAb_M and CD3-BTLA BsAb_D In this disclosure, the bi-specific antibody targeted CD3 and inhibitory molecule BTLA on human T cell is named as CD3-BTLA BsAb.
1. CD3-BTLA BsAb_M and CD3-BTLA BsAb_D Construction Design CD3-BTLA BsAb_M Monomer construction design: the sequence of anti-CD3 scFv and BTLA scFv is linked by (GGGGS) 3 Linker.

CD3-BTLA BsAb_D Dimer construction design: the sequence of anti-CD3 scFv and BTLA scFv is linked by IgD hinge region Linker.

In order to express the bi-specific antibody in mammalian cells, codon optimization of mammalian system was performed for the sequence of anti-CD3 scFv, BTLA scFv and Linker.

The nucleotide sequence of anti-CD3 scFv heavy chain variable region is shown as SEQ ID NO. 264 in detail.

The nucleotide sequence of anti-CD3 scFv light chain variable region is shown as SEQ ID NO. 265 in detail.

The nucleotide sequence of anti-CD3 scFv is shown as SEQ ID NO. 263 in detail.

The nucleotide sequence of BTLA scFv heavy chain variable region is shown as SEQ ID NO. 282 in detail.

The nucleotide sequence of BTLA scFv light chain variable region is shown as SEQ ID NO. 283 in detail.

The nucleotide sequence of BTLA scFv is shown as SEQ ID NO. 281 in detail.

The nucleotide sequence of CD3-BTLA BsAb_M monomer linker is shown as SEQ ID NO. 209 in detail.

The nucleotide sequence of CD3-BTLA BsAb_D dimer linker is shown as SEQ ID NO. 211 in detail.

In order to make bi-specific antibody successfully expressed in CHO-S cells and secreted into medium, signal peptide of antibody secretory expression was selected in this Embodiment.

The amino acid sequence of this secretory signal peptide is shown as SEQ ID NO.284 in detail.

The nucleotide sequence of this secretory signal peptide is shown as SEQ ID NO. 285 in detail.
2. Construction of Eukaryotic Expression Vector of CD3-BTLA BsAb_M and CD3-BTLA BsAb_D The construction and expression of this bi-specific antibody disclosure chose mammalian cell protein transient expression vector pcDNA3.1 (purchased from Invitrogen, Shanghai). In order to construct the monomer and dimer of bi-specific antibodys, primers were designed as in table 4-6. All the primers were synthesized by Genewiz, Suzhou, and DNA template for PCR was synthesized by Synbio Technologies, Suzhou.

The cloning construct for CD3-BTLA BsAb_M amplified signal peptide first by primers pcDNA3.1-Sig-F and Sig-R, and then amplified anti-CD3 scFv, (GGGGS); Linker and BTLA scFv by primers Sig-CD3-F&CD3-R, and CD3-(GGGGS)₃-BTLA-F&pcDNA3.1-BTLA-R. The cloning construct for CD3-BTLA BsAb_D amplified signal peptide first by primers pcDNA3.1-Sig-F and Sig-R, and then amplified anti-CD3 scFv, IgD hinge region Linker, and BTLA scFv by primers Sig-CD3-F&CD3-R, CD3-IgD-F&IgD-R, and IgD-BTLA-F&pcDNA3.1-BTLA-R. After PCR amplification, the full sequence of bi-specific antibody monomer and dimer were seperately ligated and seamlessly cloned into the pcDNA3.1 vector which was linearized by EcoRI and HindIII. The target vector was transformed into *E. Coli* DH5a, colony PCR was used for positive cloning identification, and the recombinant (recombinant plasmid) identified as positive was performed sequencing identification. The recombinants (recombinant plasmid) with right sequence were purified by midi-prep, and then transfected into CHO-S cells.

After sequencing, the CD3-BTLA BsAb_M monomer and CD3-BTLA BsAb_D dimer both had the right full DNA sequence as expected.

The nucleotide sequence of CD3-BTLA BsAb_M monomer is shown as SEQ ID NO.239 in detail.

The nucleotide sequence of CD3-BTLA BsAb_D dimer is shown as SEQ ID NO.241 in detail.

TABLE 4-6

Primers used in CD3-BTLA bi-specific antibody gene cloning

| Primer name | Sequence | No. |
|---|---|---|
| CD3-(GGGG S)₃-BTLA-F | GGCACCAAGCTGGAGCTGAAGGGCGGCGGCGG CAGCGGCGGCGGCGGCAGCGGCGGCGGCGGCA GCGAGGTGCAGCTGGTGGAGAGC | SEQ ID NO.307 |
| pcDNA3.1-BTLA-R | CTGATCAGCGGTTTAAACTTAAGCTTTCAGCGCT TGATCTCCAGGCGGG | SEQ ID NO.308 |
| IgD-BTLA-F | CACACCCAGCCCCTGGGCGTGGAGGTGCAGCTG GTGGAGAGC | SEQ ID NO.309 |

Embodiment 4-27: The Expression and Purification of CD3-BTLA BsAb_M and CD3-BTLA BsAb_D 1. The Expression of CD3-BTLA BsAb_M and CD3-BTLA BsAb_D 1.1 The cell density of CHO-S cells (purchased from Thermo Fisher Scientific) was 0.5~0.6×106/ml one day before transfection.

1.2 Calculating cell density at the day of transfection, performing plasmid transfection when the density is in the range of 1~1.4×106/ml and live percentage is >90%.

1.3 Transfection complex recipes: each project (CD3-BTLA BsAb_M and CD3-BTLA BsAb_D) needs two centrifuge tubes/flasks. Take total 20 ml as an example, put the recombinant plasmids from Embodiment 4-26 separately:

Tube 1: 600 μl PBS, 20 μg recombinant plasmid, mixing well.

Tube 2: 600 μl PBS, 20 μl FreeStyle™ MAX Transfection Reagent (purchased from Thermo Fisher Scientific), mixing well.

1.4 Mixing the diluted transfection reagent into the diluted recombinant plasmid, mixing well, which is transfection complex.

1.5 Keeping transfection complex for 15~20 min, adding it into cell culture by drops steadily.

1.6 Keeping cell culture after transfection at 37° C., $CO_2$ 8%, 130 rpm on cell shaker. Collecting medium after 5 days for the target protein test.

2. The Purification of CD3-BTLA BsAb_M and CD3-BTLA BsAb_D 2.1 Sample Pretreatment Get 20 ml cell medium after transfection, adding 20 mM PB, 200 mM NaCl, and adjusting pH to 7.5;

2.2 Purification of Protein L Affinity Chromatography Column

Protein purification chromatography column: Protein L affinity chromatography column (purchased from GE Healthcare, column volume: 1.0 ml)

Buffer A: PBS, pH7.4

Buffer B: 0.1M Glycine, pH3.0

Buffer C: 0.1M Glycine, pH2.7

Purification procedure: AKTA explorer 100 protein purification system (purchased from GE Healthcare) was used for purification. Pretreat Protein L affinity chromatography column with Buffer A, running culture medium sample, and collecting flowthrough sample. After running sample, balance chromatography column with at least 1.5 ml Buffer A, washing with Buffer B and Buffer C respectively after balance, and collecting flowthrough sample with target protein (the collection tube for flowthrough sample needs pretreated with 1% 1M Tris, pH8.0 to neutralize the pH of flowthrough sample, and the final concentration of Tris is about 10 mM). Finally, concentrate and dialyse into buffer PBS.

The final purified CD3-BTLA BsAb_M and CD3-BTLA BsAb_D recombinant protein was analyzed by SDS-PAGE, and the protein electrophoresis data under reduced and unreduced conditions were shown as FIG. 4-22. It shows that both purity of CD3-BTLA BsAb_M and CD3-BTLA BsAb_D recombinant protein are >95%. The theoretical molecular weight for CD3-BTLA BsAb_M is 53.1 kDa, and protein displayed the same single band under reduced and unreduced conditions. The molecular weight of these bands is consistent with monomer, so this bi-specific antibody is monomer (FIG. 4-22A, Lane 1: protein marker for molecular weight; Lane 2: reduced CD3-BTLA BsAb_M; Lane 3: unreduced CD3-BTLA BsAb_M). The theoretical molecular weight for CD3-BTLA BsAb_D is 61.0 kDa, and protein displayed the same molecular weight as monomer under reduced condition, but the molecular weight is consistent with dimer under unreduced condition (FIG. 4-22B, Lane 1: protein marker for molecular weight; Lane 2: reduced CD3-BTLA BsAb_D; Lane 3: unreduced CD3-BTLA BsAb_D), which indicate two protein link to each other by disulfide bond so that this bi-specific antibody is dimer.

Moreover, the N/C terminal sequence analysis for purified recombinant protein shows the reading frame has no error, consistent with the theoretical N/C terminal amino acid sequence. Mass spectrometry analysis further confirmed that CD3-BTLA BsAb_M is monomer and CD3-BTLA BsAb_D is dimer.

Therefore, the amino acid sequence of CD3-BTLA BsAb_M monomer is shown as SEQ ID NO.238 in detail.

The amino acid sequence of CD3-BTLA BsAb_D dimer is shown as SEQ ID NO.240 in detail.

The amino acid sequence of anti-CD3 scFv is shown as SEQ ID NO.242 in detail.

The amino acid sequence of anti-CD3 scFv heavy chain variable region is shown as SEQ ID NO.243 in detail.

The amino acid sequence of anti-CD3 scFv light chain variable region is shown as SEQ ID NO.244 in detail.

The amino acid sequence of anti-BTLA scFv is shown as SEQ ID NO.260 in detail.

The amino acid sequence of anti-BTLA scFv heavy chain variable region is shown as SEQ ID NO.261 in detail.

The amino acid sequence of anti-BTLA scFv light chain variable region is shown as SEQ ID NO.262 in detail.

The amino acid sequence of CD3-BTLA BsAb_M monomer linker is shown as SEQ ID NO.208 in detail.

The amino acid sequence of CD3-BTLA BsAb_D dimer linker is shown as SEQ ID NO.210 in detail.

Embodiment 4-28: Antigen-Binding Activity Test of CD3-BTLA BsAb_M and CD3-BTLA BsAb_D by ELISA ELISA Procedure:

1. Recombinant antigen coating: 96-well plates were coated by human CD3-hFc and human BTLA-hFc recombinant protein (purchased from Novoprotein, Wujiang) 100 μl per well in concentration 1 μg/ml. The coated plates were kept at 37° C. for 1 hour or at 4° C. overnight. The recipe for coating buffer is: 3.58 g $Na_2HPO_4$, 0.24 g $NaH_2PO_4$, 0.2 g KCl, 8.2 g NaCl, 950 ml $H_2O$, adjusting pH to 7.4 by 1 mol/L HCl or 1 mol/L NaOH, adding water to 1 L for total volume.

2. Blocking: washing plates with PBS for 4 times, and adding PBSA (PBS+2% BSA (V/W)) 200 μl per well to block 1 hour at 37° C.

3. Adding sample: washing plates with PBS for 4 times, adding 100 μl per well of bi-specific antibody samples respectively and keeping plates at 37° C. for 1 hour. Sample serial dilution includes: using 10 μg/ml of purified CD3-BTLA BsAb_M or CD3-BTLA BsAb_D as starting concentration, diluting it into 6 gradient concentrations, and using 2 duplicate wells for each gradient.

4. Color developing: washing plates with PBST (PBS+ 0.05% Tween-20 (V/V)) for 4 times, diluting 1/5000 HRP labeled color-developing antibody (purchased from Abcam) by blocking buffer PBSA, adding 100 μl per well and keeping plates at 37° C. for 1 hour. Washing plates with PBS for 4 times, adding 100 μl per well color-developing TMB (purchased from KPL), developing in dark for 5~10 min at room temperature.

5. Reaction termination and result test: adding 100 μl per well of stop buffer (1M HCl) to stop the reaction, and reading OD value of 450 nm absorbance on ELISA reader.

The results of ELISA are shown in FIGS. 4-23A and 4-23B. The three lines in the figure represent three test results: ■ coated with 1 μg/ml CD3-hFc recombinant antigen, ♦ coated with 1 μg/ml BTLA-hFc recombinant antigen; ▲ no antigen coated result. FIG. 4-23A displays that CD3-BTLA BsAb_M has antigen-binding activity with CD3-hFc and BTLA-hFc in vitro, among which BTLA has higher binding activity than that of CD3. FIG. 4-23B displays that CD3-BTLA BsAb_D has antigen-binding activity with CD3-hFc and BTLA-hFc in vitro as well, and BTLA has higher binding activity.

Embodiment 4-29: Cell Proliferation of Cytokine Induced Killer (CIK) Mediated by CD3-BTLA Bi-Specific Antibody Human PBMC (Peripheral blood mononuclear cell, PBMC) was used as experiment material. CD3-BTLA BsAb_M monomer and CD3-BTLA BsAb_D dimer produced by this disclosure, as well as full-length antibody anti-CD3/28 combination were added to PBMC from the same donor, respectively. Cells are counted after being cultured to compare cell proliferation.

1. Separating PBMC: adding the physiological saline of same volume into the anticoagulant blood, and adding Ficoll (purchased from GE Healthcare) of same volume into the mixed-blood slowly along the centrifuge tube wall. Keeping different liquid surface clear, centrifuging at 2000 rpm for 20 min, and removing the white cell layer in the middle into new centrifuge tube. Adding PBS with volume more than 2 times of the extracted cell layer to wash cells, centrifuging for 10 min at 1000 rpm, repeat washing once more, and adding some pre-cooling X-vivo 15 serum-free medium (purchased from Lonza) to resuspend cells. Counting the cells for use.

2. CIK cell culture and expansion: Resuspending PBMC with CIK basic medium (90% X-vivo15+10% FBS), and adjusting cell density to 1×106/ml. Setup three experiment groups: Control (coating plate with 5 μg/ml of anti-CD3 and 5 μg/ml of anti-CD28, full-length antibodies are all purchased from Novoprotein, Wujiang); Experiment 1 (adding 10 ng/ml of soluble bi-specific CD3-BTLA BsAb_M); Experiment 2 (adding 10 ng/ml of soluble bi-specific CD3-BTLA BsAb_D). All of the three groups were added with IFN-γ (200 ng/ml, purchased from Novoprotein, Wujiang) and IL-1B (2 ng/ml, purchased from Novoprotein, Wujiang), the cell culture was kept in incubator under the condition of saturated humidity, 37° C. and 5.0% CO2. After overnight, adding 500U/ml of IL-2 (purchased from Novoprotein, Wujiang) into cell medium and keeping culture. Every 2-3 days, counting the cells and passaging cell at the density of 1×106/ml in CIK basic medium with 500U/ml of IL-2. Keeping cell culture in this way for 30 days, counting the cells for expansion fold calculation, and drawing the cell growth curve.

The experiment results were shown as FIG. 4-24. CD3-BTLA bi-specific antibody monomer and dimer can better induce CIK expansion than anti-CD3/anti-CD28 monoclonal full-length antibody combination. Anti-CD3/anti-CD28 monoclonal full-length antibody combination induced severe cell death after culturing 18 days, and cell proliferation rate significantly reduced; meanwhile, neither CD3-BTLA BsAb_M monomer nor CD3-BTLA BsAb_D dimer induced cell death, but the cell proliferation rate was relatively slow. Therefore, both monomer and dimer of CD3-BTLA bi-specific antibodies can effectively promote cell expansion and prolong the survival of CIK cell, among which dimer has better effect.

Embodiment 4-30: IFN-γ of CIK Induced by CD3-BTLA Bi-Specific Antibody

Procedure:

1. Collecting 100 μl CIK cell culture supernatant after 25 days from Embodiment 4-29 (adjusting to the same cell density, cell number is 2×10$^5$), incubate for 45 min at 37° C., and test by Human IFN-γ ELISA kit (purchase from Boster Biological Technology). Triplet for three group samples.

2. Washing with PBS for three times, adding HRP labeled IFN-γ antibody, and incubate for 45 min at 37° C.

3. Washing with PBS for three times, and then adding TIMB 100 μl to develop color. Developing at room temperature for 5-10 min.

4. Stop reaction with stop buffer HCL (1M), and then reading OD value of 450 nm wavelength.

The experiment results were shown as FIG. 4-25. The amount of IFN-γ secreted by CIK cultured with anti-CD3/anti-CD28 monoclonal full-length antibody combination was defined as 1, so the relative amount of IFN-γ secreted by CIK cultured with soluble CD3-BTLA BsAb_M monomer is 1.54 and the relative amount of IFN-γ secreted by CIK cultured with soluble CD3-BTLA BsAb_D dimer is 2.24. Therefore, both monomer and dimer of CD3-BTLA bi-specific antibody can effectively activate CIK cells and induce IFN-γ secretion, among which dimer has better effect.

Embodiments as shown above are only the optical examples of this disclosure, not limitation in nomenclature and in substance. It should be noted that embodiments of the present disclosure may take on various modifications and alteration without departing from the method of this disclosure for people in this technical field, which should be under the scope of protection of the present disclosure. For the technical personnel familiar with this field, all the slight change, modification and evolution of the equivalent changes without breaking away from the spirit and scope of the present disclosure are the equivalent embodiment of the present disclosure. Meanwhile, all the change, modification and evolution of equivalent changes for the above embodiments according to the essential technique of this disclosure are controlled by the limitations set forth in the claims.

Table of Sequence

See TXT. file in detail. Please review every sequence.

The invention claimed is:

1. A bifunctional molecule comprising a first function domain capable of binding to and activating a CD3 molecule on the surface of T cell, and a second function domain capable of binding to and activating a T cell positive costimulatory molecule;
wherein the first function domain is an anti-CD3 scFv, the second function domain is a scFv against a T cell positive costimulatory molecule or a ligand extracellular domain of a T cell positive costimulatory molecule;
wherein the first function domain and the second function domain are connected by a linker fragment;
wherein the linker fragment is a hinge domain fragment of immunoglobulin IgD, and the amino acid sequence of the hinge domain fragment of immunoglobulin IgD is as shown in SEQ ID NO. 19.

2. The bifunctional molecule according to claim 1, wherein
the scFv against T cell positive costimulatory molecule is selected from the group consisting of anti-CD28 scFv, anti-4-1BB scFv, anti-ICOS scFv, anti-OX40 scFv, anti-GITR scFv, anti-CD40L, scFv, or anti-CD27 scFv;
the ligand extracellular domain of the T cell positive costimulatory molecule is selected from the group consisting of 4-1BBL, B7RP-1, OX40L, GITRL or CD70 ligand extracellular domains.

3. The bifunctional molecule according to claim 2,
wherein the scFv comprises a heavy chain variable region and a light chain variable region;
wherein the amino acid sequence of the heavy chain variable region of the anti-CD3 scFv is shown in SEQ ID NO. 6, the amino acid sequence of the light chain variable region of the anti-CD3 scFv is shown in SEQ ID NO. 7;
the amino acid sequence of the heavy chain variable region of the anti-CD28 scFv is shown in SEQ ID NO. 9, the amino acid sequence of the light chain variable region of the anti-CD28 scFv is shown in SEQ ID NO. 10;
the amino acid sequence of the heavy chain variable region of the anti-4-1BB scFv is shown in SEQ ID NO. 71, the amino acid sequence of the light chain variable region of the anti-4-1BB scFv is shown in SEQ ID NO. 72;
the amino acid sequence of the heavy chain variable region of the anti-ICOS scFv is shown in SEQ ID NO. 74, the amino acid sequence of the light chain variable region of the anti-ICOS scFv is shown in SEQ ID NO.75;
the amino acid sequence of the heavy chain variable region of the anti-OX40 scFv is shown in SEQ ID NO. 77, the amino acid sequence of the light chain variable region of the anti-OX40 scFv is shown in SEQ ID NO. 78;
the amino acid sequence of the heavy chain variable region of the anti-GITR scFv is shown in SEQ ID NO. 80, the amino acid sequence of the light chain variable region of the anti-GITR scFv is shown in SEQ ID NO. 81;
the amino acid sequence of the heavy chain variable region of the anti-CD40L scFv is shown in SEQ ID NO. 83, the amino acid sequence of the light chain variable region of the anti-CD40L scFv is shown in SEQ ID NO. 84;
the amino acid sequence of the heavy chain variable region of the anti-CD27 scFv is shown in SEQ ID NO. 86, the amino acid sequence of the light chain variable region of the anti-CD27 is shown in SEQ ID NO. 87.

4. The bifunctional molecule according to claim 2, wherein
the amino acid sequence of the anti-CD3 scFv is shown in SEQ ID NO. 5;
the amino acid sequence of the anti-CD28 scFv is shown in SEQ ID NO. 8;
the amino acid sequence of the anti-4-1BB scFv is shown in SEQ ID NO. 70;
the amino acid sequence of the anti-ICOS scFv is shown in SEQ ID NO. 73;
the amino acid sequence of the anti-OX40 scFv is shown in SEQ ID NO. 76;
the amino acid sequence of the anti-GITR scFv is shown in SEQ ID NO. 79;
the amino acid sequence of the anti-CD40L scFv is shown in SEQ ID NO. 82;
the amino acid sequence of the anti-CD27 scFv is shown in SEQ ID NO. 85;
the amino acid sequence of 4-IBBL extracellular domain is shown in SEQ ID NO. 172;
the amino acid sequence of B7RP-1 extracellular domain is shown in SEQ ID NO. 173;
the amino acid sequence of OX40L extracellular domain is shown in SEQ ID NO. 174;
the amino acid sequence of GITRL extracellular domain is shown in SEQ ID NO. 175;
the amino acid sequence of CD70 extracellular domain is shown in SEQ ID NO. 176.

5. The bifunctional molecule according to claim 1, wherein
the amino acid sequence of the bifunctional molecule is as shown in any one of SEQ ID NO. 3, SEQ ID NO. 45, SEQ ID NO.49, SEQ ID NO. 53, SEQ ID NO. 57, SEQ ID NO. 61, SEQ ID NO. 65, SEQ ID NO. 151, SEQ ID NO. 155, SEQ ID NO. 159, SEQ ID NO. 163 or SEQ ID NO. 167.

6. A polynucleotide encoding a bifunctional molecule according to claim 1.

7. An expression vector comprising the polynucleotide of claim 6.

8. A host cell transfected with the expression vector of claim 7.

9. A method for preparing a bifunctional molecule of claim 1, comprising: constructing an expression vector containing a bifunctional molecule gene sequence, transfecting the expression vector into a host cell to induce expression, and separating bifunctional molecule from an expression product.

10. A method for expanding T cell in vitro, comprising administering the bifunctional molecule according to claim 1 working on T cells.

\* \* \* \* \*

SEQUENCE LISTING

```
<160> NUMBER OF SEQ ID NOS: 309

<210> SEQ ID NO 1
<211> LENGTH: 501
<212> TYPE: PRT
<213> ORGANISM: Artificial
<220> FEATURE:
```

<223> OTHER INFORMATION: The amino acid sequence of CD3-CD28 BsAb_M

<400> SEQUENCE: 1

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Gly Gly Gly Gly Ser Gly Gly Gly Gly Ser Gly Gly Gly
                245                 250                 255

Gly Ser Gln Val Gln Leu Val Gln Ser Gly Ala Glu Val Lys Lys Pro
            260                 265                 270

Gly Ala Ser Val Lys Val Ser Cys Lys Ala Ser Gly Tyr Thr Phe Thr
        275                 280                 285

Ser Tyr Tyr Ile His Trp Val Arg Gln Ala Pro Gly Gln Gly Leu Glu
    290                 295                 300

Trp Ile Gly Cys Ile Tyr Pro Gly Asn Val Asn Thr Asn Tyr Asn Glu
305                 310                 315                 320

Lys Phe Lys Asp Arg Ala Thr Leu Thr Val Asp Thr Ser Ile Ser Thr
                325                 330                 335

Ala Tyr Met Glu Leu Ser Arg Leu Arg Ser Asp Asp Thr Ala Val Tyr
            340                 345                 350

Phe Cys Thr Arg Ser His Tyr Gly Leu Asp Trp Asn Phe Asp Val Trp
        355                 360                 365

Gly Gln Gly Thr Thr Val Thr Val Ser Ser Gly Gly Gly Gly Ser Gly
    370                 375                 380

Gly Gly Gly Ser Gly Gly Gly Gly Ser Asp Ile Gln Met Thr Gln Ser
385                 390                 395                 400
```

```
Pro Ser Ser Leu Ser Ala Ser Val Gly Asp Arg Val Thr Ile Thr Cys
                405                 410                 415

His Ala Ser Gln Asn Ile Tyr Val Trp Leu Asn Trp Tyr Gln Gln Lys
            420                 425                 430

Pro Gly Lys Ala Pro Lys Leu Leu Ile Tyr Lys Ala Ser Asn Leu His
        435                 440                 445

Thr Gly Val Pro Ser Arg Phe Ser Gly Ser Gly Ser Gly Thr Asp Phe
    450                 455                 460

Thr Leu Thr Ile Ser Ser Leu Gln Pro Glu Asp Phe Ala Thr Tyr Tyr
465                 470                 475                 480

Cys Gln Gln Gly Gln Thr Tyr Pro Tyr Thr Phe Gly Gly Gly Thr Lys
                485                 490                 495

Val Glu Ile Lys Arg
            500

<210> SEQ ID NO 2
<211> LENGTH: 1503
<212> TYPE: DNA
<213> ORGANISM: Artificial
<220> FEATURE:
<223> OTHER INFORMATION: The nucleotide sequence of CD3-CD28 BsAb_M

<400> SEQUENCE: 2
gacatcaagc tgcagcagag cggcgccgag ctggcccgcc ccggcgccag cgtgaagatg     60
agctgcaaga ccagcggcta caccttcacc cgctacacca tgcactgggt gaagcagcgc    120
cccggccagg gcctggagtg gatcggctac atcaaccccg ccgcggcta caccaactac    180 aaccagaagt tcaaggacaa ggccaccctg accaccgaca gagcagcag caccgcctac    240 atgcagctga gcagcctgac cagcgaggac agcgccgtgt actactgcgc ccgctactac    300
gacgaccact actgcctgga ctactggggc cagggcacca ccctgaccgt gagcagcgtg    360
gagggcggca gcggcggcag cggcggcagc ggcggcagcg gcggcgtgga cgacatccag    420
ctgacccaga gccccgccat catgagcgcc agccccggcg agaaggtgac catgacctgc    480
cgcgccagca gcagcgtgag ctacatgaac tggtaccagc agaagagcgg caccagcccc    540
aagcgctgga tctacgacac cagcaaggtg gccagcggcg tgccctaccg cttcagcggc    600
agcggcagcg gcaccagcta cagcctgacc atcagcagca tggaggccga ggacgccgcc    660
acctactact gccagcagtg gagcagcaac ccctgacct cggcgccgg caccaagctg    720 gagctgaagg gcggcggcgg cagcggcggc ggcggcagcg gcggcggcgg cagccaggtg    780
cagctggtgc agagcggcgc cgaggtgaag aagcccggcg ccagcgtgaa ggtgagctgc    840
aaggccagcg gctacacctt caccagctac tacatccact gggtgcgcca ggccccggc    900 cagggcctgg agtggatcgg ctgcatctac cccggcaacg tgaacaccaa ctacaacgag    960
aagttcaagg accgcgccac cctgaccgtg gacaccagca tcagcaccgc ctacatggag   1020
ctgagccgcc tgcgcagcga cgacaccgcc gtgtacttct gcacccgcag ccactacggc   1080
ctggactgga acttcgacgt gtggggccag ggcaccaccg tgaccgtgag cagcggcggc   1140
ggcggcagcg gcggcggcgg cagcggcggc ggcggcagcg acatccagat gacccagagc   1200
cccagcagcc tgagcgccag cgtgggcgac cgcgtgacca tcacctgcca cgccagccag   1260
aacatctacg tgtggctgaa ctggtaccag cagaagcccg gcaaggcccc caagctgctg   1320
atctacaagg ccagcaacct gcacaccggc gtgcccagcc gcttcagcgg cagcggcagc   1380
ggcaccgact tcaccctgac catcagcagc ctgcagcccg aggacttcgc cacctactac   1440
```

```
tgccagcagg gccagaccta ccccctacacc ttcggcggcg gcaccaaggt ggagatcaag    1500
cgc                                                                  1503

<210> SEQ ID NO 3
<211> LENGTH: 567
<212> TYPE: PRT
<213> ORGANISM: Artificial
<220> FEATURE:
<223> OTHER INFORMATION: The amino acid sequence of CD3-CD28 BSAB_D

<400> SEQUENCE: 3
```

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Ala Ser Lys Ser Lys Glu Ile Phe Arg Trp Pro Glu
                245                 250                 255

Ser Pro Lys Ala Gln Ala Ser Ser Val Pro Thr Ala Gln Pro Gln Ala
            260                 265                 270

Glu Gly Ser Leu Ala Lys Ala Thr Thr Ala Pro Ala Thr Thr Arg Asn
        275                 280                 285

Thr Gly Arg Gly Gly Glu Glu Lys Lys Lys Glu Lys Glu Lys Glu Glu
    290                 295                 300

Gln Glu Glu Arg Glu Thr Lys Thr Pro Glu Cys Pro Ser His Thr Gln
305                 310                 315                 320

Pro Leu Gly Val Gln Val Gln Leu Val Gln Ser Gly Ala Glu Val Lys
                325                 330                 335

Lys Pro Gly Ala Ser Val Lys Val Ser Cys Lys Ala Ser Gly Tyr Thr
            340                 345                 350

```
Phe Thr Ser Tyr Tyr Ile His Trp Val Arg Gln Ala Pro Gly Gln Gly
        355                 360                 365

Leu Glu Trp Ile Gly Cys Ile Tyr Pro Gly Asn Val Asn Thr Asn Tyr
    370                 375                 380

Asn Glu Lys Phe Lys Asp Arg Ala Thr Leu Thr Val Asp Thr Ser Ile
385                 390                 395                 400

Ser Thr Ala Tyr Met Glu Leu Ser Arg Leu Arg Ser Asp Asp Thr Ala
                405                 410                 415

Val Tyr Phe Cys Thr Arg Ser His Tyr Gly Leu Asp Trp Asn Phe Asp
            420                 425                 430

Val Trp Gly Gln Gly Thr Thr Val Thr Val Ser Ser Gly Gly Gly Gly
        435                 440                 445

Ser Gly Gly Gly Gly Ser Gly Gly Gly Gly Ser Asp Ile Gln Met Thr
    450                 455                 460

Gln Ser Pro Ser Ser Leu Ser Ala Ser Val Gly Asp Arg Val Thr Ile
465                 470                 475                 480

Thr Cys His Ala Ser Gln Asn Ile Tyr Val Trp Leu Asn Trp Tyr Gln
                485                 490                 495

Gln Lys Pro Gly Lys Ala Pro Lys Leu Leu Ile Tyr Lys Ala Ser Asn
            500                 505                 510

Leu His Thr Gly Val Pro Ser Arg Phe Ser Gly Ser Gly Ser Gly Thr
        515                 520                 525

Asp Phe Thr Leu Thr Ile Ser Ser Leu Gln Pro Glu Asp Phe Ala Thr
    530                 535                 540

Tyr Tyr Cys Gln Gln Gly Gln Thr Tyr Pro Tyr Thr Phe Gly Gly Gly
545                 550                 555                 560

Thr Lys Val Glu Ile Lys Arg
                565
```

<210> SEQ ID NO 4
<211> LENGTH: 1701
<212> TYPE: DNA
<213> ORGANISM: Artificial
<220> FEATURE:
<223> OTHER INFORMATION: The nucleotide sequence of CD3-CD28 BsAb_D

<400> SEQUENCE: 4

```
gacatcaagc tgcagcagag cggcgccgag ctggcccgcc ccggcgccag cgtgaagatg      60
agctgcaaga ccagcggcta caccttcacc cgctacacca tgcactgggt gaagcagcgc     120
cccggccagg gcctggagtg gatcggctac atcaaccccc gccgcggcta caccaactac     180
aaccagaagt tcaaggacaa ggccaccctg accaccgaca gagcagcag caccgcctac     240
atgcagctga gcagcctgac cagcgaggac agcgccgtgt actactgcgc cgctactac     300
gacgaccact actgcctgga ctactggggc cagggcacca ccctgaccgt gagcagcgtg     360
gagggcggca gcggcggcag cggcggcagc ggcggcagcg gcggcgtgga cgacatccag     420
ctgacccaga gccccgccat catgagcgcc agccccggcg agaaggtgac catgacctgc     480
cgcgccagca gcagcgtgag ctacatgaac tggtaccagc agaagagcgg caccagcccc     540
aagcgctgga tctacgacac cagcaaggtg gccagcggcg tgccctaccg cttcagcggc     600
agcggcagcg gcaccagcta cagcctgacc atcagcagca tggaggccga ggacgccgcc     660
acctactact gccagcagtg gagcagcaac cccctgacct cggcgccgg caccaagctg     720
gagctgaagg ccagcaagag caagaaggag atcttccgct ggcccgagag ccccaaggcc     780
```

-continued

| | |
|---|---|
| caggccagca gcgtgcccac cgcccagccc caggccgagg gcagcctggc caaggccacc | 840 |
| accgccccg ccaccacccg caacaccggc cgcggcggcg aggagaagaa gaaggagaag | 900 |
| gagaaggagg agcaggagga gcgcgagacc aagaccccg agtgcccag ccacacccag | 960 |
| cccctgggcg tgcaggtgca gctggtgcag agcggcgccg aggtgaagaa gcccggcgcc | 1020 |
| agcgtgaagg tgagctgcaa ggccagcggc tacaccttca ccagctacta catccactgg | 1080 |
| gtgcgccagg cccccggcca gggcctggag tggatcggct gcatctaccc cggcaacgtg | 1140 |
| aacaccaact acaacgagaa gttcaaggac cgcgccaccc tgaccgtgga caccagcatc | 1200 |
| agcaccgcct acatggagct gagccgcctg cgcagcgacg acaccgccgt gtacttctgc | 1260 |
| acccgcagcc actacggcct ggactggaac ttcgacgtgt ggggccaggg caccaccgtg | 1320 |
| accgtgagca gcggcggcgg cggcagcggc ggcggcggca gcggcggcgg cggcagcgac | 1380 |
| atccagatga cccagagccc cagcagcctg agcgccagcg tgggcgaccg cgtgaccatc | 1440 |
| acctgccacg ccagccagaa catctacgtg tggctgaact ggtaccagca gaagcccggc | 1500 |
| aaggcccca agctgctgat ctacaaggcc agcaacctgc acaccggcgt gcccagccgc | 1560 |
| ttcagcggca gcggcagcgg caccgacttc accctgacca tcagcagcct gcagcccgag | 1620 |
| gacttcgcca cctactactg ccagcagggc cagacctacc cctacacctt cggcggcggc | 1680 |
| accaaggtgg agatcaagcg c | 1701 |

<210> SEQ ID NO 5
<211> LENGTH: 243
<212> TYPE: PRT
<213> ORGANISM: Artificial
<220> FEATURE:
<223> OTHER INFORMATION: The amino acid sequence of anti-CD3 scFv

<400> SEQUENCE: 5

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser

-continued

```
                195                 200                 205
Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys

<210> SEQ ID NO 6
<211> LENGTH: 119
<212> TYPE: PRT
<213> ORGANISM: Artificial
<220> FEATURE:
<223> OTHER INFORMATION: The amino acid sequence of anti-CD3 scFv heavy
      chain variable region

<400> SEQUENCE: 6

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Thr Leu Thr Val Ser Ser
            115

<210> SEQ ID NO 7
<211> LENGTH: 106
<212> TYPE: PRT
<213> ORGANISM: Artificial
<220> FEATURE:
<223> OTHER INFORMATION: The amino acid sequence of anti-CD3 scFv light
      chain variable region

<400> SEQUENCE: 7

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Val Ala Ser Gly Val Pro Tyr Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
                100                 105

<210> SEQ ID NO 8
```

<211> LENGTH: 243
<212> TYPE: PRT
<213> ORGANISM: Artificial
<220> FEATURE:
<223> OTHER INFORMATION: The amino acid sequence of anti-CD28 scFv

<400> SEQUENCE: 8

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys His Ala
145                 150                 155                 160

Ser Gln Asn Ile Tyr Val Trp Leu Asn Trp Tyr Gln Gln Lys Pro Gly
                165                 170                 175

Lys Ala Pro Lys Leu Leu Ile Tyr Lys Ala Ser Asn Leu His Thr Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln Gly Gln Thr Tyr Pro Tyr Thr Phe Gly Gly Gly Thr Lys Val Glu
225                 230                 235                 240

Ile Lys Arg
```

<210> SEQ ID NO 9
<211> LENGTH: 120
<212> TYPE: PRT
<213> ORGANISM: Artificial
<220> FEATURE:
<223> OTHER INFORMATION: The amino acid sequence of anti-CD28 scFv heavy
      chain variable region

<400> SEQUENCE: 9

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
```

```
                65                  70                  75                  80
Met Glu Leu Ser Arg Leu Arg Ser Asp Asp Thr Ala Val Tyr Phe Cys
                        85                  90                  95

Thr Arg Ser His Tyr Gly Leu Asp Trp Asn Phe Asp Val Trp Gly Gln
                        100                 105                 110

Gly Thr Thr Val Thr Val Ser Ser
                115                 120

<210> SEQ ID NO 10
<211> LENGTH: 108
<212> TYPE: PRT
<213> ORGANISM: Artificial
<220> FEATURE:
<223> OTHER INFORMATION: The amino acid sequence of anti-CD28 scFv light
      chain variable region

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
                20                  25                  30

Leu Asn Trp Tyr Gln Gln Lys Pro Gly Lys Ala Pro Lys Leu Leu Ile
                35                  40                  45

Tyr Lys Ala Ser Asn Leu His Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys Arg
                100                 105

<210> SEQ ID NO 11
<211> LENGTH: 729
<212> TYPE: DNA
<213> ORGANISM: Artificial
<220> FEATURE:
<223> OTHER INFORMATION: The nucleotide sequence of anti-CD3 scFv

<400> SEQUENCE: 11
gacatcaagc tgcagcagag cggcgccgag ctggcccgcc ccggcgccag cgtgaagatg      60
agctgcaaga ccagcggcta caccttcacc cgctacacca tgcactgggt gaagcagcgc     120
cccggccagg gcctggagtg gatcggctac atcaacccca gcgcggcta caccaactac      180 aaccagaagt tcaaggacaa ggccaccctg accaccgaca gagcagcag caccgcctac      240 atgcagctga gcagcctgac cagcgaggac agcgccgtgt actactgcgc cgctactac      300 gacgaccact actgcctgga ctactggggc cagggcacca ccctgaccgt gagcagcgtg     360
gagggcggca gcggcggcag cggcggcagc ggcggcagcg gcggcgtgga cgacatccag     420
ctgacccaga gccccgccat catgagcgcc agccccggcg agaaggtgac catgacctgc     480
cgcgccagca gcagcgtgag ctacatgaac tggtaccagc agaagagcgg caccagcccc     540
aagcgctgga tctacgacac cagcaaggtg gccagcggcg tgccctaccg cttcagcggc     600
agcggcagcg gcaccagcta cagcctgacc atcagcagca tggaggccga ggacgccgcc     660
acctactact gccagcagtg gagcagcaac cccctgacct tcggcgccgg caccaagctg     720
gagctgaag                                                             729
```

<210> SEQ ID NO 12
<211> LENGTH: 357
<212> TYPE: DNA
<213> ORGANISM: Artificial
<220> FEATURE:
<223> OTHER INFORMATION: The nucleotide sequence of anti-CD3 scFv heavy
      chain variable region

<400> SEQUENCE: 12

| | | | | | |
|---|---|---|---|---|---|
| gacatcaagc | tgcagcagag | cggcgccgag | ctggcccgcc | ccggcgccag | cgtgaagatg | 60 |
| agctgcaaga | ccagcggcta | caccttcacc | cgctacacca | tgcactgggt | gaagcagcgc | 120 |
| cccggccagg | gcctggagtg | gatcggctac | atcaacccca | gcgcggcta | caccaactac | 180 |
| aaccagaagt | tcaaggacaa | ggccaccctg | accaccgaca | agagcagcag | caccgcctac | 240 |
| atgcagctga | gcagcctgac | cagcgaggac | agcgccgtgt | actactgcgc | cgctactac | 300 |
| gacgaccact | actgcctgga | ctactggggc | cagggcacca | ccctgaccgt | gagcagc | 357 |

<210> SEQ ID NO 13
<211> LENGTH: 318
<212> TYPE: DNA
<213> ORGANISM: Artificial
<220> FEATURE:
<223> OTHER INFORMATION: The nucleotide sequence of anti-CD3 scFv light
      chain variable region

<400> SEQUENCE: 13

| | | | | | |
|---|---|---|---|---|---|
| gacatccagc | tgacccagag | ccccgccatc | atgagcgcca | gccccggcga | gaaggtgacc | 60 |
| atgacctgcc | gcgccagcag | cagcgtgagc | tacatgaact | ggtaccagca | gaagagcggc | 120 |
| accagcccca | agcgctggat | ctacgacacc | agcaaggtgg | ccagcggcgt | gccctaccgc | 180 |
| ttcagcggca | gcggcagcgg | caccagctac | agcctgacca | tcagcagcat | ggaggccgag | 240 |
| gacgccgcca | cctactactg | ccagcagtgg | agcagcaacc | ccctgacctt | cggcgccggc | 300 |
| accaagctgg | agctgaag | | | | | 318 |

<210> SEQ ID NO 14
<211> LENGTH: 729
<212> TYPE: DNA
<213> ORGANISM: Artificial
<220> FEATURE:
<223> OTHER INFORMATION: The nucleotide sequence of anti-CD28 scFv

<400> SEQUENCE: 14

| | | | | | |
|---|---|---|---|---|---|
| caggtgcagc | tggtgcagag | cggcgccgag | gtgaagaagc | ccggcgccag | cgtgaaggtg | 60 |
| agctgcaagg | ccagcggcta | caccttcacc | agctactaca | tccactgggt | gcgccaggcc | 120 |
| cccggccagg | gcctggagtg | gatcggctgc | atctaccccg | caacgtgaa | caccaactac | 180 |
| aacgagaagt | tcaaggaccg | cgccaccctg | accgtggaca | ccagcatcag | caccgcctac | 240 |
| atggagctga | gccgcctgcg | cagcgacgac | accgccgtgt | acttctgcac | ccgcagccac | 300 |
| tacggcctgg | actggaactt | cgacgtgtgg | ggccagggca | ccaccgtgac | cgtgagcagc | 360 |
| ggcggcggcg | gcagcggcgg | cggcggcagc | ggcggcggcg | gcagcgacat | ccagatgacc | 420 |
| cagagcccca | gcagcctgag | cgccagcgtg | ggcgaccgcg | tgaccatcac | ctgccacgcc | 480 |
| agccagaaca | tctacgtgtg | gctgaactgg | taccagcaga | agcccggcaa | ggcccccaag | 540 |
| ctgctgatct | acaaggccag | caacctgcac | accggcgtgc | ccagccgctt | cagcggcagc | 600 |
| ggcagcggca | ccgacttcac | cctgaccatc | agcagcctgc | agcccgagga | cttcgccacc | 660 |
| tactactgcc | agcagggcca | gacctacccc | tacaccttcg | gcggcggcac | caaggtggag | 720 |

```
<210> SEQ ID NO 15
<211> LENGTH: 360
<212> TYPE: DNA
<213> ORGANISM: Artificial
<220> FEATURE:
<223> OTHER INFORMATION: The nucleotide sequence of anti-CD28 scFv heavy
      chain variable region

<400> SEQUENCE: 15
caggtgcagc tggtgcagag cggcgccgag gtgaagaagc ccggcgccag cgtgaaggtg      60
agctgcaagg ccagcggcta caccttcacc agctactaca tccactgggt gcgccaggcc     120
cccggccagg gcctggagtg gatcggctgc atctaccccg gcaacgtgaa caccaactac     180
aacgagaagt tcaaggaccg cgccaccctg accgtggaca ccagcatcag caccgcctac     240
atggagctga gccgcctgcg cagcgacgac accgccgtgt acttctgcac ccgcagccac     300
tacggcctgg actggaactt cgacgtgtgg ggccagggca ccaccgtgac cgtgagcagc     360

<210> SEQ ID NO 16
<211> LENGTH: 324
<212> TYPE: DNA
<213> ORGANISM: Artificial
<220> FEATURE:
<223> OTHER INFORMATION: The nucleotide sequence of anti-CD28 scFv light
      chain variable region

<400> SEQUENCE: 16
gacatccaga tgacccagag ccccagcagc ctgagcgcca gcgtgggcga ccgcgtgacc      60
atcacctgcc acgccagcca gaacatctac gtgtggctga actggtacca gcagaagccc     120
ggcaaggccc ccaagctgct gatctacaag gccagcaacc tgcacaccgg cgtgcccagc     180
cgcttcagcg gcagcggcag cggcaccgac ttcaccctga ccatcagcag cctgcagccc     240
gaggacttcg ccacctacta ctgccagcag ggccagacct accctacac cttcggcggc     300 ggcaccaagg tggagatcaa gcgc                                            324

<210> SEQ ID NO 17
<211> LENGTH: 15
<212> TYPE: PRT
<213> ORGANISM: Artificial
<220> FEATURE:
<223> OTHER INFORMATION: The amino acid sequence of the CD3-CD28 BsAb_M
      linker

<400> SEQUENCE: 17

Gly Gly Gly Gly Ser Gly Gly Gly Gly Ser Gly Gly Gly Gly Ser
1               5                   10                  15

<210> SEQ ID NO 18
<211> LENGTH: 45
<212> TYPE: DNA
<213> ORGANISM: Artificial
<220> FEATURE:
<223> OTHER INFORMATION: The nucleotide sequence of the CD3-CD28 BsAb_M
      linker

<400> SEQUENCE: 18
ggcggcggcg gcagcggcgg cggcggcagc ggcggcggcg gcagc                      45

<210> SEQ ID NO 19
<211> LENGTH: 81
```

```
<212> TYPE: PRT
<213> ORGANISM: Artificial
<220> FEATURE:
<223> OTHER INFORMATION: The amino acid sequence of the CD3-CD28 BsAb_D
      linker

<400> SEQUENCE: 19

Ala Ser Lys Ser Lys Lys Glu Ile Phe Arg Trp Pro Glu Ser Pro Lys
1               5                   10                  15

Ala Gln Ala Ser Ser Val Pro Thr Ala Gln Pro Gln Ala Glu Gly Ser
                20                  25                  30

Leu Ala Lys Ala Thr Thr Ala Pro Ala Thr Thr Arg Asn Thr Gly Arg
            35                  40                  45

Gly Gly Glu Glu Lys Lys Lys Glu Lys Glu Lys Glu Glu Gln Glu Glu
        50                  55                  60

Arg Glu Thr Lys Thr Pro Glu Cys Pro Ser His Thr Gln Pro Leu Gly
65                  70                  75                  80

Val

<210> SEQ ID NO 20
<211> LENGTH: 243
<212> TYPE: DNA
<213> ORGANISM: Artificial
<220> FEATURE:
<223> OTHER INFORMATION: The nucleotide sequence of the CD3-CD28 BsAb_D
      linker

<400> SEQUENCE: 20
gccagcaaga gcaagaagga gatcttccgc tggcccgaga gccccaaggc ccaggccagc      60
agcgtgccca ccgcccagcc ccaggccgag ggcagcctgg ccaaggccac caccgccccc     120
gccaccaccc gcaacaccgg ccgcggcggc gaggagaaga agaaggagaa ggagaaggag     180
gagcaggagg agcgcgagac caagaccccc gagtgcccca gccacaccca gcccctgggc     240
gtg                                                                   243

<210> SEQ ID NO 21
<211> LENGTH: 19
<212> TYPE: PRT
<213> ORGANISM: Artificial
<220> FEATURE:
<223> OTHER INFORMATION: The amino acid sequence of the secretory signal
      peptide

<400> SEQUENCE: 21

Met Thr Arg Leu Thr Val Leu Ala Leu Leu Ala Gly Leu Leu Ala Ser
1               5                   10                  15

Ser Arg Ala

<210> SEQ ID NO 22
<211> LENGTH: 57
<212> TYPE: DNA
<213> ORGANISM: Artificial
<220> FEATURE:
<223> OTHER INFORMATION: The nucleotide sequence of the secretory signal
      peptide

<400> SEQUENCE: 22
atgacccggc tgaccgtgct ggccctgctg gccggcctgc tggcctcctc cagggcc        57

<210> SEQ ID NO 23
<211> LENGTH: 59
<212> TYPE: DNA
```

-continued

<213> ORGANISM: Artificial
<220> FEATURE:
<223> OTHER INFORMATION: pcDNA3.1-Sig-F

<400> SEQUENCE: 23
gtgctggata tctgcagaat tcgccgccac catgacccgg ctgaccgtgc tggccctgc    59

<210> SEQ ID NO 24
<211> LENGTH: 49
<212> TYPE: DNA
<213> ORGANISM: Artificial
<220> FEATURE:
<223> OTHER INFORMATION: Sig-R

<400> SEQUENCE: 24
ggccctggag gaggccagca ggccggccag cagggccagc acggtcagc    49

<210> SEQ ID NO 25
<211> LENGTH: 41
<212> TYPE: DNA
<213> ORGANISM: Artificial
<220> FEATURE:
<223> OTHER INFORMATION: Sig-CD3-F

<400> SEQUENCE: 25
gctggcctcc tccagggccg acatcaagct gcagcagagc g    41

<210> SEQ ID NO 26
<211> LENGTH: 20
<212> TYPE: DNA
<213> ORGANISM: Artificial
<220> FEATURE:
<223> OTHER INFORMATION: CD3-R

<400> SEQUENCE: 26
cttcagctcc agcttggtgc    20

<210> SEQ ID NO 27
<211> LENGTH: 86
<212> TYPE: DNA
<213> ORGANISM: Artificial
<220> FEATURE:
<223> OTHER INFORMATION: CD3-(GGGGS)3-CD28-F

<400> SEQUENCE: 27
gcaccaagct ggagctgaag ggcggcggcg gcagcggcgg cggcggcagc ggcggcggcg    60
gcagccaggt gcagctggtg cagagc    86

<210> SEQ ID NO 28
<211> LENGTH: 51
<212> TYPE: DNA
<213> ORGANISM: Artificial
<220> FEATURE:
<223> OTHER INFORMATION: pcDNA3.1-CD28-R

<400> SEQUENCE: 28
ctgatcagcg gtttaaactt aagctttcag cgcttgatct ccaccttggt g    51

<210> SEQ ID NO 29
<211> LENGTH: 41
<212> TYPE: DNA
<213> ORGANISM: Artificial
<220> FEATURE:
<223> OTHER INFORMATION: CD3-IgD-F

<400> SEQUENCE: 29

```
gcaccaagct ggagctgaag gccagcaaga gcaagaagga g                               41
```

<210> SEQ ID NO 30
<211> LENGTH: 21
<212> TYPE: DNA
<213> ORGANISM: Artificial
<220> FEATURE:
<223> OTHER INFORMATION: IgD-R

<400> SEQUENCE: 30

```
cacgcccagg ggctgggtgt g                                                    21
```

<210> SEQ ID NO 31
<211> LENGTH: 42
<212> TYPE: DNA
<213> ORGANISM: Artificial
<220> FEATURE:
<223> OTHER INFORMATION: IgD-CD28-F

<400> SEQUENCE: 31

```
cacacccagc ccctgggcgt gcaggtgcag ctggtgcaga gc                             42
```

<210> SEQ ID NO 32
<211> LENGTH: 15
<212> TYPE: PRT
<213> ORGANISM: Artificial
<220> FEATURE:
<223> OTHER INFORMATION: The amino acid sequence of CD3-4-1BB BsAb_M
      monomer linker

<400> SEQUENCE: 32

Gly Gly Gly Gly Ser Gly Gly Gly Gly Ser Gly Gly Gly Gly Ser
1               5                   10                  15

<210> SEQ ID NO 33
<211> LENGTH: 45
<212> TYPE: DNA
<213> ORGANISM: Artificial
<220> FEATURE:
<223> OTHER INFORMATION: The nucleotide sequence of CD3-4-1BB BsAb_M
      monomer linker

<400> SEQUENCE: 33

```
ggcggcggcg gcagcggcgg cggcggcagc ggcggcggcg gcagc                          45
```

<210> SEQ ID NO 34
<211> LENGTH: 81
<212> TYPE: PRT
<213> ORGANISM: Artificial
<220> FEATURE:
<223> OTHER INFORMATION: The amino acid sequence of CD3-4-1BB BsAb_D
      dimer linker

<400> SEQUENCE: 34

Ala Ser Lys Ser Lys Lys Glu Ile Phe Arg Trp Pro Glu Ser Pro Lys
1               5                   10                  15

Ala Gln Ala Ser Ser Val Pro Thr Ala Gln Pro Gln Ala Glu Gly Ser
                20                  25                  30

Leu Ala Lys Ala Thr Thr Ala Pro Ala Thr Thr Arg Asn Thr Gly Arg
            35                  40                  45

Gly Gly Glu Glu Lys Lys Lys Glu Lys Glu Lys Glu Glu Gln Glu Glu
        50                  55                  60

Arg Glu Thr Lys Thr Pro Glu Cys Pro Ser His Thr Gln Pro Leu Gly
65                  70                  75                  80

Val

<210> SEQ ID NO 35
<211> LENGTH: 243
<212> TYPE: DNA
<213> ORGANISM: Artificial
<220> FEATURE:
<223> OTHER INFORMATION: The nucleotide sequence of CD3-4-1BB BsAb_D dimer linker

<400> SEQUENCE: 35

```
gccagcaaga gcaagaagga gatcttccgc tggcccgaga gccccaaggc ccaggccagc    60
agcgtgccca ccgcccagcc ccaggccgag ggcagcctgg ccaaggccac caccgccccc   120
gccaccaccc gcaacaccgg ccgcggcggc gaggagaaga agaaggagaa ggagaaggag   180
gagcaggagg agcgcgagac caagaccccc gagtgcccca gccacaccca gccctgggc   240
gtg                                                                243
```

<210> SEQ ID NO 36
<211> LENGTH: 134
<212> TYPE: PRT
<213> ORGANISM: Artificial
<220> FEATURE:
<223> OTHER INFORMATION: The amino acid sequence of the human T cell positive costimulatory molecule CD28 extracellular domain

<400> SEQUENCE: 36

```
Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
            20                  25                  30

Phe Arg Ala Ser Leu His Lys Gly Leu Asp Ser Ala Val Glu Val Cys
        35                  40                  45

Val Val Tyr Gly Asn Tyr Ser Gln Gln Leu Gln Val Tyr Ser Lys Thr
    50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
            100                 105                 110

Thr Ile Ile His Val Lys Gly Lys His Leu Cys Pro Ser Pro Leu Phe
        115                 120                 125

Pro Gly Pro Ser Lys Pro
    130
```

<210> SEQ ID NO 37
<211> LENGTH: 163
<212> TYPE: PRT
<213> ORGANISM: Artificial
<220> FEATURE:
<223> OTHER INFORMATION: The amino acid sequence of the human T cell positive costimulatory molecule 4-1BB extracellular domain

<400> SEQUENCE: 37

```
Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30
```

```
Ala Gly Gly Gln Arg Thr Cys Asp Ile Cys Arg Gln Cys Lys Gly Val
            35                  40                  45

Phe Arg Thr Arg Lys Glu Cys Ser Ser Thr Ser Asn Ala Glu Cys Asp
 50                  55                  60

Cys Thr Pro Gly Phe His Cys Leu Gly Ala Gly Cys Ser Met Cys Glu
 65                  70                  75                  80

Gln Asp Cys Lys Gln Gly Gln Glu Leu Thr Lys Lys Gly Cys Lys Asp
                 85                  90                  95

Cys Cys Phe Gly Thr Phe Asn Asp Gln Lys Arg Gly Ile Cys Arg Pro
                100                 105                 110

Trp Thr Asn Cys Ser Leu Asp Gly Lys Ser Val Leu Val Asn Gly Thr
            115                 120                 125

Lys Glu Arg Asp Val Val Cys Gly Pro Ser Pro Ala Asp Leu Ser Pro
130                 135                 140

Gly Ala Ser Ser Val Thr Pro Pro Ala Pro Ala Arg Glu Pro Gly His
145                 150                 155                 160

Ser Pro Gln

<210> SEQ ID NO 38
<211> LENGTH: 120
<212> TYPE: PRT
<213> ORGANISM: Artificial
<220> FEATURE:
<223> OTHER INFORMATION: The amino acid sequence of the human T cell
      positive costimulatory molecule ICOS extracellular domain

<400> SEQUENCE: 38

Glu Ile Asn Gly Ser Ala Asn Tyr Glu Met Phe Ile Phe His Asn Gly
 1               5                  10                  15

Gly Val Gln Ile Leu Cys Lys Tyr Pro Asp Ile Val Gln Gln Phe Lys
            20                  25                  30

Met Gln Leu Leu Lys Gly Gly Gln Ile Leu Cys Asp Leu Thr Lys Thr
            35                  40                  45

Lys Gly Ser Gly Asn Thr Val Ser Ile Lys Ser Leu Lys Phe Cys His
 50                  55                  60

Ser Gln Leu Ser Asn Asn Ser Val Ser Phe Phe Leu Tyr Asn Leu Asp
65                  70                  75                  80

His Ser His Ala Asn Tyr Tyr Phe Cys Asn Leu Ser Ile Phe Asp Pro
                85                  90                  95

Pro Pro Phe Lys Val Thr Leu Thr Gly Gly Tyr Leu His Ile Tyr Glu
                100                 105                 110

Ser Gln Leu Cys Cys Gln Leu Lys
            115                 120

<210> SEQ ID NO 39
<211> LENGTH: 186
<212> TYPE: PRT
<213> ORGANISM: Artificial
<220> FEATURE:
<223> OTHER INFORMATION: The amino acid sequence of the human T cell
      positive costimulatory molecule OX40 extracellular domain

<400> SEQUENCE: 39

Leu His Cys Val Gly Asp Thr Tyr Pro Ser Asn Asp Arg Cys Cys His
 1               5                  10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
```

```
              35                  40                  45
Ser Ser Lys Pro Cys Lys Pro Cys Thr Trp Cys Asn Leu Arg Ser Gly
 50                  55                  60

Ser Glu Arg Lys Gln Leu Cys Thr Ala Thr Gln Asp Thr Val Cys Arg
 65                  70                  75                  80

Cys Arg Ala Gly Thr Gln Pro Leu Asp Ser Tyr Lys Pro Gly Val Asp
                 85                  90                  95

Cys Ala Pro Cys Pro Gly His Phe Ser Pro Gly Asp Asn Gln Ala
                100                 105                 110

Cys Lys Pro Trp Thr Asn Cys Thr Leu Ala Gly Lys His Thr Leu Gln
                115                 120                 125

Pro Ala Ser Asn Ser Ser Asp Ala Ile Cys Glu Asp Arg Asp Pro Pro
130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala
                180                 185

<210> SEQ ID NO 40
<211> LENGTH: 137
<212> TYPE: PRT
<213> ORGANISM: Artificial
<220> FEATURE:
<223> OTHER INFORMATION: The amino acid sequence of the human T cell
      positive costimulatory molecule GITR extracellular domain

<400> SEQUENCE: 40

Gln Arg Pro Thr Gly Gly Pro Gly Cys Gly Pro Gly Arg Leu Leu Leu
 1               5                  10                  15

Gly Thr Gly Thr Asp Ala Arg Cys Cys Arg Val His Thr Thr Arg Cys
                 20                  25                  30

Cys Arg Asp Tyr Pro Gly Glu Glu Cys Cys Ser Glu Trp Asp Cys Met
                 35                  40                  45

Cys Val Gln Pro Glu Phe His Cys Gly Asp Pro Cys Cys Thr Thr Cys
 50                  55                  60

Arg His His Pro Cys Pro Pro Gly Gln Gly Val Gln Ser Gln Gly Lys
 65                  70                  75                  80

Phe Ser Phe Gly Phe Gln Cys Ile Asp Cys Ala Ser Gly Thr Phe Ser
                 85                  90                  95

Gly Gly His Glu Gly His Cys Lys Pro Trp Thr Asp Cys Thr Gln Phe
                100                 105                 110

Gly Phe Leu Thr Val Phe Pro Gly Asn Lys Thr His Asn Ala Val Cys
                115                 120                 125

Val Pro Gly Ser Pro Pro Ala Glu Pro
130                 135

<210> SEQ ID NO 41
<211> LENGTH: 215
<212> TYPE: PRT
<213> ORGANISM: Artificial
<220> FEATURE:
<223> OTHER INFORMATION: The amino acid sequence of the human T cell
      positive costimulatory molecule CD40L extracellular domain

<400> SEQUENCE: 41

His Arg Arg Leu Asp Lys Ile Glu Asp Glu Arg Asn Leu His Glu Asp
```

```
                1               5                   10                  15
            Phe Val Phe Met Lys Thr Ile Gln Arg Cys Asn Thr Gly Glu Arg Ser
                            20                  25                  30

Leu Ser Leu Leu Asn Cys Glu Glu Ile Lys Ser Gln Phe Glu Gly Phe
                            35                  40                  45

Val Lys Asp Ile Met Leu Asn Lys Glu Glu Thr Lys Lys Glu Asn Ser
                50                  55                  60

Phe Glu Met Gln Lys Gly Asp Gln Asn Pro Gln Ile Ala Ala His Val
             65                 70                  75                  80

Ile Ser Glu Ala Ser Ser Lys Thr Thr Ser Val Leu Gln Trp Ala Glu
                            85                  90                  95

Lys Gly Tyr Tyr Thr Met Ser Asn Asn Leu Val Thr Leu Glu Asn Gly
                            100                 105                 110

Lys Gln Leu Thr Val Lys Arg Gln Gly Leu Tyr Tyr Ile Tyr Ala Gln
                            115                 120                 125

Val Thr Phe Cys Ser Asn Arg Glu Ala Ser Ser Gln Ala Pro Phe Ile
                130                 135                 140

Ala Ser Leu Cys Leu Lys Ser Pro Gly Arg Phe Glu Arg Ile Leu Leu
            145                 150                 155                 160

Arg Ala Ala Asn Thr His Ser Ser Ala Lys Pro Cys Gly Gln Gln Ser
                            165                 170                 175

Ile His Leu Gly Gly Val Phe Glu Leu Gln Pro Gly Ala Ser Val Phe
                            180                 185                 190

Val Asn Val Thr Asp Pro Ser Gln Val Ser His Gly Thr Gly Phe Thr
                            195                 200                 205

Ser Phe Gly Leu Leu Lys Leu
                            210                 215

<210> SEQ ID NO 42
<211> LENGTH: 172
<212> TYPE: PRT
<213> ORGANISM: Artificial
<220> FEATURE:
<223> OTHER INFORMATION: The amino acid sequence of the human T cell
      positive costimulatory molecule CD27 extracellular domain

<400> SEQUENCE: 42

Ala Thr Pro Ala Pro Lys Ser Cys Pro Glu Arg His Tyr Trp Ala Gln
            1               5                   10                  15

Gly Lys Leu Cys Cys Gln Met Cys Glu Pro Gly Thr Phe Leu Val Lys
                            20                  25                  30

Asp Cys Asp Gln His Arg Lys Ala Ala Gln Cys Asp Pro Cys Ile Pro
                            35                  40                  45

Gly Val Ser Phe Ser Pro Asp His His Thr Arg Pro His Cys Glu Ser
                50                  55                  60

Cys Arg His Cys Asn Ser Gly Leu Leu Val Arg Asn Cys Thr Ile Thr
             65                 70                  75                  80

Ala Asn Ala Glu Cys Ala Cys Arg Asn Gly Trp Gln Cys Arg Asp Lys
                            85                  90                  95

Glu Cys Thr Glu Cys Asp Pro Leu Pro Asn Pro Ser Leu Thr Ala Arg
                            100                 105                 110

Ser Ser Gln Ala Leu Ser Pro His Pro Gln Pro Thr His Leu Pro Tyr
                            115                 120                 125

Val Ser Glu Met Leu Glu Ala Arg Thr Ala Gly His Met Gln Thr Leu
                130                 135                 140
```

```
Ala Asp Phe Arg Gln Leu Pro Ala Arg Thr Leu Ser Thr His Trp Pro
145                 150                 155                 160

Pro Gln Arg Ser Leu Cys Ser Ser Asp Phe Ile Arg
                165                 170
```

<210> SEQ ID NO 43
<211> LENGTH: 504
<212> TYPE: PRT
<213> ORGANISM: Artificial
<220> FEATURE:
<223> OTHER INFORMATION: The amino acid sequence of CD3-4-1BB BsAb_M monomer

<400> SEQUENCE: 43

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Thr Leu Thr Val Ser Ser Val Glu Gly Gly Ser Gly Gly Ser Gly
            115                 120                 125

Gly Ser Gly Gly Ser Gly Gly Val Asp Asp Ile Gln Leu Thr Gln Ser
        130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
210                 215                 220

Gln Gln Trp Ser Ser Asn Pro Leu Thr Phe Gly Ala Gly Thr Lys Leu
225                 230                 235                 240

Glu Leu Lys Gly Gly Gly Gly Ser Gly Gly Gly Gly Ser Gly Gly Gly
                245                 250                 255

Gly Ser Gln Val Gln Leu Gln Gln Trp Gly Ala Gly Leu Leu Lys Pro
            260                 265                 270

Ser Glu Thr Leu Ser Leu Thr Cys Ala Val Tyr Gly Gly Ser Phe Ser
        275                 280                 285

Gly Tyr Tyr Trp Ser Trp Ile Arg Gln Ser Pro Glu Lys Gly Leu Glu
        290                 295                 300

Trp Ile Gly Glu Ile Asn His Gly Gly Tyr Val Thr Tyr Asn Pro Ser
305                 310                 315                 320

Leu Glu Ser Arg Val Thr Ile Ser Val Asp Thr Ser Lys Asn Gln Phe
                325                 330                 335
```

Ser Leu Lys Leu Ser Ser Val Thr Ala Ala Asp Thr Ala Val Tyr Tyr
                340                 345                 350

Cys Ala Arg Asp Tyr Gly Pro Gly Asn Tyr Asp Trp Tyr Phe Asp Leu
            355                 360                 365

Trp Gly Arg Gly Thr Leu Val Thr Val Ser Ser Gly Gly Gly Gly Ser
370                 375                 380

Gly Gly Gly Gly Ser Gly Gly Gly Ser Glu Ile Val Leu Thr Gln
385                 390                 395                 400

Ser Pro Ala Thr Leu Ser Leu Ser Pro Gly Glu Arg Ala Thr Leu Ser
                405                 410                 415

Cys Arg Ala Ser Gln Ser Val Ser Ser Tyr Leu Ala Trp Tyr Gln Gln
            420                 425                 430

Lys Pro Gly Gln Ala Pro Arg Leu Leu Ile Tyr Asp Ala Ser Asn Arg
        435                 440                 445

Ala Thr Gly Ile Pro Ala Arg Phe Ser Gly Ser Gly Ser Gly Thr Asp
    450                 455                 460

Phe Thr Leu Thr Ile Ser Ser Leu Glu Pro Glu Asp Phe Ala Val Tyr
465                 470                 475                 480

Tyr Cys Gln Gln Arg Ser Asn Trp Pro Pro Ala Leu Thr Phe Cys Gly
                485                 490                 495

Gly Thr Lys Val Glu Ile Lys Arg
            500

<210> SEQ ID NO 44
<211> LENGTH: 1512
<212> TYPE: DNA
<213> ORGANISM: Artificial
<220> FEATURE:
<223> OTHER INFORMATION: The nucleotide sequence of CD3-4-1BB BsAb_M
      monomer

<400> SEQUENCE: 44

```
gacatcaagc tgcagcagag cggcgccgag ctggcccgcc ccggcgccag cgtgaagatg      60
agctgcaaga ccagcggcta caccttcacc cgctacacca tgcactgggt gaagcagcgc     120
cccggccagg gcctggagtg gatcggctac atcaaccccg ccgcggcta caccaactac     180 aaccagaagt tcaaggacaa ggccaccctg accaccgaca gagcagcag caccgcctac     240 atgcagctga gcagcctgac cagcgaggac agcgccgtgt actactgcgc ccgctactac     300
gacgaccact actgcctgga ctactgggc cagggcacca ccctgaccgt gagcagcgtg     360
gagggcggca gcggcggcag cggcggcagc ggcggcagcg gcggcgtgga cgacatccag     420
ctgacccaga gccccgccat catgagcgcc agccccggcg agaaggtgac catgacctgc     480
cgcgccagca gcagcgtgag ctacatgaac tggtaccagc agaagagcgg caccagcccc     540
aagcgctgga tctacgacac cagcaaggtg gccagcggcg tgccctaccg cttcagcggc     600
agcggcagcg gcaccagcta cagcctgacc atcagcagca tggaggccga ggacgccgcc     660
acctactact gccagcagtg gagcagcaac cccctgacct tcggcgccgg caccaagctg     720
gagctgaagg gcggcggcgg cagcggcggc ggcggcagcg gcggcggcgg cagccaggtg     780
cagctgcagc agtggggcgc cggcctgctg aagcccagcg agaccctgag cctgacctgc     840
gccgtgtacg gcggcagctt cagcggctac tactggagct ggatccgcca gagccccgag     900
aagggcctgg agtggatcgg cgagatcaac cacggcggct acgtgaccta caaccccagc     960
ctggagagcc gcgtgaccat cagcgtggac accagcaaga accagttcag cctgaagctg    1020
```

-continued

```
agcagcgtga ccgccgccga caccgccgtg tactactgcg cccgcgacta cggcccccggc    1080 aactacgact ggtacttcga cctgtggggc cgcggcaccc tggtgaccgt gagcagcggc    1140
ggcggcggca gcggcggcgg cggcagcggc ggcggcggca gcgagatcgt gctgacccag    1200
agccccgcca ccctgagcct gagccccggc gagcgcgcca ccctgagctg ccgcgccagc    1260
cagagcgtga gcagctacct ggcctggtac cagcagaagc ccggccaggc cccccgcctg    1320
ctgatctacg acgccagcaa ccgcgccacc ggcatccccg cccgcttcag cggcagcggc    1380
agcggcaccg acttcaccct gaccatcagc agcctggagc ccgaggactt cgccgtgtac    1440
tactgccagc agcgcagcaa ctggcccccc gccctgacct tctgcggcgg caccaaggtg    1500
gagatcaagc gc                                                        1512
```

<210> SEQ ID NO 45
<211> LENGTH: 570
<212> TYPE: PRT
<213> ORGANISM: Artificial
<220> FEATURE:
<223> OTHER INFORMATION: The amino acid sequence of CD3-4-1BB BsAb_D dimer

<400> SEQUENCE: 45

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Ala Ser Lys Ser Lys Glu Ile Phe Arg Trp Pro Glu
                245                 250                 255

Ser Pro Lys Ala Gln Ala Ser Ser Val Pro Thr Ala Gln Pro Gln Ala
            260                 265                 270
```

```
Glu Gly Ser Leu Ala Lys Ala Thr Thr Ala Pro Ala Thr Thr Arg Asn
        275                 280                 285
Thr Gly Arg Gly Gly Glu Glu Lys Lys Lys Glu Lys Glu Lys Glu Glu
        290                 295                 300
Gln Glu Glu Arg Glu Thr Lys Thr Pro Glu Cys Pro Ser His Thr Gln
305                 310                 315                 320
Pro Leu Gly Val Gln Val Gln Leu Gln Gln Trp Gly Ala Gly Leu Leu
                325                 330                 335
Lys Pro Ser Glu Thr Leu Ser Leu Thr Cys Ala Val Tyr Gly Gly Ser
                340                 345                 350
Phe Ser Gly Tyr Tyr Trp Ser Trp Ile Arg Gln Ser Pro Glu Lys Gly
                355                 360                 365
Leu Glu Trp Ile Gly Glu Ile Asn His Gly Gly Tyr Val Thr Tyr Asn
        370                 375                 380
Pro Ser Leu Glu Ser Arg Val Thr Ile Ser Val Asp Thr Ser Lys Asn
385                 390                 395                 400
Gln Phe Ser Leu Lys Leu Ser Ser Val Thr Ala Ala Asp Thr Ala Val
                405                 410                 415
Tyr Tyr Cys Ala Arg Asp Tyr Gly Pro Gly Asn Tyr Asp Trp Tyr Phe
                420                 425                 430
Asp Leu Trp Gly Arg Gly Thr Leu Val Thr Val Ser Ser Gly Gly Gly
                435                 440                 445
Gly Ser Gly Gly Gly Gly Ser Gly Gly Gly Gly Ser Glu Ile Val Leu
        450                 455                 460
Thr Gln Ser Pro Ala Thr Leu Ser Leu Ser Pro Gly Glu Arg Ala Thr
465                 470                 475                 480
Leu Ser Cys Arg Ala Ser Gln Ser Val Ser Ser Tyr Leu Ala Trp Tyr
                485                 490                 495
Gln Gln Lys Pro Gly Gln Ala Pro Arg Leu Leu Ile Tyr Asp Ala Ser
                500                 505                 510
Asn Arg Ala Thr Gly Ile Pro Ala Arg Phe Ser Gly Ser Gly Ser Gly
                515                 520                 525
Thr Asp Phe Thr Leu Thr Ile Ser Ser Leu Glu Pro Glu Asp Phe Ala
        530                 535                 540
Val Tyr Tyr Cys Gln Gln Arg Ser Asn Trp Pro Pro Ala Leu Thr Phe
545                 550                 555                 560
Cys Gly Gly Thr Lys Val Glu Ile Lys Arg
                565                 570

<210> SEQ ID NO 46
<211> LENGTH: 1710
<212> TYPE: DNA
<213> ORGANISM: Artificial
<220> FEATURE:
<223> OTHER INFORMATION: The nucleotide sequence of CD3-4-1BB BsAb_D
      dimer

<400> SEQUENCE: 46
gacatcaagc tgcagcagag cggcgccgag ctggcccgcc ccggcgccag cgtgaagatg      60
agctgcaaga ccagcggcta caccttcacc cgctacacca tgcactgggt gaagcagcgc     120
cccggccagg gcctggagtg gatcggctac atcaacccca gccgcggcta caccaactac     180
aaccagaagt tcaaggacaa ggccaccctg accaccgaca gagcagcag caccgcctac     240 atgcagctga gcagcctgac cagcgaggac agcgccgtgt actactgcgc ccgctactac     300
```

```
gacgaccact actgcctgga ctactggggc cagggcacca ccctgaccgt gagcagcgtg    360
gagggcggca gcggcggcag cggcggcagc ggcggcagcg gcggcgtgga cgacatccag    420
ctgacccaga gccccgccat catgagcgcc agccccggcg agaaggtgac catgacctgc    480
cgcgccagca gcagcgtgag ctacatgaac tggtaccagc agaagagcgg caccagcccc    540
aagcgctgga tctacgacac cagcaaggtg gccagcggcg tgccctaccg cttcagcggc    600
agcggcagcg gcaccagcta cagcctgacc atcagcagca tggaggccga ggacgccgcc    660
acctactact gccagcagtg gagcagcaac cccctgacct tcggcgccgg caccaagctg    720
gagctgaagg ccagcaagag caagaaggag atcttccgct ggcccgagag ccccaaggcc    780
caggccagca gcgtgcccac cgcccagccc caggccgagg cagcctggc caaggccacc    840
accgccccg ccaccacccg caacaccggc cgcggcggcg aggagaagaa gaaggagaag    900
gagaaggagg agcaggagga gcgcgagacc aagacccccg agtgccccag ccacacccag    960
cccctgggcg tgcaggtgca gctgcagcag tggggcgccg gcctgctgaa gcccagcgag   1020
accctgagcc tgacctgcgc cgtgtacggc ggcagcttca gcggctacta ctggagctgg   1080
atccgccaga gccccgagaa gggcctggag tggatcggcg agatcaacca cggcggctac   1140
gtgacctaca accccagcct ggagagccgc gtgaccatca gcgtggacac cagcaagaac   1200
cagttcagcc tgaagctgag cagcgtgacc gccgccgaca ccgccgtgta ctactgcgcc   1260
cgcgactacg cccccggcaa ctacgactgg tacttcgacc tgtggggccg cggcaccctg   1320
gtgaccgtga gcagcggcgg cggcggcagc ggcggcggcg gcagcggcgg cggcggcagc   1380
gagatcgtgc tgacccagag ccccgccacc ctgagcctga gccccggcga gcgcgccacc   1440
ctgagctgcc gcgccagcca gagcgtgagc agctacctgg cctggtacca gcagaagccc   1500
ggccaggccc ccgcgctgct gatctacgac gccagcaacc gcgccaccgg catccccgcc   1560
cgcttcagcg gcagcggcag cggcaccgac ttcaccctga ccatcagcag cctggagccc   1620
gaggacttcg ccgtgtacta ctgccagcag cgcagcaact ggccccccgc cctgaccttc   1680
tgcggcggca ccaaggtgga gatcaagcgc                                    1710
```

<210> SEQ ID NO 47
<211> LENGTH: 505
<212> TYPE: PRT
<213> ORGANISM: Artificial
<220> FEATURE:
<223> OTHER INFORMATION: The amino acid sequence of CD3-ICOS BsAb_M
      monomer

<400> SEQUENCE: 47

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Ser Gly Gly Ser Gly
            115                 120                 125

Gly Ser Gly Gly Ser Gly Val Asp Asp Ile Gln Leu Thr Gln Ser
        130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Gly Gly Gly Gly Ser Gly Gly Gly Gly Ser Gly Gly Gly
                245                 250                 255

Gly Ser Gln Val Gln Leu Val Gln Ser Gly Ala Glu Val Lys Lys Pro
        260                 265                 270

Gly Ala Ser Val Lys Val Ser Cys Lys Ala Ser Gly Tyr Thr Phe Thr
    275                 280                 285

Gly Tyr Tyr Met His Trp Val Arg Gln Ala Pro Gly Gln Gly Leu Glu
        290                 295                 300

Trp Met Gly Trp Ile Asn Pro His Ser Gly Thr Asn Tyr Ala Gln
305                 310                 315                 320

Lys Phe Gln Gly Arg Val Thr Met Thr Arg Asp Thr Ser Ile Ser Thr
                325                 330                 335

Ala Tyr Met Glu Leu Ser Arg Leu Arg Ser Asp Asp Thr Ala Val Tyr
            340                 345                 350

Tyr Cys Ala Arg Thr Tyr Tyr Asp Ser Ser Gly Tyr Tyr His Asp
        355                 360                 365

Ala Phe Asp Ile Trp Gly Gln Gly Thr Met Val Thr Val Ser Ser Gly
    370                 375                 380

Gly Gly Gly Ser Gly Gly Gly Gly Ser Gly Gly Gly Gly Ser Asp Ile
385                 390                 395                 400

Gln Met Thr Gln Ser Pro Ser Ser Val Ser Ala Ser Val Gly Asp Arg
                405                 410                 415

Val Thr Ile Thr Cys Arg Ala Ser Gln Gly Ile Ser Arg Leu Leu Ala
            420                 425                 430

Trp Tyr Gln Gln Lys Pro Gly Lys Ala Pro Lys Leu Leu Ile Tyr Val
        435                 440                 445

Ala Ser Ser Leu Gln Ser Gly Val Pro Ser Arg Phe Ser Gly Ser Gly
    450                 455                 460

Ser Gly Thr Asp Phe Thr Leu Thr Ile Ser Ser Leu Gln Pro Glu Asp
465                 470                 475                 480

Phe Ala Thr Tyr Tyr Cys Gln Gln Ala Asn Ser Phe Pro Trp Thr Phe
                485                 490                 495

Gly Gln Gly Thr Lys Val Glu Ile Lys
            500                 505

<210> SEQ ID NO 48
<211> LENGTH: 1515

```
<212> TYPE: DNA
<213> ORGANISM: Artificial
<220> FEATURE:
<223> OTHER INFORMATION: The nucleotide sequence of CD3-ICOS BsAb_M
      monomer

<400> SEQUENCE: 48
gacatcaagc tgcagcagag cggcgccgag ctggcccgcc ccggcgccag cgtgaagatg      60
agctgcaaga ccagcggcta caccttcacc cgctacacca tgcactgggt gaagcagcgc    120
cccggccagg gcctggagtg gatcggctac atcaaccccag gccgcggcta caccaactac    180
aaccagaagt tcaaggacaa ggccacccctg accaccgaca gagcagcag caccgcctac    240 atgcagctga gcagcctgac cagcgaggac agcgccgtgt actactgcgc ccgctactac    300
gacgaccact actgcctgga ctactggggc cagggcacca ccctgaccgt gagcagcgtg    360
gagggcggca gcggcggcag cggcggcagc ggcggcagcg gcggcgtgga cgacatccag    420
ctgacccaga gccccgccat catgagcgcc agccccggcg agaaggtgac catgacctgc    480
cgcgccagca gcagcgtgag ctacatgaac tggtaccagc agaagagcgg caccagcccc    540
aagcgctgga tctacgacac cagcaaggtg gccagcggcg tgccctaccg cttcagcggc    600
agcggcagcg gcaccagcta cagcctgacc atcagcagca tggaggccga ggacgccgcc    660
acctactact gccagcagtg gagcagcaac cccctgacct tcggcgccgg caccaagctg    720
gagctgaagg gcggcggcgg cagcggcggc ggcggcagcg gcggcggcgg cagccaggtg    780
cagctggtgc agagcggcgc cgaggtgaag aagcccggcg ccagcgtgaa ggtgagctgc    840
aaggccagcg gctacacctt caccggctac tacatgcact gggtgcgcca ggcccccggc    900
cagggcctgg agtggatggg ctggatcaac cccacagcg gcggcaccaa ctacgcccag    960
aagttccagg gccgcgtgac catgacccgc gacaccagca tcagcaccgc ctacatggag   1020
ctgagccgcc tgcgcagcga cgacaccgcc gtgtactact gcgcccgcac ctactactac   1080
gacagcagcg gctactacca cgacgccttc gacatctggg gccagggcac catggtgacc   1140
gtgagcagcg gcggcggcgg cagcggcggc ggcggcagcg gcggcggcgg cagcgacatc   1200
cagatgaccc agagccccag cagcgtgagc gccagcgtgg gcgaccgcgt gaccatcacc   1260
tgccgcgcca gccagggcat cagccgcctg ctggcctggt accagcagaa gcccggcaag   1320
gcccccaagc tgctgatcta cgtggccagc agcctgcaga gcggcgtgcc cagccgcttc   1380
agcggcagcg gcagcggcac cgacttcacc ctgaccatca gcagcctgca gcccgaggac   1440
ttcgccacct actactgcca gcaggccaac agcttcccct ggaccttcgg ccagggcacc   1500
aaggtggaga tcaag                                                    1515

<210> SEQ ID NO 49
<211> LENGTH: 571
<212> TYPE: PRT
<213> ORGANISM: Artificial
<220> FEATURE:
<223> OTHER INFORMATION: The amino acid sequence of CD3-ICOS BsAb_D
      dimer

<400> SEQUENCE: 49

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45
```

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Ala Ser Lys Ser Lys Lys Glu Ile Phe Arg Trp Pro Glu
                245                 250                 255

Ser Pro Lys Ala Gln Ala Ser Ser Val Pro Thr Ala Gln Pro Gln Ala
            260                 265                 270

Glu Gly Ser Leu Ala Lys Ala Thr Thr Ala Pro Ala Thr Thr Arg Asn
        275                 280                 285

Thr Gly Arg Gly Gly Glu Glu Lys Lys Lys Glu Lys Glu Lys Glu Glu
    290                 295                 300

Gln Glu Glu Arg Glu Thr Lys Thr Pro Glu Cys Pro Ser His Thr Gln
305                 310                 315                 320

Pro Leu Gly Val Gln Val Gln Leu Val Gln Ser Gly Ala Glu Val Lys
                325                 330                 335

Lys Pro Gly Ala Ser Val Lys Val Ser Cys Lys Ala Ser Gly Tyr Thr
            340                 345                 350

Phe Thr Gly Tyr Tyr Met His Trp Val Arg Gln Ala Pro Gly Gln Gly
        355                 360                 365

Leu Glu Trp Met Gly Trp Ile Asn Pro His Ser Gly Gly Thr Asn Tyr
    370                 375                 380

Ala Gln Lys Phe Gln Gly Arg Val Thr Met Thr Arg Asp Thr Ser Ile
385                 390                 395                 400

Ser Thr Ala Tyr Met Glu Leu Ser Arg Leu Arg Ser Asp Asp Thr Ala
                405                 410                 415

Val Tyr Tyr Cys Ala Arg Thr Tyr Tyr Tyr Asp Ser Ser Gly Tyr Tyr
            420                 425                 430

His Asp Ala Phe Asp Ile Trp Gly Gln Gly Thr Met Val Thr Val Ser
        435                 440                 445

Ser Gly Gly Gly Gly Ser Gly Gly Gly Gly Ser Gly Gly Gly Gly Ser
    450                 455                 460

```
Asp Ile Gln Met Thr Gln Ser Pro Ser Ser Val Ala Ser Val Gly
465                 470                 475                 480

Asp Arg Val Thr Ile Thr Cys Arg Ala Ser Gln Gly Ile Ser Arg Leu
            485                 490                 495

Leu Ala Trp Tyr Gln Gln Lys Pro Gly Lys Ala Pro Lys Leu Leu Ile
            500                 505                 510

Tyr Val Ala Ser Ser Leu Gln Ser Gly Val Pro Ser Arg Phe Ser Gly
            515                 520                 525

Ser Gly Ser Gly Thr Asp Phe Thr Leu Thr Ile Ser Ser Leu Gln Pro
            530                 535                 540

Glu Asp Phe Ala Thr Tyr Tyr Cys Gln Gln Ala Asn Ser Phe Pro Trp
545                 550                 555                 560

Thr Phe Gly Gln Gly Thr Lys Val Glu Ile Lys
                565                 570
```

<210> SEQ ID NO 50
<211> LENGTH: 1713
<212> TYPE: DNA
<213> ORGANISM: Artificial
<220> FEATURE:
<223> OTHER INFORMATION: The nucleotide sequence of CD3-ICOS BsAb_D dimer

<400> SEQUENCE: 50

```
gacatcaagc tgcagcagag cggcgccgag ctggcccgcc ccggcgccag cgtgaagatg      60
agctgcaaga ccagcggcta caccttcacc cgctacacca tgcactgggt gaagcagcgc     120
cccggccagg gcctggagtg gatcggctac atcaacccca gcgcggcta caccaactac      180
aaccagaagt tcaaggacaa ggccaccctg accaccgaca gagcagcag caccgcctac      240
atgcagctga gcagcctgac cagcgaggac agcgccgtgt actactgcgc cgctactac      300
gacgaccact actgcctgga ctactggggc cagggcacca ccctgaccgt gagcagcgtg     360
gagggcggca gcggcggcag cggcggcagc ggcggcagcg gcggcgtgga cgacatccag     420
ctgacccaga gccccgccat catgagcgcc agccccggcg agaaggtgac catgacctgc     480
cgcgccagca gcagcgtgag ctacatgaac tggtaccagc agaagagcgg caccagcccc     540
aagcgctgga tctacgacac cagcaaggtg gccagcggcg tgccctaccg cttcagcggc     600
agcggcagcg gcaccagcta cagcctgacc atcagcagca tggaggccga ggacgccgcc     660
acctactact gccagcagtg gagcagcaac cccctgacct tcggcgccgg caccaagctg     720
gagctgaagg ccagcaagag caagaaggag atcttccgct ggcccgagag ccccaaggcc     780
caggccagca gcgtgcccac cgcccagccc caggccgagg gcagcctggc caaggccacc     840
accgccccg ccaccacccg caacaccggc cgcggcggcg aggagaagaa gaaggagaag     900
gagaaggagg agcaggagga gcgcgagacc aagaccccg agtgccccag ccacacccag     960
cccctgggcg tgcaggtgca gctggtgcag agcggcgccg aggtgaagaa gcccggcgcc    1020
agcgtgaagg tgagctgcaa ggccagcggc tacaccttca ccggctacta catgcactgg    1080
gtgcgccagg ccccggcca gggcctggag tggatgggct ggatcaaccc ccacagcggc    1140
ggcaccaact acgcccagaa gttccagggc cgcgtgacca tgacccgcga caccagcatc    1200
agcaccgcct acatggagct gagccgcctg cgcagcgacg acaccgccgt gtactactgc    1260
gcccgcacct actactacga cagcagcggc tactaccacg acgccttcga catctggggc    1320
cagggcacca tggtgaccgt gagcagcggc ggcggcggca gcggcggcgg cggcagcggc    1380
ggcggcggca gcgacatcca gatgacccag agccccagca gcgtgagcgc cagcgtgggc    1440
```

```
gaccgcgtga ccatcacctg ccgcgccagc cagggcatca gccgcctgct ggcctggtac    1500
cagcagaagc ccggcaaggc ccccaagctg ctgatctacg tggccagcag cctgcagagc    1560
ggcgtgccca gccgcttcag cggcagcggc agcggcaccg acttcaccct gaccatcagc    1620
agcctgcagc ccgaggactt cgccacctac tactgccagc aggccaacag cttccccctgg   1680 accttcggcc agggcaccaa ggtggagatc aag                                  1713
```

<210> SEQ ID NO 51
<211> LENGTH: 500
<212> TYPE: PRT
<213> ORGANISM: Artificial
<220> FEATURE:
<223> OTHER INFORMATION: The amino acid sequence of CD3-OX40 BsAb_M monomer

<400> SEQUENCE: 51

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Gly Gly Gly Gly Ser Gly Gly Gly Gly Ser Gly Gly Gly
                245                 250                 255

Gly Ser Gln Leu Val Glu Ser Gly Gly Gly Leu Val Gln Pro Gly Gly
            260                 265                 270

Ser Leu Arg Leu Ser Cys Ala Ala Ser Gly Phe Thr Phe Ser Ser Tyr
        275                 280                 285

Ser Met Asn Trp Val Arg Gln Ala Pro Gly Lys Gly Leu Glu Trp Val
    290                 295                 300
```

Ser Tyr Ile Ser Ser Ser Ser Thr Ile Tyr Ala Asp Ser Val
305                 310                 315                 320

Lys Gly Arg Phe Thr Ile Ser Arg Asp Asn Ala Lys Asn Ser Leu Tyr
            325                 330                 335

Leu Gln Met Asn Ser Leu Arg Asp Glu Asp Thr Ala Val Tyr Tyr Cys
            340                 345                 350

Ala Arg Gly Val Tyr His Asn Gly Trp Ser Phe Phe Asp Tyr Trp Gly
            355                 360                 365

Gln Gly Thr Leu Leu Thr Val Ser Ser Gly Gly Gly Ser Gly Gly
            370                 375                 380

Gly Gly Ser Gly Gly Gly Ser Asp Ile Gln Met Thr Gln Ser Pro
385                 390                 395                 400

Ser Ser Leu Ser Ala Ser Val Gly Asn Arg Val Thr Ile Thr Cys Arg
            405                 410                 415

Ala Ser Gln Asp Ile Ser Ser Trp Leu Ala Trp Tyr Gln Gln Lys Pro
            420                 425                 430

Glu Lys Ala Pro Lys Ser Leu Ile Tyr Ala Ala Ser Ser Leu Gln Ser
            435                 440                 445

Gly Val Pro Ser Arg Phe Ser Gly Ser Gly Ser Gly Thr Asp Phe Thr
450                 455                 460

Leu Thr Ile Ser Ser Leu Gln Pro Glu Asp Phe Ala Thr Tyr Tyr Cys
465                 470                 475                 480

Gln Gln Tyr Asn Ser Tyr Pro Leu Thr Phe Gly Gln Gly Thr Arg Leu
            485                 490                 495

Glu Ile Lys Arg
            500

<210> SEQ ID NO 52
<211> LENGTH: 1500
<212> TYPE: DNA
<213> ORGANISM: Artificial
<220> FEATURE:
<223> OTHER INFORMATION: The nucleotide sequence of CD3-OX40 BsAb_M
      monomer

<400> SEQUENCE: 52
gacatcaagc tgcagcagag cggcgccgag ctggcccgcc ccggcgccag cgtgaagatg      60
agctgcaaga ccagcggcta caccttcacc cgctacacca tgcactgggt gaagcagcgc     120
cccggccagg gcctggagtg gatcggctac atcaacccca gccgcggcta caccaactac     180
aaccagaagt tcaaggacaa ggccaccctg accaccgaca gagcagcag caccgcctac     240 atgcagctga gcagcctgac cagcgaggac agcgccgtgt actactgcgc ccgctactac     300
gacgaccact actgcctgga ctactggggc cagggcacca ccctgaccgt gagcagcgtg     360
gagggcggca gcggcggcag cggcggcagc ggcggcagcg gcggcgtgga cgacatccag     420
ctgacccaga gccccgccat catgagcgcc agccccggcg agaaggtgac catgacctgc     480
cgcgccagca gcagcgtgag ctacatgaac tggtaccagc agaagagcgg caccagcccc     540
aagcgctgga tctacgacac cagcaaggtg gccagcggcg tgccctaccg cttcagcggc     600
agcggcagcg gcaccagcta cagcctgacc atcagcagca tggaggccga ggacgccgcc     660
acctactact gccagcagtg gagcagcaac ccctgacct tcggcgccgg caccaagctg     720
gagctgaagg gcggcggcgg cagcggcggc ggcggcagcg gcggcggcgg cagccagctg     780
gtggagagcg gcggcggcct ggtgcagccc ggcggcagcc tgcgcctgag ctgcgccgcc     840
agcggcttca ccttcagcag ctacagcatg aactgggtgc gccaggcccc cggcaagggc     900

```
ctggagtggg tgagctacat cagcagcagc agcagcacca tctactacgc cgacagcgtg    960
aagggccgct tcaccatcag ccgcgacaac gccaagaaca gcctgtacct gcagatgaac   1020
agcctgcgcg acgaggacac cgccgtgtac tactgcgccc gcggcgtgta ccacaacggc   1080
tggagcttct tcgactactg gggccagggc accctgctga ccgtgagcag cggcggcggc   1140
ggcagcggcg gcggcggcag cggcggcggc ggcagcgaca tccagatgac ccagagcccc   1200
agcagcctga gcgccagcgt gggcaaccgc gtgaccatca cctgccgcgc cagccaggac   1260
atcagcagct ggctggcctg gtaccagcag aagcccgaga aggcccccaa gagcctgatc   1320
tacgccgcca gcagcctgca gagcggcgtg cccagccgct tcagcggcag cggcagcggc   1380
accgacttca ccctgaccat cagcagcctg cagcccgagg acttcgccac ctactactgc   1440
cagcagtaca acagctaccc cctgaccttc ggccagggca cccgcctgga gatcaagcgc   1500
```

<210> SEQ ID NO 53
<211> LENGTH: 566
<212> TYPE: PRT
<213> ORGANISM: Artificial
<220> FEATURE:
<223> OTHER INFORMATION: The amino acid sequence of CD3-OX40 BsAb_D
      dimer

<400> SEQUENCE: 53

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Ala Ser Lys Ser Lys Lys Glu Ile Phe Arg Trp Pro Glu
                245                 250                 255

Ser Pro Lys Ala Gln Ala Ser Ser Val Pro Thr Ala Gln Pro Gln Ala
                260                 265                 270

Glu Gly Ser Leu Ala Lys Ala Thr Thr Ala Pro Ala Thr Thr Arg Asn
            275                 280                 285

Thr Gly Arg Gly Gly Glu Glu Lys Lys Lys Glu Lys Glu Lys Glu Glu
        290                 295                 300

Gln Glu Glu Arg Glu Thr Lys Thr Pro Glu Cys Pro Ser His Thr Gln
305                 310                 315                 320

Pro Leu Gly Val Gln Leu Val Glu Ser Gly Gly Gly Leu Val Gln Pro
                325                 330                 335

Gly Gly Ser Leu Arg Leu Ser Cys Ala Ala Ser Gly Phe Thr Phe Ser
            340                 345                 350

Ser Tyr Ser Met Asn Trp Val Arg Gln Ala Pro Gly Lys Gly Leu Glu
        355                 360                 365

Trp Val Ser Tyr Ile Ser Ser Ser Ser Thr Ile Tyr Tyr Ala Asp
        370                 375                 380

Ser Val Lys Gly Arg Phe Thr Ile Ser Arg Asp Asn Ala Lys Asn Ser
385                 390                 395                 400

Leu Tyr Leu Gln Met Asn Ser Leu Arg Asp Glu Asp Thr Ala Val Tyr
                405                 410                 415

Tyr Cys Ala Arg Gly Val Tyr His Asn Gly Trp Ser Phe Phe Asp Tyr
            420                 425                 430

Trp Gly Gln Gly Thr Leu Leu Thr Val Ser Ser Gly Gly Gly Gly Ser
        435                 440                 445

Gly Gly Gly Gly Ser Gly Gly Gly Ser Asp Ile Gln Met Thr Gln
        450                 455                 460

Ser Pro Ser Ser Leu Ser Ala Ser Val Gly Asn Arg Val Thr Ile Thr
465                 470                 475                 480

Cys Arg Ala Ser Gln Asp Ile Ser Ser Trp Leu Ala Trp Tyr Gln Gln
                485                 490                 495

Lys Pro Glu Lys Ala Pro Lys Ser Leu Ile Tyr Ala Ala Ser Ser Leu
            500                 505                 510

Gln Ser Gly Val Pro Ser Arg Phe Ser Gly Ser Gly Ser Gly Thr Asp
        515                 520                 525

Phe Thr Leu Thr Ile Ser Ser Leu Gln Pro Glu Asp Phe Ala Thr Tyr
        530                 535                 540

Tyr Cys Gln Gln Tyr Asn Ser Tyr Pro Leu Thr Phe Gly Gln Gly Thr
545                 550                 555                 560

Arg Leu Glu Ile Lys Arg
                565

<210> SEQ ID NO 54
<211> LENGTH: 1698
<212> TYPE: DNA
<213> ORGANISM: Artificial
<220> FEATURE:
<223> OTHER INFORMATION: The nucleotide sequence of CD3-OX40 BsAb_D
      dimer

<400> SEQUENCE: 54
gacatcaagc tgcagcagag cggcgccgag ctggcccgcc ccggcgccag cgtgaagatg    60
agctgcaaga ccagcggcta caccttcacc cgctacacca tgcactgggt gaagcagcgc   120
cccggccagg gcctggagtg gatcggctac atcaaccccea gccgcggcta caccaactac   180
aaccagaagt tcaaggacaa ggccaccctg accaccgaca gagcagcag caccgcctac   240

```
atgcagctga gcagcctgac cagcgaggac agcgccgtgt actactgcgc ccgctactac    300
gacgaccact actgcctgga ctactggggc cagggcacca ccctgaccgt gagcagcgtg    360
gagggcggca gcggcggcag cggcggcagc ggcggcagcg gcggcgtgga cgacatccag    420
ctgacccaga gccccgccat catgagcgcc agccccggcg agaaggtgac catgacctgc    480
cgcgccagca gcagcgtgag ctacatgaac tggtaccagc agaagagcgg caccagcccc    540
aagcgctgga tctacgacac cagcaaggtg gccagcggcg tgccctaccg cttcagcggc    600
agcggcagcg gcaccagcta cagcctgacc atcagcagca tggaggccga ggacgccgcc    660
acctactact gccagcagtg gagcagcaac ccctgacct cggcgccgg caccaagctg    720 gagctgaagg ccagcaagag caagaaggag atcttccgct ggccccgagag ccccaaggcc    780 caggccagca gcgtgcccac cgcccagccc caggccgagg cagcctggc caaggccacc    840 accgccccg ccaccacccg caacaccggc cgcggcggcg aggagaagaa gaaggagaag    900
gagaaggagg agcaggagga gcgcgagacc aagacccccg agtgccccag ccacacccag    960
cccctgggcg tgcagctggt ggagagcggc ggcggcctgg tgcagcccgg cggcagcctg   1020
cgcctgagct gcgccgccag cggcttcacc ttcagcagct acagcatgaa ctgggtgcgc   1080
caggcccccg gcaagggcct ggagtgggtg agctacatca gcagcagcag cagcaccatc   1140
tactacgccg acagcgtgaa gggccgcttc accatcagcc gcgacaacgc caagaacagc   1200
ctgtacctgc agatgaacag cctgcgcgac gaggacaccg ccgtgtacta ctgcgcccgc   1260
ggcgtgtacc acaacggctg gagcttcttc gactactggg gccagggcac cctgctgacc   1320
gtgagcagcg gcggcggcgg cagcggcggc ggcggcagcg gcggcggcgg cagcgacatc   1380
cagatgaccc agagcccag cagcctgagc gccagcgtgg gcaaccgcgt gaccatcacc   1440
tgccgcgcca gccaggacat cagcagctgg ctggcctggt accagcagaa gcccgagaag   1500
gcccccaaga gcctgatcta cgccgccagc agcctgcaga gcggcgtgcc cagccgcttc   1560
agcggcagcg gcagcggcac cgacttcacc ctgaccatca gcagcctgca gcccgaggac   1620
ttcgccacct actactgcca gcagtacaac agctacccc tgaccttcgg ccagggcacc   1680
cgcctggaga tcaagcgc                                                 1698
```

<210> SEQ ID NO 55
<211> LENGTH: 499
<212> TYPE: PRT
<213> ORGANISM: Artificial
<220> FEATURE:
<223> OTHER INFORMATION: The amino acid sequence of CD3-GITR BsAb_M
      monomer

<400> SEQUENCE: 55

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95
```

```
Ala Arg Tyr Tyr Asp Asp His Tyr Cys Leu Asp Tyr Trp Gly Gln Gly
            100                 105                 110

Thr Thr Leu Thr Val Ser Ser Val Glu Gly Ser Gly Gly Ser Gly
            115                 120                 125

Gly Ser Gly Gly Ser Gly Gly Val Asp Asp Ile Gln Leu Thr Gln Ser
            130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
            195                 200                 205

Leu Thr Ile Ser Ser Met Glu Ala Glu Asp Ala Ala Thr Tyr Tyr Cys
            210                 215                 220

Gln Gln Trp Ser Ser Asn Pro Leu Thr Phe Gly Ala Gly Thr Lys Leu
225                 230                 235                 240

Glu Leu Lys Gly Gly Gly Gly Ser Gly Gly Gly Gly Ser Gly Gly Gly
                245                 250                 255

Gly Ser Gln Val Thr Leu Lys Glu Ser Gly Pro Gly Ile Leu Lys Pro
            260                 265                 270

Ser Gln Thr Leu Ser Leu Thr Cys Ser Phe Ser Gly Phe Ser Leu Ser
            275                 280                 285

Thr Ser Gly Met Gly Val Gly Trp Ile Arg Gln Pro Ser Gly Lys Gly
            290                 295                 300

Leu Glu Trp Leu Ala His Ile Trp Trp Asp Asp Asp Lys Tyr Tyr Asn
305                 310                 315                 320

Pro Ser Leu Lys Ser Gln Leu Thr Ile Ser Lys Asp Thr Ser Arg Asn
                325                 330                 335

Gln Val Phe Leu Lys Ile Thr Ser Val Asp Thr Ala Asp Ala Ala Thr
            340                 345                 350

Tyr Tyr Cys Ala Arg Thr Arg Arg Tyr Phe Pro Phe Ala Tyr Trp Gly
            355                 360                 365

Gln Gly Thr Leu Val Thr Val Ser Ser Gly Gly Gly Gly Ser Gly Gly
            370                 375                 380

Gly Gly Ser Gly Gly Gly Gly Ser Asp Ile Val Met Thr Gln Ser Gln
385                 390                 395                 400

Lys Phe Met Ser Thr Ser Val Gly Asp Arg Val Ser Val Thr Cys Lys
                405                 410                 415

Ala Ser Gln Asn Val Gly Thr Asn Val Ala Trp Tyr Gln Gln Lys Pro
            420                 425                 430

Gly Gln Ser Pro Lys Ala Leu Ile Tyr Ser Ala Ser Tyr Arg Tyr Ser
            435                 440                 445

Gly Val Pro Asp Arg Phe Thr Gly Ser Gly Ser Gly Thr Asp Phe Thr
            450                 455                 460

Leu Thr Ile Asn Asn Val His Ser Glu Asp Leu Ala Glu Tyr Phe Cys
465                 470                 475                 480

Gln Gln Tyr Asn Thr Asp Pro Leu Thr Phe Gly Ala Gly Thr Lys Leu
                485                 490                 495

Glu Ile Lys
```

-continued

```
<210> SEQ ID NO 56
<211> LENGTH: 1497
<212> TYPE: DNA
<213> ORGANISM: Artificial
<220> FEATURE:
<223> OTHER INFORMATION: The nucleotide sequence of CD3-GITR BsAb_M
      monomer

<400> SEQUENCE: 56
gacatcaagc tgcagcagag cggcgccgag ctggcccgcc ccggcgccag cgtgaagatg      60
agctgcaaga ccagcggcta caccttcacc cgctacacca tgcactgggt gaagcagcgc    120
cccggccagg gcctggagtg gatcggctac atcaacccca gccgcggcta caccaactac    180
aaccagaagt tcaaggacaa ggccaccctg accaccgaca gagcagcag caccgcctac    240 atgcagctga gcagcctgac cagcgaggac agcgccgtgt actactgcgc cgctactac    300 gacgaccact actgcctgga ctactggggc cagggcacca ccctgaccgt gagcagcgtg    360
gagggcggca gcggcggcag cggcggcagc ggcggcagcg gcggcgtgga cgacatccag    420
ctgacccaga gccccgccat catgagcgcc agccccggcg agaaggtgac catgacctgc    480
cgcgccagca gcagcgtgag ctacatgaac tggtaccagc agaagagcgg caccagcccc    540
aagcgctgga tctacgacac cagcaaggtg gccagcggcg tgccctaccg cttcagcggc    600
agcggcagcg gcaccagcta cagcctgacc atcagcagca tggaggccga ggacgccgcc    660
acctactact gccagcagtg gagcagcaac ccctgacct cggcgccgg caccaagctg    720 gagctgaagg gcggcggcgg cagcggcggc ggcggcagcg gcggcggcgg cagccaggtg    780
accctgaagg agagcggccc cggcatcctg aagcccagcc agaccctgag cctgacctgc    840
agcttcagcg gcttcagcct gagcaccagc ggcatgggcg tgggctggat ccgccagccc    900
agcggcaagg gcctggagtg gctggcccac atctggtggg acgacgacaa gtactacaac    960
cccagcctga gagccagct gaccatcagc aaggacacca gccgcaacca ggtgttcctg   1020
aagatcacca gcgtggacac cgccgacgcc gccacctact actgcgcccg cacccgccgc   1080
tacttcccct cgcctactg gggccagggc accctggtga ccgtgagcag cggcggcggc   1140
ggcagcggcg gcggcggcag cggcggcggc ggcagcgaca tcgtgatgac ccagagccag   1200
aagttcatga gcaccagcgt gggcgaccgc gtgagcgtga cctgcaaggc cagccagaac   1260
gtgggcacca acgtggcctg gtaccagcag aagcccggcc agagccccaa ggccctgatc   1320
tacagcgcca gctaccgcta cagcggcgtg cccgaccgct tcaccggcag cggcagcggc   1380
accgacttca ccctgaccat caacaacgtg cacagcgagg acctggccga gtacttctgc   1440
cagcagtaca acaccgaccc cctgaccttc ggcgccggca ccaagctgga gatcaag     1497

<210> SEQ ID NO 57
<211> LENGTH: 565
<212> TYPE: PRT
<213> ORGANISM: Artificial
<220> FEATURE:
<223> OTHER INFORMATION: The amino acid sequence of CD3-GITR BsAb_D
      dimer

<400> SEQUENCE: 57

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45
```

```
Gly Tyr Ile Asn Pro Ser Arg Gly Tyr Thr Asn Tyr Asn Gln Lys Phe
         50                  55                  60

Lys Asp Lys Ala Thr Leu Thr Thr Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
                100                 105                 110

Thr Thr Leu Thr Val Ser Ser Val Glu Gly Gly Ser Gly Gly Ser Gly
            115                 120                 125

Gly Ser Gly Gly Ser Gly Gly Val Asp Asp Ile Gln Leu Thr Gln Ser
        130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Ala Ser Lys Ser Lys Lys Glu Ile Phe Arg Trp Pro Glu
                245                 250                 255

Ser Pro Lys Ala Gln Ala Ser Ser Val Pro Thr Ala Gln Pro Gln Ala
            260                 265                 270

Glu Gly Ser Leu Ala Lys Ala Thr Thr Ala Pro Ala Thr Thr Arg Asn
        275                 280                 285

Thr Gly Arg Gly Gly Glu Glu Lys Lys Lys Glu Lys Glu Lys Glu Glu
    290                 295                 300

Gln Glu Glu Arg Glu Thr Lys Thr Pro Glu Cys Pro Ser His Thr Gln
305                 310                 315                 320

Pro Leu Gly Val Gln Val Thr Leu Lys Glu Ser Gly Pro Gly Ile Leu
                325                 330                 335

Lys Pro Ser Gln Thr Leu Ser Leu Thr Cys Ser Phe Ser Gly Phe Ser
            340                 345                 350

Leu Ser Thr Ser Gly Met Gly Val Gly Trp Ile Arg Gln Pro Ser Gly
        355                 360                 365

Lys Gly Leu Glu Trp Leu Ala His Ile Trp Trp Asp Asp Asp Lys Tyr
    370                 375                 380

Tyr Asn Pro Ser Leu Lys Ser Gln Leu Thr Ile Ser Lys Asp Thr Ser
385                 390                 395                 400

Arg Asn Gln Val Phe Leu Lys Ile Thr Ser Val Asp Thr Ala Asp Ala
                405                 410                 415

Ala Thr Tyr Tyr Cys Ala Arg Thr Arg Arg Tyr Phe Pro Phe Ala Tyr
            420                 425                 430

Trp Gly Gln Gly Thr Leu Val Thr Val Ser Ser Gly Gly Gly Gly Ser
        435                 440                 445

Gly Gly Gly Gly Ser Gly Gly Gly Gly Ser Asp Ile Val Met Thr Gln
    450                 455                 460
```

```
Ser Gln Lys Phe Met Ser Thr Ser Val Gly Asp Arg Val Ser Val Thr
465                 470                 475                 480

Cys Lys Ala Ser Gln Asn Val Gly Thr Asn Val Ala Trp Tyr Gln Gln
                485                 490                 495

Lys Pro Gly Gln Ser Pro Lys Ala Leu Ile Tyr Ser Ala Ser Tyr Arg
            500                 505                 510

Tyr Ser Gly Val Pro Asp Arg Phe Thr Gly Ser Gly Ser Gly Thr Asp
        515                 520                 525

Phe Thr Leu Thr Ile Asn Asn Val His Ser Glu Asp Leu Ala Glu Tyr
            530                 535                 540

Phe Cys Gln Gln Tyr Asn Thr Asp Pro Leu Thr Phe Gly Ala Gly Thr
545                 550                 555                 560

Lys Leu Glu Ile Lys
            565

<210> SEQ ID NO 58
<211> LENGTH: 1695
<212> TYPE: DNA
<213> ORGANISM: Artificial
<220> FEATURE:
<223> OTHER INFORMATION: The nucleotide sequence of CD3-GITR BsAb_D
      dimer

<400> SEQUENCE: 58
gacatcaagc tgcagcagag cggcgccgag ctggcccgcc ccggcgccag cgtgaagatg      60
agctgcaaga ccagcggcta caccttcacc cgctacacca tgcactgggt gaagcagcgc     120
cccggccagg gcctggagtg gatcggctac atcaaccccg ccgcggcta caccaactac     180 aaccagaagt tcaaggacaa ggccaccctg accaccgaca gagcagcag caccgcctac     240 atgcagctga gcagcctgac cagcgaggac agcgccgtgt actactgcgc cgctactac     300 gacgaccact actgcctgga ctactggggc cagggcacca ccctgaccgt gagcagcgtg     360
gagggcggca gcggcggcag cggcggcagc ggcggcagcg gcggcgtgga cgacatccag     420
ctgacccaga gccccgccat catgagcgcc agcccggcg agaaggtgac catgacctgc     480
cgcgccagca gcagcgtgag ctacatgaac tggtaccagc agaagagcgg caccagcccc     540
aagcgctgga tctacgacac cagcaaggtg gccagcggcg tgccctaccg cttcagcggc     600
agcggcagcg gcaccagcta cagcctgacc atcagcagca tggaggccga ggacgccgcc     660
acctactact gccagcagtg gagcagcaac ccctgacct tcggcgccgg caccaagctg     720
gagctgaagg ccagcaagag caagaaggag atcttccgct ggcccgagag ccccaaggcc     780
caggccagca gcgtgcccac cgcccagccc caggccgagg gcagcctggc caaggccacc     840 accgccccg ccaccacccg caacaccggc cgcggcggcg aggagaagaa gaaggagaag     900
gagaaggagg agcaggagga gcgcgagacc aagaccccg agtgccccag ccacacccag     960
cccctgggcg tgcaggtgac cctgaaggag agcggcccg gcatcctgaa gcccagccag     1020
accctgagcc tgacctgcag cttcagcggc ttcagcctga gcaccagcgg catgggcgtg     1080
ggctggatcc gccagcccag cggcaagggc ctggagtggc tggcccacat ctggtgggac     1140
gacgacaagt actacaaccc cagcctgaag agccagctga ccatcagcaa ggacaccagc     1200
cgcaaccagg tgttcctgaa gatcaccagc gtggacaccg ccgacgccgc cacctactac     1260
tgcgcccgca cccgccgcta cttccccttc gcctactggg gccagggcac cctggtgacc     1320
gtgagcagcg gcggcggcgg cagcggcggc ggcggcagcg gcggcggcgg cagcgacatc     1380
gtgatgaccc agagccagaa gttcatgagc accagcgtgg gcgaccgcgt gagcgtgacc     1440
```

-continued

```
tgcaaggcca gccagaacgt gggcaccaac gtggcctggt accagcagaa gcccggccag      1500
agccccaagg ccctgatcta cagcgccagc taccgctaca gcggcgtgcc cgaccgcttc      1560
accggcagcg gcagcggcac cgacttcacc ctgaccatca acaacgtgca gagcgaggac      1620
ctggccgagt acttctgcca gcagtacaac accgaccccc tgaccttcgg cgccggcacc      1680
aagctggaga tcaag                                                       1695
```

<210> SEQ ID NO 59
<211> LENGTH: 497
<212> TYPE: PRT
<213> ORGANISM: Artificial
<220> FEATURE:
<223> OTHER INFORMATION: The amino acid sequence of CD3-CD40L BsAb_M monomer

<400> SEQUENCE: 59

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Gly Gly Gly Gly Ser Gly Gly Gly Gly Ser Gly Gly Gly
                245                 250                 255

Gly Ser Glu Val Gln Leu Leu Glu Ser Gly Gly Gly Leu Val Gln Pro
            260                 265                 270

Gly Gly Ser Leu Arg Leu Ser Cys Ala Ala Ser Gly Phe Thr Phe Ser
        275                 280                 285

Ser Tyr Ala Met Ser Trp Val Arg Gln Ala Pro Gly Lys Gly Leu Glu
    290                 295                 300
```

Trp Val Ser Ala Ile Ser Gly Ser Gly Gly Ser Thr Tyr Tyr Ala Asp
305                 310                 315                 320

Ser Val Lys Gly Arg Phe Thr Ile Ser Arg Asp Asn Ser Lys Asn Thr
            325                 330                 335

Leu Tyr Leu Gln Met Asn Ser Leu Arg Ala Glu Asp Thr Ala Val Tyr
        340                 345                 350

Tyr Cys Ala Lys Ser Tyr Gly Ala Phe Asp Tyr Trp Gly Gln Gly Thr
    355                 360                 365

Leu Val Thr Val Ser Ser Gly Gly Gly Ser Gly Gly Gly Gly Ser
370                 375                 380

Gly Gly Gly Gly Ser Asp Ile Gln Met Thr Gln Ser Pro Ser Ser Leu
385                 390                 395                 400

Ser Ala Ser Val Gly Asp Arg Val Thr Ile Thr Cys Arg Ala Ser Gln
            405                 410                 415

Ser Ile Ser Ser Tyr Leu Asn Trp Tyr Gln Gln Lys Pro Gly Lys Ala
        420                 425                 430

Pro Lys Leu Leu Ile Tyr Ala Ala Ser Ser Leu Gln Ser Gly Val Pro
    435                 440                 445

Ser Arg Phe Ser Gly Ser Gly Ser Gly Thr Asp Phe Thr Leu Thr Ile
450                 455                 460

Ser Ser Leu Gln Pro Glu Asp Phe Ala Thr Tyr Tyr Cys Gln Gln Ser
465                 470                 475                 480

Tyr Ser Thr Pro Asn Thr Phe Gly Gln Gly Thr Lys Val Glu Ile Lys
            485                 490                 495

Arg

<210> SEQ ID NO 60
<211> LENGTH: 1491
<212> TYPE: DNA
<213> ORGANISM: Artificial
<220> FEATURE:
<223> OTHER INFORMATION: The nucleotide sequence of CD3-CD40L BsAb_M
      monomer

<400> SEQUENCE: 60
gacatcaagc tgcagcagag cggcgccgag ctggcccgcc ccggcgccag cgtgaagatg      60
agctgcaaga ccagcggcta caccttcacc cgctacacca tgcactgggt gaagcagcgc    120
cccggccagg gcctggagtg gatcggctac atcaacccca gccgcggcta caccaactac    180
aaccagaagt tcaaggacaa ggccaccctg accaccgaca gagcagcag caccgcctac    240 atgcagctga gcagcctgac cagcgaggac agcgccgtgt actactgcgc cgctactac    300 gacgaccact actgcctgga ctactggggc cagggcacca ccctgaccgt gagcagcgtg    360
gagggcggca gcggcggcag cggcggcagc ggcggcgtgga cgacatccag    420 ctgacccaga gccccgccat catgagcgcc agccccggcg agaaggtgac catgacctgc    480
cgcgccagca gcagcgtgag ctacatgaac tggtaccagc agaagagcgg caccagcccc    540
aagcgctgga tctacgacac cagcaaggtg gccagcggcg tgccctaccg cttcagcggc    600
agcggcagcg gcaccagcta cagcctgacc atcagcagca tggaggccga ggacgccgcc    660
acctactact gccagcagtg gagcagcaac cccctgacct cggcgccgg caccaagctg    720 gagctgaagg gcggcggcgg cagcggcggc ggcggcagcg gcggcggcgg cagcgaggtg    780
cagctgctgg agagcggcgg cggcctggtg cagcccggcg gcagcctgcg cctgagctgc    840
gccgccagcg gcttcacctt cagcagctac gccatgagct gggtgcgcca ggcccccggc    900

```
aagggcctgg agtgggtgag cgccatcagc ggcagcggcg gcagcaccta ctacgccgac    960
agcgtgaagg ccgcttcac catcagccgc gacaacagca agaacaccct gtacctgcag   1020
atgaacagcc tgcgcgccga ggacaccgcc gtgtactact gcgccaagag ctacggcgcc   1080
ttcgactact ggggccaggg caccctggtg accgtgagca gcggcggcgg cggcagcggc   1140
ggcggcggca gcggcggcgg cggcagcgac atccagatga cccagagccc cagcagcctg   1200
agcgccagcg tgggcgaccg cgtgaccatc acctgccgcg ccagccagag catcagcagc   1260
tacctgaact ggtaccagca gaagcccggc aaggcccca agctgctgat ctacgccgcc   1320
agcagcctgc agagcggcgt gcccagccgc ttcagcggca gcggcagcgg caccgacttc   1380
accctgacca tcagcagcct gcagcccgag gacttcgcca cctactactg ccagcagagc   1440
tacagcaccc ccaacacctt cggccagggc accaaggtgg agatcaagcg c            1491
```

<210> SEQ ID NO 61
<211> LENGTH: 563
<212> TYPE: PRT
<213> ORGANISM: Artificial
<220> FEATURE:
<223> OTHER INFORMATION: The amino acid sequence of CD3-CD40L BsAb_D
      dimer

<400> SEQUENCE: 61

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Ala Ser Lys Ser Lys Glu Ile Phe Arg Trp Pro Glu
                245                 250                 255
```

Ser Pro Lys Ala Gln Ala Ser Ser Val Pro Thr Ala Gln Pro Gln Ala
            260                 265                 270

Glu Gly Ser Leu Ala Lys Ala Thr Thr Ala Pro Ala Thr Thr Arg Asn
        275                 280                 285

Thr Gly Arg Gly Gly Glu Glu Lys Lys Lys Glu Lys Glu Lys Glu Glu
        290                 295                 300

Gln Glu Glu Arg Glu Thr Lys Thr Pro Glu Cys Pro Ser His Thr Gln
305                 310                 315                 320

Pro Leu Gly Val Glu Val Gln Leu Leu Glu Ser Gly Gly Gly Leu Val
                325                 330                 335

Gln Pro Gly Gly Ser Leu Arg Leu Ser Cys Ala Ala Ser Gly Phe Thr
            340                 345                 350

Phe Ser Ser Tyr Ala Met Ser Trp Val Arg Gln Ala Pro Gly Lys Gly
        355                 360                 365

Leu Glu Trp Val Ser Ala Ile Ser Gly Ser Gly Gly Ser Thr Tyr Tyr
        370                 375                 380

Ala Asp Ser Val Lys Gly Arg Phe Thr Ile Ser Arg Asp Asn Ser Lys
385                 390                 395                 400

Asn Thr Leu Tyr Leu Gln Met Asn Ser Leu Arg Ala Glu Asp Thr Ala
                405                 410                 415

Val Tyr Tyr Cys Ala Lys Ser Tyr Gly Ala Phe Asp Tyr Trp Gly Gln
            420                 425                 430

Gly Thr Leu Val Thr Val Ser Ser Gly Gly Gly Gly Ser Gly Gly Gly
        435                 440                 445

Gly Ser Gly Gly Gly Gly Ser Asp Ile Gln Met Thr Gln Ser Pro Ser
    450                 455                 460

Ser Leu Ser Ala Ser Val Gly Asp Arg Val Thr Ile Thr Cys Arg Ala
465                 470                 475                 480

Ser Gln Ser Ile Ser Ser Tyr Leu Asn Trp Tyr Gln Gln Lys Pro Gly
                485                 490                 495

Lys Ala Pro Lys Leu Leu Ile Tyr Ala Ala Ser Ser Leu Gln Ser Gly
            500                 505                 510

Val Pro Ser Arg Phe Ser Gly Ser Gly Ser Gly Thr Asp Phe Thr Leu
        515                 520                 525

Thr Ile Ser Ser Leu Gln Pro Glu Asp Phe Ala Thr Tyr Tyr Cys Gln
        530                 535                 540

Gln Ser Tyr Ser Thr Pro Asn Thr Phe Gly Gln Gly Thr Lys Val Glu
545                 550                 555                 560

Ile Lys Arg

<210> SEQ ID NO 62
<211> LENGTH: 1689
<212> TYPE: DNA
<213> ORGANISM: Artificial
<220> FEATURE:
<223> OTHER INFORMATION: The nucleotide sequence of CD3-CD40L BsAb_D
      dimer

<400> SEQUENCE: 62
gacatcaagc tgcagcagag cggcgccgag ctggcccgcc ccggcgccag cgtgaagatg      60
agctgcaaga ccagcggcta caccttcacc cgctacacca tgcactgggt gaagcagcgc     120
cccggccagg gcctggagtg gatcggctac atcaacccca gccgcggcta caccaactac     180
aaccagaagt tcaaggacaa ggccaccctg accaccgaca gagcagcag caccgcctac     240 atgcagctga gcagcctgac cagcgaggac agcgccgtgt actactgcgc ccgctactac     300

-continued

```
gacgaccact actgcctgga ctactggggc cagggcacca ccctgaccgt gagcagcgtg    360
gagggcggca gcggcggcag cggcggcagc ggcggcagcg gcggcgtgga cgacatccag    420
ctgacccaga gccccgccat catgagcgcc agcccggcg agaaggtgac catgacctgc     480
cgcgccagca gcagcgtgag ctacatgaac tggtaccagc agaagagcgg caccagcccc    540
aagcgctgga tctacgacac cagcaaggtg gccagcggcg tgccctaccg cttcagcggc    600
agcggcagcg gcaccagcta cagcctgacc atcagcagca tggaggccga ggacgccgcc    660
acctactact gccagcagtg gagcagcaac cccctgacct tcggcgccgg caccaagctg    720
gagctgaagg ccagcaagag caagaaggag atcttccgct ggcccgagag ccccaaggcc    780
caggccagca gcgtgcccac cgcccagccc caggccgagg cagcctggc caaggccacc      840 accgcccccg ccaccacccg caacaccggc cgcggcggcg aggagaagaa gaaggagaag    900
gagaaggagg agcaggagga gcgcgagacc aagacccccg agtgccccag ccacacccag    960
cccctgggcg tggaggtgca gctgctggag agcggcggcg gcctggtgca gcccggcggc   1020
agcctgcgcc tgagctgcgc cgccagcggc ttcaccttca gcagctacgc catgagctgg   1080
gtgcgccagg cccccggcaa gggcctggag tgggtgagcg ccatcagcgg cagcggcggc   1140
agcacctact acgccgacag cgtgaagggc cgcttcacca tcagccgcga caacagcaag   1200
aacaccctgt acctgcagat gaacagcctg cgcgccgagg acaccgccgt gtactactgc   1260
gccaagagct acggcgcctt cgactactgg ggccagggca ccctggtgac cgtgagcagc   1320
ggcggcggcg gcagcggcgg cggcggcagc ggcggcggcg gcagcgacat ccagatgacc   1380
cagagcccca gcagcctgag cgccagcgtg ggcgaccgcg tgaccatcac ctgccgcgcc   1440
agccagagca tcagcagcta cctgaactgg taccagcaga agcccggcaa ggccccaag    1500 ctgctgatct acgccgccag cagcctgcag agcggcgtgc ccagccgctt cagcggcagc   1560
ggcagcggca ccgacttcac cctgaccatc agcagcctgc agcccgagga cttcgccacc   1620
tactactgcc agcagagcta cagcaccccc aacaccttcg gccagggcac caaggtggag   1680
atcaagcgc                                                           1689
```

<210> SEQ ID NO 63
<211> LENGTH: 499
<212> TYPE: PRT
<213> ORGANISM: Artificial
<220> FEATURE:
<223> OTHER INFORMATION: The amino acid sequence of CD3-CD27 BsAb_M monomer

<400> SEQUENCE: 63

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly

```
                    100                 105                 110
Thr Thr Leu Thr Val Ser Ser Val Glu Gly Ser Gly Gly Ser Gly
            115                 120                 125
Gly Ser Gly Gly Ser Gly Gly Val Asp Asp Ile Gln Leu Thr Gln Ser
            130                 135             140
Pro Ala Ile Met Ser Ala Ser Pro Gly Glu Lys Val Thr Met Thr Cys
145                 150                 155                 160
Arg Ala Ser Ser Val Ser Tyr Met Asn Trp Tyr Gln Gln Lys Ser
                165                 170                 175
Gly Thr Ser Pro Lys Arg Trp Ile Tyr Asp Thr Ser Lys Val Ala Ser
            180                 185                 190
Gly Val Pro Tyr Arg Phe Ser Gly Ser Gly Ser Gly Thr Ser Tyr Ser
            195                 200                 205
Leu Thr Ile Ser Ser Met Glu Ala Glu Asp Ala Ala Thr Tyr Tyr Cys
            210                 215                 220
Gln Gln Trp Ser Ser Asn Pro Leu Thr Phe Gly Ala Gly Thr Lys Leu
225                 230                 235                 240
Glu Leu Lys Gly Gly Gly Gly Ser Gly Gly Gly Gly Ser Gly Gly Gly
                245                 250                 255
Gly Ser Gln Val Gln Leu Val Glu Ser Gly Gly Val Val Gln Pro
            260                 265                 270
Gly Arg Ser Leu Arg Leu Ser Cys Ala Ala Ser Gly Phe Thr Phe Ser
            275                 280                 285
Ser Tyr Asp Met His Trp Val Arg Gln Ala Pro Gly Lys Gly Leu Glu
            290                 295                 300
Trp Val Ala Val Ile Trp Tyr Asp Gly Ser Asn Lys Tyr Tyr Ala Asp
305                 310                 315                 320
Ser Val Lys Gly Arg Phe Thr Ile Ser Arg Asp Asn Ser Lys Asn Thr
                325                 330                 335
Leu Tyr Leu Gln Met Asn Ser Leu Arg Ala Glu Asp Thr Ala Val Tyr
            340                 345                 350
Tyr Cys Ala Arg Gly Ser Gly Asn Trp Gly Phe Phe Asp Tyr Trp Gly
            355                 360                 365
Gln Gly Thr Leu Val Thr Val Ser Ser Gly Gly Gly Gly Ser Gly Gly
            370                 375             380
Gly Gly Ser Gly Gly Gly Gly Ser Asp Ile Gln Met Thr Gln Ser Pro
385                 390                 395                 400
Ser Ser Leu Ser Ala Ser Val Gly Asp Arg Val Thr Ile Thr Cys Arg
                405                 410                 415
Ala Ser Gln Gly Ile Ser Arg Trp Leu Ala Trp Tyr Gln Gln Lys Pro
            420                 425                 430
Glu Lys Ala Pro Lys Ser Leu Ile Tyr Ala Ala Ser Ser Leu Gln Ser
            435                 440                 445
Gly Val Pro Ser Arg Phe Ser Gly Ser Gly Ser Gly Thr Asp Phe Thr
            450                 455                 460
Leu Thr Ile Ser Ser Leu Gln Pro Glu Asp Phe Ala Thr Tyr Tyr Cys
465                 470                 475                 480
Gln Gln Tyr Asn Thr Tyr Pro Arg Thr Phe Gly Gln Gly Thr Lys Val
                485                 490                 495
Glu Ile Lys

<210> SEQ ID NO 64
<211> LENGTH: 1497
```

<212> TYPE: DNA
<213> ORGANISM: Artificial
<220> FEATURE:
<223> OTHER INFORMATION: The nucleotide sequence of CD3-CD27 BsAb_M monomer

<400> SEQUENCE: 64

| | | | | | |
|---|---|---|---|---|---|
| gacatcaagc | tgcagcagag | cggcgccgag | ctggcccgcc | ccggcgccag | cgtgaagatg | 60 |
| agctgcaaga | ccagcggcta | caccttcacc | cgctacacca | tgcactgggt | gaagcagcgc | 120 |
| cccggccagg | gcctggagtg | gatcggctac | atcaacccca | gccgcggcta | caccaactac | 180 |
| aaccagaagt | tcaaggacaa | ggccaccctg | accaccgaca | agagcagcag | caccgcctac | 240 |
| atgcagctga | gcagcctgac | cagcgaggac | agcgccgtgt | actactgcgc | ccgctactac | 300 |
| gacgaccact | actgcctgga | ctactggggc | cagggcacca | ccctgaccgt | gagcagcgtg | 360 |
| gagggcggca | gcggcggcag | cggcggcagc | ggcggcagcg | gcggcgtgga | cgacatccag | 420 |
| ctgacccaga | gccccgccat | catgagcgcc | agccccggcg | agaaggtgac | catgacctgc | 480 |
| cgcgccagca | gcagcgtgag | ctacatgaac | tggtaccagc | agaagagcgg | caccagcccc | 540 |
| aagcgctgga | tctacgacac | cagcaaggtg | gccagcggcg | tgccctaccg | cttcagcggc | 600 |
| agcggcagcg | gcaccagcta | cagcctgacc | atcagcagca | tggaggccga | ggacgccgcc | 660 |
| acctactact | gccagcagtg | gagcagcaac | cccctgacct | tcggcgccgg | caccaagctg | 720 |
| gagctgaagg | gcggcggcgg | cagcggcggc | ggcggcagcg | gcggcggcgg | cagccaggtg | 780 |
| cagctggtgg | agagcggcgg | cggcgtggtg | cagcccggcc | gcagcctgcg | cctgagctgc | 840 |
| gccgccagcg | gcttcacctt | cagcagctac | gacatgcact | gggtgcgcca | ggcccccggc | 900 |
| aagggcctgg | agtgggtggc | cgtgatctgg | tacgacggca | gcaacaagta | ctacgccgac | 960 |
| agcgtgaagg | gccgcttcac | catcagccgc | gacaacagca | agaacaccct | gtacctgcag | 1020 |
| atgaacagcc | tgcgcgccga | ggacaccgcc | gtgtactact | gcgcccgcgg | cagcggcaac | 1080 |
| tggggcttct | tcgactactg | gggccagggc | accctggtga | ccgtgagcag | cggcggcggc | 1140 |
| ggcagcggcg | gcggcggcag | cggcggcggc | ggcagcgaca | tccagatgac | ccagagcccc | 1200 |
| agcagcctga | gcgccagcgt | gggcgaccgc | gtgaccatca | cctgccgcgc | cagccagggc | 1260 |
| atcagccgct | ggctggcctg | gtaccagcag | aagcccgaga | aggcccccaa | gagcctgatc | 1320 |
| tacgccgcca | gcagcctgca | gagcggcgtg | cccagccgct | tcagcggcag | cggcagcggc | 1380 |
| accgacttca | ccctgaccat | cagcagcctg | cagcccgagg | acttcgccac | ctactactgc | 1440 |
| cagcagtaca | acacctaccc | ccgcaccttc | ggccagggca | ccaaggtgga | gatcaag | 1497 |

<210> SEQ ID NO 65
<211> LENGTH: 565
<212> TYPE: PRT
<213> ORGANISM: Artificial
<220> FEATURE:
<223> OTHER INFORMATION: The amino acid sequence of CD3-CD27 BsAb_D dimer

<400> SEQUENCE: 65

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe

-continued

```
                50                  55                  60
Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                     85                  90                  95

Ala Arg Tyr Tyr Asp Asp His Tyr Cys Leu Asp Tyr Trp Gly Gln Gly
                100                 105                 110

Thr Thr Leu Thr Val Ser Ser Val Glu Gly Gly Ser Gly Gly Ser Gly
                115                 120                 125

Gly Ser Gly Gly Ser Gly Gly Val Asp Asp Ile Gln Leu Thr Gln Ser
130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
                180                 185                 190

Gly Val Pro Tyr Arg Phe Ser Gly Ser Gly Ser Gly Thr Ser Tyr Ser
                195                 200                 205

Leu Thr Ile Ser Ser Met Glu Ala Glu Asp Ala Ala Thr Tyr Tyr Cys
210                 215                 220

Gln Gln Trp Ser Ser Asn Pro Leu Thr Phe Gly Ala Gly Thr Lys Leu
225                 230                 235                 240

Glu Leu Lys Ala Ser Lys Ser Lys Lys Glu Ile Phe Arg Trp Pro Glu
                245                 250                 255

Ser Pro Lys Ala Gln Ala Ser Ser Val Pro Thr Ala Gln Pro Gln Ala
                260                 265                 270

Glu Gly Ser Leu Ala Lys Ala Thr Thr Ala Pro Ala Thr Thr Arg Asn
                275                 280                 285

Thr Gly Arg Gly Gly Glu Glu Lys Lys Lys Glu Lys Glu Lys Glu Glu
                290                 295                 300

Gln Glu Glu Arg Glu Thr Lys Thr Pro Glu Cys Pro Ser His Thr Gln
305                 310                 315                 320

Pro Leu Gly Val Gln Val Gln Leu Val Glu Ser Gly Gly Gly Val Val
                325                 330                 335

Gln Pro Gly Arg Ser Leu Arg Leu Ser Cys Ala Ala Ser Gly Phe Thr
                340                 345                 350

Phe Ser Ser Tyr Asp Met His Trp Val Arg Gln Ala Pro Gly Lys Gly
                355                 360                 365

Leu Glu Trp Val Ala Val Ile Trp Tyr Asp Gly Ser Asn Lys Tyr Tyr
                370                 375                 380

Ala Asp Ser Val Lys Gly Arg Phe Thr Ile Ser Arg Asp Asn Ser Lys
385                 390                 395                 400

Asn Thr Leu Tyr Leu Gln Met Asn Ser Leu Arg Ala Glu Asp Thr Ala
                405                 410                 415

Val Tyr Tyr Cys Ala Arg Gly Ser Gly Asn Trp Gly Phe Phe Asp Tyr
                420                 425                 430

Trp Gly Gln Gly Thr Leu Val Thr Val Ser Ser Gly Gly Gly Gly Ser
                435                 440                 445

Gly Gly Gly Gly Ser Gly Gly Gly Gly Ser Asp Ile Gln Met Thr Gln
                450                 455                 460

Ser Pro Ser Ser Leu Ser Ala Ser Val Gly Asp Arg Val Thr Ile Thr
465                 470                 475                 480
```

Cys Arg Ala Ser Gln Gly Ile Ser Arg Trp Leu Ala Trp Tyr Gln Gln
            485                 490                 495

Lys Pro Glu Lys Ala Pro Lys Ser Leu Ile Tyr Ala Ala Ser Ser Leu
        500                 505                 510

Gln Ser Gly Val Pro Ser Arg Phe Ser Gly Ser Gly Ser Gly Thr Asp
        515                 520                 525

Phe Thr Leu Thr Ile Ser Ser Leu Gln Pro Glu Asp Phe Ala Thr Tyr
        530                 535                 540

Tyr Cys Gln Gln Tyr Asn Thr Tyr Pro Arg Thr Phe Gly Gln Gly Thr
545                 550                 555                 560

Lys Val Glu Ile Lys
            565

<210> SEQ ID NO 66
<211> LENGTH: 1695
<212> TYPE: DNA
<213> ORGANISM: Artificial
<220> FEATURE:
<223> OTHER INFORMATION: The nucleotide sequence of CD3-CD27 BsAb_D
      dimer

<400> SEQUENCE: 66
gacatcaagc tgcagcagag cggcgccgag ctggcccgcc ccggcgccag cgtgaagatg      60
agctgcaaga ccagcggcta caccttcacc cgctacacca tgcactgggt gaagcagcgc    120
cccggccagg gcctggagtg gatcggctac atcaacccca ccgcggcta caccaactac     180
aaccagaagt tcaaggacaa ggccaccctg accaccgaca gagcagcag caccgcctac    240
atgcagctga gcagcctgac cagcgaggac agcgccgtgt actactgcgc ccgctactac    300
gacgaccact actgcctgga ctactggggc cagggcacca ccctgaccgt gagcagcgtg    360
gagggcggca gcggcggcag cggcggcagc ggcggcagcg gcggcgtgga cgacatccag    420
ctgacccaga gccccgccat catgagcgcc agccccggcg agaaggtgac catgacctgc    480
cgcgccagca gcagcgtgag ctacatgaac tggtaccagc agaagagcgg caccagcccc    540
aagcgctgga tctacgacac cagcaaggtg ccagcggcg tgccctaccg cttcagcggc    600
agcggcagcg gcaccagcta cagcctgacc atcagcagca tggaggccga ggacgccgcc    660
acctactact gccagcagtg gagcagcaac cccctgacct cggcgccgg caccaagctg    720
gagctgaagg ccagcaagag caagaaggag atcttccgct ggcccgagag ccccaaggcc    780
caggccagca gcgtgcccac cgcccagccc caggccgagg cagcctggc caaggccacc    840
accgccccg ccaccacccg caacaccggc cgcggcggcg aggagaagaa gaaggagaag    900
gagaaggagg agcaggagga gcgcgagacc aagaccccg agtgccccag ccacaccag     960
ccccctgggcg tgcaggtgca gctggtggag agcggcggcg gcgtggtgca gccgccgc    1020
agcctgcgcc tgagctgcgc cgccagcggc ttcaccttca gcagctacga catgcactgg    1080
gtgcgccagg ccccggcaa gggcctggag tgggtggccg tgatctggta cgacggcagc    1140
aacaagtact acgccgacag cgtgaagggc cgcttcacca tcagccgcga caacagcaag    1200
aacaccctgt acctgcagat gaacagcctg cgcgccgagg acaccgccgt gtactactgc    1260
gcccgcggca gcggcaactg gggcttcttc gactactggg gccagggcac cctggtgacc    1320
gtgagcagcg gcggcggcgg cagcggcggc ggcggcagcg gcggcggcgg cagcgacatc    1380
cagatgaccc agagccccag cagcctgagc gccagcgtgg gcgaccgcgt gaccatcacc    1440
tgccgcgcca gccagggcat cagccgctgg ctggcctggt accagcagaa gcccgagaag    1500
gcccccaaga gcctgatcta cgccgccagc agcctgcaga gcggcgtgcc cagccgcttc    1560
agcggcagcg gcagcggcac cgacttcacc ctgaccatca gcagcctgca gcccgaggac    1620
ttcgccacct actactgcca gcagtacaac acctaccccc gcaccttcgg ccagggcacc    1680
aaggtggaga tcaag                                                     1695

<210> SEQ ID NO 67
<211> LENGTH: 243
<212> TYPE: PRT
<213> ORGANISM: Artificial
<220> FEATURE:
<223> OTHER INFORMATION: The amino acid sequence of anti-CD3 scFv

<400> SEQUENCE: 67

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys

<210> SEQ ID NO 68
<211> LENGTH: 119
<212> TYPE: PRT
<213> ORGANISM: Artificial
<220> FEATURE:
<223> OTHER INFORMATION: The amino acid sequence of anti-CD3 scFv heavy
      chain variable region

<400> SEQUENCE: 68

Asp Ile Lys Leu Gln Gln Ser Gly Ala Glu Leu Ala Arg Pro Gly Ala
1               5                   10                  15

```
Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
            115

<210> SEQ ID NO 69
<211> LENGTH: 106
<212> TYPE: PRT
<213> ORGANISM: Artificial
<220> FEATURE:
<223> OTHER INFORMATION: The amino acid sequence of anti-CD3 scFv light
      chain variable region

<400> SEQUENCE: 69

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
            35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 70
<211> LENGTH: 246
<212> TYPE: PRT
<213> ORGANISM: Artificial
<220> FEATURE:
<223> OTHER INFORMATION: The amino acid sequence of anti-4-1BB scFv

<400> SEQUENCE: 70

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
            35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80
```

```
Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Gly Gly Gly Ser Gly Gly
        115                 120                 125

Gly Gly Ser Gly Gly Gly Ser Glu Ile Val Leu Thr Gln Ser Pro
    130                 135                 140

Ala Thr Leu Ser Leu Ser Pro Gly Glu Arg Ala Thr Leu Ser Cys Arg
145                 150                 155                 160

Ala Ser Gln Ser Val Ser Ser Tyr Leu Ala Trp Tyr Gln Gln Lys Pro
                165                 170                 175

Gly Gln Ala Pro Arg Leu Leu Ile Tyr Asp Ala Ser Asn Arg Ala Thr
            180                 185                 190

Gly Ile Pro Ala Arg Phe Ser Gly Ser Gly Ser Gly Thr Asp Phe Thr
        195                 200                 205

Leu Thr Ile Ser Ser Leu Glu Pro Glu Asp Phe Ala Val Tyr Tyr Cys
        210                 215                 220

Gln Gln Arg Ser Asn Trp Pro Pro Ala Leu Thr Phe Cys Gly Gly Thr
225                 230                 235                 240

Lys Val Glu Ile Lys Arg
                245
```

<210> SEQ ID NO 71
<211> LENGTH: 121
<212> TYPE: PRT
<213> ORGANISM: Artificial
<220> FEATURE:
<223> OTHER INFORMATION: The amino acid sequence of anti-4-1BB scFv heavy chain variable region

<400> SEQUENCE: 71

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser
        115                 120
```

<210> SEQ ID NO 72
<211> LENGTH: 110
<212> TYPE: PRT
<213> ORGANISM: Artificial
<220> FEATURE:
<223> OTHER INFORMATION: The amino acid sequence of anti-4-1BB scFv light chain variable region

<400> SEQUENCE: 72

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Cys Gly Gly Thr Lys Val Glu Ile Lys Arg
            100                 105                 110

<210> SEQ ID NO 73
<211> LENGTH: 247
<212> TYPE: PRT
<213> ORGANISM: Artificial
<220> FEATURE:
<223> OTHER INFORMATION: The amino acid sequence of ICOS scFv

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro His Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Thr Tyr Tyr Tyr Asp Ser Ser Gly Tyr Tyr His Asp Ala Phe
            100                 105                 110

Asp Ile Trp Gly Gln Gly Thr Met Val Thr Val Ser Ser Gly Gly Gly
    115                 120                 125

Gly Ser Gly Gly Gly Gly Ser Gly Gly Gly Gly Ser Asp Ile Gln Met
130                 135                 140

Thr Gln Ser Pro Ser Ser Val Ser Ala Ser Val Gly Asp Arg Val Thr
145                 150                 155                 160

Ile Thr Cys Arg Ala Ser Gln Gly Ile Ser Arg Leu Leu Ala Trp Tyr
                165                 170                 175

Gln Gln Lys Pro Gly Lys Ala Pro Lys Leu Leu Ile Tyr Val Ala Ser
            180                 185                 190

Ser Leu Gln Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
210                 215                 220

Thr Tyr Tyr Cys Gln Gln Ala Asn Ser Phe Pro Trp Thr Phe Gly Gln
225                 230                 235                 240

Gly Thr Lys Val Glu Ile Lys
            245
```

<210> SEQ ID NO 74
<211> LENGTH: 125
<212> TYPE: PRT
<213> ORGANISM: Artificial
<220> FEATURE:
<223> OTHER INFORMATION: The amino acid sequence of the ICOS scFv heavy
      chain variable region

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro His Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Thr Tyr Tyr Tyr Asp Ser Ser Gly Tyr Tyr His Asp Ala Phe
            100                 105                 110

Asp Ile Trp Gly Gln Gly Thr Met Val Thr Val Ser Ser
        115                 120                 125

<210> SEQ ID NO 75
<211> LENGTH: 107
<212> TYPE: PRT
<213> ORGANISM: Artificial
<220> FEATURE:
<223> OTHER INFORMATION: The amino acid sequence of the ICOS scFv light
      chain variable region

<400> SEQUENCE: 75

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Leu
            20                  25                  30

Leu Ala Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys Val Glu Ile Lys
            100                 105

<210> SEQ ID NO 76
<211> LENGTH: 242
<212> TYPE: PRT
<213> ORGANISM: Artificial
<220> FEATURE:
<223> OTHER INFORMATION: The amino acid sequence of OX40 scFv

<400> SEQUENCE: 76

Gln Leu Val Glu Ser Gly Gly Gly Leu Val Gln Pro Gly Gly Ser Leu
1               5                   10                  15

```
Arg Leu Ser Cys Ala Ala Ser Gly Phe Thr Phe Ser Ser Tyr Ser Met
            20                  25                  30

Asn Trp Val Arg Gln Ala Pro Gly Lys Gly Leu Glu Trp Val Ser Tyr
            35                  40                  45

Ile Ser Ser Ser Ser Thr Ile Tyr Tyr Ala Asp Ser Val Lys Gly
 50                  55                  60

Arg Phe Thr Ile Ser Arg Asp Asn Ala Lys Asn Ser Leu Tyr Leu Gln
65                   70                  75                  80

Met Asn Ser Leu Arg Asp Glu Asp Thr Ala Val Tyr Tyr Cys Ala Arg
                85                  90                  95

Gly Val Tyr His Asn Gly Trp Ser Phe Phe Asp Tyr Trp Gly Gln Gly
                100                 105                 110

Thr Leu Leu Thr Val Ser Ser Gly Gly Gly Ser Gly Gly Gly
            115                 120                 125

Ser Gly Gly Gly Gly Ser Asp Ile Gln Met Thr Gln Ser Pro Ser Ser
    130                 135                 140

Leu Ser Ala Ser Val Gly Asn Arg Val Thr Ile Thr Cys Arg Ala Ser
145                 150                 155                 160

Gln Asp Ile Ser Ser Trp Leu Ala Trp Tyr Gln Gln Lys Pro Glu Lys
                165                 170                 175

Ala Pro Lys Ser Leu Ile Tyr Ala Ala Ser Ser Leu Gln Ser Gly Val
            180                 185                 190

Pro Ser Arg Phe Ser Gly Ser Gly Ser Gly Thr Asp Phe Thr Leu Thr
                195                 200                 205

Ile Ser Ser Leu Gln Pro Glu Asp Phe Ala Thr Tyr Tyr Cys Gln Gln
    210                 215                 220

Tyr Asn Ser Tyr Pro Leu Thr Phe Gly Gln Gly Thr Arg Leu Glu Ile
225                 230                 235                 240

Lys Arg

<210> SEQ ID NO 77
<211> LENGTH: 119
<212> TYPE: PRT
<213> ORGANISM: Artificial
<220> FEATURE:
<223> OTHER INFORMATION: The amino acid sequence of OX40 scFv heavy
      chain variable region

<400> SEQUENCE: 77

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Ser Tyr Ser Met
            20                  25                  30

Asn Trp Val Arg Gln Ala Pro Gly Lys Gly Leu Glu Trp Val Ser Tyr
            35                  40                  45

Ile Ser Ser Ser Ser Thr Ile Tyr Tyr Ala Asp Ser Val Lys Gly
 50                  55                  60

Arg Phe Thr Ile Ser Arg Asp Asn Ala Lys Asn Ser Leu Tyr Leu Gln
65                   70                  75                  80

Met Asn Ser Leu Arg Asp Glu Asp Thr Ala Val Tyr Tyr Cys Ala Arg
                85                  90                  95

Gly Val Tyr His Asn Gly Trp Ser Phe Phe Asp Tyr Trp Gly Gln Gly
                100                 105                 110

Thr Leu Leu Thr Val Ser Ser
            115
```

<210> SEQ ID NO 78
<211> LENGTH: 108
<212> TYPE: PRT
<213> ORGANISM: Artificial
<220> FEATURE:
<223> OTHER INFORMATION: The amino acid sequence of OX40 scFv light
      chain variable region

<400> SEQUENCE: 78

Asp Ile Gln Met Thr Gln Ser Pro Ser Ser Leu Ser Ala Ser Val Gly
1               5                   10                  15

Asn Arg Val Thr Ile Thr Cys Arg Ala Ser Gln Asp Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gln Gly Thr Arg Leu Glu Ile Lys Arg
            100                 105

<210> SEQ ID NO 79
<211> LENGTH: 241
<212> TYPE: PRT
<213> ORGANISM: Artificial
<220> FEATURE:
<223> OTHER INFORMATION: The amino acid sequence of GITR scFv

<400> SEQUENCE: 79

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Ala Ala Thr Tyr Tyr
                85                  90                  95

Cys Ala Arg Thr Arg Arg Tyr Phe Pro Phe Ala Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Asp Ile Val Met Thr Gln Ser Gln Lys Phe
    130                 135                 140

Met Ser Thr Ser Val Gly Asp Arg Val Ser Val Thr Cys Lys Ala Ser
145                 150                 155                 160

Gln Asn Val Gly Thr Asn Val Ala Trp Tyr Gln Gln Lys Pro Gly Gln
                165                 170                 175

Ser Pro Lys Ala Leu Ile Tyr Ser Ala Ser Tyr Arg Tyr Ser Gly Val
            180                 185                 190

```
Pro Asp Arg Phe Thr Gly Ser Gly Ser Gly Thr Asp Phe Thr Leu Thr
        195                 200                 205

Ile Asn Asn Val His Ser Glu Asp Leu Ala Glu Tyr Phe Cys Gln Gln
    210                 215                 220

Tyr Asn Thr Asp Pro Leu Thr Phe Gly Ala Gly Thr Lys Leu Glu Ile
225                 230                 235                 240

Lys

<210> SEQ ID NO 80
<211> LENGTH: 119
<212> TYPE: PRT
<213> ORGANISM: Artificial
<220> FEATURE:
<223> OTHER INFORMATION: The amino acid sequence of GITR scFv heavy
      chain variable region

<400> SEQUENCE: 80

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ser
50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Ala Ala Thr Tyr Tyr
                85                  90                  95

Cys Ala Arg Thr Arg Arg Tyr Phe Pro Phe Ala Tyr Trp Gly Gln Gly
            100                 105                 110

Thr Leu Val Thr Val Ser Ser
        115

<210> SEQ ID NO 81
<211> LENGTH: 107
<212> TYPE: PRT
<213> ORGANISM: Artificial
<220> FEATURE:
<223> OTHER INFORMATION: The amino acid sequence of GITR scFv light
      chain variable region

<400> SEQUENCE: 81

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Asn Asn Val His Ser
65                  70                  75                  80

Glu Asp Leu Ala Glu Tyr Phe Cys Gln Gln Tyr Asn Thr Asp Pro Leu
                85                  90                  95

Thr Phe Gly Ala Gly Thr Lys Leu Glu Ile Lys
            100                 105
```

```
<210> SEQ ID NO 82
<211> LENGTH: 239
<212> TYPE: PRT
<213> ORGANISM: Artificial
<220> FEATURE:
<223> OTHER INFORMATION: The amino acid sequence of CD40L scFv

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser Gly Gly Gly Gly Ser Gly Gly Gly Ser Gly Gly
        115                 120                 125

Gly Gly Ser Asp Ile Gln Met Thr Gln Ser Pro Ser Ser Leu Ser Ala
    130                 135                 140

Ser Val Gly Asp Arg Val Thr Ile Thr Cys Arg Ala Ser Gln Ser Ile
145                 150                 155                 160

Ser Ser Tyr Leu Asn Trp Tyr Gln Gln Lys Pro Gly Lys Ala Pro Lys
                165                 170                 175

Leu Leu Ile Tyr Ala Ala Ser Ser Leu Gln Ser Gly Val Pro Ser Arg
            180                 185                 190

Phe Ser Gly Ser Gly Ser Gly Thr Asp Phe Thr Leu Thr Ile Ser Ser
        195                 200                 205

Leu Gln Pro Glu Asp Phe Ala Thr Tyr Tyr Cys Gln Gln Ser Tyr Ser
    210                 215                 220

Thr Pro Asn Thr Phe Gly Gln Gly Thr Lys Val Glu Ile Lys Arg
225                 230                 235

<210> SEQ ID NO 83
<211> LENGTH: 116
<212> TYPE: PRT
<213> ORGANISM: Artificial
<220> FEATURE:
<223> OTHER INFORMATION: The amino acid sequence of CD40L scFv heavy
      chain variable region

<400> SEQUENCE: 83

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser
        115

<210> SEQ ID NO 84
<211> LENGTH: 108
<212> TYPE: PRT
<213> ORGANISM: Artificial
<220> FEATURE:
<223> OTHER INFORMATION: The amino acid sequence of CD40L scFv light
      chain variable region

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys Arg
            100                 105

<210> SEQ ID NO 85
<211> LENGTH: 241
<212> TYPE: PRT
<213> ORGANISM: Artificial
<220> FEATURE:
<223> OTHER INFORMATION: The amino acid sequence of CD27 scFv

<400> SEQUENCE: 85

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Asn Trp Gly Phe Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140
```

Leu Ser Ala Ser Val Gly Asp Arg Val Thr Ile Thr Cys Arg Ala Ser
145                 150                 155                 160

Gln Gly Ile Ser Arg Trp Leu Ala Trp Tyr Gln Gln Lys Pro Glu Lys
            165                 170                 175

Ala Pro Lys Ser Leu Ile Tyr Ala Ala Ser Ser Leu Gln Ser Gly Val
            180                 185                 190

Pro Ser Arg Phe Ser Gly Ser Gly Ser Gly Thr Asp Phe Thr Leu Thr
            195                 200                 205

Ile Ser Ser Leu Gln Pro Glu Asp Phe Ala Thr Tyr Tyr Cys Gln Gln
            210                 215                 220

Tyr Asn Thr Tyr Pro Arg Thr Phe Gly Gln Gly Thr Lys Val Glu Ile
225                 230                 235                 240

Lys

<210> SEQ ID NO 86
<211> LENGTH: 119
<212> TYPE: PRT
<213> ORGANISM: Artificial
<220> FEATURE:
<223> OTHER INFORMATION: The amino acid sequence of CD27 scFv heavy
      chain variable region

<400> SEQUENCE: 86

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Asp Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Asn Trp Gly Phe Phe Asp Tyr Trp Gly Gln Gly
            100                 105                 110

Thr Leu Val Thr Val Ser Ser
        115

<210> SEQ ID NO 87
<211> LENGTH: 107
<212> TYPE: PRT
<213> ORGANISM: Artificial
<220> FEATURE:
<223> OTHER INFORMATION: The amino acid sequence of CD27 scFv light
      chain variable region

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Arg Trp
                20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro

```
               65                  70                  75                  80
          Glu Asp Phe Ala Thr Tyr Tyr Cys Gln Gln Tyr Asn Thr Tyr Pro Arg
                          85                  90                  95

Thr Phe Gly Gln Gly Thr Lys Val Glu Ile Lys
                        100                 105

<210> SEQ ID NO 88
<211> LENGTH: 729
<212> TYPE: DNA
<213> ORGANISM: Artificial
<220> FEATURE:
<223> OTHER INFORMATION: The nucleotide sequence of anti-CD3 scFv

<400> SEQUENCE: 88
gacatcaagc tgcagcagag cggcgccgag ctggcccgcc ccggcgccag cgtgaagatg       60
agctgcaaga ccagcggcta caccttcacc cgctacacca tgcactgggt gaagcagcgc      120
cccggccagg gcctggagtg gatcggctac atcaacccca gccgcggcta caccaactac      180
aaccagaagt tcaaggacaa ggccaccctg accaccgaca gagcagcag caccgcctac      240 atgcagctga gcagcctgac cagcgaggac agcgccgtgt actactgcgc ccgctactac      300
gacgaccact actgcctgga ctactggggc cagggcacca ccctgaccgt gagcagcgtg      360
gagggcggca gcggcggcag cggcggcagc ggcggcagcg gcggcgtgga cgacatccag      420
ctgacccaga gccccgccat catgagcgcc agccccggcg agaaggtgac catgacctgc      480
cgcgccagca gcagcgtgag ctacatgaac tggtaccagc agaagagcgg caccagcccc      540
aagcgctgga tctacgacac cagcaaggtg gccagcggcg tgccctaccg cttcagcggc      600
agcggcagcg gcaccagcta cagcctgacc atcagcagca tggaggccga ggacgccgcc      660
acctactact gccagcagtg gagcagcaac cccctgacct tcggcgccgg caccaagctg      720
gagctgaag                                                             729

<210> SEQ ID NO 89
<211> LENGTH: 255
<212> TYPE: DNA
<213> ORGANISM: Artificial
<220> FEATURE:
<223> OTHER INFORMATION: The nucleotide sequence of anti-CD3 scFv heavy
      chain variable region

<400> SEQUENCE: 89
gacatcaagc tgcagcagag cggcgccgag ctggcccgcc ccggcgccag cgtgaagatg       60
agctgcaaga ccagcggcta caccttcacc cgctacacca tgcactgggt gaagcagcgc      120
cccggccagg gcctggagtg gatcggctac atcaacccca gccgcggcta caccaactac      180
aaccagaagt tcaaggacaa ggccaccctg accaccgaca gagcagcag caccgcctac      240 atgcagctga gcagc                                                      255

<210> SEQ ID NO 90
<211> LENGTH: 318
<212> TYPE: DNA
<213> ORGANISM: Artificial
<220> FEATURE:
<223> OTHER INFORMATION: The nucleotide sequence of anti-CD3 scFv light
      chain variable region

<400> SEQUENCE: 90
gacatccagc tgacccagag ccccgccatc atgagcgcca gccccggcga gaaggtgacc       60
atgacctgcc gcgccagcag cagcgtgagc tacatgaact ggtaccagca gaagagcggc      120
```

| | |
|---|---|
| accagcccca agcgctggat ctacgacacc agcaaggtgg ccagcggcgt gccctaccgc | 180 |
| ttcagcggca gcggcagcgg caccagctac agcctgacca tcagcagcat ggaggccgag | 240 |
| gacgccgcca cctactactg ccagcagtgg agcagcaacc cctgaccttc ggcgccggc | 300 |
| accaagctgg agctgaag | 318 |

<210> SEQ ID NO 91
<211> LENGTH: 738
<212> TYPE: DNA
<213> ORGANISM: Artificial
<220> FEATURE:
<223> OTHER INFORMATION: The nucleotide sequence of anti-4-1BB scFv

<400> SEQUENCE: 91

| | |
|---|---|
| caggtgcagc tgcagcagtg gggcgccggc ctgctgaagc ccagcgagac cctgagcctg | 60 |
| acctgcgccg tgtacggcgg cagcttcagc ggctactact ggagctggat ccgccagagc | 120 |
| cccgagaagg gcctggagtg gatcggcgag atcaaccacg gcggctacgt gacctacaac | 180 |
| cccagcctgg agagccgcgt gaccatcagc gtggacacca gcaagaacca gttcagcctg | 240 |
| aagctgagca gcgtgaccgc cgccgacacc gccgtgtact actgcgcccg cgactacggc | 300 |
| cccggcaact acgactggta cttcgacctg tggggccgcg gcaccctggt gaccgtgagc | 360 |
| agcggcggcg gcggcagcgg cggcggcggc agcggcggcg gcggcagcga gatcgtgctg | 420 |
| acccagagcc ccgccaccct gagcctgagc cccggcgagc gcgccaccct gagctgccgc | 480 |
| gccagccaga gcgtgagcag ctacctggcc tggtaccagc agaagcccgg ccaggccccc | 540 |
| cgcctgctga tctacgacgc cagcaaccgc gccaccggca tccccgcccg cttcagcggc | 600 |
| agcggcagcg gcaccgactt caccctgacc atcagcagcc tggagcccga ggacttcgcc | 660 |
| gtgtactact gccagcagcg cagcaactgg ccccccgccc tgaccttctg cggcggcacc | 720 |
| aaggtggaga tcaagcgc | 738 |

<210> SEQ ID NO 92
<211> LENGTH: 363
<212> TYPE: DNA
<213> ORGANISM: Artificial
<220> FEATURE:
<223> OTHER INFORMATION: The nucleotide sequence of anti-4-1BB scFv heavy chain variable region

<400> SEQUENCE: 92

| | |
|---|---|
| caggtgcagc tgcagcagtg gggcgccggc ctgctgaagc ccagcgagac cctgagcctg | 60 |
| acctgcgccg tgtacggcgg cagcttcagc ggctactact ggagctggat ccgccagagc | 120 |
| cccgagaagg gcctggagtg gatcggcgag atcaaccacg gcggctacgt gacctacaac | 180 |
| cccagcctgg agagccgcgt gaccatcagc gtggacacca gcaagaacca gttcagcctg | 240 |
| aagctgagca gcgtgaccgc cgccgacacc gccgtgtact actgcgcccg cgactacggc | 300 |
| cccggcaact acgactggta cttcgacctg tggggccgcg gcaccctggt gaccgtgagc | 360 |
| agc | 363 |

<210> SEQ ID NO 93
<211> LENGTH: 330
<212> TYPE: DNA
<213> ORGANISM: Artificial
<220> FEATURE:
<223> OTHER INFORMATION: The nucleotide sequence of anti-4-1BB scFv light chain variable region

<400> SEQUENCE: 93

```
gagatcgtgc tgacccagag ccccgccacc ctgagcctga gccccggcga gcgcgccacc    60
ctgagctgcc gcgccagcca gagcgtgagc agctacctgg cctggtacca gcagaagccc   120
ggccaggccc cccgcctgct gatctacgac gccagcaacc gcgccaccgg catccccgcc   180
cgcttcagcg gcagcggcag cggcaccgac ttcaccctga ccatcagcag cctggagccc   240
gaggacttcg ccgtgtacta ctgccagcag cgcagcaact ggcccccgc cctgaccttc    300 tgcggcggca ccaaggtgga gatcaagcgc                                    330
```

<210> SEQ ID NO 94
<211> LENGTH: 741
<212> TYPE: DNA
<213> ORGANISM: Artificial
<220> FEATURE:
<223> OTHER INFORMATION: The nucleotide sequence of anti-ICOS scFv

<400> SEQUENCE: 94

```
caggtgcagc tggtgcagag cggcgccgag gtgaagaagc ccggcgccag cgtgaaggtg    60
agctgcaagg ccagcggcta caccttcacc ggctactaca tgcactgggt gcgccaggcc   120
cccggccagg gctggagtg gatgggctgg atcaacccc acagcggcgg caccaactac    180
gcccagaagt tccagggccg cgtgaccatg acccgcgaca ccagcatcag caccgcctac   240
atggagctga gccgcctgcg cagcgacgac accgccgtgt actactgcgc ccgcacctac   300
tactacgaca gcagcggcta ctaccacgac gccttcgaca tctggggcca gggcaccatg   360
gtgaccgtga gcagcggcgg cggcggcagc ggcggcggcg gcagcggcgg cggcggcagc   420
gacatccaga tgacccagag ccccagcagc gtgagcgcca gcgtgggcga ccgcgtgacc   480
atcacctgcc gcgccagcca gggcatcagc cgcctgctgg cctggtacca gcagaagccc   540
ggcaaggccc ccaagctgct gatctacgtg gccagcagcc tgcagagcgg cgtgcccagc   600
cgcttcagcg gcagcggcag cggcaccgac ttcaccctga ccatcagcag cctgcagccc   660
gaggacttcg ccacctacta ctgccagcag gccaacagct tccctggac cttcggccag   720 ggcaccaagg tggagatcaa g                                              741
```

<210> SEQ ID NO 95
<211> LENGTH: 375
<212> TYPE: DNA
<213> ORGANISM: Artificial
<220> FEATURE:
<223> OTHER INFORMATION: The nucleotide sequence of anti-ICOS scFv heavy
      chain variable region

<400> SEQUENCE: 95

```
caggtgcagc tggtgcagag cggcgccgag gtgaagaagc ccggcgccag cgtgaaggtg    60
agctgcaagg ccagcggcta caccttcacc ggctactaca tgcactgggt gcgccaggcc   120
cccggccagg gctggagtg gatgggctgg atcaacccc acagcggcgg caccaactac    180
gcccagaagt tccagggccg cgtgaccatg acccgcgaca ccagcatcag caccgcctac   240
atggagctga gccgcctgcg cagcgacgac accgccgtgt actactgcgc ccgcacctac   300
tactacgaca gcagcggcta ctaccacgac gccttcgaca tctggggcca gggcaccatg   360
gtgaccgtga gcagc                                                   375
```

<210> SEQ ID NO 96
<211> LENGTH: 321
<212> TYPE: DNA

<213> ORGANISM: Artificial
<220> FEATURE:
<223> OTHER INFORMATION: The nucleotide sequence of anti-ICOS scFv light
chain variable region

<400> SEQUENCE: 96

```
gacatccaga tgacccagag ccccagcagc gtgagcgcca gcgtgggcga ccgcgtgacc    60
atcacctgcc gcgccagcca gggcatcagc cgcctgctgg cctggtacca gcagaagccc   120
ggcaaggccc ccaagctgct gatctacgtg ccagcagcc tgcagagcgg cgtgcccagc   180
cgcttcagcg gcagcggcag cggcaccgac ttcaccctga ccatcagcag cctgcagccc   240
gaggacttcg ccacctacta ctgccagcag gccaacagct cccctggac cttcggccag   300
ggcaccaagg tggagatcaa g                                             321
```

<210> SEQ ID NO 97
<211> LENGTH: 726
<212> TYPE: DNA
<213> ORGANISM: Artificial
<220> FEATURE:
<223> OTHER INFORMATION: The nucleotide sequence of anti-OX40 scFv

<400> SEQUENCE: 97

```
cagctggtgg agagcggcgg cggcctggtg cagcccggcg gcagcctgcg cctgagctgc    60
gccgccagcg gcttcacctt cagcagctac agcatgaact gggtgcgcca ggccccggc   120
aagggcctgg agtgggtgag ctacatcagc agcagcagca gcaccatcta ctacgccgac   180
agcgtgaagg gccgcttcac catcagccgc gacaacgcca gaacagcct gtacctgcag   240
atgaacagcc tgcgcgacga ggacaccgcc gtgtactact gcgcccgcgg cgtgtaccac   300
aacggctgga gcttcttcga ctactggggc cagggcaccc tgctgaccgt gagcagcggc   360
ggcggcggca gcggcggcgg cggcagcggc ggcggcggca gcgacatcca gatgacccag   420
agccccagca gcctgagcgc cagcgtgggc aaccgcgtga ccatcacctg ccgcgccagc   480
caggacatca gcagctggct ggcctggtac cagcagaagc cgagaaggc ccccaagagc   540
ctgatctacg ccgccagcag cctgcagagc ggcgtgccca gccgcttcag cggcagcggc   600
agcggcaccg acttcaccct gaccatcagc agcctgcagc cgaggactt cgccacctac   660
tactgccagc agtacaacag ctaccccctg accttcggcc agggcacccg cctggagatc   720
aagcgc                                                              726
```

<210> SEQ ID NO 98
<211> LENGTH: 357
<212> TYPE: DNA
<213> ORGANISM: Artificial
<220> FEATURE:
<223> OTHER INFORMATION: The nucleotide sequence of anti-OX40 scFv heavy
chain variable region

<400> SEQUENCE: 98

```
cagctggtgg agagcggcgg cggcctggtg cagcccggcg gcagcctgcg cctgagctgc    60
gccgccagcg gcttcacctt cagcagctac agcatgaact gggtgcgcca ggccccggc   120
aagggcctgg agtgggtgag ctacatcagc agcagcagca gcaccatcta ctacgccgac   180
agcgtgaagg gccgcttcac catcagccgc gacaacgcca gaacagcct gtacctgcag   240
atgaacagcc tgcgcgacga ggacaccgcc gtgtactact gcgcccgcgg cgtgtaccac   300
aacggctgga gcttcttcga ctactggggc cagggcaccc tgctgaccgt gagcagc     357
```

```
<210> SEQ ID NO 99
<211> LENGTH: 324
<212> TYPE: DNA
<213> ORGANISM: Artificial
<220> FEATURE:
<223> OTHER INFORMATION: The nucleotide sequence of anti-OX40 scFv light
      chain variable region

<400> SEQUENCE: 99
gacatccaga tgacccagag ccccagcagc ctgagcgcca gcgtgggcaa ccgcgtgacc      60
atcacctgcc gcgccagcca ggacatcagc agctggctgg cctggtacca gcagaagccc     120
gagaaggccc ccaagagcct gatctacgcc gccagcagcc tgcagagcgg cgtgcccagc     180
cgcttcagcg gcagcggcag cggcaccgac ttcaccctga ccatcagcag cctgcagccc     240
gaggacttcg ccacctacta ctgccagcag tacaacagct accccctgac cttcggccag     300
ggcacccgcc tggagatcaa gcgc                                            324

<210> SEQ ID NO 100
<211> LENGTH: 723
<212> TYPE: DNA
<213> ORGANISM: Artificial
<220> FEATURE:
<223> OTHER INFORMATION: The nucleotide sequence of anti-GITR scFv

<400> SEQUENCE: 100
caggtgaccc tgaaggagag cggccccggc atcctgaagc ccagccagac cctgagcctg      60
acctgcagct tcagcggctt cagcctgagc accagcggca tgggcgtggg ctggatccgc     120
cagcccagcg gcaagggcct ggagtggctg gcccacatct ggtgggacga cgacaagtac     180
tacaacccca gcctgaagag ccagctgacc atcagcaagg acaccagccg caaccaggtg     240
ttcctgaaga tcaccagcgt ggacaccgcc gacgccgcca cctactactg cgcccgcacc     300
cgccgctact tccccttcgc ctactggggc cagggcaccc tggtgaccgt gagcagcggc     360
ggcggcggca gcggcggcgg cggcagcggc ggcggcggca gcgacatcgt gatgacccag     420
agccagaagt tcatgagcac cagcgtgggc gaccgcgtga gcgtgacctg caaggccagc     480
cagaacgtgg gcaccaacgt ggcctggtac cagcagaagc ccggccagag ccccaaggcc     540
ctgatctaca gcgccagcta ccgctacagc ggcgtgcccg accgcttcac cggcagcggc     600
agcggcaccg acttcaccct gaccatcaac aacgtgcaca gcgaggacct ggccgagtac     660
ttctgccagc agtacaacac cgacccctg accttcggcg ccggcaccaa gctggagatc     720
aag                                                                   723

<210> SEQ ID NO 101
<211> LENGTH: 357
<212> TYPE: DNA
<213> ORGANISM: Artificial
<220> FEATURE:
<223> OTHER INFORMATION: The nucleotide sequence of anti-GITR scFv heavy
      chain variable region

<400> SEQUENCE: 101
caggtgaccc tgaaggagag cggccccggc atcctgaagc ccagccagac cctgagcctg      60
acctgcagct tcagcggctt cagcctgagc accagcggca tgggcgtggg ctggatccgc     120
cagcccagcg gcaagggcct ggagtggctg gcccacatct ggtgggacga cgacaagtac     180
tacaacccca gcctgaagag ccagctgacc atcagcaagg acaccagccg caaccaggtg     240
ttcctgaaga tcaccagcgt ggacaccgcc gacgccgcca cctactactg cgcccgcacc     300
```
cgccgctact tccccttcgc ctactggggc cagggcaccc tggtgaccgt gagcagc      357

<210> SEQ ID NO 102
<211> LENGTH: 321
<212> TYPE: DNA
<213> ORGANISM: Artificial
<220> FEATURE:
<223> OTHER INFORMATION: The nucleotide sequence of anti-GITR scFv light
      chain variable region

<400> SEQUENCE: 102
gacatcgtga tgacccagag ccagaagttc atgagcacca gcgtgggcga ccgcgtgagc       60
gtgacctgca aggccagcca gaacgtgggc accaacgtgg cctggtacca gcagaagccc      120
ggccagagcc ccaaggccct gatctacagc gccagctacc gctacagcgg cgtgcccgac      180
cgcttcaccg gcagcggcag cggcaccgac ttcaccctga ccatcaacaa cgtgcacagc      240
gaggacctgg ccgagtactt ctgccagcag tacaacaccg acccctgac cttcggcgcc       300 ggcaccaagc tggagatcaa g                                                321

<210> SEQ ID NO 103
<211> LENGTH: 717
<212> TYPE: DNA
<213> ORGANISM: Artificial
<220> FEATURE:
<223> OTHER INFORMATION: The nucleotide sequence of anti-CD40L scFv

<400> SEQUENCE: 103
gaggtgcagc tgctggagag cggcggcggc ctggtgcagc ccggcggcag cctgcgcctg       60
agctgcgccg ccagcggctt caccttcagc agctacgcca tgagctgggt gcgccaggcc      120
cccggcaagg gcctggagtg ggtgagcgcc atcagcggca gcggcggcag cacctactac      180
gccgacagcg tgaagggccg cttcaccatc agccgcgaca acagcaagaa caccctgtac      240
ctgcagatga acagcctgcg cgccgaggac accgccgtgt actactgcgc caagagctac      300
ggcgccttcg actactgggg ccagggcacc ctggtgaccg tgagcagcgg cggcggcggc      360
agcggcggcg gcggcagcgg cggcggcggc agcgacatcc agatgaccca gagccccagc      420
agcctgagcg ccagcgtggg cgaccgcgtg accatcacct gccgcgccag ccagagcatc      480
agcagctacc tgaactggta ccagcagaag cccggcaagg cccccaagct gctgatctac      540
gccgccagca gcctgcagag cggcgtgccc agcgcttca gcggcagcgg cagcggcacc      600
gacttcaccc tgaccatcag cagcctgcag cccgaggact tcgccaccta ctactgccag      660
cagagctaca gcacccccaa caccttcggc cagggcacca aggtggagat caagcgc        717

<210> SEQ ID NO 104
<211> LENGTH: 348
<212> TYPE: DNA
<213> ORGANISM: Artificial
<220> FEATURE:
<223> OTHER INFORMATION: The nucleotide sequence of anti-CD40L scFv
      heavy chain variable region

<400> SEQUENCE: 104
gaggtgcagc tgctggagag cggcggcggc ctggtgcagc ccggcggcag cctgcgcctg       60
agctgcgccg ccagcggctt caccttcagc agctacgcca tgagctgggt gcgccaggcc      120
cccggcaagg gcctggagtg ggtgagcgcc atcagcggca gcggcggcag cacctactac      180
gccgacagcg tgaagggccg cttcaccatc agccgcgaca acagcaagaa caccctgtac      240
ctgcagatga acagcctgcg cgccgaggac accgccgtgt actactgcgc caagagctac      300

```
ggcgccttcg actactgggg ccagggcacc ctggtgaccg tgagcagc          348
```

<210> SEQ ID NO 105
<211> LENGTH: 324
<212> TYPE: DNA
<213> ORGANISM: Artificial
<220> FEATURE:
<223> OTHER INFORMATION: The nucleotide sequence of anti-CD40L scFv
light chain variable region

<400> SEQUENCE: 105

```
gacatccaga tgacccagag ccccagcagc ctgagcgcca gcgtgggcga ccgcgtgacc    60
atcacctgcc gcgccagcca gagcatcagc agctacctga actggtacca gcagaagccc   120
ggcaaggccc ccaagctgct gatctacgcc gccagcagcc tgcagagcgg cgtgcccagc   180
cgcttcagcg gcagcggcag cggcaccgac ttcaccctga ccatcagcag cctgcagccc   240
gaggacttcg ccacctacta ctgccagcag agctacagca cccccaacac cttcggccag   300
ggcaccaagg tggagatcaa gcgc                                          324
```

<210> SEQ ID NO 106
<211> LENGTH: 723
<212> TYPE: DNA
<213> ORGANISM: Artificial
<220> FEATURE:
<223> OTHER INFORMATION: The nucleotide sequence of anti-CD27 scFv

<400> SEQUENCE: 106

```
caggtgcagc tggtggagag cggcggcggc gtggtgcagc ccggccgcag cctgcgcctg    60
agctgcgccg ccagcggctt caccttcagc agctacgaca tgcactgggt gcgccaggcc   120
cccggcaagg gcctggagtg ggtggccgtg atctggtacg acggcagcaa caagtactac   180
gccgacagcg tgaagggccg cttcaccatc agccgcgaca acagcaagaa caccctgtac   240
ctgcagatga acagcctgcg cgccgaggac accgccgtgt actactgcgc cgcggcagc   300 ggcaactggg gcttcttcga ctactggggc cagggcaccc tggtgaccgt gagcagcggc   360
ggcggcggca gcggcggcgg cggcagcggc ggcggcggca gcgacatcca gatgacccag   420
agccccagca gcctgagcgc cagcgtgggc gaccgcgtga ccatcacctg ccgcgccagc   480
cagggcatca gccgctggct ggcctggtac cagcagaagc ccgagaaggc ccccaagagc   540
ctgatctacg ccgccagcag cctgcagagc ggcgtgccca gccgcttcag cggcagcggc   600
agcggcaccg acttcaccct gaccatcagc agcctgcagc ccgaggactt cgccacctac   660
tactgccagc agtacaacac ctaccccgc accttcggcc agggcaccaa ggtggagatc   720
aag                                                                 723
```

<210> SEQ ID NO 107
<211> LENGTH: 357
<212> TYPE: DNA
<213> ORGANISM: Artificial
<220> FEATURE:
<223> OTHER INFORMATION: The nucleotide sequence of anti-CD27 scFv heavy
chain variable region

<400> SEQUENCE: 107

```
caggtgcagc tggtggagag cggcggcggc gtggtgcagc ccggccgcag cctgcgcctg    60
agctgcgccg ccagcggctt caccttcagc agctacgaca tgcactgggt gcgccaggcc   120
cccggcaagg gcctggagtg ggtggccgtg atctggtacg acggcagcaa caagtactac   180
```

```
gccgacagcg tgaagggccg cttcaccatc agccgcgaca acagcaagaa cacccctgtac    240 ctgcagatga acagcctgcg cgccgaggac accgccgtgt actactgcgc ccgcggcagc    300
ggcaactggg gcttcttcga ctactggggc cagggcaccc tggtgaccgt gagcagc       357
```

```
<210> SEQ ID NO 108
<211> LENGTH: 321
<212> TYPE: DNA
<213> ORGANISM: Artificial
<220> FEATURE:
<223> OTHER INFORMATION: The nucleotide sequence of anti-CD27 scFv light
      chain variable region

<400> SEQUENCE: 108
gacatccaga tgacccagag ccccagcagc ctgagcgcca gcgtgggcga ccgcgtgacc    60
atcacctgcc gcgccagcca gggcatcagc cgctggctgg cctggtacca gcagaagccc    120
gagaaggccc ccaagagcct gatctacgcc gccagcagcc tgcagagcgg cgtgcccagc    180
cgcttcagcg gcagcggcag cggcaccgac ttcaccctga ccatcagcag cctgcagccc    240
gaggacttcg ccacctacta ctgccagcag tacaacacct accccgcac cttcggccag    300 ggcaccaagg tggagatcaa g                                              321
```

```
<210> SEQ ID NO 109
<211> LENGTH: 19
<212> TYPE: PRT
<213> ORGANISM: Artificial
<220> FEATURE:
<223> OTHER INFORMATION: The amino acid sequence of the secretory signal
      peptide

<400> SEQUENCE: 109

Met Thr Arg Leu Thr Val Leu Ala Leu Leu Ala Gly Leu Leu Ala Ser
1               5                   10                  15

Ser Arg Ala
```

```
<210> SEQ ID NO 110
<211> LENGTH: 57
<212> TYPE: DNA
<213> ORGANISM: Artificial
<220> FEATURE:
<223> OTHER INFORMATION: The nucleotide sequence of the secretory signal
      peptide

<400> SEQUENCE: 110
atgacccggc tgaccgtgct ggccctgctg gccggcctgc tggcctcctc cagggcc       57
```

```
<210> SEQ ID NO 111
<211> LENGTH: 59
<212> TYPE: DNA
<213> ORGANISM: Artificial
<220> FEATURE:
<223> OTHER INFORMATION: pcDNA3.1-Sig-F

<400> SEQUENCE: 111
gtgctggata tctgcagaat tcgccgccac catgacccgg ctgaccgtgc tggccctgc     59
```

```
<210> SEQ ID NO 112
<211> LENGTH: 49
<212> TYPE: DNA
<213> ORGANISM: Artificial
<220> FEATURE:
<223> OTHER INFORMATION: Sig-R

<400> SEQUENCE: 112
```

```
ggccctggag gaggccagca ggccggccag cagggccagc acggtcagc                      49
```

<210> SEQ ID NO 113
<211> LENGTH: 41
<212> TYPE: DNA
<213> ORGANISM: Artificial
<220> FEATURE:
<223> OTHER INFORMATION: Sig-CD3-F

<400> SEQUENCE: 113

```
gctggcctcc tccagggccg acatcaagct gcagcagagc g                              41
```

<210> SEQ ID NO 114
<211> LENGTH: 20
<212> TYPE: DNA
<213> ORGANISM: Artificial
<220> FEATURE:
<223> OTHER INFORMATION: CD3-R

<400> SEQUENCE: 114

```
cttcagctcc agcttggtgc                                                      20
```

<210> SEQ ID NO 115
<211> LENGTH: 85
<212> TYPE: DNA
<213> ORGANISM: Artificial
<220> FEATURE:
<223> OTHER INFORMATION: CD3-(GGGGS)3-4-1BB-F

<400> SEQUENCE: 115

```
gcaccaagct ggagctgaag ggcggcggcg gcagcggcgg cggcggcagc ggcggcggcg          60
gcagccaggt gcagctgcag cagtg                                                85
```

<210> SEQ ID NO 116
<211> LENGTH: 51
<212> TYPE: DNA
<213> ORGANISM: Artificial
<220> FEATURE:
<223> OTHER INFORMATION: pcDNA3.1-4-1BB-R

<400> SEQUENCE: 116

```
ctgatcagcg gtttaaactt aagctttcag cgcttgatct ccaccttggt g                   51
```

<210> SEQ ID NO 117
<211> LENGTH: 41
<212> TYPE: DNA
<213> ORGANISM: Artificial
<220> FEATURE:
<223> OTHER INFORMATION: CD3-IgD-F

<400> SEQUENCE: 117

```
gcaccaagct ggagctgaag gccagcaaga gcaagaagga g                              41
```

<210> SEQ ID NO 118
<211> LENGTH: 21
<212> TYPE: DNA
<213> ORGANISM: Artificial
<220> FEATURE:
<223> OTHER INFORMATION: IgD-R

<400> SEQUENCE: 118

```
cacgcccagg ggctgggtgt g                                                    21
```

<210> SEQ ID NO 119

```
<211> LENGTH: 42
<212> TYPE: DNA
<213> ORGANISM: Artificial
<220> FEATURE:
<223> OTHER INFORMATION: IgD-4-1BB-F

<400> SEQUENCE: 119
cacacccagc ccctgggcgt gcaggtgcag ctgcagcagt gg                    42

<210> SEQ ID NO 120
<211> LENGTH: 86
<212> TYPE: DNA
<213> ORGANISM: Artificial
<220> FEATURE:
<223> OTHER INFORMATION: CD3-(GGGGS)3-ICOS-F

<400> SEQUENCE: 120
gcaccaagct ggagctgaag ggcggcggcg gcagcggcgg cggcggcagc ggcggcggcg    60
gcagccaggt gcagctggtg cagagc                                        86

<210> SEQ ID NO 121
<211> LENGTH: 50
<212> TYPE: DNA
<213> ORGANISM: Artificial
<220> FEATURE:
<223> OTHER INFORMATION: pcDNA3.1-ICOS -R

<400> SEQUENCE: 121
ctgatcagcg gtttaaactt aagctttcac ttgatctcca ccttggtgcc               50

<210> SEQ ID NO 122
<211> LENGTH: 42
<212> TYPE: DNA
<213> ORGANISM: Artificial
<220> FEATURE:
<223> OTHER INFORMATION: IgD-ICOS-F

<400> SEQUENCE: 122
cacacccagc ccctgggcgt gcaggtgcag ctggtgcaga gc                      42

<210> SEQ ID NO 123
<211> LENGTH: 85
<212> TYPE: DNA
<213> ORGANISM: Artificial
<220> FEATURE:
<223> OTHER INFORMATION: CD3-(GGGGS)3- OX40-F

<400> SEQUENCE: 123
gcaccaagct ggagctgaag ggcggcggcg gcagcggcgg cggcggcagc ggcggcggcg    60
gcagccagct ggtggagagc ggcgg                                         85

<210> SEQ ID NO 124
<211> LENGTH: 52
<212> TYPE: DNA
<213> ORGANISM: Artificial
<220> FEATURE:
<223> OTHER INFORMATION: pcDNA3.1-OX40 -R

<400> SEQUENCE: 124
ctgatcagcg gtttaaactt aagctttcag cgcttgatct ccaggcgggt gc            52

<210> SEQ ID NO 125
<211> LENGTH: 45
<212> TYPE: DNA
<213> ORGANISM: Artificial
```

```
<220> FEATURE:
<223> OTHER INFORMATION: IgD-OX40-F

<400> SEQUENCE: 125
gccacaccca gccctgggc gtgcagctgg tggagagcgg cggcg            45

<210> SEQ ID NO 126
<211> LENGTH: 85
<212> TYPE: DNA
<213> ORGANISM: Artificial
<220> FEATURE:
<223> OTHER INFORMATION: CD3-(GGGGS)3- GITR-F

<400> SEQUENCE: 126
gcaccaagct ggagctgaag ggcggcggcg gcagcggcgg cggcggcagc ggcggcggcg   60
gcagccaggt gaccctgaag gagag                                        85

<210> SEQ ID NO 127
<211> LENGTH: 52
<212> TYPE: DNA
<213> ORGANISM: Artificial
<220> FEATURE:
<223> OTHER INFORMATION: pcDNA3.1-GITR -R

<400> SEQUENCE: 127
ctgatcagcg gtttaaactt aagctttcac ttgatctcca gcttggtgcc gg          52

<210> SEQ ID NO 128
<211> LENGTH: 43
<212> TYPE: DNA
<213> ORGANISM: Artificial
<220> FEATURE:
<223> OTHER INFORMATION: IgD-GITR-F

<400> SEQUENCE: 128
gccacaccca gccctgggc gtgcaggtga ccctgaagga gag                    43

<210> SEQ ID NO 129
<211> LENGTH: 87
<212> TYPE: DNA
<213> ORGANISM: Artificial
<220> FEATURE:
<223> OTHER INFORMATION: CD3-(GGGGS)3- CD40L-F

<400> SEQUENCE: 129
ggcaccaagc tggagctgaa gggcggcggc ggcagcggcg gcggcggcag cggcggcggc   60
ggcagcgagg tgcagctgct ggagagc                                      87

<210> SEQ ID NO 130
<211> LENGTH: 51
<212> TYPE: DNA
<213> ORGANISM: Artificial
<220> FEATURE:
<223> OTHER INFORMATION: pcDNA3.1-CD40L -R

<400> SEQUENCE: 130
ctgatcagcg gtttaaactt aagctttcag cgcttgatct ccaccttggt g           51

<210> SEQ ID NO 131
<211> LENGTH: 43
<212> TYPE: DNA
<213> ORGANISM: Artificial
<220> FEATURE:
<223> OTHER INFORMATION: IgD-CD40L-F
```

<400> SEQUENCE: 131
gccacaccca gccctgggc gtggaggtgc agctgctgga gag					43

<210> SEQ ID NO 132
<211> LENGTH: 86
<212> TYPE: DNA
<213> ORGANISM: Artificial
<220> FEATURE:
<223> OTHER INFORMATION: CD3-(GGGGS)3- CD27-F

<400> SEQUENCE: 132
gcaccaagct ggagctgaag ggcggcggcg gcagcggcgg cggcggcagc ggcggcggcg					60 gcagccaggt gcagctggtg gagagc					86

<210> SEQ ID NO 133
<211> LENGTH: 51
<212> TYPE: DNA
<213> ORGANISM: Artificial
<220> FEATURE:
<223> OTHER INFORMATION: pcDNA3.1-CD27 -R

<400> SEQUENCE: 133
ctgatcagcg gtttaaactt aagctttcac ttgatctcca ccttggtgcc c					51

<210> SEQ ID NO 134
<211> LENGTH: 43
<212> TYPE: DNA
<213> ORGANISM: Artificial
<220> FEATURE:
<223> OTHER INFORMATION: IgD-CD27-F

<400> SEQUENCE: 134
gccacaccca gccctgggc gtgcaggtgc agctggtgga gag					43

<210> SEQ ID NO 135
<211> LENGTH: 15
<212> TYPE: PRT
<213> ORGANISM: Artificial
<220> FEATURE:
<223> OTHER INFORMATION: The amino acid sequence of CD3-4-1BBL BsM_M monomer linker

<400> SEQUENCE: 135

Gly Gly Gly Gly Ser Gly Gly Gly Gly Ser Gly Gly Gly Gly Ser
1               5                   10                  15

<210> SEQ ID NO 136
<211> LENGTH: 45
<212> TYPE: DNA
<213> ORGANISM: Artificial
<220> FEATURE:
<223> OTHER INFORMATION: The nucleotide sequence of CD3-4-1BBL BsM_M monomer linker

<400> SEQUENCE: 136
ggcggcggcg gcagcggcgg cggcggcagc ggcggcggcg gcagc					45

<210> SEQ ID NO 137
<211> LENGTH: 81
<212> TYPE: PRT
<213> ORGANISM: Artificial
<220> FEATURE:
<223> OTHER INFORMATION: The amino acid sequence of CD3-4-1BBL BsM_D dimer linker

<400> SEQUENCE: 137

-continued

```
Ala Ser Lys Ser Lys Lys Glu Ile Phe Arg Trp Pro Glu Ser Pro Lys
1               5                   10                  15

Ala Gln Ala Ser Ser Val Pro Thr Ala Gln Pro Gln Ala Glu Gly Ser
            20                  25                  30

Leu Ala Lys Ala Thr Thr Ala Pro Ala Thr Thr Arg Asn Thr Gly Arg
        35                  40                  45

Gly Gly Glu Glu Lys Lys Lys Glu Lys Glu Lys Glu Glu Gln Glu Glu
    50                  55                  60

Arg Glu Thr Lys Thr Pro Glu Cys Pro Ser His Thr Gln Pro Leu Gly
65                  70                  75                  80

Val

<210> SEQ ID NO 138
<211> LENGTH: 243
<212> TYPE: DNA
<213> ORGANISM: Artificial
<220> FEATURE:
<223> OTHER INFORMATION: The nucleotide sequence of CD3-4-1BBL BsM_D
      dimer linker

<400> SEQUENCE: 138
gccagcaaga gcaagaagga gatcttccgc tggcccgaga gccccaaggc ccaggccagc      60
agcgtgccca ccgcccagcc ccaggccgag ggcagcctgg ccaaggccac caccgccccc    120
gccaccaccc gcaacaccgg ccgcggcggc gaggagaaga agaaggagaa ggagaaggag    180
gagcaggagg agcgcgagac caagaccccc gagtgcccca gccacaccca gcccctgggc    240
gtg                                                                  243

<210> SEQ ID NO 139
<211> LENGTH: 232
<212> TYPE: PRT
<213> ORGANISM: Artificial
<220> FEATURE:
<223> OTHER INFORMATION: The amino acid sequence of  the T cell positive
      costimulatory molecule human 4-1BB

<400> SEQUENCE: 139

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
            85                  90                  95

Cys Cys Phe Gly Thr Phe Asn Asp Gln Lys Arg Gly Ile Cys Arg Pro
        100                 105                 110

Trp Thr Asn Cys Ser Leu Asp Gly Lys Ser Val Leu Val Asn Gly Thr
    115                 120                 125

Lys Glu Arg Asp Val Val Cys Gly Pro Ser Pro Ala Asp Leu Ser Pro
130                 135                 140

Gly Ala Ser Ser Val Thr Pro Pro Ala Pro Ala Arg Glu Pro Gly His
145                 150                 155                 160
```

```
Ser Pro Gln Ile Ile Ser Phe Phe Leu Ala Leu Thr Ser Thr Ala Leu
            165                 170                 175

Leu Phe Leu Leu Phe Phe Leu Thr Leu Arg Phe Ser Val Val Lys Arg
            180                 185                 190

Gly Arg Lys Lys Leu Leu Tyr Ile Phe Lys Gln Pro Phe Met Arg Pro
            195                 200                 205

Val Gln Thr Thr Gln Glu Glu Asp Gly Cys Ser Cys Arg Phe Pro Glu
        210                 215                 220

Glu Glu Glu Gly Gly Cys Glu Leu
225                 230
```

<210> SEQ ID NO 140
<211> LENGTH: 254
<212> TYPE: PRT
<213> ORGANISM: Artificial
<220> FEATURE:
<223> OTHER INFORMATION: the amino acid sequence of the T cell positive
      costimulatory ligand human 4-1BBL

<400> SEQUENCE: 140

```
Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
            85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
            115                 120                 125

Asp Thr Lys Glu Leu Val Val Ala Lys Ala Gly Val Tyr Tyr Val Phe
        130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
            165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
            195                 200                 205

Gly Gln Arg Leu Gly Val His Leu His Thr Glu Ala Arg Ala Arg His
        210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
            245                 250
```

<210> SEQ ID NO 141
<211> LENGTH: 179
<212> TYPE: PRT

<213> ORGANISM: Artificial
<220> FEATURE:
<223> OTHER INFORMATION: The amino acid sequence of the T cell positive costimulatory molecule human ICOS

<400> SEQUENCE: 141

```
Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Gln Phe Lys
            20                  25                  30

Met Gln Leu Leu Lys Gly Gly Gln Ile Leu Cys Asp Leu Thr Lys Thr
        35                  40                  45

Lys Gly Ser Gly Asn Thr Val Ser Ile Lys Ser Leu Lys Phe Cys His
    50                  55                  60

Ser Gln Leu Ser Asn Asn Ser Val Ser Phe Phe Leu Tyr Asn Leu Asp
65                  70                  75                  80

His Ser His Ala Asn Tyr Tyr Phe Cys Asn Leu Ser Ile Phe Asp Pro
                85                  90                  95

Pro Pro Phe Lys Val Thr Leu Thr Gly Gly Tyr Leu His Ile Tyr Glu
            100                 105                 110

Ser Gln Leu Cys Cys Gln Leu Lys Phe Trp Leu Pro Ile Gly Cys Ala
        115                 120                 125

Ala Phe Val Val Val Cys Ile Leu Gly Cys Ile Leu Ile Cys Trp Leu
    130                 135                 140

Thr Lys Lys Lys Tyr Ser Ser Ser Val His Asp Pro Asn Gly Glu Tyr
145                 150                 155                 160

Met Phe Met Arg Ala Val Asn Thr Ala Lys Lys Ser Arg Leu Thr Asp
                165                 170                 175

Val Thr Leu
```

<210> SEQ ID NO 142
<211> LENGTH: 284
<212> TYPE: PRT
<213> ORGANISM: Artificial
<220> FEATURE:
<223> OTHER INFORMATION: The amino acid sequence of the T cell positive costimulatory ligand human B7RP-1

<400> SEQUENCE: 142

```
Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Asn Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140
```

```
Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser
            180                 185                 190

Val Asn Ile Gly Cys Cys Ile Glu Asn Val Leu Leu Gln Gln Asn Leu
        195                 200                 205

Thr Val Gly Ser Gln Thr Gly Asn Asp Ile Gly Glu Arg Asp Lys Ile
    210                 215                 220

Thr Glu Asn Pro Val Ser Thr Gly Glu Lys Asn Ala Ala Thr Trp Ser
225                 230                 235                 240

Ile Leu Ala Val Leu Cys Leu Leu Val Val Ala Val Ala Ile Gly
                245                 250                 255

Trp Val Cys Arg Asp Arg Cys Leu Gln His Ser Tyr Ala Gly Ala Trp
                260                 265                 270

Ala Val Ser Pro Glu Thr Glu Leu Thr Gly His Val
                275                 280

<210> SEQ ID NO 143
<211> LENGTH: 249
<212> TYPE: PRT
<213> ORGANISM: Artificial
<220> FEATURE:
<223> OTHER INFORMATION: The amino acid sequence of the T cell positive
      costimulatory molecule human OX40

<400> SEQUENCE: 143

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala Val Ala Ala Ile Leu Gly
            180                 185                 190

Leu Gly Leu Val Leu Gly Leu Leu Gly Pro Leu Ala Ile Leu Leu Ala
        195                 200                 205

Leu Tyr Leu Leu Arg Arg Asp Gln Arg Leu Pro Pro Asp Ala His Lys
```

```
                210                 215                 220
Pro Pro Gly Gly Gly Ser Phe Arg Thr Pro Ile Gln Glu Gln Ala
225                 230                 235                 240

Asp Ala His Ser Thr Leu Ala Lys Ile
                245

<210> SEQ ID NO 144
<211> LENGTH: 183
<212> TYPE: PRT
<213> ORGANISM: Artificial
<220> FEATURE:
<223> OTHER INFORMATION: The amino acid sequence of the T cell positive
      costimulatory ligand human OX40L

<400> SEQUENCE: 144

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
                20                  25                  30

Gly Leu Gly Leu Leu Leu Cys Phe Thr Tyr Ile Cys Leu His Phe Ser
            35                  40                  45

Ala Leu Gln Val Ser His Arg Tyr Pro Arg Ile Gln Ser Ile Lys Val
50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 145
<211> LENGTH: 216
<212> TYPE: PRT
<213> ORGANISM: Artificial
<220> FEATURE:
<223> OTHER INFORMATION: The amino acid sequence of the T cell positive
      costimulatory molecule human GITR

<400> SEQUENCE: 145

Gln Arg Pro Thr Gly Gly Pro Gly Cys Gly Pro Gly Arg Leu Leu Leu
1               5                   10                  15

Gly Thr Gly Thr Asp Ala Arg Cys Cys Arg Val His Thr Thr Arg Cys
                20                  25                  30

Cys Arg Asp Tyr Pro Gly Glu Glu Cys Cys Ser Glu Trp Asp Cys Met
            35                  40                  45

Cys Val Gln Pro Glu Phe His Cys Gly Asp Pro Cys Cys Thr Thr Cys
50                  55                  60

Arg His His Pro Cys Pro Pro Gly Gln Gly Val Gln Ser Gln Gly Lys
```

```
            65                  70                  75                  80

Phe Ser Phe Gly Phe Gln Cys Ile Asp Cys Ala Ser Gly Thr Phe Ser
                        85                  90                  95

Gly Gly His Glu Gly His Cys Lys Pro Trp Thr Asp Cys Thr Gln Phe
                    100                 105                 110

Gly Phe Leu Thr Val Phe Pro Gly Asn Lys Thr His Asn Ala Val Cys
                    115                 120                 125

Val Pro Gly Ser Pro Pro Ala Glu Pro Leu Gly Trp Leu Thr Val Val
                130                 135                 140

Leu Leu Ala Val Ala Ala Cys Val Leu Leu Thr Ser Ala Gln Leu
        145                 150                 155                 160

Gly Leu His Ile Trp Gln Leu Arg Ser Gln Cys Met Trp Pro Arg Glu
                            165                 170                 175

Thr Gln Leu Leu Leu Glu Val Pro Pro Ser Thr Glu Asp Ala Arg Ser
                        180                 185                 190

Cys Gln Phe Pro Glu Glu Glu Arg Gly Glu Arg Ser Ala Glu Glu Lys
                    195                 200                 205

Gly Arg Leu Gly Asp Leu Trp Val
                210                 215

<210> SEQ ID NO 146
<211> LENGTH: 199
<212> TYPE: PRT
<213> ORGANISM: Artificial
<220> FEATURE:
<223> OTHER INFORMATION: The amino acid sequence of the T cell positive
      costimulatory ligand human GITRL

<400> SEQUENCE: 146

Met Thr Leu His Pro Ser Pro Ile Thr Cys Glu Phe Leu Phe Ser Thr
        1               5                   10                  15

Ala Leu Ile Ser Pro Lys Met Cys Leu Ser His Leu Glu Asn Met Pro
                        20                  25                  30

Leu Ser His Ser Arg Thr Gln Gly Ala Gln Arg Ser Ser Trp Lys Leu
                    35                  40                  45

Trp Leu Phe Cys Ser Ile Val Met Leu Leu Phe Leu Cys Ser Phe Ser
            50                  55                  60

Trp Leu Ile Phe Ile Phe Leu Gln Leu Glu Thr Ala Lys Glu Pro Cys
        65                  70                  75                  80

Met Ala Lys Phe Gly Pro Leu Pro Ser Lys Trp Gln Met Ala Ser Ser
                        85                  90                  95

Glu Pro Pro Cys Val Asn Lys Val Ser Asp Trp Lys Leu Glu Ile Leu
                    100                 105                 110

Gln Asn Gly Leu Tyr Leu Ile Tyr Gly Gln Val Ala Pro Asn Ala Asn
                115                 120                 125

Tyr Asn Asp Val Ala Pro Phe Glu Val Arg Leu Tyr Lys Asn Lys Asp
            130                 135                 140

Met Ile Gln Thr Leu Thr Asn Lys Ser Lys Ile Gln Asn Val Gly Gly
        145                 150                 155                 160

Thr Tyr Glu Leu His Val Gly Asp Thr Ile Asp Leu Ile Phe Asn Ser
                        165                 170                 175

Glu His Gln Val Leu Lys Asn Asn Thr Tyr Trp Gly Ile Ile Leu Leu
                    180                 185                 190

Ala Asn Pro Gln Phe Ile Ser
                195
```

<210> SEQ ID NO 147
<211> LENGTH: 241
<212> TYPE: PRT
<213> ORGANISM: Artificial
<220> FEATURE:
<223> OTHER INFORMATION: The amino acid sequence of the T cell positive
      costimulatory molecule human CD27

<400> SEQUENCE: 147

Ala Thr Pro Ala Pro Lys Ser Cys Pro Glu Arg His Tyr Trp Ala Gln
1               5                   10                  15

Gly Lys Leu Cys Cys Gln Met Cys Glu Pro Gly Thr Phe Leu Val Lys
            20                  25                  30

Asp Cys Asp Gln His Arg Lys Ala Ala Gln Cys Asp Pro Cys Ile Pro
        35                  40                  45

Gly Val Ser Phe Ser Pro Asp His His Thr Arg Pro His Cys Glu Ser
    50                  55                  60

Cys Arg His Cys Asn Ser Gly Leu Leu Val Arg Asn Cys Thr Ile Thr
65                  70                  75                  80

Ala Asn Ala Glu Cys Ala Cys Arg Asn Gly Trp Gln Cys Arg Asp Lys
                85                  90                  95

Glu Cys Thr Glu Cys Asp Pro Leu Pro Asn Pro Ser Leu Thr Ala Arg
            100                 105                 110

Ser Ser Gln Ala Leu Ser Pro His Pro Gln Pro Thr His Leu Pro Tyr
        115                 120                 125

Val Ser Glu Met Leu Glu Ala Arg Thr Ala Gly His Met Gln Thr Leu
    130                 135                 140

Ala Asp Phe Arg Gln Leu Pro Ala Arg Thr Leu Ser Thr His Trp Pro
145                 150                 155                 160

Pro Gln Arg Ser Leu Cys Ser Ser Asp Phe Ile Arg Ile Leu Val Ile
                165                 170                 175

Phe Ser Gly Met Phe Leu Val Phe Thr Leu Ala Gly Ala Leu Phe Leu
            180                 185                 190

His Gln Arg Arg Lys Tyr Arg Ser Asn Lys Gly Glu Ser Pro Val Glu
        195                 200                 205

Pro Ala Glu Pro Cys His Tyr Ser Cys Pro Arg Glu Glu Glu Gly Ser
    210                 215                 220

Thr Ile Pro Ile Gln Glu Asp Tyr Arg Lys Pro Glu Pro Ala Cys Ser
225                 230                 235                 240

Pro

<210> SEQ ID NO 148
<211> LENGTH: 193
<212> TYPE: PRT
<213> ORGANISM: Artificial
<220> FEATURE:
<223> OTHER INFORMATION: The amino acid sequence of the T cell positive
      costimulatory ligand human CD70

<400> SEQUENCE: 148

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His

```
                    50                  55                  60
Thr Gly Pro Gln Gln Asp Pro Arg Leu Tyr Trp Gln Gly Pro Ala
 65                  70                  75                  80

Leu Gly Arg Ser Phe Leu His Gly Pro Glu Leu Asp Lys Gly Gln Leu
                     85                  90                  95

Arg Ile His Arg Asp Gly Ile Tyr Met Val His Ile Gln Val Thr Leu
                100                 105                 110

Ala Ile Cys Ser Ser Thr Thr Ala Ser Arg His His Pro Thr Thr Leu
                115                 120                 125

Ala Val Gly Ile Cys Ser Pro Ala Ser Arg Ser Ile Ser Leu Leu Arg
            130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                    165                 170                 175

Pro Ser Arg Asn Thr Asp Glu Thr Phe Phe Gly Val Gln Trp Val Arg
                180                 185                 190

Pro

<210> SEQ ID NO 149
<211> LENGTH: 463
<212> TYPE: PRT
<213> ORGANISM: Artificial
<220> FEATURE:
<223> OTHER INFORMATION: The amino acid sequence of CD3-4-1BBL BsM_M
      monomer

<400> SEQUENCE: 149

Asp Ile Lys Leu Gln Gln Ser Gly Ala Glu Leu Ala Arg Pro Gly Ala
 1               5                  10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
 50                  55                  60

Lys Asp Lys Ala Thr Leu Thr Thr Asp Lys Ser Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Thr Leu Thr Val Ser Ser Val Glu Gly Gly Ser Gly Gly Ser Gly
            115                 120                 125

Gly Ser Gly Gly Ser Gly Gly Val Asp Asp Ile Gln Leu Thr Gln Ser
        130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                    165                 170                 175

Gly Thr Ser Pro Lys Arg Trp Ile Tyr Asp Thr Ser Lys Val Ala Ser
                180                 185                 190

Gly Val Pro Tyr Arg Phe Ser Gly Ser Gly Ser Gly Thr Ser Tyr Ser
                195                 200                 205

Leu Thr Ile Ser Ser Met Glu Ala Glu Asp Ala Ala Thr Tyr Tyr Cys
```

```
                        210                 215                 220
Gln Gln Trp Ser Ser Asn Pro Leu Thr Phe Gly Ala Gly Thr Lys Leu
225                 230                 235                 240

Glu Leu Lys Gly Gly Gly Ser Gly Gly Gly Ser Gly Gly Gly
                245                 250                 255

Gly Ser Ala Cys Pro Trp Ala Val Ser Gly Ala Arg Ala Ser Pro Gly
                260                 265                 270

Ser Ala Ala Ser Pro Arg Leu Arg Glu Gly Pro Glu Leu Ser Pro Asp
                275                 280                 285

Asp Pro Ala Gly Leu Leu Asp Leu Arg Gln Gly Met Phe Ala Gln Leu
290                 295                 300

Val Ala Gln Asn Val Leu Leu Ile Asp Gly Pro Leu Ser Trp Tyr Ser
305                 310                 315                 320

Asp Pro Gly Leu Ala Gly Val Ser Leu Thr Gly Gly Leu Ser Tyr Lys
                325                 330                 335

Glu Asp Thr Lys Glu Leu Val Val Ala Lys Ala Gly Val Tyr Tyr Val
                340                 345                 350

Phe Phe Gln Leu Glu Leu Arg Arg Val Val Ala Gly Glu Gly Ser Gly
                355                 360                 365

Ser Val Ser Leu Ala Leu His Leu Gln Pro Leu Arg Ser Ala Ala Gly
                370                 375                 380

Ala Ala Ala Leu Ala Leu Thr Val Asp Leu Pro Pro Ala Ser Ser Glu
385                 390                 395                 400

Ala Arg Asn Ser Ala Phe Gly Phe Gln Gly Arg Leu Leu His Leu Ser
                405                 410                 415

Ala Gly Gln Arg Leu Gly Val His Leu His Thr Glu Ala Arg Ala Arg
                420                 425                 430

His Ala Trp Gln Leu Thr Gln Gly Ala Thr Val Leu Gly Leu Phe Arg
                435                 440                 445

Val Thr Pro Glu Ile Pro Ala Gly Leu Pro Ser Pro Arg Ser Glu
450                 455                 460

<210> SEQ ID NO 150
<211> LENGTH: 1389
<212> TYPE: DNA
<213> ORGANISM: Artificial
<220> FEATURE:
<223> OTHER INFORMATION: The nucleotide sequence of CD3-4-1BBL BsM_M
      monomer

<400> SEQUENCE: 150
gacatcaagc tgcagcagag cggcgccgag ctggccccgcc ccggcgccag cgtgaagatg      60
agctgcaaga ccagcggcta caccttcacc cgctacacca tgcactgggt gaagcagcgc     120
cccggccagg gcctggagtg gatcggctac atcaacccca gccgcggcta caccaactac     180
aaccagaagt tcaaggacaa ggccaccctg accaccgaca gagcagcag caccgcctac     240 atgcagctga gcagcctgac cagcgaggac agcgccgtgt actactgcgc ccgctactac     300
gacgaccact actgcctgga ctactggggc cagggcacca ccctgaccgt gagcagcgtg     360
gagggcggca gcgcggcag cggcggcagc ggcggcagcg gcggcgtgga cgacatccag     420
ctgacccaga gccccgccat catgagcgcc agccccggcg agaaggtgac catgacctgc     480
cgcgccagca gcagcgtgag ctacatgaac tggtaccagc agaagagcgg caccagcccc     540
aagcgctgga tctacgacac cagcaaggtg gccagcggcg tgccctaccg cttcagcggc     600
agcggcagcg gcaccagcta cagcctgacc atcagcagca tggaggccga ggacgccgcc     660
```

```
acctactact gccagcagtg gagcagcaac ccctgacct tcggcgccgg caccaagctg      720
gagctgaagg gcggcggcgg cagcggcggc ggcggcagcg gcggcggcgg cagcgcctgc      780
ccctgggccg tgagcggcgc ccgcgccagc cccggcagcg ccgccagccc ccgcctgcgc      840
gagggccccg agctgagccc cgacgacccc gccggcctgc tggacctgcg ccagggcatg      900
ttcgcccagc tggtggccca gaacgtgctg ctgatcgacg ccccctgag ctggtacagc      960
gaccccggcc tggccggcgt gagcctgacc ggcggcctga gctacaagga ggacaccaag     1020
gagctggtgg tggccaaggc cggcgtgtac tacgtgttct tccagctgga gctgcgccgc     1080
gtggtggccg gcgagggcag cggcagcgtg agcctggccc tgcacctgca gcccctgcgc     1140
agcgccgccg gcgccgccgc cctggccctg accgtggacc tgcccccgc cagcagcgag     1200
gcccgcaaca gcgccttcgg cttccagggc cgcctgctgc acctgagcgc cggccagcgc     1260
ctgggcgtgc acctgcacac cgaggcccgc gcccgccacg cctggcagct gacccagggc     1320
gccaccgtgc tgggcctgtt ccgcgtgacc cccgagatcc ccgccggcct gcccagcccc     1380
cgcagcgag                                                              1389
```

<210> SEQ ID NO 151
<211> LENGTH: 529
<212> TYPE: PRT
<213> ORGANISM: Artificial
<220> FEATURE:
<223> OTHER INFORMATION: The amino acid sequence of CD3-4-1BBL BsM_D dimer

<400> SEQUENCE: 151

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220
```

Gln Gln Trp Ser Ser Asn Pro Leu Thr Phe Gly Ala Gly Thr Lys Leu
225                 230                 235                 240

Glu Leu Lys Ala Ser Lys Ser Lys Lys Glu Ile Phe Arg Trp Pro Glu
                245                 250                 255

Ser Pro Lys Ala Gln Ala Ser Ser Val Pro Thr Ala Gln Pro Gln Ala
            260                 265                 270

Glu Gly Ser Leu Ala Lys Ala Thr Thr Ala Pro Ala Thr Thr Arg Asn
        275                 280                 285

Thr Gly Arg Gly Gly Glu Glu Lys Lys Lys Glu Lys Glu Lys Glu Glu
290                 295                 300

Gln Glu Glu Arg Glu Thr Lys Thr Pro Glu Cys Pro Ser His Thr Gln
305                 310                 315                 320

Pro Leu Gly Val Ala Cys Pro Trp Ala Val Ser Gly Ala Arg Ala Ser
                325                 330                 335

Pro Gly Ser Ala Ala Ser Pro Arg Leu Arg Glu Gly Pro Glu Leu Ser
            340                 345                 350

Pro Asp Asp Pro Ala Gly Leu Leu Asp Leu Arg Gln Gly Met Phe Ala
        355                 360                 365

Gln Leu Val Ala Gln Asn Val Leu Leu Ile Asp Gly Pro Leu Ser Trp
370                 375                 380

Tyr Ser Asp Pro Gly Leu Ala Gly Val Ser Leu Thr Gly Gly Leu Ser
385                 390                 395                 400

Tyr Lys Glu Asp Thr Lys Glu Leu Val Val Ala Lys Ala Gly Val Tyr
                405                 410                 415

Tyr Val Phe Phe Gln Leu Glu Leu Arg Arg Val Val Ala Gly Glu Gly
            420                 425                 430

Ser Gly Ser Val Ser Leu Ala Leu His Leu Gln Pro Leu Arg Ser Ala
        435                 440                 445

Ala Gly Ala Ala Ala Leu Ala Leu Thr Val Asp Leu Pro Pro Ala Ser
450                 455                 460

Ser Glu Ala Arg Asn Ser Ala Phe Gly Phe Gln Gly Arg Leu Leu His
465                 470                 475                 480

Leu Ser Ala Gly Gln Arg Leu Gly Val His Leu His Thr Glu Ala Arg
                485                 490                 495

Ala Arg His Ala Trp Gln Leu Thr Gln Gly Ala Thr Val Leu Gly Leu
            500                 505                 510

Phe Arg Val Thr Pro Glu Ile Pro Ala Gly Leu Pro Ser Pro Arg Ser
        515                 520                 525

Glu

<210> SEQ ID NO 152
<211> LENGTH: 1587
<212> TYPE: DNA
<213> ORGANISM: Artificial
<220> FEATURE:
<223> OTHER INFORMATION: The nucleotide sequence of CD3-4-1BBL BsM_D
      dimer

<400> SEQUENCE: 152
gacatcaagc tgcagcagag cggcgccgag ctggcccgcc ccggcgccag cgtgaagatg      60
agctgcaaga ccagcggcta caccttcacc cgctacacca tgcactgggt gaagcagcgc     120
cccggccagg gcctggagtg gatcggctac atcaaccccc agcgcggcta caccaactac     180
aaccagaagt tcaaggacaa ggccaccctg accaccgaca gagcagcag caccgcctac     240

```
atgcagctga gcagcctgac cagcgaggac agcgccgtgt actactgcgc ccgctactac    300
gacgaccact actgcctgga ctactggggc cagggcacca cccctgaccgt gagcagcgtg    360 gagggcggca gcggcggcag cggcggcagc ggcggcagcg gcggcgtgga cgacatccag    420
ctgacccaga gccccgccat catgagcgcc agccccggcg agaaggtgac catgacctgc    480
cgcgccagca gcagcgtgag ctacatgaac tggtaccagc agaagagcgg caccagcccc    540
aagcgctgga tctacgacac cagcaaggtg gccagcggcg tgccctaccg cttcagcggc    600
agcggcagcg gcaccagcta cagcctgacc atcagcagca tggaggccga ggacgccgcc    660
acctactact gccagcagtg gagcagcaac ccctgacct cggcgccgg caccaagctg    720 gagctgaagg ccagcaagag caagaaggag atcttccgct ggccccgagag ccccaaggcc    780 caggccagca gcgtgcccac cgcccagccc caggccgagg gcagcctggc caaggccacc    840 accgccccg ccaccacccg caacaccggc cgcggcggcg aggagaagaa gaaggagaag    900
gagaaggagg agcaggagga gcgcgagacc aagacccccg agtgccccag ccacacccag    960
cccctgggcg tggcctgccc ctgggccgtg agcgcgccc cgccagccc cggcagcgcc    1020 gccagccccc gcctgcgcga gggccccgag ctgagccccg acgacccgc cggcctgctg    1080 gacctgcgcc agggcatgtt cgcccagctg gtggcccaga acgtgctgct gatcgacggc    1140
cccctgagct ggtacagcga ccccggcctg gccggcgtga gcctgaccgg cggcctgagc    1200
tacaaggagg acaccaagga gctggtggtg gccaaggccg cgtgtacta cgtgttcttc    1260 cagctggagc tgcgccgcgt ggtggccggc gagggcagcg gcagcgtgag cctggccctg    1320
cacctgcagc ccctgcgcag cgccgccggc gccgccgccc tggccctgac cgtggacctg    1380
ccccccgcca gcagcgaggc ccgcaacagc gccttcggct ccagggccg cctgctgcac    1440 ctgagcgccg ccagcgcct gggcgtgcac ctgcacaccg aggcccgcgc cgccacgcc    1500 tggcagctga cccagggcgc caccgtgctg ggcctgttcc gcgtgacccc cgagatcccc    1560
gccggcctgc ccagccccg cagcgag                                         1587

<210> SEQ ID NO 153
<211> LENGTH: 496
<212> TYPE: PRT
<213> ORGANISM: Artificial
<220> FEATURE:
<223> OTHER INFORMATION: The amino acid sequence of CD3-B7RP-1 BsM_M
      monomer

<400> SEQUENCE: 153

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Thr Leu Thr Val Ser Ser Val Glu Gly Gly Ser Gly Gly Ser Gly
```

```
            115                 120                 125
Gly Ser Gly Gly Ser Gly Gly Val Asp Asp Ile Gln Leu Thr Gln Ser
        130                 135                 140
Pro Ala Ile Met Ser Ala Ser Pro Gly Glu Lys Val Thr Met Thr Cys
145                 150                 155                 160
Arg Ala Ser Ser Ser Val Ser Tyr Met Asn Trp Tyr Gln Gln Lys Ser
                165                 170                 175
Gly Thr Ser Pro Lys Arg Trp Ile Tyr Asp Thr Ser Lys Val Ala Ser
            180                 185                 190
Gly Val Pro Tyr Arg Phe Ser Gly Ser Gly Ser Gly Thr Ser Tyr Ser
        195                 200                 205
Leu Thr Ile Ser Ser Met Glu Ala Glu Asp Ala Ala Thr Tyr Tyr Cys
    210                 215                 220
Gln Gln Trp Ser Ser Asn Pro Leu Thr Phe Gly Ala Gly Thr Lys Leu
225                 230                 235                 240
Glu Leu Lys Gly Gly Gly Gly Ser Gly Gly Gly Gly Ser Gly Gly Gly
                245                 250                 255
Gly Ser Asp Thr Gln Glu Lys Glu Val Arg Ala Met Val Gly Ser Asp
            260                 265                 270
Val Glu Leu Ser Cys Ala Cys Pro Glu Gly Ser Arg Phe Asp Leu Asn
        275                 280                 285
Asp Val Tyr Val Tyr Trp Gln Thr Ser Glu Ser Lys Thr Val Val Thr
    290                 295                 300
Tyr His Ile Pro Gln Asn Ser Ser Leu Glu Asn Val Asp Ser Arg Tyr
305                 310                 315                 320
Arg Asn Arg Ala Leu Met Ser Pro Ala Gly Met Leu Arg Gly Asp Phe
                325                 330                 335
Ser Leu Arg Leu Phe Asn Val Thr Pro Gln Asp Glu Gln Lys Phe His
            340                 345                 350
Cys Leu Val Leu Ser Gln Ser Leu Gly Phe Gln Glu Val Leu Ser Val
        355                 360                 365
Glu Val Thr Leu His Val Ala Ala Asn Phe Ser Val Pro Val Val Ser
    370                 375                 380
Ala Pro His Ser Pro Ser Gln Asp Glu Leu Thr Phe Thr Cys Thr Ser
385                 390                 395                 400
Ile Asn Gly Tyr Pro Arg Pro Asn Val Tyr Trp Ile Asn Lys Thr Asp
                405                 410                 415
Asn Ser Leu Leu Asp Gln Ala Leu Gln Asn Asp Thr Val Phe Leu Asn
            420                 425                 430
Met Arg Gly Leu Tyr Asp Val Val Ser Val Leu Arg Ile Ala Arg Thr
        435                 440                 445
Pro Ser Val Asn Ile Gly Cys Cys Ile Glu Asn Val Leu Leu Gln Gln
    450                 455                 460
Asn Leu Thr Val Gly Ser Gln Thr Gly Asn Asp Ile Gly Glu Arg Asp
465                 470                 475                 480
Lys Ile Thr Glu Asn Pro Val Ser Thr Gly Glu Lys Asn Ala Ala Thr
                485                 490                 495
```

<210> SEQ ID NO 154
<211> LENGTH: 1488
<212> TYPE: DNA
<213> ORGANISM: Artificial
<220> FEATURE:
<223> OTHER INFORMATION: The nucleotide sequence of CD3-B7RP-1 BsM_M monomer

<400> SEQUENCE: 154

```
gacatcaagc tgcagcagag cggcgccgag ctggcccgcc ccggcgccag cgtgaagatg      60
agctgcaaga ccagcggcta caccttcacc cgctacacca tgcactgggt gaagcagcgc    120
cccggccagg gcctggagtg gatcggctac atcaaccccca gccgcggcta caccaactac    180
aaccagaagt tcaaggacaa ggccaccctg accaccgaca agagcagcag caccgcctac    240
atgcagctga gcagcctgac cagcgaggac agcgccgtgt actactgcgc cgctactac    300
gacgaccact actgcctgga ctactggggc cagggcacca ccctgaccgt gagcagcgtg    360
gagggcggca gcggcggcag cggcggcagc ggcggcagcg gcggcgtgga cgacatccag    420
ctgacccaga gccccgccat catgagcgcc agccccggcg agaaggtgac catgacctgc    480
cgcgccagca gcagcgtgag ctacatgaac tggtaccagc agaagagcgg caccagcccc    540
aagcgctgga tctacgacac cagcaaggtg gccagcggcg tgccctaccg cttcagcggc    600
agcggcagcg gcaccagcta cagcctgacc atcagcagca tggaggccga ggacgccgcc    660
acctactact gccagcagtg gagcagcaac cccctgacct tcggcgccgg caccaagctg    720
gagctgaagg gcggcggcgg cagcggcggc ggcggcagcg gcggcggcgg cagcgacacc    780
caggagaagg aggtgcgcgc catggtgggc agcgacgtgg agctgagctg cgcctgcccc    840
gagggcagcc gcttcgacct gaacgacgtg tacgtgtact ggcagaccag cgagagcaag    900
accgtggtga cctaccacat cccccagaac agcagcctgg agaacgtgga cagccgctac    960
cgcaaccgcg ccctgatgag ccccgccggc atgctgcgcg gcgacttcag cctgcgcctg   1020
ttcaacgtga ccccccagga cgagcagaag ttccactgcc tggtgctgag ccagagcctg   1080
ggcttccagg aggtgctgag cgtggaggtg accctgcacg tggccgccaa cttcagcgtg   1140
cccgtggtga gcgcccccca gcccccagc caggacgagc tgaccttcac ctgcaccagc   1200
atcaacggct acccccgccc caacgtgtac tggatcaaca agaccgacaa cagcctgctg   1260
gaccaggccc tgcagaacga caccgtgttc ctgaacatgc gcggcctgta cgacgtggtg   1320
agcgtgctgc gcatcgcccg cacccccagc gtgaacatcg gctgctgcat cgagaacgtg   1380
ctgctgcagc agaacctgac cgtgggcagc cagaccggca cgacatcgg cgagcgcgac   1440
aagatcaccg agaaccccgt gagcaccggc gagaagaacg ccgccacc               1488
```

<210> SEQ ID NO 155
<211> LENGTH: 562
<212> TYPE: PRT
<213> ORGANISM: Artificial
<220> FEATURE:
<223> OTHER INFORMATION: The amino acid sequence of CD3-B7RP-1 BsM_D dimer

<400> SEQUENCE: 155

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80
```

```
Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
            115                 120                 125

Gly Ser Gly Gly Ser Gly Val Asp Asp Ile Gln Leu Thr Gln Ser
        130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
            195                 200                 205

Leu Thr Ile Ser Ser Met Glu Ala Glu Asp Ala Ala Thr Tyr Tyr Cys
            210                 215                 220

Gln Gln Trp Ser Ser Asn Pro Leu Thr Phe Gly Ala Gly Thr Lys Leu
225                 230                 235                 240

Glu Leu Lys Ala Ser Lys Ser Lys Lys Glu Ile Phe Arg Trp Pro Glu
                245                 250                 255

Ser Pro Lys Ala Gln Ala Ser Ser Val Pro Thr Ala Gln Pro Gln Ala
            260                 265                 270

Glu Gly Ser Leu Ala Lys Ala Thr Thr Ala Pro Ala Thr Thr Arg Asn
            275                 280                 285

Thr Gly Arg Gly Gly Glu Glu Lys Lys Lys Glu Lys Glu Lys Glu Glu
            290                 295                 300

Gln Glu Glu Arg Glu Thr Lys Thr Pro Glu Cys Pro Ser His Thr Gln
305                 310                 315                 320

Pro Leu Gly Val Asp Thr Gln Glu Lys Glu Val Arg Ala Met Val Gly
            325                 330                 335

Ser Asp Val Glu Leu Ser Cys Ala Cys Pro Glu Gly Ser Arg Phe Asp
            340                 345                 350

Leu Asn Asp Val Tyr Val Tyr Trp Gln Thr Ser Glu Ser Lys Thr Val
            355                 360                 365

Val Thr Tyr His Ile Pro Gln Asn Ser Ser Leu Glu Asn Val Asp Ser
            370                 375                 380

Arg Tyr Arg Asn Arg Ala Leu Met Ser Pro Ala Gly Met Leu Arg Gly
385                 390                 395                 400

Asp Phe Ser Leu Arg Leu Phe Asn Val Thr Pro Gln Asp Glu Gln Lys
                405                 410                 415

Phe His Cys Leu Val Leu Ser Gln Ser Leu Gly Phe Gln Glu Val Leu
            420                 425                 430

Ser Val Glu Val Thr Leu His Val Ala Ala Asn Phe Ser Val Pro Val
            435                 440                 445

Val Ser Ala Pro His Ser Pro Ser Gln Asp Glu Leu Thr Phe Thr Cys
450                 455                 460

Thr Ser Ile Asn Gly Tyr Pro Arg Pro Asn Val Tyr Trp Ile Asn Lys
465                 470                 475                 480

Thr Asp Asn Ser Leu Leu Asp Gln Ala Leu Gln Asn Asp Thr Val Phe
                485                 490                 495

Leu Asn Met Arg Gly Leu Tyr Asp Val Val Ser Val Leu Arg Ile Ala
```

```
                500            505            510
Arg Thr Pro Ser Val Asn Ile Gly Cys Cys Ile Glu Asn Val Leu Leu
              515               520              525

Gln Gln Asn Leu Thr Val Gly Ser Gln Thr Gly Asn Asp Ile Gly Glu
          530                  535             540

Arg Asp Lys Ile Thr Glu Asn Pro Val Ser Thr Gly Glu Lys Asn Ala
545             550                  555              560

Ala Thr

<210> SEQ ID NO 156
<211> LENGTH: 1686
<212> TYPE: DNA
<213> ORGANISM: Artificial
<220> FEATURE:
<223> OTHER INFORMATION: The nucleotide sequence of CD3-B7RP-1 BsM_D
      dimer

<400> SEQUENCE: 156
gacatcaagc tgcagcagag cggcgccgag ctggcccgcc ccggcgccag cgtgaagatg    60
agctgcaaga ccagcggcta caccttcacc cgctacacca tgcactgggt gaagcagcgc   120
cccggccagg gctggagtg atcggctac atcaacccca ccgcgggcta caccaactac   180
aaccagaagt tcaaggacaa ggccaccctg accaccgaca agagcagcag caccgcctac   240
atgcagctga gcagcctgac cagcgaggac agcgccgtgt actactgcgc ccgctactac   300
gacgaccact actgcctgga ctactgggc cagggcacca ccctgaccgt gagcagcgtg   360
gagggcggca gcggcggcag cggcggcagc ggcggcagcg gcggcgtgga cgacatccag   420
ctgacccaga gccccgccat catgagcgcc agccccggcg agaaggtgac catgacctgc   480
cgcgccagca gcagcgtgag ctacatgaac tggtaccagc agaagagcgg caccagcccc   540
aagcgctgga tctacgacac cagcaaggtg gccagcggcg tgccctaccg cttcagcggc   600
agcggcagcg gcaccagcta cagcctgacc atcagcagca tggaggccga ggacgccgcc   660
acctactact gccagcagtg gagcagcaac cccctgacct tcggcgccgg caccaagctg   720
gagctgaagg ccagcaagag caagaaggag atcttccgct ggcccgagag ccccaaggcc   780
caggccagca gcgtgcccac cgcccagccc caggccgagg cagcctggc caaggccacc   840 accgccccg ccaccaccg caacaccggc cgcggcggcg aggagaagaa gaaggagaag   900
gagaaggagg agcaggagga gcgcgagacc aagacccccg agtgccccag ccacacccag   960
cccctgggcg tggacaccca ggagaaggag gtgcgcgcca tggtgggcag cgacgtggag  1020
ctgagctgcg cctgccccga gggcagccgc ttcgacctga cgacgtgta cgtgtactgg  1080 cagaccagcg agagcaagac cgtggtgacc taccacatcc cccagaacag cagcctggag  1140
aacgtggaca gccgctaccg caaccgcgcc ctgatgagcc ccgccggcat gctgcgcggc  1200
gacttcagcc tgcgcctgtt caacgtgacc ccccaggacg agcagaagtt ccactgcctg  1260
gtgctgagcc agagcctggg cttccaggag gtgctgagcg tggaggtgac cctgcacgtg  1320
gccgccaact tcagcgtgcc cgtggtgagc gcccccaca gccccagcca ggacgagctg  1380
accttcacct gcaccagcat caacggctac cccgcccca cgtgtactg atcaacaag  1440 accgacaaca gcctgctgga ccaggccctg cagaacgaca ccgtgttcct gaacatgcgc  1500
ggcctgtacg acgtggtgag cgtgctgcgc atcgcccgca cccccagcgt gaacatcggc  1560
tgctgcatcg agaacgtgct gctgcagcag aacctgaccg tgggcagcca gaccggcaac  1620
gacatcggcg agcgcgacaa gatcaccgag aaccccgtga gcaccggcga gaagaacgcc  1680
```

```
gccacc                                                                          1686
```

<210> SEQ ID NO 157
<211> LENGTH: 391
<212> TYPE: PRT
<213> ORGANISM: Artificial
<220> FEATURE:
<223> OTHER INFORMATION: The amino acid sequence of CD3-OX40L BsM_M monomer

<400> SEQUENCE: 157

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Gly Gly Gly Gly Ser Gly Gly Gly Ser Gly Gly
                245                 250                 255

Gly Ser Gln Val Ser His Arg Tyr Pro Arg Ile Gln Ser Ile Lys Val
            260                 265                 270

Gln Phe Thr Glu Tyr Lys Lys Glu Lys Gly Phe Ile Leu Thr Ser Gln
        275                 280                 285

Lys Glu Asp Glu Ile Met Lys Val Gln Asn Asn Ser Val Ile Ile Asn
    290                 295                 300

Cys Asp Gly Phe Tyr Leu Ile Ser Leu Lys Gly Tyr Phe Ser Gln Glu
305                 310                 315                 320

Val Asn Ile Ser Leu His Tyr Gln Lys Asp Glu Glu Pro Leu Phe Gln
                325                 330                 335

Leu Lys Lys Val Arg Ser Val Asn Ser Leu Met Val Ala Ser Leu Thr
            340                 345                 350
```

Tyr Lys Asp Lys Val Tyr Leu Asn Val Thr Thr Asp Asn Thr Ser Leu
            355                 360                 365

Asp Asp Phe His Val Asn Gly Gly Glu Leu Ile Leu Ile His Gln Asn
        370                 375                 380

Pro Gly Glu Phe Cys Val Leu
385                 390

<210> SEQ ID NO 158
<211> LENGTH: 1173
<212> TYPE: DNA
<213> ORGANISM: Artificial
<220> FEATURE:
<223> OTHER INFORMATION: The nucleotide sequence of CD3-OX40L BsM_M
      monomer

<400> SEQUENCE: 158

| | | | | | |
|---|---|---|---|---|---|
| gacatcaagc | tgcagcagag | cggcgccgag | ctggcccgcc | ccggcgccag | cgtgaagatg | 60 |
| agctgcaaga | ccagcggcta | caccttcacc | cgctacacca | tgcactgggt | gaagcagcgc | 120 |
| cccggccagg | gcctggagtg | gatcggctac | atcaacccca | gccgcggcta | caccaactac | 180 |
| aaccagaagt | tcaaggacaa | ggccaccctg | accaccgaca | gagcagcag | caccgcctac | 240 |
| atgcagctga | gcagcctgac | cagcgaggac | agcgccgtgt | actactgcgc | ccgctactac | 300 |
| gacgaccact | actgcctgga | ctactggggc | cagggcacca | ccctgaccgt | gagcagcgtg | 360 |
| gagggcggca | gcggcggcag | cggcggcagc | ggcggcagcg | gcggcgtgga | cgacatccag | 420 |
| ctgacccaga | gccccgccat | catgagcgcc | agccccggcg | agaaggtgac | catgacctgc | 480 |
| cgcgccagca | gcagcgtgag | ctacatgaac | tggtaccagc | agaagagcgg | caccagcccc | 540 |
| aagcgctgga | tctacgacac | cagcaaggtg | gccagcggcg | tgccctaccg | cttcagcggc | 600 |
| agcggcagcg | gcaccagcta | cagcctgacc | atcagcagca | tggaggccga | ggacgccgcc | 660 |
| acctactact | gccagcagtg | gagcagcaac | cccctgacct | tcggcgccgg | caccaagctg | 720 |
| gagctgaagg | gcggcggcgg | cagcggcggc | ggcggcagcg | gcggcggcgg | cagccaggtg | 780 |
| agccaccgct | acccccgcat | ccagagcatc | aaggtgcagt | tcaccgagta | caagaaggag | 840 |
| aagggcttca | tcctgaccag | ccagaaggag | gacgagatca | tgaaggtgca | gaacaacagc | 900 |
| gtgatcatca | actgcgacgg | cttctacctg | atcagcctga | agggctactt | cagccaggag | 960 |
| gtgaacatca | gcctgcacta | ccagaaggac | gaggagcccc | tgttccagct | gaagaaggtg | 1020 |
| cgcagcgtga | cagcctgat | ggtggccagc | ctgacctaca | aggacaaggt | gtacctgaac | 1080 |
| gtgaccaccg | acaacaccag | cctggacgac | ttccacgtga | acggcggcga | gctgatcctg | 1140 |
| atccaccaga | accccggcga | gttctgcgtg | ctg | | | 1173 |

<210> SEQ ID NO 159
<211> LENGTH: 457
<212> TYPE: PRT
<213> ORGANISM: Artificial
<220> FEATURE:
<223> OTHER INFORMATION: The amino acid sequence of CD3-OX40L BsM_D
      dimer

<400> SEQUENCE: 159

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile

```
                35                  40                  45
Gly Tyr Ile Asn Pro Ser Arg Gly Tyr Thr Asn Tyr Asn Gln Lys Phe
 50                  55                  60

Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
                100                 105                 110

Thr Thr Leu Thr Val Ser Ser Val Glu Gly Gly Ser Gly Gly Ser Gly
                115                 120                 125

Gly Ser Gly Gly Ser Gly Gly Val Asp Asp Ile Gln Leu Thr Gln Ser
                130                 135                 140

Pro Ala Ile Met Ser Ala Ser Pro Gly Glu Lys Val Thr Met Thr Cys
145                 150                 155                 160

Arg Ala Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
                180                 185                 190

Gly Val Pro Tyr Arg Phe Ser Gly Ser Gly Ser Gly Thr Ser Tyr Ser
                195                 200                 205

Leu Thr Ile Ser Ser Met Glu Ala Glu Asp Ala Ala Thr Tyr Tyr Cys
210                 215                 220

Gln Gln Trp Ser Ser Asn Pro Leu Thr Phe Gly Ala Gly Thr Lys Leu
225                 230                 235                 240

Glu Leu Lys Ala Ser Lys Ser Lys Glu Ile Phe Arg Trp Pro Glu
                245                 250                 255

Ser Pro Lys Ala Gln Ala Ser Ser Val Pro Thr Ala Gln Pro Gln Ala
                260                 265                 270

Glu Gly Ser Leu Ala Lys Ala Thr Thr Ala Pro Ala Thr Thr Arg Asn
                275                 280                 285

Thr Gly Arg Gly Gly Glu Glu Lys Lys Lys Glu Lys Glu Lys Glu Glu
                290                 295                 300

Gln Glu Glu Arg Glu Thr Lys Thr Pro Glu Cys Pro Ser His Thr Gln
305                 310                 315                 320

Pro Leu Gly Val Gln Val Ser His Arg Tyr Pro Arg Ile Gln Ser Ile
                325                 330                 335

Lys Val Gln Phe Thr Glu Tyr Lys Lys Glu Lys Gly Phe Ile Leu Thr
                340                 345                 350

Ser Gln Lys Glu Asp Glu Ile Met Lys Val Gln Asn Asn Ser Val Ile
                355                 360                 365

Ile Asn Cys Asp Gly Phe Tyr Leu Ile Ser Leu Lys Gly Tyr Phe Ser
                370                 375                 380

Gln Glu Val Asn Ile Ser Leu His Tyr Gln Lys Asp Glu Glu Pro Leu
385                 390                 395                 400

Phe Gln Leu Lys Lys Val Arg Ser Val Asn Ser Leu Met Val Ala Ser
                405                 410                 415

Leu Thr Tyr Lys Asp Lys Val Tyr Leu Asn Val Thr Thr Asp Asn Thr
                420                 425                 430

Ser Leu Asp Asp Phe His Val Asn Gly Gly Glu Leu Ile Leu Ile His
                435                 440                 445

Gln Asn Pro Gly Glu Phe Cys Val Leu
450                 455
```

<210> SEQ ID NO 160
<211> LENGTH: 1371
<212> TYPE: DNA
<213> ORGANISM: Artificial
<220> FEATURE:
<223> OTHER INFORMATION: The nucleotide sequence of CD3-OX40L BsM_D dimer

<400> SEQUENCE: 160

```
gacatcaagc tgcagcagag cggcgccgag ctggcccgcc ccggcgccag cgtgaagatg      60
agctgcaaga ccagcggcta caccttcacc cgctacacca tgcactgggt gaagcagcgc     120
cccggccagg gcctggagtg gatcggctac atcaaccccag ccgcggcta caccaactac     180
aaccagaagt tcaaggacaa ggccacccctg accaccgaca gagcagcag caccgcctac     240
atgcagctga gcagcctgac cagcgaggac agcgccgtgt actactgcgc ccgctactac     300
gacgaccact actgcctgga ctactgggggc cagggcacca ccctgaccgt gagcagcgtg     360
gagggcggca gcggcggcag cggcggcagc ggcggcagcg gcggcgtgga cgacatccag     420
ctgacccaga gccccgccat catgagcgcc agccccggcg agaaggtgac catgacctgc     480
cgcgccagca gcagcgtgag ctacatgaac tggtaccagc agaagagcgg caccagcccc     540
aagcgctgga tctacgacac cagcaaggtg gccagcggcg tgccctaccg cttcagcggc     600
agcggcagcg gcaccagcta cagcctgacc atcagcagca tggaggccga ggacgccgcc     660
acctactact gccagcagtg gagcagcaac cccctgacct tcggcgccgg caccaagctg     720
gagctgaagg ccagcaagag caagaaggag atcttccgct ggcccgagag ccccaaggcc     780
caggccagca gcgtgcccac cgcccagccc caggccgagg cagcctggc caaggccacc     840
accgccccg ccaccacccg caacaccggc cgcggcggcg aggagaagaa gaaggagaag     900
gagaaggagg agcaggagga cgcgagacc aagaccccg agtgccccag ccacacccag     960
cccctgggcg tgcaggtgag ccaccgctac cccgcatcc agagcatcaa ggtgcagttc    1020
accgagtaca gaaggagaa gggcttcatc ctgaccagcc agaaggagga cgagatcatg    1080
aaggtgcaga caacagcgt gatcatcaac tgcgacggc tctacctgat cagcctgaag    1140
ggctacttca gccaggaggt gaacatcagc ctgcactacc agaaggacga ggagcccctg    1200
ttccagctga agaaggtgcg cagcgtgaac agcctgatgg tggccagcct gacctacaag    1260
gacaaggtgt acctgaacgt gaccaccgac aacaccagcc tggacgactt ccacgtgaac    1320
ggcggcgagc tgatcctgat ccaccagaac cccggcgagt ctgcgtgct g             1371
```

<210> SEQ ID NO 161
<211> LENGTH: 386
<212> TYPE: PRT
<213> ORGANISM: Artificial
<220> FEATURE:
<223> OTHER INFORMATION: The amino acid sequence of CD3-GITRL BsM_M monomer

<400> SEQUENCE: 161

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
```

```
            50                  55                  60
Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
            115                 120                 125

Gly Ser Gly Gly Ser Gly Gly Val Asp Asp Ile Gln Leu Thr Gln Ser
            130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
            195                 200                 205

Leu Thr Ile Ser Ser Met Glu Ala Glu Asp Ala Ala Thr Tyr Tyr Cys
            210                 215                 220

Gln Gln Trp Ser Ser Asn Pro Leu Thr Phe Gly Ala Gly Thr Lys Leu
225                 230                 235                 240

Glu Leu Lys Gly Gly Gly Gly Ser Gly Gly Gly Gly Ser Gly Gly Gly
                245                 250                 255

Gly Ser Gln Leu Glu Thr Ala Lys Glu Pro Cys Met Ala Lys Phe Gly
            260                 265                 270

Pro Leu Pro Ser Lys Trp Gln Met Ala Ser Ser Glu Pro Pro Cys Val
            275                 280                 285

Asn Lys Val Ser Asp Trp Lys Leu Glu Ile Leu Gln Asn Gly Leu Tyr
            290                 295                 300

Leu Ile Tyr Gly Gln Val Ala Pro Asn Ala Asn Tyr Asn Asp Val Ala
305                 310                 315                 320

Pro Phe Glu Val Arg Leu Tyr Lys Asn Lys Asp Met Ile Gln Thr Leu
                325                 330                 335

Thr Asn Lys Ser Lys Ile Gln Asn Val Gly Gly Thr Tyr Glu Leu His
            340                 345                 350

Val Gly Asp Thr Ile Asp Leu Ile Phe Asn Ser Glu His Gln Val Leu
            355                 360                 365

Lys Asn Asn Thr Tyr Trp Gly Ile Ile Leu Leu Ala Asn Pro Gln Phe
            370                 375                 380

Ile Ser
385

<210> SEQ ID NO 162
<211> LENGTH: 1158
<212> TYPE: DNA
<213> ORGANISM: Artificial
<220> FEATURE:
<223> OTHER INFORMATION: The nucleotide sequence of CD3-GITRL BsM_M
      monomer

<400> SEQUENCE: 162
gacatcaagc tgcagcagag cggcgccgag ctggcccgcc cggcgccag cgtgaagatg      60 agctgcaaga ccagcggcta caccttcacc cgctacacca tgcactgggt gaagcagcgc     120
```

```
cccggccagg gcctggagtg gatcggctac atcaacccca gccgcggcta caccaactac      180
aaccagaagt tcaaggacaa ggccaccctg accaccgaca agagcagcag caccgcctac      240
atgcagctga gcagcctgac cagcgaggac agcgccgtgt actactgcgc ccgctactac      300
gacgaccact actgcctgga ctactggggc cagggcacca ccctgaccgt gagcagcgtg      360
gagggcggca gcggcggcag cggcggcagc ggcggcagcg gcggcgtgga cgacatccag      420
ctgacccaga gccccgccat catgagcgcc agccccggcg agaaggtgac catgacctgc      480
cgcgccagca gcagcgtgag ctacatgaac tggtaccagc agaagagcgg caccagcccc      540
aagcgctgga tctacgacac cagcaaggtg gccagcggcg tgccctaccg cttcagcggc      600
agcggcagcg gcaccagcta cagcctgacc atcagcagca tggaggccga ggacgccgcc      660
acctactact gccagcagtg gagcagcaac ccctgacct cggcgccgg caccaagctg       720 gagctgaagg gcggcggcgg cagcggcggc ggcggcagcg gcggcggcgg cagccagctg      780
gagaccgcca aggagccctg catggccaag ttcggccccc tgcccagcaa gtggcagatg      840
gccagcagcg agccccctg cgtgaacaag gtgagcgact ggaagctgga gatcctgcag      900
aacggcctgt acctgatcta cggccaggtg gcccccaacg ccaactacaa cgacgtggcc      960
cccttcgagg tgcgcctgta caagaacaag gacatgatcc agaccctgac caacaagagc     1020
aagatccaga cgtgggcgg cacctacgag ctgcacgtgg gcgacaccat cgacctgatc      1080
ttcaacagcg agcaccaggt gctgaagaac aacacctact ggggcatcat cctgctggcc      1140 aaccccagt tcatcagc                                                    1158

<210> SEQ ID NO 163
<211> LENGTH: 452
<212> TYPE: PRT
<213> ORGANISM: Artificial
<220> FEATURE:
<223> OTHER INFORMATION: The amino acid sequence of CD3-GITRL BsM_D
      dimer

<400> SEQUENCE: 163

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
```

```
                   165                 170                 175
Gly Thr Ser Pro Lys Arg Trp Ile Tyr Asp Thr Ser Lys Val Ala Ser
                180                 185                 190

Gly Val Pro Tyr Arg Phe Ser Gly Ser Gly Ser Gly Thr Ser Tyr Ser
                195                 200                 205

Leu Thr Ile Ser Ser Met Glu Ala Glu Asp Ala Ala Thr Tyr Tyr Cys
                210                 215                 220

Gln Gln Trp Ser Ser Asn Pro Leu Thr Phe Gly Ala Gly Thr Lys Leu
225                 230                 235                 240

Glu Leu Lys Ala Ser Lys Ser Lys Lys Glu Ile Phe Arg Trp Pro Glu
                245                 250                 255

Ser Pro Lys Ala Gln Ala Ser Ser Val Pro Thr Ala Gln Pro Gln Ala
                260                 265                 270

Glu Gly Ser Leu Ala Lys Ala Thr Thr Ala Pro Ala Thr Thr Arg Asn
                275                 280                 285

Thr Gly Arg Gly Gly Glu Glu Lys Lys Glu Lys Glu Lys Glu Glu
                290                 295                 300

Gln Glu Glu Arg Glu Thr Lys Thr Pro Glu Cys Pro Ser His Thr Gln
305                 310                 315                 320

Pro Leu Gly Val Gln Leu Glu Thr Ala Lys Glu Pro Cys Met Ala Lys
                325                 330                 335

Phe Gly Pro Leu Pro Ser Lys Trp Gln Met Ala Ser Ser Glu Pro Pro
                340                 345                 350

Cys Val Asn Lys Val Ser Asp Trp Lys Leu Glu Ile Leu Gln Asn Gly
                355                 360                 365

Leu Tyr Leu Ile Tyr Gly Gln Val Ala Pro Asn Ala Asn Tyr Asn Asp
                370                 375                 380

Val Ala Pro Phe Glu Val Arg Leu Tyr Lys Asn Lys Asp Met Ile Gln
385                 390                 395                 400

Thr Leu Thr Asn Lys Ser Lys Ile Gln Asn Val Gly Gly Thr Tyr Glu
                405                 410                 415

Leu His Val Gly Asp Thr Ile Asp Leu Ile Phe Asn Ser Glu His Gln
                420                 425                 430

Val Leu Lys Asn Asn Thr Tyr Trp Gly Ile Ile Leu Leu Ala Asn Pro
435                 440                 445

Gln Phe Ile Ser
                450

<210> SEQ ID NO 164
<211> LENGTH: 1356
<212> TYPE: DNA
<213> ORGANISM: Artificial
<220> FEATURE:
<223> OTHER INFORMATION: The nucleotide sequence of CD3-GITRL BsM_D
      dimer

<400> SEQUENCE: 164
gacatcaagc tgcagcagag cggcgccgag ctggcccgcc ccggcgccag cgtgaagatg      60
agctgcaaga ccagcggcta caccttcacc cgctacacca tgcactgggt gaagcagcgc     120
cccggccagg gcctggagtg gatcggctac atcaacccca ccgcgggcta caccaactac    180
aaccagaagt tcaaggacaa ggccaccctg accaccgaca gagcagcag caccgcctac     240 atgcagctga gcagcctgac cagcgaggac agcgccgtgt actactgcgc cgctactac    300 gacgaccact actgcctgga ctactgggc cagggcacca ccctgaccgt gagcagcgtg    360
```

| | |
|---|---|
| gagggcggca gcggcggcag cggcggcagc ggcggcagcg gcggcgtgga cgacatccag | 420 |
| ctgacccaga gccccgccat catgagcgcc agccccggcg agaaggtgac catgacctgc | 480 |
| cgcgccagca gcagcgtgag ctacatgaac tggtaccagc agaagagcgg caccagcccc | 540 |
| aagcgctgga tctacgacac cagcaaggtg gccagcggcg tgccctaccg cttcagcggc | 600 |
| agcggcagcg gcaccagcta cagcctgacc atcagcagca tggaggccga ggacgccgcc | 660 |
| acctactact gccagcagtg gagcagcaac cccctgacct cggcgccgg caccaagctg | 720 |
| gagctgaagg ccagcaagag caagaaggag atcttccgct ggccccgagag ccccaaggcc | 780 |
| caggccagca gcgtgcccac cgcccagccc caggccgagg cagcctggc caaggccacc | 840 |
| accgcccccg ccaccacccg caacaccggc cgcggcggcg aggagaagaa gaaggagaag | 900 |
| gagaaggagg agcaggagga gcgcgagacc aagacccccg agtgccccag ccacacccag | 960 |
| cccctgggcg tgcagctgga accgccaag gagccctgca tggccaagtt cggcccctg | 1020 |
| cccagcaagt ggcagatggc cagcagcgag ccccctgcg tgaacaaggt gagcgactgg | 1080 |
| aagctggaga tcctgcagaa cggcctgtac ctgatctacg ccaggtggc ccccaacgcc | 1140 |
| aactacaacg acgtggcccc cttcgaggtg cgcctgtaca gaacaagga catgatccag | 1200 |
| accctgacca acaagagcaa gatccagaac gtgggcggca cctacgagct gcacgtgggc | 1260 |
| gacaccatcg acctgatctt caacagcgag caccaggtgc tgaagaacaa cacctactgg | 1320 |
| ggcatcatcc tgctggccaa ccccagttc atcagc | 1356 |

<210> SEQ ID NO 165
<211> LENGTH: 413
<212> TYPE: PRT
<213> ORGANISM: Artificial
<220> FEATURE:
<223> OTHER INFORMATION: The amino acid sequence of CD3-CD70 BsM_M monomer

<400> SEQUENCE: 165

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Thr Leu Thr Val Ser Ser Val Glu Gly Gly Ser Gly Gly Ser Gly
            115                 120                 125

Gly Ser Gly Gly Ser Gly Gly Val Asp Asp Ile Gln Leu Thr Gln Ser
        130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
```

```
                180             185              190
Gly Val Pro Tyr Arg Phe Ser Gly Ser Gly Ser Gly Thr Ser Tyr Ser
            195                 200             205

Leu Thr Ile Ser Ser Met Glu Ala Glu Asp Ala Ala Thr Tyr Tyr Cys
210             215                 220

Gln Gln Trp Ser Ser Asn Pro Leu Thr Phe Gly Ala Gly Thr Lys Leu
225                 230                 235                 240

Glu Leu Lys Gly Gly Gly Gly Ser Gly Gly Gly Gly Ser Gly Gly Gly
                245                 250                 255

Gly Ser Gln Arg Phe Ala Gln Ala Gln Gln Leu Pro Leu Glu Ser
            260                 265             270

Leu Gly Trp Asp Val Ala Glu Leu Gln Leu Asn His Thr Gly Pro Gln
            275                 280             285

Gln Asp Pro Arg Leu Tyr Trp Gln Gly Gly Pro Ala Leu Gly Arg Ser
            290                 295             300

Phe Leu His Gly Pro Glu Leu Asp Lys Gly Gln Leu Arg Ile His Arg
305             310                 315                 320

Asp Gly Ile Tyr Met Val His Ile Gln Val Thr Leu Ala Ile Cys Ser
                325                 330                 335

Ser Thr Thr Ala Ser Arg His His Pro Thr Thr Leu Ala Val Gly Ile
            340                 345                 350

Cys Ser Pro Ala Ser Arg Ser Ile Ser Leu Leu Arg Leu Ser Phe His
            355                 360                 365

Gln Gly Cys Thr Ile Ala Ser Gln Arg Leu Thr Pro Leu Ala Arg Gly
            370                 375                 380

Asp Thr Leu Cys Thr Asn Leu Thr Gly Thr Leu Leu Pro Ser Arg Asn
385                 390                 395                 400

Thr Asp Glu Thr Phe Phe Gly Val Gln Trp Val Arg Pro
                405                 410

<210> SEQ ID NO 166
<211> LENGTH: 1239
<212> TYPE: DNA
<213> ORGANISM: Artificial
<220> FEATURE:
<223> OTHER INFORMATION: The nucleotide sequence of CD3-CD70 BsM_M
      monomer

<400> SEQUENCE: 166
gacatcaagc tgcagcagag cggcgccgag ctggcccgcc ccggcgccag cgtgaagatg        60
agctgcaaga ccagcggcta caccttcacc cgctacacca tgcactgggt gaagcagcgc       120
cccggccagg gcctggagtg gatcggctac atcaacccca gccgcggcta caccaactac       180
aaccagaagt tcaaggacaa ggccaccctg accaccgaca gagcagcag caccgcctac        240 atgcagctga gcagcctgac cagcgaggac agcgccgtgt actactgcgc cgctactac        300 gacgaccact actgcctgga ctactggggc cagggcacca ccctgaccgt gagcagcgtg       360
gagggcggca gcggcggcag cggcggcagc ggcggcagcg gcggcgtgga cgacatccag       420
ctgacccaga gccccgccat catgagcgcc agccccggcg agaaggtgac catgacctgc       480
cgcgccagca gcagcgtgag ctacatgaac tggtaccagc agaagagcgg caccagcccc       540
aagcgctgga tctacgacac cagcaaggtg gccagcggcg tgccctaccg cttcagcggc       600
agcggcagcg gcaccagcta cagcctgacc atcagcagca tggaggccga ggacgccgcc       660
acctactact gccagcagtg gagcagcaac cccctgacct tcggcgccgg caccaagctg       720
```

-continued

```
gagctgaagg gcggcggcgg cagcggcggc ggcggcagcg gcggcggcgg cagccagcgc      780
ttcgcccagg cccagcagca gctgcccctg gagagcctgg gctgggacgt ggccgagctg      840
cagctgaacc acaccggccc ccagcaggac ccccgcctgt actggcaggg cggccccgcc      900
ctgggccgca gcttcctgca cggccccgag ctggacaagg ccagctgcg catccaccgc       960 gacggcatct acatggtgca catccaggtg accctggcca tctgcagcag caccaccgcc     1020
agccgccacc accccaccac cctggccgtg ggcatctgca gccccgccag ccgcagcatc     1080
agcctgctgc gcctgagctt ccaccagggc tgcaccatcg ccagccagcg cctgaccccc     1140
ctggcccgcg cgacaccct gtgcaccaac ctgaccggca ccctgctgcc cagccgcaac      1200
accgacgaga ccttcttcgg cgtgcagtgg gtgcgcccc                            1239
```

<210> SEQ ID NO 167
<211> LENGTH: 479
<212> TYPE: PRT
<213> ORGANISM: Artificial
<220> FEATURE:
<223> OTHER INFORMATION: The amino acid sequence of CD3-CD70 BsM_D dimer

<400> SEQUENCE: 167

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Ala Ser Lys Ser Lys Glu Ile Phe Arg Trp Pro Glu
                245                 250                 255

Ser Pro Lys Ala Gln Ala Ser Ser Val Pro Thr Ala Gln Pro Gln Ala
            260                 265                 270
```

Glu Gly Ser Leu Ala Lys Ala Thr Ala Pro Ala Thr Thr Arg Asn
            275                 280                 285

Thr Gly Arg Gly Gly Glu Glu Lys Lys Lys Glu Lys Glu Glu
        290                 295                 300

Gln Glu Glu Arg Glu Thr Lys Thr Pro Glu Cys Pro Ser His Thr Gln
305                 310                 315                 320

Pro Leu Gly Val Gln Arg Phe Ala Gln Ala Gln Gln Leu Pro Leu
            325                 330                 335

Glu Ser Leu Gly Trp Asp Val Ala Glu Leu Gln Leu Asn His Thr Gly
            340                 345                 350

Pro Gln Gln Asp Pro Arg Leu Tyr Trp Gln Gly Gly Pro Ala Leu Gly
            355                 360                 365

Arg Ser Phe Leu His Gly Pro Glu Leu Asp Lys Gly Gln Leu Arg Ile
            370                 375                 380

His Arg Asp Gly Ile Tyr Met Val His Ile Gln Val Thr Leu Ala Ile
385                 390                 395                 400

Cys Ser Ser Thr Thr Ala Ser Arg His His Pro Thr Thr Leu Ala Val
                405                 410                 415

Gly Ile Cys Ser Pro Ala Ser Arg Ser Ile Ser Leu Leu Arg Leu Ser
            420                 425                 430

Phe His Gln Gly Cys Thr Ile Ala Ser Gln Arg Leu Thr Pro Leu Ala
            435                 440                 445

Arg Gly Asp Thr Leu Cys Thr Asn Leu Thr Gly Thr Leu Leu Pro Ser
            450                 455                 460

Arg Asn Thr Asp Glu Thr Phe Phe Gly Val Gln Trp Val Arg Pro
465                 470                 475

<210> SEQ ID NO 168
<211> LENGTH: 1437
<212> TYPE: DNA
<213> ORGANISM: Artificial
<220> FEATURE:
<223> OTHER INFORMATION: The nucleotide sequence of CD3-CD70 BsM_D dimer

<400> SEQUENCE: 168
gacatcaagc tgcagcagag cggcgccgag ctggcccgcc ccggcgccag cgtgaagatg      60
agctgcaaga ccagcggcta caccttcacc cgctacacca tgcactgggt gaagcagcgc     120
cccggccagg gcctggagtg gatcggctac atcaaccccg ccgcggctac accaactac     180 aaccagaagt tcaaggacaa ggccaccctg accaccgaca gagcagcag caccgcctac     240 atgcagctga gcagcctgac cagcgaggac agcgccgtgt actactgcgc cgctactac     300 gacgaccact actgcctgga ctactggggc cagggcacca ccctgaccgt gagcagcgtg     360
gagggcggca gcggcggcag cggcggcagc ggcggcagcg gcggcgtgga cgacatccag     420
ctgacccaga gccccgccat catgagcgcc agccccggcg agaaggtgac catgacctgc     480
cgcgccagca gcagcgtgag ctacatgaac tggtaccagc agaagagcgg caccagcccc     540
aagcgctgga tctacgacac cagcaaggtg gccagcggcg tgccctaccg cttcagcggc     600
agcggcagcg gcaccagcta cagcctgacc atcagcagca tggaggccga ggacgccgcc     660
acctactact gccagcagtg gagcagcaac cccctgacct cggcgccgg caccaagctg     720 gagctgaagg ccagcaagag caagaaggag atcttccgct ggcccgagag ccccaaggcc     780
caggccagca gcgtgcccac cgcccagccc caggccgagg cagcctggc caaggccacc     840 accgccccg ccaccaccg caacaccggc cgcggcggcg aggagaagaa gaaggagaag     900

```
gagaaggagg agcaggagga gcgcgagacc aagaccccg  agtgcccag  ccacacccag    960 cccctgggcg tgcagcgctt cgcccaggcc cagcagcagc tgcccctgga gagcctgggc   1020
tgggacgtgg ccgagctgca gctgaaccac accggccccc agcaggaccc ccgcctgtac   1080 tgcagggcg  ccccgccct  gggccgcagc ttcctgcacg ccccgagct  ggacaagggc   1140 cagctgcgca tccaccgcga cggcatctac atggtgcaca tccaggtgac cctggccatc   1200
tgcagcagca ccaccgccag ccgccaccac cccaccaccc tggccgtggg catctgcagc   1260 ccgccagcc  gcagcatcag cctgctgcgc ctgagcttcc accagggctg caccatcgcc   1320
agccagcgcc tgacccccct ggccgcggc  gacaccctgt gcaccaacct gaccggcacc   1380
ctgctgccca gccgcaacac cgacgagacc ttcttcggcg tgcagtgggt gcgcccc     1437
```

<210> SEQ ID NO 169
<211> LENGTH: 243
<212> TYPE: PRT
<213> ORGANISM: Artificial
<220> FEATURE:
<223> OTHER INFORMATION: The amino acid sequence of anti-CD3 scFv

<400> SEQUENCE: 169

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys
```

<210> SEQ ID NO 170
<211> LENGTH: 119
<212> TYPE: PRT

<213> ORGANISM: Artificial
<220> FEATURE:
<223> OTHER INFORMATION: The amino acid sequence of anti-CD3 scFv heavy chain variable region

<400> SEQUENCE: 170

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
            115
```

<210> SEQ ID NO 171
<211> LENGTH: 106
<212> TYPE: PRT
<213> ORGANISM: Artificial
<220> FEATURE:
<223> OTHER INFORMATION: The amino acid sequence of anti-CD3 scFv light chain variable region

<400> SEQUENCE: 171

```
Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105
```

<210> SEQ ID NO 172
<211> LENGTH: 205
<212> TYPE: PRT
<213> ORGANISM: Artificial
<220> FEATURE:
<223> OTHER INFORMATION: The amino acid sequence of 4-1BBL extracellular domain

<400> SEQUENCE: 172

```
Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
            20                  25                  30
```

Ala Gly Leu Leu Asp Leu Arg Gln Gly Met Phe Ala Gln Leu Val Ala
            35                  40                  45

Gln Asn Val Leu Leu Ile Asp Gly Pro Leu Ser Trp Tyr Ser Asp Pro
        50                  55                  60

Gly Leu Ala Gly Val Ser Leu Thr Gly Gly Leu Ser Tyr Lys Glu Asp
65                  70                  75                  80

Thr Lys Glu Leu Val Val Ala Lys Ala Gly Val Tyr Tyr Val Phe Phe
                85                  90                  95

Gln Leu Glu Leu Arg Arg Val Val Ala Gly Glu Gly Ser Gly Ser Val
            100                 105                 110

Ser Leu Ala Leu His Leu Gln Pro Leu Arg Ser Ala Ala Gly Ala Ala
        115                 120                 125

Ala Leu Ala Leu Thr Val Asp Leu Pro Pro Ala Ser Ser Glu Ala Arg
130                 135                 140

Asn Ser Ala Phe Gly Phe Gln Gly Arg Leu Leu His Leu Ser Ala Gly
145                 150                 155                 160

Gln Arg Leu Gly Val His Leu His Thr Glu Ala Arg Ala Arg His Ala
            165                 170                 175

Trp Gln Leu Thr Gln Gly Ala Thr Val Leu Gly Leu Phe Arg Val Thr
        180                 185                 190

Pro Glu Ile Pro Ala Gly Leu Pro Ser Pro Arg Ser Glu
        195                 200                 205

<210> SEQ ID NO 173
<211> LENGTH: 238
<212> TYPE: PRT
<213> ORGANISM: Artificial
<220> FEATURE:
<223> OTHER INFORMATION: The amino acid sequence of B7RP-1 extracellular
      domain

<400> SEQUENCE: 173

Asp Thr Gln Glu Lys Glu Val Arg Ala Met Val Gly Ser Asp Val Glu
1               5                   10                  15

Leu Ser Cys Ala Cys Pro Glu Gly Ser Arg Phe Asp Leu Asn Asp Val
            20                  25                  30

Tyr Val Tyr Trp Gln Thr Ser Glu Ser Lys Thr Val Val Thr Tyr His
        35                  40                  45

Ile Pro Gln Asn Ser Ser Leu Glu Asn Val Asp Ser Arg Tyr Arg Asn
    50                  55                  60

Arg Ala Leu Met Ser Pro Ala Gly Met Leu Arg Gly Asp Phe Ser Leu
65                  70                  75                  80

Arg Leu Phe Asn Val Thr Pro Gln Asp Glu Gln Lys Phe His Cys Leu
                85                  90                  95

Val Leu Ser Gln Ser Leu Gly Phe Gln Glu Val Leu Ser Val Glu Val
            100                 105                 110

Thr Leu His Val Ala Ala Asn Phe Ser Val Pro Val Val Ser Ala Pro
        115                 120                 125

His Ser Pro Ser Gln Asp Glu Leu Thr Phe Thr Cys Thr Ser Ile Asn
    130                 135                 140

Gly Tyr Pro Arg Pro Asn Val Tyr Trp Ile Asn Lys Thr Asp Asn Ser
145                 150                 155                 160

Leu Leu Asp Gln Ala Leu Gln Asn Asp Thr Val Phe Leu Asn Met Arg
                165                 170                 175

Gly Leu Tyr Asp Val Val Ser Val Leu Arg Ile Ala Arg Thr Pro Ser

```
                180               185               190
Val Asn Ile Gly Cys Cys Ile Glu Asn Val Leu Leu Gln Gln Asn Leu
            195                 200                 205

Thr Val Gly Ser Gln Thr Gly Asn Asp Ile Gly Glu Arg Asp Lys Ile
            210                 215                 220

Thr Glu Asn Pro Val Ser Thr Gly Glu Lys Asn Ala Ala Thr
225                 230                 235

<210> SEQ ID NO 174
<211> LENGTH: 133
<212> TYPE: PRT
<213> ORGANISM: Artificial
<220> FEATURE:
<223> OTHER INFORMATION: The amino acid sequence of OX40L extracellular
      domain

<400> SEQUENCE: 174

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130

<210> SEQ ID NO 175
<211> LENGTH: 128
<212> TYPE: PRT
<213> ORGANISM: Artificial
<220> FEATURE:
<223> OTHER INFORMATION: The amino acid sequence of GITRL extracellular
      domain

<400> SEQUENCE: 175

Gln Leu Glu Thr Ala Lys Glu Pro Cys Met Ala Lys Phe Gly Pro Leu
1               5                   10                  15

Pro Ser Lys Trp Gln Met Ala Ser Ser Glu Pro Pro Cys Val Asn Lys
            20                  25                  30

Val Ser Asp Trp Lys Leu Glu Ile Leu Gln Asn Gly Leu Tyr Leu Ile
        35                  40                  45

Tyr Gly Gln Val Ala Pro Asn Ala Asn Tyr Asn Asp Val Ala Pro Phe
    50                  55                  60

Glu Val Arg Leu Tyr Lys Asn Lys Asp Met Ile Gln Thr Leu Thr Asn
65                  70                  75                  80

Lys Ser Lys Ile Gln Asn Val Gly Gly Thr Tyr Glu Leu His Val Gly
                85                  90                  95

Asp Thr Ile Asp Leu Ile Phe Asn Ser Glu His Gln Val Leu Lys Asn
```

```
            100                 105                 110
Asn Thr Tyr Trp Gly Ile Ile Leu Leu Ala Asn Pro Gln Phe Ile Ser
        115                 120                 125
```

<210> SEQ ID NO 176
<211> LENGTH: 155
<212> TYPE: PRT
<213> ORGANISM: Artificial
<220> FEATURE:
<223> OTHER INFORMATION: The amino acid sequence of CD70 extracellular
      domain

<400> SEQUENCE: 176

```
Gln Arg Phe Ala Gln Ala Gln Gln Gln Leu Pro Leu Glu Ser Leu Gly
1               5                   10                  15

Trp Asp Val Ala Glu Leu Gln Leu Asn His Thr Gly Pro Gln Gln Asp
            20                  25                  30

Pro Arg Leu Tyr Trp Gln Gly Gly Pro Ala Leu Gly Arg Ser Phe Leu
        35                  40                  45

His Gly Pro Glu Leu Asp Lys Gly Gln Leu Arg Ile His Arg Asp Gly
    50                  55                  60

Ile Tyr Met Val His Ile Gln Val Thr Leu Ala Ile Cys Ser Ser Thr
65                  70                  75                  80

Thr Ala Ser Arg His His Pro Thr Thr Leu Ala Val Gly Ile Cys Ser
                85                  90                  95

Pro Ala Ser Arg Ser Ile Ser Leu Leu Arg Leu Ser Phe His Gln Gly
            100                 105                 110

Cys Thr Ile Ala Ser Gln Arg Leu Thr Pro Leu Ala Arg Gly Asp Thr
        115                 120                 125

Leu Cys Thr Asn Leu Thr Gly Thr Leu Leu Pro Ser Arg Asn Thr Asp
    130                 135                 140

Glu Thr Phe Phe Gly Val Gln Trp Val Arg Pro
145                 150                 155
```

<210> SEQ ID NO 177
<211> LENGTH: 729
<212> TYPE: DNA
<213> ORGANISM: Artificial
<220> FEATURE:
<223> OTHER INFORMATION: The nucleotide sequence of anti-CD3 scFv

<400> SEQUENCE: 177

```
gacatcaagc tgcagcagag cggcgccgag ctggcccgcc ccggcgccag cgtgaagatg      60
agctgcaaga ccagcggcta caccttcacc cgctacacca tgcactgggt gaagcagcgc     120
cccggccagg gcctggagtg gatcggctac atcaaccccg ccgcggcta caccaactac      180 aaccagaagt tcaaggacaa ggccaccctg accaccgaca gagcagcag caccgcctac     240 atgcagctga gcagcctgac cagcgaggac agcgccgtgt actactgcgc ccgctactac     300
gacgaccact actgcctgga ctactggggc cagggcacca ccctgaccgt gagcagcgtg     360
gagggcggca gcggcggcag cggcggcagc ggcggcagcg gcggcgtgga cgacatccag     420
ctgacccaga gccccgccat catgagcgcc agccccggcg agaaggtgac catgacctgc     480
cgcgccagca gcagcgtgag ctacatgaac tggtaccagc agaagagcgg caccagcccc     540
aagcgctgga tctacgacac cagcaaggtg gccagcggcg tgccctaccg cttcagcggc     600
agcggcagcg gcaccagcta cagcctgacc atcagcagca tggaggccga ggacgccgcc     660
acctactact gccagcagtg gagcagcaac cccctgacct cggcgccgg caccaagctg     720
```

```
gagctgaag                                                                729
```

<210> SEQ ID NO 178
<211> LENGTH: 357
<212> TYPE: DNA
<213> ORGANISM: Artificial
<220> FEATURE:
<223> OTHER INFORMATION: The nucleotide sequence of anti-CD3 scFv heavy
      chain variable region

<400> SEQUENCE: 178

```
gacatcaagc tgcagcagag cggcgccgag ctggcccgcc ccggcgccag cgtgaagatg    60
agctgcaaga ccagcggcta caccttcacc cgctacacca tgcactgggt gaagcagcgc   120
cccggccagg gcctggagtg gatcggctac atcaacccca gccgcggcta caccaactac   180
aaccagaagt tcaaggacaa ggccaccctg accaccgaca gagcagcag caccgcctac   240 atgcagctga gcagcctgac cagcgaggac agcgccgtgt actactgcgc cgctactac   300 gacgaccact actgcctgga ctactggggc cagggcacca ccctgaccgt gagcagc     357
```

<210> SEQ ID NO 179
<211> LENGTH: 318
<212> TYPE: DNA
<213> ORGANISM: Artificial
<220> FEATURE:
<223> OTHER INFORMATION: The nucleotide sequence of anti-CD3 scFv light
      chain variable region

<400> SEQUENCE: 179

```
gacatccagc tgacccagag ccccgccatc atgagcgcca gccccggcga aaggtgacc    60 atgacctgcc gcgccagcag cagcgtgagc tacatgaact ggtaccagca aaagagcggc   120
accagcccca gcgctggat ctacgacacc agcaaggtgg ccagcggcgt gccctaccgc   180
ttcagcggca gcggcagcgg caccagctac agcctgacca tcagcagcat ggaggccgag   240
gacgccgcca cctactactg ccagcagtgg agcagcaacc ccctgacctt cggcgccggc   300
accaagctgg agctgaag                                                318
```

<210> SEQ ID NO 180
<211> LENGTH: 615
<212> TYPE: DNA
<213> ORGANISM: Artificial
<220> FEATURE:
<223> OTHER INFORMATION: The nucleotide sequence of 4-1BBL extracellular
      region

<400> SEQUENCE: 180

```
gcctgcccct gggccgtgag cggcgcccgc gccagccccg gcagcgccgc cagccccgc    60 ctgcgcgagg gccccgagct gagccccgac gaccccgccg gcctgctgga cctgcgccag   120
ggcatgttcg cccagctggt ggcccagaac gtgctgctga tcgacggccc cctgagctgg   180
tacagcgacc ccggcctggc cggcgtgagc ctgaccggcg gcctgagcta caaggaggac   240
accaaggagc tggtggtggc caaggccggc gtgtactacg tgttcttcca gctggagctg   300
cgccgcgtgg tggccggcga gggcagcggc agcgtgagcc tggccctgca cctgcagccc   360
ctgcgcagcg ccgccggcgc cgccgccctg gccctgaccg tggacctgcc cccgccagc   420 agcgaggccc gcaacagcgc cttcggcttc cagggccgcc tgctgcacct gagcgccggc   480
cagcgcctgg gcgtgcacct gcacaccgag gcccgcgccc gccacgcctg gcagctgacc   540
cagggcgcca ccgtgctggg cctgttccgc gtgaccccg agatccccgc cggcctgccc   600
```

```
agcccccgca gcgag                                                   615

<210> SEQ ID NO 181
<211> LENGTH: 714
<212> TYPE: DNA
<213> ORGANISM: Artificial
<220> FEATURE:
<223> OTHER INFORMATION: The nucleotide sequence of B7RP-1 extracellular
      domain

<400> SEQUENCE: 181
gacacccagg agaaggaggt gcgcgccatg gtgggcagcg acgtggagct gagctgcgcc    60
tgccccgagg gcagccgctt cgacctgaac gacgtgtacg tgtactggca gaccagcgag   120
agcaagaccg tggtgaccta ccacatcccc cagaacagca gcctggagaa cgtggacagc   180
cgctaccgca accgcgccct gatgagcccc gccggcatgc tgcgcggcga cttcagcctg   240
cgcctgttca cgtgaccccc caggacgag cagaagttcc actgcctggt gctgagccag   300
agcctgggct tccaggaggt gctgagcgtg aggtgaccc tgcacgtggc cgccaacttc   360
agcgtgcccg tggtgagcgc ccccacagc cccagccagg acgagctgac cttcacctgc   420
accagcatca acggctaccc ccgccccaac gtgtactgga tcaacaagac cgacaacagc   480
ctgctggacc aggccctgca gaacgacacc gtgttcctga acatgcgcgg cctgtacgac   540
gtggtgagcg tgctgcgcat cgcccgcacc cccagcgtga acatcggctg ctgcatcgag   600
aacgtgctgc tgcagcagaa cctgaccgtg ggcagccaga ccggcaacga catcggcgag   660
cgcgacaaga tcaccgagaa ccccgtgagc accggcgaga agaacgccgc cacc         714

<210> SEQ ID NO 182
<211> LENGTH: 399
<212> TYPE: DNA
<213> ORGANISM: Artificial
<220> FEATURE:
<223> OTHER INFORMATION: The nucleotide sequence of OX40L extracellular
      region

<400> SEQUENCE: 182
caggtgagcc accgctaccc ccgcatccag agcatcaagg tgcagttcac cgagtacaag    60
aaggagaagg gcttcatcct gaccagccag aaggaggacg agatcatgaa ggtgcagaac   120
aacagcgtga tcatcaactg cgacggcttc tacctgatca gcctgaaggg ctacttcagc   180
caggaggtga acatcagcct gcactaccag aaggacgagg agcccctgtt ccagctgaag   240
aaggtgcgca gcgtgaacag cctgatggtg gccagcctga cctacaagga caaggtgtac   300
ctgaacgtga ccaccgacaa caccagcctg gacgacttcc acgtgaacgg cggcgagctg   360
atcctgatcc accagaaccc cggcgagttc tgcgtgctg                          399

<210> SEQ ID NO 183
<211> LENGTH: 384
<212> TYPE: DNA
<213> ORGANISM: Artificial
<220> FEATURE:
<223> OTHER INFORMATION: The nucleotide sequence of GITRL extracellular
      region

<400> SEQUENCE: 183
cagctggaga ccgccaagga gccctgcatg gccaagttcg gccccctgcc cagcaagtgg    60
cagatggcca gcagcgagcc ccctgcgtg aacaaggtga gcgactggaa gctggagatc   120
ctgcagaacg gcctgtacct gatctacggc caggtggccc ccaacgccaa ctacaacgac   180
```

-continued

```
gtggcccct tcgaggtgcg cctgtacaag aacaaggaca tgatccagac cctgaccaac    240
aagagcaaga tccagaacgt gggcggcacc tacgagctgc acgtgggcga ccatcgac     300 ctgatcttca acagcgagca ccaggtgctg aagaacaaca cctactgggg catcatcctg   360
ctggccaacc cccagttcat cagc                                          384
```

<210> SEQ ID NO 184
<211> LENGTH: 465
<212> TYPE: DNA
<213> ORGANISM: Artificial
<220> FEATURE:
<223> OTHER INFORMATION: The nucleotide sequence of CD70 extracellular
      region

<400> SEQUENCE: 184

```
cagcgcttcg cccaggccca gcagcagctg cccctggaga gcctgggctg ggacgtggcc    60
gagctgcagc tgaaccacac cggcccccag caggaccccc gcctgtactg gcagggcggc   120
cccgccctgg gccgcagctt cctgcacggc cccgagctgg acaagggcca gctgcgcatc   180
caccgcgacg gcatctacat ggtgcacatc caggtgaccc tggccatctg cagcagcacc   240
accgccagcc gccaccaccc caccaccctg gccgtgggca tctgcagccc cgccagccgc   300
agcatcagcc tgctgcgcct gagcttccac cagggctgca ccatcgccag ccagcgcctg   360 accccctgg cccgcggcga caccctgtgc accaacctga ccggcaccct gctgcccagc    420
cgcaacaccg acgagacctt cttcggcgtg cagtgggtgc ccccc                  465
```

<210> SEQ ID NO 185
<211> LENGTH: 19
<212> TYPE: PRT
<213> ORGANISM: Artificial
<220> FEATURE:
<223> OTHER INFORMATION: The amino acid sequence of the secretory signal
      peptide

<400> SEQUENCE: 185

Met Thr Arg Leu Thr Val Leu Ala Leu Leu Ala Gly Leu Leu Ala Ser
1               5                   10                  15

Ser Arg Ala

<210> SEQ ID NO 186
<211> LENGTH: 57
<212> TYPE: DNA
<213> ORGANISM: Artificial
<220> FEATURE:
<223> OTHER INFORMATION: The nucleotide sequence of the secretory signal
      peptide

<400> SEQUENCE: 186

```
atgacccgcc tgaccgtgct ggccctgctg gccggcctgc tggccagcag ccgcgcc       57
```

<210> SEQ ID NO 187
<211> LENGTH: 59
<212> TYPE: DNA
<213> ORGANISM: Artificial
<220> FEATURE:
<223> OTHER INFORMATION: pcDNA3.1-Sig-F

<400> SEQUENCE: 187

```
gtgctggata tctgcagaat tcgccgccac catgacccgg ctgaccgtgc tggccctgc     59
```

<210> SEQ ID NO 188

```
<211> LENGTH: 49
<212> TYPE: DNA
<213> ORGANISM: Artificial
<220> FEATURE:
<223> OTHER INFORMATION: Sig-R

<400> SEQUENCE: 188
ggccctggag gaggccagca ggccggccag cagggccagc acggtcagc                    49

<210> SEQ ID NO 189
<211> LENGTH: 41
<212> TYPE: DNA
<213> ORGANISM: Artificial
<220> FEATURE:
<223> OTHER INFORMATION: Sig-CD3-F

<400> SEQUENCE: 189
gctggcctcc tcagggccg acatcaagct gcagcagagc g                             41

<210> SEQ ID NO 190
<211> LENGTH: 20
<212> TYPE: DNA
<213> ORGANISM: Artificial
<220> FEATURE:
<223> OTHER INFORMATION: CD3-R

<400> SEQUENCE: 190
cttcagctcc agcttggtgc                                                    20

<210> SEQ ID NO 191
<211> LENGTH: 86
<212> TYPE: DNA
<213> ORGANISM: Artificial
<220> FEATURE:
<223> OTHER INFORMATION: CD3-(GGGGS)3-4-1BBL-F

<400> SEQUENCE: 191
gcaccaagct ggagctgaag ggcggcggcg gcagcggcgg cggcggcagc ggcggcggcg        60
gcagcgcctg ccctgggcc gtgagc                                              86

<210> SEQ ID NO 192
<211> LENGTH: 52
<212> TYPE: DNA
<213> ORGANISM: Artificial
<220> FEATURE:
<223> OTHER INFORMATION: pcDNA3.1-4-1BBL-R

<400> SEQUENCE: 192
ctgatcagcg gtttaaactt aagctttcac tcgctgcggg ggctgggcag gc                52

<210> SEQ ID NO 193
<211> LENGTH: 41
<212> TYPE: DNA
<213> ORGANISM: Artificial
<220> FEATURE:
<223> OTHER INFORMATION: CD3-IgD-F

<400> SEQUENCE: 193
gcaccaagct ggagctgaag gccagcaaga gcaagaagga g                            41

<210> SEQ ID NO 194
<211> LENGTH: 21
<212> TYPE: DNA
<213> ORGANISM: Artificial
<220> FEATURE:
<223> OTHER INFORMATION: IgD-R
```

```
<400> SEQUENCE: 194
cacgcccagg ggctgggtgt g                                         21

<210> SEQ ID NO 195
<211> LENGTH: 44
<212> TYPE: DNA
<213> ORGANISM: Artificial
<220> FEATURE:
<223> OTHER INFORMATION: IgD-4-1BBL-F

<400> SEQUENCE: 195
gccacaccca gccctgggc gtggcctgcc cctgggccgt gagc                 44

<210> SEQ ID NO 196
<211> LENGTH: 89
<212> TYPE: DNA
<213> ORGANISM: Artificial
<220> FEATURE:
<223> OTHER INFORMATION: CD3-(GGGGS)3-B7RP-1-F

<400> SEQUENCE: 196
cggcaccaag ctggagctga agggcggcgg cggcagcggc ggcggcggca gcggcggcgg    60
cggcagcgac acccaggaga aggaggtgc                                     89

<210> SEQ ID NO 197
<211> LENGTH: 50
<212> TYPE: DNA
<213> ORGANISM: Artificial
<220> FEATURE:
<223> OTHER INFORMATION: pcDNA3.1-B7RP-1-R

<400> SEQUENCE: 197
ctgatcagcg gtttaaactt aagctttcag gtggcggcgt tcttctcgcc              50

<210> SEQ ID NO 198
<211> LENGTH: 45
<212> TYPE: DNA
<213> ORGANISM: Artificial
<220> FEATURE:
<223> OTHER INFORMATION: IgD-B7RP-1-F

<400> SEQUENCE: 198
gccacaccca gccctgggc gtggacaccc aggagaagga ggtgc                    45

<210> SEQ ID NO 199
<211> LENGTH: 90
<212> TYPE: DNA
<213> ORGANISM: Artificial
<220> FEATURE:
<223> OTHER INFORMATION: CD3-(GGGGS)3-OX40L-F

<400> SEQUENCE: 199
cggcaccaag ctggagctga agggcggcgg cggcagcggc ggcggcggca gcggcggcgg    60
cggcagccag gtgagccacc gctaccccg                                     90

<210> SEQ ID NO 200
<211> LENGTH: 48
<212> TYPE: DNA
<213> ORGANISM: Artificial
<220> FEATURE:
<223> OTHER INFORMATION: pcDNA3.1-OX40L-R

<400> SEQUENCE: 200
```
ctgatcagcg gtttaaactt aagctttcac agcacgcaga actcgccg        48

<210> SEQ ID NO 201
<211> LENGTH: 44
<212> TYPE: DNA
<213> ORGANISM: Artificial
<220> FEATURE:
<223> OTHER INFORMATION: IgD-OX40L-F

<400> SEQUENCE: 201
cacacccagc ccctgggcgt gcaggtgagc caccgctacc cccg        44

<210> SEQ ID NO 202
<211> LENGTH: 88
<212> TYPE: DNA
<213> ORGANISM: Artificial
<220> FEATURE:
<223> OTHER INFORMATION: CD3-(GGGGS)3-GITRL-F

<400> SEQUENCE: 202
ggcaccaagc tggagctgaa gggcggcggc ggcagcggcg cggcggcag cggcggcggc        60 ggcagccagc tggagaccgc caaggagc        88

<210> SEQ ID NO 203
<211> LENGTH: 50
<212> TYPE: DNA
<213> ORGANISM: Artificial
<220> FEATURE:
<223> OTHER INFORMATION: pcDNA3.1-GITRL-R

<400> SEQUENCE: 203
ctgatcagcg gtttaaactt aagctttcag ctgatgaact gggggttggc        50

<210> SEQ ID NO 204
<211> LENGTH: 43
<212> TYPE: DNA
<213> ORGANISM: Artificial
<220> FEATURE:
<223> OTHER INFORMATION: IgD-GITRL-F

<400> SEQUENCE: 204
cacacccagc ccctgggcgt gcagctggag accgccaagg agc        43

<210> SEQ ID NO 205
<211> LENGTH: 88
<212> TYPE: DNA
<213> ORGANISM: Artificial
<220> FEATURE:
<223> OTHER INFORMATION: CD3-(GGGGS)3-CD70-F

<400> SEQUENCE: 205
ggcaccaagc tggagctgaa gggcggcggc ggcagcggcg cggcggcag cggcggcggc        60 ggcagccagc gcttcgccca ggcccagc        88

<210> SEQ ID NO 206
<211> LENGTH: 49
<212> TYPE: DNA
<213> ORGANISM: Artificial
<220> FEATURE:
<223> OTHER INFORMATION: pcDNA3.1-CD70-R

<400> SEQUENCE: 206
ctgatcagcg gtttaaactt aagctttcag gggcgcaccc actgcacgc        49

<210> SEQ ID NO 207
<211> LENGTH: 43
<212> TYPE: DNA
<213> ORGANISM: Artificial
<220> FEATURE:
<223> OTHER INFORMATION: IgD-CD70-F

<400> SEQUENCE: 207
cacacccagc ccctgggcgt gcagcgcttc gcccaggccc agc           43

<210> SEQ ID NO 208
<211> LENGTH: 15
<212> TYPE: PRT
<213> ORGANISM: Artificial
<220> FEATURE:
<223> OTHER INFORMATION: The amino acid sequence of CD3-PD-1 BsAb_M
    monomer linker

<400> SEQUENCE: 208

Gly Gly Gly Gly Ser Gly Gly Gly Gly Ser Gly Gly Gly Gly Ser
1               5                   10                  15

<210> SEQ ID NO 209
<211> LENGTH: 45
<212> TYPE: DNA
<213> ORGANISM: Artificial
<220> FEATURE:
<223> OTHER INFORMATION: The nucleotide sequence of CD3-PD-1 BsAb_M
    monomer linker

<400> SEQUENCE: 209
ggcggcggcg gcagcggcgg cggcggcagc ggcggcggcg gcagc          45

<210> SEQ ID NO 210
<211> LENGTH: 81
<212> TYPE: PRT
<213> ORGANISM: Artificial
<220> FEATURE:
<223> OTHER INFORMATION: The amino acid sequence of CD3-PD-1 BsAb_D
    dimer linker

<400> SEQUENCE: 210

Ala Ser Lys Ser Lys Glu Ile Phe Arg Trp Pro Glu Ser Pro Lys
1               5                   10                  15

Ala Gln Ala Ser Ser Val Pro Thr Ala Gln Pro Gln Ala Glu Gly Ser
            20                  25                  30

Leu Ala Lys Ala Thr Thr Ala Pro Ala Thr Thr Arg Asn Thr Gly Arg
        35                  40                  45

Gly Gly Glu Glu Lys Lys Lys Glu Lys Glu Lys Glu Glu Gln Glu Glu
    50                  55                  60

Arg Glu Thr Lys Thr Pro Glu Cys Pro Ser His Thr Gln Pro Leu Gly
65                  70                  75                  80

Val

<210> SEQ ID NO 211
<211> LENGTH: 243
<212> TYPE: DNA
<213> ORGANISM: Artificial
<220> FEATURE:
<223> OTHER INFORMATION: The nucleotide sequence of CD3-PD-1 BsAb_D
    dimer linker

<400> SEQUENCE: 211
gccagcaaga gcaagaagga gatcttccgc tggcccgaga gccccaaggc ccaggccagc   60

```
agcgtgccca ccgcccagcc ccaggccgag ggcagcctgg ccaaggccac caccgccccc    120
gccaccaccc gcaacaccgg ccgcggcggc gaggagaaga agaaggagaa ggagaaggag    180
gagcaggagg agcgcgagac caagacccccc gagtgcccca gccacaccca gcccctgggc    240
gtg                                                                  243
```

```
<210> SEQ ID NO 212
<211> LENGTH: 150
<212> TYPE: PRT
<213> ORGANISM: Artificial
<220> FEATURE:
<223> OTHER INFORMATION: The amino acid sequence of the extracellular
      domain of the human T cell inhibitory molecule PD-1

<400> SEQUENCE: 212
```

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

```
<210> SEQ ID NO 213
<211> LENGTH: 126
<212> TYPE: PRT
<213> ORGANISM: Artificial
<220> FEATURE:
<223> OTHER INFORMATION: The amino acid sequence of the extracellular
      domain of the human T cell inhibitory molecule CTLA-4

<400> SEQUENCE: 213
```

Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr

```
                    100                 105                 110
Gln Ile Tyr Val Ile Asp Pro Glu Pro Cys Pro Asp Ser Asp
            115                 120                 125
```

<210> SEQ ID NO 214
<211> LENGTH: 422
<212> TYPE: PRT
<213> ORGANISM: Artificial
<220> FEATURE:
<223> OTHER INFORMATION: The amino acid sequence of the extracellular
      domain of the human T cell inhibitory molecule LAG-3

<400> SEQUENCE: 214

```
Val Pro Val Val Trp Ala Gln Glu Gly Ala Pro Ala Gln Leu Pro Cys
1               5                   10                  15
Ser Pro Thr Ile Pro Leu Gln Asp Leu Ser Leu Leu Arg Arg Ala Gly
                20                  25                  30
Val Thr Trp Gln His Gln Pro Asp Ser Gly Pro Pro Ala Ala Ala Pro
            35                  40                  45
Gly His Pro Leu Ala Pro Gly Pro His Pro Ala Ala Pro Ser Ser Trp
        50                  55                  60
Gly Pro Arg Pro Arg Arg Tyr Thr Val Leu Ser Val Gly Pro Gly Gly
65                  70                  75                  80
Leu Arg Ser Gly Arg Leu Pro Leu Gln Pro Arg Val Gln Leu Asp Glu
                85                  90                  95
Arg Gly Arg Gln Arg Gly Asp Phe Ser Leu Trp Leu Arg Pro Ala Arg
            100                 105                 110
Arg Ala Asp Ala Gly Glu Tyr Arg Ala Ala Val His Leu Arg Asp Arg
        115                 120                 125
Ala Leu Ser Cys Arg Leu Arg Leu Arg Leu Gly Gln Ala Ser Met Thr
130                 135                 140
Ala Ser Pro Pro Gly Ser Leu Arg Ala Ser Asp Trp Val Ile Leu Asn
145                 150                 155                 160
Cys Ser Phe Ser Arg Pro Asp Arg Pro Ala Ser Val His Trp Phe Arg
                165                 170                 175
Asn Arg Gly Gln Gly Arg Val Pro Val Arg Glu Ser Pro His His His
            180                 185                 190
Leu Ala Glu Ser Phe Leu Phe Leu Pro Gln Val Ser Pro Met Asp Ser
        195                 200                 205
Gly Pro Trp Gly Cys Ile Leu Thr Tyr Arg Asp Gly Phe Asn Val Ser
        210                 215                 220
Ile Met Tyr Asn Leu Thr Val Leu Gly Leu Glu Pro Pro Thr Pro Leu
225                 230                 235                 240
Thr Val Tyr Ala Gly Ala Gly Ser Arg Val Gly Leu Pro Cys Arg Leu
                245                 250                 255
Pro Ala Gly Val Gly Thr Arg Ser Phe Leu Thr Ala Lys Trp Thr Pro
            260                 265                 270
Pro Gly Gly Gly Pro Asp Leu Leu Val Thr Gly Asp Asn Gly Asp Phe
        275                 280                 285
Thr Leu Arg Leu Glu Asp Val Ser Gln Ala Gln Ala Gly Thr Tyr Thr
        290                 295                 300
Cys His Ile His Leu Gln Glu Gln Gln Leu Asn Ala Thr Val Thr Leu
305                 310                 315                 320
Ala Ile Ile Thr Val Thr Pro Lys Ser Phe Gly Ser Pro Gly Ser Leu
                325                 330                 335
```

Gly Lys Leu Leu Cys Glu Val Thr Pro Val Ser Gly Gln Glu Arg Phe
            340                 345                 350

Val Trp Ser Ser Leu Asp Thr Pro Ser Gln Arg Ser Phe Ser Gly Pro
        355                 360                 365

Trp Leu Glu Ala Gln Glu Ala Gln Leu Leu Ser Gln Pro Trp Gln Cys
        370                 375                 380

Gln Leu Tyr Gln Gly Glu Arg Leu Leu Gly Ala Ala Val Tyr Phe Thr
385                 390                 395                 400

Glu Leu Ser Ser Pro Gly Ala Gln Arg Ser Gly Arg Ala Pro Gly Ala
                405                 410                 415

Leu Pro Ala Gly His Leu
            420

<210> SEQ ID NO 215
<211> LENGTH: 181
<212> TYPE: PRT
<213> ORGANISM: Artificial
<220> FEATURE:
<223> OTHER INFORMATION: The amino acid sequence of the extracellular
      domain of the human T cell inhibitory molecule TIM-3

<400> SEQUENCE: 215

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
            20                  25                  30

Gly Lys Gly Ala Cys Pro Val Phe Glu Cys Gly Asn Val Val Leu Arg
        35                  40                  45

Thr Asp Glu Arg Asp Val Asn Tyr Trp Thr Ser Arg Tyr Trp Leu Asn
    50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

Met Asn Asp Glu Lys Phe Asn Leu Lys Leu Val Ile Lys Pro Ala Lys
            100                 105                 110

Val Thr Pro Ala Pro Thr Arg Gln Arg Asp Phe Thr Ala Ala Phe Pro
        115                 120                 125

Arg Met Leu Thr Thr Arg Gly His Gly Pro Ala Glu Thr Gln Thr Leu
    130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg Ile Gly
            180

<210> SEQ ID NO 216
<211> LENGTH: 120
<212> TYPE: PRT
<213> ORGANISM: Artificial
<220> FEATURE:
<223> OTHER INFORMATION: The amino acid sequence of the extracellular
      domain of the human T cell inhibitory molecule TIGIT

<400> SEQUENCE: 216

Met Met Thr Gly Thr Ile Glu Thr Thr Gly Asn Ile Ser Ala Glu Lys
1               5                   10                  15

```
Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Val Ala Glu
            100                 105                 110

His Gly Ala Arg Phe Gln Ile Pro
        115                 120

<210> SEQ ID NO 217
<211> LENGTH: 127
<212> TYPE: PRT
<213> ORGANISM: Artificial
<220> FEATURE:
<223> OTHER INFORMATION: The amino acid sequence of the extracellular
      domain of the human T cell inhibitory molecule BTLA

<400> SEQUENCE: 217

Lys Glu Ser Cys Asp Val Gln Leu Tyr Ile Lys Arg Gln Ser Glu His
1               5                   10                  15

Ser Ile Leu Ala Gly Asp Pro Phe Glu Leu Glu Cys Pro Val Lys Tyr
            20                  25                  30

Cys Ala Asn Arg Pro His Val Thr Trp Cys Lys Leu Asn Gly Thr Thr
        35                  40                  45

Cys Val Lys Leu Glu Asp Arg Gln Thr Ser Trp Lys Glu Glu Lys Asn
    50                  55                  60

Ile Ser Phe Phe Ile Leu His Phe Glu Pro Val Leu Pro Asn Asp Asn
65                  70                  75                  80

Gly Ser Tyr Arg Cys Ser Ala Asn Phe Gln Ser Asn Leu Ile Glu Ser
                85                  90                  95

His Ser Thr Thr Leu Tyr Val Thr Asp Val Lys Ser Ala Ser Glu Arg
            100                 105                 110

Pro Ser Lys Asp Glu Met Ala Ser Arg Pro Trp Leu Leu Tyr Arg
        115                 120                 125

<210> SEQ ID NO 218
<211> LENGTH: 494
<212> TYPE: PRT
<213> ORGANISM: Artificial
<220> FEATURE:
<223> OTHER INFORMATION: The amino acid sequence of CD3-PD-1 BsAb_M
      monomer

<400> SEQUENCE: 218

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60
```

```
Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Gly Gly Gly Gly Ser Gly Gly Gly Ser Gly Gly Gly
                245                 250                 255

Gly Ser Gln Val Gln Leu Val Glu Ser Gly Gly Val Val Gln Pro
            260                 265                 270

Gly Arg Ser Leu Arg Leu Asp Cys Lys Ala Ser Gly Ile Thr Phe Ser
        275                 280                 285

Asn Ser Gly Met His Trp Val Arg Gln Ala Pro Gly Lys Gly Leu Glu
    290                 295                 300

Trp Val Ala Val Ile Trp Tyr Asp Gly Ser Lys Arg Tyr Tyr Ala Asp
305                 310                 315                 320

Ser Val Lys Gly Arg Phe Thr Ile Ser Arg Asp Asn Ser Lys Asn Thr
                325                 330                 335

Leu Phe Leu Gln Met Asn Ser Leu Arg Ala Glu Asp Thr Ala Val Tyr
            340                 345                 350

Tyr Cys Ala Thr Asn Asp Asp Tyr Trp Gly Gln Gly Thr Leu Val Thr
        355                 360                 365

Val Ser Ser Gly Gly Gly Gly Ser Gly Gly Gly Gly Ser Gly Gly Gly
    370                 375                 380

Gly Ser Glu Ile Val Leu Thr Gln Ser Pro Ala Thr Leu Ser Leu Ser
385                 390                 395                 400

Pro Gly Glu Arg Ala Thr Leu Ser Cys Arg Ala Ser Gln Ser Val Ser
            405                 410                 415

Ser Tyr Leu Ala Trp Tyr Gln Gln Lys Pro Gly Gln Ala Pro Arg Leu
        420                 425                 430

Leu Ile Tyr Asp Ala Ser Asn Arg Ala Thr Gly Ile Pro Ala Arg Phe
    435                 440                 445

Ser Gly Ser Gly Ser Gly Thr Asp Phe Thr Leu Thr Ile Ser Ser Leu
        450                 455                 460

Glu Pro Glu Asp Phe Ala Val Tyr Tyr Cys Gln Gln Ser Ser Asn Trp
465                 470                 475                 480

Pro Arg Thr Phe Gly Gln Gly Thr Lys Val Glu Ile Lys Arg
```

<210> SEQ ID NO 219
<211> LENGTH: 1482
<212> TYPE: DNA
<213> ORGANISM: Artificial
<220> FEATURE:
<223> OTHER INFORMATION: The nucleotide sequence of CD3-PD-1 BsAb_M monomer

<400> SEQUENCE: 219

```
gacatcaagc tgcagcagag cggcgccgag ctggcccgcc ccggcgccag cgtgaagatg      60
agctgcaaga ccagcggcta caccttcacc cgctacacca tgcactgggt gaagcagcgc     120
cccggccagg gcctggagtg gatcggctac atcaacccca gccgcggcta caccaactac     180
aaccagaagt tcaaggacaa ggccaccctg accaccgaca gagcagcag caccgcctac     240
atgcagctga gcagcctgac cagcgaggac agcgccgtgt actactgcgc ccgctactac     300
gacgaccact actgcctgga ctactggggc cagggcacca ccctgaccgt gagcagcgtg     360
gagggcggca gcggcggcag cggcggcagc ggcggcagcg gcggcgtgga cgacatccag     420
ctgacccaga gccccgccat catgagcgcc agccccggcg agaaggtgac catgacctgc     480
cgcgccagca gcagcgtgag ctacatgaac tggtaccagc agaagagcgg caccagcccc     540
aagcgctgga tctacgacac cagcaaggtg gccagcggcg tgccctaccg cttcagcggc     600
agcggcagcg gcaccagcta cagcctgacc atcagcagca tggaggccga ggacgccgcc     660
acctactact gccagcagtg gagcagcaac cccctgacct cggcgccgg caccaagctg     720
gagctgaagg gcggcggcgg cagcggcggc ggcggcagcg gcggcggcgg cagccaggtg     780
cagctggtgg agagcggcgg cggcgtggtg cagcccggcc gcagcctgcg cctggactgc     840
aaggccagcg gcatcacctt cagcaacagc ggcatgcact gggtgcgcca ggcccccggc     900
aagggcctgg agtgggtggc cgtgatctgg tacgacggca gcaagcgcta ctacgccgac     960
agcgtgaagg gccgcttcac catcagccgc gacaacagca gaacaccct gttcctgcag    1020
atgaacagcc tgcgcgccga ggacaccgcc gtgtactact gcgccaccaa cgacgactac    1080
tggggccagg gcaccctggt gaccgtgagc agcggcggcg gcggcagcgg cggcggcggc    1140
agcggcggcg gcggcagcga gatcgtgctg acccagagcc ccgccaccct gagcctgagc    1200
cccggcgagc gcgccaccct gagctgccgc gccagccaga gcgtgagcag ctacctggcc    1260
tggtaccagc agaagcccgg ccaggccccc cgcctgctga tctacgacgc cagcaaccgc    1320
gccaccggca tccccgcccg cttcagcggc agcggcagcg gcaccgactt cacccctgacc    1380
atcagcagcc tggagcccga ggacttcgcc gtgtactact gccagcagag cagcaactgg    1440
ccccgcacct cggccaggg caccaaggtg gagatcaagc gc                        1482
```

<210> SEQ ID NO 220
<211> LENGTH: 560
<212> TYPE: PRT
<213> ORGANISM: Artificial
<220> FEATURE:
<223> OTHER INFORMATION: The amino acid sequence of CD3-PD-1 BsAb_D dimer

<400> SEQUENCE: 220

```
Asp Ile Lys Leu Gln Gln Ser Gly Ala Glu Leu Ala Arg Pro Gly Ala
1               5                   10                  15
Ser Val Lys Met Ser Cys Lys Thr Ser Gly Tyr Thr Phe Thr Arg Tyr
            20                  25                  30
```

```
Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Thr Leu Thr Val Ser Ser Val Glu Gly Gly Ser Gly Gly Ser Gly
                115                 120                 125

Gly Ser Gly Gly Ser Gly Gly Val Asp Asp Ile Gln Leu Thr Gln Ser
        130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
                180                 185                 190

Gly Val Pro Tyr Arg Phe Ser Gly Ser Gly Ser Gly Thr Ser Tyr Ser
                195                 200                 205

Leu Thr Ile Ser Ser Met Glu Ala Glu Asp Ala Ala Thr Tyr Tyr Cys
        210                 215                 220

Gln Gln Trp Ser Ser Asn Pro Leu Thr Phe Gly Ala Gly Thr Lys Leu
225                 230                 235                 240

Glu Leu Lys Ala Ser Lys Ser Lys Lys Glu Ile Phe Arg Trp Pro Glu
                245                 250                 255

Ser Pro Lys Ala Gln Ala Ser Ser Val Pro Thr Ala Gln Pro Gln Ala
                260                 265                 270

Glu Gly Ser Leu Ala Lys Ala Thr Thr Ala Pro Ala Thr Thr Arg Asn
                275                 280                 285

Thr Gly Arg Gly Gly Glu Glu Lys Lys Lys Glu Lys Glu Lys Glu Glu
        290                 295                 300

Gln Glu Glu Arg Glu Thr Lys Thr Pro Glu Cys Pro Ser His Thr Gln
305                 310                 315                 320

Pro Leu Gly Val Gln Val Gln Leu Val Glu Ser Gly Gly Gly Val Val
                325                 330                 335

Gln Pro Gly Arg Ser Leu Arg Leu Asp Cys Lys Ala Ser Gly Ile Thr
                340                 345                 350

Phe Ser Asn Ser Gly Met His Trp Val Arg Gln Ala Pro Gly Lys Gly
                355                 360                 365

Leu Glu Trp Val Ala Val Ile Trp Tyr Asp Gly Ser Lys Arg Tyr Tyr
        370                 375                 380

Ala Asp Ser Val Lys Gly Arg Phe Thr Ile Ser Arg Asp Asn Ser Lys
385                 390                 395                 400

Asn Thr Leu Phe Leu Gln Met Asn Ser Leu Arg Ala Glu Asp Thr Ala
                405                 410                 415

Val Tyr Tyr Cys Ala Thr Asn Asp Asp Tyr Trp Gly Gln Gly Thr Leu
                420                 425                 430

Val Thr Val Ser Ser Gly Gly Gly Gly Ser Gly Gly Gly Gly Ser Gly
                435                 440                 445
```

Gly Gly Gly Ser Glu Ile Val Leu Thr Gln Ser Pro Ala Thr Leu Ser
            450                 455                 460

Leu Ser Pro Gly Glu Arg Ala Thr Leu Ser Cys Arg Ala Ser Gln Ser
465                 470                 475                 480

Val Ser Ser Tyr Leu Ala Trp Tyr Gln Gln Lys Pro Gly Gln Ala Pro
                485                 490                 495

Arg Leu Leu Ile Tyr Asp Ala Ser Asn Arg Ala Thr Gly Ile Pro Ala
                500                 505                 510

Arg Phe Ser Gly Ser Gly Ser Gly Thr Asp Phe Thr Leu Thr Ile Ser
            515                 520                 525

Ser Leu Glu Pro Glu Asp Phe Ala Val Tyr Tyr Cys Gln Gln Ser Ser
530                 535                 540

Asn Trp Pro Arg Thr Phe Gly Gln Gly Thr Lys Val Glu Ile Lys Arg
545                 550                 555                 560

<210> SEQ ID NO 221
<211> LENGTH: 1680
<212> TYPE: DNA
<213> ORGANISM: Artificial
<220> FEATURE:
<223> OTHER INFORMATION: The nucleotide sequence of CD3-PD-1 BsAb_D
      dimer

<400> SEQUENCE: 221
gacatcaagc tgcagcagag cggcgccgag ctggcccgcc ccggcgccag cgtgaagatg      60
agctgcaaga ccagcggcta caccttcacc cgctacacca tgcactgggt gaagcagcgc     120
cccggccagg gctggagtg atcggctac atcaaccca gccgcggcta caccaactac     180
aaccagaagt tcaaggacaa ggccaccctg accaccgaca gagcagcag caccgcctac     240 atgcagctga gcagcctgac cagcgaggac agcgccgtgt actactgcgc cgctactac     300 gacgaccact actgcctgga ctactgggc cagggcacca ccctgaccgt gagcagcgtg     360
gagggcggca gcggcggcag cggcggcagc ggcggcgtgga cgacatccag     420 ctgacccaga gccccgccat catgagcgcc agccccggcg agaaggtgac catgacctgc     480
cgcgccagca gcagcgtgag ctacatgaac tggtaccagc agaagagcgg caccagcccc     540
aagcgctgga tctacgacac cagcaaggtg gccagcggcg tgccctaccg cttcagcggc     600
agcggcagcg gcaccagcta cagcctgacc atcagcagca tggaggccga ggacgccgcc     660
acctactact gccagcagtg gagcagcaac cccctgacct tcggcgccgg caccaagctg     720
gagctgaagg ccagcaagag caagaaggag atcttccgct ggcccgagag ccccaaggcc     780
caggccagca gcgtgcccac cgcccagccc caggccgagg cagcctggc caaggccacc     840 accgccccg ccaccacccg caacaccggc cgcggcggcg aggagaagaa gaaggagaag     900
gagaaggagg agcaggagga gcgcgagacc aagacccccg agtgccccag ccacacccag     960
cccctgggcg tgcaggtgca gctggtggag agcggcggcg cgtggtgca gcccggccgc    1020 agcctgcgcc tggactgcaa ggccagcggc atcaccttca gcaacagcgg catgcactgg    1080
gtgcgccagg cccccggcaa gggcctggag tgggtggccg tgatctggta cgacggcagc    1140
aagcgctact acgccgacag cgtgaagggc cgcttcacca tcagccgcga caacagcaag    1200
aacaccctgt tcctgcagat gaacagcctg cgcgccgagg acaccgccgt gtactactgc    1260
gccaccaacg acgactactg gggccagggc accctggtga ccgtgagcag cggcggcggc    1320
ggcagcggcg gcggcggcag cggcggcggc ggcagcgaga tcgtgctgac ccagagcccc    1380
gccaccctga gcctgagccc cggcgagcgc gccacccctga gctgccgcgc cagccagagc    1440

```
gtgagcagct acctggcctg gtaccagcag aagcccggcc aggcccccg cctgctgatc    1500 tacgacgcca gcaaccgcgc caccggcatc ccgcccgct tcagcggcag cggcagcggc    1560
accgacttca ccctgaccat cagcagcctg agcccgagg acttcgccgt gtactactgc    1620
cagcagagca gcaactggcc ccgcaccttc ggccagggca ccaaggtgga gatcaagcgc    1680
```

<210> SEQ ID NO 222
<211> LENGTH: 500
<212> TYPE: PRT
<213> ORGANISM: Artificial
<220> FEATURE:
<223> OTHER INFORMATION: The amino acid sequence of CD3-CTLA-4 BsAb_M
      monomer

<400> SEQUENCE: 222

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Gly Gly Gly Gly Ser Gly Gly Gly Gly Ser Gly Gly Gly
                245                 250                 255

Gly Ser Gln Val Gln Leu Val Glu Ser Gly Gly Val Val Gln Pro
            260                 265                 270

Gly Arg Ser Leu Arg Leu Ser Cys Ala Ala Ser Gly Phe Thr Phe Ser
        275                 280                 285

Ser Tyr Thr Met His Trp Val Arg Gln Ala Pro Gly Lys Gly Leu Glu
    290                 295                 300

Trp Val Thr Phe Ile Ser Tyr Asp Gly Asn Asn Lys Tyr Tyr Ala Asp
305                 310                 315                 320
```

Ser Val Lys Gly Arg Phe Thr Ile Ser Arg Asp Asn Ser Lys Asn Thr
          325                 330                 335

Leu Tyr Leu Gln Met Asn Ser Leu Arg Ala Glu Asp Thr Ala Ile Tyr
          340                 345                 350

Tyr Cys Ala Arg Thr Gly Trp Leu Gly Pro Phe Asp Tyr Trp Gly Gln
          355                 360                 365

Gly Thr Leu Val Thr Val Ser Ser Gly Gly Gly Ser Gly Gly Gly
          370                 375                 380

Gly Ser Gly Gly Gly Ser Glu Ile Val Leu Thr Gln Ser Pro Gly
385                 390                 395                 400

Thr Leu Ser Leu Ser Pro Gly Glu Arg Ala Thr Leu Ser Cys Arg Ala
          405                 410                 415

Ser Gln Ser Val Gly Ser Ser Tyr Leu Ala Trp Tyr Gln Gln Lys Pro
          420                 425                 430

Gly Gln Ala Pro Arg Leu Leu Ile Tyr Gly Ala Phe Ser Arg Ala Thr
          435                 440                 445

Gly Ile Pro Asp Arg Phe Ser Gly Ser Gly Ser Gly Thr Asp Phe Thr
          450                 455                 460

Leu Thr Ile Ser Arg Leu Glu Pro Glu Asp Phe Ala Val Tyr Tyr Cys
465                 470                 475                 480

Gln Gln Tyr Gly Ser Ser Pro Trp Thr Phe Gly Gln Gly Thr Lys Val
          485                 490                 495

Glu Ile Lys Arg
          500

```
<210> SEQ ID NO 223
<211> LENGTH: 1500
<212> TYPE: DNA
<213> ORGANISM: Artificial
<220> FEATURE:
<223> OTHER INFORMATION: The nucleotide sequence of CD3-CTLA-4 BsAb_M
      monomer

<400> SEQUENCE: 223
gacatcaagc tgcagcagag cggcgccgag ctggcccgcc ccggcgccag cgtgaagatg      60
agctgcaaga ccagcggcta caccttcacc cgctacacca tgcactgggt gaagcagcgc     120
cccggccagg gcctggagtg gatcggctac atcaaccccagccgcggcta caccaactac     180 aaccagaagt tcaaggacaa ggccaccctg accaccgaca gagcagcag caccgcctac     240 atgcagctga gcagcctgac cagcgaggac agcgccgtgt actactgcgc cgctactac      300 gacgaccact actgcctgga ctactggggc cagggcacca ccctgaccgt gagcagcgtg     360
gagggcggca gcggcggcag cggcggcagc ggcggcagcg gcggcgtgga cgacatccag     420
ctgacccaga gccccgccat catgagcgcc agccccggcg agaaggtgac catgacctgc     480
cgcgccagca gcagcgtgag ctacatgaac tggtaccagc agaagagcgg caccagcccc     540
aagcgctgga tctacgacac cagcaaggtg gccagcggcg tgccctaccg cttcagcggc     600
agcggcagcg gcaccagcta cagcctgacc atcagcagca tggaggccga ggacgccgcc     660
acctactact gccagcagtg gagcagcaac cccctgacct cggcgccgg caccaagctg      720 gagctgaagg gcggcggcgg cagcggcggc ggcggcagcg gcggcggcgg cagccaggtg     780
cagctggtgg agagcggcgg cggcgtggtg cagcccggcc gcagcctgcg cctgagctgc     840
gccgccagcg gcttcacctt cagcagctac accatgcact gggtgcgcca ggcccccggc     900
aagggcctgg agtgggtgac cttcatcagc tacgacggca caacaagta ctacgccgac     960
```

-continued

```
agcgtgaagg gccgcttcac catcagccgc gacaacagca agaacaccct gtacctgcag    1020
atgaacagcc tgcgcgccga ggacaccgcc atctactact gcgcccgcac cggctggctg    1080
ggccccttcg actactgggg ccagggcacc ctggtgaccg tgagcagcgg cggcggcggc    1140
agcggcggcg gcggcagcgg cggcggcggc agcgagatcg tgctgaccca gagccccggc    1200
accctgagcc tgagccccgg cgagcgcgcc accctgagct gccgcgccag ccagagcgtg    1260
ggcagcagct acctggcctg gtaccagcag aagcccggcc aggccccccg cctgctgatc    1320
tacggcgcct tcagccgcgc caccggcatc cccgaccgct cagcggcag cggcagcggc    1380 accgacttca ccctgaccat cagccgcctg gagcccgagg acttcgccgt gtactactgc    1440
cagcagtacg gcagcagccc ctggaccttc ggccagggca ccaaggtgga gatcaagcgc    1500
```

<210> SEQ ID NO 224
<211> LENGTH: 566
<212> TYPE: PRT
<213> ORGANISM: Artificial
<220> FEATURE:
<223> OTHER INFORMATION: The amino acid sequence of CD3-CTLA-4 BsAb_D dimer

<400> SEQUENCE: 224

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Ala Ser Lys Ser Lys Glu Ile Phe Arg Trp Pro Glu
                245                 250                 255

Ser Pro Lys Ala Gln Ala Ser Ser Val Pro Thr Ala Gln Pro Gln Ala
```

```
                260             265             270
Glu Gly Ser Leu Ala Lys Ala Thr Thr Ala Pro Ala Thr Thr Arg Asn
                275             280             285

Thr Gly Arg Gly Gly Glu Glu Lys Lys Lys Glu Lys Glu Lys Glu Glu
            290             295             300

Gln Glu Glu Arg Glu Thr Lys Thr Pro Glu Cys Pro Ser His Thr Gln
305             310             315             320

Pro Leu Gly Val Gln Val Gln Leu Val Glu Ser Gly Gly Gly Val Val
                325             330             335

Gln Pro Gly Arg Ser Leu Arg Leu Ser Cys Ala Ala Ser Gly Phe Thr
            340             345             350

Phe Ser Ser Tyr Thr Met His Trp Val Arg Gln Ala Pro Gly Lys Gly
            355             360             365

Leu Glu Trp Val Thr Phe Ile Ser Tyr Asp Gly Asn Asn Lys Tyr Tyr
            370             375             380

Ala Asp Ser Val Lys Gly Arg Phe Thr Ile Ser Arg Asp Asn Ser Lys
385             390             395             400

Asn Thr Leu Tyr Leu Gln Met Asn Ser Leu Arg Ala Glu Asp Thr Ala
                405             410             415

Ile Tyr Tyr Cys Ala Arg Thr Gly Trp Leu Gly Pro Phe Asp Tyr Trp
                420             425             430

Gly Gln Gly Thr Leu Val Thr Val Ser Ser Gly Gly Gly Gly Ser Gly
            435             440             445

Gly Gly Gly Ser Gly Gly Gly Ser Glu Ile Val Leu Thr Gln Ser
450             455             460

Pro Gly Thr Leu Ser Leu Ser Pro Gly Glu Arg Ala Thr Leu Ser Cys
465             470             475             480

Arg Ala Ser Gln Ser Val Gly Ser Ser Tyr Leu Ala Trp Tyr Gln Gln
                485             490             495

Lys Pro Gly Gln Ala Pro Arg Leu Leu Ile Tyr Gly Ala Phe Ser Arg
            500             505             510

Ala Thr Gly Ile Pro Asp Arg Phe Ser Gly Ser Gly Ser Gly Thr Asp
            515             520             525

Phe Thr Leu Thr Ile Ser Arg Leu Glu Pro Glu Asp Phe Ala Val Tyr
            530             535             540

Tyr Cys Gln Gln Tyr Gly Ser Ser Pro Trp Thr Phe Gly Gln Gly Thr
545             550             555             560

Lys Val Glu Ile Lys Arg
            565

<210> SEQ ID NO 225
<211> LENGTH: 1698
<212> TYPE: DNA
<213> ORGANISM: Artificial
<220> FEATURE:
<223> OTHER INFORMATION: The nucleotide sequence of CD3-CTLA-4 BsAb_D
      dimer

<400> SEQUENCE: 225
gacatcaagc tgcagcagag cggcgccgag ctggcccgcc ccggcgccag cgtgaagatg      60
agctgcaaga ccagcggcta caccttcacc cgctacacca tgcactgggt gaagcagcgc     120
cccggccagg gcctggagtg gatcggctac atcaacccca gccgcggcta caccaactac     180
aaccagaagt tcaaggacaa ggccaccctg accaccgaca gagcagcag caccgcctac     240 atgcagctga gcagcctgac cagcgaggac agcgccgtgt actactgcgc ccgctactac     300
```

```
gacgaccact actgcctgga ctactggggc cagggcacca ccctgaccgt gagcagcgtg    360
gagggcggca gcggcggcag cggcggcagc ggcggcagcg gcggcgtgga cgacatccag    420
ctgacccaga gccccgccat catgagcgcc agccccggcg agaaggtgac catgacctgc    480
cgcgccagca gcagcgtgag ctacatgaac tggtaccagc agaagagcgg caccagcccc    540
aagcgctgga tctacgacac cagcaaggtg gccagcggcg tgccctaccg cttcagcggc    600
agcggcagcg gcaccagcta cagcctgacc atcagcagca tggaggccga ggacgccgcc    660
acctactact gccagcagtg gagcagcaac cccctgacct tcggcgccgg caccaagctg    720
gagctgaagg ccagcaagag caagaaggag atcttccgct ggcccgagag ccccaaggcc    780
caggccagca gcgtgcccac cgcccagccc caggccgagg cagcctggc caaggccacc    840 accgcccccg ccaccacccg caacaccggc cgcggcggcg aggagaagaa gaaggagaag    900
gagaaggagg agcaggagga gcgcgagacc aagacccccg agtgccccag ccacacccag    960
cccctggggc tgcaggtgca gctggtggag agcggcggcg gcgtggtgca gcccggccgc   1020
agcctgcgcc tgagctgcgc cgccagcggc ttcaccttca gcagctacac catgcactgg   1080
gtgcgccagg cccccggcaa gggcctggag tgggtgacct tcatcagcta cgacggcaac   1140
aacaagtact acgccgacag cgtgaagggc cgcttcacca tcagccgcga caacagcaag   1200
aacaccctgt acctgcagat gaacagcctg cgcgccgagg acaccgccat ctactactgc   1260
gcccgcaccg gctggctggg ccccttcgac tactggggcc agggcaccct ggtgaccgtg   1320
agcagcggcg gcggcggcag cggcggcggc ggcagcggcg gcggcggcag cgagatcgtg   1380
ctgacccaga gccccggcac cctgagcctg agccccggcg agcgcgccac cctgagctgc   1440
cgcgccagcc agagcgtggg cagcagctac ctggcctggt accagcagaa gcccggccag   1500
gccccccgcc tgctgatcta cggcgccttc agccgcgcca ccggcatccc cgaccgcttc   1560
agcggcagcg gcagcggcac cgacttcacc ctgaccatca gccgcctgga gcccgaggac   1620
ttcgccgtgt actactgcca gcagtacggc agcagcccct ggaccttcgg ccagggcacc   1680
aaggtggaga tcaagcgc                                                  1698
```

<210> SEQ ID NO 226
<211> LENGTH: 501
<212> TYPE: PRT
<213> ORGANISM: Artificial
<220> FEATURE:
<223> OTHER INFORMATION: The amino acid sequence of CD3-LAG-3 BsAb_M monomer

<400> SEQUENCE: 226

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
```

-continued

```
                100                 105                 110
Thr Thr Leu Thr Val Ser Ser Val Glu Gly Gly Ser Gly Gly Ser Gly
            115                 120                 125

Gly Ser Gly Gly Ser Gly Gly Val Asp Asp Ile Gln Leu Thr Gln Ser
            130                 135                 140

Pro Ala Ile Met Ser Ala Ser Pro Gly Glu Lys Val Thr Met Thr Cys
145                 150                 155                 160

Arg Ala Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
                180                 185                 190

Gly Val Pro Tyr Arg Phe Ser Gly Ser Gly Ser Gly Thr Ser Tyr Ser
            195                 200                 205

Leu Thr Ile Ser Ser Met Glu Ala Glu Asp Ala Ala Thr Tyr Tyr Cys
            210                 215                 220

Gln Gln Trp Ser Ser Asn Pro Leu Thr Phe Gly Ala Gly Thr Lys Leu
225                 230                 235                 240

Glu Leu Lys Gly Gly Gly Gly Ser Gly Gly Gly Gly Ser Gly Gly Gly
                245                 250                 255

Gly Ser Gln Val Gln Leu Gln Gln Trp Gly Ala Gly Leu Leu Lys Pro
            260                 265                 270

Ser Glu Thr Leu Ser Leu Thr Cys Ala Val Tyr Gly Gly Ser Phe Ser
            275                 280                 285

Asp Tyr Tyr Trp Asn Trp Ile Arg Gln Pro Pro Gly Lys Gly Leu Glu
            290                 295                 300

Trp Ile Gly Glu Ile Asn His Arg Gly Ser Thr Asn Ser Asn Pro Ser
305                 310                 315                 320

Leu Lys Ser Arg Val Thr Leu Ser Leu Asp Thr Ser Lys Asn Gln Phe
                325                 330                 335

Ser Leu Lys Leu Arg Ser Val Thr Ala Ala Asp Thr Ala Val Tyr Tyr
                340                 345                 350

Cys Ala Phe Gly Tyr Ser Asp Tyr Glu Tyr Asn Trp Phe Asp Pro Trp
            355                 360                 365

Gly Gln Gly Thr Leu Val Thr Val Ser Ser Gly Gly Gly Gly Ser Gly
            370                 375                 380

Gly Gly Gly Ser Gly Gly Gly Gly Ser Glu Ile Val Leu Thr Gln Ser
385                 390                 395                 400

Pro Ala Thr Leu Ser Leu Ser Pro Gly Glu Arg Ala Thr Leu Ser Cys
                405                 410                 415

Arg Ala Ser Gln Ser Ile Ser Ser Tyr Leu Ala Trp Tyr Gln Gln Lys
                420                 425                 430

Pro Gly Gln Ala Pro Arg Leu Leu Ile Tyr Asp Ala Ser Asn Arg Ala
            435                 440                 445

Thr Gly Ile Pro Ala Arg Phe Ser Gly Ser Gly Ser Gly Thr Asp Phe
            450                 455                 460

Thr Leu Thr Ile Ser Ser Leu Glu Pro Glu Asp Phe Ala Val Tyr Tyr
465                 470                 475                 480

Cys Gln Gln Arg Ser Asn Trp Pro Leu Thr Phe Gly Gln Gly Thr Asn
                485                 490                 495

Leu Glu Ile Lys Arg
                500

<210> SEQ ID NO 227
```

```
<211> LENGTH: 1503
<212> TYPE: DNA
<213> ORGANISM: Artificial
<220> FEATURE:
<223> OTHER INFORMATION: The nucleotide sequence of CD3-LAG-3 BsAb_M
      monomer

<400> SEQUENCE: 227
gacatcaagc tgcagcagag cggcgccgag ctggcccgcc ccggcgccag cgtgaagatg      60
agctgcaaga ccagcggcta caccttcacc cgctacacca tgcactgggt gaagcagcgc    120
cccggccagg gcctggagtg gatcggctac atcaaccccc gccgcggcta caccaactac    180
aaccagaagt tcaaggacaa ggccaccctg accaccgaca gagcagcag caccgcctac    240 atgcagctga gcagcctgac cagcgaggac agcgccgtgt actactgcgc ccgctactac    300
gacgaccact actgcctgga ctactggggc cagggcacca ccctgaccgt gagcagcgtg    360
gagggcggca gcggcggcag cggcggcagc ggcggcagcg gcggcgtgga cgacatccag    420
ctgacccaga gccccgccat catgagcgcc agccccggcg agaaggtgac catgacctgc    480
cgcgccagca gcagcgtgag ctacatgaac tggtaccagc agaagagcgg caccagcccc    540
aagcgctgga tctacgacac cagcaaggtg gccagcggcg tgccctaccg cttcagcggc    600
agcggcagcg gcaccagcta cagcctgacc atcagcagca tggaggccga ggacgccgcc    660
acctactact gccagcagtg gagcagcaac ccccctgacct tcggcgccgg caccaagctg    720
gagctgaagg gcggcggcgg cagcggcggc ggcggcagcg gcggcggcgg cagccaggtg    780
cagctgcagc agtggggcgc cggcctgctg aagcccagcg agaccctgag cctgacctgc    840
gccgtgtacg gcggcagctt cagcgactac tactggaact ggatccgcca gccccccggc    900
aagggcctgg agtggatcgg cgagatcaac caccgcggca gcaccaacag caaccccagc    960
ctgaagagcc gcgtgaccct gagcctggac accagcaaga ccagttcag cctgaagctg   1020 cgcagcgtga ccgccgccga caccgccgtg tactactgcg ccttcggcta cagcgactac   1080
gagtacaact ggttcgaccc ctggggccag ggcaccctgg tgaccgtgag cagcggcggc   1140
ggcggcagcg gcggcggcgg cagcggcggc ggcggcagcg agatcgtgct gacccagagc   1200
cccgccaccc tgagcctgag ccccggcgag cgcgccaccc tgagctgccg cgccagccag   1260
agcatcagca gctacctggc ctggtaccag cagaagcccg gccaggcccc cgcctgctg    1320 atctacgacg ccagcaaccg cgccaccggc atccccgccc gcttcagcgg cagcggcagc   1380
ggcaccgact tcaccctgac catcagcagc ctggagcccg aggacttcgc cgtgtactac   1440
tgccagcagc gcagcaactg gccccctgacc ttcggccagg gcaccaacct ggagatcaag   1500
cgc                                                                  1503

<210> SEQ ID NO 228
<211> LENGTH: 567
<212> TYPE: PRT
<213> ORGANISM: Artificial
<220> FEATURE:
<223> OTHER INFORMATION: The amino acid sequence of CD3-LAG-3 BsAb_D
      dimer

<400> SEQUENCE: 228

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
```

-continued

```
               35                  40                  45
Gly Tyr Ile Asn Pro Ser Arg Gly Tyr Thr Asn Tyr Asn Gln Lys Phe
 50                  55                  60

Lys Asp Lys Ala Thr Leu Thr Thr Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
                100                 105                 110

Thr Thr Leu Thr Val Ser Ser Val Glu Gly Gly Ser Gly Gly Ser Gly
                115                 120                 125

Gly Ser Gly Gly Ser Gly Gly Val Asp Asp Ile Gln Leu Thr Gln Ser
 130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
                180                 185                 190

Gly Val Pro Tyr Arg Phe Ser Gly Ser Gly Ser Gly Thr Ser Tyr Ser
                195                 200                 205

Leu Thr Ile Ser Ser Met Glu Ala Glu Asp Ala Ala Thr Tyr Tyr Cys
 210                 215                 220

Gln Gln Trp Ser Ser Asn Pro Leu Thr Phe Gly Ala Gly Thr Lys Leu
225                 230                 235                 240

Glu Leu Lys Ala Ser Lys Ser Lys Glu Ile Phe Arg Trp Pro Glu
                245                 250                 255

Ser Pro Lys Ala Gln Ala Ser Ser Val Pro Thr Ala Gln Pro Gln Ala
                260                 265                 270

Glu Gly Ser Leu Ala Lys Ala Thr Thr Ala Pro Ala Thr Thr Arg Asn
                275                 280                 285

Thr Gly Arg Gly Gly Glu Glu Lys Lys Lys Glu Lys Glu Lys Glu Glu
290                 295                 300

Gln Glu Glu Arg Glu Thr Lys Thr Pro Glu Cys Pro Ser His Thr Gln
305                 310                 315                 320

Pro Leu Gly Val Gln Val Gln Leu Gln Gln Trp Gly Ala Gly Leu Leu
                325                 330                 335

Lys Pro Ser Glu Thr Leu Ser Leu Thr Cys Ala Val Tyr Gly Gly Ser
                340                 345                 350

Phe Ser Asp Tyr Tyr Trp Asn Trp Ile Arg Gln Pro Pro Gly Lys Gly
                355                 360                 365

Leu Glu Trp Ile Gly Glu Ile Asn His Arg Gly Ser Thr Asn Ser Asn
                370                 375                 380

Pro Ser Leu Lys Ser Arg Val Thr Leu Ser Leu Asp Thr Ser Lys Asn
385                 390                 395                 400

Gln Phe Ser Leu Lys Leu Arg Ser Val Thr Ala Ala Asp Thr Ala Val
                405                 410                 415

Tyr Tyr Cys Ala Phe Gly Tyr Ser Asp Tyr Glu Tyr Asn Trp Phe Asp
                420                 425                 430

Pro Trp Gly Gln Gly Thr Leu Val Thr Val Ser Ser Gly Gly Gly Gly
                435                 440                 445

Ser Gly Gly Gly Gly Ser Gly Gly Gly Ser Glu Ile Val Leu Thr
450                 455                 460
```

Gln Ser Pro Ala Thr Leu Ser Leu Ser Pro Gly Glu Arg Ala Thr Leu
465                 470                 475                 480

Ser Cys Arg Ala Ser Gln Ser Ile Ser Ser Tyr Leu Ala Trp Tyr Gln
                485                 490                 495

Gln Lys Pro Gly Gln Ala Pro Arg Leu Leu Ile Tyr Asp Ala Ser Asn
            500                 505                 510

Arg Ala Thr Gly Ile Pro Ala Arg Phe Ser Gly Ser Gly Ser Gly Thr
        515                 520                 525

Asp Phe Thr Leu Thr Ile Ser Ser Leu Glu Pro Glu Asp Phe Ala Val
    530                 535                 540

Tyr Tyr Cys Gln Gln Arg Ser Asn Trp Pro Leu Thr Phe Gly Gln Gly
545                 550                 555                 560

Thr Asn Leu Glu Ile Lys Arg
            565

<210> SEQ ID NO 229
<211> LENGTH: 1701
<212> TYPE: DNA
<213> ORGANISM: Artificial
<220> FEATURE:
<223> OTHER INFORMATION: The nucleotide sequence of CD3-LAG-3 BsAb_D
      dimer

<400> SEQUENCE: 229

| | |
|---|---|
| gacatcaagc tgcagcagag cggcgccgag ctggcccgcc ccggcgccag cgtgaagatg | 60 |
| agctgcaaga ccagcggcta caccttcacc cgctacacca tgcactgggt gaagcagcgc | 120 |
| cccggccagg gcctggagtg gatcggctac atcaacccca gccgcggcta caccaactac | 180 |
| aaccagaagt tcaaggacaa ggccaccctg accaccgaca gagcagcag caccgcctac | 240 |
| atgcagctga gcagcctgac cagcgaggac agcgccgtgt actactgcgc ccgctactac | 300 |
| gacgaccact actgcctgga ctactgggc caggcacca ccctgaccgt gagcagcgtg | 360 |
| gagggcggca gcggcggcag cggcggcagc ggcggcagcg gcggcgtgga cgacatccag | 420 |
| ctgacccaga gccccgccat catgagcgcc agccccggcg agaaggtgac catgacctgc | 480 |
| cgcgccagca gcagcgtgag ctacatgaac tggtaccagc agaagagcgg caccagcccc | 540 |
| aagcgctgga tctacgacac cagcaaggtg gccagcggcg tgccctaccg cttcagcggc | 600 |
| agcggcagcg gcaccagcta cagcctgacc atcagcagca tggaggccga ggacgccgcc | 660 |
| acctactact gccagcagtg gagcagcaac cccctgacct tcggcgccgg caccaagctg | 720 |
| gagctgaagg ccagcaagag caagaaggag atcttccgct ggcccgagag ccccaaggcc | 780 |
| caggccagca gcgtgcccac cgcccagccc caggccgagg cagcctggc caaggccacc | 840 |
| accgccccg ccaccacccg caacaccggc cgcggcggcg aggagaagaa gaaggagaag | 900 |
| gagaaggagg agcaggagga gcgcgagacc aagaccccg agtgccccag ccacacccag | 960 |
| cccctgggcg tgcaggtgca gctgcagcag tggggcgccg gcctgctgaa gcccagcgag | 1020 |
| accctgagcc tgacctgcgc cgtgtacggc ggcagcttca gcgactacta ctggaactgg | 1080 |
| atccgccagc cccccggcaa gggcctggag tggatcggcg agatcaacca ccgcggcagc | 1140 |
| accaacagca accccagcct gaagagccgc gtgaccctga gcctggacac cagcaagaac | 1200 |
| cagttcagcc tgaagctgcg cagcgtgacc gccgccgaca ccgccgtgta ctactgcgcc | 1260 |
| ttcggctaca gcgactacga gtacaactgg ttcgacccct ggggccaggg caccctggtg | 1320 |
| accgtgagca gcggcggcgg cggcagcggc ggcggcggca gcggcggcgg cggcagcgag | 1380 |

```
atcgtgctga cccagagccc cgccaccctg agcctgagcc ccggcgagcg cgccaccctg   1440
agctgccgcg ccagccagag catcagcagc tacctggcct ggtaccagca gaagcccggc   1500
caggcccccc gcctgctgat ctacgacgcc agcaaccgcg ccaccggcat ccccgcccgc   1560
ttcagcggca gcggcagcgg caccgacttc accctgacca tcagcagcct ggagcccgag   1620
gacttcgccg tgtactactg ccagcagcgc agcaactggc ccctgacctt cggccagggc   1680
accaacctgg agatcaagcg c                                             1701
```

<210> SEQ ID NO 230
<211> LENGTH: 503
<212> TYPE: PRT
<213> ORGANISM: Artificial
<220> FEATURE:
<223> OTHER INFORMATION: The amino acid sequence of CD3-TIM-3 BsAb_M monomer

<400> SEQUENCE: 230

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Gly Gly Gly Gly Ser Gly Gly Gly Gly Ser Gly Gly Gly
                245                 250                 255

Gly Ser Gln Val Gln Leu Val Ser Gly Ala Glu Val Lys Lys Pro
            260                 265                 270

Gly Ala Ser Val Lys Val Ser Cys Lys Ala Ser Gly Tyr Thr Phe Thr
        275                 280                 285

Ser Tyr Asn Met His Trp Val Arg Gln Ala Pro Gly Gln Gly Leu Glu
    290                 295                 300

Trp Ile Gly Asp Ile Tyr Pro Gly Gln Gly Asp Thr Ser Tyr Asn Gln
305                 310                 315                 320

Lys Phe Lys Gly Arg Ala Thr Met Thr Ala Asp Lys Ser Thr Ser Thr
            325                 330                 335

Val Tyr Met Glu Leu Ser Ser Leu Arg Ser Glu Asp Thr Ala Val Tyr
        340                 345                 350

Tyr Cys Ala Arg Val Gly Gly Ala Phe Pro Met Asp Tyr Trp Gly Gln
    355                 360                 365

Gly Thr Leu Val Thr Val Ser Ser Gly Gly Gly Ser Gly Gly Gly
    370                 375                 380

Gly Ser Gly Gly Gly Gly Ser Asp Ile Val Leu Thr Gln Ser Pro Asp
385                 390                 395                 400

Ser Leu Ala Val Ser Leu Gly Glu Arg Ala Thr Ile Asn Cys Arg Ala
                405                 410                 415

Ser Glu Ser Val Glu Tyr Tyr Gly Thr Ser Leu Met Gln Trp Tyr Gln
            420                 425                 430

Gln Lys Pro Gly Gln Pro Pro Lys Leu Leu Ile Tyr Ala Ala Ser Asn
        435                 440                 445

Val Glu Ser Gly Val Pro Asp Arg Phe Ser Gly Ser Gly Ser Gly Thr
    450                 455                 460

Asp Phe Thr Leu Thr Ile Ser Ser Leu Gln Ala Glu Asp Val Ala Val
465                 470                 475                 480

Tyr Tyr Cys Gln Gln Ser Arg Lys Asp Pro Ser Thr Phe Gly Gly Gly
                485                 490                 495

Thr Lys Val Glu Ile Lys Arg
            500

<210> SEQ ID NO 231
<211> LENGTH: 1509
<212> TYPE: DNA
<213> ORGANISM: Artificial
<220> FEATURE:
<223> OTHER INFORMATION: The nucleotide sequence of CD3-TIM-3 BsAb_M
      monomer

<400> SEQUENCE: 231
gacatcaagc tgcagcagag cggcgccgag ctggcccgcc ccggcgccag cgtgaagatg     60
agctgcaaga ccagcggcta caccttcacc cgctacacca tgcactgggt gaagcagcgc    120
cccggccagg gcctggagtg gatcggctac atcaacccca gccgcggcta caccaactac    180
aaccagaagt tcaaggacaa ggccaccctg accaccgaca gagcagcag caccgcctac    240 atgcagctga gcagcctgac cagcgaggac agcgccgtgt actactgcgc ccgctactac    300
gacgaccact actgcctgga ctactggggc cagggcacca ccctgaccgt gagcagcgtg    360
gagggcggca gcggcggcag cggcggcagc ggcggcagcg gcggcgtgga cgacatccag    420
ctgacccaga gccccgccat catgagcgcc agccccggcg agaaggtgac catgacctgc    480
cgcgccagca gcagcgtgag ctacatgaac tggtaccagc agaagagcgg caccagcccc    540
aagcgctgga tctacgacac cagcaaggtg gccagcggcg tgccctaccg cttcagcggc    600
agcggcagcg gcaccagcta cagcctgacc atcagcagca tggaggccga ggacgccgcc    660
acctactact gccagcagtg gagcagcaac cccctgacct tcggcgccgg caccaagctg    720
gagctgaagg gcggcggcgg cagcggcggc ggcggcagcg gcggcggcgg cagccaggtg    780
cagctggtgc agagcggcgc cgaggtgaag aagcccggcg ccagcgtgaa ggtgagctgc    840

-continued

```
aaggccagcg gctacacctt caccagctac aacatgcact gggtgcgcca ggccccggc       900 cagggcctgg agtggatcgg cgacatctac cccggccagg gcgacaccag ctacaaccag      960
aagttcaagg gccgcgccac catgaccgcc gacaagagca ccagcaccgt gtacatggag     1020
ctgagcagcc tgcgcagcga ggacaccgcc gtgtactact gcgcccgcgt gggcggcgcc     1080
ttccccatgg actactgggg ccagggcacc ctggtgaccg tgagcagcgg cggcggcggc     1140
agcggcggcg gcggcagcgg cggcggcggc agcgacatcg tgctgaccca gagccccgac     1200
agcctggccg tgagcctggg cgagcgcgcc accatcaact gccgcgccag cgagagcgtg     1260
gagtactacg gcaccagcct gatgcagtgg taccagcaga agcccggcca gccccccaag     1320
ctgctgatct acgccgccag caacgtggag agcggcgtgc ccgaccgctt cagcggcagc     1380
ggcagcggca ccgacttcac cctgaccatc agcagcctgc aggccgagga cgtggccgtg     1440
tactactgcc agcagagccg caaggacccc agcaccttcg gcggcggcac caaggtggag     1500
atcaagcgc                                                              1509
```

```
<210> SEQ ID NO 232
<211> LENGTH: 569
<212> TYPE: PRT
<213> ORGANISM: Artificial
<220> FEATURE:
<223> OTHER INFORMATION: The amino acid sequence of CD3-TIM-3 BsAb_D
      dimer

<400> SEQUENCE: 232

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240
```

Glu Leu Lys Ala Ser Lys Ser Lys Glu Ile Phe Arg Trp Pro Glu
             245                 250                 255

Ser Pro Lys Ala Gln Ala Ser Ser Val Pro Thr Ala Gln Pro Gln Ala
             260                 265                 270

Glu Gly Ser Leu Ala Lys Ala Thr Thr Ala Pro Ala Thr Thr Arg Asn
             275                 280                 285

Thr Gly Arg Gly Gly Glu Glu Lys Lys Lys Glu Lys Glu Lys Glu Glu
             290                 295                 300

Gln Glu Glu Arg Glu Thr Lys Thr Pro Glu Cys Pro Ser His Thr Gln
305                  310                 315                 320

Pro Leu Gly Val Gln Val Gln Leu Val Gln Ser Gly Ala Glu Val Lys
             325                 330                 335

Lys Pro Gly Ala Ser Val Lys Val Ser Cys Lys Ala Ser Gly Tyr Thr
             340                 345                 350

Phe Thr Ser Tyr Asn Met His Trp Val Arg Gln Ala Pro Gly Gln Gly
             355                 360                 365

Leu Glu Trp Ile Gly Asp Ile Tyr Pro Gly Gln Gly Asp Thr Ser Tyr
             370                 375                 380

Asn Gln Lys Phe Lys Gly Arg Ala Thr Met Thr Ala Asp Lys Ser Thr
385                  390                 395                 400

Ser Thr Val Tyr Met Glu Leu Ser Ser Leu Arg Ser Glu Asp Thr Ala
             405                 410                 415

Val Tyr Tyr Cys Ala Arg Val Gly Gly Ala Phe Pro Met Asp Tyr Trp
             420                 425                 430

Gly Gln Gly Thr Leu Val Thr Val Ser Ser Gly Gly Gly Ser Gly
             435                 440                 445

Gly Gly Gly Ser Gly Gly Gly Ser Asp Ile Val Leu Thr Gln Ser
             450                 455                 460

Pro Asp Ser Leu Ala Val Ser Leu Gly Glu Arg Ala Thr Ile Asn Cys
465                  470                 475                 480

Arg Ala Ser Glu Ser Val Glu Tyr Tyr Gly Thr Ser Leu Met Gln Trp
             485                 490                 495

Tyr Gln Gln Lys Pro Gly Gln Pro Pro Lys Leu Leu Ile Tyr Ala Ala
             500                 505                 510

Ser Asn Val Glu Ser Gly Val Pro Asp Arg Phe Ser Gly Ser Gly Ser
             515                 520                 525

Gly Thr Asp Phe Thr Leu Thr Ile Ser Ser Leu Gln Ala Glu Asp Val
             530                 535                 540

Ala Val Tyr Tyr Cys Gln Gln Ser Arg Lys Asp Pro Ser Thr Phe Gly
545                  550                 555                 560

Gly Gly Thr Lys Val Glu Ile Lys Arg
             565

<210> SEQ ID NO 233
<211> LENGTH: 1707
<212> TYPE: DNA
<213> ORGANISM: Artificial
<220> FEATURE:
<223> OTHER INFORMATION: The nucleotide sequence of CD3-TIM-3 BsAb_D
      dimer

<400> SEQUENCE: 233
gacatcaagc tgcagcagag cggcgccgag ctggcccgcc ccggcgccag cgtgaagatg      60
agctgcaaga ccagcggcta caccttcacc cgctacacca tgcactgggt gaagcagcgc     120

|  |  |
|---|---|
| cccggccagg gcctggagtg atcggctac atcaaccca gccgcggcta caccaactac | 180 |
| aaccagaagt tcaaggacaa ggccacctg accaccgaca agagcagcag caccgcctac | 240 |
| atgcagctga gcagcctgac cagcgaggac agcgccgtgt actactgcgc ccgctactac | 300 |
| gacgaccact actgcctgga ctactggggc cagggcacca ccctgaccgt gagcagcgtg | 360 |
| gagggcggca gcggcggcag cggcggcagc ggcggcagcg gcggcgtgga cgacatccag | 420 |
| ctgacccaga gccccgccat catgagcgcc agccccggcg agaaggtgac catgacctgc | 480 |
| cgcgccagca gcagcgtgag ctacatgaac tggtaccagc agaagagcgg caccagcccc | 540 |
| aagcgctgga tctacgacac cagcaaggtg gccagcggcg tgccctaccg cttcagcggc | 600 |
| agcggcagcg gcaccagcta cagcctgacc atcagcagca tggaggccga ggacgccgcc | 660 |
| acctactact gccagcagtg gagcagcaac ccctgacct cggcgccgg caccaagctg | 720 |
| gagctgaagg ccagcaagag caagaaggag atcttccgct ggcccgagag ccccaaggcc | 780 |
| caggccagca gcgtgcccac cgcccagccc caggccgagg cagcctggc caaggccacc | 840 |
| accgccccg ccaccacccg caacaccggc cgcggcggcg aggagaagaa gaaggagaag | 900 |
| gagaaggagg agcaggagga gcgcgagacc aagacccccg agtgccccag ccacacccag | 960 |
| cccctgggcg tgcaggtgca gctggtgcag agcggcgccg aggtgaagaa gcccggcgcc | 1020 |
| agcgtgaagg tgagctgcaa ggccagcggc tacaccttca ccagctacaa catgcactgg | 1080 |
| gtgcgccagg ccccggcca gggcctggag tggatcggcg acatctaccc cggccagggc | 1140 |
| gacaccagct acaaccagaa gttcaagggc cgcgccacca tgaccgccga caagagcacc | 1200 |
| agcaccgtgt acatggagct gagcagcctg cgcagcgagg acaccgccgt gtactactgc | 1260 |
| gcccgcgtgg gcggcgcctt ccccatggac tactggggcc agggcaccct ggtgaccgtg | 1320 |
| agcagcggcg gcggcggcag cggcggcggc ggcagcggcg gcggcggcag cgacatcgtg | 1380 |
| ctgacccaga gccccgacag cctggccgtg agcctgggcg agcgcgccac catcaactgc | 1440 |
| cgcgccagcg agagcgtgga gtactacggc accagcctga tgcagtggta ccagcagaag | 1500 |
| cccggccagc cccccaagct gctgatctac gccgccagca acgtggagag cggcgtgccc | 1560 |
| gaccgcttca gcggcagcgg cagcggcacc gacttcaccc tgaccatcag cagcctgcag | 1620 |
| gccgaggacg tggccgtgta ctactgccag cagagccgca aggaccccag caccttcggc | 1680 |
| ggcggcacca aggtggagat caagcgc | 1707 |

<210> SEQ ID NO 234
<211> LENGTH: 507
<212> TYPE: PRT
<213> ORGANISM: Artificial
<220> FEATURE:
<223> OTHER INFORMATION: The amino acid sequence of CD3-TIGIT BsAb_M
      monomer

<400> SEQUENCE: 234

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

```
Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
            115                 120                 125

Gly Ser Gly Gly Ser Gly Gly Val Asp Asp Ile Gln Leu Thr Gln Ser
        130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
            195                 200                 205

Leu Thr Ile Ser Ser Met Glu Ala Glu Asp Ala Ala Thr Tyr Tyr Cys
            210                 215                 220

Gln Gln Trp Ser Ser Asn Pro Leu Thr Phe Gly Ala Gly Thr Lys Leu
225                 230                 235                 240

Glu Leu Lys Gly Gly Gly Gly Ser Gly Gly Gly Gly Ser Gly Gly Gly
                245                 250                 255

Gly Ser Glu Val Gln Leu Gln Glu Ser Gly Pro Gly Leu Val Lys Pro
            260                 265                 270

Ser Gln Ser Leu Ser Leu Thr Cys Ser Val Thr Gly Ser Ser Ile Ala
            275                 280                 285

Ser Asp Tyr Trp Gly Trp Ile Arg Lys Phe Pro Gly Asn Lys Met Glu
290                 295                 300

Trp Met Gly Phe Ile Thr Tyr Ser Gly Ser Thr Ser Tyr Asn Pro Ser
305                 310                 315                 320

Leu Lys Ser Arg Ile Ser Ile Thr Arg Asp Thr Ser Lys Asn Gln Phe
                325                 330                 335

Phe Leu Gln Leu His Ser Val Thr Thr Asp Thr Ala Thr Tyr Ser
                340                 345                 350

Cys Ala Arg Met Pro Ser Phe Ile Thr Leu Ala Ser Leu Ser Thr Trp
            355                 360                 365

Glu Gly Tyr Phe Asp Phe Trp Gly Pro Gly Thr Met Val Thr Val Ser
            370                 375                 380

Ser Gly Gly Gly Gly Ser Gly Gly Gly Gly Ser Gly Gly Gly Gly Ser
385                 390                 395                 400

Asp Ile Gln Met Thr Gln Ser Pro Ser Leu Leu Ser Ala Ser Val Gly
                405                 410                 415

Asp Arg Val Thr Leu Asn Cys Lys Ala Ser Gln Ser Ile His Lys Asn
            420                 425                 430

Leu Ala Trp Tyr Gln Gln Lys Leu Gly Glu Ala Pro Lys Phe Leu Ile
            435                 440                 445

Tyr Tyr Ala Asn Ser Leu Gln Thr Gly Ile Pro Ser Arg Phe Ser Gly
450                 455                 460

Ser Gly Ser Gly Thr Asp Phe Thr Leu Thr Ile Ser Gly Leu Gln Pro
465                 470                 475                 480

Glu Asp Val Ala Thr Tyr Phe Cys Gln Gln Tyr Tyr Ser Gly Trp Thr
                485                 490                 495
```

Phe Gly Gly Gly Thr Lys Val Glu Leu Lys Arg
          500                 505

<210> SEQ ID NO 235
<211> LENGTH: 1521
<212> TYPE: DNA
<213> ORGANISM: Artificial
<220> FEATURE:
<223> OTHER INFORMATION: The nucleotide sequence of CD3-TIGIT BsAb_M
      monomer

<400> SEQUENCE: 235

| | | | | |
|---|---|---|---|---|
| gacatcaagc | tgcagcagag | cggcgccgag | ctggcccgcc | ccggcgccag cgtgaagatg | 60 |
| agctgcaaga | ccagcggcta | caccttcacc | cgctacacca | tgcactgggt gaagcagcgc | 120 |
| cccggccagg | gcctggagtg | gatcggctac | atcaacccca | gccgcggcta caccaactac | 180 |
| aaccagaagt | tcaaggacaa | ggccaccctg | accaccgaca | gagcagcag caccgcctac | 240 |
| atgcagctga | gcagcctgac | cagcgaggac | agcgccgtgt | actactgcgc ccgctactac | 300 |
| gacgaccact | actgcctgga | ctactggggc | cagggcacca | ccctgaccgt gagcagcgtg | 360 |
| gagggcggca | gcggcggcag | cggcggcagc | ggcggcagcg | gcggcgtgga cgacatccag | 420 |
| ctgacccaga | gccccgccat | catgagcgcc | agccccggcg | agaaggtgac catgacctgc | 480 |
| cgcgccagca | gcagcgtgag | ctacatgaac | tggtaccagc | agaagagcgg caccagcccc | 540 |
| aagcgctgga | tctacgacac | cagcaaggtg | gccagcggcg | tgccctaccg cttcagcggc | 600 |
| agcggcagcg | gcaccagcta | cagcctgacc | atcagcagca | tggaggccga ggacgccgcc | 660 |
| acctactact | gccagcagtg | gagcagcaac | cccctgacct | tcggcgccgg caccaagctg | 720 |
| gagctgaagg | gcggcggcgg | cagcggcggc | ggcggcagcg | gcggcggcgg cagcgaggtg | 780 |
| cagctgcagg | agagcggccc | cggcctggtg | aagcccagcc | agagcctgag cctgacctgc | 840 |
| agcgtgaccg | gcagcagcat | cgccagcgac | tactggggct | ggatccgcaa gttccccggc | 900 |
| aacaagatgg | agtggatggg | cttcatcacc | tacagcggca | gcaccagcta caacccagc | 960 |
| ctgaagagcc | gcatcagcat | caccccgcgac | accagcaaga | accagttctt cctgcagctg | 1020 |
| cacagcgtga | ccaccgacga | caccgccacc | tacagctgcg | cccgcatgcc cagcttcatc | 1080 |
| accctggcca | gcctgagcac | ctgggagggc | tacttcgact | tctggggccc cggcaccatg | 1140 |
| gtgaccgtga | gcgcggcgg | cggcggcagc | ggcggcggcg | gcagcggcgg cggcggcagc | 1200 |
| gacatccaga | tgacccagag | ccccagcctg | ctgagcgcca | gcgtgggcga ccgcgtgacc | 1260 |
| ctgaactgca | aggccagcca | gagcatccac | aagaacctgg | cctggtacca gcagaagctg | 1320 |
| ggcgaggccc | ccaagttcct | gatctactac | gccaacagcc | tgcagaccgg catccccagc | 1380 |
| cgcttcagcg | gcagcggcag | cggcaccgac | ttcaccctga | ccatcagcgg cctgcagccc | 1440 |
| gaggacgtgg | ccacctactt | ctgccagcag | tactacagcg | gctggacctt cggcggcggc | 1500 |
| accaaggtgg | agctgaagcg | c | | | 1521 |

<210> SEQ ID NO 236
<211> LENGTH: 573
<212> TYPE: PRT
<213> ORGANISM: Artificial
<220> FEATURE:
<223> OTHER INFORMATION: The amino acid sequence of CD3-TIGIT BsAb_D
      dimer

<400> SEQUENCE: 236

Asp Ile Lys Leu Gln Gln Ser Gly Ala Glu Leu Ala Arg Pro Gly Ala
1               5                   10                  15

-continued

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Ala Ser Lys Ser Lys Lys Glu Ile Phe Arg Trp Pro Glu
                245                 250                 255

Ser Pro Lys Ala Gln Ala Ser Ser Val Pro Thr Ala Gln Pro Gln Ala
            260                 265                 270

Glu Gly Ser Leu Ala Lys Ala Thr Thr Ala Pro Ala Thr Thr Arg Asn
        275                 280                 285

Thr Gly Arg Gly Gly Glu Glu Lys Lys Lys Glu Lys Glu Lys Glu Glu
    290                 295                 300

Gln Glu Glu Arg Glu Thr Lys Thr Pro Glu Cys Pro Ser His Thr Gln
305                 310                 315                 320

Pro Leu Gly Val Glu Val Gln Leu Gln Glu Ser Gly Pro Gly Leu Val
                325                 330                 335

Lys Pro Ser Gln Ser Leu Ser Leu Thr Cys Ser Val Thr Gly Ser Ser
            340                 345                 350

Ile Ala Ser Asp Tyr Trp Gly Trp Ile Arg Lys Phe Pro Gly Asn Lys
        355                 360                 365

Met Glu Trp Met Gly Phe Ile Thr Tyr Ser Gly Ser Thr Ser Tyr Asn
    370                 375                 380

Pro Ser Leu Lys Ser Arg Ile Ser Ile Thr Arg Asp Thr Ser Lys Asn
385                 390                 395                 400

Gln Phe Phe Leu Gln Leu His Ser Val Thr Thr Asp Asp Thr Ala Thr
                405                 410                 415

Tyr Ser Cys Ala Arg Met Pro Ser Phe Ile Thr Leu Ala Ser Leu Ser
            420                 425                 430

```
Thr Trp Glu Gly Tyr Phe Asp Phe Trp Gly Pro Gly Thr Met Val Thr
            435                 440                 445
Val Ser Ser Gly Gly Gly Ser Gly Gly Gly Ser Gly Gly Gly
    450                 455                 460
Gly Ser Asp Ile Gln Met Thr Gln Ser Pro Ser Leu Leu Ser Ala Ser
465                 470                 475                 480
Val Gly Asp Arg Val Thr Leu Asn Cys Lys Ala Ser Gln Ser Ile His
                485                 490                 495
Lys Asn Leu Ala Trp Tyr Gln Gln Lys Leu Gly Glu Ala Pro Lys Phe
            500                 505                 510
Leu Ile Tyr Tyr Ala Asn Ser Leu Gln Thr Gly Ile Pro Ser Arg Phe
        515                 520                 525
Ser Gly Ser Gly Ser Gly Thr Asp Phe Thr Leu Thr Ile Ser Gly Leu
    530                 535                 540
Gln Pro Glu Asp Val Ala Thr Tyr Phe Cys Gln Gln Tyr Tyr Ser Gly
545                 550                 555                 560
Trp Thr Phe Gly Gly Gly Thr Lys Val Glu Leu Lys Arg
                565                 570
```

<210> SEQ ID NO 237
<211> LENGTH: 1719
<212> TYPE: DNA
<213> ORGANISM: Artificial
<220> FEATURE:
<223> OTHER INFORMATION: The nucleotide sequence of CD3-TIGIT BsAb_D dimer

<400> SEQUENCE: 237

```
gacatcaagc tgcagcagag cggcgccgag ctggcccgcc ccggcgccag cgtgaagatg      60
agctgcaaga ccagcggcta caccttcacc cgctacacca tgcactgggt gaagcagcgc     120
cccggccagg gcctggagtg gatcggctac atcaacccca gccgcggcta caccaactac     180
aaccagaagt tcaaggacaa ggccaccctg accaccgaca gagcagcag caccgcctac     240
atgcagctga gcagcctgac cagcgaggac agcgccgtgt actactgcgc cgctactac     300
gacgaccact actgcctgga ctactggggc cagggcacca ccctgaccgt gagcagcgtg     360
gagggcggca gcggcggcag cggcggcagc ggcggcagcg gcggcgtgga cgacatccag     420
ctgacccaga gccccgccat catgagcgcc agccccggcg agaaggtgac catgacctgc     480
cgcgccagca gcagcgtgag ctacatgaac tggtaccagc agaagagcgg caccagcccc     540
aagcgctgga tctacgacac cagcaaggtg gccagcggcg tgccctaccg cttcagcggc     600
agcggcagcg gcaccagcta cagcctgacc atcagcagca tggaggccga ggacgccgcc     660
acctactact gccagcagtg gagcagcaac cccctgacct tcggcgccgg caccaagctg     720
gagctgaagg ccagcaagag caagaaggag atcttccgct ggcccgagag ccccaaggcc     780
caggccagca gcgtgcccac cgcccagccc caggccgagg cagcctggc caaggccacc     840
accgccccg ccaccacccg caacaccggc cgcggcggc aggagaagaa gaaggagaag     900
gagaaggagg agcaggagga gcgcgagacc aagacccccg agtgccccag ccacacccag     960
cccctgggcg tggaggtgca gctgcaggag agcggcccg gcctggtgaa gcccagccag    1020
agcctgagcc tgacctgcag cgtgaccggc agcagcatcg ccagcgacta ctggggctgg    1080
atccgcaagt tccccggcaa caagatggag tggatgggct tcatcaccta cagcggcagc    1140
accagctaca accccagcct gaagagccgc atcagcatca cccgcgacac cagcaagaac    1200
cagttcttcc tgcagctgca cagcgtgacc accgacgaca ccgccaccta cagctgcgcc    1260
```

```
cgcatgccca gcttcatcac cctggccagc ctgagcacct gggagggcta cttcgacttc    1320
tggggccccg gcaccatggt gaccgtgagc agcggcggcg gcggcagcgg cggcggcggc    1380
agcggcggcg gcggcagcga catccagatg acccagagcc ccagcctgct gagcgccagc    1440
gtgggcgacc gcgtgaccct gaactgcaag gccagccaga gcatccacaa gaacctggcc    1500
tggtaccagc agaagctggg cgaggccccc aagttcctga tctactacgc caacagcctg    1560
cagaccggca tccccagccg cttcagcggc agcggcagcg gcaccgactt caccctgacc    1620
atcagcggcc tgcagcccga ggacgtggcc acctacttct gccagcagta ctacagcggc    1680
tggaccttcg gcggcggcac caaggtggag ctgaagcgc                            1719
```

<210> SEQ ID NO 238
<211> LENGTH: 503
<212> TYPE: PRT
<213> ORGANISM: Artificial
<220> FEATURE:
<223> OTHER INFORMATION: the amino acid sequence of CD3-BTLA BsAb_M monomer

<400> SEQUENCE: 238

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys Gly Gly Gly Gly Ser Gly Gly Gly Gly Ser Gly Gly Gly
                245                 250                 255

Gly Ser Glu Val Gln Leu Val Glu Ser Gly Gly Gly Leu Val Gln Pro
            260                 265                 270
```

Gly Gly Ser Leu Arg Leu Ser Cys Ala Ala Ser Gly Phe Thr Ile Ser
            275                 280                 285

Ser Tyr Asp Met His Trp Val Arg Gln Ala Thr Gly Lys Gly Leu Glu
    290                 295                 300

Trp Val Ser Val Ile Gly Pro Ala Gly Asp Thr Tyr Tyr Pro Gly Ser
305                 310                 315                 320

Val Lys Gly Arg Phe Thr Ile Ser Arg Glu Asn Ala Lys Asn Ser Leu
                325                 330                 335

Tyr Leu Gln Met Asn Ser Leu Arg Ala Gly Asp Thr Ala Val Tyr Tyr
            340                 345                 350

Cys Ala Arg Glu Gly Met Ala Ala His Asn Tyr Tyr Gly Met Asp Val
        355                 360                 365

Trp Gly Gln Gly Thr Thr Val Thr Val Ser Ser Gly Gly Gly Gly Ser
370                 375                 380

Gly Gly Gly Gly Ser Gly Gly Gly Ser Glu Ile Val Leu Thr Gln
385                 390                 395                 400

Ser Pro Ala Thr Leu Ser Leu Ser Pro Gly Glu Arg Ala Thr Leu Ser
                405                 410                 415

Cys Arg Ala Ser Gln Ser Val Ser Ser Tyr Leu Ala Trp Tyr Gln Gln
            420                 425                 430

Lys Pro Gly Gln Ala Pro Arg Leu Leu Ile Tyr Asp Ala Ser Asn Arg
        435                 440                 445

Ala Thr Gly Ile Pro Ala Arg Phe Ser Gly Ser Gly Ser Gly Thr Asp
    450                 455                 460

Phe Thr Leu Thr Ile Ser Ser Leu Glu Pro Glu Asp Phe Ala Val Tyr
465                 470                 475                 480

Tyr Cys Gln Gln Arg Ser Asn Trp Pro Pro Ile Thr Phe Gly Gln Gly
                485                 490                 495

Thr Arg Leu Glu Ile Lys Arg
            500

```
<210> SEQ ID NO 239
<211> LENGTH: 1509
<212> TYPE: DNA
<213> ORGANISM: Artificial
<220> FEATURE:
<223> OTHER INFORMATION: The nucleotide sequence of CD3-BTLA BsAb_M
      monomer

<400> SEQUENCE: 239
gacatcaagc tgcagcagag cggcgccgag ctggcccgcc ccggcgccag cgtgaagatg    60
agctgcaaga ccagcggcta caccttcacc cgctacacca tgcactgggt gaagcagcgc   120
cccggccagg gcctggagtg gatcggctac atcaaccccc gccgcggcta caccaactac   180
aaccagaagt tcaaggacaa ggccaccctg accaccgaca gagcagcag caccgcctac   240 atgcagctga gcagcctgac cagcgaggac agcgccgtgt actactgcgc ccgctactac   300
gacgaccact actgcctgga ctactggggc cagggcacca ccctgaccgt gagcagcgtg   360
gagggcggca gcggcggcag cggcggcagc ggcggcagcg gcggcgtgga cgacatccag   420
ctgacccaga gccccgccat catgagcgcc agccccggcg agaaggtgac catgacctgc   480
cgcgccagca gcagcgtgag ctacatgaac tggtaccagc agaagagcgg caccagcccc   540
aagcgcctgg atctacgaca ccagcaaggtg gccagcggcg tgccctaccg cttcagcggc   600
agcggcagcg gcaccagcta cagcctgacc atcagcagca tggaggccga ggacgccgcc   660
acctactact gccagcagtg gagcagcaac cccctgacct tcggcgccgg caccaagctg   720
```

-continued

```
gagctgaagg cggcggcgg cagcggcggc ggcggcagcg gcggcggcgg cagcgaggtg    780
cagctggtgg agagcggcgg cggcctggtg cagcccggcg cagcctgcg  cctgagctgc    840 gccgccagcg gcttcaccat cagcagctac gacatgcact gggtgcgcca ggccaccggc    900
aagggcctgg agtgggtgag cgtgatcggc cccgccggcg acacctacta ccccggcagc    960
gtgaagggcc gcttcaccat cagccgcgag aacgccaaga acagcctgta cctgcagatg   1020
aacagcctgc gcgccggcga caccgccgtg tactactgcg cccgcgaggg catggccgcc   1080
cacaactact acggcatgga cgtgtggggc cagggcacca ccgtgaccgt gagcagcggc   1140
ggcggcggca gcggcggcgg cggcagcggc ggcggcggca gcgagatcgt gctgacccag   1200
agccccgcca ccctgagcct gagccccggc gagcgcgcca ccctgagctg ccgcgccagc   1260
cagagcgtga gcagctacct ggcctggtac cagcagaagc ccggccaggc ccccgcctg   1320 ctgatctacg acgccagcaa ccgcgccacc ggcatccccg cccgcttcag cggcagcggc   1380
agcggcaccg acttcaccct gaccatcagc agcctggagc ccgaggactt cgccgtgtac   1440
tactgccagc agcgcagcaa ctggccccc atcaccttcg gccagggcac ccgcctggag   1500
atcaagcgc                                                          1509
```

<210> SEQ ID NO 240
<211> LENGTH: 569
<212> TYPE: PRT
<213> ORGANISM: Artificial
<220> FEATURE:
<223> OTHER INFORMATION: The amino acid sequence of CD3-BTLA BsAb_D dimer

<400> SEQUENCE: 240

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205
```

Leu Thr Ile Ser Ser Met Glu Ala Glu Asp Ala Ala Thr Tyr Tyr Cys
            210                 215                 220

Gln Gln Trp Ser Ser Asn Pro Leu Thr Phe Gly Ala Gly Thr Lys Leu
225                 230                 235                 240

Glu Leu Lys Ala Ser Lys Ser Lys Glu Ile Phe Arg Trp Pro Glu
            245                 250                 255

Ser Pro Lys Ala Gln Ala Ser Ser Val Pro Thr Ala Gln Pro Gln Ala
            260                 265                 270

Glu Gly Ser Leu Ala Lys Ala Thr Thr Ala Pro Ala Thr Thr Arg Asn
            275                 280                 285

Thr Gly Arg Gly Gly Glu Glu Lys Lys Lys Glu Lys Glu Lys Glu Glu
290                 295                 300

Gln Glu Glu Arg Glu Thr Lys Thr Pro Glu Cys Pro Ser His Thr Gln
305                 310                 315                 320

Pro Leu Gly Val Glu Val Gln Leu Val Glu Ser Gly Gly Gly Leu Val
            325                 330                 335

Gln Pro Gly Gly Ser Leu Arg Leu Ser Cys Ala Ala Ser Gly Phe Thr
            340                 345                 350

Ile Ser Ser Tyr Asp Met His Trp Val Arg Gln Ala Thr Gly Lys Gly
            355                 360                 365

Leu Glu Trp Val Ser Val Ile Gly Pro Ala Gly Asp Thr Tyr Tyr Pro
370                 375                 380

Gly Ser Val Lys Gly Arg Phe Thr Ile Ser Arg Glu Asn Ala Lys Asn
385                 390                 395                 400

Ser Leu Tyr Leu Gln Met Asn Ser Leu Arg Ala Gly Asp Thr Ala Val
            405                 410                 415

Tyr Tyr Cys Ala Arg Glu Gly Met Ala Ala His Asn Tyr Tyr Gly Met
            420                 425                 430

Asp Val Trp Gly Gln Gly Thr Thr Val Thr Val Ser Ser Gly Gly Gly
            435                 440                 445

Gly Ser Gly Gly Gly Gly Ser Gly Gly Gly Gly Ser Glu Ile Val Leu
            450                 455                 460

Thr Gln Ser Pro Ala Thr Leu Ser Leu Ser Pro Gly Glu Arg Ala Thr
465                 470                 475                 480

Leu Ser Cys Arg Ala Ser Gln Ser Val Ser Ser Tyr Leu Ala Trp Tyr
            485                 490                 495

Gln Gln Lys Pro Gly Gln Ala Pro Arg Leu Leu Ile Tyr Asp Ala Ser
            500                 505                 510

Asn Arg Ala Thr Gly Ile Pro Ala Arg Phe Ser Gly Ser Gly Ser Gly
            515                 520                 525

Thr Asp Phe Thr Leu Thr Ile Ser Ser Leu Glu Pro Glu Asp Phe Ala
            530                 535                 540

Val Tyr Tyr Cys Gln Gln Arg Ser Asn Trp Pro Pro Ile Thr Phe Gly
545                 550                 555                 560

Gln Gly Thr Arg Leu Glu Ile Lys Arg
            565

<210> SEQ ID NO 241
<211> LENGTH: 1707
<212> TYPE: DNA
<213> ORGANISM: Artificial
<220> FEATURE:
<223> OTHER INFORMATION: The nucleotide sequence of CD3-BTLA BsAb_D
      dimer

<400> SEQUENCE: 241

```
gacatcaagc tgcagcagag cggcgccgag ctggcccgcc ccggcgccag cgtgaagatg      60
agctgcaaga ccagcggcta caccttcacc cgctacacca tgcactgggt gaagcagcgc     120
cccggccagg gcctggagtg gatcggctac atcaacccca gccgcggcta caccaactac     180
aaccagaagt tcaaggacaa ggccaccctg accaccgaca gagcagcagc accgcctac      240 atgcagctga gcagcctgac cagcgaggac agcgccgtgt actactgcgc ccgctactac     300
gacgaccact actgcctgga ctactggggc cagggcacca ccctgaccgt gagcagcgtg     360
gagggcggca gcggcggcag cggcggcagc ggcggcagcg gcggcgtgga cgacatccag     420
ctgacccaga gccccgccat catgagcgcc agccccggcg agaaggtgac catgacctgc     480
cgcgccagca gcagcgtgag ctacatgaac tggtaccagc agaagagcgg caccagcccc     540
aagcgctgga tctacgacac cagcaaggtg gccagcggcg tgccctaccg cttcagcggc     600
agcggcagcg gcaccagcta cagcctgacc atcagcagca tggaggccga ggacgccgcc     660
acctactact gccagcagtg gagcagcaac cccctgacct tcggcgccgg caccaagctg     720
gagctgaagg ccagcaagag caagaaggag atcttccgct ggcccgagag ccccaaggcc     780
caggccagca gcgtgcccac cgcccagccc caggccgagg cagcctggc caaggccacc     840 accgcccccg ccaccacccg caacaccggc cgcggcggcg aggagaagaa gaaggagaag     900
gagaaggagg agcaggagga gcgcgagacc aagacccccg agtgccccag ccacacccag     960
cccctgggcg tggaggtgca gctggtggag agcggcggcg gcctggtgca gcccggcggc    1020
agcctgcgcc tgagctgcgc cgccagcggc ttcaccatca gcagctacga catgcactgg    1080
gtgcgccagg ccaccggcaa gggcctggag tgggtgagcg tgatcggccc cgccggcgac    1140
acctactacc ccggcagcgt gaagggccgc ttcaccatca gccgcgagaa cgccaagaac    1200
agcctgtacc tgcagatgaa cagcctgcgc gccggcgaca ccgccgtgta ctactgcgcc    1260
cgcgagggca tggccgccca caactactac ggcatggacg tgtggggcca gggcaccacc    1320
gtgaccgtga gcagcggcgg cggcggcagc ggcggcggcg gcagcggcgg cggcggcagc    1380
gagatcgtgc tgacccagag ccccgccacc ctgagcctga ccccggcga gcgcgccacc    1440 ctgagctgcc gcgccagcca gagcgtgagc agctacctgg cctggtacca gcagaagccc    1500
ggccaggccc cccgcctgct gatctacgac gccagcaacc gcgccaccgg catccccgcc    1560
cgcttcagcg gcagcggcag cggcaccgac ttcaccctga ccatcagcag cctggagccc    1620
gaggacttcg ccgtgtacta ctgccagcag cgcagcaact ggccccccat caccttcggc    1680
cagggcaccc gcctggagat caagcgc                                        1707
```

<210> SEQ ID NO 242
<211> LENGTH: 243
<212> TYPE: PRT
<213> ORGANISM: Artificial
<220> FEATURE:
<223> OTHER INFORMATION: The amino acid sequence of anti-CD3 scFv

<400> SEQUENCE: 242

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
```

-continued

```
                 50                  55                  60
Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
                100                 105                 110

Thr Thr Leu Thr Val Ser Ser Val Glu Gly Gly Ser Gly Ser Gly
                115                 120                 125

Gly Ser Gly Gly Ser Gly Gly Val Asp Asp Ile Gln Leu Thr Gln Ser
                130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
                180                 185                 190

Gly Val Pro Tyr Arg Phe Ser Gly Ser Gly Ser Gly Thr Ser Tyr Ser
                195                 200                 205

Leu Thr Ile Ser Ser Met Glu Ala Glu Asp Ala Ala Thr Tyr Tyr Cys
                210                 215                 220

Gln Gln Trp Ser Ser Asn Pro Leu Thr Phe Gly Ala Gly Thr Lys Leu
225                 230                 235                 240

Glu Leu Lys
```

<210> SEQ ID NO 243
<211> LENGTH: 119
<212> TYPE: PRT
<213> ORGANISM: Artificial
<220> FEATURE:
<223> OTHER INFORMATION: The amino acid sequence of anti-CD3 scFv heavy
      chain variable region

<400> SEQUENCE: 243

```
Asp Ile Lys Leu Gln Gln Ser Gly Ala Glu Leu Ala Arg Pro Gly Ala
 1                   5                  10                  15

Ser Val Lys Met Ser Cys Lys Thr Ser Gly Tyr Thr Phe Thr Arg Tyr
                 20                  25                  30

Thr Met His Trp Val Lys Gln Arg Pro Gly Gln Gly Leu Glu Trp Ile
                 35                  40                  45

Gly Tyr Ile Asn Pro Ser Arg Gly Tyr Thr Asn Tyr Asn Gln Lys Phe
                 50                  55                  60

Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
                100                 105                 110

Thr Thr Leu Thr Val Ser Ser
                115
```

<210> SEQ ID NO 244
<211> LENGTH: 106
<212> TYPE: PRT
<213> ORGANISM: Artificial
<220> FEATURE:
<223> OTHER INFORMATION: The amino acid sequence of anti-CD3 scFv light chain variable region

<400> SEQUENCE: 244

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 245
<211> LENGTH: 236
<212> TYPE: PRT
<213> ORGANISM: Artificial
<220> FEATURE:
<223> OTHER INFORMATION: The amino acid sequence of anti-PD-1 scFv

<400> SEQUENCE: 245

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Gly Gly Gly Gly Ser Gly Gly Gly Ser Gly Gly Gly Gly Ser
        115                 120                 125

Glu Ile Val Leu Thr Gln Ser Pro Ala Thr Leu Ser Leu Ser Pro Gly
    130                 135                 140

Glu Arg Ala Thr Leu Ser Cys Arg Ala Ser Gln Ser Val Ser Ser Tyr
145                 150                 155                 160

Leu Ala Trp Tyr Gln Gln Lys Pro Gly Gln Ala Pro Arg Leu Leu Ile
                165                 170                 175

Tyr Asp Ala Ser Asn Arg Ala Thr Gly Ile Pro Ala Arg Phe Ser Gly
            180                 185                 190

Ser Gly Ser Gly Thr Asp Phe Thr Leu Thr Ile Ser Ser Leu Glu Pro
        195                 200                 205

Glu Asp Phe Ala Val Tyr Tyr Cys Gln Gln Ser Ser Asn Trp Pro Arg
    210                 215                 220

Thr Phe Gly Gln Gly Thr Lys Val Glu Ile Lys Arg
225                 230                 235

<210> SEQ ID NO 246
<211> LENGTH: 113
<212> TYPE: PRT
<213> ORGANISM: Artificial
<220> FEATURE:
<223> OTHER INFORMATION: The amino acid sequence of anti-PD-1 scFv heavy
      chain variable region

<400> SEQUENCE: 246

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 247
<211> LENGTH: 108
<212> TYPE: PRT
<213> ORGANISM: Artificial
<220> FEATURE:
<223> OTHER INFORMATION: The amino acid sequence of anti-PD-1 scFv light
      chain variable region

<400> SEQUENCE: 247

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg
            100                 105

<210> SEQ ID NO 248
<211> LENGTH: 242
<212> TYPE: PRT
<213> ORGANISM: Artificial
<220> FEATURE:
<223> OTHER INFORMATION: The amino acid sequence of anti-CTLA-4 scFv

<400> SEQUENCE: 248

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
            35                  40                  45

Thr Phe Ile Ser Tyr Asp Gly Asn Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Glu Ile Val Leu Thr Gln Ser Pro Gly Thr Leu
130                 135                 140

Ser Leu Ser Pro Gly Glu Arg Ala Thr Leu Ser Cys Arg Ala Ser Gln
145                 150                 155                 160

Ser Val Gly Ser Ser Tyr Leu Ala Trp Tyr Gln Gln Lys Pro Gly Gln
                165                 170                 175

Ala Pro Arg Leu Leu Ile Tyr Gly Ala Phe Ser Arg Ala Thr Gly Ile
            180                 185                 190

Pro Asp Arg Phe Ser Gly Ser Gly Ser Gly Thr Asp Phe Thr Leu Thr
            195                 200                 205

Ile Ser Arg Leu Glu Pro Glu Asp Phe Ala Val Tyr Tyr Cys Gln Gln
            210                 215                 220

Tyr Gly Ser Ser Pro Trp Thr Phe Gly Gln Gly Thr Lys Val Glu Ile
225                 230                 235                 240

Lys Arg

<210> SEQ ID NO 249
<211> LENGTH: 118
<212> TYPE: PRT
<213> ORGANISM: Artificial
<220> FEATURE:
<223> OTHER INFORMATION: The amino acid sequence of anti-CTLA-4 scFv
      heavy chain variable region

<400> SEQUENCE: 249

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
            35                  40                  45

Thr Phe Ile Ser Tyr Asp Gly Asn Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
            115

<210> SEQ ID NO 250
<211> LENGTH: 109
<212> TYPE: PRT
<213> ORGANISM: Artificial
<220> FEATURE:
<223> OTHER INFORMATION: The amino acid sequence of anti-CTLA-4 scFv
      light chain variable region

<400> SEQUENCE: 250

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg
            100                 105

<210> SEQ ID NO 251
<211> LENGTH: 243
<212> TYPE: PRT
<213> ORGANISM: Artificial
<220> FEATURE:
<223> OTHER INFORMATION: The amino acid sequence of anti-LAG-3 scFv

<400> SEQUENCE: 251

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Ser Glu Ile Val Leu Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Ser Ile Ser Ser Tyr Leu Ala Trp Tyr Gln Gln Lys Pro Gly
                165                 170                 175

Gln Ala Pro Arg Leu Leu Ile Tyr Asp Ala Ser Asn Arg Ala Thr Gly
            180                 185                 190

```
Ile Pro Ala Arg Phe Ser Gly Ser Gly Ser Gly Thr Asp Phe Thr Leu
            195                 200                 205

Thr Ile Ser Ser Leu Glu Pro Glu Asp Phe Ala Val Tyr Tyr Cys Gln
        210                 215                 220

Gln Arg Ser Asn Trp Pro Leu Thr Phe Gly Gln Gly Thr Asn Leu Glu
225                 230                 235                 240

Ile Lys Arg

<210> SEQ ID NO 252
<211> LENGTH: 120
<212> TYPE: PRT
<213> ORGANISM: Artificial
<220> FEATURE:
<223> OTHER INFORMATION: The amino acid sequence of anti-LAG-3 scFv
      heavy chain variable region

<400> SEQUENCE: 252

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser
        115                 120

<210> SEQ ID NO 253
<211> LENGTH: 108
<212> TYPE: PRT
<213> ORGANISM: Artificial
<220> FEATURE:
<223> OTHER INFORMATION: The amino acid sequence of anti-LAG-3 scFv
      light chain variable region

<400> SEQUENCE: 253

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys Arg
            100                 105
```

-continued

```
<210> SEQ ID NO 254
<211> LENGTH: 245
<212> TYPE: PRT
<213> ORGANISM: Artificial
<220> FEATURE:
<223> OTHER INFORMATION: The amino acid sequence of anti-TIM-3 scFv

<400> SEQUENCE: 254

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Ile
        35                  40                  45

Gly Asp Ile Tyr Pro Gly Gln Gly Asp Thr Ser Tyr Asn Gln Lys Phe
    50                  55                  60

Lys Gly Arg Ala Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Val Leu Thr Gln Ser Pro Asp Ser Leu
    130                 135                 140

Ala Val Ser Leu Gly Glu Arg Ala Thr Ile Asn Cys Arg Ala Ser Glu
145                 150                 155                 160

Ser Val Glu Tyr Tyr Gly Thr Ser Leu Met Gln Trp Tyr Gln Gln Lys
                165                 170                 175

Pro Gly Gln Pro Pro Lys Leu Leu Ile Tyr Ala Ala Ser Asn Val Glu
            180                 185                 190

Ser Gly Val Pro Asp Arg Phe Ser Gly Ser Gly Ser Gly Thr Asp Phe
        195                 200                 205

Thr Leu Thr Ile Ser Ser Leu Gln Ala Glu Asp Val Ala Val Tyr Tyr
    210                 215                 220

Cys Gln Gln Ser Arg Lys Asp Pro Ser Thr Phe Gly Gly Gly Thr Lys
225                 230                 235                 240

Val Glu Ile Lys Arg
                245

<210> SEQ ID NO 255
<211> LENGTH: 118
<212> TYPE: PRT
<213> ORGANISM: Artificial
<220> FEATURE:
<223> OTHER INFORMATION: The amino acid sequence of anti-TIM-3 scFv
      heavy chain variable region

<400> SEQUENCE: 255

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Ile
        35                  40                  45

Gly Asp Ile Tyr Pro Gly Gln Gly Asp Thr Ser Tyr Asn Gln Lys Phe
    50                  55                  60
```

```
Lys Gly Arg Ala Thr Met Thr Ala Asp Lys Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Val Gly Gly Ala Phe Pro Met Asp Tyr Trp Gly Gln Gly Thr
            100                 105                 110

Leu Val Thr Val Ser Ser
        115

<210> SEQ ID NO 256
<211> LENGTH: 112
<212> TYPE: PRT
<213> ORGANISM: Artificial
<220> FEATURE:
<223> OTHER INFORMATION: The amino acid sequence of anti-TIM-3 scFv
      light chain variable region

<400> SEQUENCE: 256

Asp Ile Val Leu Thr Gln Ser Pro Asp Ser Leu Ala Val Ser Leu Gly
 1               5                  10                  15

Glu Arg Ala Thr Ile Asn Cys Arg Ala Ser Glu Ser Val Glu Tyr Tyr
             20                  25                  30

Gly Thr Ser Leu Met Gln Trp Tyr Gln Gln Lys Pro Gly Gln Pro Pro
         35                  40                  45

Lys Leu Leu Ile Tyr Ala Ala Ser Asn Val Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Arg
                 85                  90                  95

Lys Asp Pro Ser Thr Phe Gly Gly Gly Thr Lys Val Glu Ile Lys Arg
            100                 105                 110

<210> SEQ ID NO 257
<211> LENGTH: 249
<212> TYPE: PRT
<213> ORGANISM: Artificial
<220> FEATURE:
<223> OTHER INFORMATION: The amino acid sequence of anti-TIGIT scFv

<400> SEQUENCE: 257

Glu Val Gln Leu Gln Glu Ser Gly Pro Gly Leu Val Lys Pro Ser Gln
 1               5                  10                  15

Ser Leu Ser Leu Thr Cys Ser Val Thr Gly Ser Ser Ile Ala Ser Asp
             20                  25                  30

Tyr Trp Gly Trp Ile Arg Lys Phe Pro Gly Asn Lys Met Glu Trp Met
         35                  40                  45

Gly Phe Ile Thr Tyr Ser Gly Ser Thr Ser Tyr Asn Pro Ser Leu Lys
 50                  55                  60

Ser Arg Ile Ser Ile Thr Arg Asp Thr Ser Lys Asn Gln Phe Phe Leu
 65                  70                  75                  80

Gln Leu His Ser Val Thr Thr Asp Asp Thr Ala Thr Tyr Ser Cys Ala
                 85                  90                  95

Arg Met Pro Ser Phe Ile Thr Leu Ala Ser Leu Ser Thr Trp Glu Gly
            100                 105                 110

Tyr Phe Asp Phe Trp Gly Pro Gly Thr Met Val Thr Val Ser Ser Gly
        115                 120                 125
```

```
Gly Gly Gly Ser Gly Gly Gly Ser Gly Gly Gly Ser Asp Ile
    130             135             140

Gln Met Thr Gln Ser Pro Ser Leu Leu Ser Ala Ser Val Gly Asp Arg
145                 150                 155                 160

Val Thr Leu Asn Cys Lys Ala Ser Gln Ser Ile His Lys Asn Leu Ala
                165                 170                 175

Trp Tyr Gln Gln Lys Leu Gly Glu Ala Pro Lys Phe Leu Ile Tyr Tyr
            180                 185                 190

Ala Asn Ser Leu Gln Thr Gly Ile Pro Ser Arg Phe Ser Gly Ser Gly
        195                 200                 205

Ser Gly Thr Asp Phe Thr Leu Thr Ile Ser Gly Leu Gln Pro Glu Asp
    210                 215                 220

Val Ala Thr Tyr Phe Cys Gln Gln Tyr Tyr Ser Gly Trp Thr Phe Gly
225                 230                 235                 240

Gly Gly Thr Lys Val Glu Leu Lys Arg
                245

<210> SEQ ID NO 258
<211> LENGTH: 127
<212> TYPE: PRT
<213> ORGANISM: Artificial
<220> FEATURE:
<223> OTHER INFORMATION: The amino acid sequence of anti-TIGIT scFv
      heavy chain variable region

<400> SEQUENCE: 258

Glu Val Gln Leu Gln Glu Ser Gly Pro Gly Leu Val Lys Pro Ser Gln
1               5                   10                  15

Ser Leu Ser Leu Thr Cys Ser Val Thr Gly Ser Ser Ile Ala Ser Asp
            20                  25                  30

Tyr Trp Gly Trp Ile Arg Lys Phe Pro Gly Asn Lys Met Glu Trp Met
        35                  40                  45

Gly Phe Ile Thr Tyr Ser Gly Ser Thr Ser Tyr Asn Pro Ser Leu Lys
    50                  55                  60

Ser Arg Ile Ser Ile Thr Arg Asp Thr Ser Lys Asn Gln Phe Phe Leu
65                  70                  75                  80

Gln Leu His Ser Val Thr Thr Asp Asp Thr Ala Thr Tyr Ser Cys Ala
                85                  90                  95

Arg Met Pro Ser Phe Ile Thr Leu Ala Ser Leu Ser Thr Trp Glu Gly
            100                 105                 110

Tyr Phe Asp Phe Trp Gly Pro Gly Thr Met Val Thr Val Ser Ser
        115                 120                 125

<210> SEQ ID NO 259
<211> LENGTH: 107
<212> TYPE: PRT
<213> ORGANISM: Artificial
<220> FEATURE:
<223> OTHER INFORMATION: The amino acid sequence of anti-TIGIT scFv
      light chain variable region

<400> SEQUENCE: 259

Asp Ile Gln Met Thr Gln Ser Pro Ser Leu Leu Ser Ala Ser Val Gly
1               5                   10                  15

Asp Arg Val Thr Leu Asn Cys Lys Ala Ser Gln Ser Ile His Lys Asn
            20                  25                  30

Leu Ala Trp Tyr Gln Gln Lys Leu Gly Glu Ala Pro Lys Phe Leu Ile
        35                  40                  45
```

-continued

Tyr Tyr Ala Asn Ser Leu Gln Thr Gly Ile Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Val Ala Thr Tyr Phe Cys Gln Gln Tyr Tyr Ser Gly Trp Thr
                85                  90                  95

Phe Gly Gly Gly Thr Lys Val Glu Leu Lys Arg
            100                 105

<210> SEQ ID NO 260
<211> LENGTH: 245
<212> TYPE: PRT
<213> ORGANISM: Artificial
<220> FEATURE:
<223> OTHER INFORMATION: The amino acid sequence of anti-BTLA scFv

<400> SEQUENCE: 260

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Tyr
                20                  25                  30

Asp Met His Trp Val Arg Gln Ala Thr Gly Lys Gly Leu Glu Trp Val
            35                  40                  45

Ser Val Ile Gly Pro Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Met Ala Ala His Asn Tyr Tyr Gly Met Asp Val Trp Gly
            100                 105                 110

Gln Gly Thr Thr Val Thr Val Ser Ser Gly Gly Gly Ser Gly Gly
        115                 120                 125

Gly Gly Ser Gly Gly Gly Ser Glu Ile Val Leu Thr Gln Ser Pro
        130                 135                 140

Ala Thr Leu Ser Leu Ser Pro Gly Glu Arg Ala Thr Leu Ser Cys Arg
145                 150                 155                 160

Ala Ser Gln Ser Val Ser Ser Tyr Leu Ala Trp Tyr Gln Gln Lys Pro
                165                 170                 175

Gly Gln Ala Pro Arg Leu Leu Ile Tyr Asp Ala Ser Asn Arg Ala Thr
            180                 185                 190

Gly Ile Pro Ala Arg Phe Ser Gly Ser Gly Ser Gly Thr Asp Phe Thr
        195                 200                 205

Leu Thr Ile Ser Ser Leu Glu Pro Glu Asp Phe Ala Val Tyr Tyr Cys
    210                 215                 220

Gln Gln Arg Ser Asn Trp Pro Pro Ile Thr Phe Gly Gln Gly Thr Arg
225                 230                 235                 240

Leu Glu Ile Lys Arg
            245

<210> SEQ ID NO 261
<211> LENGTH: 121
<212> TYPE: PRT
<213> ORGANISM: Artificial
<220> FEATURE:
<223> OTHER INFORMATION: The amino acid sequence of anti-BTLA scFv heavy
      chain variable region

<400> SEQUENCE: 261

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Tyr
            20                  25                  30

Asp Met His Trp Val Arg Gln Ala Thr Gly Lys Gly Leu Glu Trp Val
        35                  40                  45

Ser Val Ile Gly Pro Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Met Ala Ala His Asn Tyr Tyr Gly Met Asp Val Trp Gly
            100                 105                 110

Gln Gly Thr Thr Val Thr Val Ser Ser
        115                 120

<210> SEQ ID NO 262
<211> LENGTH: 109
<212> TYPE: PRT
<213> ORGANISM: Artificial
<220> FEATURE:
<223> OTHER INFORMATION: The amino acid sequence of anti-BTLA scFv light
      chain variable region

<400> SEQUENCE: 262

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ile Thr Phe Gly Gln Gly Thr Arg Leu Glu Ile Lys Arg
            100                 105

<210> SEQ ID NO 263
<211> LENGTH: 729
<212> TYPE: DNA
<213> ORGANISM: Artificial
<220> FEATURE:
<223> OTHER INFORMATION: The nucleotide sequence of anti-CD3 scFv

<400> SEQUENCE: 263
gacatcaagc tgcagcagag cggcgccgag ctggccccgcc ccggcgccag cgtgaagatg      60
agctgcaaga ccagcggcta caccttcacc cgctacacca tgcactgggt gaagcagcgc     120
cccggccagg gcctggagtg gatcggctac atcaaccccca gccgcggcta caccaactac     180
aaccagaagt tcaaggacaa ggccacccctg accaccgaca agagcagcag caccgcctac     240
atgcagctga gcagcctgac cagcgaggac agcgccgtgt actactgcgc cgctactac     300 gacgaccact actgcctgga ctactggggc cagggcacca ccctgaccgt gagcagcgtg     360

```
gagggcggca gcggcggcag cggcggcagc ggcggcagcg gcggcgtgga cgacatccag    420
ctgacccaga gccccgccat catgagcgcc agccccggcg agaaggtgac catgacctgc    480
cgcgccagca gcagcgtgag ctacatgaac tggtaccagc agaagagcgg caccagcccc    540
aagcgctgga tctacgacac cagcaaggtg gccagcggct gccctaccg cttcagcggc    600 agcggcagcg gcaccagcta cagcctgacc atcagcagca tggaggccga ggacgccgcc    660
acctactact gccagcagtg gagcagcaac cccctgacct cggcgccgg caccaagctg    720 gagctgaag                                                            729
```

<210> SEQ ID NO 264
<211> LENGTH: 357
<212> TYPE: DNA
<213> ORGANISM: Artificial
<220> FEATURE:
<223> OTHER INFORMATION: The nucleotide sequence of anti-CD3 scFv heavy
      chain variable region

<400> SEQUENCE: 264

```
gacatcaagc tgcagcagag cggcgccgag ctggcccgcc ccggcgccag cgtgaagatg    60
agctgcaaga ccagcggcta caccttcacc cgctacacca tgcactgggt gaagcagcgc    120
cccggccagg gcctggagtg gatcggctac atcaacccca gccgcggcta caccaactac    180
aaccagaagt tcaaggacaa ggccaccctg accaccgaca gagcagcag caccgcctac    240 atgcagctga gcagcctgac cagcgaggac agcgccgtgt actactgcgc ccgctactac    300
gacgaccact actgcctgga ctactggggc cagggcacca ccctgaccgt gagcagc      357
```

<210> SEQ ID NO 265
<211> LENGTH: 318
<212> TYPE: DNA
<213> ORGANISM: Artificial
<220> FEATURE:
<223> OTHER INFORMATION: The nucleotide sequence of anti-CD3 scFv light
      chain variable region

<400> SEQUENCE: 265

```
gacatccagc tgacccagag ccccgccatc atgagcgcca gccccggcga gaaggtgacc    60
atgacctgcc gcgccagcag cagcgtgagc tacatgaact ggtaccagca gaagagcggc    120
accagcccca gcgctggat ctacgacacc agcaaggtgg ccagcggcgt gccctaccgc    180
ttcagcggca gcggcagcgg caccagctac agcctgacca tcagcagcat ggaggccgag    240
gacgccgcca cctactactg ccagcagtgg agcagcaacc ccctgacctt cggcgccggc    300
accaagctgg agctgaag                                                  318
```

<210> SEQ ID NO 266
<211> LENGTH: 708
<212> TYPE: DNA
<213> ORGANISM: Artificial
<220> FEATURE:
<223> OTHER INFORMATION: The nucleotide sequence of PD-1 scFv

<400> SEQUENCE: 266

```
caggtgcagc tggtggagag cggcggcggc gtggtgcagc ccggccgcag cctgcgcctg    60
gactgcaagg ccagcggcat caccttcagc aacagcggca tgcactgggt gcgccaggcc    120
cccggcaagg gcctggagtg ggtggccgtg atctggtacg acggcagcaa gcgctactac    180
gccgacagcg tgaagggccg cttcaccatc agccgcgaca acagcaagaa cacccctgttc    240
```

```
ctgcagatga acagcctgcg cgccgaggac accgccgtgt actactgcgc caccaacgac    300
gactactggg gccagggcac cctggtgacc gtgagcagcg gcggcggcgg cagcggcggc    360
ggcggcagcg gcggcggcgg cagcgagatc gtgctgaccc agagccccgc caccctgagc    420
ctgagccccg gcgagcgcgc caccctgagc tgccgcgcca gcagagcgt gagcagctac     480 ctggcctggt accagcagaa gcccggccag gccccccgcc tgctgatcta cgacgccagc    540
aaccgcgcca ccggcatccc cgcccgcttc agcggcagcg gcagcggcac cgacttcacc    600
ctgaccatca gcagcctgga gcccgaggac ttcgccgtgt actactgcca gcagagcagc    660
aactggcccc gcaccttcgg ccagggcacc aaggtggaga tcaagcgc               708
```

<210> SEQ ID NO 267
<211> LENGTH: 339
<212> TYPE: DNA
<213> ORGANISM: Artificial
<220> FEATURE:
<223> OTHER INFORMATION: The nucleotide sequence of PD-1 scFv heavy
      chain variable region

<400> SEQUENCE: 267

```
caggtgcagc tggtggagag cggcggcggc gtggtgcagc ccggccgcag cctgcgcctg    60
gactgcaagg ccagcggcat caccttcagc aacagcggca tgcactgggt cgccaggcc    120 cccggcaagg gcctggagtg gtggccgtg atctggtacg acggcagcaa cgctactac     180 gccgacagcg tgaagggccg cttcaccatc agccgcgaca cagcaagaa caccctgttc    240 ctgcagatga acagcctgcg cgccgaggac accgccgtgt actactgcgc caccaacgac    300
gactactggg gccagggcac cctggtgacc gtgagcagc                         339
```

<210> SEQ ID NO 268
<211> LENGTH: 324
<212> TYPE: DNA
<213> ORGANISM: Artificial
<220> FEATURE:
<223> OTHER INFORMATION: The nucleotide sequence of PD-1 scFv light
      chain variable region

<400> SEQUENCE: 268

```
gagatcgtgc tgacccagag ccccgccacc ctgagcctga gccccggcga gcgcgccacc    60
ctgagctgcc gcgccagcca gagcgtgagc agctacctgg cctggtacca gcagaagccc    120
ggccaggccc ccgcctgct gatctacgac gccagcaacc gccaccgg catccccgcc      180 cgcttcagcg gcagcggcag cggcaccgac ttcaccctga ccatcagcag cctggagccc    240
gaggacttcg ccgtgtacta ctgccagcag agcagcaact ggccccgcac cttcggccag    300
ggcaccaagg tggagatcaa gcgc                                          324
```

<210> SEQ ID NO 269
<211> LENGTH: 726
<212> TYPE: DNA
<213> ORGANISM: Artificial
<220> FEATURE:
<223> OTHER INFORMATION: The nucleotide sequence of CTLA-4 scFv

<400> SEQUENCE: 269

```
caggtgcagc tggtggagag cggcggcggc gtggtgcagc ccggccgcag cctgcgcctg    60
agctgcgccg ccagcggctt caccttcagc agctacacca tgcactgggt cgccaggcc    120 cccggcaagg gcctggagtg gtgaccttc atcagctacg acggcaacaa caagtactac    180
gccgacagcg tgaagggccg cttcaccatc agccgcgaca cagcaagaa caccctgtac    240
```

```
ctgcagatga acagcctgcg cgccgaggac accgccatct actactgcgc cgcaccggc    300 tggctgggcc ccttcgacta ctggggccag ggcaccctgg tgaccgtgag cagcggcggc    360
ggcggcagcg gcggcggcgg cagcggcggc ggcggcagcg agatcgtgct gacccagagc    420
cccggcaccc tgagcctgag ccccggcgag cgcgccaccc tgagcctgcc cgccagccag    480
agcgtgggca gcagctacct ggcctggtac cagcagaagc ccggccaggc ccccgcctg     540 ctgatctacg gcgccttcag ccgcgccacc ggcatccccg accgcttcag cggcagcggc    600
agcggcaccg acttcaccct gaccatcagc cgcctggagc ccgaggactt cgccgtgtac    660
tactgccagc agtacggcag cagcccctgg accttcggcc agggcaccaa ggtggagatc    720
aagcgc                                                               726

<210> SEQ ID NO 270
<211> LENGTH: 354
<212> TYPE: DNA
<213> ORGANISM: Artificial
<220> FEATURE:
<223> OTHER INFORMATION: The nucleotide sequence of CTLA-4 scFv heavy
      chain variable region

<400> SEQUENCE: 270
caggtgcagc tggtggagag cggcggcggc gtggtgcagc ccggccgcag cctgcgcctg    60
agctgcgccg ccagcggctt cacctttcagc agctacacca tgcactgggt cgccaggcc    120 cccggcaagg gcctggagtg ggtgaccttc atcagctacg acggcaacaa caagtactac    180
gccgacagcg tgaagggccg cttcaccatc agccgcgaca caagcaagaa cacccctgtac    240 ctgcagatga acagcctgcg cgccgaggac accgccatct actactgcgc cgcaccggc    300 tggctgggcc ccttcgacta ctggggccag ggcaccctgg tgaccgtgag cagc          354

<210> SEQ ID NO 271
<211> LENGTH: 327
<212> TYPE: DNA
<213> ORGANISM: Artificial
<220> FEATURE:
<223> OTHER INFORMATION: The nucleotide sequence of CTLA-4 scFv light
      chain variable region

<400> SEQUENCE: 271
gagatcgtgc tgacccagag ccccggcacc ctgagcctga gccccggcga gcgcgccacc    60
ctgagctgcc gcgccagcca gagcgtgggc agcagctacc tggcctggta ccagcagaag    120
cccggccagg ccccccgcct gctgatctac ggcgccttca gccgcgccac cggcatcccc    180
gaccgcttca gcggcagcgg cagcggcacc gacttcaccc tgaccatcag ccgcctggag    240
cccgaggact tcgccgtgta ctactgccag cagtacggca gcagcccctg gaccttcggc    300
cagggcacca aggtggagat caagcgc                                        327

<210> SEQ ID NO 272
<211> LENGTH: 729
<212> TYPE: DNA
<213> ORGANISM: Artificial
<220> FEATURE:
<223> OTHER INFORMATION: The nucleotide sequence of LAG-3 scFv

<400> SEQUENCE: 272
caggtgcagc tgcagcagtg gggcgccggc ctgctgaagc ccagcgagac cctgagcctg    60
acctgcgccg tgtacggcgg cagcttcagc gactactact ggaactggat ccgccagccc    120
```

```
cccggcaagg gcctggagtg atcggcgag atcaaccacc gcggcagcac caacagcaac      180
cccagcctga agagccgcgt gaccctgagc ctggacacca gcaagaacca gttcagcctg      240
aagctgcgca gcgtgaccgc cgccgacacc gccgtgtact actgcgcctt cggctacagc      300
gactacgagt acaactggtt cgaccccctgg ggccagggca ccctggtgac cgtgagcagc      360
ggcggcggcg gcagcggcgg cggcggcagc ggcggcggcg gcagcgagat cgtgctgacc      420
cagagccccg ccaccctgag cctgagcccc ggcgagcgcg ccaccctgag ctgccgcgcc      480
agccagagca tcagcagcta cctggcctgg taccagcaga agcccggcca ggcccccgc       540 ctgctgatct acgacgccag caaccgcgcc accggcatcc ccgcccgctt cagcggcagc      600
ggcagcggca ccgacttcac cctgaccatc agcagcctgg agcccgagga cttcgccgtg      660
tactactgcc agcagcgcag caactggccc ctgaccttcg gccagggcac caacctggag      720
atcaagcgc                                                              729
```

<210> SEQ ID NO 273
<211> LENGTH: 360
<212> TYPE: DNA
<213> ORGANISM: Artificial
<220> FEATURE:
<223> OTHER INFORMATION: The nucleotide sequence of LAG-3 scFv heavy
      chain variable region

<400> SEQUENCE: 273

```
caggtgcagc tgcagcagtg gggcgccggc ctgctgaagc ccagcgagac cctgagcctg      60
acctgcgccg tgtacggcgg cagcttcagc gactactact ggaactggat ccgccagccc      120
cccggcaagg gcctggagtg atcggcgag atcaaccacc gcggcagcac caacagcaac      180
cccagcctga agagccgcgt gaccctgagc ctggacacca gcaagaacca gttcagcctg      240
aagctgcgca gcgtgaccgc cgccgacacc gccgtgtact actgcgcctt cggctacagc      300
gactacgagt acaactggtt cgaccccctgg ggccagggca ccctggtgac cgtgagcagc      360
```

<210> SEQ ID NO 274
<211> LENGTH: 324
<212> TYPE: DNA
<213> ORGANISM: Artificial
<220> FEATURE:
<223> OTHER INFORMATION: The nucleotide sequence of LAG-3 scFv light
      chain variable region

<400> SEQUENCE: 274

```
gagatcgtgc tgacccagag ccccgccacc ctgagcctga gccccggcga gcgcgccacc      60
ctgagctgcc gcgccagcca gagcatcagc agctacctgg cctggtacca gcagaagccc      120
ggccaggccc ccgcctgct gatctacgac gccagcaacc gcgccaccgg catccccgcc      180
cgcttcagcg gcagcggcag cggcaccgac ttcaccctga ccatcagcag cctggagccc      240
gaggacttcg ccgtgtacta ctgccagcag cgcagcaact ggcccctgac cttcggccag      300
ggcaccaacc tggagatcaa gcgc                                             324
```

<210> SEQ ID NO 275
<211> LENGTH: 735
<212> TYPE: DNA
<213> ORGANISM: Artificial
<220> FEATURE:
<223> OTHER INFORMATION: The nucleotide sequence of TIM-3 scFv

<400> SEQUENCE: 275

```
caggtgcagc tggtgcagag cggcgccgag gtgaagaagc ccggcgccag cgtgaaggtg      60
```

```
agctgcaagg ccagcggcta ccttcacc agctacaaca tgcactgggt gcgccaggcc      120
cccggccagg gcctggagtg gatcggcgac atctaccccg ccagggcga caccagctac      180 aaccagaagt tcaagggccg cgccaccatg accgccgaca gagcaccag caccgtgtac      240 atggagctga gcagcctgcg cagcgaggac accgccgtgt actactgcgc ccgcgtgggc      300
ggcgccttcc ccatggacta ctggggccag ggcaccctgg tgaccgtgag cagcggcggc      360
ggcggcagcg gcggcggcgg cagcggcggc ggcggcagcg acatcgtgct gacccagagc      420
cccgacagcc tggccgtgag cctgggcgag cgcgccacca tcaactgccg cgccagcgag      480
agcgtggagt actacggcac cagcctgatg cagtggtacc agcagaagcc cggccagccc      540
cccaagctgc tgatctacgc cgccagcaac gtggagagcg gcgtgcccga ccgcttcagc      600
ggcagcggca gcggcaccga cttcaccctg accatcagca gcctgcaggc cgaggacgtg      660
gccgtgtact actgccagca gagccgcaag gaccccagca ccttcggcgg cggcaccaag      720
gtggagatca agcgc                                                      735

<210> SEQ ID NO 276
<211> LENGTH: 354
<212> TYPE: DNA
<213> ORGANISM: Artificial
<220> FEATURE:
<223> OTHER INFORMATION: The nucleotide sequence of TIM-3 scFv heavy
      chain variable region

<400> SEQUENCE: 276
caggtgcagc tggtgcagag cggcgccgag gtgaagaagc ccggcgccag cgtgaaggtg       60
agctgcaagg ccagcggcta ccttcacc agctacaaca tgcactgggt gcgccaggcc      120
cccggccagg gcctggagtg gatcggcgac atctaccccg ccagggcga caccagctac      180 aaccagaagt tcaagggccg cgccaccatg accgccgaca gagcaccag caccgtgtac      240 atggagctga gcagcctgcg cagcgaggac accgccgtgt actactgcgc ccgcgtgggc      300
ggcgccttcc ccatggacta ctggggccag ggcaccctgg tgaccgtgag cagc           354

<210> SEQ ID NO 277
<211> LENGTH: 336
<212> TYPE: DNA
<213> ORGANISM: Artificial
<220> FEATURE:
<223> OTHER INFORMATION: The nucleotide sequence of TIM-3 scFv light
      chain variable region

<400> SEQUENCE: 277
gacatcgtgc tgacccagag ccccgacagc ctggccgtga gcctgggcga gcgcgccacc       60
atcaactgcc gcgccagcga gagcgtggag tactacggca ccagcctgat gcagtggtac      120
cagcagaagc ccggccagcc ccccaagctg ctgatctacg ccgccagcaa cgtggagagc      180
ggcgtgcccg accgcttcag cggcagcggc agcggcaccg acttcaccct gaccatcagc      240
agcctgcagg ccgaggacgt ggccgtgtac tactgccagc agagccgcaa ggaccccagc      300
accttcggcg gcggcaccaa ggtggagatc aagcgc                                336

<210> SEQ ID NO 278
<211> LENGTH: 747
<212> TYPE: DNA
<213> ORGANISM: Artificial
<220> FEATURE:
<223> OTHER INFORMATION: The nucleotide sequence of TIGIT scFv
```

<400> SEQUENCE: 278

```
gaggtgcagc tgcaggagag cggccccggc ctggtgaagc ccagccagag cctgagcctg      60
acctgcagcg tgaccggcag cagcatcgcc agcgactact ggggctggat ccgcaagttc     120
cccggcaaca gatggagtg gatgggcttc atcacctaca gcggcagcac cagctacaac     180
cccagcctga agagccgcat cagcatcacc cgcgacacca gcaagaacca gttcttcctg     240
cagctgcaca gcgtgaccac cgacgacacc gccacctaca gctgcgcccg catgcccagc     300
ttcatcaccc tggccagcct gagcacctgg gagggctact tcgacttctg ggccccggc     360
accatggtga ccgtgagcag cggcggcggc ggcagcggcg gcggcggcag cggcggcggc     420
ggcagcgaca tccagatgac ccagagcccc agcctgctga gcgccagcgt gggcgaccgc     480
gtgaccctga actgcaaggc cagccagagc atccacaaga acctggcctg gtaccagcag     540
aagctgggcg aggcccccaa gttcctgatc tactacgcca acagcctgca gaccggcatc     600
cccagccgct cagcggcag cggcagcggc accgacttca ccctgaccat cagcggcctg     660
cagcccgagg acgtggccac ctacttctgc cagcagtact acagcggctg gaccttcggc     720
ggcggcacca aggtggagct gaagcgc                                         747
```

<210> SEQ ID NO 279
<211> LENGTH: 381
<212> TYPE: DNA
<213> ORGANISM: Artificial
<220> FEATURE:
<223> OTHER INFORMATION: The nucleotide sequence of TIGIT scFv heavy chain variable region

<400> SEQUENCE: 279

```
gaggtgcagc tgcaggagag cggccccggc ctggtgaagc ccagccagag cctgagcctg      60
acctgcagcg tgaccggcag cagcatcgcc agcgactact ggggctggat ccgcaagttc     120
cccggcaaca gatggagtg gatgggcttc atcacctaca gcggcagcac cagctacaac     180
cccagcctga agagccgcat cagcatcacc cgcgacacca gcaagaacca gttcttcctg     240
cagctgcaca gcgtgaccac cgacgacacc gccacctaca gctgcgcccg catgcccagc     300
ttcatcaccc tggccagcct gagcacctgg gagggctact tcgacttctg ggccccggc     360
accatggtga ccgtgagcag c                                               381
```

<210> SEQ ID NO 280
<211> LENGTH: 321
<212> TYPE: DNA
<213> ORGANISM: Artificial
<220> FEATURE:
<223> OTHER INFORMATION: The nucleotide sequence of TIGIT scFv light chain variable region

<400> SEQUENCE: 280

```
gacatccaga tgacccagag ccccagcctg ctgagcgcca gcgtgggcga ccgcgtgacc      60
ctgaactgca aggccagcca gagcatccac aagaacctgg cctggtacca gcagaagctg     120
ggcgaggccc ccaagttcct gatctactac gccaacagcc tgcagaccgg catccccagc     180
cgcttcagcg gcagcggcag cggcaccgac ttcaccctga ccatcagcgg cctgcagccc     240
gaggacgtgg ccacctactt ctgccagcag tactacagcg gctggacctt cggcggcggc     300
accaaggtgg agctgaagcg c                                               321
```

<210> SEQ ID NO 281
<211> LENGTH: 735

<212> TYPE: DNA
<213> ORGANISM: Artificial
<220> FEATURE:
<223> OTHER INFORMATION: The nucleotide sequence of BTLA scFv

<400> SEQUENCE: 281

```
gaggtgcagc tggtggagag cggcggcggc ctggtgcagc ccggcggcag cctgcgcctg      60
agctgcgccg ccagcggctt caccatcagc agctacgaca tgcactgggt gcgccaggcc     120
accggcaagg gcctggagtg ggtgagcgtg atcggccccg ccggcgacac ctactacccc     180
ggcagcgtga agggccgctt caccatcagc cgcgagaacg ccaagaacag cctgtacctg     240
cagatgaaca gcctgcgcgc cggcgacacc gccgtgtact actgcgcccg cgagggcatg     300
gccgcccaca actactacgg catggacgtg tggggccagg gcaccaccgt gaccgtgagc     360
agcggcggcg gcggcagcgg cggcggcggc agcggcggcg gcggcagcga gatcgtgctg     420
acccagagcc ccgccaccct gagcctgagc cccggcgagc gcgccaccct gagctgccgc     480
gccagccaga gcgtgagcag ctacctggcc tggtaccagc agaagcccgg ccaggccccc     540
cgcctgctga tctacgacgc cagcaaccgc gccaccggca tccccgcccg cttcagcggc     600
agcggcagcg gcaccgactt cacgctgacc atcagcagcc tggagcccga ggacttcgcc     660
gtgtactact gccagcagcg cagcaactgg ccccccatca ccttcggcca gggcaccgcc     720
ctggagatca gcgc                                                        735
```

<210> SEQ ID NO 282
<211> LENGTH: 363
<212> TYPE: DNA
<213> ORGANISM: Artificial
<220> FEATURE:
<223> OTHER INFORMATION: The nucleotide sequence of BTLA scFv heavy
      chain variable region

<400> SEQUENCE: 282

```
gaggtgcagc tggtggagag cggcggcggc ctggtgcagc ccggcggcag cctgcgcctg      60
agctgcgccg ccagcggctt caccatcagc agctacgaca tgcactgggt gcgccaggcc     120
accggcaagg gcctggagtg ggtgagcgtg atcggccccg ccggcgacac ctactacccc     180
ggcagcgtga agggccgctt caccatcagc cgcgagaacg ccaagaacag cctgtacctg     240
cagatgaaca gcctgcgcgc cggcgacacc gccgtgtact actgcgcccg cgagggcatg     300
gccgcccaca actactacgg catggacgtg tggggccagg gcaccaccgt gaccgtgagc     360
agc                                                                    363
```

<210> SEQ ID NO 283
<211> LENGTH: 327
<212> TYPE: DNA
<213> ORGANISM: Artificial
<220> FEATURE:
<223> OTHER INFORMATION: The nucleotide sequence of BTLA scFv light
      chain variable region

<400> SEQUENCE: 283

```
gagatcgtgc tgacccagag ccccgccacc ctgagcctga gccccggcga gcgcgccacc     60
ctgagctgcc gcgccagcca gagcgtgagc agctacctgg cctggtacca gcagaagccc    120
ggccaggccc ccgcctgctg atctacgac gccagcaacc gcgccaccgg catccccgcc     180
cgcttcagcg gcagcggcag cggcaccgac ttcaccctga ccatcagcag cctggagccc    240
gaggacttcg ccgtgtacta ctgccagcag cgcagcaact ggccccccat caccttcggc    300
```
cagggcaccc gcctggagat caagcgc     327

<210> SEQ ID NO 284
<211> LENGTH: 19
<212> TYPE: PRT
<213> ORGANISM: Artificial
<220> FEATURE:
<223> OTHER INFORMATION: The amino acid sequence of the secretory signal
      peptide

<400> SEQUENCE: 284

Met Thr Arg Leu Thr Val Leu Ala Leu Leu Ala Gly Leu Leu Ala Ser
1               5                   10                  15

Ser Arg Ala

<210> SEQ ID NO 285
<211> LENGTH: 57
<212> TYPE: DNA
<213> ORGANISM: Artificial
<220> FEATURE:
<223> OTHER INFORMATION: The nucleotide sequence of the secretory signal
      peptide

<400> SEQUENCE: 285
atgacccgcc tgaccgtgct ggccctgctg gccggcctgc tggccagcag ccgcgcc     57

<210> SEQ ID NO 286
<211> LENGTH: 59
<212> TYPE: DNA
<213> ORGANISM: Artificial
<220> FEATURE:
<223> OTHER INFORMATION: pcDNA3.1-Sig-F

<400> SEQUENCE: 286
gtgctggata tctgcagaat tcgccgccac catgacccgg ctgaccgtgc tggccctgc     59

<210> SEQ ID NO 287
<211> LENGTH: 49
<212> TYPE: DNA
<213> ORGANISM: Artificial
<220> FEATURE:
<223> OTHER INFORMATION: Sig-R

<400> SEQUENCE: 287
ggccctggag gaggccagca ggccggccag cagggccagc acggtcagc     49

<210> SEQ ID NO 288
<211> LENGTH: 41
<212> TYPE: DNA
<213> ORGANISM: Artificial
<220> FEATURE:
<223> OTHER INFORMATION: Sig-CD3-F

<400> SEQUENCE: 288
gctggcctcc tccagggccg acatcaagct gcagcagagc g     41

<210> SEQ ID NO 289
<211> LENGTH: 20
<212> TYPE: DNA
<213> ORGANISM: Artificial
<220> FEATURE:
<223> OTHER INFORMATION: CD3-R

<400> SEQUENCE: 289
cttcagctcc agcttggtgc     20

<210> SEQ ID NO 290
<211> LENGTH: 91
<212> TYPE: DNA
<213> ORGANISM: Artificial
<220> FEATURE:
<223> OTHER INFORMATION: CD3-(GGGGS)3-PD-1-F

<400> SEQUENCE: 290
ggcaccaagc tggagctgaa gggcggcggc ggcagcggcg gcggcggcag cggcggcggc    60
ggcagccagg tgcagctggt ggagagcggc g                                  91

<210> SEQ ID NO 291
<211> LENGTH: 49
<212> TYPE: DNA
<213> ORGANISM: Artificial
<220> FEATURE:
<223> OTHER INFORMATION: pcDNA3.1-PD-1-R

<400> SEQUENCE: 291
ctgatcagcg gtttaaactt aagctttcag cgcttgatct ccaccttgg               49

<210> SEQ ID NO 292
<211> LENGTH: 41
<212> TYPE: DNA
<213> ORGANISM: Artificial
<220> FEATURE:
<223> OTHER INFORMATION: CD3-IgD-F

<400> SEQUENCE: 292
gcaccaagct ggagctgaag gccagcaaga gcaagaagga g                       41

<210> SEQ ID NO 293
<211> LENGTH: 21
<212> TYPE: DNA
<213> ORGANISM: Artificial
<220> FEATURE:
<223> OTHER INFORMATION: IgD-R

<400> SEQUENCE: 293
cacgcccagg ggctgggtgt g                                             21

<210> SEQ ID NO 294
<211> LENGTH: 43
<212> TYPE: DNA
<213> ORGANISM: Artificial
<220> FEATURE:
<223> OTHER INFORMATION: IgD-PD-1-F

<400> SEQUENCE: 294
cacacccagc ccctgggcgt gcaggtgcag ctggtggaga gcg                     43

<210> SEQ ID NO 295
<211> LENGTH: 87
<212> TYPE: DNA
<213> ORGANISM: Artificial
<220> FEATURE:
<223> OTHER INFORMATION: CD3-(GGGGS)3-CTLA-4-F

<400> SEQUENCE: 295
ggcaccaagc tggagctgaa gggcggcggc ggcagcggcg gcggcggcag cggcggcggc    60
ggcagccagg tgcagctggt ggagagc                                       87

<210> SEQ ID NO 296
<211> LENGTH: 49

```
<212> TYPE: DNA
<213> ORGANISM: Artificial
<220> FEATURE:
<223> OTHER INFORMATION: pcDNA3.1-CTLA-4-R

<400> SEQUENCE: 296
ctgatcagcg gtttaaactt aagctttcag cgcttgatct ccaccttgg          49

<210> SEQ ID NO 297
<211> LENGTH: 40
<212> TYPE: DNA
<213> ORGANISM: Artificial
<220> FEATURE:
<223> OTHER INFORMATION: IgD-CTLA-4-F

<400> SEQUENCE: 297
acacccagcc cctgggcgtg ccaaggtgga gatcaagcgc                    40

<210> SEQ ID NO 298
<211> LENGTH: 87
<212> TYPE: DNA
<213> ORGANISM: Artificial
<220> FEATURE:
<223> OTHER INFORMATION: CD3-(GGGGS)3-LAG-3-F

<400> SEQUENCE: 298
ggcaccaagc tggagctgaa gggcggcggc ggcagcggcg gcggcggcag cggcggcggc   60
ggcagccagg tgcagctgca gcagtgg                                      87

<210> SEQ ID NO 299
<211> LENGTH: 49
<212> TYPE: DNA
<213> ORGANISM: Artificial
<220> FEATURE:
<223> OTHER INFORMATION: pcDNA3.1-LAG-3-R

<400> SEQUENCE: 299
ctgatcagcg gtttaaactt aagctttcag cgcttgatct ccaggttgg          49

<210> SEQ ID NO 300
<211> LENGTH: 40
<212> TYPE: DNA
<213> ORGANISM: Artificial
<220> FEATURE:
<223> OTHER INFORMATION: IgD-LAG-3-F

<400> SEQUENCE: 300
acacccagcc cctgggcgtg ccaacctgga gatcaagcgc                    40

<210> SEQ ID NO 301
<211> LENGTH: 87
<212> TYPE: DNA
<213> ORGANISM: Artificial
<220> FEATURE:
<223> OTHER INFORMATION: CD3-(GGGGS)3-TIM-3-F

<400> SEQUENCE: 301
ggcaccaagc tggagctgaa gggcggcggc ggcagcggcg gcggcggcag cggcggcggc   60
ggcagccagg tgcagctggt gcagagc                                      87

<210> SEQ ID NO 302
<211> LENGTH: 50
<212> TYPE: DNA
<213> ORGANISM: Artificial
<220> FEATURE:
```

<223> OTHER INFORMATION: pcDNA3.1-TIM-3-R

<400> SEQUENCE: 302
ctgatcagcg gtttaaactt aagctttcag cgcttgatct ccaccttggt                50

<210> SEQ ID NO 303
<211> LENGTH: 40
<212> TYPE: DNA
<213> ORGANISM: Artificial
<220> FEATURE:
<223> OTHER INFORMATION: IgD-TIM-3-F

<400> SEQUENCE: 303
acacccagcc cctgggcgtg ccaaggtgga gatcaagcgc                           40

<210> SEQ ID NO 304
<211> LENGTH: 87
<212> TYPE: DNA
<213> ORGANISM: Artificial
<220> FEATURE:
<223> OTHER INFORMATION: CD3-(GGGGS)3-TIGIT-F

<400> SEQUENCE: 304
ggcaccaagc tggagctgaa gggcggcggc ggcagcggcg gcggcggcag cggcggcggc     60
ggcagcgagg tgcagctgca ggagagc                                        87

<210> SEQ ID NO 305
<211> LENGTH: 49
<212> TYPE: DNA
<213> ORGANISM: Artificial
<220> FEATURE:
<223> OTHER INFORMATION: pcDNA3.1-TIGIT-R

<400> SEQUENCE: 305
ctgatcagcg gtttaaactt aagctttcag cgcttcagct ccaccttgg                 49

<210> SEQ ID NO 306
<211> LENGTH: 40
<212> TYPE: DNA
<213> ORGANISM: Artificial
<220> FEATURE:
<223> OTHER INFORMATION: IgD-TIGIT-F

<400> SEQUENCE: 306
acacccagcc cctgggcgtg ccaaggtgga gctgaagcgc                           40

<210> SEQ ID NO 307
<211> LENGTH: 87
<212> TYPE: DNA
<213> ORGANISM: Artificial
<220> FEATURE:
<223> OTHER INFORMATION: CD3-(GGGGS)3-BTLA-F

<400> SEQUENCE: 307
ggcaccaagc tggagctgaa gggcggcggc ggcagcggcg gcggcggcag cggcggcggc     60
ggcagcgagg tgcagctggt ggagagc                                        87

<210> SEQ ID NO 308
<211> LENGTH: 49
<212> TYPE: DNA
<213> ORGANISM: Artificial
<220> FEATURE:
<223> OTHER INFORMATION: pcDNA3.1-BTLA-R

<400> SEQUENCE: 308

```
ctgatcagcg gtttaaactt aagctttcag cgcttgatct ccaggcggg                49
```

<210> SEQ ID NO 309
<211> LENGTH: 42
<212> TYPE: DNA
<213> ORGANISM: Artificial
<220> FEATURE:
<223> OTHER INFORMATION: IgD-BTLA-F

<400> SEQUENCE: 309

```
cacacccagc ccctgggcgt ggaggtgcag ctggtggaga gc                       42
```